United States Patent
Azuma et al.

(10) Patent No.: US 10,077,254 B2
(45) Date of Patent: Sep. 18, 2018

(54) TETRAZOLINONE COMPOUND AND USE THEREOF

(71) Applicant: SUMITOMO CHEMICAL COMPANY, LIMITED, Tokyo (JP)

(72) Inventors: Shuhei Azuma, Takarazuha (JP); Teruki Takahashi, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/029,377

(22) PCT Filed: Oct. 15, 2014

(86) PCT No.: PCT/JP2014/078005
§ 371 (c)(1),
(2) Date: Apr. 14, 2016

(87) PCT Pub. No.: WO2015/056811
PCT Pub. Date: Apr. 23, 2015

(65) Prior Publication Data
US 2016/0272622 A1    Sep. 22, 2016

(30) Foreign Application Priority Data
Oct. 17, 2013 (JP) .................. 2013-216079

(51) Int. Cl.
| | |
|---|---|
| C07D 401/04 | (2006.01) |
| A01N 43/713 | (2006.01) |
| C07D 403/04 | (2006.01) |
| A01N 43/80 | (2006.01) |
| C07D 401/14 | (2006.01) |
| C07D 409/14 | (2006.01) |
| C07D 417/14 | (2006.01) |
| A01N 43/78 | (2006.01) |
| C07D 403/14 | (2006.01) |

(52) U.S. Cl.
CPC ......... C07D 403/04 (2013.01); A01N 43/713 (2013.01); A01N 43/78 (2013.01); A01N 43/80 (2013.01); C07D 401/14 (2013.01); C07D 403/14 (2013.01); C07D 409/14 (2013.01); C07D 417/14 (2013.01)

(58) Field of Classification Search
CPC .......................... C07D 401/14; C07D 403/04
USPC ....................................................... 514/341
See application file for complete search history.

(56) References Cited

U.S. PATENT DOCUMENTS

| | | | |
|---|---|---|---|
| 5,589,439 A | 12/1996 | Goto et al. | |
| 5,641,727 A | 6/1997 | Goto et al. | |
| 6,294,503 B1 | 9/2001 | Gupta et al. | |
| 9,380,782 B2 * | 7/2016 | Yoshimoto | A01N 43/76 |

(Continued)

FOREIGN PATENT DOCUMENTS

| | | |
|---|---|---|
| CN | 102875540 A | 1/2013 |
| EP | 0 902 028 A1 | 3/1999 |

(Continued)

OTHER PUBLICATIONS

Office Action issued in Chinese counterpart application 201480056941.5 dated Dec. 30, 2016 (with English language translation).

(Continued)

*Primary Examiner* — Sabiha N Qazi
(74) *Attorney, Agent, or Firm* — Birch, Stewart, Kolasch & Birch, LLP

(57) ABSTRACT

A tetrazolinone compound represented by formula (1)

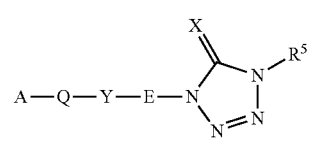

(1)

wherein E represents the following group E16;

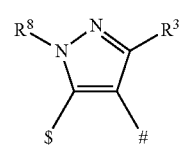

E16

Y represents —O—CH$_2$—;
Q represents the following group Q46;

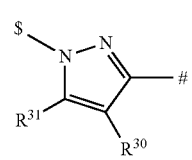

Q46

$R^8$ represents a C1-C6 alkyl group; $R^3$, $R^{30}$ and $R^{31}$ are the same or different and represent a hydrogen atom; A represents a C6-C16 aryl group optionally having one or more atoms or groups selected from Group $P^1$; $R^5$ represents a C1-C3 alkyl group; and X represents an oxygen atom or a sulfur atom, has excellent control activity against pests.

5 Claims, No Drawings

(56) References Cited

U.S. PATENT DOCUMENTS

| | | | |
|---|---|---|---|
| 9,635,857 B2* | 5/2017 | Shioda | A01N 43/713 |
| 9,675,072 B2* | 6/2017 | Arimori | C07D 403/12 |
| 9,781,933 B2* | 10/2017 | Hou | C07D 401/14 |
| 9,822,096 B2* | 11/2017 | Johnson | C07D 239/95 |
| 9,828,389 B2* | 11/2017 | Arimori | C07D 403/12 |
| 2015/0031733 A1 | 1/2015 | Yoshimoto et al. | |
| 2015/0051171 A1 | 2/2015 | Yoshimoto et al. | |
| 2015/0203511 A1 | 7/2015 | Arimori et al. | |
| 2015/0223460 A1 | 8/2015 | Arimori et al. | |
| 2015/0299146 A1 | 10/2015 | Hasegawa et al. | |
| 2015/0336908 A1 | 11/2015 | Shioda et al. | |
| 2016/0081339 A1 | 3/2016 | Yoshimoto et al. | |
| 2016/0081340 A1 | 3/2016 | Arimori et al. | |
| 2016/0150787 A1* | 6/2016 | Azuma | C07D 403/12 514/252.05 |
| 2016/0157489 A1 | 6/2016 | Shioda et al. | |
| 2016/0159755 A1 | 6/2016 | Shioda et al. | |
| 2016/0174558 A1 | 6/2016 | Hou et al. | |
| 2016/0205935 A1 | 7/2016 | Akioka et al. | |

FOREIGN PATENT DOCUMENTS

| | | |
|---|---|---|
| JP | 8-81459 A | 3/1996 |
| JP | 8-99975 A | 4/1996 |
| JP | 9-87281 A | 3/1997 |
| JP | 9-100272 A | 4/1997 |
| JP | 9-100277 A | 4/1997 |
| JP | 9-110863 A | 4/1997 |
| JP | 9-208565 * | 8/1997 |
| JP | 11-152278 A | 6/1999 |
| JP | 2001-512460 A | 8/2001 |
| WO | WO 96/36229 | 11/1996 |
| WO | WO 98/23156 | 6/1998 |
| WO | WO 98/25912 A1 | 6/1998 |
| WO | WO 98/35961 A1 | 8/1998 |
| WO | WO 98/35961 A1 | 11/1998 |
| WO | WO 98/51683 A1 | 11/1998 |
| WO | WO 99/11129 | 3/1999 |
| WO | WO 99/48890 A1 | 9/1999 |
| WO | WO 2013/162072 A1 | 10/2013 |
| WO | WO 2013/162077 A1 | 10/2013 |
| WO | WO 2014/051161 A1 | 4/2014 |
| WO | WO 2014/051165 A1 | 4/2014 |
| WO | WO 2014/084223 A1 | 6/2014 |
| WO | WO 2014/104268 A1 | 7/2014 |
| WO | WO 2014/104382 A1 | 7/2014 |
| WO | WO 2014/104384 A1 | 7/2014 |
| WO | WO 2014/175465 A1 | 10/2014 |
| WO | WO 2014/192953 A1 | 12/2014 |
| WO | WO 2015/005499 A1 | 1/2015 |
| WO | WO 2015/016335 A1 | 2/2015 |
| WO | WO 2015/016372 A1 | 2/2015 |
| WO | WO 2015/016373 A1 | 2/2015 |
| WO | WO 2015/030217 A1 | 3/2015 |
| WO | WO 2015/041360 A1 | 3/2015 |
| WO | WO 2015/046480 A1 | 4/2015 |
| WO | WO 2015/056806 A1 | 4/2015 |
| WO | WO 2015/060461 A1 | 4/2015 |

OTHER PUBLICATIONS

English translation of the Written Opinion of the International Searching Authority (Form PCT/ISA/237), dated Nov. 25, 2014, for International Application No. PCT/JP2014/078005.

International Search Report for PCT/JP2014/078005 dated Nov. 25, 2014.

Extended European Search Report dated Mar. 6, 2017, for European Application No. 14853630.3.

* cited by examiner

TETRAZOLINONE COMPOUND AND USE THEREOF

TECHNICAL FIELD

The present invention relates to a tetrazolinone compound and application for same.

BACKGROUND ART

Heretofore, various chemicals have been developed so as to control pests and provided in practice use, but in some cases, these chemicals may not exert enough activity.

Meanwhile, there have been known, as compounds having a tetrazolinone ring substituted with a 6-membered ring heterocycle, compounds represented by the following formulas (A1) and (A2):

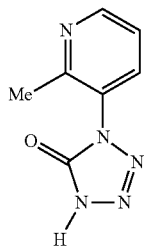

(A1)

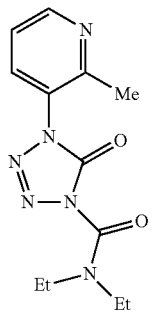

(A2)

(see EP 0692482 A).

Meanwhile, there have been known, as compounds having a tetrazolinone ring substituted with a 5-membered ring heterocycle, compounds represented by the following formulas (B1) and (B2):

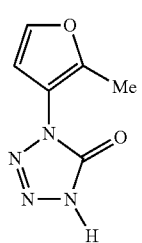

(B1)

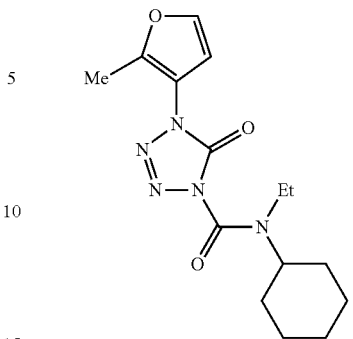

(B2)

(see EP 0695748 A).

The present invention provides compounds having excellent control activity against pests.

DISCLOSURE OF THE INVENTION

The present inventors have intensively studied so as to find compounds having excellent control activity against pests, and found that a tetrazolinone compound represented by the following formula (1) has excellent control activity against pests, thus completing the present invention.

The present invention includes the followings [1] to [6].

[1] A tetrazolinone compound represented by formula (1):

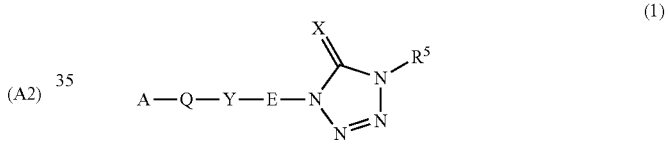

(1)

wherein $R^5$ represents a C1-C3 alkyl group optionally having one or more halogen atoms;

E represents a divalent 5-membered heteroaryl group or a divalent 6-membered heteroaryl group;

Y represents *—$(CH_2)_n$-G-&, *-G-$(CH_2)_n$—&, *-G-$(CH_2)_n$-G-&, *-G-$CH_2CH_2$-G-$CH_2CH_2$-G-&, *—$CH_2$-G-$CH_2CH_2$-G-&, *-G-$CH_2CH_2$-G-$CH_2$—&, *—CH=CH—&, *—CH=CH-G-&, *-G-CH=CH—&, *—CH=CH—$CH_2$-G-&, *-G-$CH_2$—CH=CH—&, *-G-CH=CH—$CH_2$—&, *—$CH_2$—CH=CH-G-&, *—CH=CH-G-$CH_2$—&, *—$CH_2$-G-CH=CH—&, *—CH=CH—$CH_2$-G-$CH_2$—&, *—$CH_2$-G-$CH_2$—CH=CH—&, *—CH=CH-G-$CH_2CH_2$—&, *—$CH_2CH_2$-G-CH=CH—&, *-G-CH=CH—$CH_2CH_2$—&, *—$CH_2CH_2$—CH=CH-G-&, *—CH=CH-G-CH=CH—&, *—C≡C—&, *—C≡C—$CH_2$-G-&, *-G-$CH_2$—C≡C—&, *—C≡C—$CH_2$-G-$CH_2$—&, or *—$CH_2$-G-$CH_2$—C≡C—& wherein all hydrogen atoms of Y including hydrogen atoms of G are optionally substituted with one or more atoms or groups selected from the group consisting of a halogen atom and a C1-C3 alkyl group and, when substituted with two or more atoms or groups, the atoms and groups may be the same or different to each other; G represents an oxygen atom, a sulfur atom, or $NR^B$ wherein $R^B$ represents a hydrogen atom or a C1-C3 alkyl group, n represents an integer of 1 to 10, the symbol * in Y represents a binding site for Q, and the symbol & represents a binding site for E;

Q represents a divalent C6-C10 aryl group, wherein the divalent C6-C10 aryl group optionally has one or more atoms or groups elected from Group P² or a divalent 5- to 10-membered heterocyclic group wherein the divalent 5- to 10-membered heterocyclic group optionally has one or more atoms or groups selected from Group P², and has, as a ring-constituent atom, one or more atoms selected from the group consisting of a nitrogen atom, an oxygen atom, and a sulfur atom, and, when two or more atoms are present, the atoms may be the same or different to each other;

X represents an oxygen atom or a sulfur atom;

A represents a C6-C10 aryl group, an adamantyl group, a C6-C10 aryloxy group, a C6-C10 arylthio group, a C6-C10 arylamino group, a C3-C10 cycloalkyl group, a 5- to 10-membered heterocyclic group, wherein the 5- to 10-membered heterocyclic group has, as a ring-constituent atom, one or more atoms selected from the group consisting of a nitrogen atom, an oxygen atom, and a sulfur atom, and, when two or more atoms are present, the atoms may be the same or different to each other, a 5- to 10-membered heteroaryloxy group wherein the 5- to 10-membered heteroaryloxy group has, as a ring-constituent atom, one or more atoms selected from the group consisting of a nitrogen atom, an oxygen atom, and a sulfur atom, and when two or more atoms are present, the atoms may be the same or different to each other, a 5- to 10-membered heteroarylthio group, wherein the 5- to 10-membered heteroarylthio group has, as a ring-constituent atom, one or more atoms selected from the group consisting of a nitrogen atom, an oxygen atom, and a sulfur atom, and, when two or more atoms are present, the atoms may be the same or different to each other, a 5- to 10-membered heteroarylamino group, wherein the 5- to 10-membered heteroarylamino group has, as a ring-constituent atom, one or more atoms selected from the group consisting of a nitrogen atom, an oxygen atom, and a sulfur atom, and, when two or more atoms are present, the atoms may be the same or different to each other, a C6-C10 arylsulfonyl group, a C6-C10 arylsulfinyl group, or —CH=NH optionally having one or two groups selected from Group P³, wherein, when —CH=NH has two groups selected from Group P³, the groups may be the same or different to each other, and wherein the C6-C10 aryl group, the adamantyl group, the C6-C10 aryloxy group, the C6-C10 arylthio group, the C6-C10 arylamino group, the C3-C10 cycloalkyl group, the 5- to 10-membered heterocyclic group, the 5- to 10-membered heteroaryloxy group, the 5- to 10-membered heteroarylthio group, and the 5- to 10-membered heteroarylamino group, the C6-C10 arylsulfonyl group, and the C6-C10 arylsulfinyl group optionally have one or more atoms or groups selected from Group P¹, and, when two or more atoms or groups are present, the atoms or groups may be the same or different to each other:

Group P¹: Group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a carboxy group, a formyl group, a C2-C6 alkoxycarbonyl group, a nitro group, a cyano group, a hydroxy group, a C1-C6 alkylsulfonyl group, a C1-C6 haloalkylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, and an aminocarbonyl group optionally having a C1-C6 alkyl group;

Group P²: Group consisting of a halogen atom, a cyano group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group; and Group P³: Group consisting of a C1-C6 alkyl group, a C1-C6 haloalkyl group, a C3-C6 cycloalkyl group, and a C3-C6 halocycloalkyl group.

[2] The tetrazolinone compound according to [1], wherein E is any one group selected from Group P⁴:

Group P⁴: Group consisting of E1 to E7:

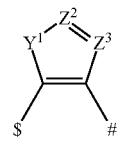

E1

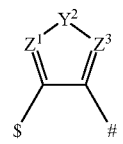

E2

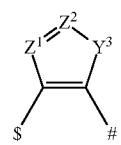

E3

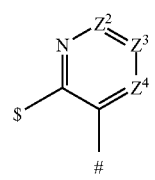

E4

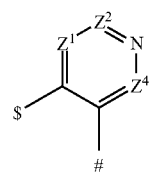

E5

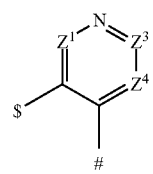

E6

-continued

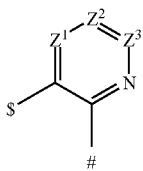

E7 in which the symbol # represents a binding site for a tetrazolinone ring, and the symbol $ represents a binding site for Y; and $Z^1$ represents a nitrogen atom or $CR^1$; $Z^2$ represents a nitrogen atom or $CR^2$; $Z^3$ represents a nitrogen atom or $CR^3$; $Z^4$ represents a nitrogen atom or $CR^4$;

$Y^1$ represents an oxygen atom, a sulfur atom, or $NR^8$; $Y^2$ represents an oxygen atom, a sulfur atom, or $NR^8$; $Y^3$ represents an oxygen atom, a sulfur atom, or $NR^7$;

$R^1$ represents a hydrogen atom, a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, a thiol group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group;

$R^2$, $R^3$, and $R^4$ each independently represents a hydrogen atom, a halogen atom, a C1-C3 alkyl group, a C1-C3 haloalkyl group, a C2-C3 alkenyl group, a C2-C3 haloalkenyl group, or a C1-C3 alkoxy group;

$R^6$ and $R^7$ each independently represents a hydrogen atom, a C1-C3 alkyl group, a C1-C3 haloalkyl group, a C2-C3 alkenyl group, a C2-C3 haloalkenyl group, or a C1-C3 alkoxy group;

$R^8$ represents a hydrogen atom, a C1-C6 alkyl group, a C3-C6 cycloalkyl group, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group.

[3] The tetrazolinone compound according to [1] or [2], wherein Y is —O—CH$_2$—.

[4] A pest control agent comprising the tetrazolinone compound according to any one of [1] to [3].

[5] A method for controlling pests, which comprises applying an effective amount of the tetrazolinone compound according to any one of [1] to [3] to plants or soil.

[6] Use of the tetrazolinone compound according to any one of [1] to [3] for controlling pests.

According to the present invention, pests can be controlled.

MODE FOR CARRYING OUT THE INVENTION

A compound of the present invention is a tetrazolinone compound represented by formula (1):

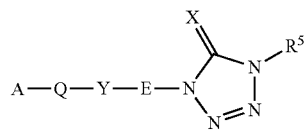

$R^5$, X, E, Y, Q, and A are the same as defined above (hereinafter referred to as the present compound).

Substituents as used herein will be mentioned below.

In the present invention, "membered" represents the number of atoms constituting the ring of aryl, hetero ring, heteroaryl, and the like. For example, it is referred to as "10-membered" for naphthalene, or referred to as "9-membered" for benzofuran mentioned below.

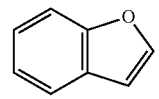

Examples of the halogen atom include a fluorine atom, a chlorine atom, a bromine atom and iodine atom.

Examples the C1-C3 alkyl group include a methyl group, an ethyl group, a propyl group, and an isopropyl group.

The C1-C3 alkyl group optionally having one or more halogen atoms represents a C1-C3 alkyl group in which one or more hydrogen atoms of a C1-C3 alkyl group are optionally substituted with a halogen atom, and examples thereof include a methyl group, an ethyl group, a propyl group, an isopropyl group, a fluoromethyl group, a chloromethyl group, a difluoromethyl group, a trifluoromethyl group, a 2,2,2-trifluoroethyl group, a pentafluoroethyl group, a 2,2-difluoroethyl group, a 2-fluoropropyl group, a 3-fluoropropyl group, a 2,2-difluoropropyl group, a 3,3,3-trifluoropropyl group, and a 3-(fluoromethyl)-2-fluoroethyl group.

The 5-membered heteroaryl group represents a group having, as a ring-constituent atom, one or more atoms selected from the group consisting of a nitrogen atom, an oxygen atom, and a sulfur atom and, when having two or more atoms, the atoms may be the same or different to each other.

Examples of the divalent 5-membered heteroaryl group include a thiophene-di-yl group, a furan-di-yl group, a pyrrole-di-yl group, a pyrazole-di-yl group, an imidazole-di-yl group, a thiazole-di-yl group, an isothiazole-di-yl group, an oxazole-di-yl group, an isoxazole-di-yl group, a triazole-di-yl group, an oxadiazole-di-yl group, and a thiadiazole-di-yl group.

Examples thereof include the following groups E11 to E46 (in which the symbol # represents a binding site for a tetrazolinone ring, and the symbol $ represents a binding site for Y):

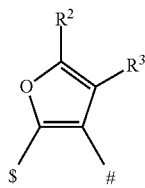
E11

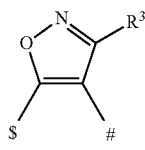
E12

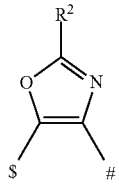
E13

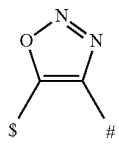
E14

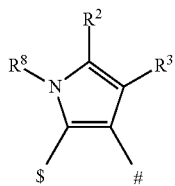
E15

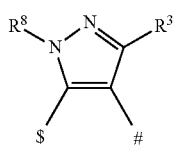
E16

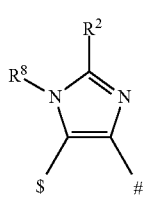
E17

-continued

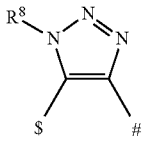
E18

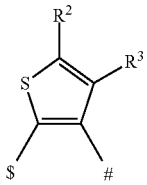
E19

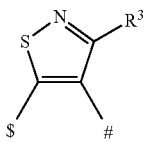
E20

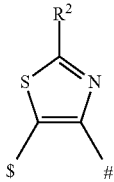
E21

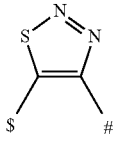
E22

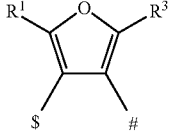
E23

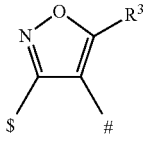
E24

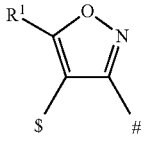
E25

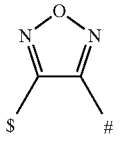
E26

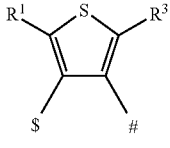
E27

-continued
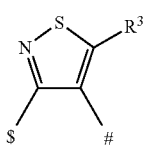 E28
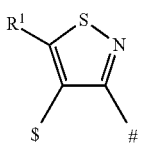 E29
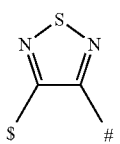 E30
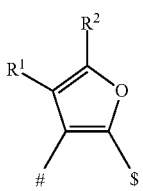 E31
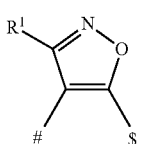 E32
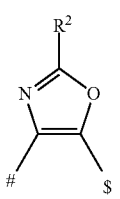 E33
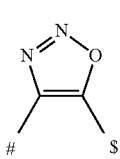 E34
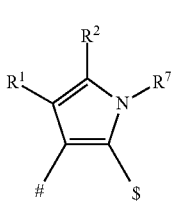 E35
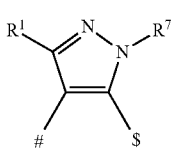 E36
-continued
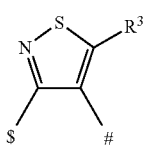 E37
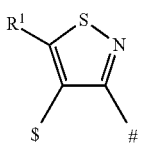 E38
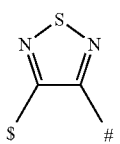 E39
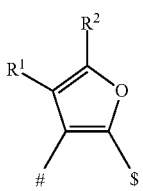 E40
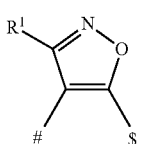 E41
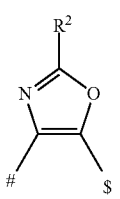 E42
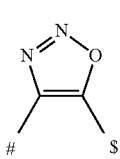 E43
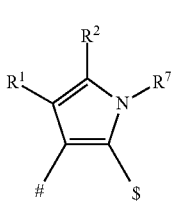 E44

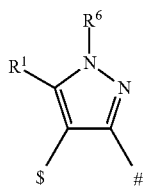 E45

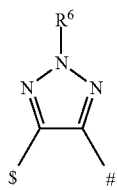 E46 wherein $R^1$, $R^2$, $R^3$, $R^4$, $R^5$, $R^6$, $R^7$, and $R^8$ are the same as defined above.

The 6-membered heteroaryl group represents a group having, as a ring-constituent atom, one or more atoms selected from the group consisting of a nitrogen atom, an oxygen atom, and a sulfur atom and, when having two or more atoms, the atoms may be the same or different to each other.

Examples of the divalent 6-membered heteroaryl group include a pyridine-di-yl group, a pyrimidine-di-yl group, a pyrazine-di-yl group, a pyridazine-di-yl group, a triazine-di-yl group, and a tetrazine-di-yl group.

Examples thereof include the following groups E50 to E65 (in which the symbol # represents a binding site for a tetrazolinone ring, and the symbol $ represents a binding site for Y):

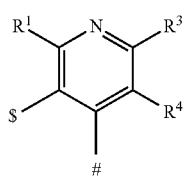 E50

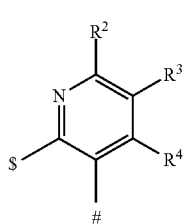 E51

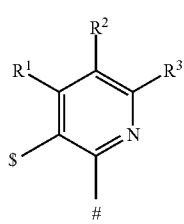 E52

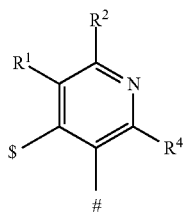 E53

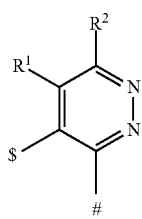 E54

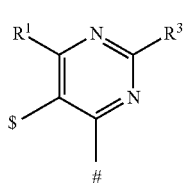 E55

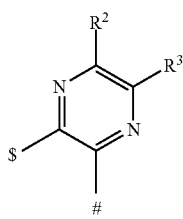 E56

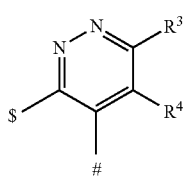 E57

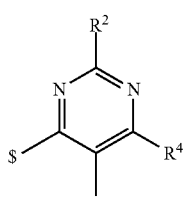 E58

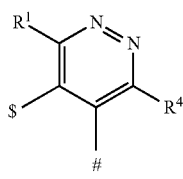 E59

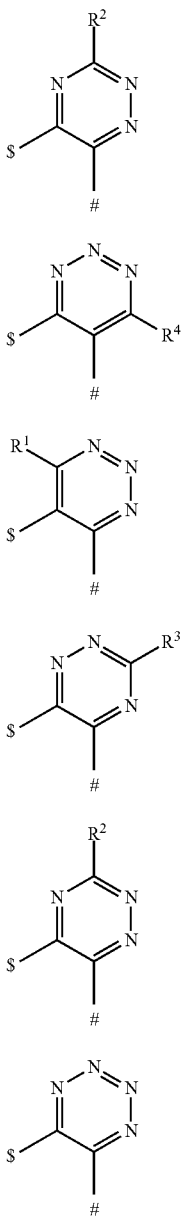

wherein R¹, R², R³, R⁴, R⁵, R⁶, R⁷, and R⁸ are the same as defined above.

Examples of the divalent C6-C10 aryl group include a benzene-1,2-di-yl group, a benzene-1,3-di-yl group, a benzene-1,4-di-yl group, a naphthalene-1,2-di-yl group, a naphthyl-1,6-di-yl group, and a naphthyl-1,8-di-yl group.

The 5- to 10-membered heterocyclic group represents a group having, as a ring-constituent atom, one or more atoms selected from the group consisting of a nitrogen atom, an oxygen atom, and a sulfur atom and, when having two or more atoms, the atoms may be the same or different to each other.

Examples of the divalent 5- to 10-membered heterocyclic group include a pyridine-di-yl group, a pyrimidine-di-yl group, a pyrazine-di-yl group, a pyridazine-di-yl group, a thiophene-di-yl group, a furan-di-yl group, a pyrrole-di-yl group, a pyrazole-di-yl group, an imidazole-di-yl group, a thiazole-di-yl group, an isothiazole-di-yl group, an oxazole-di-yl group, an isoxazole-di-yl group, a triazole-di-yl group, a tetrazole-di-yl group, an oxadiazole-di-yl group, a thiadiazole-di-yl group, a benzofuran-di-yl group, a benzothiophene-di-yl group, an indole-di-yl group, a benzoimidazole-di-yl group, an indazole-di-yl group, a benzothiazole-di-yl group, a benzoxazole-di-yl group, a benzoisothiazole-di-yl group, a benzoisoxazole-di-yl group, a pyrazolopyrrole-di-yl group, a pyrazolopyrazole-di-yl group, a pyrazoloimidazole-di-yl group, an imidazopyrimidine-di-yl group, an imidazopyrazine-di-yl group, a triazopyridine-di-yl group, a triazopyrimidine-di-yl group, a triazoquinoline-di-yl group, a 2,3-dihydrobenzofuran-di-yl group, a 2,3-dihydrobenzothiophene-di-yl group, a 1,3-benzodioxole-di-yl group, a quinoline-di-yl group, an isoquinoline-di-yl group, a cinnoline-di-yl group, a phthalazine-di-yl group, a quinazoline-di-yl group, a quinoxaline-di-yl group, a naphthyridine-di-yl group, a chroman-di-yl group, an isochroman-di-yl group, a thienopyridine-di-yl group, a thienopyrazole-di-yl group, and a thienoquinoline-di-yl group, and a pyrazole-di-yl group and a thiazole-di-yl group are preferably exemplified.

Examples thereof include the following groups Q1 to Q366 (in which the symbol # represents a binding site for Y, and the symbol $ represents a binding site for A):

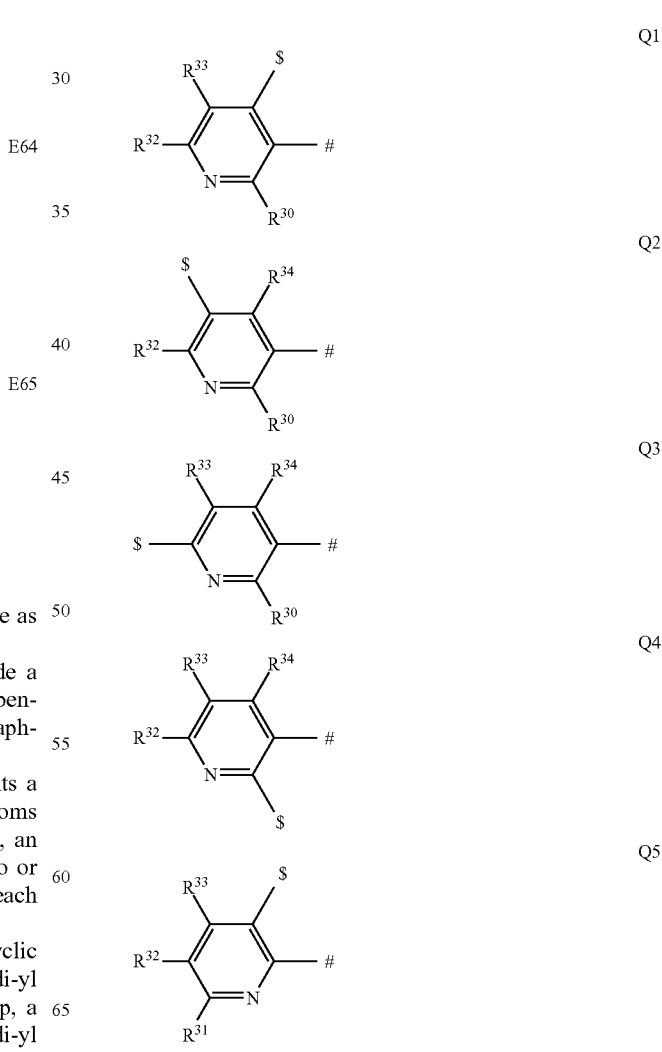

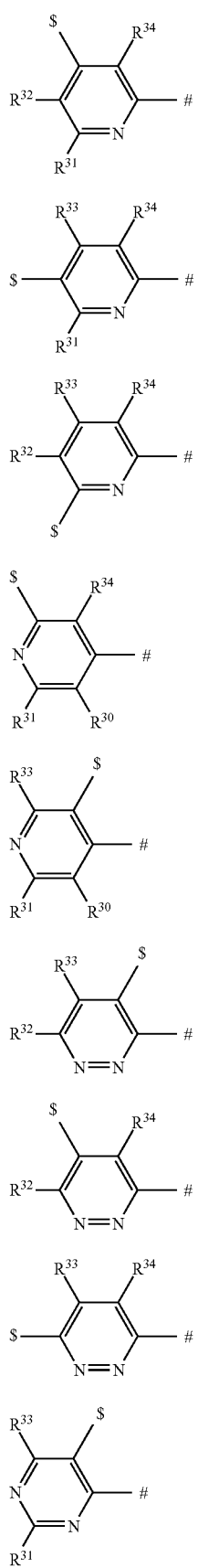
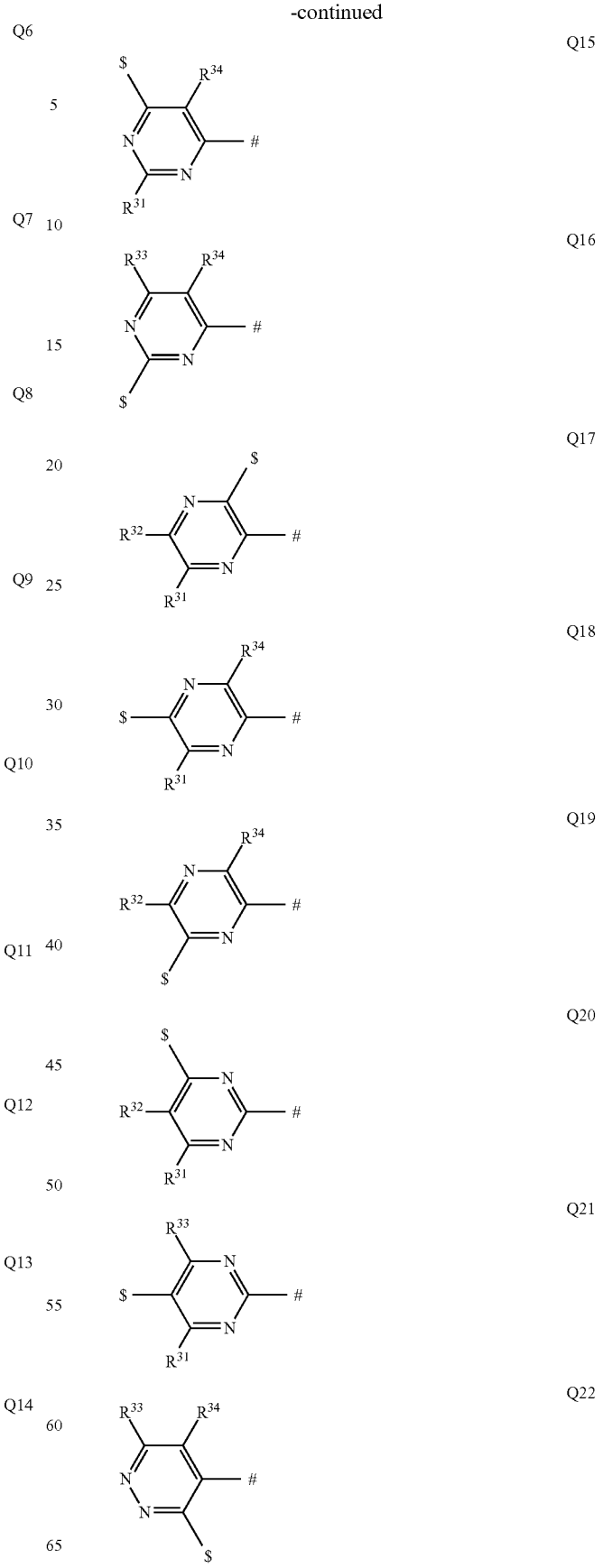

| | |
|---|---|
| 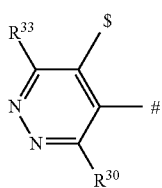 | Q23 |
| 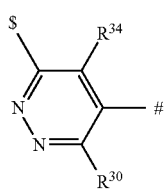 | Q24 |
| 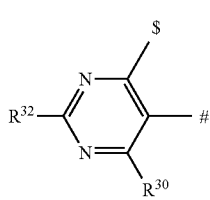 | Q25 |
| 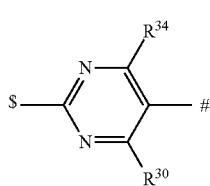 | Q26 |
| 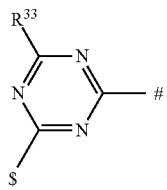 | Q27 |
| 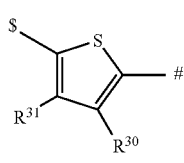 | Q28 |
| 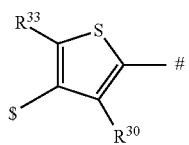 | Q29 |
| 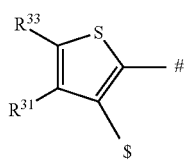 | Q30 |
| 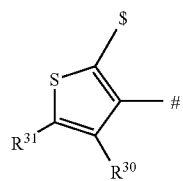 | Q31 |
| 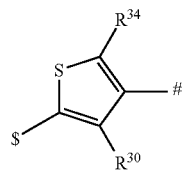 | Q32 |
| 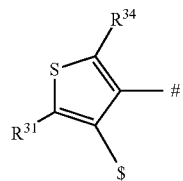 | Q33 |
| 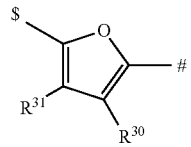 | Q34 |
| 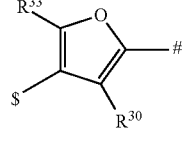 | Q35 |
| 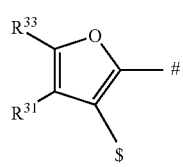 | Q36 |
| 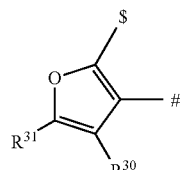 | Q37 |
| 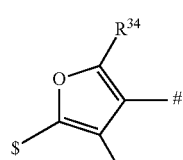 | Q38 |
| 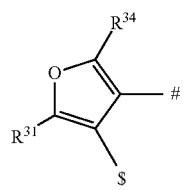 | Q39 |

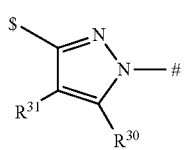
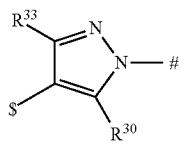
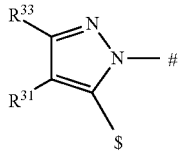
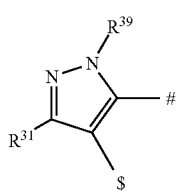
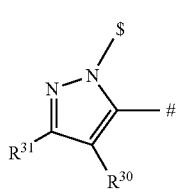
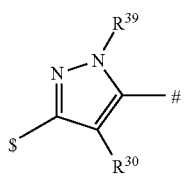
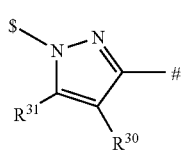
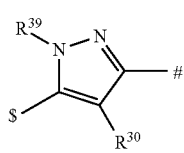
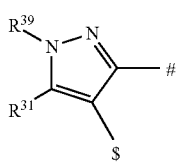
Q40
Q41
Q42
Q43
Q44
Q45
Q46
Q47
Q48
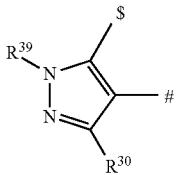
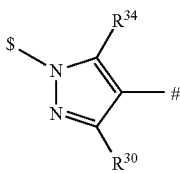
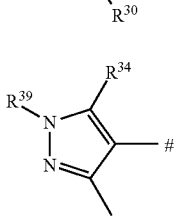
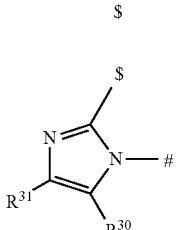
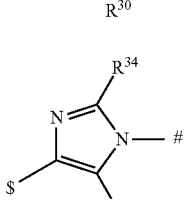
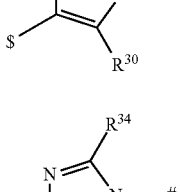
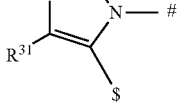
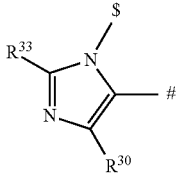
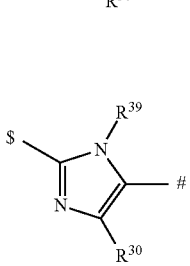
Q49
Q50
Q51
Q52
Q53
Q54
Q55
Q56

| | | |
|---|---|---|
| 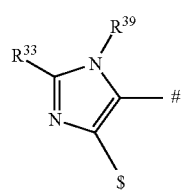 | Q57 | 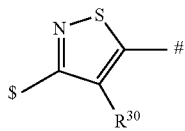 Q67 |
| 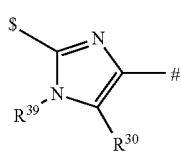 | Q58 | 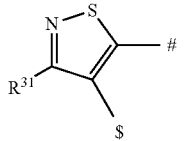 Q68 |
| 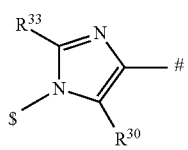 | Q59 | 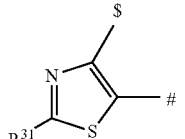 Q69 |
| 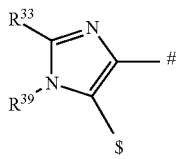 | Q60 | 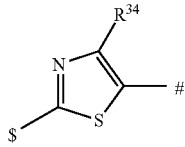 Q70 |
| 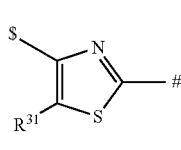 | Q61 | 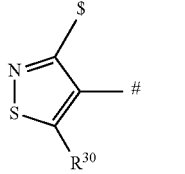 Q71 |
| 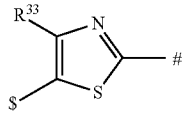 | Q62 | 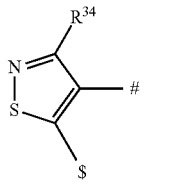 Q72 |
| 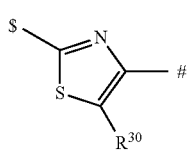 | Q63 | 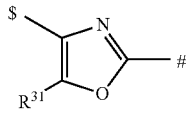 Q73 |
| 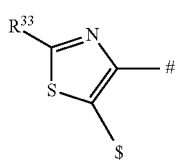 | Q64 | 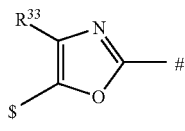 Q74 |
| 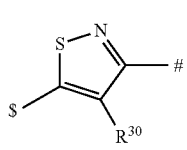 | Q65 | 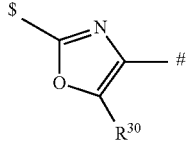 Q75 |
| 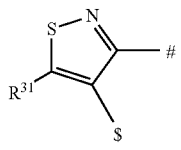 | Q66 | 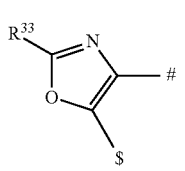 Q76 |

| | |
|---|---|
| 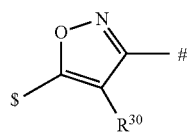 Q77 | 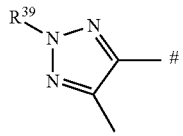 Q86 |
| 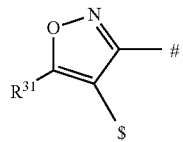 Q78 | 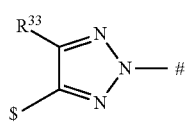 Q87 |
| 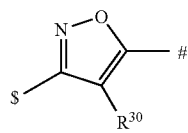 Q79 | 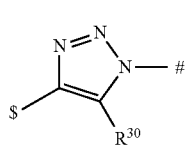 Q88 |
| 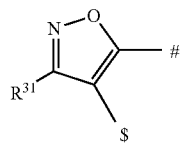 Q80 | 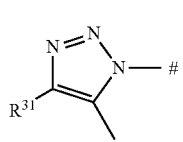 Q89 |
| 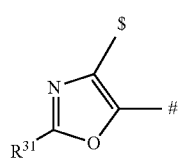 Q81 | 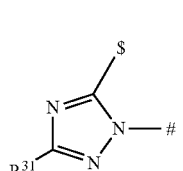 Q90 |
| 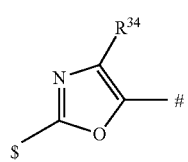 Q82 | 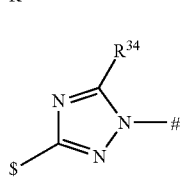 Q91 |
| 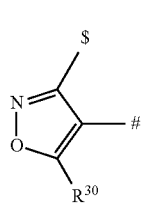 Q83 | 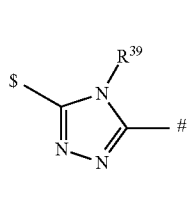 Q92 |
| 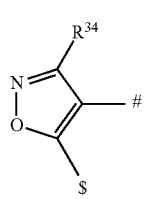 Q84 | 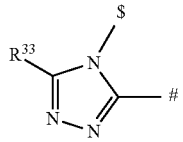 Q93 |
| | 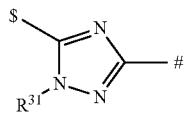 Q94 |
| 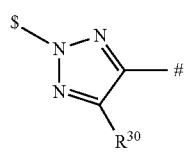 Q85 | 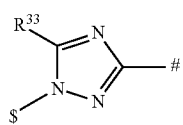 Q95 |

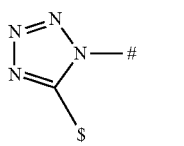 Q96
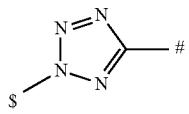 Q97
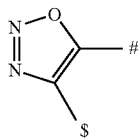 Q98
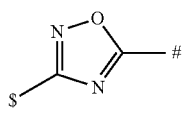 Q99
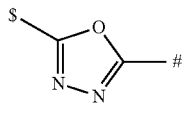 Q100
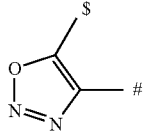 Q101
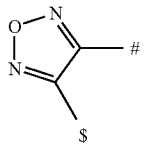 Q102
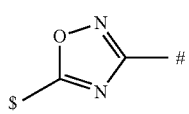 Q103
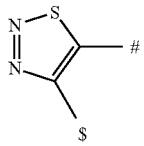 Q104
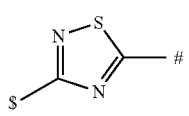 Q105
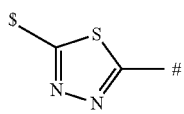 Q106
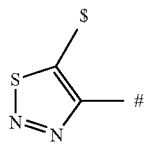 Q107
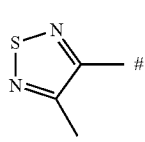 Q108
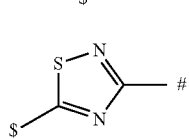 Q109
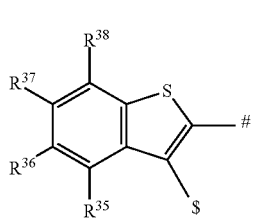 Q110
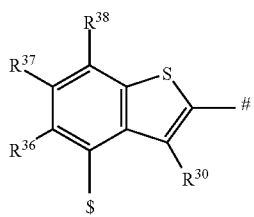 Q111
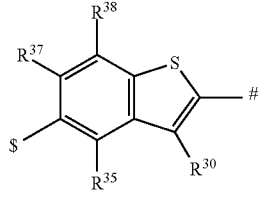 Q112
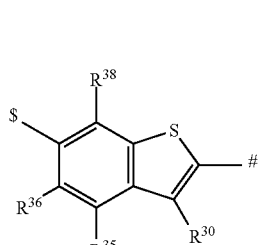 Q113
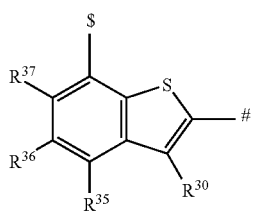 Q114

-continued
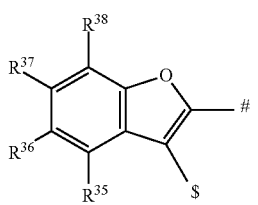
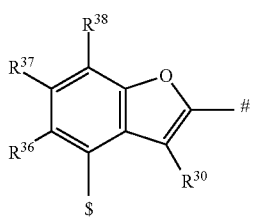
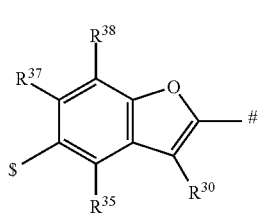
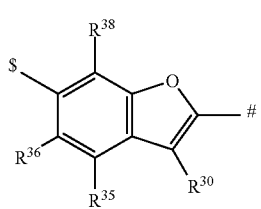
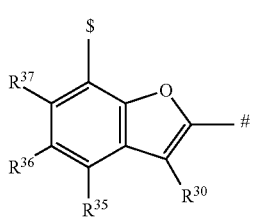
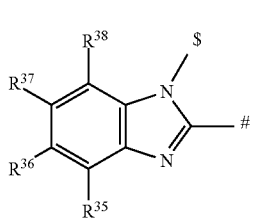
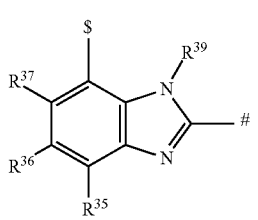
Q115
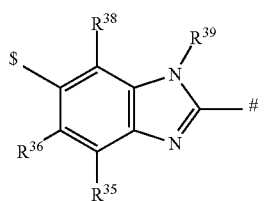
Q116
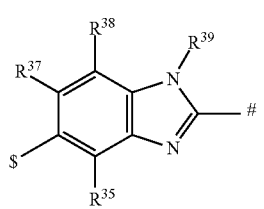
Q117
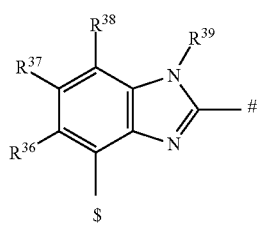
Q118
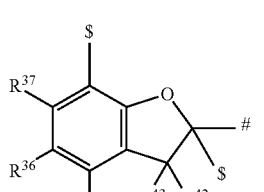
Q119
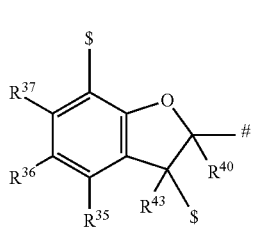
Q120
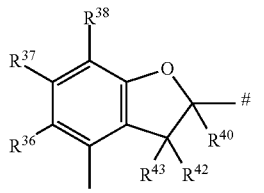
Q121
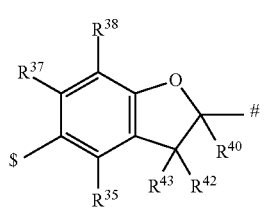
Q122
Q123
Q124
Q125
Q126
Q127
Q128

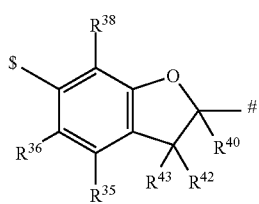 Q129
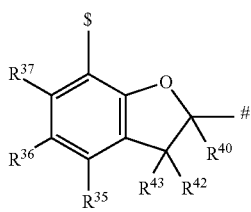 Q130
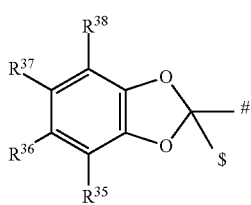 Q131
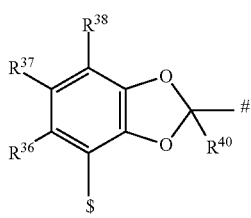 Q132
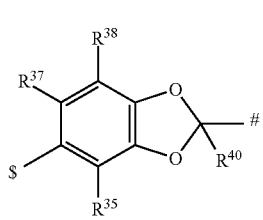 Q133
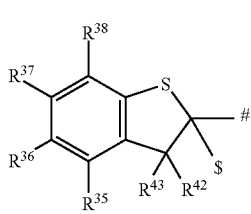 Q134
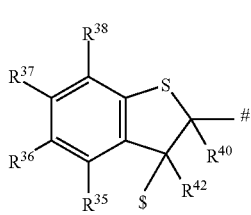 Q135
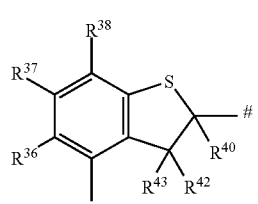 Q136
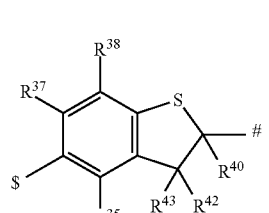 Q137
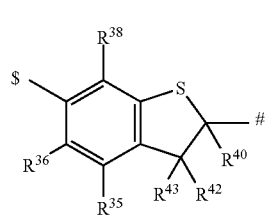 Q138
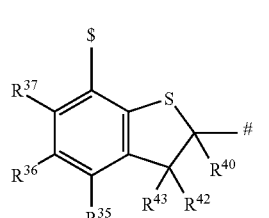 Q139
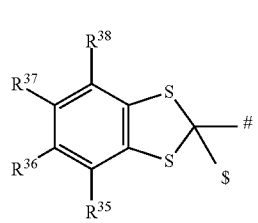 Q140
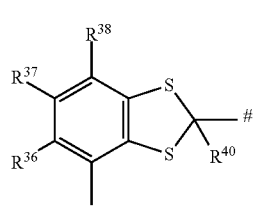 Q141
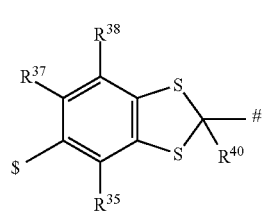 Q142

-continued
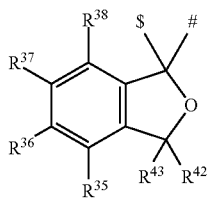
Q143
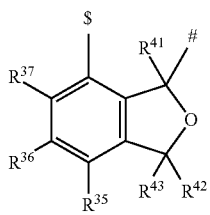
Q144
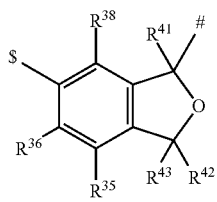
Q145
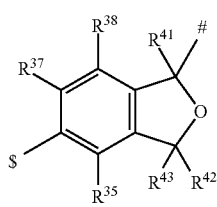
Q146
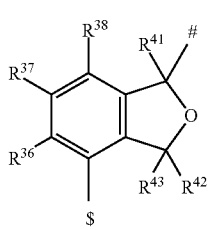
Q147
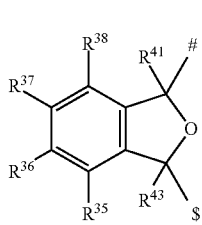
Q148
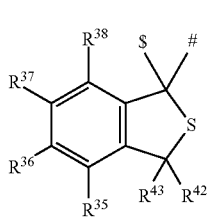
Q149
-continued
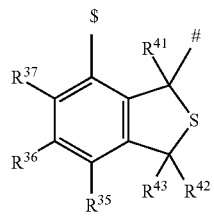
Q150
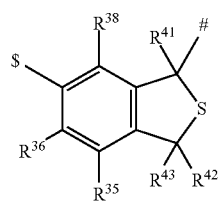
Q151
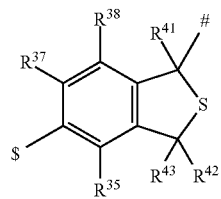
Q152
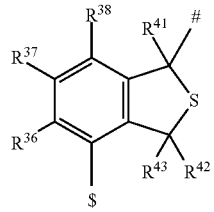
Q153
Q154
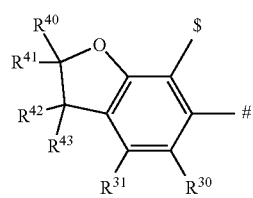
Q155
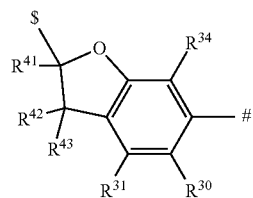
Q156

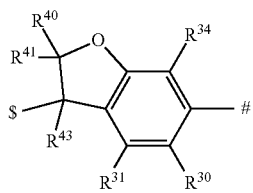 Q157
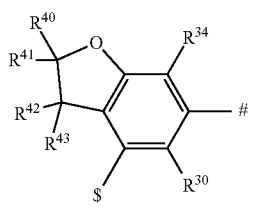 Q158
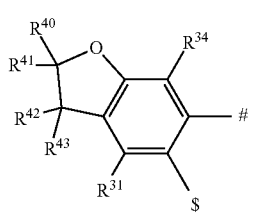 Q159
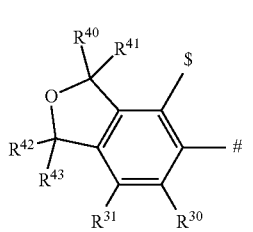 Q160
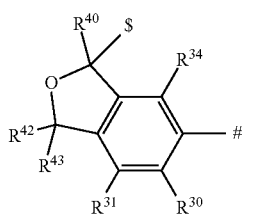 Q161
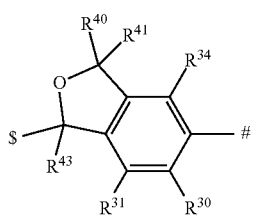 Q162
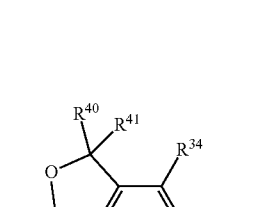 Q163
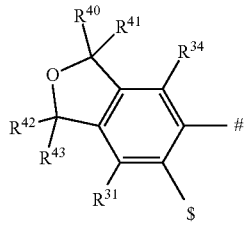 Q164
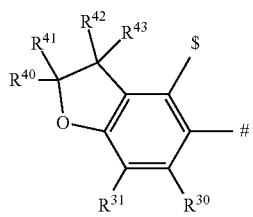 Q165
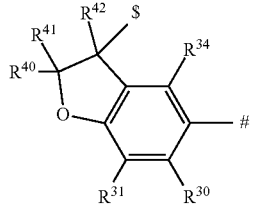 Q166
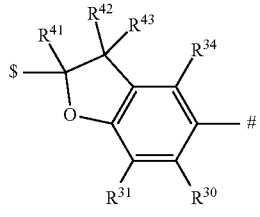 Q167
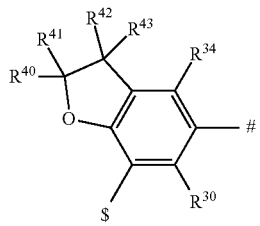 Q168
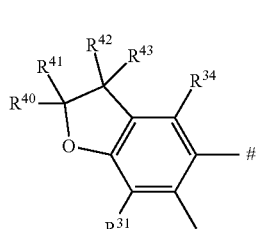 Q169
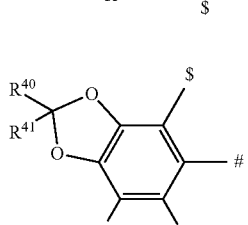 Q170

US 10,077,254 B2
35
-continued
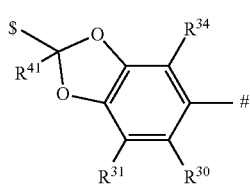 Q171
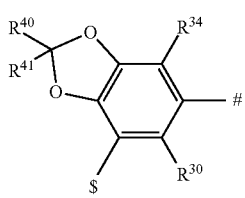 Q172
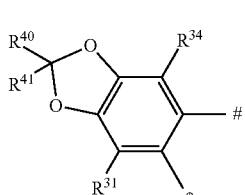 Q173
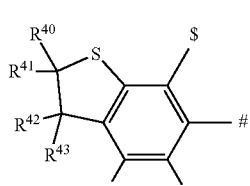 Q174
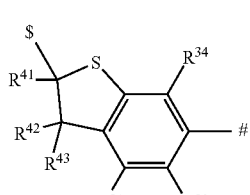 Q175
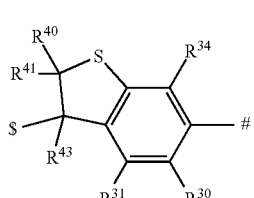 Q176
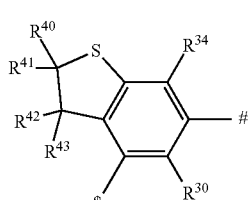 Q177
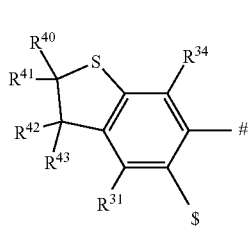 Q178
36
-continued
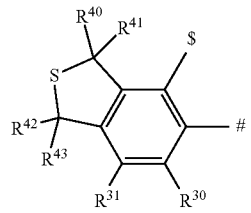 Q179
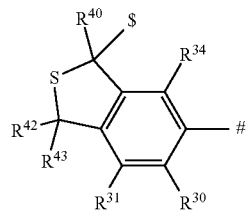 Q180
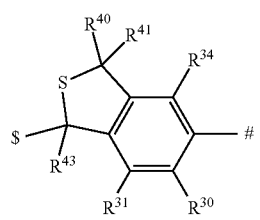 Q181
 Q182
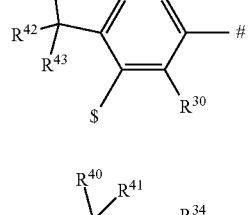 Q183
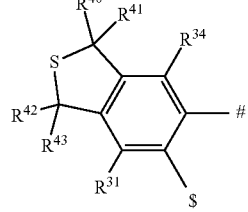 Q184
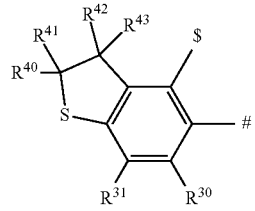 Q185
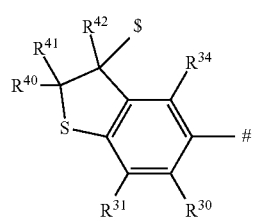

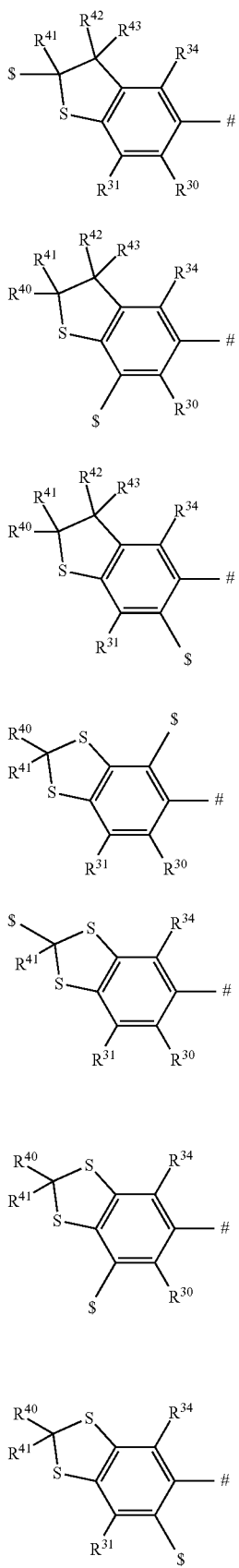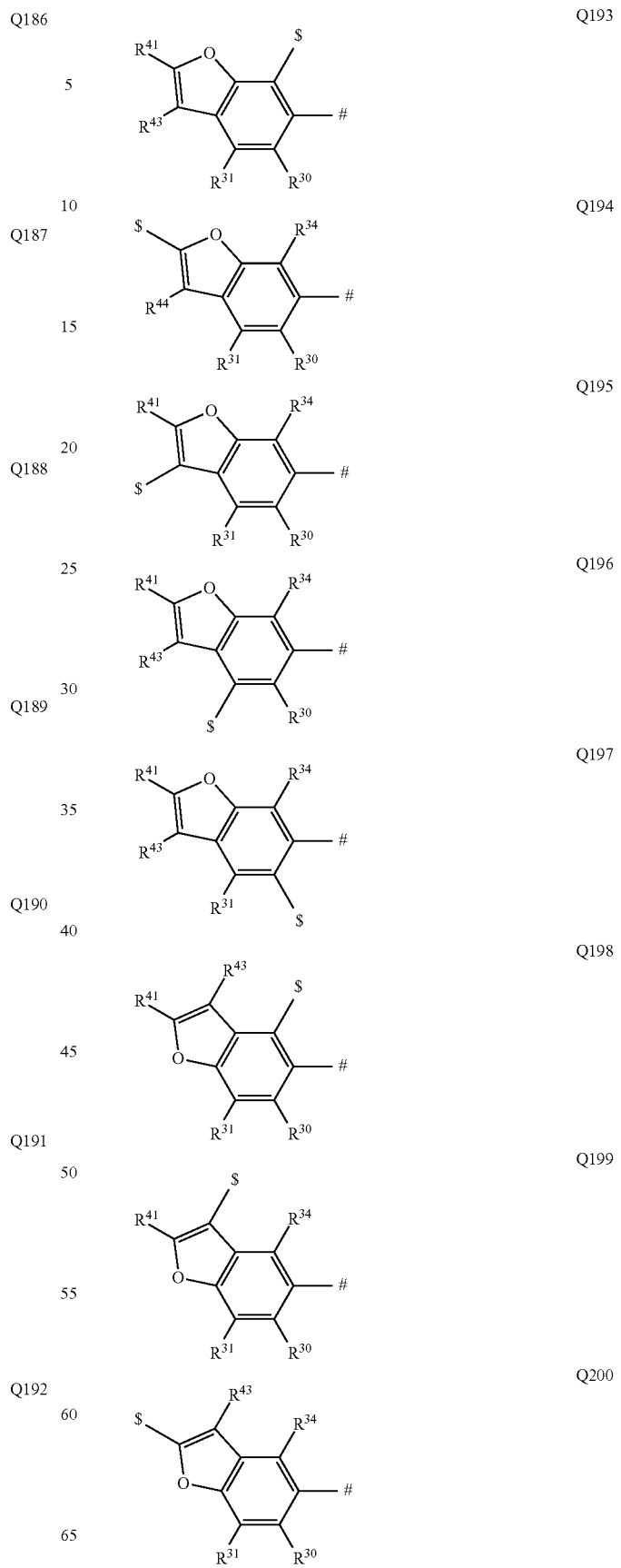

-continued
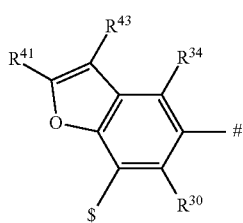 Q201
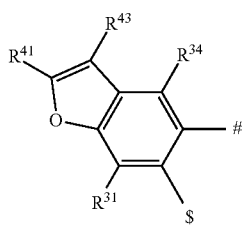 Q202
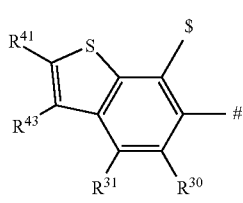 Q203
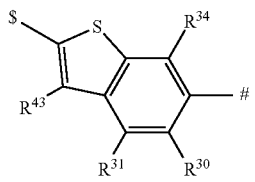 Q204
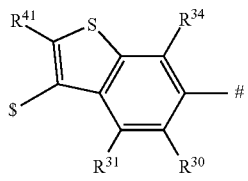 Q205
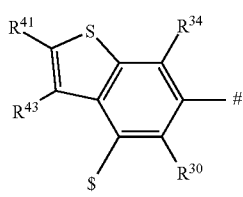 Q206
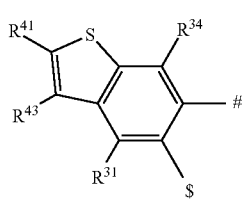 Q207
-continued
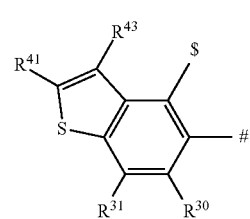 Q208
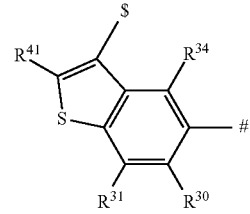 Q209
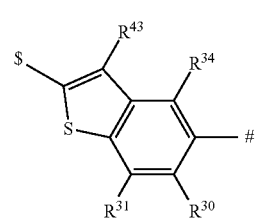 Q210
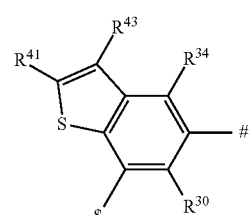 Q211
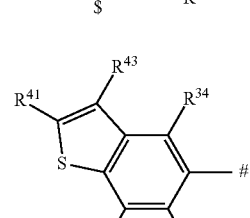 Q212
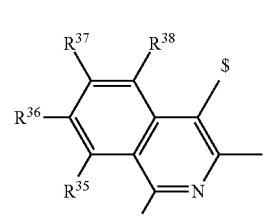 Q213
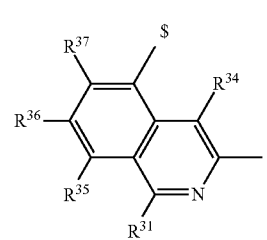 Q214

Q215 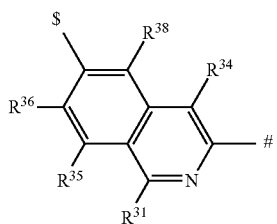
Q216 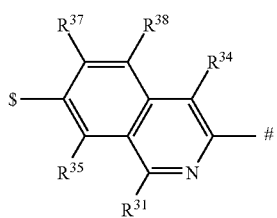
Q217 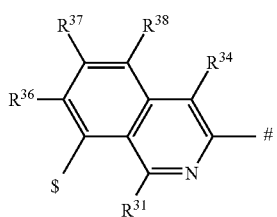
Q218 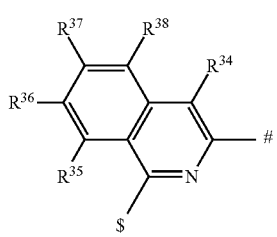
Q219 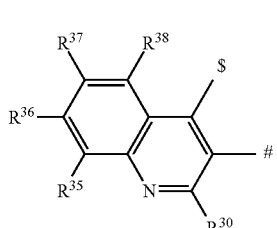
Q220 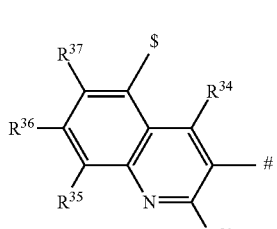
Q221 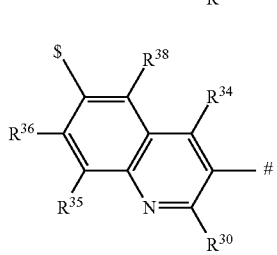
Q222 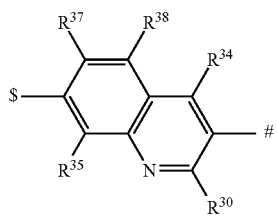
Q223 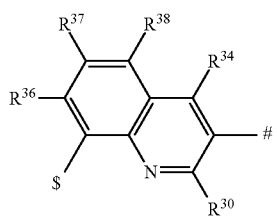
Q224 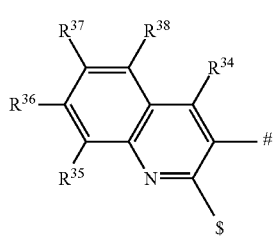
Q225 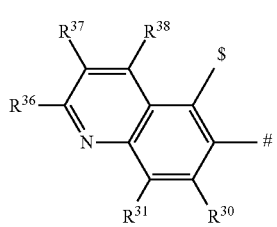
Q226 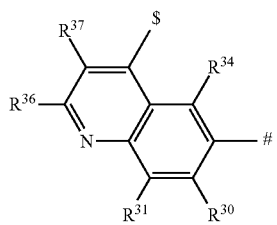
Q227 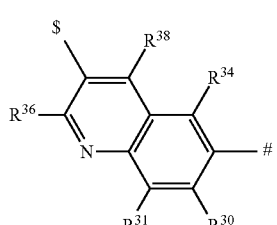
Q228 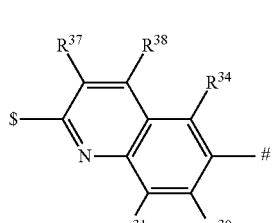

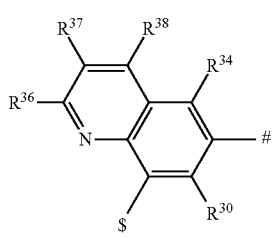 Q229
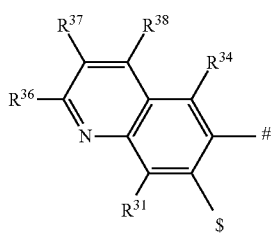 Q230
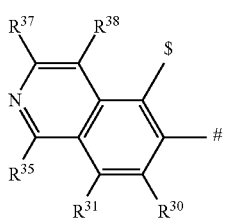 Q231
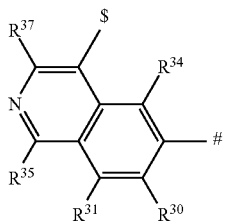 Q232
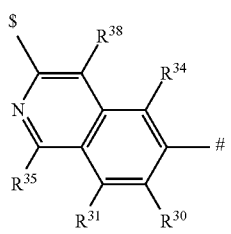 Q233
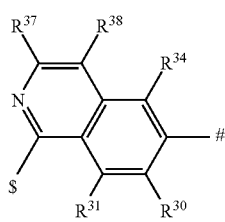 Q234
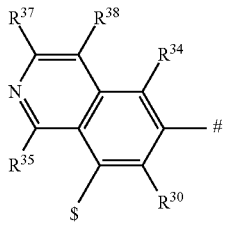 Q235
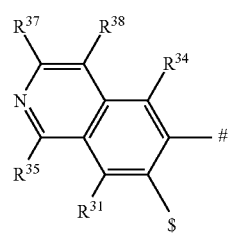 Q236
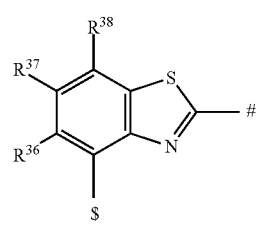 Q237
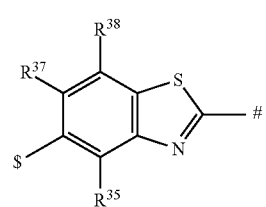 Q238
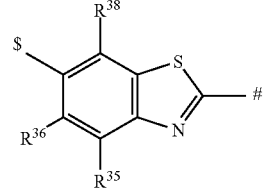 Q239
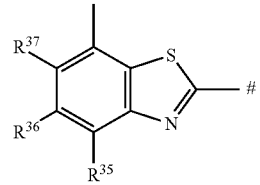 Q240
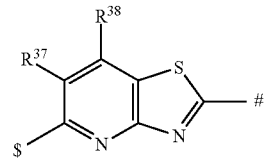 Q241
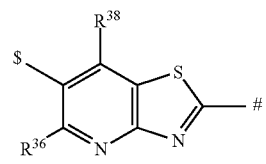 Q242
Q243

-continued
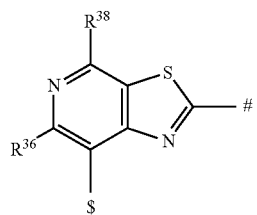
Q244
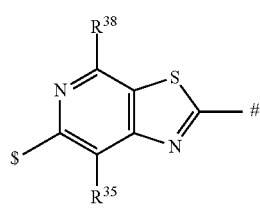
Q245
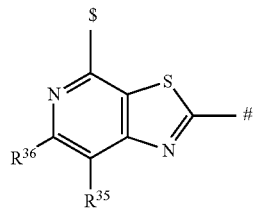
Q246
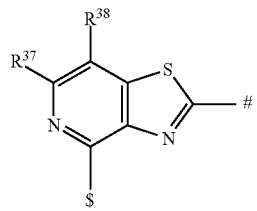
Q247
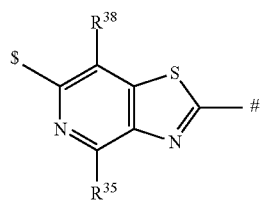
Q248
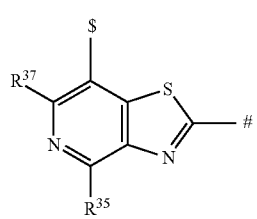
Q249
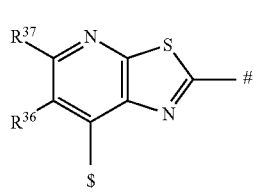
Q250
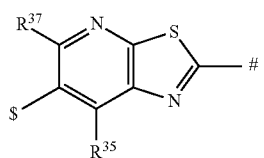
Q251
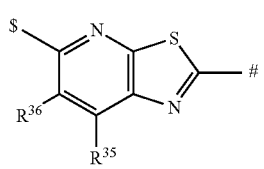
Q252
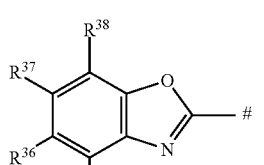
Q253
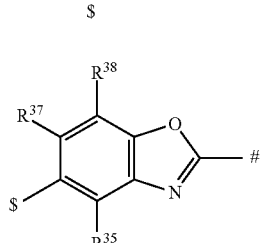
Q254
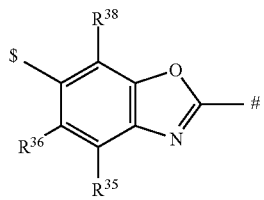
Q255
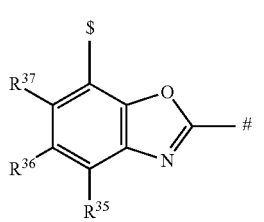
Q256
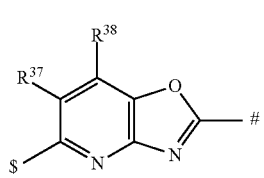
Q257
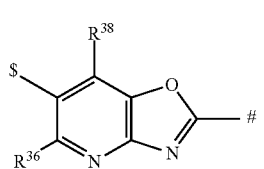
Q258

| | |
|---|---|
| 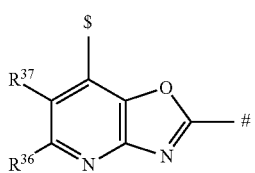 | Q259 |
| 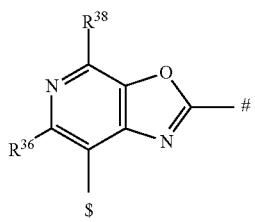 | Q260 |
| 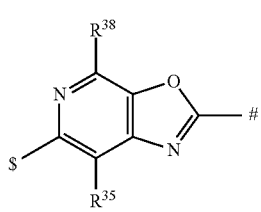 | Q261 |
| 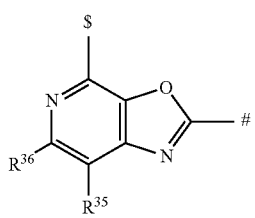 | Q262 |
| 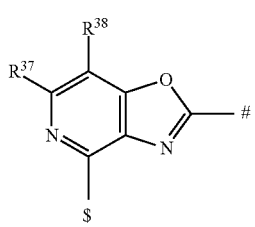 | Q263 |
| 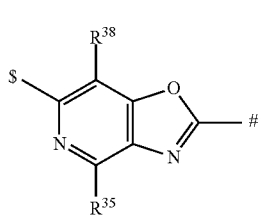 | Q264 |
| 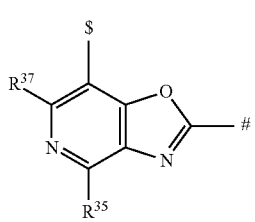 | Q265 |
| | |
|---|---|
| 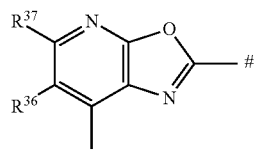 | Q267 |
| 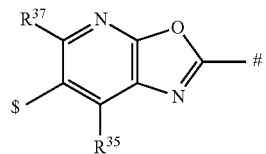 | Q268 |
| 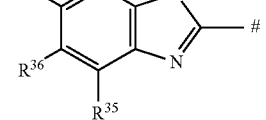 | Q269 |
| 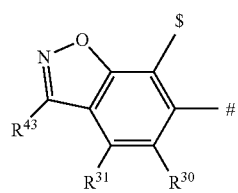 | Q270 |
| 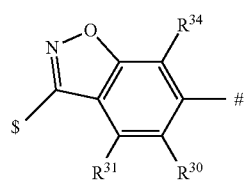 | Q271 |
| 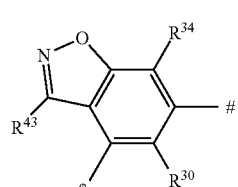 | Q272 |
| 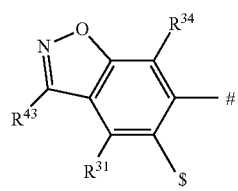 | Q273 |
| 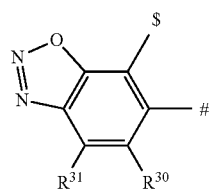 | Q274 |

-continued
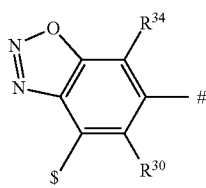 Q275
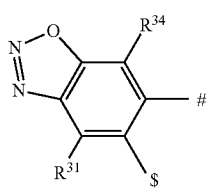 Q276
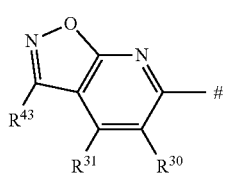 Q277
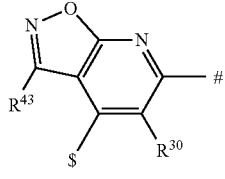 Q278
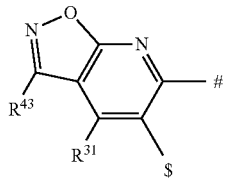 Q279
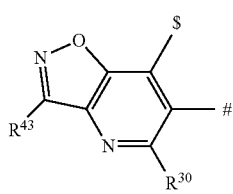 Q280
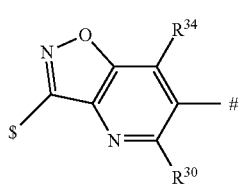 Q281
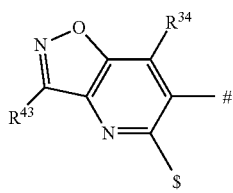 Q282
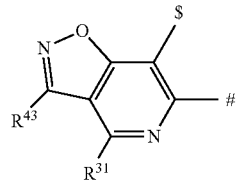 Q283
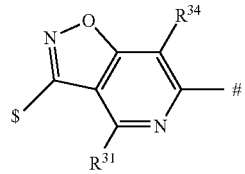 Q284
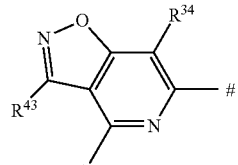 Q285
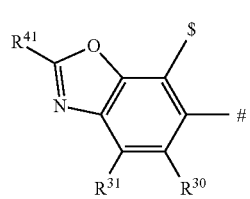 Q286
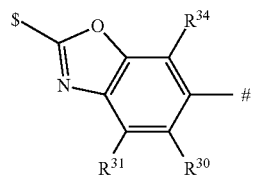 Q287
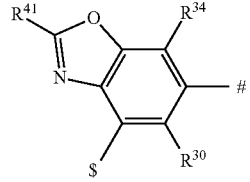 Q288
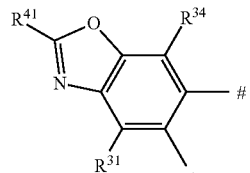 Q289
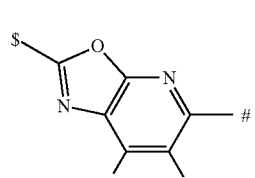 Q290

-continued
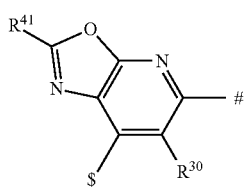 Q291
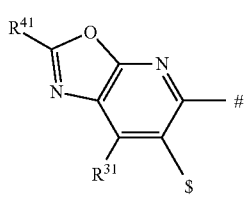 Q292
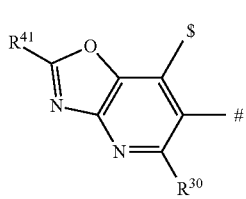 Q293
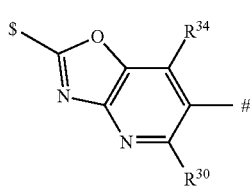 Q294
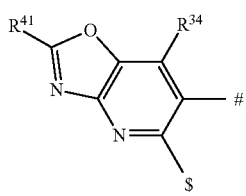 Q295
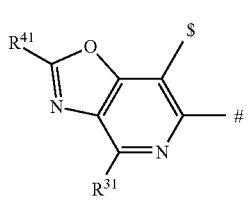 Q296
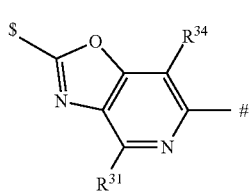 Q297
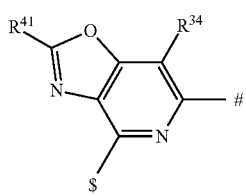 Q298
-continued
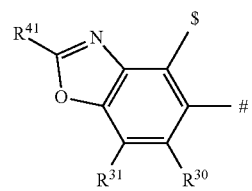 Q299
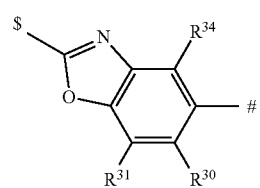 Q300
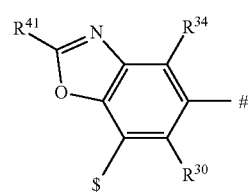 Q301
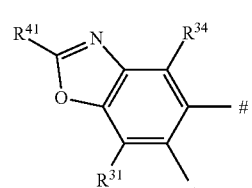 Q302
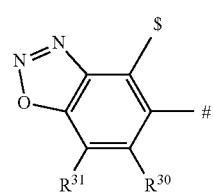 Q303
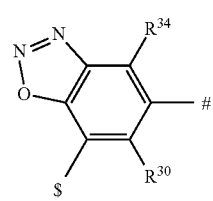 Q304
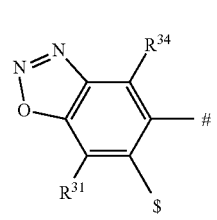 Q305
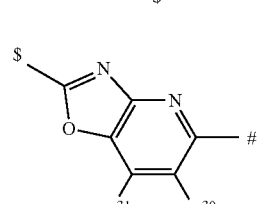 Q306

-continued
Q307 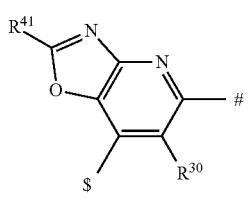
Q308 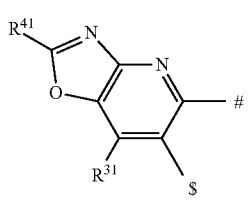
Q309 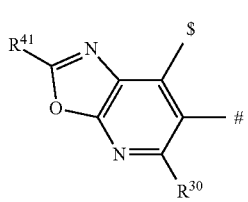
Q310 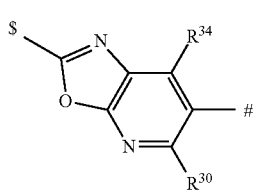
Q311 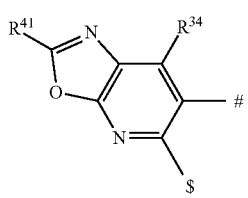
Q312 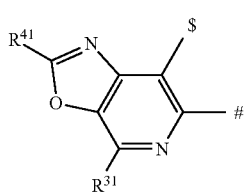
Q313 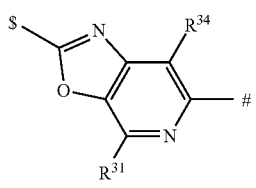
Q314 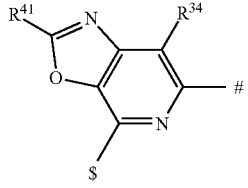
-continued
Q315 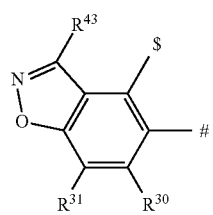
Q316 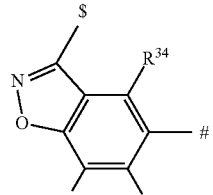
Q317 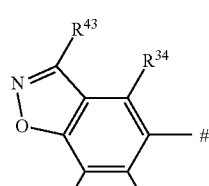
Q318 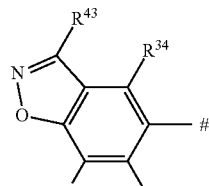
Q319 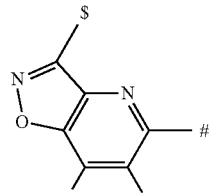
Q320 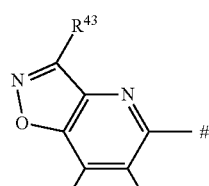
Q321 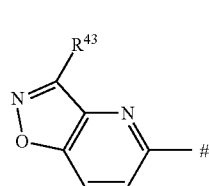

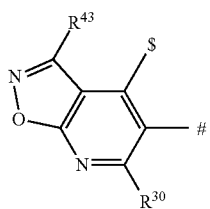 Q322
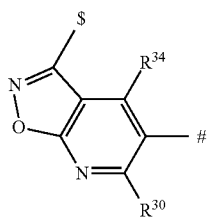 Q323
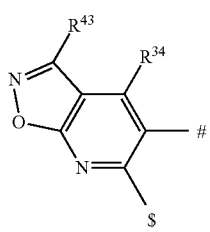 Q324
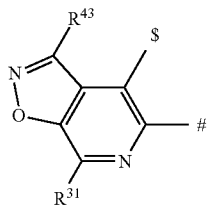 Q325
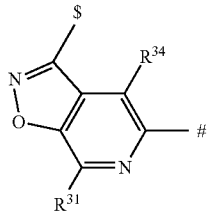 Q326
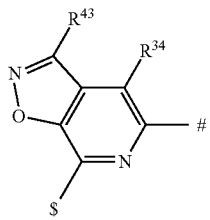 Q327
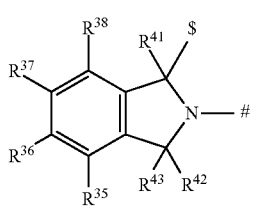 Q328
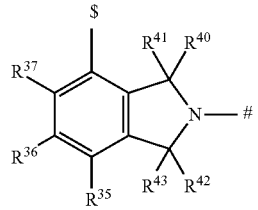 Q329
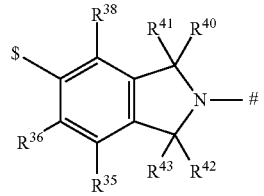 Q330
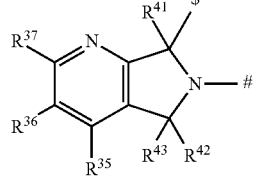 Q331
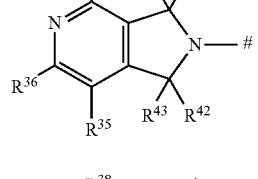 Q332
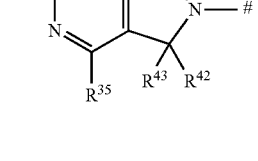 Q333
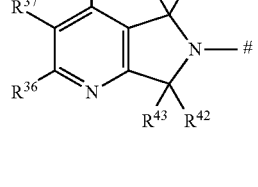 Q334
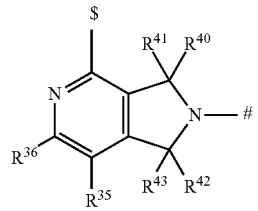 Q335

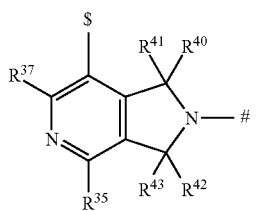
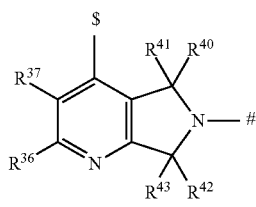
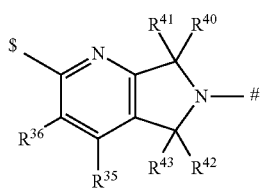
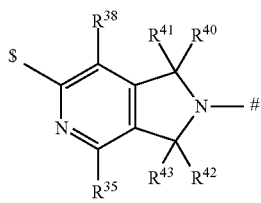
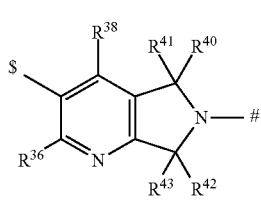
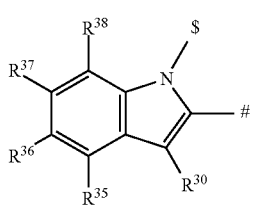
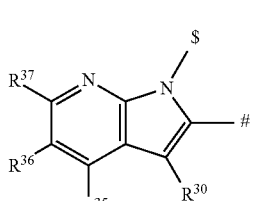
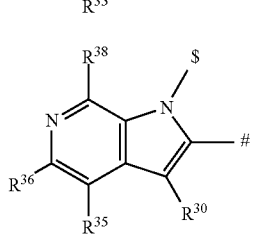
Q336
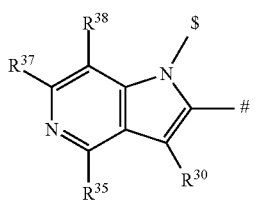
Q337
Q338
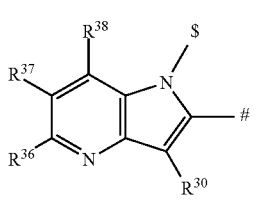
Q339
Q340
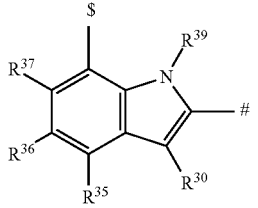
Q341
Q342
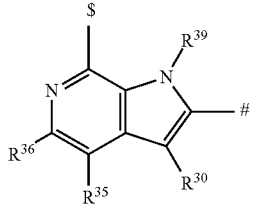
Q343
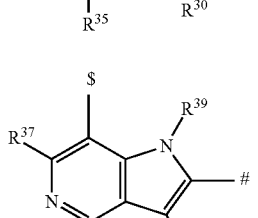
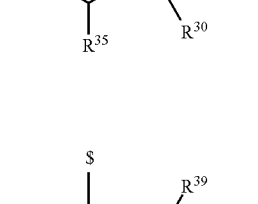
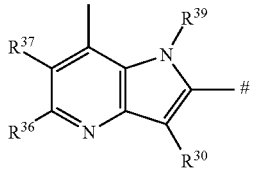
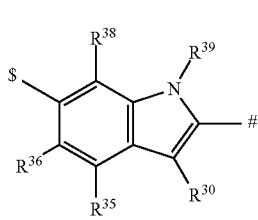
Q344
Q345
Q346
Q347
Q348
Q349
Q350

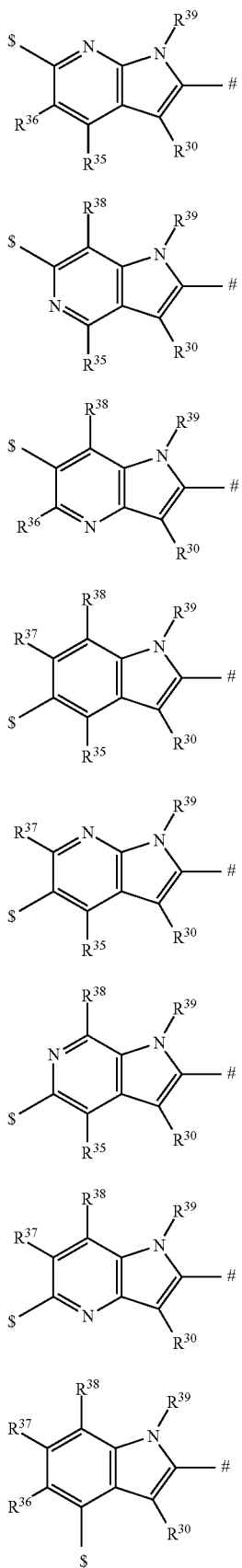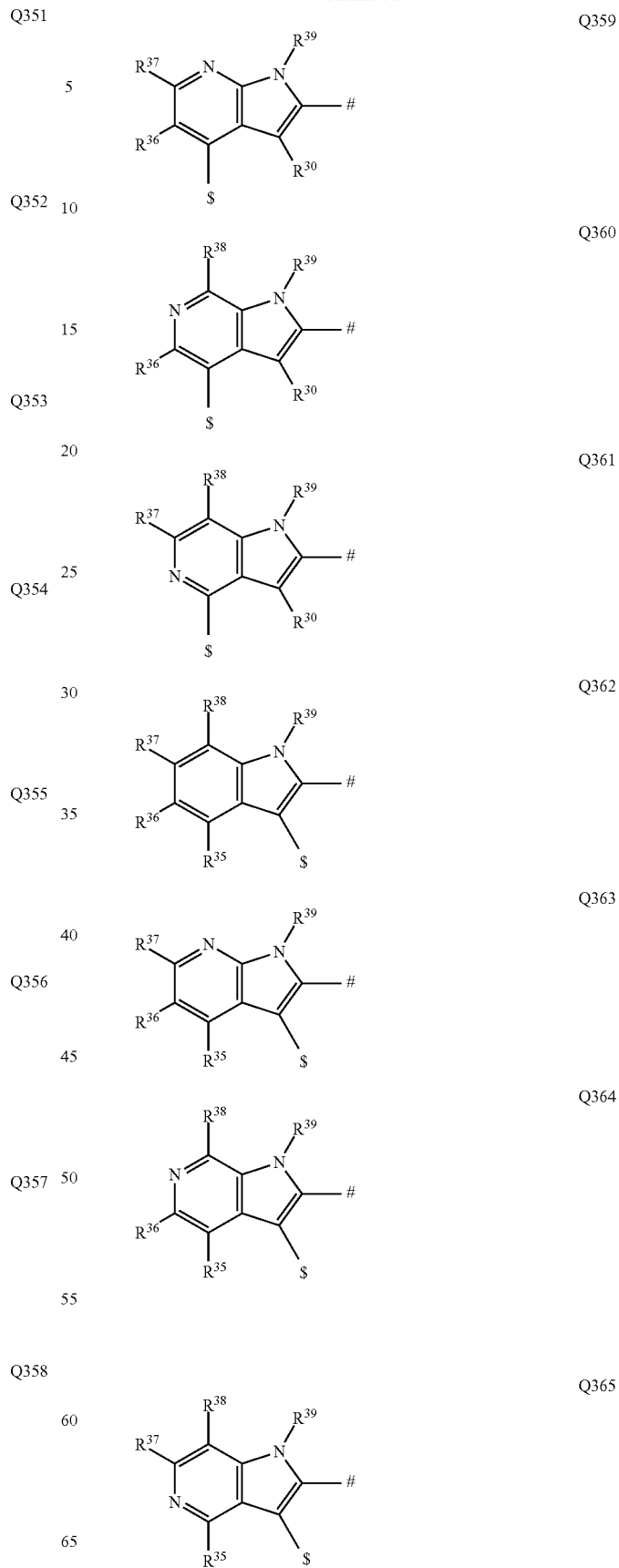

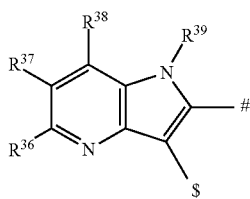
Q366 wherein R³⁰, R³¹, R³², R³³, R³⁴, R³⁵, R³⁶, R³⁷, R³⁸, R⁴⁰, R⁴¹, R⁴², and R⁴³ each independently represents a hydrogen atom, a halogen atom, a cyano group, a C3-C6 cycloalkyl group, a C3-C6 halocycloalkyl group, a C1-C4 alkoxy group, a C1-C4 haloalkoxy group, a C1-C4 alkylthio group, or a C1-C4 haloalkylthio group; and R³⁹ represents a hydrogen atom, a cyano group, a C3-C6 cycloalkyl group, a C3-C6 halocycloalkyl group, a C1-C4 alkoxy group, a C1-C4 haloalkoxy group, a C1-C4 alkylthio group, or a C1-C4 haloalkylthio group.

The C6-C10 aryl group specifically represents a phenyl group, a 1-naphthyl group, and a 2-naphthyl group.

The C6-C10 aryloxy group specifically represents a phenoxy group, a 1-naphthyloxy group, and a 2-naphthyloxy group.

The C6-C10 arylthio group specifically represents a phenylthio group, a 1-naphthylthio group, and a 2-naphthylthio group.

The C6-C10 arylamino group specifically represents a phenylamino group, a (1-naphthyl)amino group, and a (2-naphthyl)amino group.

The C3-C10 cycloalkyl group specifically represents a cyclopropyl group, a cyclobutyl group, a cyclopentyl group, a cyclohexyl group, a cycloheptyl group, a cyclooctyl group, a cyclononyl group, and a cyclodecyl group.

The C6-C10 arylsulfonyl group specifically represents a phenylsulfonyl group, a 1-naphthylsulfonyl group, and a 2-naphthylsulfonyl group.

The C6-C10 arylsulfinyl group specifically represents a phenylsulfinyl group, a 1-naphthylfinyl group, and a 2-naphthylsulfinyl group.

Examples of the 5- to 10-membered heterocyclic group include a pyridyl group, a pyrimidinyl group, a pyrazinyl group, a pyridazinyl group, a thienyl group, a furyl group, a pyrrolyl group, a pyrazolyl group, an imidazolyl group, a thiazolyl group, an isothiazolyl group, an oxazolyl group, an isoxazolyl group, a triazolyl group, a tetrazolyl group, an oxadiazolyl group, a thiadiazolyl group, a benzofuryl group, a benzothienyl group, an indolyl group, a benzoimidazolyl group, an indazolyl group, a benzothiazolyl group, a benzoxazolyl group, a benzoisothiazolyl group, a benzoisoxazolyl group, a pyrazolopyrrolyl group, a pyrazolopyrazolyl group, a pyrazoloimidazolyl group, an imidazopyrimidinyl group, an imidazopyrazinyl group, a triazolopyridyl group, a triazolopyrimidinyl group, a triazoloquinolyl group, a 2,3-dihydrobenzofuryl group, a 2,3-dihydrobenzothienyl group, a 1,3-benzodioxolyl group, a quinolyl group, an isoquinolyl group, a cinnolinyl group, a phthalazinyl group, a quinazolinyl group, a quinoxalinyl group, a naphthylidinyl group, a chromanyl group, an isochromanyl group, a thienopyridyl group, a thienopyrazolyl group, and a thienoquinolyl group, and a pyridyl group is preferably exemplified.

Examples thereof include the following groups A1 to A133 (in which the symbol # represents a binding site for Q):

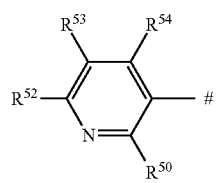
A1

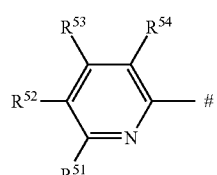
A2

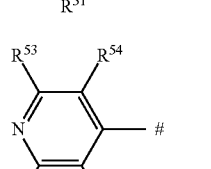
A3

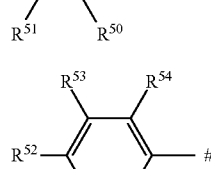
A4

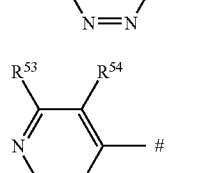
A5

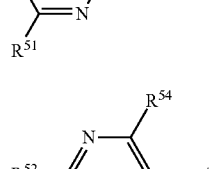
A6

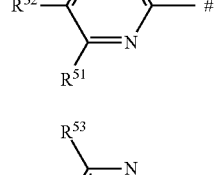
A7

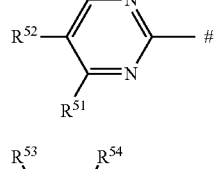
A8

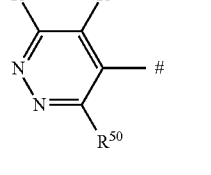
A9

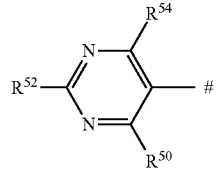

-continued
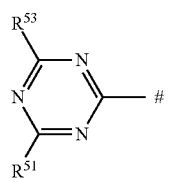 A10
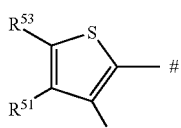 A11
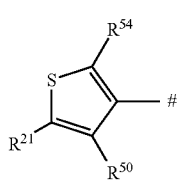 A12
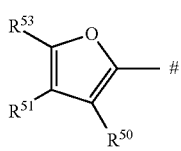 A13
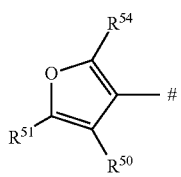 A14
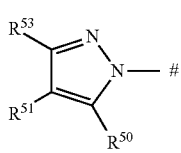 A15
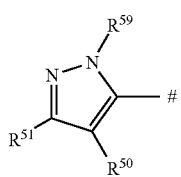 A16
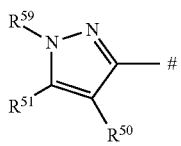 A17
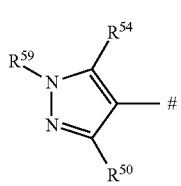 A18
-continued
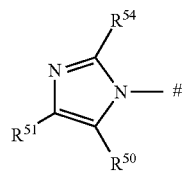 A19
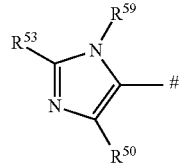 A20
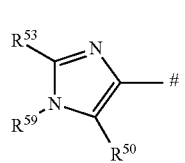 A21
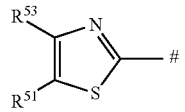 A22
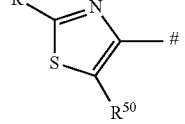 A23
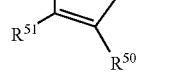 A24
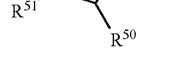 A25
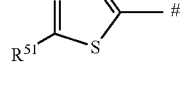 A26
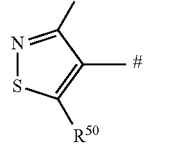 A27
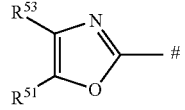 A28

-continued
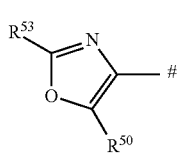 A29
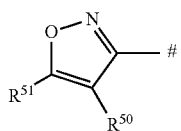 A30
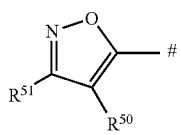 A31
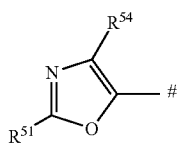 A32
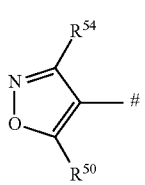 A33
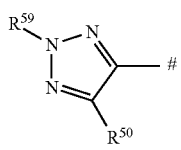 A34
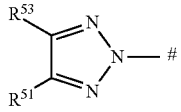 A35
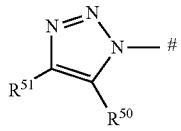 A36
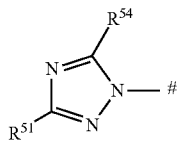 A37
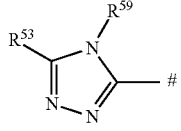 A38
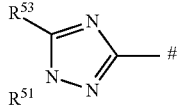 A39
-continued
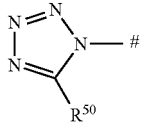 A40
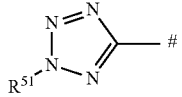 A41
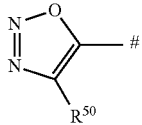 A42
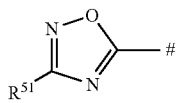 A43
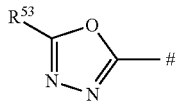 A44
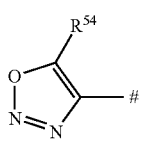 A45
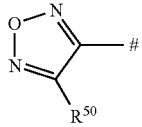 A46
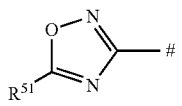 A47
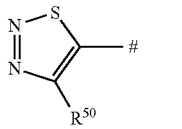 A48
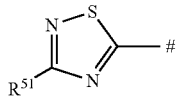 A49
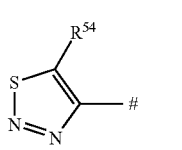 A50
A51

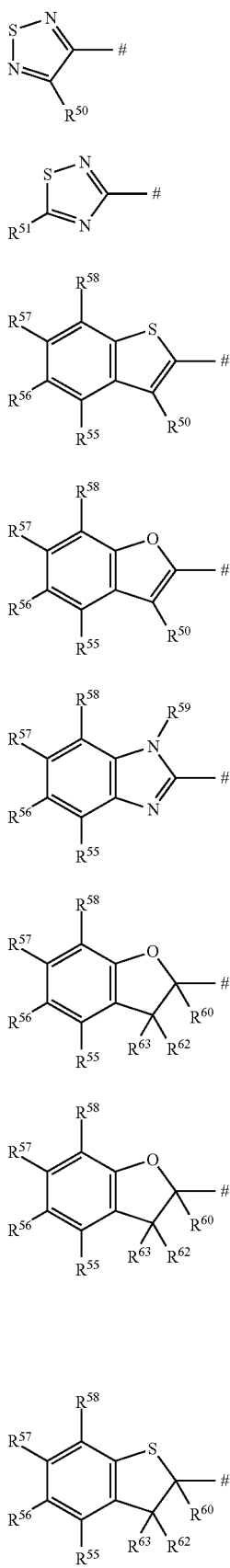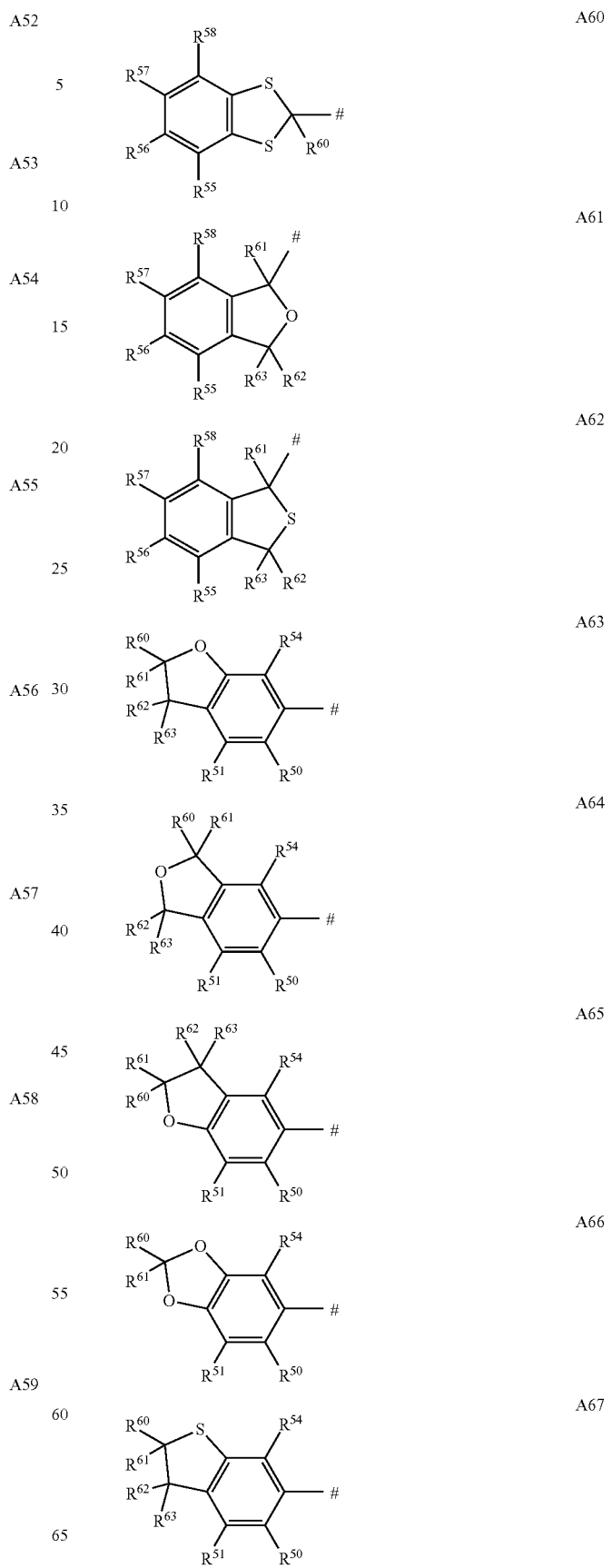

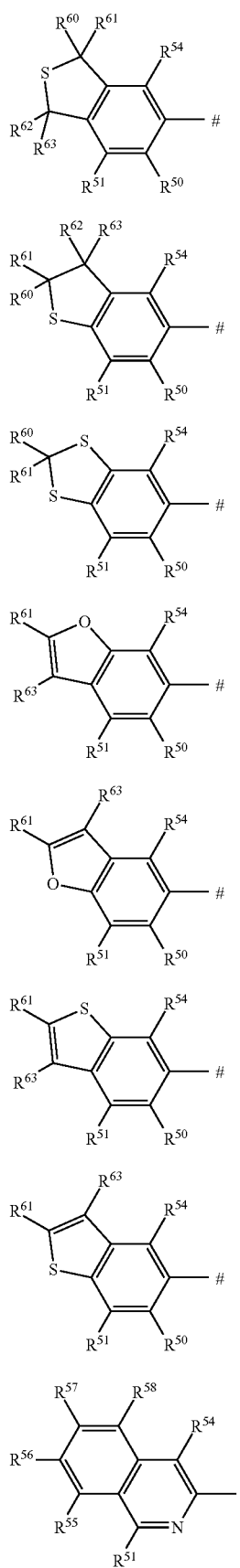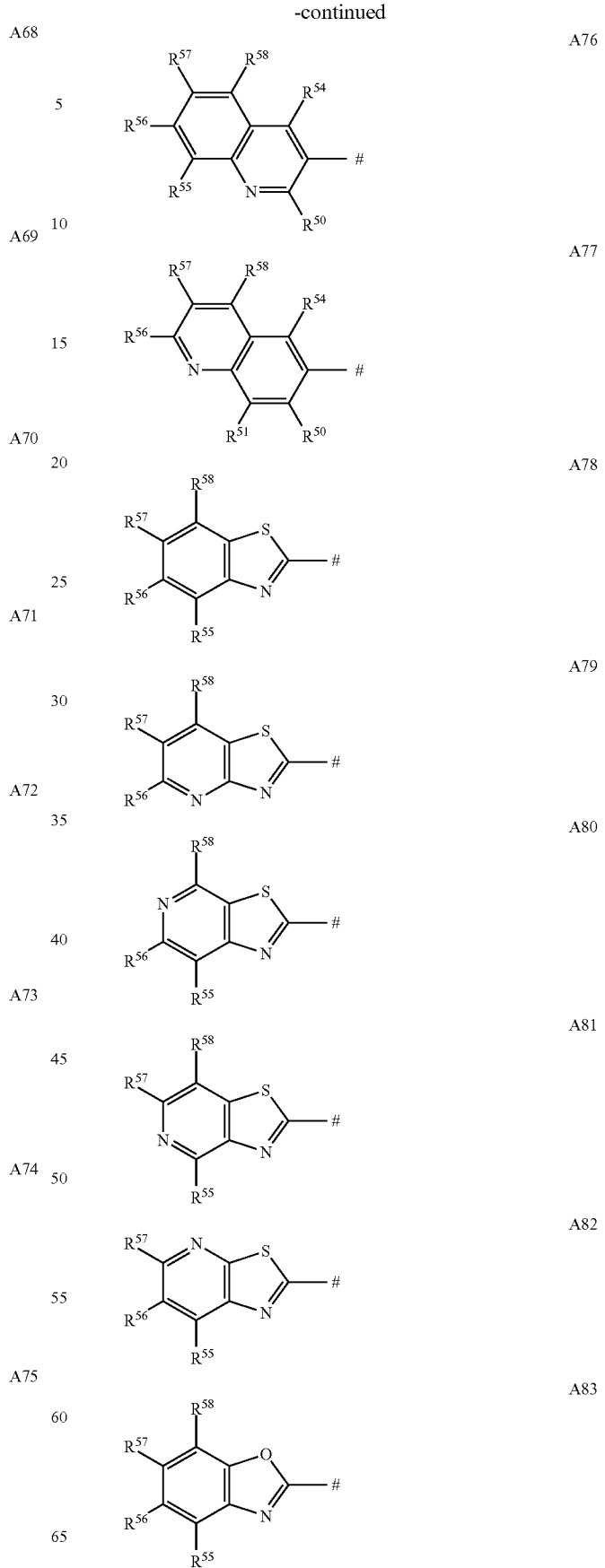

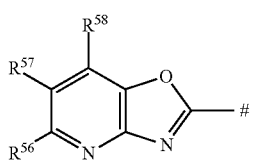 A84
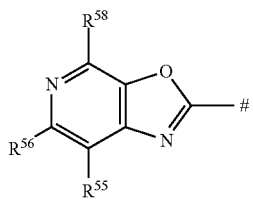 A85
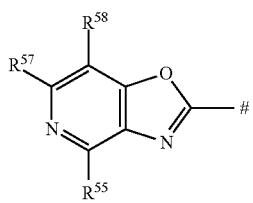 A86
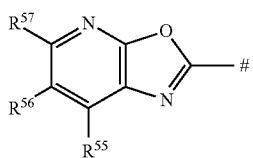 A87
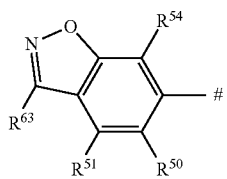 A88
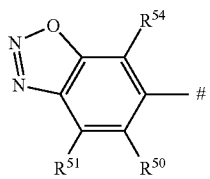 A89
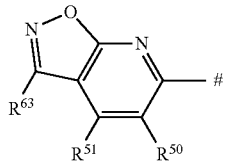 A90
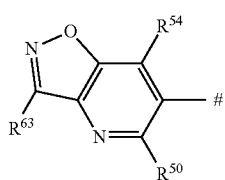 A91
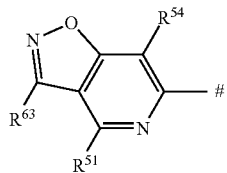 A92
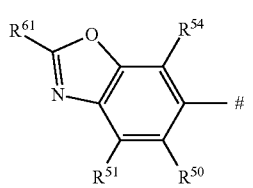 A93
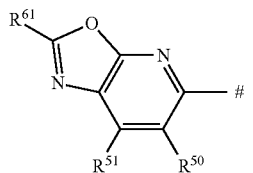 A94
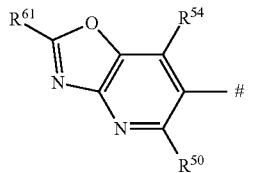 A95
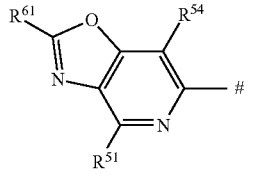 A96
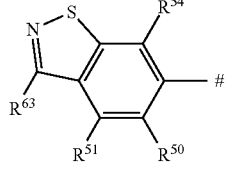 A97
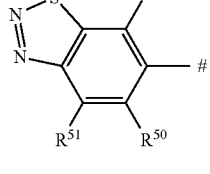 A98
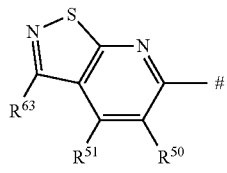 A99

-continued
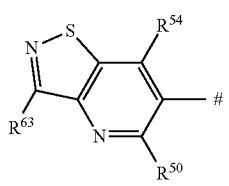 A100
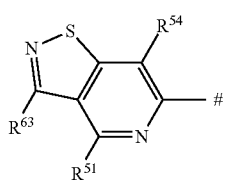 A101
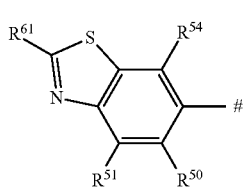 A102
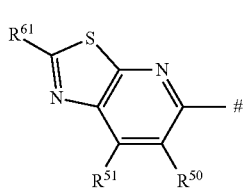 A103
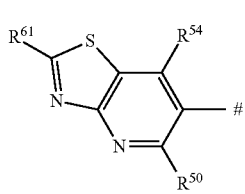 A104
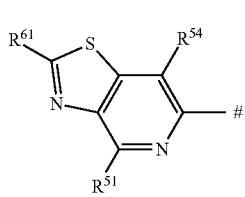 A105
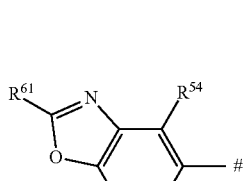 A106
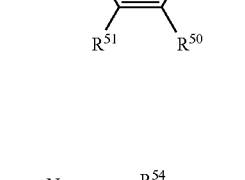 A107
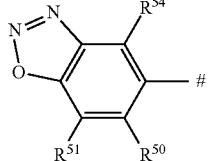
-continued
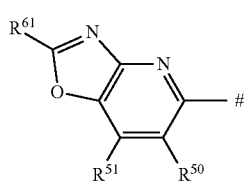 A108
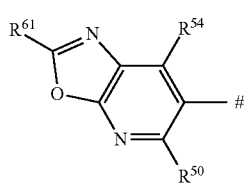 A109
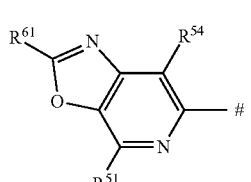 A110
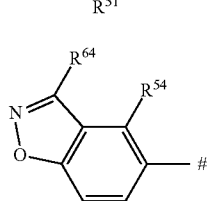 A111
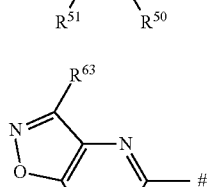 A112
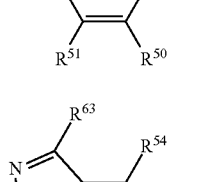 A113
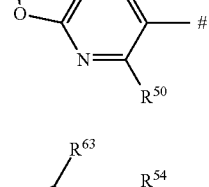 A114
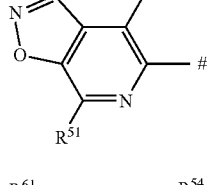 A115
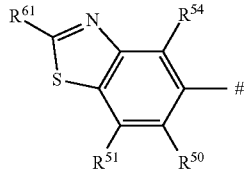

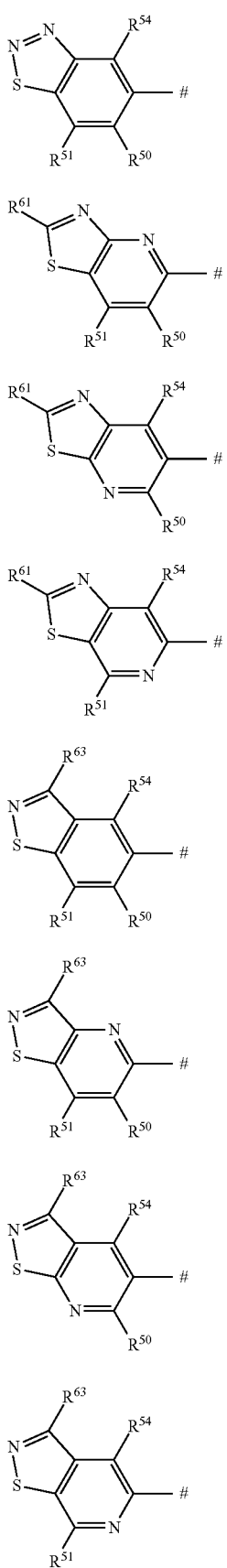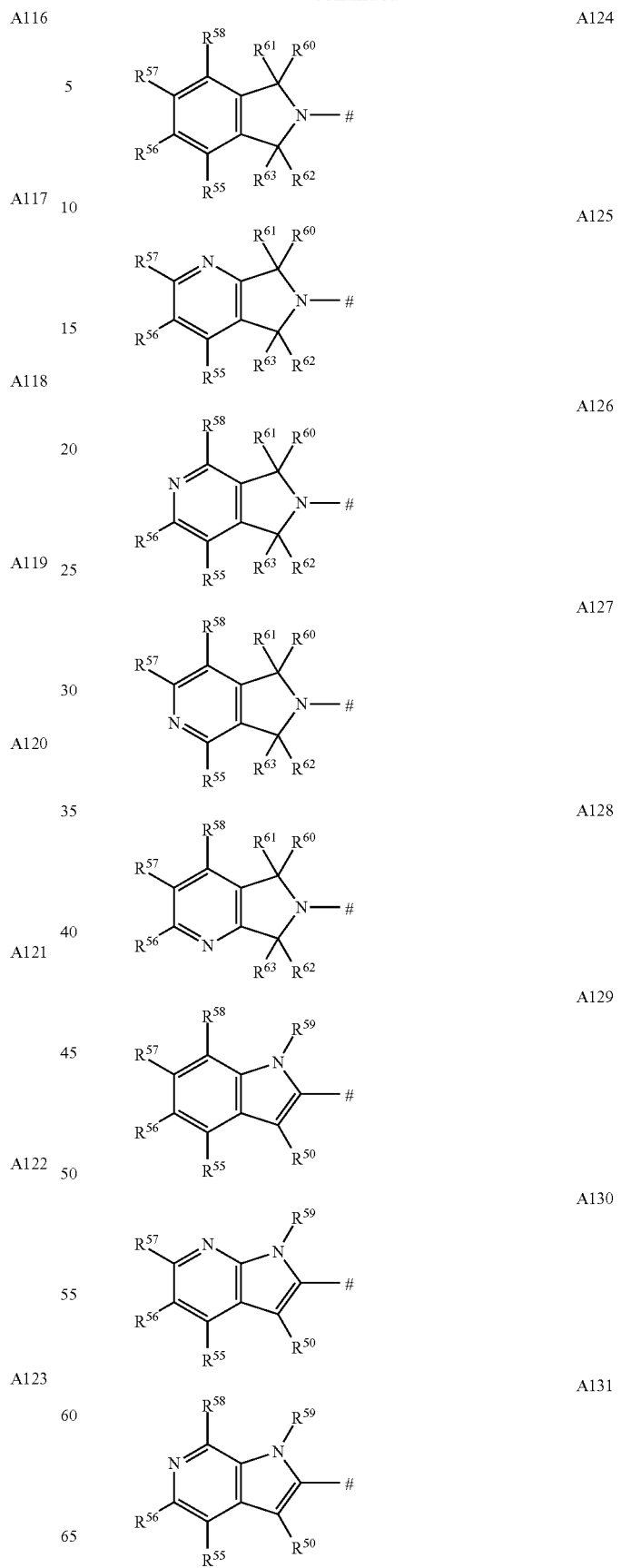

-continued

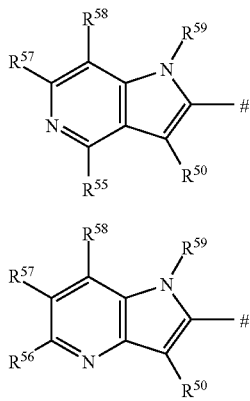

A132

A133 wherein $R^{50}$, $R^{51}$, $R^{52}$, $R^{53}$, $R^{54}$, $R^{55}$, $R^{56}$, $R^{57}$, $R^{58}$, $R^{60}$, $R^{61}$, $R^{62}$, and $R^{63}$ each independently represents a hydrogen atom, a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a carboxy group, a formyl group, a C2-C6 alkoxycarbonyl group, a nitro group, a cyano group, a hydroxy group, a C1-C6 alkylsulfonyl group, a C1-C6 haloalkylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, or an aminocarbonyl group optionally having a C1-C6 alkyl group; and $R^{59}$ represents a hydrogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a formyl group, a C2-C6 alkoxycarbonyl group, a nitro group, a cyano group, a hydroxy group, a C1-C6 alkylsulfonyl group, a C1-C6 haloalkylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, or an aminocarbonyl group optionally having a C1-C6 alkyl group.

The 5- to 10-membered heteroaryl represents a 5- to 10-membered heteroaryl which has, as a ring-constituent atom, one or more atoms selected from the group consisting of a nitrogen atom, an oxygen atom, and a sulfur atom and, when having a two or more atoms, the atoms may be the same or different to each other, and examples thereof include pyridine, pyrimidine, pyrazine, pyridazine, thiophene, furan, pyrrole, and oxazole.

Examples of the 5- to 10-membered heteroaryloxy group include a pyridyloxy group, a pyrimidinyloxy group, a pyrazinyloxy group, a pyridazinyloxy group, a thienyloxy group, a furyloxy group, a pyrrolyloxy group, a pyrazolyloxy group, an imidazolyloxy group, a thiazolyloxy group, an isothiazolyloxy group, an oxazolyloxy group, an isoxazolyloxy group, a triazolyloxy group, a tetrazolyloxy group, an oxadiazolyloxy group, a thiadiazolyloxy group, a benzofuryloxy group, a benzothienyloxy group, an indolyloxy group, a benzoimidazolyloxy group, an indazolyloxy group, a benzothiazolyloxy group, a benzoxazolyloxy group, a benzoisothiazolyloxy group, a benzoisoxazolyloxy group, a pyrazolopyrrolyloxy group, a pyrazolopyrazolyloxy group, a pyrazoloimidazolyloxy group, an imidazopyrimidinyloxy group, an imidazopyrazinyloxy group, a triazolopyridyloxy group, a triazolopyrimidinyloxy group, a triazoloquinolyloxy group, a 2,3-dihydrobenzofuryloxy group, a 2,3-dihydrobenzothienyloxy group, a 1,3-benzodioxolyloxy group, a quinolyloxy group, an isoquinolyloxy group, a cinnolinyloxy group, a phthalazinyloxy group, a quinazolinyloxy group, a quinoxalinyloxy group, a naphthyridinyloxy group, a chromanyloxy group, an isochromanyloxy group, a thienopyridyloxy group, a thienopyrazolyloxy group, and a thienoquinolyloxy group.

Examples of the 5- to 10-membered heteroarylthio group include a pyridylthio group, a pyrimidinylthio group, a pyrazinylthio group, a pyridazinylthio group, a thienylthio group, a furylthio group, a pyrrolylthio group, a pyrazolylthio group, an imidazolylthio group, a thiazolylthio group, an isothiazolylthio group, an oxazolylthio group, an isoxazolylthio group, a triazolylthio group, a tetrazolylthio group, an oxadiazolylthio group, a thiadiazolylthio group, a benzofurylthio group, a benzothienylthio group, an indolylthio group, a benzoimidazolylthio group, an indazolylthio group, a benzothiazolylthio group, a benzoxazolylthio group, a benzoisothiazolylthio group, a benzoisoxazolylthio group, a pyrazolopyrrolylthio group, a pyrazolopyrazolylthio group, a pyrazoloimidazolylthio group, an imidazopyrimidinylthio group, an imidazopyrazinylthio group, a triazolopyridylthio group, a triazolopyrimidinylthio group, a triazoloquinolylthio group, a 2,3-dihydrobenzofurylthio group, a 2,3-dihydrobenzothienylthio group, a 1,3-benzodioxolylthio group, a quinolylthio group, an isoquinolylthio group, a cinnolinylthio group, a phthalazinylthio group, a quinazolinylthio group, a quinoxalinylthio group, a naphthyridinylthio group, a chromanylthio group, an isochromanylthio group, a thienopyridylthio group, a thienopyrazolylthio group, and a thienoquinolylthio group.

The 5- to 10-membered heteroarylamino group represents a group in which one hydrogen atom on nitrogen of an amino group is substituted with a 5- to 10-membered heteroaryl group, and examples thereof include a pyridylamino group, a pyrimidylamino group, a pyrazylamino group, a pyridazylamino group, a thienylamino group, a furylamino group, a pyrrolylamino group, a pyrazolylamino group, an imidazolylamino group, a thiazolylamino group, an isothiazolylamino group, an oxazolylamino group, an isoxazolylamino group, a triazolylamino group, a tetrazolylamino group, an oxadiazolylamino group, a thiadiazolylamino group, a benzofurylamino group, a benzothienylamino group, an indolylamino group, a benzoimidazolylamino group, an indazolylamino group, a benzothiazolylamino group, a benzoxazolylamino group, a benzoisothiazolylamino group, a benzoisoxazolylamino group, a pyrazolopyrrolylamino group, a pyrazolopyrazolylamino group, a pyrazoloimidazolylamino group, an imidazopyrimidylamino group, an imidazopyrazinylamino group, a triazopyridylamino group, a triazopyrimidylamino group, a triazoquinolylamino group, a 2,3-dihydrobenzofurylamino group, a 2,3-dihydrobenzothienylamino group, a 1,3-benzodioxolylamino group, a quinolylamino group, an isoquinolylamino group, a cinnolinylamino group, a phthalazinylamino group, a quinazolinylamino group, a quinoxalylamino group, a naphthylidinylamino group, a chromanylamino group, an isochromanylamino group, a thienopyridylamino group, a thienopyrazolylamino group, and a thienoquinolylamino group.

Examples of the C1-C6 alkyl group include a methyl group, an ethyl group, a propyl group, an isopropyl group, a butyl group, an isobutyl group, a sec-butyl group, a tert-butyl group, a pentyl group, and a hexyl group.

The C1-C6 haloalkyl group represents a group in which at least one hydrogen atom of a C1-C6 alkyl group is substituted with a halogen atom, and examples thereof include a fluoromethyl group, a chloromethyl group, a dichloromethyl group, a difluoromethyl group, a trifluoromethyl group, a trichloromethyl group, a tribromomethyl group, a chlorofluoromethyl group, a dichlorofluoromethyl group, a 2,2,2-trifluoroethyl group, a 2,2,2-trichloroethyl group, a pentafluoroethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3,4-difluorobutyl group, a 4-fluorobutyl group, a 5-fluoropentyl group, and a 2,2-difluorohexyl group.

Examples of the C2-C6 alkenyl group include a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, a 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group, and a 5-hexenyl group.

The C2-C6 haloalkenyl group represents a group in which at least one hydrogen atom of a C2-C6 alkenyl group is substituted with a halogen atom, and examples thereof include a 2-chlorovinyl group, a 2-bromovinyl group, a 2-iodovinyl group, a 1-trifluoromethylvinyl group, a 1-trifluoromethyl-2,2-difluorovinyl group, a 3,3-difluoro-2-propenyl group, a perfluoro-1-butenyl group, a perfluoro-3-butenyl group, a perfluoro-1-pentenyl group, a perfluoro-4-pentenyl group, a perfluoro-1-hexenyl group, and a perfluoro-5-hexenyl group.

Examples of the C2-C6 alkynyl group include an ethynyl group, a propargyl group, a 3-butyn-2-yl group, a 2-butynyl group, a 3-butynyl group, a 2-methyl-3-butyn-2-yl group, a 2-pentynyl group, a 3-pentynyl group, a 4-pentynyl group, a 1-hexynyl group, and a 5-hexynyl group.

The C2-C6 haloalkynyl group represents a group in which at least one hydrogen atom of a C2-C6 alkynyl group is substituted with a halogen atom, and examples thereof include a fluoroethynyl group, a 3-chloro-2-propynyl group, a 3-bromo-2-propynyl group, a 3-iodo-2-propynyl group, a 3-chloro-1-propynyl group, a 5-chloro-4-pentynyl group, a 3,3,3-trifluoro-1-propynyl group, a 3,3,3-trifluoro-1-propynyl group, a perfluoro-2-butynyl group, a perfluoro-3-butynyl group, a perfluoro-2-pentynyl group, a perfluoro-3-pentynyl group, a perfluoro-4-pentynyl group, a perfluoro-1-hexynyl group, and a perfluoro-5-hexynyl group.

Examples of the C3-C6 cycloalkyl group include a cyclopropyl group, a cyclobutyl group, a cyclopentyl group, and a cyclohexyl group.

The C3-C6 halocycloalkyl group represents a group in which at least one hydrogen atom of a C3-C6 cycloalkyl group is substituted with a halogen atom, and examples thereof include a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2,3,3-tetrafluorocyclobutyl group, a 2-chlorocyclopentyl group, a 2-chlorocyclohexyl group, a 4,4-difluorocyclohexyl group, and a 4-chlorocyclohexyl group.

The C1-C6 alkoxy group represents an alkoxy group, and examples thereof include a methoxy group, an ethoxy group, a propoxy group, an isopropoxy group, a butoxy group, an isobutoxy group, a sec-butoxy group, a tert-butoxy group, a pentyloxy group, an isoamyloxy group, a neopentyloxy group, a 2-pentyloxy group, a 3-pentyloxy group, a 2-methylbutyloxy group, a hexyloxy group, an isohexyloxy group, a 3-methylpentyloxy group, and a 4-methylpentyloxy group.

The C1-C6 haloalkoxy group represents a group in which at least one hydrogen atom of a C1-C6 alkoxy group is substituted with a halogen atom, and examples thereof include a trifluoromethoxy group, a trichloromethoxy group, a chloromethoxy group, a dichloromethoxy group, a fluoromethoxy group, a difluoromethoxy group, a pentafluoroethoxy group, a 2,2,2-trifluoroethoxy group, a 2-fluoroethoxy group, a 2,2-difluoroethoxy group, a heptafluoropropoxy group, a 3,3,3-trifluoropropoxy group, a 2-fluoropropoxy group, a 3-fluoropropoxy group, a 2,2-difluoropropoxy group, a 2,3-difluoropropoxy group, a 3,3,3-trifluoropropoxy group, a nonafluorobutoxy group, a perfluoropentyloxy group, and a perfluorohexyloxy group.

Examples of the C1-C6 alkylthio group include a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, an isoamylthio group, a 2-pentylthio group, a 3-pentylthio group, a 2-methylbutylthio group, a hexylthio group, an isohexylthio group, a sec-hexylthio group, a 3-methylpentylthio group, and a 4-methylpentylthio group.

The C1-C6 haloalkylthio group represents a group in which at least one hydrogen atom of a straight or branched C1-C6 alkylthio group is substituted with a halogen atom, and examples thereof include a fluoromethylthio group, a difluoromethylthio group, a trifluoromethylthio group, a pentafluoroethylthio group, a 2,2,2-trifluoroethylthio group, a 2,2-difluoroethylthio group, a heptafluoropropylthio group, a 3,3,3-trifluoropropylthio group, a 2,2-difluoropropylthio group, a 3,3,3-trifluoropropylthio group, a nonafluorobutylthio group, a perfluoropentylthio group, and a perfluorohexylthio group.

Examples of the C3-C6 cycloalkyloxy group include a cyclopropyloxy group, a cyclobutyloxy group, a cyclopentyloxy group, and a cyclohexyloxy group.

The C3-C6 halocycloalkyloxy group represents a group in which at least one hydrogen atom of a C3-C6 cycloalkyloxy group is substituted with a halogen atom, and examples thereof include a 2-fluorocyclopropyloxy group, a 2,2-difluorocyclopropyloxy group, a 2-chloro-2-fluorocyclopropyloxy group, a 2,2-dichlorocyclopropyloxy group, a 2,2-dibromocyclopropyloxy group, a 2,2-difluoro-1-methylcyclopropyloxy group, a 2,2-dichloro-1-methylcyclopropyloxy group, a 2,2-dibromo-1-methylcyclopropyloxy group, a 1-(trifluoromethyl)cyclopropyloxy group, a 2,2,3,3-tetrafluorocyclobutyloxy group, a 2-chlorocyclohexyloxy group, a 4,4-difluorocyclohexyloxy group, and a 4-chlorocyclohexyloxy group.

Examples of the C3-C6 cycloalkylthio group include a cyclopropylthio group, a cyclobutylthio group, a cyclopentylthio group, and a cyclohexylthio group.

Examples of the C2-C6 alkenyloxy group include a vinyloxy group, a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-3-butenyloxy group, a 1-vinyl-2-propenyloxy group, and a 5-hexenyloxy group.

The C2-C6 haloalkenyloxy group represents a group in which at least one hydrogen atom of a C2-C6 alkenyloxy group is substituted with a halogen atom, and examples thereof include a 1-fluorovinyloxy group, a 2-fluorovinyloxy group, a 3,3-difluoro-2-propenyloxy group, a 4,4,4-trifluoro-2-butenyloxy group, a 3,4,4-trifluoro-3-butenyloxy group, a 3,3-difluoro-2-methyl-2-propenyloxy group, a perfluoro-3-butenyloxy group, and a perfluoro-5-hexenyloxy group.

Examples of the C2-C6 alkynyloxy group include an ethynyloxy group, a propargyloxy group, a 3-butyn-2-yloxy group, a 2-butynyloxy group, a 3-butynyloxy group, a 2-methyl-3-butyn-2-yloxy group, a 2-pentynyloxy group, a 3-pentynyloxy group, a 4-pentynyloxy group, and a 5-hexynyloxy group.

C2-C6 haloalkynyloxy group represents a group in which at least one hydrogen atom of a C2-C6 alkynyloxy group is substituted with a halogen atom, and examples thereof include a bromoethynyloxy group, a 3-chloro-2-propynyloxy group, a 3-bromo-2-propynyloxy group, a 3-iodo-2-propynyloxy group, a 5-chloro-4-pentynyloxy group, a 3,3,3-trifluoro-1-propynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group, and a perfluoro-5-hexynyloxy group.

Examples of the C3-C6 alkenylthio group include a vinylthio group, a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group, and a 5-hexenylthio group.

The C3-C6 haloalkenylthio group represents a group in which at least one hydrogen atom of a C3-C6 alkenylthio group is substituted with a halogen atom, and examples thereof include a 1-fluorovinylthio group, a 2-fluorovinylthio group, a 3-chloro-2-propenylthio group, a 3-bromo-2-propenylthio group, a 3,3-difluoro-2-propenylthio group, a 4,4,4-trifluoro-2-butenylthio group, a 3,4,4-trifluoro-3-butenylthio group, a 3,3-difluoro-2-methyl-2-propenylthio group, a perfluoro-3-butenylthio group, and a perfluoro-5-hexenylthio group.

Examples of the C3-C6 alkynylthio group include an ethynylthio group, a propargylthio group, a 3-butyn-2-ylthio group, a 2-butynylthio group, a 3-butynylthio group, a 2-methyl-3-butyn-2-ylthio group, a 2-pentynylthio group, a 3-pentynylthio group, a 4-pentynylthio group, and a 5-hexynylthio group.

The C3-C6 haloalkynylthio group represents a group in which at least one hydrogen atom of a C3-C6 alkynylthio group is substituted with a halogen atom, and examples thereof include a bromoethynylthio group, a 3-chloro-2-propynylthio group, a 3-bromo-2-propynylthio group, a 3-iodo-2-propynylthio group, a 5-chloro-4-pentynylthio group, a 3,3,3-trifluoro-1-propynylthio group, a perfluoro-2-butynylthio group, a perfluoro-3-butynylthio group, a perfluoro-2-pentynylthio group, a perfluoro-3-pentynylthio group, a perfluoro-4-pentynylthio group, and a perfluoro-5-hexynylthio group.

The C2-C6 alkylcarbonyl group represents an alkylcarbonyl group in which the total number of carbon atoms including carbon of carbonyl is within a range of 2 to 6, and examples thereof include an acetyl group, a propionyl group, a butanoyl group, a pentanoyl group, and a hexanoyl group.

The C2-C6 haloalkylcarbonyl group represents a group in which at least one hydrogen atom of a C2-C6 alkylcarbonyl group is substituted with a halogen atom, and examples thereof include a trichloroacetyl group, a fluoroacetyl group, a difluoroacetyl group, a trifluoroacetyl group, a pentafluoropropionyl group, a pentachloropropionyl group, a pentabromopropionyl group, a pentaiodopropionyl group, a 3,3,3-trichloropropionyl group, a 3,3,3-trifluoropropionyl group, a 3,3,3-tribromopropionyl group, a 3,3,3-triiodopropionyl group, a heptafluorobutanoyl group, a heptachlorobutanoyl group, a heptabromobutanoyl group, a heptaiodobutanoyl group, a 4,4,4-trifluorobutanoyl group, a 4,4,4-trichlorobutanoyl group, a 4,4,4-tribromobutanoyl group, a 4,4,4-triiodobutanoyl group, a nonafluoropentanoyl group, a nonachloropentanoyl group, a nonabromopentanoyl group, a nonaiodopentanoyl group, and a perfluorohexanoyl group.

The C2-C6 alkylcarbonyloxy group represents an alkylcarbonyloxy group in which the total number of carbon atoms including carbon of carbonyl is within a range of 2 to 6, and examples thereof include an acetoxy group, a propionyloxy group, a butanoyloxy group, a pentanoyloxy group, and a hexanoyloxy group.

The C2-C6 alkylcarbonylthio group represents a group in which the total number of carbon atoms including carbon of carbonyl is within a range of 2 to 6, and examples thereof include an acetylthio group, a propionylthio group, a butanoylthio group, a pentanoylthio group, and a hexanoylthio group.

The C2-C6 alkoxycarbonyl group represents a group in which the total number of carbon atoms of the alkoxy moiety and carbonyl is within a range of 2 to 6, and examples thereof include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isoamyloxycarbonyl group, a neopentyloxycarbonyl group, a 2-pentyloxycarbonyl group, a 3-pentyloxycarbonyl group, and a 2-methylbutoxycarbonyl group.

Examples of the C1-C6 alkylsulfonyl group include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, an isopentylsulfonyl group, a neopentylsulfonyl group, an isoamylsulfonyl group, a 2-pentylsulfonyl group, a 3-pentylsulfonyl group, a 2-methylbutylsulfonyl group, a hexylsulfonyl group, an isohexylsulfonyl group, a sec-hexylsulfonyl group, a 3-methylpentylsulfonyl group, and a 4-methylpentylsulfonyl group.

The C1-C6 haloalkylsulfonyl group represents a group in which at least one hydrogen atom of a C1-C6 alkylsulfonyl group is substituted with a halogen atom, and examples thereof include a fluoromethylsulfonyl group, a bromodifluoromethylsulfonyl group, a difluoromethylsulfonyl group, a trifluoromethylsulfonyl group, a trichloromethylsulfonyl group, a tribromomethylsulfonyl group, a triiodomethylsulfonyl group, a chlorofluoromethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-trifluoroethylsulfonyl group, a 2,2,2-tribromoethylsulfonyl group, a 2,2,2-triiodoethylsulfonyl group, a 2,2-difluoroethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a 2,2-difluoropropylsulfonyl group, a 3,3,3-trifluoropropylsulfonyl group, a nonafluorobutylsulfonyl group, a nonachlorobutylsulfonyl group, a nonabromobutylsulfonyl group, a nonaiodobutylsulfonyl group, a perfluoropentylsulfonyl group, a perchloropentylsulfonyl group, a perbromopentylsulfonyl group, a perfluorohexylsulfonyl group, a perchlorohexylsulfonyl group, a perbromohexylsulfonyl group, and a periodohexylsulfonyl group.

Examples of the C1-C6 alkylsulfinyl group include a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a pentylsulfinyl group, an isopentylsulfinyl group, a neopentylsulfinyl group, an isoamylsulfinyl group, a 2-pentylsulfinyl group, a 3-pentylsulfinyl group, a 2-methylbutylsulfinyl group, a hexylsulfinyl group, an isohexylsulfinyl group, a sec-hexylsulfinyl group, a 3-methylpentylsulfinyl group, and a 4-methylpentylsulfinyl group.

The C1-C6 haloalkylsulfinyl group represents a group in which at least one hydrogen atom of a C1-C6 alkylsulfinyl group is substituted with a halogen atom, and examples thereof include a monofluoromethylsulfinyl group, a difluoromethylsulfinyl group, a trifluoromethylsulfinyl group, a trichloromethylsulfinyl group, a pentafluoroethylsulfinyl group, a 2,2,2-trifluoroethylsulfinyl group, a 2,2-difluoroethylsulfinyl group, a heptafluoropropylsulfinyl group, a 3,3,3-trifluoropropylsulfinyl group, a 2,2-difluoropropylsulfinyl group, a 3,3,3-trifluoropropylsulfinyl group, a nonafluorobutylsulfinyl group, a perfluoropentylsulfinyl group, and a perfluorohexylsulfinyl group.

The amino group optionally having a C1-C6 alkyl group is an amino group in which one or two hydrogen atoms of an amino group are optionally substituted with a C1-C6 alkyl group and, in the case of a dialkylamino group, alkyl groups on the nitrogen atom may be the same or different to each other. Examples of the amino group optionally having a C1-C6 alkyl group include an amino group, an N-methylamino group, an N,N-dimethylamino group, an N-ethylamino group, an N-ethyl-N-methylamino group, an N,N-diethylamino group, an N-propylamino group, an N-isopropylamino group, an N-propyl-N-methylamino group, an N,N-dipropylamino group, an N,N-diisopropylamino group, an N-butylamino group, an N-butyl-N-methylamino group, an N,N-dibutylamino group, an N-pentylamino group, an N-pentyl-N-methylamino group, and an N-hexylamino group.

The aminocarbonyl group optionally having a C1-C6 alkyl group is an aminocarbonyl group in which one or two hydrogen atoms of an aminocarbonyl group are optionally substituted with a C1-C6 alkyl group and, in the case of a dialkylaminocarbonyl group, alkyl groups on the nitrogen atom may be the same or different to each other. Examples of the aminocarbonyl group optionally having a C1-C6 alkyl group include an aminocarbonyl group, an N-methylaminocarbonyl group, an N-ethylaminocarbonyl group, an N-propylaminocarbonyl group, an N-isopropylaminocarbonyl group, an N-butylaminocarbonyl group, and an N-pentylaminocarbonyl group.

The aminosulfonyl group optionally having a C1-C6 alkyl group represents an aminosulfonyl group in which one or two hydrogen atoms of an aminosulfonyl group are optionally substituted with a C1-C6 alkyl group and, in the case of a dialkylaminosulfonyl group, alkyl groups on the nitrogen atom may be the same or different to each other. Examples of the aminosulfonyl group optionally having a C1-C6 alkyl group include an aminosulfonyl group, an N-methylaminosulfonyl group, an N-ethylaminosulfonyl group, an N-propylaminosulfonyl group, an N-isopropylaminosulfonyl group, an N-butylaminosulfonyl group, an N-pentylaminosulfonyl group, and an N-hexylaminosulfonyl group.

Examples of the C1-C4 alkoxy group include a methoxy group, an ethoxy group, a propoxy group, an isopropoxy group, a butoxy group, an isobutoxy group, a sec-butoxy group, and a tert-butoxy group.

The C1-C4 haloalkoxy group represents a group in which at least one hydrogen atom of a C1-C4 alkoxy group is substituted with a halogen atom, and examples thereof include a trifluoromethoxy group, a trichloromethoxy group, a chloromethoxy group, a dichloromethoxy group, a fluoromethoxy group, a difluoromethoxy group, a pentafluoroethoxy group, a 2,2,2-trifluoroethoxy group, a 2-fluoroethoxy group, a 2,2-difluoroethoxy group, a heptafluoropropoxy group, a 3,3,3-trifluoropropoxy group, a 2-fluoropropoxy group, a 3-fluoropropoxy group, a 2,2-difluoropropoxy group, a 2,3-difluoropropoxy group, a 3,3,3-trifluoropropoxy group, and a nonafluorobutoxy group.

Examples of the C1-C4 alkylthio group include a methylthio group, an ethylthio group, a propylthio group, an isopropylthio group, a butylthio group, an isobutylthio group, a sec-butylthio group, and a tert-butylthio group.

The C1-C4 haloalkylthio group represents a group in which at least one hydrogen atom of a C1-C4 alkylthio group is substituted with a halogen atom, and examples thereof include a trifluoromethylthio group, a trichloromethylthio group, a chloromethylthio group, a dichloromethylthio group, a fluoromethylthio group, a difluoromethylthio group, a pentafluoroethylthio group, a 2,2,2-trichloroethylthio group, a 2,2,2-trifluoroethylthio group, a 2-fluoroethylthio group, a 2,2-difluoroethylthio group, a heptafluoropropylthio group, a 3,3,3-trifluoropropylthio group, a 2-fluoropropylthio group, a 3-fluoropropylthio group, a 2,2-difluoropropylthio group, a 2,3-difluoropropylthio group, a 3,3,3-trifluoropropylthio group, and a nonafluorobutylthio group.

Examples of the C1-C4 alkylsulfonyl group include a methylsulfonyl group, an ethylsulfonyl group, a propylsulfonyl group, an isopropylsulfonyl group, a butylsulfonyl group, an isobutylsulfonyl group, a sec-butylsulfonyl group, and a tert-butylsulfonyl group.

The C1-C4 haloalkylsulfonyl group represents a group in which at least one hydrogen atom of a C1-C4 alkylsulfonyl group is substituted with a halogen atom, and examples thereof include a trifluoromethylsulfonyl group, a trichloromethylsulfonyl group, a chloromethylsulfonyl group, a dichloromethylsulfonyl group, a fluoromethylsulfonyl group, a difluoromethylsulfonyl group, a pentafluoroethylsulfonyl group, a 2,2,2-trifluoroethylsulfonyl group, a 2-fluoroethylsulfonyl group, a 2,2-difluoroethylsulfonyl group, a heptafluoropropylsulfonyl group, a 3,3,3-trifluoropropylsulfonyl group, a 2-fluoropropylsulfonyl group, a 3-fluoropropylsulfonyl group, a 2,2-difluoropropylsulfonyl group, a 2,3-difluoropropylsulfonyl group, a 3,3,3-trifluoropropylsulfonyl group, and a nonafluorobutylsulfonyl group.

Examples of the C3-C9 trialkylsilyl group include a trimethylsilyl group, a tert-butyldimethylsilyl group, a triethylsilyl group, an isopropyldimethylsilyl group, and a triisopropylsilyl group.

The C5-C14 trialkylsilylethynyl group represents an ethynyl group having a trialkylsilyl group bound thereto, in which the number of carbon atoms including carbon of an ethynyl group is within a range of 5 to 14 and three alkyl groups on a silyl group may be the same or different to each other, and examples thereof include a trimethylsilylethynyl group, a tert-butyldimethylsilylethynyl group, a triethylsilylethynyl group, an isopropyldimethylsilylethynyl group, a triisopropylsilylethynyl group, a tri(tert-butyl)silylethynyl group, and a tributylsilylethynyl group.

Examples of the C1-C4 alkylsulfinyl group include a methylsulfinyl group, an ethylsulfinyl group, a propylsulfinyl group, an isopropylsulfinyl group, a butylsulfinyl group, an isobutylsulfinyl group, a sec-butylsulfinyl group, and a tert-butylsulfinyl group.

The C1-C4 haloalkylsulfinyl group represents a group in which at least one hydrogen atom of a C1-C4 alkylsulfinyl group is substituted with a halogen atom, and examples thereof include a trifluoromethylsulfinyl group, a trichloromethylsulfinyl group, a chloromethylsulfinyl group, a dichloromethylsulfinyl group, a fluoromethylsulfinyl group, a difluoromethylsulfinyl group, a pentafluoroethylsulfinyl group, a 2,2,2-trifluoroethylsulfinyl group, a 2-fluoroethylsulfinyl group, a 2,2-difluoroethylsulfinyl group, a heptafluoropropylsulfinyl group, a 3,3,3-trifluoropropylsulfinyl group, a 2-fluoropropylsulfinyl group, a 3-fluoropropylsulfinyl group, a 2,2-difluoropropylsulfinyl group, a 2,3-difluoropropylsulfinyl group, and a nonafluorobutylsulfinyl group.

The C2-C5 alkoxyalkyl group represents a group in which the total number of carbon atoms of the alkoxy moiety and the alkyl moiety is within a range of 2 to 5, and examples thereof include a methoxymethyl group, an ethoxymethyl group, a propoxymethyl group, an isopropoxymethyl group, a butoxymethyl group, an isobutoxymethyl group, a sec-butoxymethyl group, a 1-methoxyethyl group, a 2-methoxyethyl group, a 2-ethoxyethyl group, a 2-propoxyethyl group, a 2-isopropoxyethyl group, a 2-butoxyethyl group, a 3-methoxypropyl group, a 3-ethoxypropyl group, and a 3-methoxybutyl group.

The C2-C5 alkylthioalkyl group is a group in which the total number of the alkylthio moiety and the alkyl moiety is within a range of 2 to 5, and may be either straight or branched, and examples thereof include a methoxymethyl group, an ethoxymethyl group, a propoxymethyl group, an isopropoxymethyl group, a butoxymethyl group, an isobutoxymethyl group, a sec-butoxymethyl group, a 1-methoxyethyl group, a 2-methoxyethyl group, a 2-ethoxyethyl group, a 2-propoxyethyl group, a 2-isopropoxyethyl group, a 2-butoxyethyl group, a 3-methoxypropyl group, a 3-ethoxypropyl group, or a 3-methoxybutyl group.

The C1-C3 haloalkyl group represents a group in which at least one hydrogen atom of a C1-C3 alkyl group is substituted with a halogen atom, and examples thereof include a fluoromethyl group, a chloromethyl group, a dichloromethyl group, a difluoromethyl group, a trifluoromethyl group, a trichloromethyl group, a tribromomethyl group, a chlorofluoromethyl group, a dichlorofluoromethyl group, a 2,2,2-trifluoroethyl group, a 2,2,2-trichloroethyl group, a pentafluoroethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, and a 3,3,3-trifluoropropyl group.

Examples of the C2-C3 alkenyl group include a vinyl group, a 1-propenyl group, an isopropenyl group, and a 2-propenyl group.

The C2-C3 haloalkenyl group represents a group in which at least one hydrogen atom of a C2-3 alkenyl group is substituted with a halogen atom, and examples thereof include a 2-chlorovinyl group, a 2-bromovinyl group, a 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 3,3-dichloro-2-propenyl group, a 3,3-dibromo-2-propenyl group, and a 3-fluoro-3-chloro-2-propenyl group.

Examples of the C1-C3 alkoxy group include a methoxy group, an ethoxy group, a propoxy group, and an isopropoxy group.

Examples of the aspect of the present compound include compounds in which a substituent in formula (1) is as following.

A tetrazolinone compound in which E is E11. A tetrazolinone compound in which E is E12. A tetrazolinone compound in which E is E13. A tetrazolinone compound in which E is E14. A tetrazolinone compound in which E is E15. A tetrazolinone compound in which E is E16. A tetrazolinone compound in which E is E17. A tetrazolinone compound in which E is E18. A tetrazolinone compound in which E is E19. A tetrazolinone compound in which E is E20. A tetrazolinone compound in which E is E21. A tetrazolinone compound in which E is E22. A tetrazolinone compound in which E is E23. A tetrazolinone compound in which E is E24. A tetrazolinone compound in which E is E25. A tetrazolinone compound in which E is E26. A tetrazolinone compound in which E is E27. A tetrazolinone compound in which E is E28. A tetrazolinone compound in which E is E29. A tetrazolinone compound in which E is E30. A tetrazolinone compound in which E is E31. A tetrazolinone compound in which E is E32. A tetrazolinone compound in which E is E33. A tetrazolinone compound in which E is E34. A tetrazolinone compound in which E is E35. A tetrazolinone compound in which E is E36. A tetrazolinone compound in which E is E37. A tetrazolinone compound in which E is E38. A tetrazolinone compound in which E is E39. A tetrazolinone compound in which E is E40. A tetrazolinone compound in which E is E41. A tetrazolinone compound in which E is E42. A tetrazolinone compound in which E is E43. A tetrazolinone compound in which E is E44. A tetrazolinone compound in which E is E45. A tetrazolinone compound in which E is E46. A tetrazolinone compound in which E is E50. A tetrazolinone compound in which E is E51. A tetrazolinone compound in which E is E52. A tetrazolinone compound in which E is E53. A tetrazolinone compound in which E is E54. A tetrazolinone compound in which E is E55. A tetrazolinone compound in which E is E56. A tetrazolinone compound in which E is E57. A tetrazolinone compound in which E is E58. A tetrazolinone compound in which E is E59. A tetrazolinone compound in which E is E60. A tetrazolinone compound in which E is E61. A tetrazolinone compound in which E is E62. A tetrazolinone compound in which E is E63. A tetrazolinone compound in which E is E64. A tetrazolinone compound in which E is E65.

A tetrazolinone compound in which Q is Q46; Y is —O—CH$_2$—; $R^{30}$ and $R^{31}$ are hydrogen atoms; $R^5$ is a methyl group; X is an oxygen atom; and E is E11. A tetrazolinone compound in which Q is Q46; Y is —O—CH$_2$—; $R^{30}$ and $R^{31}$ are hydrogen atoms; $R^5$ is a methyl group; X is an oxygen atom; and E is E12. A tetrazolinone compound in which Q is Q46; Y is —O—CH$_2$—; $R^{30}$ and $R^{31}$ are hydrogen atoms; $R^5$ is a methyl group; X is an oxygen atom; and E is E13. A tetrazolinone compound in which Q is Q46; Y is —O—CH$_2$—; $R^{30}$ and $R^{31}$ are hydrogen atoms; $R^5$ is a methyl group; X is an oxygen atom; and E is E14. A tetrazolinone compound in which Q is Q46; Y is —O—CH$_2$—; $R^{30}$ and $R^{31}$ are hydrogen atoms; $R^5$ is a methyl group; X is an oxygen atom; and E is E15. A tetrazolinone compound in which Q is Q46; Y is —O—CH$_2$—; $R^{30}$ and $R^{31}$ are hydrogen atoms; $R^5$ is a methyl group; X is an oxygen atom; and E is E16. A tetrazolinone compound in which Q is Q46; Y is —O—CH$_2$—; $R^{30}$ and $R^{31}$ are hydrogen atoms; $R^5$ is a methyl group; X is an oxygen atom; and E is E17. A tetrazolinone compound in which Q is Q46; Y is —O—CH$_2$—; $R^{30}$ and $R^{31}$ are hydrogen atoms; $R^5$ is a methyl group; X is an oxygen atom; and E is E18. A tetrazolinone compound in which Q is Q46; Y is —O—CH$_2$—; $R^{30}$ and $R^{31}$ are hydrogen atoms; $R^5$ is a methyl group; X is an oxygen atom; and E is E19. A tetrazolinone compound in which Q is Q46; Y is —O—CH$_2$—; $R^{30}$ and $R^{31}$ are hydrogen atoms; $R^5$ is a methyl group; X is an oxygen atom; and E is E20. A tetrazolinone compound in which Q is Q46; Y is —O—CH$_2$—; $R^{30}$ and $R^{31}$ are hydrogen atoms; $R^5$ is a methyl group; X is an oxygen atom; and E is E21. A tetrazolinone compound in which Q is Q46; Y is —O—CH$_2$—; $R^{30}$ and $R^{31}$ are hydrogen atoms; $R^5$ is a methyl group; X is an oxygen atom; and E is E22. A tetrazolinone compound in which Q is Q46; Y is —O—CH$_2$—; $R^{30}$ and $R^{31}$ are hydrogen atoms; $R^5$ is a methyl group; X is an oxygen atom; and E is E23.

A tetrazolinone compound in which Q is Q46; Y is —O—CH$_2$—; $R^{30}$ and $R^{31}$ are hydrogen atoms; $R^5$ is a methyl group; X is an oxygen atom; and E is E24. A tetrazolinone compound in which Q is Q46; Y is —O—CH$_2$—; $R^{30}$ and $R^{31}$ are hydrogen atoms; $R^5$ is a methyl group; X is an oxygen atom; and E is E25. A tetrazolinone compound in which Q is Q46; Y is —O—CH$_2$—; $R^{30}$ and $R^{31}$ are hydrogen atoms; $R^5$ is a methyl group; X is an oxygen atom; and E is E26. A tetrazolinone compound in which Q is Q46; Y is —O—CH$_2$—; $R^{30}$ and $R^{31}$ are hydrogen atoms; $R^5$ is a methyl group; X is an oxygen atom; and E is E27. A tetrazolinone compound in which Q is Q46; Y is —O—CH$_2$—; $R^{30}$ and $R^{31}$ are hydrogen atoms; $R^5$ is a methyl group; X is an oxygen atom; and E is E28. A tetrazolinone compound in which Q is Q46; Y is —O—CH$_2$—; $R^{30}$ and $R^{31}$ are hydrogen atoms; $R^5$ is a methyl group; X is an oxygen atom; and E is E29. A tetrazolinone compound in which Q is Q46; Y is —O—CH$_2$—; $R^{30}$ and $R^{31}$ are hydrogen atoms; $R^5$ is a methyl group; X is an oxygen atom; and E is E30. A tetrazolinone compound in which Q is Q46; Y is —O—CH$_2$—; $R^{30}$ and $R^{31}$ are hydrogen atoms; $R^5$ is a methyl group; X is an oxygen atom; and E is E31. A tetrazolinone compound in which Q is Q46; Y is —O—CH$_2$—; $R^{30}$ and $R^{31}$ are hydrogen atoms; $R^5$ is a methyl group; X is an oxygen atom; and E is E32. A tetrazolinone compound in which Q is Q46; Y is —O—CH$_2$—; $R^{30}$ and $R^{31}$ are hydrogen atoms; $R^5$ is a methyl group; X is an oxygen atom; and E is E33. A tetrazolinone compound in which Q is Q46; Y is —O—CH$_2$—; $R^{30}$ and $R^{31}$ are hydrogen atoms; $R^5$ is a methyl group; X is an oxygen atom; and E is E34. A tetrazolinone compound in which Q is Q46; Y is —O—CH$_2$—; $R^{30}$ and $R^{31}$ are hydrogen atoms; $R^5$ is a methyl group; X is an oxygen atom; and E is E35. A tetrazolinone compound in which Q is Q46; Y is —O—CH$_2$—; $R^{30}$ and $R^{31}$ are hydrogen atoms; $R^5$ is a methyl group; X is an oxygen atom; and E is E36. A tetrazolinone compound in which Q is Q46; Y is —O—CH$_2$—; $R^{30}$ and $R^{31}$ are hydrogen atoms; $R^5$ is a methyl group; X is an oxygen atom; and E is E37. A tetrazolinone compound in which Q is Q46; Y is —O—CH$_2$—; $R^{30}$ and $R^{31}$ are hydrogen atoms; $R^5$ is a methyl group; X is an oxygen atom; and E is E38.

A tetrazolinone compound in which Q is Q46; Y is —O—CH$_2$—; $R^{30}$ and $R^{31}$ are hydrogen atoms; $R^5$ is a methyl group; X is an oxygen atom; and E is E39. A tetrazolinone compound in which Q is Q46; Y is —O—CH$_2$—; $R^{30}$ and $R^{31}$ are hydrogen atoms; $R^5$ is a methyl group; X is an oxygen atom; and E is E40. A tetrazolinone compound in which Q is Q46; Y is —O—CH$_2$—; $R^{30}$ and $R^{31}$ are hydrogen atoms; $R^5$ is a methyl group; X is an oxygen atom; and E is E41. A tetrazolinone compound in which Q is Q46; Y is —O—CH$_2$—; $R^{30}$ and $R^{31}$ are hydrogen atoms; $R^5$ is a methyl group; X is an oxygen atom; and E is E42. A tetrazolinone compound in which Q is Q46; Y is —O—CH$_2$—; $R^{30}$ and $R^{31}$ are hydrogen atoms; $R^5$ is a methyl group; X is an oxygen atom; and E is E43. A tetrazolinone compound in which Q is Q46; Y is —O—CH$_2$—; $R^{30}$ and $R^{31}$ are hydrogen atoms; $R^5$ is a methyl group; X is an oxygen atom; and E is E44. A tetrazolinone compound in which Q is Q46; Y is —O—CH$_2$—; $R^{30}$ and $R^{31}$ are hydrogen atoms; $R^5$ is a methyl group; X is an oxygen atom; and E is E45. A tetrazolinone compound in which Q is Q46; Y is —O—CH$_2$—; $R^{30}$ and $R^{31}$ are hydrogen atoms; $R^5$ is a methyl group; X is an oxygen atom; and E is E46. A tetrazolinone compound in which Q is Q46; Y is —O—CH$_2$—; $R^{30}$ and $R^{31}$ are hydrogen atoms; $R^5$ is a methyl group; X is an oxygen atom; and E is E50. A tetrazolinone compound in which Q is Q46; Y is —O—CH$_2$—; $R^{30}$ and $R^{31}$ are hydrogen atoms; $R^5$ is a methyl group; X is an oxygen atom; and E is E51. A tetrazolinone compound in which Q is Q46; Y is —O—CH$_2$—; $R^{30}$ and $R^{31}$ are hydrogen atoms; $R^5$ is a methyl group; X is an oxygen atom; and E is E52. A tetrazolinone compound in which Q is Q46; Y is —O—CH$_2$—; R$^{30}$ and R$^{31}$ are hydrogen atoms; R$^5$ is a methyl group; X is an oxygen atom; and E is E53. A tetrazolinone compound in which Q is Q46; Y is —O—CH$_2$—; R$^{30}$ and R$^{31}$ are hydrogen atoms; R$^5$ is a methyl group; X is an oxygen atom; and E is E54. A tetrazolinone compound in which Q is Q46; Y is —O—CH$_2$—; R$^{30}$ and R$^{31}$ are hydrogen atoms; R$^5$ is a methyl group; X is an oxygen atom; and E is E55.

A tetrazolinone compound in which Q is Q46; Y is —O—CH$_2$—; R$^{30}$ and R$^{31}$ are hydrogen atoms; R$^5$ is a methyl group; X is an oxygen atom; and E is E56. A tetrazolinone compound in which Q is Q46; Y is —O—CH$_2$—; R$^{30}$ and R$^{31}$ are hydrogen atoms; R$^5$ is a methyl group; X is an oxygen atom; and E is E57. A tetrazolinone compound in which Q is Q46; Y is —O—CH$_2$—; R$^{30}$ and R$^{31}$ are hydrogen atoms; R$^5$ is a methyl group; X is an oxygen atom; and E is E58. A tetrazolinone compound in which Q is Q46; Y is —O—CH$_2$—; R$^{30}$ and R$^{31}$ are hydrogen atoms; R$^5$ is a methyl group; X is an oxygen atom; and E is E59. A tetrazolinone compound in which Q is Q46; Y is —O—CH$_2$—; R$^{30}$ and R$^{31}$ are hydrogen atoms; R$^5$ is a methyl group; X is an oxygen atom; and E is E60. A tetrazolinone compound in which Q is Q46; Y is —O—CH$_2$—; R$^{30}$ and R$^{31}$ are hydrogen atoms; R$^5$ is a methyl group; X is an oxygen atom; and E is E61. A tetrazolinone compound in which Q is Q46; Y is —O—CH$_2$—; R$^{30}$ and R$^{31}$ are hydrogen atoms; R$^5$ is a methyl group; X is an oxygen atom; and E is E62. A tetrazolinone compound in which Q is Q46; Y is —O—CH$_2$—; R$^{30}$ and R$^{31}$ are hydrogen atoms; R$^5$ is a methyl group; X is an oxygen atom; and E is E63. A tetrazolinone compound in which Q is Q46; Y is —O—CH$_2$—; R$^{30}$ and R$^{31}$ are hydrogen atoms; R$^5$ is a methyl group; X is an oxygen atom; and E is E64. A tetrazolinone compound in which Q is Q46; Y is —O—CH$_2$—; R$^{30}$ and R$^{31}$ are hydrogen atoms; R$^5$ is a methyl group; X is an oxygen atom; and E is E65.

A tetrazolinone compound in which Q is Q61; Y is —O—CH$_2$—; R$^{31}$ is a hydrogen atom; R$^5$ is a methyl group; X is an oxygen atom; and E is E11. A tetrazolinone compound in which Q is Q61; Y is —O—CH$_2$—; R$^{31}$ is a hydrogen atom; R$^5$ is a methyl group; X is an oxygen atom; and E is E12. A tetrazolinone compound in which Q is Q61; Y is —O—CH$_2$—; R$^{31}$ is a hydrogen atom; R$^5$ is a methyl group; X is an oxygen atom; and E is E13. A tetrazolinone compound in which Q is Q61; Y is —O—CH$_2$—; R$^{31}$ is a hydrogen atom; R$^5$ is a methyl group; X is an oxygen atom; and E is E14. A tetrazolinone compound in which Q is Q61; Y is —O—CH$_2$—; R$^{31}$ is a hydrogen atom; R$^5$ is a methyl group; X is an oxygen atom; and E is E15. A tetrazolinone compound in which Q is Q61; Y is —O—CH$_2$—; R$^{31}$ is a hydrogen atom; R$^5$ is a methyl group; X is an oxygen atom; and E is E16. A tetrazolinone compound in which Q is Q61; Y is —O—CH$_2$—; R$^{31}$ is a hydrogen atom; R$^5$ is a methyl group; X is an oxygen atom; and E is E17. A tetrazolinone compound in which Q is Q61; Y is —O—CH$_2$—; R$^{31}$ is a hydrogen atom; R$^5$ is a methyl group; X is an oxygen atom; and E is E18. A tetrazolinone compound in which Q is Q61; Y is —O—CH$_2$—; R$^{31}$ is a hydrogen atom; R$^5$ is a methyl group; X is an oxygen atom; and E is E19. A tetrazolinone compound in which Q is Q61; Y is —O—CH$_2$—; R$^{31}$ is a hydrogen atom; R$^5$ is a methyl group; X is an oxygen atom; and E is E20. A tetrazolinone compound in which Q is Q61; Y is —O—CH$_2$—; R$^{31}$ is a hydrogen atom; R$^5$ is a methyl group; X is an oxygen atom; and E is E21. A tetrazolinone compound in which Q is Q61; Y is —O—CH$_2$—; R$^{31}$ is a hydrogen atom; R$^5$ is a methyl group; X is an oxygen atom; and E is E22. A tetrazolinone compound in which Q is Q61; Y is —O—CH$_2$—; R$^{31}$ is a hydrogen atom; R$^5$ is a methyl group; X is an oxygen atom; and E is E23. A tetrazolinone compound in which Q is Q61; Y is —O—CH$_2$—; R$^{31}$ is a hydrogen atom; R$^5$ is a methyl group; X is an oxygen atom; and E is E24. A tetrazolinone compound in which Q is Q61; Y is —O—CH$_2$—; R$^{31}$ is a hydrogen atom; R$^5$ is a methyl group; X is an oxygen atom; and E is E25. A tetrazolinone compound in which Q is Q61; Y is —O—CH$_2$—; R$^{31}$ is a hydrogen atom; R$^5$ is a methyl group; X is an oxygen atom; and E is E26.

A tetrazolinone compound in which Q is Q61; Y is —O—CH$_2$—; R$^{31}$ is a hydrogen atom; R$^5$ is a methyl group; X is an oxygen atom; and E is E27. A tetrazolinone compound in which Q is Q61; Y is —O—CH$_2$—; R$^{31}$ is a hydrogen atom; R$^5$ is a methyl group; X is an oxygen atom; and E is E28. A tetrazolinone compound in which Q is Q61; Y is —O—CH$_2$—; R$^{31}$ is a hydrogen atom; R$^5$ is a methyl group; X is an oxygen atom; and E is E29. A tetrazolinone compound in which Q is Q61; Y is —O—CH$_2$—; R$^{31}$ is a hydrogen atom; R$^5$ is a methyl group; X is an oxygen atom; and E is E30. A tetrazolinone compound in which Q is Q61; Y is —O—CH$_2$—; R$^{31}$ is a hydrogen atom; R$^5$ is a methyl group; X is an oxygen atom; and E is E31. A tetrazolinone compound in which Q is Q61; Y is —O—CH$_2$—; R$^{31}$ is a hydrogen atom; R$^5$ is a methyl group; X is an oxygen atom; and E is E32. A tetrazolinone compound in which Q is Q61; Y is —O—CH$_2$—; R$^{31}$ is a hydrogen atom; R$^5$ is a methyl group; X is an oxygen atom; and E is E33. A tetrazolinone compound in which Q is Q61; Y is —O—CH$_2$—; R$^{31}$ is a hydrogen atom; R$^5$ is a methyl group; X is an oxygen atom; and E is E34. A tetrazolinone compound in which Q is Q61; Y is —O—CH$_2$—; R$^{31}$ is a hydrogen atom; R$^5$ is a methyl group; X is an oxygen atom; and E is E35. A tetrazolinone compound in which Q is Q61; Y is —O—CH$_2$—; R$^{31}$ is a hydrogen atom; R$^5$ is a methyl group; X is an oxygen atom; and E is E36. A tetrazolinone compound in which Q is Q61; Y is —O—CH$_2$—; R$^{31}$ is a hydrogen atom; R$^5$ is a methyl group; X is an oxygen atom; and E is E37. A tetrazolinone compound in which Q is Q61; Y is —O—CH$_2$—; R$^{31}$ is a hydrogen atom; R$^5$ is a methyl group; X is an oxygen atom; and E is E38. A tetrazolinone compound in which Q is Q61; Y is —O—CH$_2$—; R$^{31}$ is a hydrogen atom; R$^5$ is a methyl group; X is an oxygen atom; and E is E39. A tetrazolinone compound in which Q is Q61; Y is —O—CH$_2$—; R$^{31}$ is a hydrogen atom; R$^5$ is a methyl group; X is an oxygen atom; and E is E40. A tetrazolinone compound in which Q is Q61; Y is —O—CH$_2$—; R$^{31}$ is a hydrogen atom; R$^5$ is a methyl group; X is an oxygen atom; and E is E41. A tetrazolinone compound in which Q is Q61; Y is —O—CH$_2$—; R$^{31}$ is a hydrogen atom; R$^5$ is a methyl group; X is an oxygen atom; and E is E42.

A tetrazolinone compound in which Q is Q61; Y is —O—CH$_2$—; R$^{31}$ is a hydrogen atom; R$^5$ is a methyl group; X is an oxygen atom; and E is E43. A tetrazolinone compound in which Q is Q61; Y is —O—CH$_2$—; R$^{31}$ is a hydrogen atom; R$^5$ is a methyl group; X is an oxygen atom; and E is E44. A tetrazolinone compound in which Q is Q61; Y is —O—CH$_2$—; R$^{31}$ is a hydrogen atom; R$^5$ is a methyl group; X is an oxygen atom; and E is E45. A tetrazolinone compound in which Q is Q61; Y is —O—CH$_2$—; R$^{31}$ is a hydrogen atom; R$^5$ is a methyl group; X is an oxygen atom; and E is E46. A tetrazolinone compound in which Q is Q61; Y is —O—CH$_2$—; R$^{31}$ is a hydrogen atom; R$^5$ is a methyl group; X is an oxygen atom; and E is E50. A tetrazolinone compound in which Q is Q61; Y is —O—CH$_2$—; R$^{31}$ is a hydrogen atom; R$^5$ is a methyl group; X is an oxygen atom; and E is E51. A tetrazolinone compound in which Q is Q61; Y is —O—CH$_2$—; R$^{31}$ is a hydrogen atom; R$^5$ is a methyl group; X is an oxygen atom; and E is E52. A tetrazolinone compound in which Q is Q61; Y is —O—CH$_2$—; R$^{31}$ is a hydrogen atom; R$^5$ is a methyl group; X is an oxygen atom; and E is E53. A tetrazolinone compound in which Q is Q61; Y is —O—CH$_2$—; R$^{31}$ is a hydrogen atom; R$^5$ is a methyl group; X is an oxygen atom; and E is E54. A tetrazolinone compound in which Q is Q61; Y is —O—CH$_2$—; R$^{31}$ is a hydrogen atom; R$^5$ is a methyl group; X is an oxygen atom; and E is E55. A tetrazolinone compound in which Q is Q61; Y is —O—CH$_2$—; R$^{31}$ is a hydrogen atom; R$^5$ is a methyl group; X is an oxygen atom; and E is E56. A tetrazolinone compound in which Q is Q61; Y is —O—CH$_2$—; R$^{31}$ is a hydrogen atom; R$^5$ is a methyl group; X is an oxygen atom; and E is E57. A tetrazolinone compound in which Q is Q61; Y is —O—CH$_2$—; R$^{31}$ is a hydrogen atom; R$^5$ is a methyl group; X is an oxygen atom; and E is E58. A tetrazolinone compound in which Q is Q61; Y is —O—CH$_2$—; R$^{31}$ is a hydrogen atom; R$^5$ is a methyl group; X is an oxygen atom; and E is E59. A tetrazolinone compound in which Q is Q61; Y is —O—CH$_2$—; R$^{31}$ is a hydrogen atom; R$^5$ is a methyl group; X is an oxygen atom; and E is E60.

A tetrazolinone compound in which Q is Q61; Y is —O—CH$_2$—; R$^{31}$ is a hydrogen atom; R$^5$ is a methyl group; X is an oxygen atom; and E is E61. A tetrazolinone compound in which Q is Q61; Y is —O—CH$_2$—; R$^{31}$ is a hydrogen atom; R$^5$ is a methyl group; X is an oxygen atom; and E is E62. A tetrazolinone compound in which Q is Q61; Y is —O—CH$_2$—; R$^{31}$ is a hydrogen atom; R$^5$ is a methyl group; X is an oxygen atom; and E is E63. A tetrazolinone compound in which Q is Q61; Y is —O—CH$_2$—; R$^{31}$ is a hydrogen atom; R$^5$ is a methyl group; X is an oxygen atom; and E is E64. A tetrazolinone compound in which Q is Q61; Y is —O—CH$_2$—; R$^{31}$ is a hydrogen atom; R$^5$ is a methyl group; X is an oxygen atom; and E is E65.

A tetrazolinone compound in which Q is the following formula Q400:

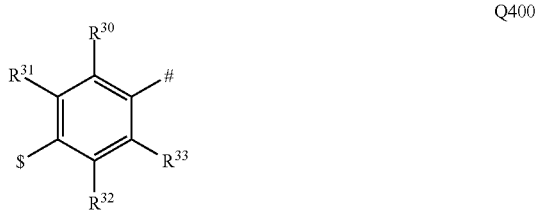

wherein R$^{30}$, R$^{31}$, R$^{32}$, and R$^{33}$ are the same as defined above, the symbol $ represents a binding site for A, the symbol # represents a binding site for Y; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E11. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E12. A tetrazolinone compound in which Q is Q400; Y is —O—CH$_2$—; R$^{30}$ is a methyl group; R$^{31}$, R$^{32}$, R$^{33}$ are hydrogen atoms; R$^5$ is a methyl group; X is an oxygen atom; and E is E13. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E14. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E15. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E16. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E17. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E18. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E19. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E20. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E21. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E22. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E23. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E24. A tetrazolinone compound in which Q is Q400; Y is —O—CH$_2$—; R$^{30}$ and R$^{31}$ are hydrogen atoms; R$^5$ is a methyl group; X is an oxygen atom; and E is E25. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E26. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E27. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E28. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E29. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E30. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E31. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E32. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E33. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E34. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E35. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E36. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E37. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E38. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E39. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E40. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E41. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E42. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E43. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E44. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E45. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E46. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E50. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E51. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E52. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E53. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E54. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E55. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E56. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E57. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E58. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E59. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E60. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E61. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E62. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E63. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E64. A tetrazolinone compound in which Q is Q400; Y is —O—CH$_2$—; R$^{30}$ is a methyl group; R$^{31}$, R$^{32}$, and R$^{33}$ are hydrogen atoms; R$^5$ is a methyl group; X is an oxygen atom; and E is E65.

A tetrazolinone compound in which E is E16, R$^8$ is a C1-C6 alkyl group, R$^3$ is a hydrogen atom, Y is —O—CH$_2$—, A is a phenyl group optionally having one or more halogen atoms, R$^5$ is a C1-C3 alkyl group, and X is an oxygen atom.

A tetrazolinone compound in which E is E16, R$^8$ is a C1-C6 alkyl group, R$^3$ is a hydrogen atom, Q is Q46, R$^{30}$ and R$^{31}$ are hydrogen atoms, Y is —O—CH$_2$—, A is a phenyl group optionally having one or more halogen atoms, R$^5$ is a C1-C3 alkyl group, and X is an oxygen atom.

A tetrazolinone compound in which E is E16, R$^8$ is a C1-C6 alkyl group, R$^3$ is a hydrogen atom, Q is Q46, R$^{30}$ and R$^{31}$ are hydrogen atoms, Y is —O—CH$_2$—, A is a phenyl group optionally having one or more C1-C3 alkoxy groups, R$^5$ is a C1-C3 alkyl group, and X is an oxygen atom.

A tetrazolinone compound in which E is E16, R$^8$ is a C1-C6 alkyl group, R$^3$ is a hydrogen atom, Q is Q61, R$^{31}$ is a hydrogen atom, Y is —O—CH$_2$—, A is an adamantyl group, R$^5$ is a C1-C3 alkyl group, and X is an oxygen atom.

A tetrazolinone compound in which E is E16, R$^8$ is a C1-C6 alkyl group, R$^3$ is a hydrogen atom, Q is Q61, R$^{31}$ is a hydrogen atom, Y is —O—CH$_2$—, A is a phenyl group optionally having one or more halogen atoms, R$^5$ is a C1-C3 alkyl group, and X is an oxygen atom.

A tetrazolinone compound in which E is E19, R$^2$ and R$^3$ are hydrogen atoms, Y is —O—CH$_2$—, A is a phenyl group optionally having one or more halogen atoms, R$^5$ is a C1-C3 alkyl group, and X is an oxygen atom.

A tetrazolinone compound in which E is E19, R$^2$ and R$^3$ is —O—CH$_2$—, A is a phenyl group optionally having one or more halogen atoms, R$^5$ is a C1-C3 alkyl group, and X is an oxygen atom.

A tetrazolinone compound in which E is E19, R$^2$ and R$^3$ are hydrogen atoms, Q is Q61, R$^{31}$ is a hydrogen atom, Y is —O—CH$_2$—, A is a phenyl group optionally having one or more halogen atoms, R$^5$ is a C1-C3 alkyl group, and X is an oxygen atom.

A tetrazolinone compound in which E is E44, R$^6$ is a C1-C6 alkyl group, R$^3$ is a hydrogen atom, Y is —O—CH$_2$—, A is a phenyl group optionally having one or more halogen atoms, R$^5$ is a C1-C3 alkyl group, and X is an oxygen atom.

A tetrazolinone compound in which E is E44, R$^6$ is a C1-C6 alkyl group, R$^3$ is a hydrogen atom, Q is Q46, R$^{30}$ and R$^{31}$ are hydrogen atoms, Y is —O—CH$_2$—, A is a phenyl group optionally having one or more halogen atoms, R$^5$ is a C1-C3 alkyl group, and X is an oxygen atom.

A tetrazolinone compound in which E is E51, $R^2$, $R^3$, and $R^4$ are hydrogen atoms, Y is —O—$CH_2$—, A is a phenyl group optionally having one or more halogen atoms, $R^5$ is a C1-C3 alkyl group, and X is an oxygen atom.

A tetrazolinone compound in which E is E51, $R^2$, $R^3$, and $R^4$ are hydrogen atoms, Q is Q46, $R^{30}$ and $R^{31}$ are hydrogen atoms, Y is —O—$CH_2$—, A is a phenyl group optionally having one or more halogen atoms, $R^5$ is a C1-C3 alkyl group, and X is an oxygen atom.

A tetrazolinone compound in which E is E16, $R^8$ is a C1-C6 alkyl group, $R^3$ is a hydrogen atom, Q is Q400, $R^{30}$ is a C1-C3 alkyl group, $R^{31}$, $R^{32}$, and $R^{33}$ are hydrogen atoms, Y is —O—$CH_2$—, A is A17, $R^{50}$ is a hydrogen atom or a C1-C3 alkyl group, $R^{51}$ is a halogen atom, $R^{59}$ is a C1-C3 alkyl group, $R^5$ is a C1-C3 alkyl group, and X is an oxygen atom.

A tetrazolinone compound in which E is E51, $R^2$, $R^3$, and $R^4$ are hydrogen atoms, Q is Q400, $R^{30}$ is a C1-C3 alkyl group, $R^{31}$, $R^{32}$, and $R^{33}$ are hydrogen atoms, Y is —O—$CH_2$—, A is A17, $R^{50}$ is a hydrogen atom or a C1-C3 alkyl group, $R^{51}$ is a halogen atom, $R^{59}$ is a C1-C3 alkyl group, $R^5$ is a C1-C3 alkyl group, and X is an oxygen atom.

Next, a process for producing the present compound will be described.

The present compound can be produced, for example, by the following Production Processes.

(Production Process A)

Among the present compounds represented by formula (1) (hereinafter referred to as the compound (1)), the present compound represented by formula (1A) can be produced by reacting a compound represented by formula (A1) (hereinafter referred to as the compound (A1)) with a compound represented by formula (A2) (hereinafter referred to as the compound (A2)) in the presence of a base:

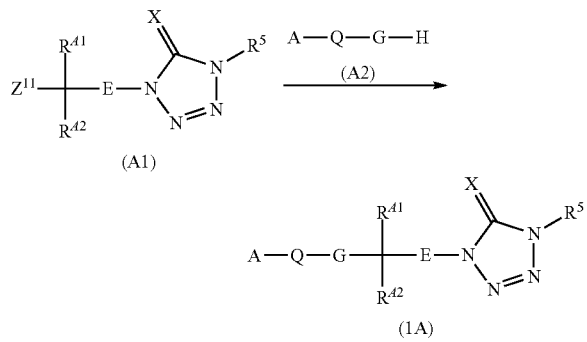

wherein $R^5$, E, A, Q, X, and G are the same as defined above, $Z^{11}$ represents a leaving group such as a chlorine atom, a bromine atom, an iodine atom, a methanesulfonyloxy group, a trifluoromethanesulfonyloxy group, or a p-toluenesulfonyloxy group, and $R^{A1}$ and $R^{A2}$ each represents a hydrogen atom, a halogen atom, or a C1-C3 alkyl group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide and potassium tert-butoxide.

In the reaction, the compound (A2) is usually used in the proportion within a range of 1 to 10 mols, and the base is usually used in the proportion within a range of 0.5 to 5 mols, based on 1 mol of the compound (A1).

The reaction temperature of the reaction is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion of 0.001 to 1.2 mols based on 1 mol of the compound (A1).

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process B)

The compound (1) can be produced by subjecting a compound represented by formula (B1) (hereinafter referred to as the compound (B1)) and a compound represented by formula (B2) (hereinafter referred to as the compound (B2)) to a coupling reaction in the presence of a base and a catalyst:

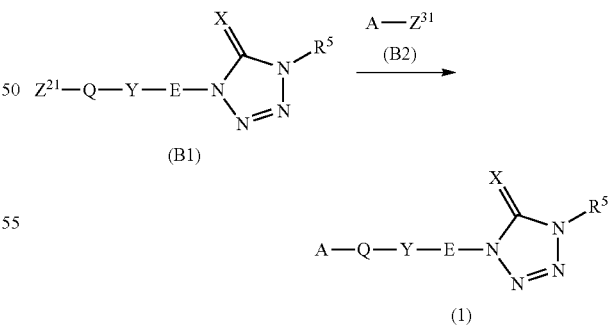

wherein A, Q, Y, E, X, and $R^5$ are the same as defined above, $Z^{21}$ represents a chlorine atom, a bromine atom, or an iodine atom, and $Z^{51}$ represents $B(OH)_2$, an alkoxyboranyl group, or a trifluoroborate ($BF_3^-K^+$).

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; alcohols such as methanol, ethanol, propanol, and butanol; water; and mixtures thereof.

It is possible to usually use, as the compound (B2) to be used in the reaction, commercially available compounds, or compounds produced by a known method mentioned in N. Miyaura and A. Suzuki, Chem. Rev., 1995, 95, 2457. It is possible to produce, as the compound (B2) to be used in the reaction, a boronic acid ester derivative by reacting an iodine compound (A-I) of A, a bromo compound (A-Br) of A, or a chloro compound (A-Cl) of A with an alkyllithium such as butyllithium, followed by a reaction with a boric acid ester. It is possible to produce a boronic acid derivative by optionally hydrolyzing the boronic acid ester derivative obtained by the above-mentioned reaction. It is also possible to produce a trifluoroborate ($BF_3^- K^+$) by fluorinating the boronic acid ester with potassium hydrogen fluoride in accordance with a known method mentioned in Molander et al. Acc. Chem. Res., 2007, 40, 275.

Examples of the catalyst to be used in the reaction include palladium(II) acetate, dichlorobis(triphenylphosphine)palladium, tetrakis(triphenylphosphine)palladium(0), palladium (II) acetate/triscyclohexylphosphine, bis(diphenylphosphinoferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium(II) acetate/dicyclohexyl(2',4',6'-triisopropylbiphenyl-2-yl)phosphine, tris(dibenzylidineacetone)dipalladium, and the like.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; alkali metal alkoxides such as sodium methoxide, sodium ethoxide, sodium tert-butoxide, and potassium tert-butoxide.

In the reaction, the compound (B2) is usually used in the proportion within a range of 1 to 10 mols, the base is usually used in the proportion within a range of 1 to 10 mols, and the catalyst is usually used in the proportion within a range of 0.0001 to 1 mols, based on 1 mol of the compound (B1).

The reaction temperature of the reaction is usually within a range of 0 to 150° C. The reaction time is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process C)

The compound (1) can be produced by subjecting a compound represented by formula (C1) (hereinafter referred to as the compound (C1)) and a compound represented by formula (C2) (hereinafter referred to as the compound (C2)) to a coupling reaction in the presence of a base and a catalyst:

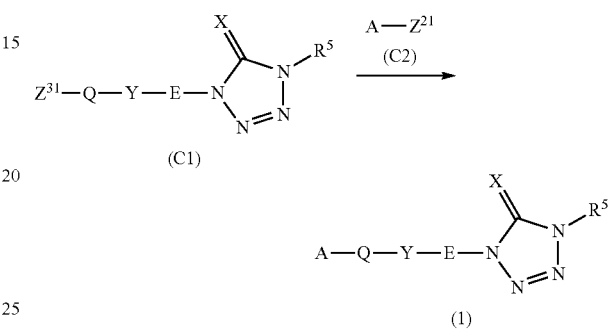

wherein A, Q, Y, E, X, $R^5$, $Z^{21}$, and $Z^{31}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

It is possible to usually use, as the compound (C2) to be used in the reaction, compounds produced by a known method or commercially available compounds.

Examples of the catalyst to be used in the reaction include palladium(II) acetate, dichlorobis(triphenylphosphine)palladium, tetrakis(triphenylphosphine)palladium(0), palladium (II) acetate/triscyclohexylphosphine, bis(diphenylphosphinoferrocenyl)palladium(II) dichloride, 1,3-bis(2,6-diisopropylphenyl)imidazol-2-ylidene(1,4-naphthoquinone) palladium dimer, allyl(chloro) (1,3-dimesityl-1,3-dihydro-2H-imidazol-2-ylidene)palladium or palladium(II) acetate/dicyclohexyl(2',4',6'-triisopropylbiphenyl-2-yl)phosphine, tris(dibenzylidineacetone)dipalladium, and the like.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (C2) is usually used in the proportion within a range of 1 to 10 mols, the base is usually used in the proportion within a range of 1 to 10 mols, and the catalyst is usually used in the proportion within a range of 0.0001 to 1 mols, based on 1 mol of the compound (C1).

The reaction temperature of the reaction is usually within a range of 0 to 150° C. The reaction time is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process D)

The compound (1) can be produced by reacting a compound represented by formula (1-3) (hereinafter referred to as the compound (1-3)) with a compound represented by formula (E1) (hereinafter referred to as the compound (E1)) in the presence of a base:

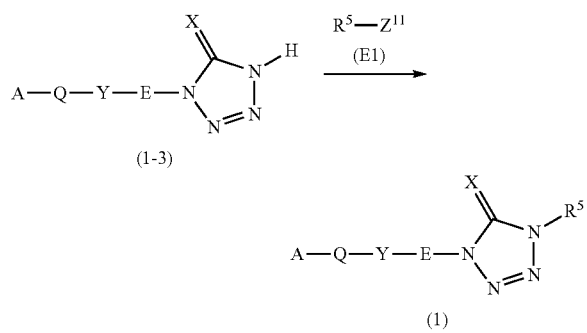

wherein A, Q, Y, E, X, $R^5$, and $Z^{11}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

It is possible to usually use, as the compound (E1) to be used in the reaction, commercially available compounds. Specific examples thereof include halogenated alkyls such as chlorodifluoromethane, methyl bromide, ethyl bromide, propyl bromide, methyl iodide, ethyl iodide, propyl iodide, and 1,1-difluoro-2-iodoethane; dialkyl sulfates such as dimethyl sulfate, diethyl sulfate; and alkyl and arylsulfonic acid esters, such as methyl p-toluenesulfonate, ethyl p-toluenesulfonate, propyl p-toluenesulfonate, methyl methanesulfonate, ethyl methanesulfonate, and propyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal hydrides such as lithium hydride, sodium hydride, and potassium hydride; and alkali metal alkoxides such as sodium tert-butoxide and potassium tert-butoxide.

In the reaction, the compound (E1) is usually used in the proportion within a range of 1 to 10 mols, and the base is usually used in the proportion within a range of 1 to 10 mols, based on 1 mol of the compound (1-3).

The reaction temperature of the reaction is usually within a range of −20 to 150° C. The reaction time is usually within a range of 0.1 to 24 hours.

After completion of the reaction, the compound (1) can be isolated by performing post-treatment operations such as extraction of the reaction mixture with an organic solvent, and drying and concentration of the organic layer. The isolated present compound can be further purified by chromatography, recrystallization, and the like.

(Production Process E)

A compound in which X is a sulfur atom (hereinafter referred to as the compound (1-S)) among the compounds (1) can be produced by reacting a compound in which X is an oxygen atom (hereinafter referred to as the compound (1-O)) among the compounds (1) with a sulfurizing agent:

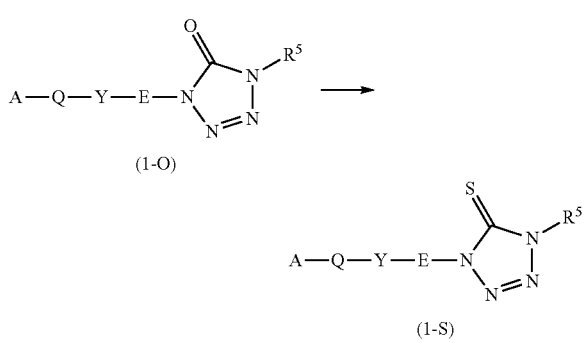

wherein A, Q, Y, E, and $R^5$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile and propionitrile; and mixtures thereof.

Examples of the sulfurizing agent to be used in the reaction include phosphorous pentasulfide and Lawesson's reagent (2,4-Bis(4-methoxyphenyl)-1,3,2,4-dithiadiphosphetane 2,4-disulfide).

In the reaction, the sulfurizing agent is preferably used in the proportion within a range of 0.5 to 1.5 mols based on 1 mol of the compound (1-O).

The reaction temperature of the reaction is usually within a range of −20 to 150° C. The reaction time is usually within a range of 0.1 to 24 hours.

In the reaction, if necessary, organic bases such as pyridine and triethylamine; and inorganic bases such as alkali metal hydroxide and alkali metal carbonate may be added, and the amount of the base to be added is within a range of 0.5 to 1.5 mols based on the compound (1-O).

After completion of the reaction, the compound (1-S) can be isolated by performing post-treatment operations such as extraction of the reaction mixture with an organic solvent, and drying and concentration of the organic layer. The isolated present compound can be further purified by chromatography, recrystallization, and the like.

(Production Process F)

Among the compounds (1), a compound represented by formula (1-4) (hereinafter referred to as the compound (1-4)) can be produced by subjecting a compound represented by formula (G1) (hereinafter referred to as the compound (G1)) and a compound represented by formula (G21) (hereinafter referred to as the compound (G21)) to a coupling reaction in the presence of a base and a catalyst:

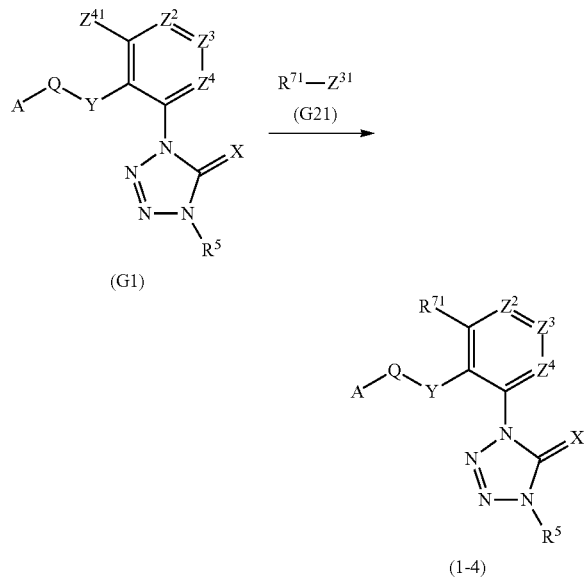

wherein A, Q, Y, X, $R^5$, $Z^2$, $Z^3$, $Z^4$, and $Z^{31}$ are the same as defined above, $Z^{41}$ represents a chlorine atom, a bromine atom, an iodine atom, or a trifluoromethanesulfonyloxy group, $R^{71}$ represents a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C cycloalkyl group, or a C3-C6 halocycloalkyl group, in which at least one of $Z^2$, $Z^3$, and $Z^4$ is a nitrogen atom.

The reaction can be carried out in accordance with Production Process B.

Among the compounds (1), a compound represented by formula (1-5) (hereinafter referred to as the compound (1-5)) can be produced by subjecting a compound represented by formula (G2) (hereinafter referred to as the compound (G2)) and a compound represented by formula (G22) (hereinafter referred to as the compound (G22)) to a coupling reaction in the presence of a base and a catalyst:

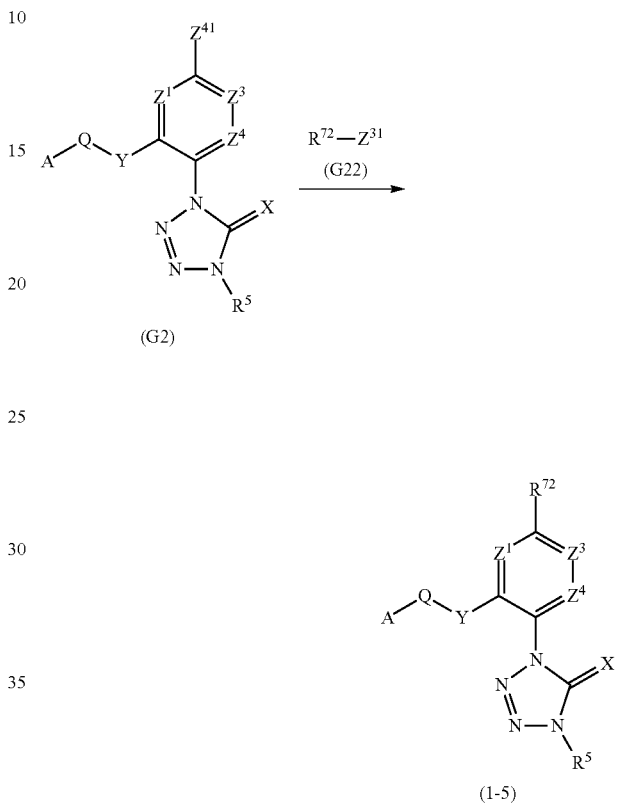

wherein A, Q, Y, X, $R^5$, $Z^1$, $Z^3$, $Z^4$, $Z^{31}$, and $Z^{41}$ are the same as defined above, and $R^{72}$ represents a C1-C3 alkyl group, in which at least one of $Z^1$, $Z^3$, and $Z^4$ is a nitrogen atom.

The reaction can be carried out in accordance with Production Process B.

Among the compounds (1), a compound represented by formula (1-6) (hereinafter referred to as the compound (1-6)) can be produced by subjecting a compound represented by formula (G3) (hereinafter referred to as the compound (G3)) and the compound (G22) to a coupling reaction in the presence of a base and a catalyst:

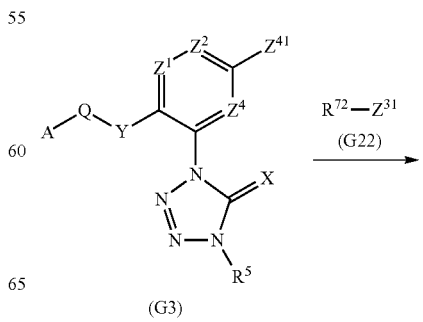

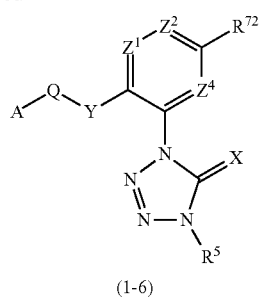

(1-6)

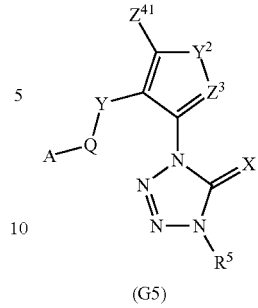

(G5)

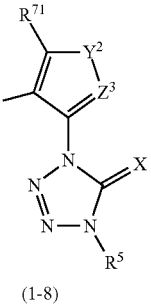

(1-8)

wherein A, Q, Y, X, $R^5$, $R^{72}$, $Z^1$, $Z^2$, $Z^4$, $Z^{31}$, and $Z^{41}$ are the same as defined above, in which at least one of $Z^1$, $Z^2$, and $Z^4$ is a nitrogen atom.

The reaction can be carried out in accordance with Production Process B.

Among the compounds (1), a compound represented by formula (1-7) (hereinafter referred to as the compound (1-7)) can be produced by subjecting a compound represented by formula (G4) (hereinafter referred to as the compound (G4)) and the compound (G22) to a coupling reaction in the presence of a base and a catalyst:

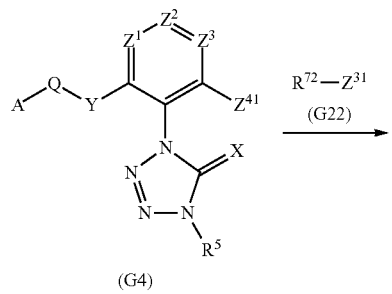

(G4)

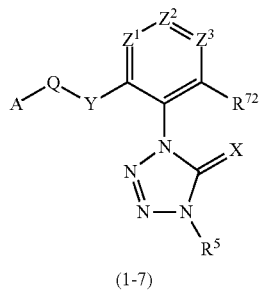

(1-7)

wherein A, Q, Y, X, $R^5$, $R^{72}$, $Z^1$, $Z^2$, $Z^3$, $Z^{31}$, and $Z^{41}$ are the same as defined above, in which at least one of $Z^1$, $Z^2$, and $Z^3$ is a nitrogen atom.

The reaction can be carried out in accordance with Production Process B.

Among the compounds (1), a compound represented by formula (1-8) (hereinafter referred to as the compound (1-8)) can be produced by subjecting a compound represented by formula (G5) (hereinafter referred to as the compound (G5)) and the compound (G21) to a coupling reaction in the presence of a base and a catalyst:

wherein A, Q, Y, $Y^2$, X, $R^5$, $R^{71}$, $Z^3$, $Z^{31}$, and $Z^{41}$, are the same as defined above.

The reaction can be carried out in accordance with Production Process B.

Among the compounds (1), a compound represented by formula (1-9) (hereinafter referred to as the compound (1-9)) can be produced by subjecting a compound represented by formula (G6) (hereinafter referred to as the compound (G6)) and the compound (G22) to a coupling reaction in the presence of a base and a catalyst:

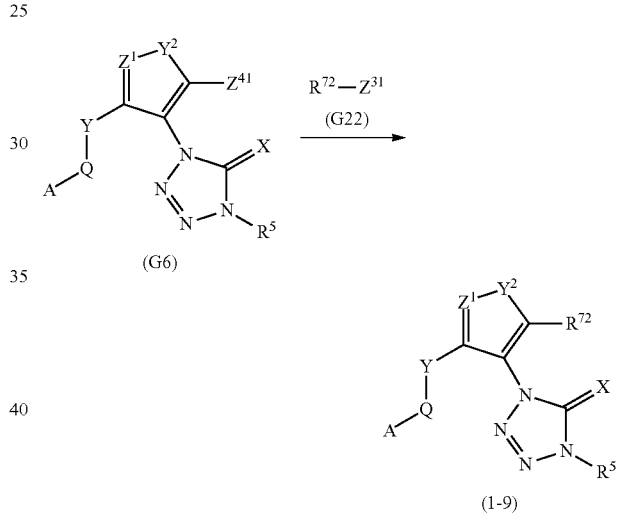

(G6)

(1-9)

wherein A, Q, Y, $Y^2$, X, $R^5$, $R^{72}$, $Z^1$, $Z^{31}$, and $Z^{41}$ are the same as defined above.

The reaction can be carried out in accordance with Production Process B.

Among the compounds (1), a compound represented by formula (1-10) (hereinafter referred to as the compound (1-10)) can be produced by subjecting a compound represented by formula (G7) (hereinafter referred to as the compound (G7)) and the compound (G21) to a coupling reaction in the presence of a base and a catalyst:

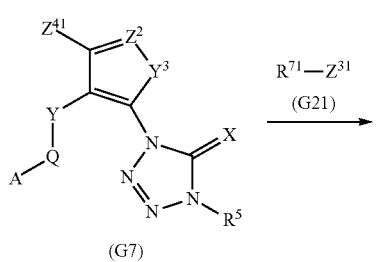

(G7)

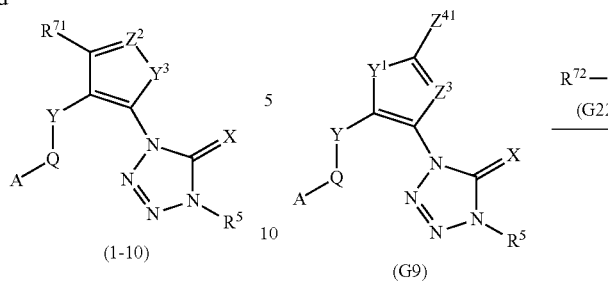

(1-10)

wherein A, Q, Y, $Y^3$, X, $R^5$, $R^{71}$, $Z^2$, $Z^{31}$, and $Z^{41}$ are the same as defined above.

The reaction can be carried out in accordance with Production Process B.

Among the compounds (1), a compound represented by formula (1-11) (hereinafter referred to as the compound (1-11)) can be produced by subjecting a compound represented by formula (G8) (hereinafter referred to as the compound (G8)) and the compound (G22) to a coupling reaction in the presence of a base and a catalyst:

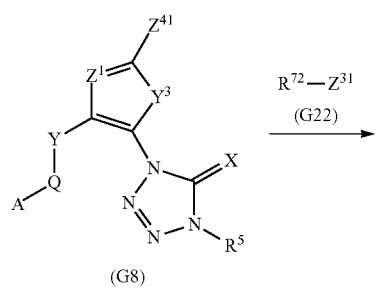

(G8)

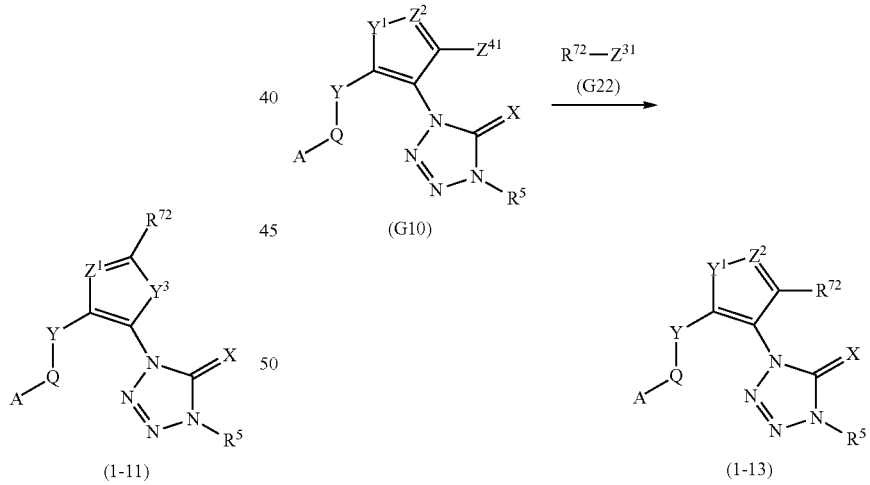

(1-11)

wherein A, Q, Y, $Y^3$, X, $R^5$, $R^{72}$, $Z^1$, $Z^{31}$, and $Z^{41}$ are the same as defined above.

The reaction can be carried out in accordance with Production Process B.

Among the compounds (1), a compound represented by formula (1-12) (hereinafter referred to as the compound (1-12)) can be produced by subjecting a compound represented by formula (G9) (hereinafter referred to as the compound (G9)) and the compound (G22) to a coupling reaction in the presence of a base and a catalyst:

(G9)

(1-12)

wherein A, Q, Y, $Y^1$, X, $R^5$, $R^{72}$, $Z^3$, $Z^{31}$, and $Z^{41}$ are the same as defined above.

The reaction can be carried out in accordance with Production Process B.

Among the compounds (1), a compound represented by formula (1-13) (hereinafter referred to as the compound (1-13)) can be produced by subjecting a compound represented by formula (G10) (hereinafter referred to as the compound (G10)) and the compound (G22) to a coupling reaction in the presence of a base and a catalyst:

(G10)

(1-13)

wherein A, Q, Y, $Y^1$, X, $R^5$, $R^{72}$, $Z^2$, $Z^{31}$, and $Z^{41}$ are the same as defined above.

The reaction can be carried out in accordance with Production Process B.

It is also possible to produce the compound (1) by using other known coupling reactions in place of the coupling reaction of Production Process B.

(Production Process G)

Among the compounds (1), a compound represented by formula (1-H) in which Q is Q46 (hereinafter referred to as the compound (1-H)) can be produced by subjecting a compound represented by formula (H1) (hereinafter referred to as the compound (H1)) and a compound represented by formula (H2) (hereinafter referred to as the compound (H2)) to a coupling reaction in the presence of a base and a catalyst:

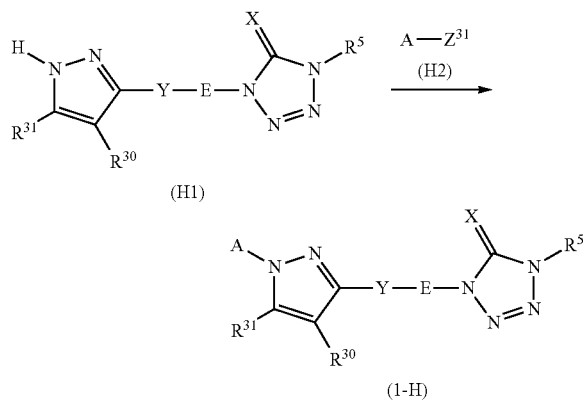

wherein A, Y, E, $R^5$, X, $R^{30}$, $R^{31}$, and $Z^{31}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

It is also possible to usually use, as the compound (H2) to be used in the reaction, commercially available compounds.

Examples of the catalyst to be used in the reaction include copper acetate, copper iodide, copper bromide, copper chloride, palladium(II) acetate, dichlorobis(triphenylphosphine)palladium, tetrakis(triphenylphosphine)palladium(0), palladium(II) acetate/tricyclohexylphosphine, bis(diphenylphosphinoferrocenyl)palladium(II) dichloride, 1,3-bis(2,6-diisopropylphenyl)imidazol-2-ylidene(1,4-naphthoquinone)palladium dimer, allyl(chloro) (1,3-dimesityl-1,3-dihydro-2H-imidazol-2-ylidene)palladium or palladium(II) acetate/dicyclohexyl(2',4',6'-triisopropylbiphenyl-2-yl)phosphine, tris(dibenzylidineacetone)dipalladium, and the like.

Examples of the base to be used in the reaction include organic bases such as pyridine, triethylamine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, the compound (H2) is usually used in the proportion within a range of 1 to 10 mols, the base is usually used in the proportion within a range of 1 to 10 mols, and the catalyst is usually used in the proportion within a range of 0.0001 to 1 mols, based on 1 mol of the compound (H1).

The reaction temperature of the reaction is usually within a range of 0 to 150° C. The reaction time is usually within a range of 0.1 to 24 hours.

After completion of the reaction, the compound (1-H) can be isolated by performing post-treatment operations such as extraction of the reaction mixture with an organic solvent, and drying and concentration of the organic layer. The isolated present compound can be further purified by chromatography, recrystallization, and the like.

The process for synthesizing an intermediate compound for production will be mentioned in detail below.

(Reference Production Process A)

A compound represented by formula (XA3) (hereinafter referred to as the compound (XA3)) can be produced by reacting a compound represented by formula (XA1) (hereinafter referred to as the compound (XA1)) or a compound represented by formula (XA2) (hereinafter referred to as the compound (XA2)) with an azidation agent:

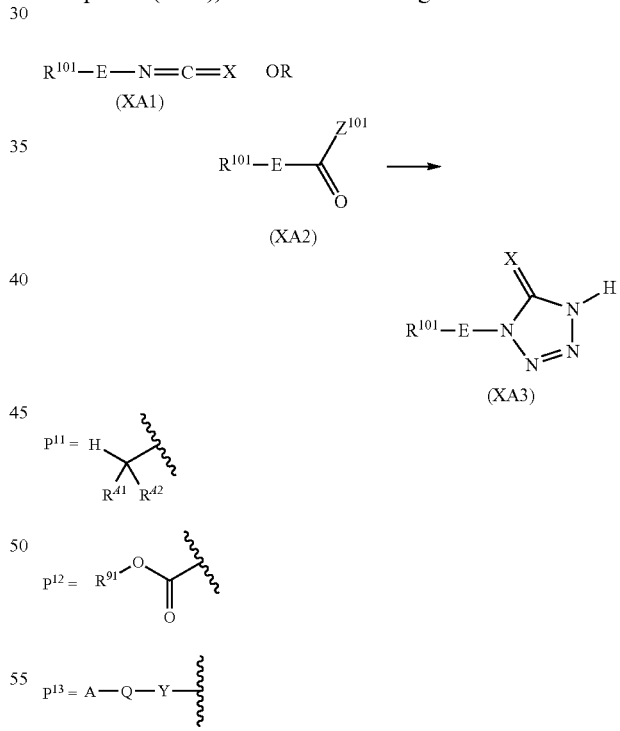

wherein $R^{41}$, $R^{42}$, Y, E, A, Q, and X are the same as defined above, $R^{101}$ represents $P^{11}$, $P^{12}$, or $P^{13}$, $R^{91}$ represents a C1-C12 alkyl group, $Z^{101}$ represents a chlorine atom or a bromine atom, and the wavy line represents a binding site.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is usually used in the proportion within a range of 1 to 10 mols based on 1 mol of the compound (XA1) or the compound (XA2).

The reaction temperature of the reaction is usually within a range of −20 to 150° C. The reaction time is usually within a range of 0.1 to 24 hours.

In the reaction, if necessary, Lewis acid such as aluminum chloride or zinc chloride may be added, and these compounds are usually used in the proportion within a range of 0.05 to 5 mols based on 1 mol of the compound (XA1) or the compound (XA2).

After completion of the reaction, the compound (XA3) can be isolated by performing post-treatment operations such as extraction of the reaction mixture with an organic solvent, and drying and concentration of the organic layer. The isolated compound (XA3) can be further purified by chromatography, recrystallization, and the like.

(Reference Production Process B)

The compound (XA1) can be produced by reacting a compound represented by formula (XB1) (hereinafter referred to as the compound (XB1)) with an isocyanating agent:

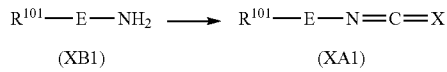

wherein $R^{101}$, E, and X are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; and mixtures thereof.

Examples of the isocyanating agent to be used in the reaction include phosgene, diphosgene, triphosgene, thiophosgene, N,N-carbodiimidazole, and N,N-thiocarbodiimidazole.

In the reaction, the isocyanating agent is usually used in the proportion within a range of 0.34 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compound are usually used in the proportion within a range of 0.05 to 5 mols based on 1 mol of the compound (XB1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process C)

The compound (XA2) can be produced by reacting a compound represented by formula (XC1) (hereinafter referred to as the compound (XC1)) with a halogenating agent:

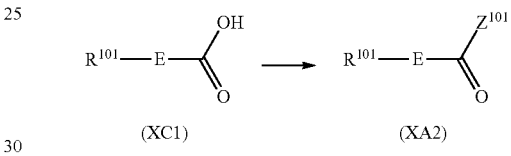

wherein $R^{101}$, E, and $Z^{101}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; and mixtures thereof.

Examples of the halogenating agent to be used in the reaction include phosphorus oxychloride, phosphorus trichloride, phosphorus pentachloride, thionyl chloride, phosphorus oxybromide, phosphorus tribromide, phosphorus pentabromide, phosphorus triiodide, oxalyl dichloride, oxalyl dibromide, triphosgene, diphosgene, phosgene, and sulfuryl chloride.

In the reaction, the halogenating agent is usually used in the proportion within a range of 1 to 10 mols based on 1 mol of the compound (XC1).

The reaction temperature of the reaction is usually within a range of −20 to 150° C. The reaction time is usually within a range of 0.1 to 24 hours.

In the reaction, the catalyst may be added, and dimethylformamide is used. The amount of the catalyst to be used is usually in the proportion within a range of 0.001 to 1 mols based on 1 mol of the compound (XC1).

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be added, and these compound are usually used in the proportion within a range of 0.05 to 5 mols based on 1 mol of the compound (XC1).

After completion of the reaction, the compound (XA2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process D)

The compound (XA1) can be produced by reacting the compound (XB1) with a carbamating agent to obtain a compound represented by formula (XD1) (hereinafter referred to as the compound (XD1)), and then reacting the compound (XD1) with an isocyanating agent:

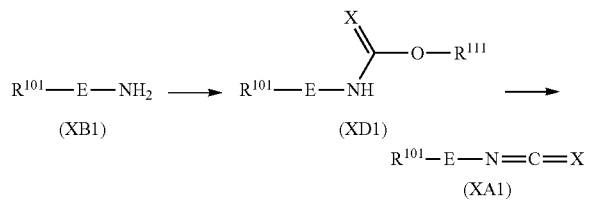

wherein $R^{101}$, E, and X are the same as defined above, and $R^{111}$ represents a C1-C12 alkyl group or a phenyl group.

The process for producing the compound (XD1) from the compound (XB1) will be described below.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the carbamating agent to be used in the reaction include phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, O-phenyl chlorothioformate, O-methyl chlorothioformate, O-ethyl chlorothioformate, and the like.

In the reaction, the carbamating agent is usually used in the proportion within a range of 1 to 10 mols based on 1 mol of the compound (XB1).

The reaction temperature of the reaction is usually within a range of −20 to 150° C. The reaction time is usually within a range of 0.1 to 24 hours.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; and alkali metal hydrogen carbonates such as lithium hydrogen carbonate, sodium hydrogen carbonate, potassium hydrogen carbonate, and cesium hydrogen carbonate may be used, and these compound are usually used in the proportion within a range of 0.05 to 5 mols based on 1 mol of the compound (XB1).

After completion of the reaction, the compound (XD1) can be isolated by performing post-treatment operations such as extraction of the reaction mixture with an organic solvent, and drying and concentration of the organic layer. The isolated compound may be further purified by operations such as distillation, chromatography, and recrystallization.

The process for producing the compound (XA1) from the compound (XD1) will be described below.

The reaction is usually performed in a solvent.

Examples of the solvent to be used in the reaction include ethers such as tetrahydrofuran, dioxane, ethylene glycol dimethyl ether, and methyl tert-butyl ether; aromatic hydrocarbons such as toluene and xylene; halogenated hydrocarbons such as carbon tetrachloride, chloroform or 1,2-dichloroethane, and chlorobenzene; nitriles such as acetonitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

It is possible to use, as the isocyanating agent to be used in the reaction, for example, phosphorus pentachloride, phosphorus oxychloride, diphosphorus pentaoxide, trichlorosilane, dichlorosilane, monochlorosilane, boron trichloride, 2-chloro-1,3,2-benzodioxaborole, diiodosilane, methyltrichlorosilane, dimethyldichlorosilane, chlorotrimethylsilane, and the like.

In the reaction, the isocyanating agent is usually used in the proportion within a range of 1 to 10 mols based on 1 mol of the compound (XD1).

The reaction temperature of the reaction is usually within a range of −20 to 250° C. The reaction time is usually within a range of 0.1 to 24 hours.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate may be added, and these compound are usually used in the proportion within a range of 0.05 to 5 mols based on 1 mol of the compound (XD1).

After completion of the reaction, the compound (XA1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process E)

A compound represented by formula (XB1) can be produced by reacting a compound represented by formula (XE1) (hereinafter referred to as the compound (XE1)) with a catalyst in an excess amount of a hydrogen atmosphere:

wherein $R^{101}$ and E are the same as defined above.

The reaction is usually performed in a solvent.

Examples of the solvent to be used in the reaction include alcohols such as methanol, ethanol, propanol, and butanol; esters such as ethyl acetate and butyl acetate; halogenated hydrocarbons such as carbon tetrachloride, chloroform, dichloromethane, 1,2-dichloroethane, tetrachloroethane, and chlorobenzene; ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; water; and mixtures thereof.

Examples of the catalyst to be used in the reaction include palladium-supported carbon (Pd/C), platinum-supported carbon (Pt/C), osmium-supported carbon (Os/C), ruthenium-supported carbon (Ru/C), rhodium-supported carbon (Rh/C), Raney nickel, and the like.

In the reaction, the catalyst is usually used in the proportion within a range of 0.0001 to 1 mols based on 1 mol of the compound (XE1).

The reaction temperature of the reaction is usually within a range of −20 to 150° C. The reaction time is usually within a range of 0.1 to 24 hours.

After completion of the reaction, the compound (XB1) can be isolated by performing post-treatment operations such as concentration of the organic layer after filtration of the catalyst. The isolated compound may be further purified by operations such as distillation, chromatography, and recrystallization.

(Reference Production Process F)

The compound (XB1) can be produced by reacting the compound (XE1) with a reducing agent in the presence of an acid:

wherein $R^{101}$ and E are the same as defined above.

The reaction is usually performed in a solvent.

Examples of the solvent to be used in the reaction include aliphatic carboxylic acids such as acetic acid; alcohols such as methanol and ethanol; water; and mixtures thereof.

Examples of the reducing agent to be used in the reaction include iron, tin, and zinc.

Examples of the acid to be used in the reaction include hydrochloric acid, sulfuric acid, acetic acid, and an aqueous ammonium chloride solution.

In the reaction, the reducing agent is usually used in the proportion within a range of 1 to 30 mols based on 1 mol of the compound (XE1).

The reaction temperature of the reaction is usually within a range of −20 to 150° C. The reaction time is usually within a range of 0.1 to 24 hours.

After completion of the reaction, the compound (XB1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process G)

A compound represented by formula (XG2) (hereinafter referred to as the compound (XG2)) can be produced by reacting a compound represented by formula (XG1) (hereinafter referred to as the compound (XG1)) with the compound (E1) in the presence of a base:

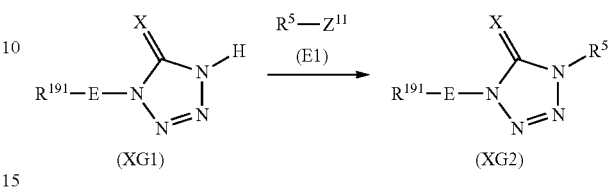

wherein $R^5$, X, and E are the same as defined above, and $R^{191}$ is $P^{11}$ or $P^{12}$.

The reaction can be carried out in accordance with Production Process E.

(Reference Production Process H)

A compound represented by formula (XH2) (hereinafter referred to as the compound (XH2)) can be produced by reacting a compound represented by formula (XH1) (hereinafter referred to as the compound (XH1)) with a halogenating agent:

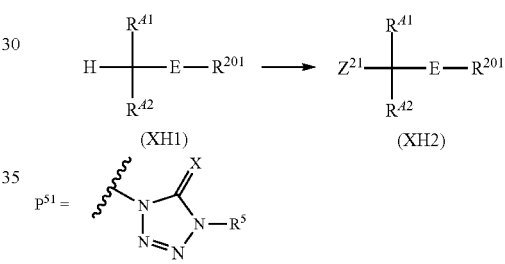

wherein $R^{A1}$, $R^{A2}$, E, $R^5$, $Z^{21}$, and X are the same as defined above, and $R^{201}$ represents $P^{51}$ or a nitro group.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene α,α,α-trifluorotoluene, and α,α,α-trichlorotoluene; esters such as ethyl acetate and methyl acetate; ketones such as acetone, methyl ethyl ketone, and methyl isobutyl ketone; nitriles such as acetonitrile and propionitrile; and mixtures thereof.

Examples of the halogenating agent usable in the reaction include a chlorinating agent, a brominating agent, or an iodinating agent, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonimide, N-bromophthalimide, and the like.

In the reaction, a radical initiator can also be used.

Examples of the radical initiator to be used in the reaction include benzoyl peroxide, azobisisobutyronitrile (AIBN), diacyl peroxide, dialkyl peroxydicarbonate, tert-alkylperoxyester, monoperoxycarbonate, di(tert-alkylperoxy)ketal, and ketone peroxide.

In the reaction, the halogenating agent is usually used in the proportion within a range of 1 to 10 mols, and the radical initiator is usually used in the proportion within a range of 0.01 to 5 mols, based on 1 mol of the compound (XH1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process I)

A compound represented by formula (XJ2) (hereinafter referred to as the compound (XJ2)) can be produced by reacting dimethyl sulfate the compound (XH2) with a compound represented by formula (XJ1) (hereinafter referred to as the compound (XJ1)):

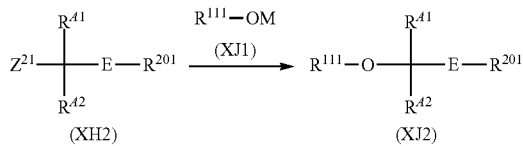

wherein $R^{41}$, $R^{42}$, E, $R^{111}$, $R^{201}$, and $Z^{21}$ are the same as defined above, and M is sodium, potassium, or lithium.

The reaction is usually performed in a solvent.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the compound (XJ1) usable in the reaction include sodium methoxide, sodium ethoxide, sodium propoxide, sodium butoxide, sodium isopropoxide, sodium sec-butoxide, sodium tert-butoxide, potassium methoxide, potassium ethoxide, potassium propoxide, potassium butoxide, potassium isopropoxide, potassium sec-butoxide, potassium tert-butoxide, sodium phenoxide, and the like.

In the reaction, the compound (XJ1) is usually used in the proportion within a range of 1 to 10 mols based on 1 mol of the compound (XH2).

The reaction temperature of the reaction is usually within a range of −20 to 150° C. The reaction time is usually within a range of 0.1 to 24 hours.

After completion of the reaction, the compound (XJ2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process J)

A compound represented by formula (XK1) (hereinafter referred to as the compound (XK1)) can be produced by reacting the compound (XH2) with water in the presence of a base:

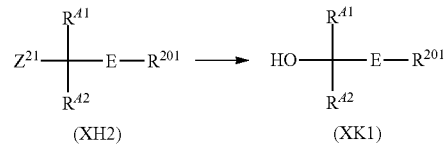

wherein $R^{41}$, $R^{42}$, E, $Z^{21}$, and $R^{201}$ are the same as defined above.

The reaction is usually performed in water, or a solvent containing water.

Examples of the solvent to be used in the reaction include ethers such as diethyl ether, tetrahydrofuran, 1,4-dioxane, ethylene glycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; metal organic acid salts such as lithium formate, lithium acetate, sodium formate, sodium acetate, potassium formate, and potassium acetate; metal nitrates such as silver nitrate and sodium nitrate; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; and alkali metal alkoxides such as sodium methoxide, sodium ethoxide, sodium tert-butoxide, and potassium tert-butoxide.

In the reaction, the base is usually used in the proportion within a range of 1 to 100 mols based on 1 mol of the compound (XH2).

In the reaction, water is usually used in the proportion within a range of 1 mol to large excess based on 1 mol of the compound (XH2).

The reaction temperature of the reaction is usually within a range of −20 to 150° C. The reaction time is usually within a range of 0.1 to 24 hours.

After completion of the reaction, the compound (XK1) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process K)

The compound (XH2) can be produced by reacting the compound (XJ2) with a halogenating agent:

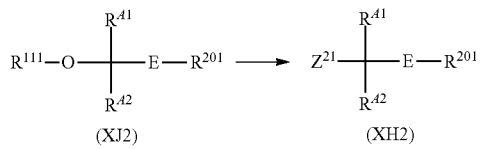

wherein $R^{41}$, $R^{42}$, $R^{111}$, $R^{201}$, E, and $Z^{21}$ are the same as defined above.

The reaction is usually performed in a solvent.

Examples of the solvent to be used in the reaction include hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include hydrochloric acid, hydrobromic acid, and hydroiodic acid.

In the reaction, the halogenating agent is usually used in the proportion of 1 mol or more based on 1 mol of the compound (XJ2).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process L)

The compound (XH2) can be produced by reacting the compound (XK1) with a halogenating agent:

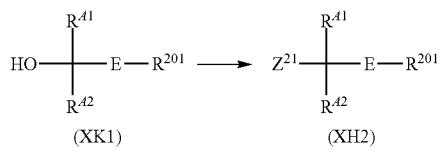

wherein $R^{41}$, $R^{42}$, $R^{201}$, E, and $Z^{21}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; esters such as ethyl acetate and methyl acetate; ketones such as acetone, methyl ethyl ketone, and methyl isobutyl ketone; nitriles such as acetonitrile and propionitrile; organic acids such as formic acid, acetic acid, and trifluoroacetic acid; water; and mixtures thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorus oxychloride, phosphorus trichloride, phosphorus pentachloride, thionyl chloride, phosphorus oxybromide, phosphorus pentabromide, phosphorus triiodide, oxalyl dichloride, oxalyl dibromide, acetyl chloride, carbon tetrabromide, N-bromosuccinimide, lithium chloride, sodium iodide, acetyl bromide, and the like.

In the reaction, the halogenating agent is usually used in the proportion within a range of 1 to 10 mols based on 1 mol of the compound (XK1).

In order to accelerate the reaction, additives may be added according to the halogenating agent to be used, and specific examples thereof include zinc chloride for acetyl chloride, triphenylphosphine for carbon tetrabromide, dimethyl sulfide for N-bromosuccinimide, boron trifluoride diethyl ether complex for sodium iodide, boron trifluoride diethyl ether complex for acetyl bromide, triethylamine and methanesulfonyl chloride for lithium chloride, aluminum chloride for sodium iodide, trimethylsilyl chloride for sodium iodide, and the like. Any additives are usually used in the proportion within a range of 0.01 to 5 mols based on 1 mol of the compound (XK1).

The reaction temperature of the reaction is usually within a range of −20 to 150° C. The reaction time is usually within a range of 0.1 to 24 hours.

After completion of the reaction, the compound (XH2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process M)

A compound represented by formula (XM3) (hereinafter referred to as the compound (XM3)) can be produced by reacting the compound (XK1) with a generally available compound represented by formula (XM2) (hereinafter referred to as the compound (XM2)) in the presence of a base:

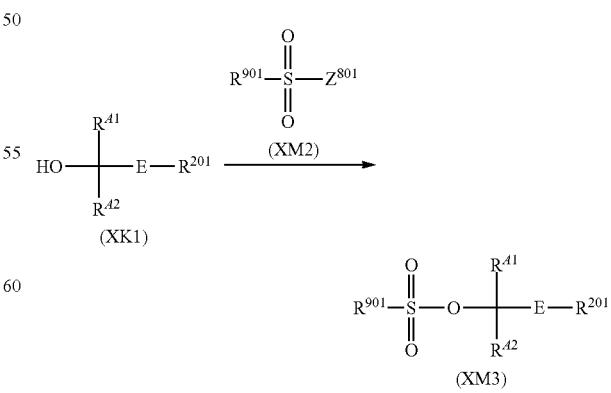

wherein $R^{41}$, $R^{42}$, E, and $R^{201}$ are the same as defined above, $R^{901}$ represents a C1-C6 alkyl group, a C1-C6 haloalkyl group, a C6-C16 aryl group, or a C6-C16 haloaryl group, and $Z^{801}$ represents a fluorine atom, a chlorine atom, a bromine atom, or an iodine atom.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; nitriles such as acetonitrile and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; and mixtures thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; alkali metal hydroxides such as lithium hydroxide, sodium hydroxide, potassium hydroxide, and cesium hydroxide; alkali metal hydrides such as lithium hydride, sodium hydride, and potassium hydride; and alkali metal alkoxides such as sodium methoxide, sodium ethoxide, sodium tert-butoxide, and potassium tert-butoxide.

In the reaction, the compound (XM2) is usually used in the proportion within a range of 1 to 10 mols, and the base is usually in the proportion within a range of 1 to 5 mols, based on 1 mol of the compound (XK1).

The reaction temperature of the reaction is usually within a range of −20 to 150° C. The reaction time is usually within a range of 0.1 to 24 hours.

In the reaction, if necessary, sodium iodide, tetrabutylammonium iodide, and the like may be added, and these compounds are usually used in the proportion within a range of 0.001 to 1.2 mols based on 1 mol of the compound (XK1).

After completion of the reaction, the compound (XM3) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process N)

Among the compounds (1), a compound represented by formula (XN12) (hereinafter referred to as the compound (XN12)) can be produced by subjecting a compound represented by formula (XN11) (hereinafter referred to as the compound (XN11)) and a compound represented by formula (G21) (hereinafter referred to as the compound (G21)) to a coupling reaction in the presence of a base and a catalyst:

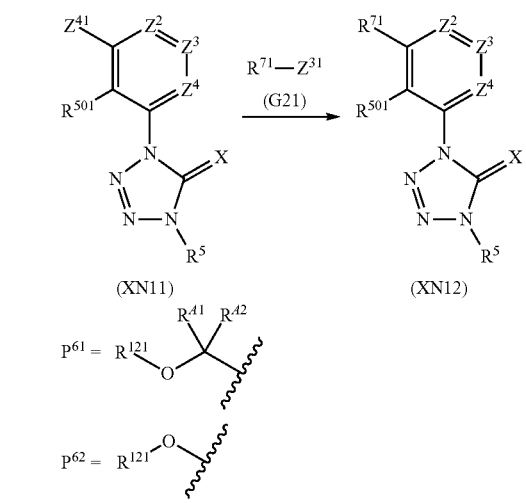

wherein $R^{501}$ represents $P^{11}$, $P^{12}$, $P^{61}$, or $P^{62}$, $R^5$, $R^{71}$, X, $Z^2$, $Z^3$, $Z^4$, $Z^{31}$, and $Z^{41}$ are the same as defined above, and $R^{121}$ represents a C1-C6 alkyl group, a C1-C6 haloalkyl group, a C2-C6 alkylcarbonyl group, a C2-C6 haloalkylcarbonyl group, a C2-C5 alkoxycarbonyl group, a C2-C5 haloalkoxycarbonyl group, a benzyl group, or a benzoyl group (in which the benzyl group or benzoyl group are optionally substituted with a group selected from the group consisting of a C1-C3 alkyl group, a C1-C3 haloalkyl group, a halogen atom, and a nitro group), in which at least one of $Z^2$, $Z^3$, and $Z^4$ is a nitrogen atom.

The reaction can be carried out in accordance with Production Process B.

Among the compounds (1), a compound represented by formula (XN22) (hereinafter referred to as the compound (XN22)) can be produced by subjecting a compound represented by formula (XN21) (hereinafter referred to as the compound (XN21)) and a compound represented by formula (G22) (hereinafter referred to as the compound (G22)) to a coupling reaction in the presence of a base and a catalyst:

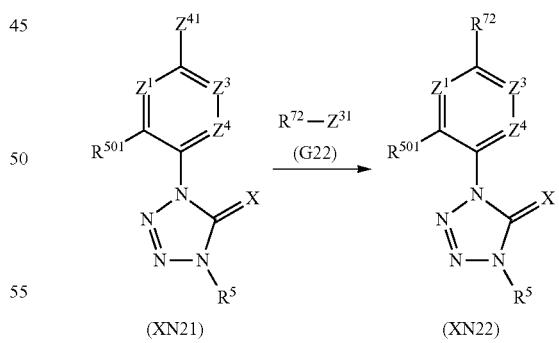

wherein $R^{501}$, X, $R^5$, $Z^1$, $Z^3$, $Z^4$, $Z^{31}$, and $Z^{41}$ are the same as defined above, and $R^{72}$ represents a C1-C3 alkyl group, in which at least one of $Z^1$, $Z^3$, and $Z^4$ is a nitrogen atom.

The reaction can be carried out in accordance with Production Process B.

Among the compounds (1), a compound represented by formula (XN32) (hereinafter referred to as the compound (XN32)) can be produced by subjecting a compound represented by formula (XN31) (hereinafter referred to as the compound (XN31)) and the compound (G22) to a coupling reaction in the presence of a base and a catalyst:

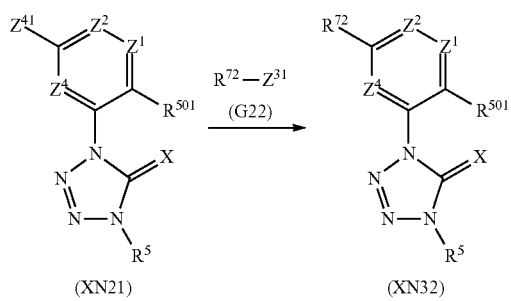

(XN21)    (XN32)

wherein $R^{501}$, X, $R^5$, $R^{72}$, $Z^1$, $Z^2$, $Z^4$, $Z^{31}$ and $Z^{41}$ are the same as defined above, in which at least one of $Z^1$, $Z^2$ and $Z^4$ is a nitrogen atom.

The reaction can be carried out in accordance with Production Process B.

Among the compounds (1), a compound represented by formula (XN42) (hereinafter referred to as the compound (XN42)) can be produced by subjecting a compound represented by formula (XN41) (hereinafter referred to as the compound (XN41)) and the compound (G22) to a coupling reaction in the presence of a base and a catalyst:

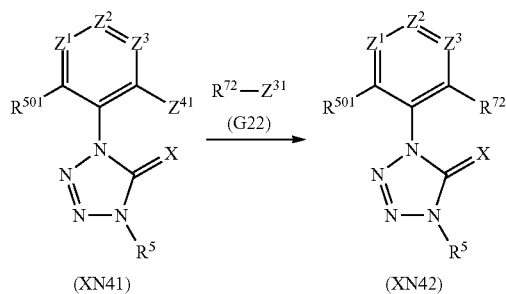

(XN41)    (XN42)

wherein $R^{501}$, X, $R^5$, $R^{72}$, $Z^1$, $Z^2$, $Z^3$, $Z^{31}$, and $Z^{41}$ are the same as defined above, in which at least one of $Z^1$, $Z^2$, and $Z^3$ is a nitrogen atom.

The reaction can be carried out in accordance with Production Process B.

Among the compounds (1), a compound represented by formula (XN52) (hereinafter referred to as the compound (XN52)) can be produced by subjecting a compound represented by formula (XN51) (hereinafter referred to as the compound (XN51)) and the compound (G21) to a coupling reaction in the presence of a base and a catalyst:

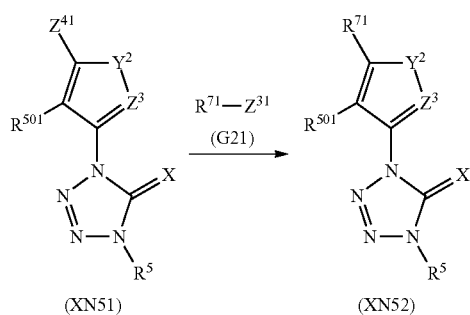

(XN51)    (XN52)

wherein $R^{501}$, $Y^2$, X, $R^5$, $R^{71}$, $Z^3$, $Z^{31}$, and $Z^{41}$ are the same as defined above.

The reaction can be carried out in accordance with Production Process B.

Among the compounds (1), a compound represented by formula (XN62) (hereinafter referred to as the compound (XN62)) can be produced by subjecting a compound represented by formula (XN61) (hereinafter referred to as the compound (XN61)) and the compound (G22) to a coupling reaction in the presence of a base and a catalyst:

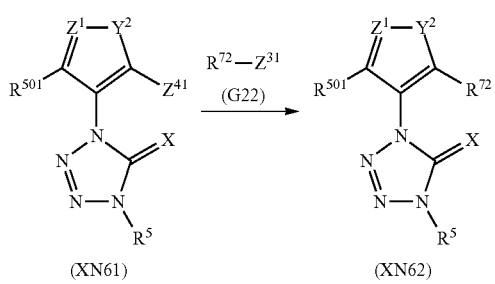

(XN61)    (XN62)

wherein $R^{501}$, $Y^2$, X, $R^5$, $R^{72}$, $Z^1$, $Z^{31}$, and $Z^{41}$ are the same as defined above.

The reaction can be carried out in accordance with Production Process B.

Among the compounds (1), a compound represented by formula (XN72) (hereinafter referred to as the compound (XN72)) can be produced by subjecting a compound represented by formula (XN71) (hereinafter referred to as the compound (XN71)) and the compound (G21) to a coupling reaction in the presence of a base and a catalyst:

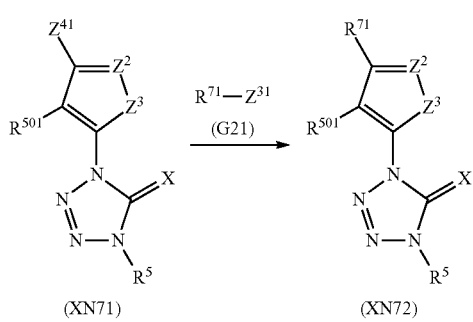

(XN71)    (XN72)

wherein $R^{501}$, $Y^2$, X, $R^5$, $R^{71}$, $Z^2$, $Z^{31}$, and $Z^{41}$ are the same as defined above.

The reaction can be carried out in accordance with Production Process B.

Among the compounds (1), a compound represented by formula (XN82) (hereinafter referred to as the compound (XN82)) can be produced by subjecting a compound represented by formula (XN81) (hereinafter referred to as the compound (XN81)) and the compound (G22) to a coupling reaction in the presence of a base and a catalyst:

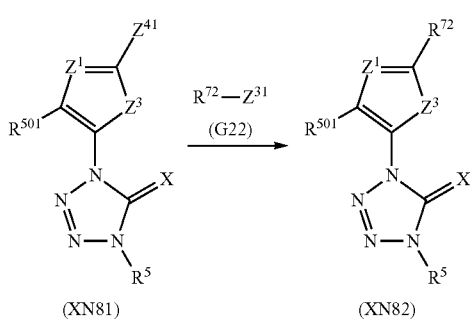

(XN81) → (XN82)

wherein $R^{501}$, $Y^3$, $X$, $R^5$, $R^{72}$, $Z^1$, $Z^{31}$, and $Z^{41}$ are the same as defined above.

The reaction can be carried out in accordance with Production Process B.

Among the compounds (1), a compound represented by formula (XN92) (hereinafter referred to as the compound (XN92)) can be produced by subjecting a compound represented by formula (XN91) (hereinafter referred to as the compound (XN91)) and the compound (G22) to a coupling reaction in the presence of a base and a catalyst:

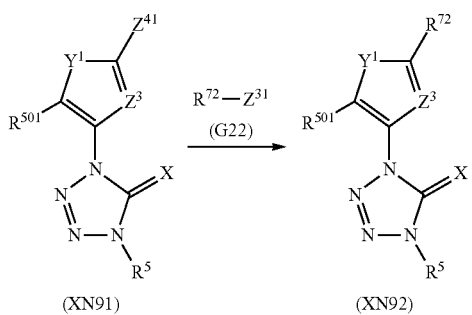

(XN91) → (XN92)

wherein $R^{501}$, $Y^1$, $X$, $R^5$, $R^{72}$, $Z^3$, $Z^{31}$, and $Z^{41}$ are the same as defined above.

The reaction can be carried out in accordance with Production Process B.

Among the compounds (1), a compound represented by formula (XN102) (hereinafter referred to as the compound (XN102)) can be produced by subjecting a compound represented by formula (XN101) (hereinafter referred to as the compound (XN101)) and the compound (G22) to a coupling reaction in the presence of a base and a catalyst:

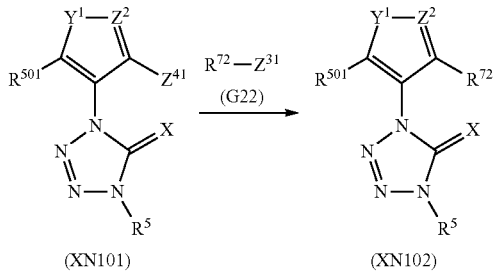

(XN101) → (XN102)

wherein $R^{501}$, $Y^1$, $X$, $R^5$, $R^{72}$, $Z^2$, $Z^{31}$, and $Z^{41}$ are the same as defined above.

The reaction can be carried out in accordance with Production Process B.

Furthermore, it is possible to produce the compound (XN12), the compound (XN32), the compound (XN42), the compound (XN52), the compound (XN62), the compound (XN72), the compound (XN82), the compound (XN92), and the compound (XN102) by using other known coupling reactions in place of the coupling reaction of Production Process N.

(Reference Production Process O)

A compound represented by formula (XW2) (hereinafter referred to as the compound (XW2)) can be produced by reacting a compound represented by formula (XW1) (hereinafter referred to as the compound (XW1)) with a compound represented by formula (XW3) (hereinafter referred to as the compound (XW3)) in the presence of a reaction accelerator:

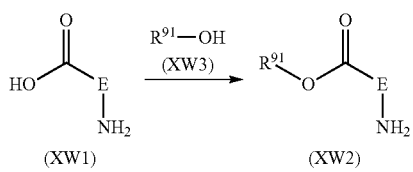

(XW1) → (XW2)

wherein E and $R^{91}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof, and the compound (XW3) may be used as the solvent.

Examples of the compound (XW3) usable in the reaction include methanol, ethanol, propyl alcohol, isopropyl alcohol, n-butyl alcohol, sec-butyl alcohol, t-butanol, n-pentanol, and the like.

Examples of the reaction accelerator to be used in the reaction include mineral acids such as hydrochloric acid and sulfuric acid; carbodiimides such as dicyclohexylcarbodiimide, diisopropylcarbodiimide, and N'-(3-dimethylaminopropyl)-N-ethylcarbodiimide; organic acids such as methanesulfonic acid and toluenesulfonic acid; Mitsunobu reaction reagents such as triphenylphosphine/diethyl azodicarboxylate; thionyl chloride, boron trifluoride-ethyl ether complex, and the like.

In the reaction, based on 1 mol of the compound (XW1), reaction accelerator is usually used in the proportion within a range of 0.01 to 10 mols.

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate may be added, and these compounds are usually used in the proportion within a range of 0.001 to 5 mols based on 1 mol of the compound (XW1).

In the reaction, an excess amount of the compound (XW3) is used based on the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process P)

The compound (XW2) can be produced by reacting the compound (XW1) with a halogenating agent to obtain a compound represented by formula (XV1) (hereinafter referred to as the compound (XV1)), and then reacting the compound (XV1) with the compound (XW3):

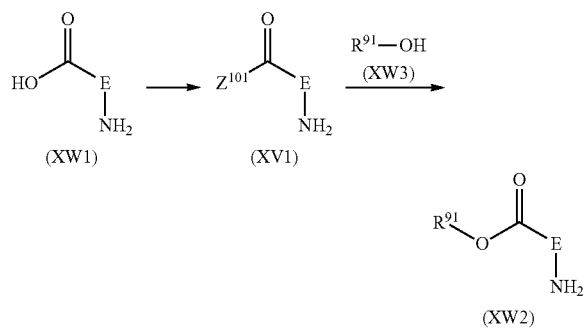

wherein E, $R^{91}$, and $Z^{101}$ are the same as defined above.

The process for producing the compound (XV1) by reacting the compound (XW1) with a halogenating agent can be carried out in accordance with Reference Production Process C.

The process for producing the compound (XW2) from the compound (XV1) will be described below.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; and mixtures thereof, and the compound (XW3) may be used as the solvent.

Examples of the compound (XW3) usable in the reaction include compounds mentioned in Reference Production Process 0.

In the reaction, an excess amount of the compound (XW3) is used based on the compound (XV1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process Q)

The compound (XW2) can be produced by reacting the compound (XW1) with an alkylating agent:

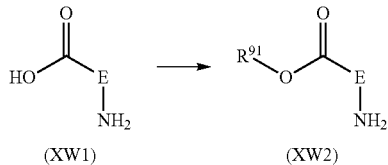

wherein E and $R^{91}$ are the same as defined above.

The reaction is usually performed in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethylene glycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate and methyl acetate; sulfoxides such as dimethyl sulfoxide; ketones such as acetone, methyl ethyl ketone, and methyl isobutyl ketone; nitriles such as acetonitrile and propionitrile; water; and mixtures thereof.

Examples of the alkylating agent usable in the reaction include halogenated alkyls such as diazomethane, trimethylsilyldiazomethane, methyl bromide, ethyl bromide, propyl bromide, methyl iodide, ethyl iodide, and propyl iodide; dialkyl sulfates such as dimethyl sulfate, diethyl sulfate, and dipropyl sulfate; and alkyl or arylsulfonic acid esters, such as methyl p-toluenesulfonate, ethyl p-toluenesulfonate, propyl p-toluenesulfonate, methyl methanesulfonate, ethyl methanesulfonate, and n-propyl methanesulfonate.

In the reaction, the alkylating agent is usually used in the proportion within a range of 1 to 10 mols based on 1 mol of the compound (XW1).

In the reaction, if necessary, organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal hydrogen carbonates such as lithium hydrogen carbonate, sodium hydrogen carbonate, potassium hydrogen carbonate, and cesium hydrogen carbonate; and quaternary ammonium salt such as tetrabutylammonium hydroxide may be added, and these compounds are usually used in the proportion within a range of 0.001 to 5 mols based on 1 mol of the compound (XW1).

The reaction temperature of the reaction is usually within a range of −78 to 100° C. The reaction time is usually within a range of 0.1 to 24 hours.

After completion of the reaction, the compound (XW2) can be isolated by performing post-treatment operations such as extraction of the reaction mixture with an organic solvent, and drying and concentration of the organic layer. The isolated compound may be further purified by operations such as distillation, chromatography, and recrystallization.

(Reference Production Process T)

A compound represented by formula (XS2) (hereinafter referred to as the compound (XS2)) can be produced by reacting a compound represented by formula (XS1) (hereinafter referred to as the compound (XS1)) with the compound (A2) in the presence of a base:

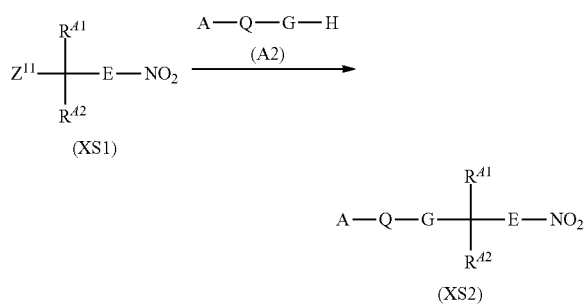

wherein $R^{A1}$, $R^{A2}$, G, E, A, Q, and $Z^{11}$ are the same as defined above.

The reaction can be carried out in accordance with Production Process A.

Although a form used for the present compound may be the present compound as itself, the present compound is usually used after mixing with solid carriers, liquid carriers, surfactants, and the like, and optionally adding auxiliary agents for formulation, such as stickers, dispersers, and stabilizers to thereby formulate into wettable powders, water dispersible granules, flowables, granules, dry flowables, emulsifiable concentrates, aqueous solutions, oil solutions, smoking agents, aerosols, microcapsules, and the like. In these formulations, the present compound is usually contained within a range of 0.1 to 99%, and preferably 0.2 to 90% by weight.

Examples of the solid carriers include clays (for example, kaolin, diatomaceous earth, synthetic hydrated silicon dioxide, Fubasami clay, bentonite, and acid clay), talcs or other inorganic minerals (for example, sericite, quartz powder, sulfur powder, activated charcoal, calcium carbonate, and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene, and methyl naphthalene), aliphatic hydrocarbons (for example, n-hexane, cyclohexanone, and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), and halogenated hydrocarbons (for example, dichloroethane, trichloroethylene, and carbon tetrachloride).

Examples of the surfactants include alkyl sulfates, alkyl sulfonates, alkyl aryl sulfonates, alkyl aryl ethers, and polyoxyethylenated compounds thereof, polyethylene glycol ethers, polyhydric alcohol esters, and sugar alcohol derivatives.

Examples of other auxiliary agents for formulation include stickers and dispersers, specifically casein, gelatin, polysaccharides (for example, starch, gum arabic, cellulose derivatives, and alginic acid), lignin derivatives, bentonite, sugars, water-soluble synthetic polymers (for example, polyvinyl alcohol, polyvinylpyrrolidone, and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or esters thereof, and the like.

The method for applying the present compound is not particularly limited, as long as the applying form is a form by which the present compound may be applied substantially, and includes, for example, an application to plants such as a foliage application; an application to area for cultivating plants such as a submerged treatment; and an application to soil such as seed disinfection.

The present control agent may be used as a mixture with various oils or surfactants such as mineral oils or vegetable oils. Specific examples of oils or surfactants, which can be used as a mixture with various oils or surfactants, include Nimbus (registered trademark), Assist (registered trademark), Aureo (registered trademark), Iharol (registered trademark), Silwet L-77 (registered trademark), BreakThru (registered trademark), SundanceII (registered trademark), Induce (registered trademark), Penetrator (registered trademark), AgriDex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), BANOLE (registered trademark), and the like.

The application amount of the present control agent varies depending on weather conditions, formulation forms, application timing, application method, application place, target diseases, target crops, and the like, and the amount of the present compound in the present control agent is usually within a range of 1 to 500 g, and preferably 2 to 200 g, per 1,000 $m^2$. The emulsifiable concentrates, wettable powders, and suspension formulations are usually applied after dilution with water. In that case, the concentration of the present compound after dilution is usually within a range of 0.0005 to 2% by weight, and preferably 0.005 to 0.1% by weight. The dusts, granules, and the like are usually applied as they are without being diluted. In the treatment for seeds, the application amount is usually within a range of 0.001 to 100 g, and preferably 0.01 to 50 g, in terms of the present compound in the present control agent per 1 kg of seeds.

The present control agent can be used as an agent for controlling plant diseases in agricultural lands such as fields, paddy fields, lawns, and orchards. The present control agent can control diseases occurred in the agricultural lands for cultivating the following "plants".

Also, in another embodiment, for example, the present compound can be administered to the inside (inside of the body) or the outside (body surface) of the above-mentioned vertebrate to thereby exterminate systemically or unsystemically the living things or parasites which are parasitic on the vertebrate. Examples of a method of the internal administration include oral administration, anal administration, transplantation, or administration via injection subcutaneously, intramuscularly or intravenously. Examples of a method of the external administration include transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., and it is desirable in general to administer the present compound so that a dose of the active ingredient (the present compound or salts thereof) is generally within a range of 0.1 mg to 2,000 mg, and preferably 0.5 mg to 1,000 mg, per 1 kg of body weight of the animal.

The present compound can be used as an agent for controlling plant diseases in agricultural lands such as fields, paddy fields, lawns, and orchards. The present compound can control diseases occurred in the agricultural lands for cultivating the following "plants".

Crops: corn, rice, wheat, barley, rye, oat, sorghum, cotton, soybean, peanut, buckwheat, beet, rapeseed, sunflower, sugar cane, tobacco, and the like; Vegetables: solanaceous vegetables (for example, eggplant, tomato, pimento, pepper, and potato), cucurbitaceous vegetables (for example, cucumber, pumpkin, zucchini, water melon, and melon), cruciferous vegetables (for example, Japanese radish, white turnip, horseradish, kohlrabi, Chinese cabbage, cabbage, leaf mustard, broccoli, and cauliflower), asteraceous vegetables (for example, burdock, crown daisy, artichoke, and lettuce), liliaceous vegetables (for example, green onion, onion, garlic, and asparagus), umbelliferous vegetables (for example, carrot, parsley, celery, and parsnip), chenopodiaceous vegetables (for example, spinach and Swiss chard), lamiaceous vegetables (for example, *Perilla frutescens*, mint, and basil), strawberry, sweet potato, *Dioscorea japonica, colocasia,* and the like; Flowers; Ornamental foliage plants;

Fruits: pomaceous fruits (for example, apple, pear, Japanese pear, Chinese quince, and quince), stone fruits (for example, peach, plum, nectarine, *Prunus mume*, cherry fruit, apricot, and prune), citrus fruits (for example, Citrus unshiu, orange, lemon, lime, and grapefruit), nuts (for example, chestnut, walnuts, hazelnuts, almond, pistachio, cashew nuts, and macadamia nuts), berry fruits (for example, blueberry, cranberry, blackberry, and raspberry), grape, persimmon, olive, loquat, banana, coffee, date palm, coconuts, and the like; Trees other than fruit trees: tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir tree, hemlock, juniper, *Pinus, Picea,* and *Taxus cuspidate*); and the like.

The above-mentioned "plants" include genetically modified crops.

The pests which can be controlled by the present compound include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*); Wheat diseases: powdery mildew (*Erysiphe graminis*), fusarium blight (*Fusarium graminearum, F. avenaceum, F. culmorum, Microdochium nivale*), rust (*Puccinia striiformis, P. graminis, P. recondita*), snow mould (*Micronectriella nivale*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), yellow spot (*Pyrenophora tritici-repentis*), damping-off by Rhizoctonia (*Rhizoctonia solani*), and take-all disease (*Gaeumannomyces graminis*); Barley diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia leaf spot (*Ramularia collo-cygni*), and damping-off by Rhizoctonia (*Rhizoctonia solani*); Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum graminicola*), gray leaf spot (*Cercospora zeae-maydis*), eyespot (*Kabatiella zeae*), and *phaeosphaeria* leaf spot (*Phaeosphaeria maydis*); Cotton diseases: anthracnose (*Colletotrichum gossypii*), grey mildew (*Ramularia areola*), and alternaria leaf spot (*Alternaria macrospora, A. gossypii*);

Coffee diseases: rust (*Hemileia vastatrix*); Rapeseed diseases: sclerotinia rot (*Sclerotinia sclerotiorum*), gray leaf spot (*Alternaria brassicae*), and root rot (*Phoma lingam*); Citrus diseases: melanose (*Diaporthe citri*), scab (*Elsinoe fawcetti*), and green mold (*Penicillium digitatum, P. italicum*); Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Glomerella cingulata, Colletotrichum acutatum*); Pear diseases: scab (*Venturia nashicola, V. pirina*), black spot (*Alternaria alternata* Japanese pear pathotype), and rust (*Gymnosporangium haraeanum*); Peach diseases: brown rot (*Monilinia fructicola*), scab (*Cladosporium carpophilum*), and Phomopsis rot (*Phomopsis* sp.); Grapes diseases: anthracnose (*Elsinoe ampelina*), ripe rot (*Glomerella cingulata, Colletotrichum acutatum*), powdery mildew (*Uncinula necator*), rust (*Phakopsora ampelopsidis*), black rot (*Guignardia bidwellii*), and downy mildew (*Plasmopara viticola*); Japanese persimmon diseases: anthracnose (*Gloeosporium kaki*) and leaf spot (*Cercospora kaki, Mycosphaerella nawae*); Diseases of gourd family: anthracnose (*Colletotrichum lagenarium*), powdery mildew (*Sphaerotheca fuliginea*), gummy stem blight (*Didymella bryoniae*), corynespora leaf spot (*Corynespora cassiicola*), fusarium wilt (*Fusarium oxysporum*), downy mildew (*Pseudoperonospora cubensis*), phytophthora rot (*Phytophthora* sp.), and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*); Eggplant diseases: brown spot (*Phomopsis vexans*) and powdery mildew (*Erysiphe cichoracearum*); Cruciferous vegetables diseases: alternaria leaf spot (*Alternaria japonica*), white spot (*Cercosporella brassicae*), clubroot (*Plasmodiophora brassicae*), and downy mildew (*Peronospora parasitica*); Welsh onion diseases: rust (*Puccinia allii*); Soybean diseases: purple stain (*Cercospora kikuchii*), sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), Rhizoctonia rot (*Rhizoctonia solani*), septoria brown spot (*Septoria glycines*), and frog eye leaf spot (*Cercospora sojina*); Kidney bean diseases: anthracnose (*Colletotrichum lindemuthianum*); Peanut diseases: leaf spot (*Cercospora personata*), brown leaf spot (*Cercospora arachidicola*), and southern blight (*Sclerotium* rolfsii); Garden pea diseases: powdery mildew (*Erysiphe pisi*); Potato diseases: early blight (*Alternaria solani*), late blight (*Phytophthora infestans*), and *verticillium* wilt (*Verticillium albo-atrum, V. dahliae, V. nigrescens*); Strawberry diseases: powdery mildew (*Sphaerotheca humuli*); Tea diseases: net blister blight (*Exobasidium reticulatum*), white scab (*Elsinoe leucospila*), gray blight (*Pestalotiopsis* sp.), and anthracnose (*Colletotrichum theae-sinensis*); Tobacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*); Sugar beet diseases: *cercospora* leaf spot (*Cercospora beticola*), leaf blight (*Thanatephorus cucumeris*), root rot (*Thanatephorus cucumeris*), and *aphanomyces* root rot (*Aphanomyces cochlioides*); Rose diseases: black spot (*Diplocarpon rosae*) and powdery mildew (*Sphaerotheca pannosa*); Chrysanthemum diseases: leaf blight (*Septoria chrysanthemi-indici*) and white rust (*Puccinia horiana*); Onion diseases: *botrytis* leaf blight (*Botrytis cinerea, B. byssoidea, B. squamosa*), graymold neck rot (*Botrytis alli*), and small sclerotial rot (*Botrytis squamosa*); various crops diseases: gray mold (*Botrytis cinerea*) and *sclerotinia* rot (*Sclerotinia sclerotiorum*); Japanese radish diseases: *alternaria* leaf spot (*Alternaria brassicicola*); Turfgrass diseases: dollar spot (*Sclerotinia homoeocarpa*) and brown patch and large patch (*Rhizoctonia solani*); and Banana diseases: Sigatoka disease (*Mycosphaerella fijiensis, Mycosphaerella musicola*).

Hemiptera: planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*) and green rice leafhopper (*Nephotettix virescens*); aphids (Aphididae) such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*), and tropical citrus aphid (*Toxoptera citricidus*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), stink bug (*Halyomorpha mista*), and tarnished plant bug (*Lygus lineolaris*); whiteflies (Aleyrodidae) such as greenhouse whitefly (*Trialeurodes vaporariorum*) and silverleaf whitefly (*Bemisia argentifolii*); scales (Coccidae) such as California red scale (*Aonidiella aurantii*), San Jose scale (*Comstockaspis perniciosa*), citrus north scale (*Unaspis citri*), red wax scale (*Ceroplastes rubens*), and cottony cushion scale (*Icerya purchasi*); lace bugs (Tingidae); jumping plant lice (Homoptera, Psylloidea); and bed bugs (*Cimex lectularius*).

Lepidoptera: pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), oriental corn borer (*Ostrinia furnacalis*), cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit *tortrix* (*Adoxophyes orana fasciata*), smaller tea *tortrix* (*Adoxophyes* sp.), oriental tea *tortrix* (*Homona magnanima*), apple *tortrix* (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); leaf miners (Gracillariidae) such as tea leafroller (*Caloptilia theivora*) and apple leafminer (*Phyllonorycter ringoneella*); codling moths (Carposimidae) such as peach fruit moth (*Carposina niponensis*); lyonetiid moths (Lyonetiidae) such as *Lyonetia* spp.; tussock moths (Lymantriidae) such as *Lymantria* spp. and *Euproctis* spp.; yponomeutid moths (Yponomeutidae) such as diamondback (*Plutella xylostella*); gelechild moths (Gelechiidae) such as pink bollworm (*Pectinophora gossypiella*) and potato tubeworm (*Phthorimaea operculella*); tiger moths and allies (Arctiidae) such as fall webworm (*Hyphantria cunea*); and tineid moths (Tineidae) such as casemaking clothes moth (*Tinea translucens*), and webbing clothes moth (*Tineola bisselliella*).

Thysanoptera: thrips such as yellow citrus *thrips* (*Frankliniella occidentalis*), melon *thrips* (*Thrips palmi*), yellow tea *thrips* (*Scirtothrips dorsalis*), onion *thrips* (*Thrips tabaci*), flower *thrips* (*Frankliniella intonsa*), and tobacco *thrips* (*Frankliniella fusca*).

Diptera: houseflies (*Musca domestica*), common mosquito (*Culex pipiens pallens*), horsefly (*Tabanus trigonus*), onion maggot (*Hylemya antiqua*), seedcorn maggot (*Hylemya platura*), *Anopheles sinensis*, rice leafminer (*Agromyza oryzae*), rice leafminer (*Hydrellia griseola*), rice stem maggot (*Chlorops oryzae*), melon fly (*Dacus cucurbitae*), Mediterranean fruit fly (*Ceratitis capitata*), and legume leafminer (*Liriomyza trifolii*).

Coleoptera: twenty-eight-spotted ladybirds (*Epilachna vigintioctopunctata*), cucurbit leaf beetle (*Aulacophora femoralis*), yellow striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*).

Orthoptera: asiatic locusts (*Locusta migratoria*), African mole cricket (*Gryllotalpa africana*), rice grasshopper (*Oxya yezoensis*), and rice grasshopper (*Oxya japonica*).

Hymenoptera: cabbage sawflies (*Athalia rosae*), leafcutting ant (*Acromyrmex* spp.), and fire ant (*Solenopsis* spp.). Nematodes: white-tip nematode (*Aphelenchoides besseyi*), strawberry bud nematode (*Nothotylenchus acris*), soybean cyst nematode (*Heterodera glycines*), southern root-knot nematode (*Meloidogyne incognita*), cobb's root-lesion nematode (*Pratylenchus penetrans*), and false root-knot nematode (*Nacobbus aberrans*).

Blattariae: German cockroach (*Blattella germanica*), smoky-brown cockroach (*Periplaneta fuliginosa*), American cockroach (*Periplaneta americana*), brown cockroach (*Periplaneta brunnea*), and oriental cockroach (*Blatta orientalis*).

Acarina: Tetranychidae (for example, two-spotted spider mite (*Tetranychus urticae*), citrus red mite (*Panonychus* citri), and *Oligonychus* spp.); Eriophyidae (for example, pink citrus rust mite (*Aculops pelekassi*)); Tarsonemidae (for example, broad mite (*Polyphagotarsonemus latus*)); Tenuipalpidae; Tuckerellidae; Tuckerellidae Acaridae (for example, common grain mite (*Tyrophagus putrescentiae*)); Pyroglyphidae (for example, American house dust mite (*Dermatophagoides farinae*) and house dust mite (*Dermatophagoides ptrenyssnus*)); Cheyletidae (for example, cheyletid mite (*Cheyletus eruditus*), *Cheyletus malaccensis*, and *Cheyletus moorei*; and Dermanyssidae.

The formulation comprising the present compound or salts thereof can be used in the field relating to a treatment of livestock diseases or livestock industry, and can exterminate the living things or parasites which are parasitic on the inside and/or the outside of vertebrates such as human being, cow, sheep, pig, poultry, dog, cat, and fish, so as to maintain public health. Examples of the pests include ticks (*Ixodes* spp.) (for example, *Ixodes scapularis*), *Boophilus* spp. (for example, cattle tick (*Boophilus microplus*)), *Amblyomma* spp., *Hyalomma* spp., *Rhipicephalus* spp. (for example, kennel tick (*Rhipicephalus sanguineus*)), *Haemaphysalis* spp. (for example, *Haemaphysalis longicornis*), *Dermacentor* spp., *Ornithodoros* spp. (for example, *Ornithodoros moubata*), red mite (*Dermanyssus gallinae*), ghost ant (*Ornithonyssus sylviarum*), *Sarcoptes* spp. (for example, *Sarcoptes scabiei*), *Psoroptes* spp., *Chorioptes* spp., *Demodex* spp., *Eutrombicula* spp., *Aedes* spp. (for example, Asian tiger mosquito (*Aedes albopictus*)), *Anopheles* spp., *Culex* spp., *Culicoides* spp., *Musca* spp., *Hypoderma* spp., *Gasterophilus* spp., *Haematobia* spp., *Tabanus* spp., *Simulium* spp., *Triatoma* spp., lice (Phthiraptera) (for example, *Damalinia* spp., *Linognathus* spp., *Haematopinus* spp.), *Ctenocephalides* spp. (for example, cat flea (*Ctenocephalides felis*)) *Xenopsylla* spp., Pharaoh's ant (*Monomorium pharaonis*) and nematodes [for example, hairworm (for example, *Nippostrongylus brasiliensis*, *Trichostrongylus axei*, *Trichostrongylus colubriformis*), *Trichinella* spp. (for example, *Trichinella spiralis*), barber pole worm (*Haemonchus contortus*), *Nematodirus* spp. (for example, *Nematodirus battus*), *Ostertagia circumcincta*, *Cooperia* spp., *Hymenolepis nana*, and the like.

EXAMPLES

The present invention will be described in more detail below by way of Production Examples, Formulation Examples, and Test Examples, but the present invention is not limited to these Examples.

First, Production Examples will be described.

Production Example 1

A mixture of 1.10 g of C02A, 1.01 g of 1-(4-chlorophenyl)-1H-pyrazol-3-ol mentioned in Reference Production Example 12, 0.94 g of potassium carbonate, and 15 mL of N,N-dimethylformamide was stirred at 80° C. for 3.5 hours. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.06 g of 1-(1-tert-butyl-5-{[1-(4-chlorophenyl)-1H-pyrazol-3-yl]oxymethyl}-1H-pyrazol-4-yl)-4-methyl-1,4-dihydrotetrazol-5-one (hereinafter referred to as the present compound 1).

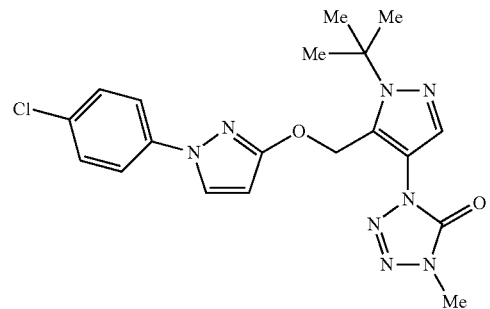 [SMILES: Cn1nnn(-c2cnn(C(C)(C)C)c2COc2ccn(-c3ccc(Cl)cc3)n2)c1=O]

$^1$H-NMR (CDCl$_3$) δ: 7.71 (1H, s), 7.67 (1H, d, J=2.4 Hz), 7.49 (2H, d, J=9.0 Hz), 7.37 (2H, d, J=8.8 Hz), 5.86 (1H, d, J=2.4 Hz), 5.45 (2H, s), 3.60 (3H, s), 1.74 (9H, s).

Production Example 2

A mixture of 0.40 g of C02A, 0.30 g of 4-(1-adamantyl)-2,3-dihydro-2-oxothiazole mentioned in Reference Production Example 16, 0.50 g of cesium carbonate, and 15 mL of N,N-dimethylformamide was stirred at 80° C. for 0.5 hour. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.56 g of 2-{[4-(4,5-dihydro-4-methyl-5-oxo-1H-tetrazol-1-yl)-2-tert-butylpyrazol-3-yl]methyloxy}-4-(1-adamantyl)thiazole (hereinafter referred to as the present compound 2).

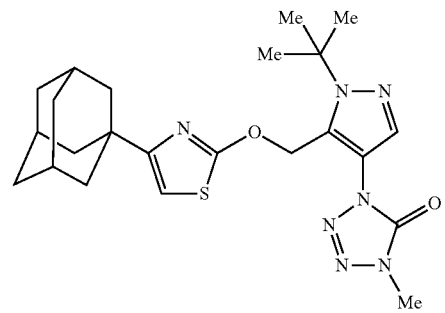 [SMILES: Cn1nnn(-c2cnn(C(C)(C)C)c2COc2nc(C34CC5CC(CC(C5)C3)C4)cs2)c1=O]

$^1$H-NMR (CDCl$_3$) δ: 1.70-1.76 (15H, br m), 1.84 (6H, d, J=2.7 Hz), 2.03-2.06 (3H, m), 3.68 (3H, s), 5.62 (2H, s), 6.17 (1H, s), 7.72 (1H, s).

Production Example 3

A mixture of 0.11 g of C02A, 0.08 g of 4-(4-chlorophenyl)-2,3-dihydro-2-oxothiazole mentioned in Reference Production Example 16, 0.13 g of cesium carbonate, and 10 mL of N,N-dimethylformamide was stirred at 80° C. for 1 hour. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.08 g of 2-(4-chlorophenyl)-4-{[4-(4,5-dihydro- 4-methyl-5-oxo-1H-tetrazol-1-yl)-2-tert-butylpyrazol-3-yl]methyloxy}thiazole (hereinafter referred to as the present compound 3).

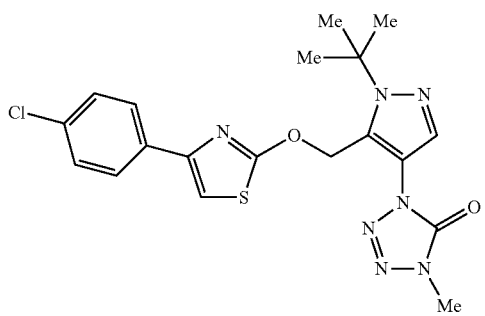 [SMILES: Cn1nnn(-c2cnn(C(C)(C)C)c2COc2nc(-c3ccc(Cl)cc3)cs2)c1=O]

¹H-NMR (CDCl₃) δ: 1.75 (9H, s), 3.56 (3H, s), 5.73 (2H, s), 6.86 (1H, s), 7.35 (2H, d, J=8.3 Hz), 7.68 (2H, d, J=8.3 Hz), 7.73 (1H, s).

Production Example 4

A mixture of 0.30 g of C02A, 0.24 g of 4-(4-bromophenyl)-2,3-dihydro-2-oxothiazole mentioned in Reference Production Example 16, 0.37 g of cesium carbonate, and 10 mL of N,N-dimethylformamide was stirred at 80° C. for 1 hour. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.25 g of 2-(4-bromophenyl)-4-{[4-(4,5-dihydro-4-methyl-5-oxo-1H-tetrazol-1-yl)-2-tert-butylpyrazol-3-yl]methyloxy}thiazole (hereinafter referred to as the present compound 4).

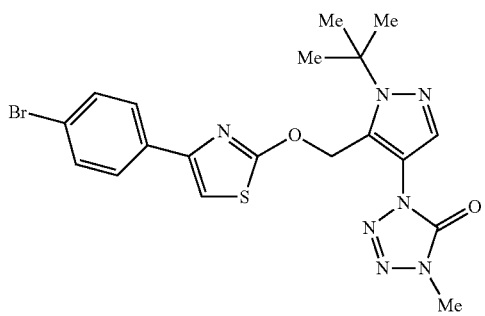

¹H-NMR (CDCl₃) δ: 1.75 (9H, s), 3.57 (3H, s), 5.73 (2H, s), 6.88 (1H, s), 7.52 (2H, d, J=8.5 Hz), 7.63 (2H, d, J=8.5 Hz), 7.73 (1H, s).

Production Example 5

A mixture of 0.30 g of C02A, 0.19 g of 4-(4-fluorophenyl)-2,3-dihydro-2-oxothiazole mentioned in Reference Production Example 16, 0.37 g of cesium carbonate, and 10 mL of N,N-dimethylformamide was stirred at 80° C. for 1.5 hours. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.20 g of 2-(4-fluorophenyl)-4-{[4-(4,5-dihydro-4-methyl-5-oxo-1H-tetrazol-1-yl)-2-tert-butylpyrazol-3-yl]methyloxy}thiazole (hereinafter referred to as the present compound 5).

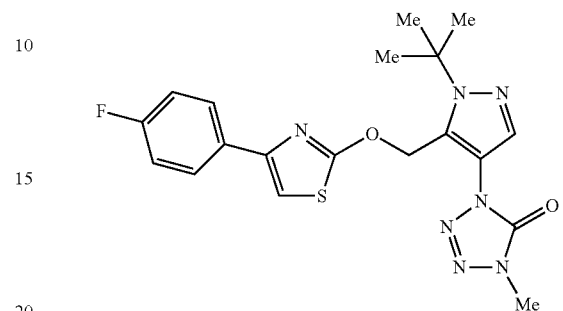

¹H-NMR (CDCl₃) δ: 7.76-7.70 (3H, m), 7.08 (2H, t, J=8.66 Hz), 6.80 (1H, s), 5.73 (2H, s), 3.56 (3H, s), 1.75 (9H, s).

Production Example 6

A mixture of 0.40 g of C05A, 0.29 g of 1-(4-chlorophenyl)-1H-pyrazol-3-ol mentioned in Reference Production Example 12, 0.41 g of potassium carbonate, and 10 mL of acetonitrile was stirred with heating under reflux for 4 hours. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.56 g of 1-(2-{[1-(4-chlorophenyl)-1H-pyrazol-3-yl]oxymethyl}-pyridin-3-yl)-4-methyl-1,4-dihydrotetrazol-5-one (hereinafter referred to as the present compound 6).

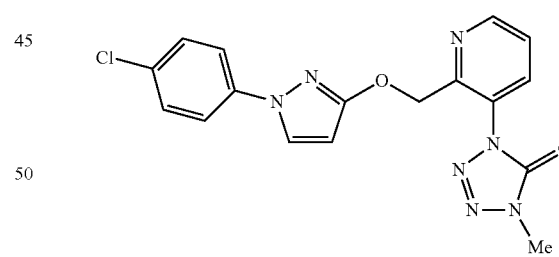

¹H-NMR (CDCl₃) δ: 8.77 (1H, dd, J=4.9, 1.5 Hz), 7.85 (1H, dd, J=8.0, 1.5 Hz), 7.63 (1H, d, J=2.7 Hz), 7.47-7.43 (3H, m), 7.37-7.33 (2H, m), 5.86 (1H, d, J=2.7 Hz), 5.55 (2H, s), 3.66 (3H, s).

Production Example 7

A mixture of 0.20 g of C07A, 0.14 g of 1-(4-chlorophenyl)-1H-pyrazol-3-ol mentioned in Reference Production Example 12, 0.20 g of potassium carbonate, and 10 mL of acetonitrile was stirred with heating under reflux for 2 hours. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.17 g of 1-(2-{[1-(4-chlorophenyl)-1H-pyrazol-3-yl]oxymethyl}-3-thienyl)-4-methyl-1,4-dihydrotetrazol-5-one (hereinafter referred to as the present compound 7).

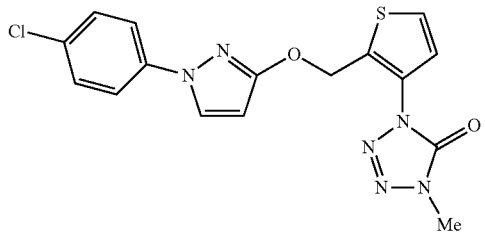 [SMILES: Cn1nnn(-c2ccsc2COc2ccn(-c3ccc(Cl)cc3)n2)c1=O]

$^1$H-NMR (CDCl$_3$) δ: 3.68 (3H, s), 5.57 (2H, s), 5.91 (1H, d, J=2.7 Hz), 7.30 (1H, d, J=5.3 Hz), 7.42-7.35 (3H, m), 7.52 (2H, dd, J=6.8, 2.2 Hz), 7.68 (1H, d, J=2.7 Hz).

Production Example 8

A mixture of 0.25 g of C07A, 0.19 g of 4-(4-chlorophenyl)-2,3-dihydro-2-oxothiazole mentioned in Reference Production Example 16, 0.36 g of cesium carbonate, and 10 mL of N,N-dimethylformamide was stirred at 80° C. for 1.5 hours. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.17 g of 2-(4-chlorophenyl)-4-{[4-(4,5-dihydro-4-methyl-5-oxo-1H-tetrazol-1-yl)-3-thienyl]methyloxy}thiazole (hereinafter referred to as the present compound 8).

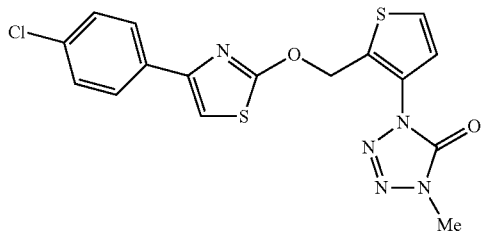

$^1$H-NMR (CDCl$_3$) δ: 3.68 (3H, s), 5.81 (2H, s), 6.87 (1H, s), 7.34 (1H, d, J=5.5 Hz), 7.36 (2H, dd, J=6.6, 1.8 Hz), 7.44 (1H, d, J=5.5 Hz), 7.74 (2H, dd, J=6.6, 1.8 Hz).

Production Example 9

A mixture of 0.20 g of C07A, 0.19 g of 4-(4-bromophenyl)-2,3-dihydro-2-oxothiazole mentioned in Reference Production Example 16, 0.28 g of cesium carbonate, and 10 mL of N,N-dimethylformamide was stirred at 80° C. for 1.5 hours. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.05 g of 2-(4-bromophenyl)-4-{[4-(4,5-dihydro-4-methyl-5-oxo-1H-tetrazol-1-yl)-3-thienyl]methyloxy}thiazole (hereinafter referred to as the present compound 9).

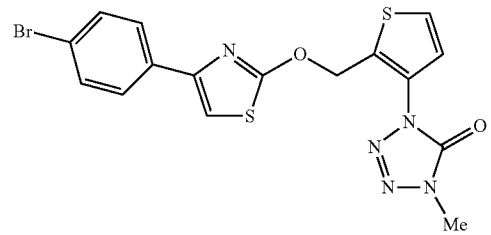 [SMILES: Cn1nnn(-c2ccsc2COc2nc(-c3ccc(Cl)cc3)cs2)c1=O]

$^1$H-NMR (CDCl$_3$) δ: 3.65 (3H, s), 5.18 (2H, s), 5.97 (1H, s), 7.03 (2H, d, J=8.5 Hz), 7.12 (1H, d, J=5.5 Hz), 7.29 (1H, d, J=5.5 Hz), 7.46 (2H, d, J=8.5 Hz).

Production Example 10

A mixture of 0.25 g of C09A, 0.18 g of 1-(4-chlorophenyl)-1H-pyrazol-3-ol mentioned in Reference Production Example 12, 0.15 g of potassium carbonate, and 10 mL of acetonitrile was stirred with heating under reflux for 5 hours. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.21 g of 1-(1-methyl-3-{[1-(4-chlorophenyl)-1H-pyrazol-3-yl]oxymethyl}-1H-pyrazol-4-yl)-4-methyl-1,4-dihydrotetrazol-5-one (hereinafter referred to as the present compound 10).

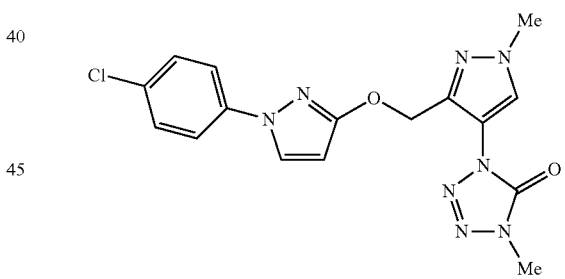

$^1$H-NMR (CDCl$_3$) δ: 7.87 (1H, s), 7.66 (1H, d, J=2.5 Hz), 7.52 (2H, dt, J=9.5, 2.6 Hz), 7.36 (2H, dt, J=9.5, 2.6 Hz), 5.91 (1H, d, J=2.5 Hz), 5.46 (2H, s), 3.97 (3H, s), 3.62 (3H, s).

Production Example 11

A mixture of 0.30 g of C11A, 0.21 g of 1-(4-chlorophenyl)-1H-pyrazol-3-ol mentioned in Reference Production Example 12, 0.18 g of potassium carbonate, and 10 mL of acetonitrile was stirred with heating under reflux for 5 hours. Water was poured into the reaction mixture allowed to cool, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.30 g of 1-(1-methyl-5-{[1-(4-chlorophenyl)-1H-pyrazol-3-yl]oxymethyl}-1H-pyrazol-4-yl)-4-methyl-1,4-dihydrotetrazol-5-one (hereinafter referred to as the present compound 11).

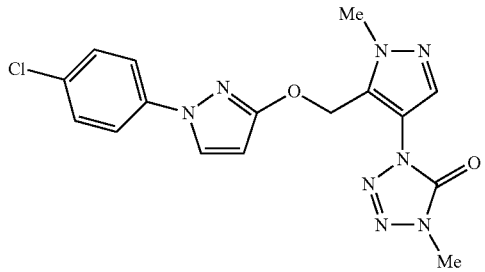 [SMILES: Cn1ncc(-n2nnn(C)c2=O)c1COc1ccn(-c2ccc(Cl)cc2)n1]

1H-NMR (CDCl$_3$) δ: 7.77 (1H, s), 7.67 (1H, d, J=2.5 Hz), 7.46 (2H, dt, J=9.4, 2.5 Hz), 7.37 (2H, dt, J=9.5, 2.5 Hz), 5.88 (1H, d, J=2.5 Hz), 5.46 (2H, s), 4.03 (3H, s), 3.64 (3H, s).

Production Example 12

A mixture of 0.50 g of C02A, 0.36 g of 1-(2-methoxyphenyl)-1H-pyrazol-3-ol mentioned in Reference Production Example 14, 0.26 g of potassium carbonate, and 26 mL of acetonitrile was stirred at 60° C. for 1 hour. To the reaction mixture, a saturated sodium bicarbonate solution was added and the mixture was extracted with ethyl acetate. The organic layer was washed with a saturated sodium bicarbonate solution, dried over anhydrous sodium sulfate, and then concentrated under reduced pressure. The residue thus obtained was subjected to silica gel column chromatography to obtain 0.17 g of 1-(1-tert-butyl-5-{[1-(2-methoxyphenyl)-1H-pyrazol-3-yl]oxymethyl}-1H-pyrazol-4-yl)-4-methyl-1,4-dihydrotetrazol-5-one (hereinafter referred to as the present compound 12).

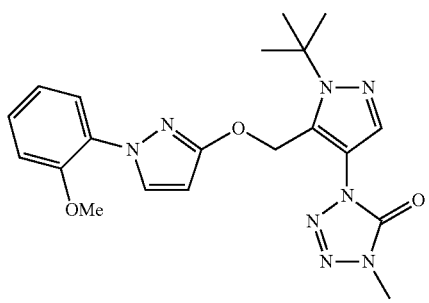 [SMILES: COc1ccccc1-n1ccc(OCc2c(-n3nnn(C)c3=O)cnn2C(C)(C)C)n1]

1H-NMR (CDCl3) δ: 7.90 (1H, d, J=2.1 Hz), 7.71 (1H, s), 7.66 (1H, dd, J=7.9, 1.7 Hz), 7.23 (1H, td, J=7.8, 1.7 Hz), 7.05-7.03 (2H, m), 5.80 (1H, d, J=2.1 Hz), 5.44 (2H, s), 3.89 (3H, s), 3.58 (3H, s), 1.75 (9H, s).

Production Example 13

A mixture of 0.30 g of C11A, 0.25 g of 1-(2-methoxyphenyl)-1H-pyrazol-3-ol mentioned in Reference Production Example 14, 0.18 g of potassium carbonate, and 18 mL of acetonitrile was stirred at 60° C. for 1 hour. To the reaction mixture, a saturated sodium bicarbonate solution was added and the mixture was extracted with ethyl acetate. The organic layer was washed with a saturated sodium bicarbonate solution, dried over anhydrous sodium sulfate, and then concentrated under reduced pressure. The residue thus obtained was subjected to silica gel column chromatography to obtain 0.13 g of 1-(1-methyl-5-{[1-(2-methoxyphenyl)-1H-pyrazol-3-yl]oxymethyl}-1H-pyrazol-4-yl)-4-methyl-1,4-dihydrotetrazol-5-one (hereinafter referred to as the present compound 13).

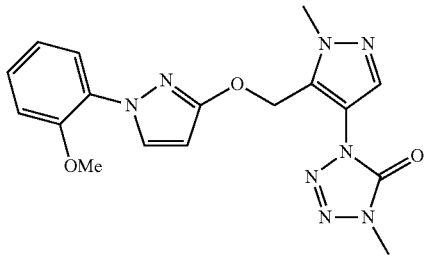 [SMILES: COc1ccccc1-n1ccc(OCc2c(-n3nnn(C)c3=O)cnn2C)n1]

1H-NMR (CDCl3) δ: 7.87 (1H, d, J=2.5 Hz), 7.76 (1H, s), 7.59 (1H, dd, J=7.8, 1.7 Hz), 7.23 (1H, ddd, J=8.8, 7.0, 1.2 Hz), 7.06-7.00 (2H, m), 5.81 (1H, d, J=2.7 Hz), 5.45 (2H, s), 4.03 (3H, s), 3.88 (3H, s), 3.61 (3H, s).

Production Example 14

A mixture of 0.50 g of C02A, 0.38 g of 4-(5-chloro-1,4-dimethyl-1H-pyrazol-3-yl)-2-methyl-phenol mentioned in Reference Production Example 21, 0.26 g of potassium carbonate, and 26 mL of N,N-dimethylformamide was stirred at 60° C. for 1 hour. To the reaction mixture, a saturated sodium bicarbonate solution was added and the mixture was extracted with ethyl acetate. The organic layer was washed with a saturated sodium bicarbonate solution, dried over anhydrous sodium sulfate, and then concentrated under reduced pressure. The residue thus obtained was subjected to silica gel column chromatography to obtain 0.25 g of 1-(1-tert-butyl-5-[2-methyl-4-(5-chloro-1,4-dimethyl-1H-pyrazol-3-yl)-phenoxymethyl]-1H-pyrazol-4-yl)-4-methyl-1,4-dihydrotetrazol-5-one (hereinafter referred to as the present compound 14).

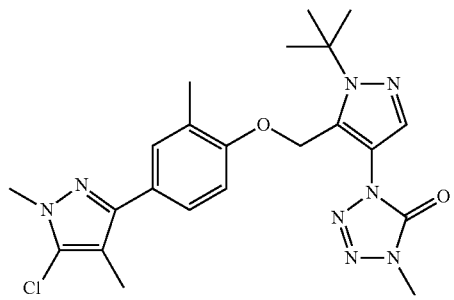 [SMILES: Cc1cc(-c2nn(C)c(Cl)c2C)ccc1OCc1c(-n2nnn(C)c2=O)cnn1C(C)(C)C]

1H-NMR (CDCl3) δ: 7.74 (1H, s), 7.44 (1H, s), 7.39 (1H, d, J=8.2 Hz), 6.88 (1H, d, J=8.5 Hz), 5.16 (2H, s), 3.86 (3H, s), 3.65 (3H, s), 2.18 (3H, s), 2.15 (3H, s), 1.74 (9H, s).

Production Example 15

A mixture of 0.30 g of C11A, 0.26 g of 4-(5-chloro-1,4-dimethyl-1H-pyrazol-3-yl)-2-methyl-phenol mentioned in Reference Production Example 22, 0.18 g of potassium carbonate, and 18 mL of N,N-dimethylformamide was stirred at 60° C. for 1 hour. To the reaction mixture, a saturated sodium bicarbonate solution was added and the mixture was extracted with ethyl acetate. The organic layer was washed with a saturated sodium bicarbonate solution, dried over anhydrous sodium sulfate, and then concentrated under reduced pressure. The residue thus obtained was subjected to silica gel column chromatography to obtain 0.39 g of 1-(1-methyl-5-[2-methyl-4-(5-chloro-1,4-dimethyl-1H-pyrazol-3-yl)-phenoxymethyl]-1H-pyrazol-4-yl)-4-methyl-1,4-dihydrotetrazol-5-one (hereinafter referred to as the present compound 15).

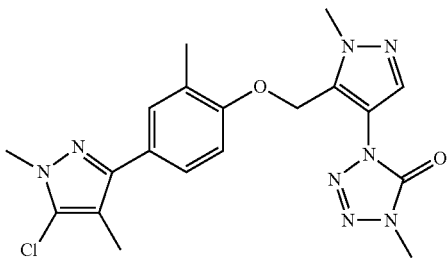 [SMILES: Cc1cc(-c2nn(C)c(Cl)c2C)ccc1OCc1c(-n2nnn(C)c2=O)cnn1C]

1H-NMR (CDCl3) δ: 7.80 (1H, s), 7.45 (1H, s), 7.40 (1H, dd, J=8.5, 2.1 Hz), 6.92 (1H, d, J=8.5 Hz), 5.20 (2H, s), 4.02 (3H, s), 3.86 (3H, s), 3.69 (3H, s), 2.21 (3H, s), 2.15 (3H, s).

Production Example 16

A mixture of 0.47 g of C05A, 0.41 g of 4-(5-chloro-1,4-dimethyl-1H-pyrazol-3-yl)-2-methyl-phenol mentioned in Reference Production Example 22, 0.29 g of potassium carbonate, and 28 mL of N,N-dimethylformamide was stirred at 60° C. for 1 hour. To the reaction mixture, a saturated sodium bicarbonate solution was added and the mixture was extracted with ethyl acetate. The organic layer was washed with a saturated sodium bicarbonate solution, dried over anhydrous sodium sulfate, and then concentrated under reduced pressure. The residue thus obtained was subjected to silica gel column chromatography to obtain 0.25 g of 1-(2-[2-methyl-4-(5-chloro-1,4-dimethyl-1H-pyrazol-3-yl)-phenoxymethyl]-pyridin-3-yl)-4-methyl-1,4-dihydrotetrazol-5-one (hereinafter referred to as the present compound 16).

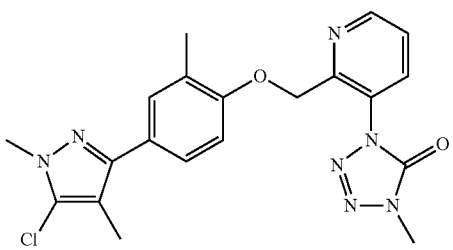 [SMILES: Cc1cc(-c2nn(C)c(Cl)c2C)ccc1OCc1ncccc1-n1nnn(C)c1=O]

1H-NMR (CDCl3) δ: 8.75 (1H, dd, J=4.8, 1.6 Hz), 7.87 (1H, dd, J=8.0, 1.6 Hz), 7.49 (1H, dd, J=8.0, 4.8 Hz), 7.38 (1H, d, J=1.4 Hz), 7.33 (1H, dd, J=8.5, 1.8 Hz), 6.88 (1H, d, J=8.5 Hz), 5.46 (2H, s), 3.84 (3H, s), 3.62 (3H, s), 2.13 (3H, s), 2.02 (3H, s).

Reference Production Example 1

A mixture of 9.50 g of 1-tert-butyl-5-methyl-1H-pyrazole-4-carboxylic acid, 7.28 g of oxalyl dichloride, about 75 mg of N,N-dimethylformamide, and 200 mL of tetrahydrofuran was stirred at 25° C. for 1 hour. The reaction mixture was concentrated under reduced pressure to obtain 1-tert-butyl-5-methyl-1H-pyrazole-4-carboxylic acid chloride. A mixture of 13.90 g of aluminum chloride, 20.34 g of sodium azide, and 100 mL of tetrahydrofuran was stirred with heating under reflux for 2 hours. After ice cooling of the reaction mixture, a mixture of 1-tert-butyl-5-methyl-1H-pyrazole-4-carboxylic acid chloride and 100 mL of tetrahydrofuran was added to the reaction mixture, followed by stirring with heating under reflux for 3 days. After cooling, the reaction mixture was added in a mixture of 31.29 g of sodium nitrite and 100 mL of water while stirring. The mixture was acidified with concentrated hydrochloric acid and then extracted with ethyl acetate. The organic layer was dried over anhydrous sodium sulfate, and then concentrated under reduced pressure to obtain 13.40 g of 1-(1-tert-butyl-5-methyl-1H-pyrazol-4-yl)-1,4-dihydrotetrazol-5-one.

A mixture of 1-(1-tert-butyl-5-methyl-1H-pyrazol-4-yl)-1,4-dihydrotetrazol-5-one, 23.78 g of potassium carbonate, 7.89 g of dimethyl sulfate, and 100 mL of N,N-dimethylformamide was stirred at 25° C. for 1 hour. A saturated sodium bicarbonate solution was poured into the reaction mixture, and the mixture was extracted with ethyl acetate. The organic layer was washed with a saturated sodium bicarbonate solution, dried over anhydrous sodium sulfate, and then concentrated under reduced pressure to obtain 8.85 g of 1-(1-tert-butyl-5-methyl-1H-pyrazol-4-yl)-4-methyl-1,4-dihydrotetrazol-5-one (referred to as C01A).

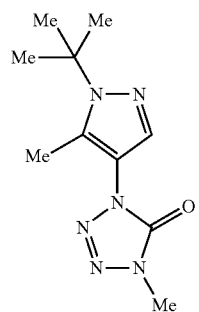

1H-NMR (CDCl3) δ: 7.58 (1H, s), 3.70 (3H, s), 2.40 (3H, s), 1.68 (9H, s).

Reference Production Example 2

A mixture of 1.00 g of C01A, 0.41 g of 1,1'-azobis(cyclohexane-1-carbonitrile), 0.87 g of N-bromosuccinimide, and 30 mL of chlorobenzene was stirred with heating under reflux for 3 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.10 g of 1-(1-tert-butyl-5-bromomethyl-1H-pyrazol-4-yl)-4-methyl-1,4-dihydrotetrazol-5-one (referred to as C02A).

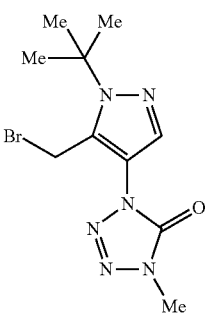

$^1$H-NMR (CDCl$_3$) δ: 7.73 (1H, s), 4.81 (2H, s), 3.72 (3H, s), 1.75 (9H, s).

Reference Production Example 3

A mixture of 5.00 g of 2-methylpyridine-3-carboxylic acid, 3.42 g of oxalyl dichloride, about 75 mg of N,N-dimethylformamide, and 200 mL of tetrahydrofuran was stirred at 25° C. for 1 hour. The reaction mixture was concentrated under reduced pressure to obtain 2-methylpyridine-3-carboxylic acid chloride. A mixture of 6.53 g of aluminum chloride, 9.55 g of sodium azide, and 100 mL of tetrahydrofuran was stirred with heating under reflux for 2 hours. After ice cooling of the reaction mixture, a mixture of 2-methylpyridine-3-carboxylic acid chloride and 100 mL of tetrahydrofuran was added to the reaction mixture, followed by stirring with heating under reflux for 2 days. After cooling, the reaction mixture was added in a mixture of 14.07 g of sodium nitrite and 100 mL of water while stirring. The mixture was acidified with concentrated hydrochloric acid and then extracted with ethyl acetate. The organic layer was dried over anhydrous sodium sulfate and then concentrated under reduced pressure to obtain 3.00 g of 1-(2-methylpyridin-3-yl)-1,4-dihydrotetrazol-5-one (referred to as C03A).

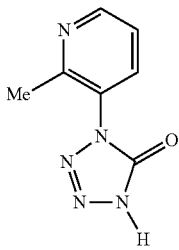 [SMILES: Cc1ncccc1-n1nn[nH]c1=O]

$^1$H-NMR (DMSO-D$_6$) δ: 8.65 (1H, dd, J=4.8, 1.4 Hz), 7.95 (1H, dd, J=8.0, 1.7 Hz), 7.50 (1H, dd, J=8.0, 4.8 Hz), 2.44 (3H, s).

Reference Production Example 4

A mixture of 0.50 g of C03A, 1.29 g of potassium carbonate, 0.43 g of dimethyl sulfate, and 15 mL of N,N-dimethylformamide was stirred at 25° C. for 1 hour. A saturated sodium bicarbonate solution was poured into the reaction mixture, and the mixture was extracted with ethyl acetate. The organic layer was washed with a saturated sodium bicarbonate solution, dried over anhydrous sodium sulfate, concentrated under reduced pressure, and then subjected to silica gel column chromatography to obtain 0.27 g of 1-(2-methylpyridin-3-yl)-4-methyl-1,4-dihydrotetrazol-5-one (referred to as C04A).

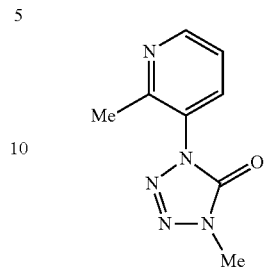

$^1$H-NMR (CDCl$_3$) δ: 8.64 (1H, dd, J=4.9, 1.6 Hz), 7.71 (1H, dd, J=8.0, 1.6 Hz), 7.32 (1H, dd, J=8.0, 4.9 Hz), 3.74 (3H, s), 2.56 (3H, s).

Reference Production Example 5

A mixture of 1.00 g of C04A, 0.51 g of 1,1'-azobis(cyclohexane-1-carbonitrile), 1.07 g of N-bromosuccinimide, and 10 mL of chlorobenzene was stirred with heating under reflux for 5 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.23 g of 1-(2-bromomethyl-pyridin-3-yl)-4-methyl-1,4-dihydrotetrazol-5-one (referred to as C05A).

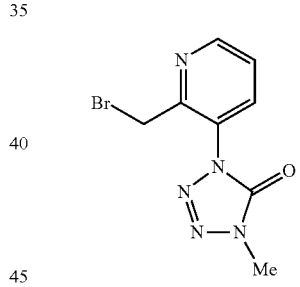

$^1$H-NMR (CDCl$_3$) δ: 8.69 (1H, dd, J=4.8, 1.5 Hz), 7.85 (1H, dd, J=8.1, 1.5 Hz), 7.46 (1H, dd, J=8.1, 4.8 Hz), 4.75 (2H, s), 3.76 (3H, s).

Reference Production Example 6

A mixture of 3.70 g of 2-methyl-3-thienylcarboxylic acid, 3.63 g of oxalyl dichloride, about 15 mg of N,N-dimethylformamide, and 50 mL of tetrahydrofuran was stirred at 25° C. for 1 hour. The reaction mixture was concentrated under reduced pressure to obtain 2-methyl-3-thienylcarboxylic acid chloride. A mixture of 10.15 g of aluminum chloride, 4.18 g of sodium azide, and 20 mL of tetrahydrofuran was stirred with heating under reflux for 2 hours. After ice cooling of the reaction mixture, a mixture of 2-methyl-3-thienylcarboxylic acid chloride and 20 mL of tetrahydrofuran was added to the reaction mixture, followed by stirring with heating under reflux for 10 hours. After cooling, the reaction mixture was added in a mixture of 15.62 g of sodium nitrite and 20 mL of water while stirring. The mixture was acidified with concentrated hydrochloric acid and then extracted with ethyl acetate. The organic layer was dried over anhydrous sodium sulfate and then concentrated under reduced pressure to obtain 1-(2-methyl-3-thienyl)-1,4-dihydrotetrazol-5-one.

A mixture of the entire amount of 1-(2-methyl-3-thienyl)-1,4-dihydrotetrazol-5-one, 11.87 g of potassium carbonate, 3.94 g of dimethyl sulfate, and 20 mL of N,N-dimethylformamide was stirred at 25° C. for 1 hour. A saturated sodium bicarbonate solution was poured into the reaction mixture, and the mixture was extracted with ethyl acetate. The organic layer was washed with a saturated sodium bicarbonate solution, and then dried over anhydrous sodium sulfate. After concentration under reduced pressure, the residue thus obtained was subjected to silica gel column chromatography to obtain 2.64 g of 1-(2-methyl-3-thienyl)-4-methyl-1,4-dihydrotetrazol-5-one (referred to as C06A).

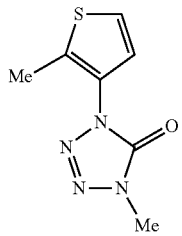

$^1$H-NMR (CDCl$_3$) δ: 2.47 (3H, s), 3.71 (3H, s), 7.13 (1H, d, J 5.5 Hz), 7.17 (1H, d, J=5.5 Hz).

Reference Production Example 7

A mixture of 0.30 g of C06A, 0.15 g of 1,1'-azobis(cyclohexane-1-carbonitrile), 0.31 g of N-bromosuccinimide, and 5 mL of chlorobenzene was stirred with heating under reflux for 5 hours. After cooling, water was poured into the reaction solution, and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.23 g of 1-(2-bromomethyl-3-thienyl)-4-methyl-1,4-dihydrotetrazol-5-one (referred to as C07A).

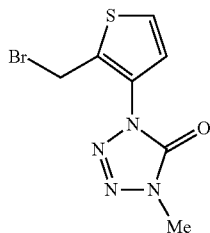 [SMILES: Cn1nnn(-c2ccsc2CBr)c1=O]

$^1$H-NMR (CDCl$_3$) δ: 3.72 (3H, s), 4.86 (2H, s), 7.32 (1H, d, J 5.6 Hz), 7.40 (1H, d, J=5.6 Hz).

Reference Production Example 8

A mixture of 1.30 g of 1,3-dimethyl-1H-pyrazole-4-carboxylic acid, 1.00 g of oxalyl dichloride, about 15 mg of N,N-dimethylformamide, and 50 mL of tetrahydrofuran was stirred at 25° C. for 1 hour. The reaction mixture was concentrated under reduced pressure to obtain 1,3-dimethyl-1H-pyrazole-4-carboxylic acid chloride. A mixture of 1.90 g of aluminum chloride, 2.78 g of sodium azide, and 50 mL of tetrahydrofuran was stirred with heating under reflux for 2 hours. After ice cooling of the reaction mixture, a mixture of 1,3-dimethyl-1H-pyrazole-4-carboxylic acid chloride and 50 mL of tetrahydrofuran was added, followed by stirring with heating under reflux for 3 days. After cooling, the reaction mixture was added in a mixture of 4.28 g of sodium nitrite and 100 mL of water while stirring. The mixture was acidified with concentrated hydrochloric acid, and the mixture was extracted with ethyl acetate. The organic layer was dried over anhydrous sodium sulfate, and then concentrated under reduced pressure to obtain 0.7 g of 1-(1,3-dimethyl-1H-pyrazol-4-yl)-1,4-dihydrotetrazol-5-one.

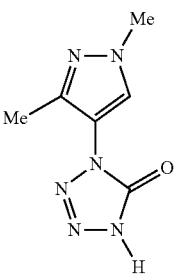

$^1$H-NMR (DMSO-D$_6$) δ: 8.07 (1H, s), 3.82 (3H, s), 2.13 (3H, s).

A mixture of 1-(1,3-dimethyl-1H-pyrazol-4-yl)-1,4-dihydrotetrazol-5-one, 3.25 g of potassium carbonate, 1.08 g of dimethyl sulfate, and 100 mL of N,N-dimethylformamide was stirred at 60° C. for 1 hour. A saturated sodium bicarbonate solution was poured into the reaction mixture, and the mixture was extracted with ethyl acetate. The organic layer was washed with a saturated sodium bicarbonate solution, dried over anhydrous sodium sulfate, and then concentrated under reduced pressure to obtain 0.50 g of 1-(1,3-dimethyl-1H-pyrazol-4-yl)-4-methyl-1,4-dihydrotetrazol-5-one (referred to as C08A).

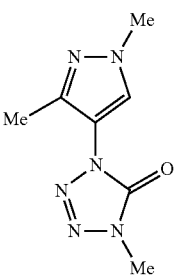 [SMILES: Cc1nn(C)cc1-n1nnn(C)c1=O]

$^1$H-NMR (CDCl$_3$) δ: 7.73 (1H, s), 3.88 (3H, s), 3.70 (3H, s), 2.33 (3H, s).

Reference Production Example 9

A mixture of 0.50 g of C08A, 0.25 g of 1,1'-azobis(cyclohexane-1-carbonitrile), 0.53 g of N-bromosuccinimide, and 30 mL of chlorobenzene was stirred with heating under reflux for 3 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 0.25 g of 1-(1-methyl-3-bromomethyl-1H-pyrazol-4-yl)-4-methyl-1,4-dihydrotetrazol-5-one (referred to as C09A).

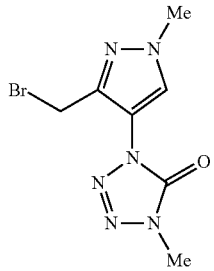

$^1$H-NMR (CDCl$_3$) δ: 7.89 (1H, s), 4.69 (2H, s), 3.94 (3H, s), 3.72 (3H, s).

Reference Production Example 10

A mixture of 1.60 g of 1,5-dimethyl-1H-pyrazole-4-carboxylic acid, 1.23 g of oxalyl dichloride, about 15 mg of N,N-dimethylformamide, and 50 mL of tetrahydrofuran was stirred at 25° C. for 1 hour. The reaction mixture was concentrated under reduced pressure to obtain 1,5-dimethyl-1H-pyrazole-4-carboxylic acid chloride. A mixture of 2.34 g of aluminum chloride, 3.42 g of sodium azide, and 50 mL of tetrahydrofuran was stirred with heating under reflux for 2 hours. After ice cooling of the reaction mixture, a mixture of 1,5-dimethyl-1H-pyrazole-4-carboxylic acid chloride and 50 mL of tetrahydrofuran was added to the reaction mixture, followed by stirring with heating under reflux for 3 days. After cooling, the reaction mixture was added in a mixture of 5.27 g of sodium nitrite and 100 mL of water while stirring. The mixture was acidified with concentrated hydrochloric acid and then extracted with ethyl acetate. The organic layer was dried over anhydrous sodium sulfate and then concentrated under reduced pressure to obtain 1.6 g of 1-(1,5-dimethyl-1H-pyrazol-4-yl)-1,4-dihydrotetrazol-5-one.

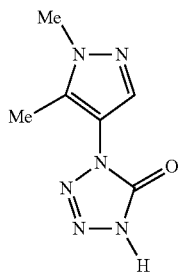

$^1$H-NMR (DMSO-D$_6$) δ: 7.62 (1H, s), 3.80 (3H, s), 2.22 (3H, s).

A mixture of 1-(1,5-dimethyl-1H-pyrazol-4-yl)-1,4-dihydrotetrazol-5-one, 4.00 g of potassium carbonate, 1.33 g of dimethyl sulfate, and 100 mL of N,N-dimethylformamide was stirred at 60° C. for 1 hour. A saturated sodium bicarbonate solution was poured into the reaction mixture, and the mixture was extracted with ethyl acetate. The organic layer was washed with a saturated sodium bicarbonate solution, dried over anhydrous sodium sulfate, and then concentrated under reduced pressure to obtain 1.40 g of 1-(1,5-dimethyl-1H-pyrazol-4-yl)-4-methyl-1,4-dihydrotetrazol-5-one (referred to as C10A).

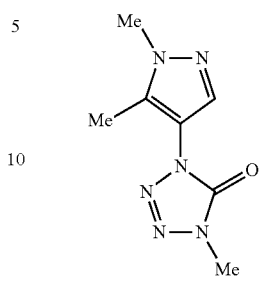

$^1$H-NMR (CDCl$_3$) δ: 7.65 (1H, s), 3.84 (3H, s), 3.70 (3H, s), 2.31 (3H, s).

Reference Production Example 11

A mixture of 1.40 g of C10A, 0.71 g of 1,1'-azobis(cyclohexane-1-carbonitrile), 1.48 g of N-bromosuccinimide, and 90 mL of chlorobenzene was stirred with heating under reflux for 3 hours. After cooling, water was poured into the reaction solution and the mixture was extracted with ethyl acetate. The organic layer was washed with water and a saturated saline solution, dried over anhydrous magnesium sulfate, and then concentrated under reduced pressure. The residue thus obtained was subjected to silica gel column chromatography to obtain 1.20 g of 1-(1-methyl-5-bromomethyl-1H-pyrazol-4-yl)-4-methyl-1,4-dihydrotetrazol-5-one (referred to as C11A).

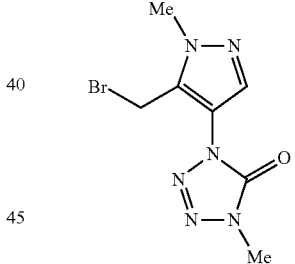

$^1$H-NMR (CDCl$_3$) δ: 7.81 (1H, s), 4.66 (2H, s), 3.97 (3H, s), 3.71 (3H, s).

Reference Production Example 12

To a mixture of 28.5 g of 4-chlorophenylhydrazine, 81.3 g of a 28% sodium methoxide-methanol solution, and 200 mL of methanol, 29.4 g of methyl propionate was added under ice cooling, followed by stirring at 100° C. for 2 hours. To the reaction mixture allowed to cool, 100 mL of ice water was added and the mixture was acidified with 30% sulfuric acid, followed by stirring at 100° C. for 2 hours. A saturated saline solution was poured into the reaction mixture allowed to cool, and the mixture was extracted with ethyl acetate. The organic layer was washed with water and a saturated saline solution, dried over anhydrous magnesium sulfate, and then concentrated under reduced pressure to obtain 15.6 g of 1-(4-chlorophenyl)-1H-pyrazol-3-ol.

1-(4-Chlorophenyl)-1H-pyrazol-3-ol

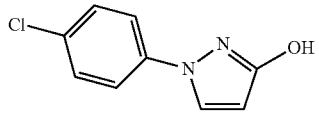 [SMILES: Oc1ccn(-c2ccc(Cl)cc2)n1]

¹H-NMR (DMSO-d₆) δ(ppm): 5.84 (1H, d, J=2.4 Hz), 7.48 (2H, d, J=8.9 Hz), 7.70 (2H, d, J=8.9 Hz), 8.25 (1H, d, J=2.7 Hz), 10.32 (1H, s).

Reference Production Example 13

A mixture of 200 g of N-hydroxysuccinimide, 287 g of sodium 3-methoxyacrylate mentioned in Reference Production Example 30, 528 g of 1-ethyl-3-(3-dimethylaminopropyl)carbodiimide hydrochloride, 269 g of pyridine, and 2 L of N,N-dimethylformamide was stirred at room temperature for 44 hours. The reaction mixture was added to a sodium bicarbonate solution, and then the mixture was extracted with ethyl acetate. The organic layer was washed with a saturated sodium bicarbonate solution, an aqueous sodium hydrogen sulfate solution, and a saturated saline solution, dried over anhydrous magnesium sulfate, and then concentrated under reduced pressure. The residue thus obtained was washed with a mixed solvent of tert-butyl methyl ether and hexane, and then dried under reduced pressure to obtain 174 g of succinimide 3-methoxyacrylate.

Succinimide 3-methoxyacrylate

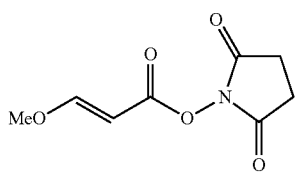 [SMILES: CO/C=C/C(=O)ON1C(=O)CCC1=O]

¹H-NMR (CDCl₃) δ(ppm): 7.84 (1H, d, J=12.7 Hz), 5.38 (1H, d, J=12.4 Hz), 3.80 (3H, s), 2.84 (4H, s).

Reference Production Example 14

A mixture of 10 g of succinimide 3-methoxyacrylate mentioned in Reference Production Example 13, 7.4 g of 2-methoxyphenylhydrazine hydrochloride, 1.9 g of sodium hydroxide, 125 mL of dioxane, and 125 mL of water was heated at 60° C. for 20 hours. To the reaction solution, water was added and the mixture was extracted with ethyl acetate. The organic layer was washed with a saturated saline solution, dried over anhydrous sodium sulfate, and then concentrated under reduced pressure. The residue thus obtained and 40 mL of concentrated hydrochloric acid were stirred at room temperature for 2 hours. To the reaction solution, an aqueous 28% sodium hydroxide solution was added under ice cooling. The residue thus obtained was washed with a mixed solvent of methyl tert-butyl ether and hexane, and then dried under reduced pressure to obtain 3.4 g of 1-(2-methoxyphenyl)-1H-pyrazol-3-ol.

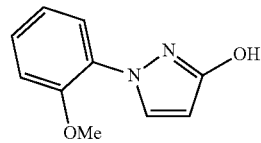 [SMILES: COc1ccccc1-n1ccc(O)n1]

¹H-NMR (CDCl₃) δ(ppm): 7.73 (1H, d, J=2.7 Hz), 7.50 (1H, dd, J=8.0, 1.6 Hz), 7.26 (1H, ddd, J=8.7, 7.0, 1.3 Hz), 7.07 (1H, td, J=7.7, 1.3 Hz), 7.02 (1H, dd, J=8.4, 1.3 Hz), 5.82 (1H, d, J=2.5 Hz), 3.88 (3H, s).

Reference Production Example 15

A mixture of 192.4 g of potassium ethylxanthate, 139.8 g of sodium chloroacetate, and 1.1 L of water was stirred at 25° C. for 8 hours, and 100 mL of concentrated ammonia water was added, followed by stirring at 25° C. for 20 hours. After the reaction mixture was extracted with methyl tert-butyl ether, the organic layer was washed with a saturated saline solution, dried over anhydrous sodium sulfate, and then concentrated under reduced pressure to obtain 58.7 g of O-ethyl thiocarbamate.

O-ethyl thiocarbamate

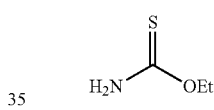

¹H-NMR (CDCl₃) δ: 1.34 (3H, t, J=7.0 Hz), 4.49 (2H, q, J=7.0 Hz), 6.01 (1H, s), 6.40 (1H, s).

Reference Production Example 16

A mixture of 10.00 g of 1-(4-chlorophenyl)-2-bromo-1-ethanone, 4.50 g of O-ethyl thiocarbamate mentioned in Reference Production Example 15, and 40 mL of ethanol was stirred with heating under reflux for 11 hours. Water was poured into the reaction mixture, and the solid thus precipitated was filtered and then washed with water to obtain 8.44 g of 4-(4-chlorophenyl)-2,3-dihydro-2-oxothiazole.

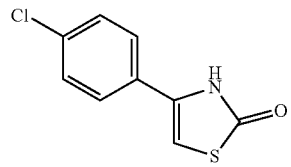 [SMILES: O=c1[nH]c(-c2ccc(Cl)cc2)cs1]

¹H-NMR (DMSO-d₆) δ: 6.88 (1H, d, J=1.7 Hz), 7.50 (2H, dt, J 2.0, 8.8 Hz), 7.68 (2H, dt, J=2.2, 8.8 Hz), 11.84 (1H, s).

The same operation was performed to obtain 4-(4-fluorophenyl)-2,3-dihydro-2-oxothiazole, 4-(4-bromophenyl)-2,3-dihydro-2-oxothiazole, and 4-(1-adamantyl)-2,3-dihydro-2-oxothiazole.

Physical properties are shown below.

4-(4-fluorophenyl)-2,3-dihydro-2-oxothiazole

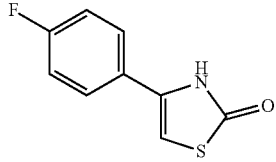

$^1$H-NMR (DMSO-d$_6$) δ: 6.76 (1H, s), 7.27 (2H, t, J=8.7 Hz), 7.68 (2H, dd, J=5.3, 8.0 Hz), 11.77 (1H, s).

4-(4-Bromophenyl)-2,3-dihydro-2-oxothiazole

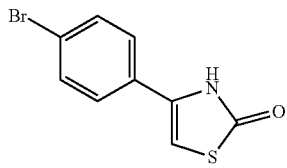

$^1$H-NMR (DMSO-d$_6$) δ: 6.89 (1H, s), 7.61 (2H, d, J=8.5 Hz), 7.64 (2H, d, J=9.2 Hz), 11.85 (1H, s).

4-(1-Adamantyl)-2,3-dihydro-2-oxothiazole

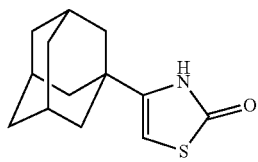 [SMILES: O=c1[nH]c(C23CC4CC(CC(C4)C2)C3)cs1]

$^1$H-NMR (CDCl$_3$) δ: 1.71-1.79 (6H, m), 1.83 (6H, d, J=2.7 Hz), 2.07 (3H, s), 5.62 (1H, d, J=2.2 Hz), 10.01 (1H, s).

Reference Production Example 17

To a mixture of 5.0 g of 4-methoxy-3-methyl-benzoic acid and 100 ml of tetrahydrofuran, 4.0 g of oxalyl chloride and 0.2 ml of dimethylformamide were added at room temperature, followed by stirring for 2.5 hours and further concentration under reduced pressure. To this mixture, 150 ml of chloroform, 3.5 g of N,O-dimethyl-hydroxylamine-hydrochloride, and 9.3 g of N,N-diisopropylethylamine were added at room temperature, followed by stirring for 4 hours. Water was added and the mixture was extracted with chloroform. The organic layer was washed with water, dried over anhydrous magnesium sulfate, and then concentrated under reduced pressure. The residue thus obtained was subjected to column chromatography to obtain 6.1 g of 4,N-dimethoxy-3-methyl-N-methylbenzamide (D2A).

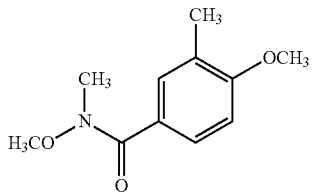

$^1$H-NMR (CDCl$_3$) δ: 7.61-7.58 (1H, m), 7.54 (1H, dd, J=2.1, 0.6 Hz), 6.81 (1H, d, J=8.5 Hz), 3.87 (3H, s), 3.57 (3H, s), 3.35 (3H, s), 2.23 (3H, s).

Reference Production Example 18

A mixture of 5.7 g of D2A mentioned in Reference Production Example 17, 100 ml of tetrahydrofuran, and 43 ml of a 0.95 mol/L ethylmagnesium bromide-tetrahydrofuran solution was stirred with heating under reflux for 6 hours. An aqueous saturated ammonium chloride solution was added at room temperature and the mixture was extracted with ethyl acetate. The organic layer was washed with water, dried over anhydrous magnesium sulfate, and then concentrated under reduced pressure. The residue thus obtained was subjected to column chromatography to obtain 4.6 g of 1-(4-methoxy-3-methylphenyl)-propan-1-one (D3A).

$^1$H-NMR (CDCl$_3$) δ: 7.83 (1H, dd, J=8.6, 2.3 Hz), 7.79-7.78 (1H, m), 6.84 (1H, d, J=8.7 Hz), 3.89 (3H, s), 2.95 (2H, q, J=7.2 Hz), 2.25 (3H, s), 1.21 (3H, t, J=7.2 Hz).

Reference Production Example 19

A mixture of 5.2 g of D3A mentioned in Reference Production Example 18, 100 ml of tetrahydrofuran, 4.1 g of potassium tert-butoxide, and 3.6 g of diethyl carbonate was stirred with heating under reflux for 5.5 hours. 6N-hydrochloric acid (20 ml) was added at room temperature and the mixture was extracted with ethyl acetate. The organic layer was washed with water, dried over anhydrous magnesium sulfate, and then concentrated under reduced pressure. The residue thus obtained was subjected to column chromatography to obtain 3.5 g of 3-(4-methoxy-3-methylphenyl)-2-methyl-3-oxopropionic acid ethyl ester (D4A).

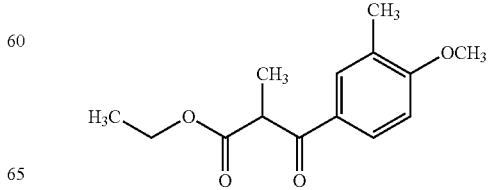

¹H-NMR (CDCl₃) δ: 7.86 (1H, dd, J=8.6, 2.3 Hz), 7.80 (1H, d, J=2.2 Hz), 6.86 (1H, d, J=8.7 Hz), 4.19-4.10 (3H, m), 3.90 (3H, s), 2.25 (3H, s), 1.47 (3H, d, J=7.2 Hz), 1.19 (3H, t, J=7.1 Hz).

Reference Production Example 20

A mixture of 3.5 g of D4A mentioned in Reference Production Example 19, 100 ml of toluene, and 7.4 g of methylhydrazine was stirred with heating under reflux for 18 hours. Toluene was distilled off and an aqueous 3N hydrochloric acid solution was added, and then the precipitate was filtered and washed with hexane to obtain 1.4 g of 3-(4-methoxy-3-methylphenyl)-1,4-dimethyl-5-hydroxy-1H-pyrazole (D5A).

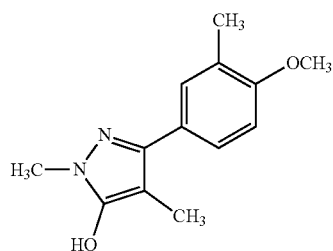 [SMILES: COc1ccc(-c2nn(C)c(O)c2C)cc1C]

¹H-NMR (DMSO-D₆) δ: 7.47-7.44 (2H, m), 7.07 (1H, d, J=8.2 Hz), 3.84 (3H, s), 3.66 (3H, s), 2.20 (3H, s), 2.05 (3H, s).

Reference Production Example 21

A mixture of 1.4 g of D5A mentioned in Reference Production Example 20 and 31.8 g of phosphorus oxychloride was stirred at 100° C. for 11 hours. The mixture was concentrated under reduced pressure and extracted with ethyl acetate. The organic layer was washed with water, dried over anhydrous magnesium sulfate, and then concentrated under reduced pressure. The residue thus obtained was subjected to column chromatography to obtain 0.4 g of 5-chloro-3-(4-methoxy-3-methylphenyl)-1,4-dimethyl-1H-pyrazole (D6A).

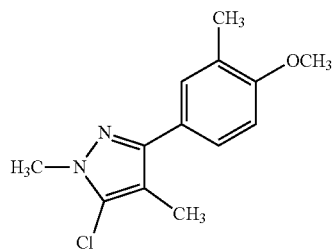 [SMILES: COc1ccc(-c2nn(C)c(Cl)c2C)cc1C]

¹H-NMR (DMSO-D₆) δ: 7.42-7.40 (2H, m), 6.98 (1H, d, J=9.2 Hz), 3.81 (3H, s), 3.80 (3H, s), 2.19 (3H, s), 2.11 (3H, s).

Reference Production Example 22

A mixture of 0.4 g of D6A mentioned in Reference Production Example 21, 3 ml of 47% hydrobromic acid, and 3 ml of acetic acid was stirred with heating under reflux for 15 hours. After the reaction solution was concentrated under reduced pressure, 20 ml of ethyl acetate was added to the residue, followed by stirring at room temperature for 1 hour. The precipitate was filtered, washed with hexane, and then dried under reduced pressure to obtain 0.3 g of 4-(5-chloro-1,4-dimethyl-1H-pyrazol-3-yl)-2-methylphenol.

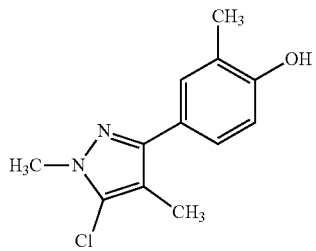 [SMILES: Cc1cc(-c2nn(C)c(Cl)c2C)ccc1O]

¹H-NMR (DMSO-D₆) δ: 7.33 (1H, s), 7.24 (1H, d, J=8.2 Hz), 6.83 (1H, d, J=8.2 Hz), 3.78 (3H, s), 2.15 (3H, s), 2.09 (3H, s).

In accordance with the process mentioned above, it is possible to obtain compounds HA1001-0001 to HA3292-7660 (hereinafter referred to as the present compounds A).

The compounds HA1001-0001 to HA3292-7660 are tetrazolinone compounds represented by the following formulas:

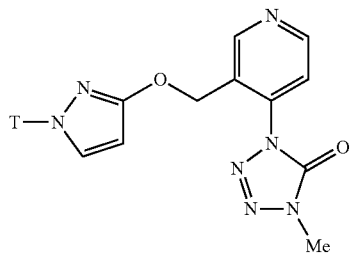

(HA1001)

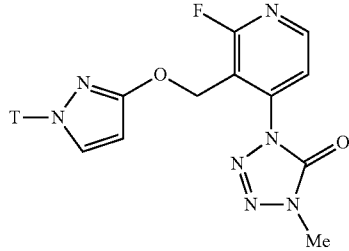

(HA1002)

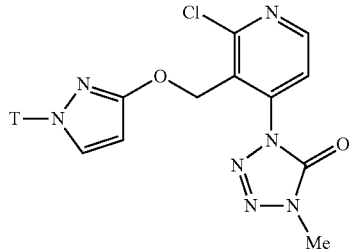

(HA1003)

(HA1004) 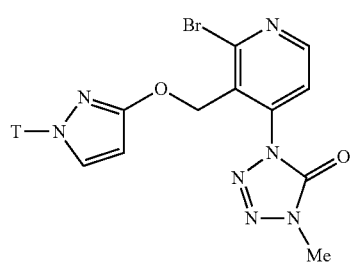
(HA1005) 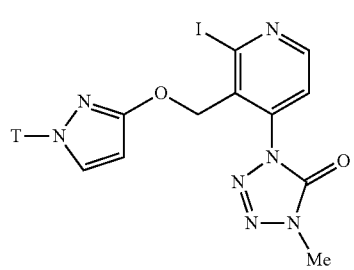
(HA1006) 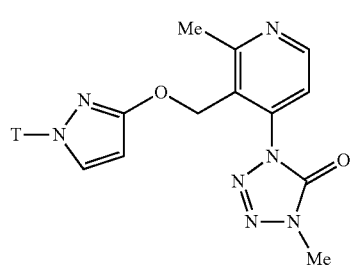
(HA1007) 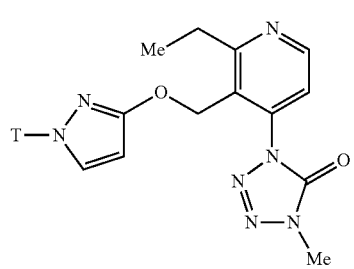
(HA1008) 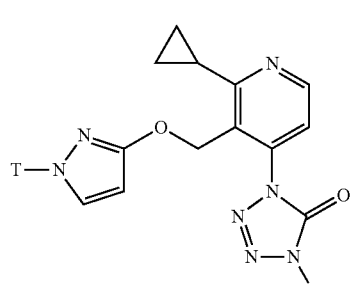
(HA1009) 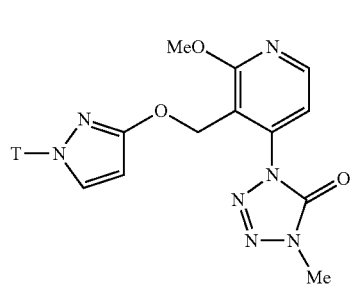
(HA1010) 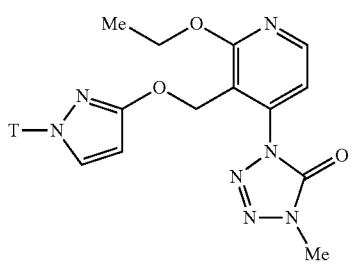
(HA1011) 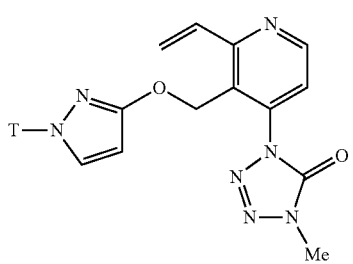
(HA1012) 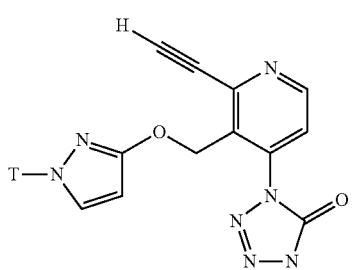
(HA1013) 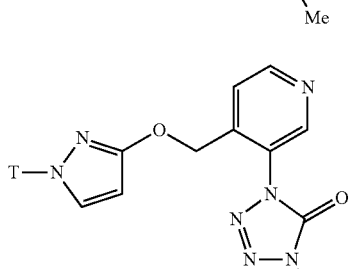
(HA1014) 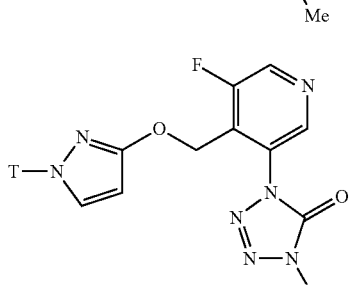
(HA1015) 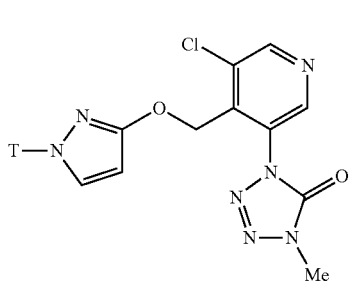

(HA1016) (HA1017) (HA1018) (HA1019) (HA1020) (HA1021) (HA1022) (HA1023) (HA1024) (HA1025) (HA1026) (HA1027)

-continued (HA1028)
(HA1029)
(HA1030)
(HA1031)
(HA1032)
(HA1033)
(HA1034)
(HA1035)
(HA1036)
(HA1037)
(HA1038)
(HA1039)

-continued
(HA1040)
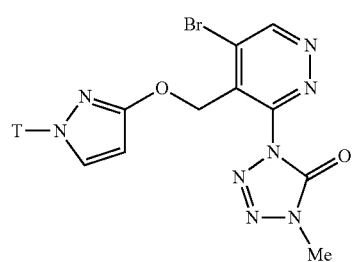
(HA1041)
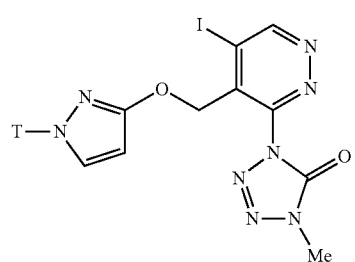
(HA1042)
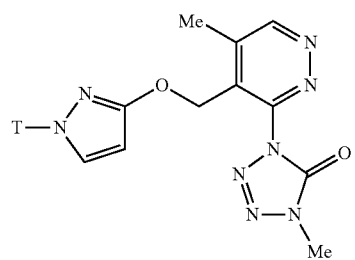
(HA1043)
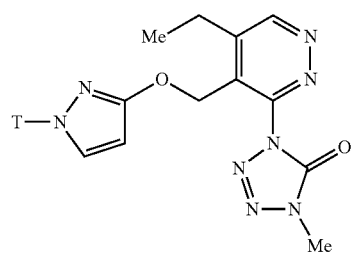
(HA1044)
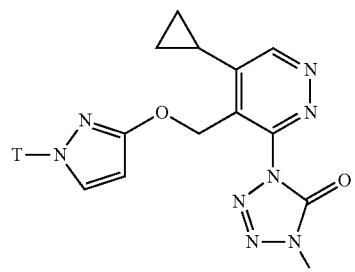
(HA1045)
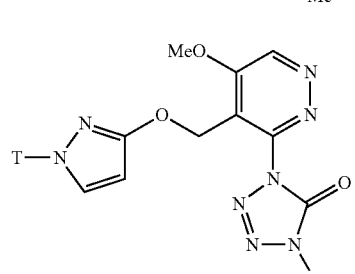
-continued
(HA1046)
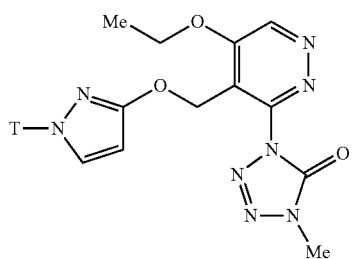
(HA1047)
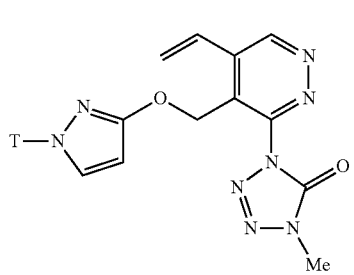
(HA1048)
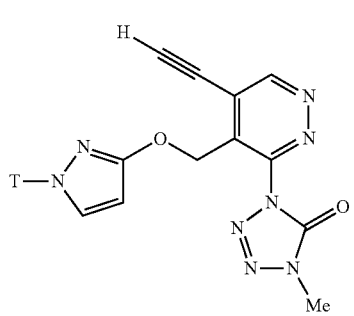
(HA1049)
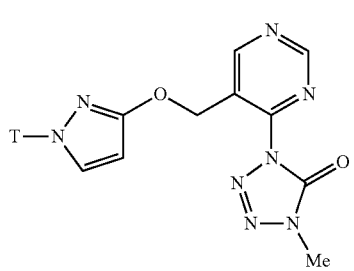
(HA1050)
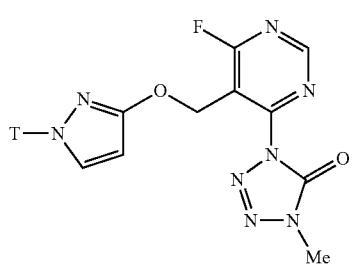
(HA1051)
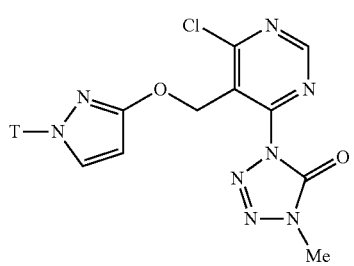

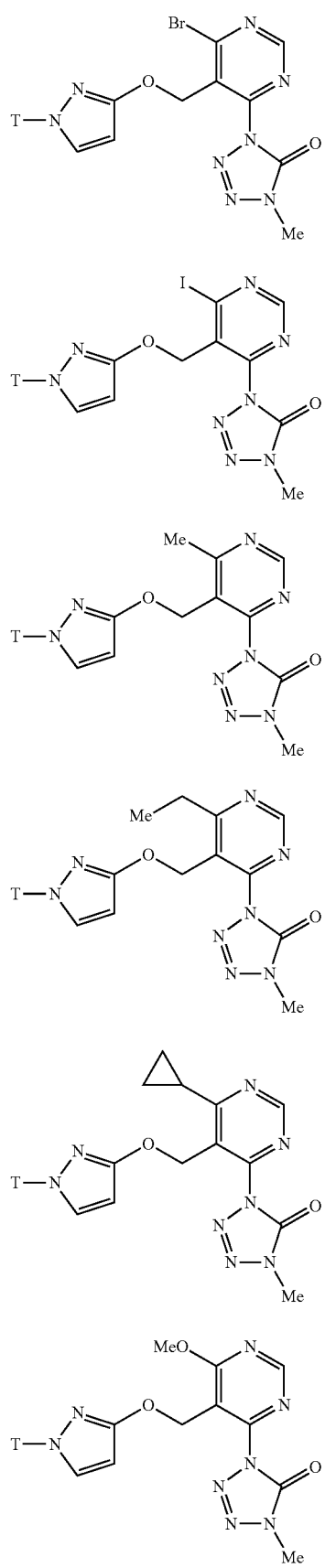
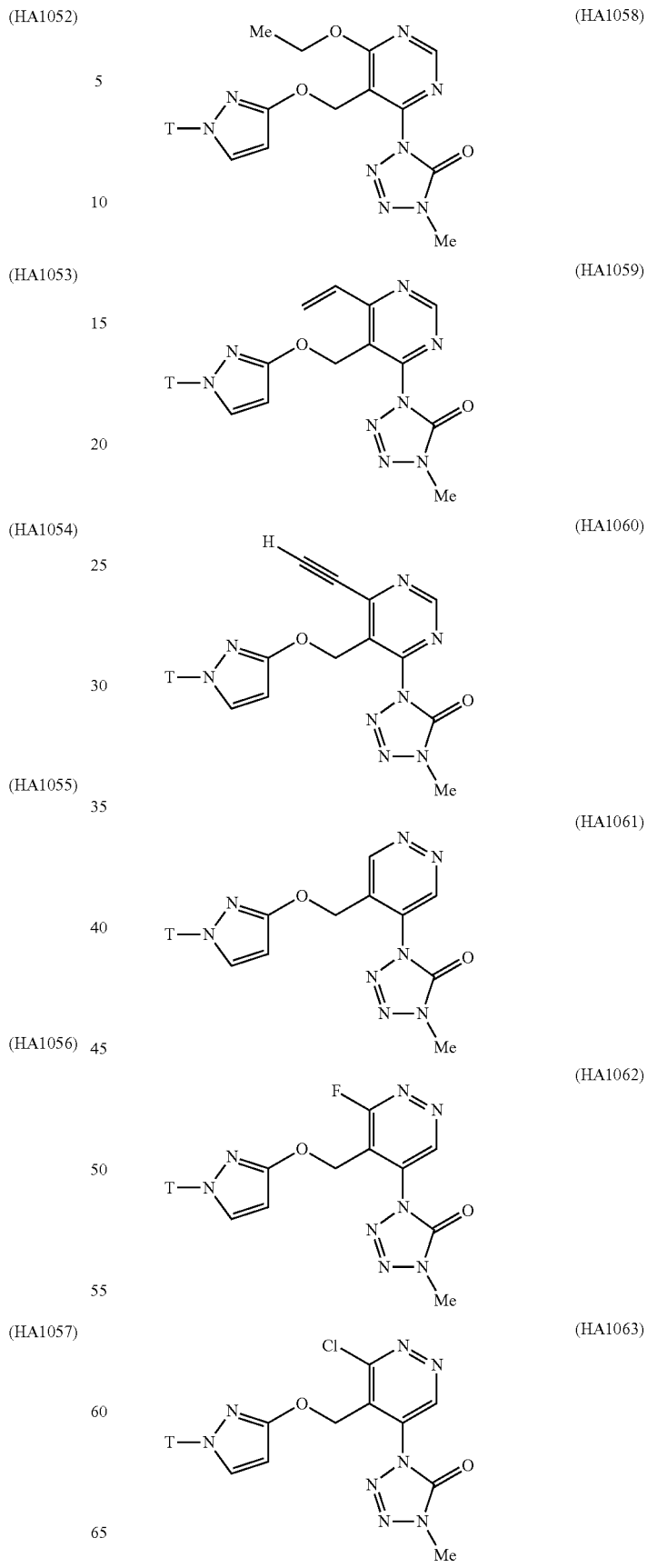

-continued (HA1064)
(HA1065)
(HA1066)
(HA1067)
(HA1068)
(HA1069)

(HA1070)
(HA1071)
(HA1072)
(HA1073)
(HA1074)
(HA1075)

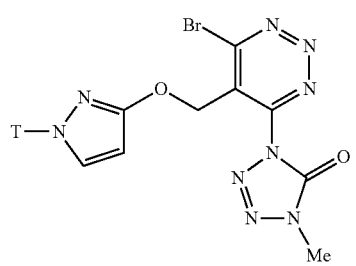
(HA1076)
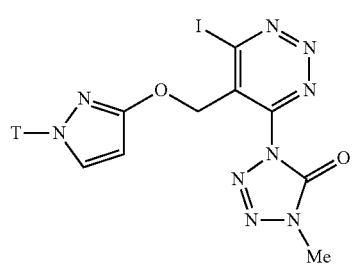
(HA1077)
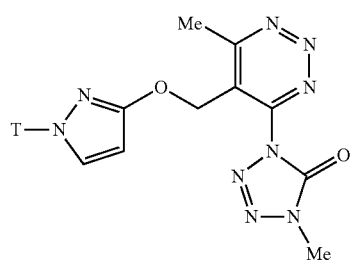
(HA1078)
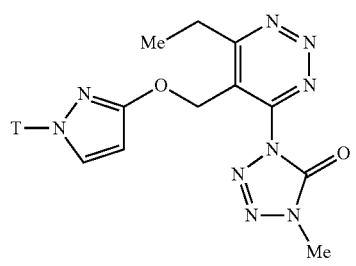
(HA1079)
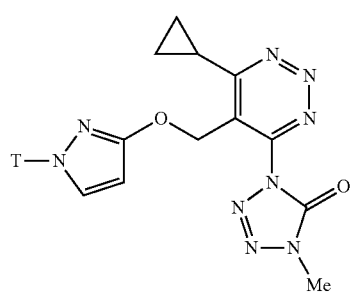
(HA1080)
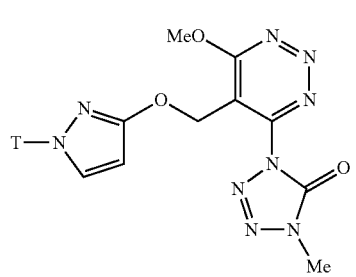
(HA1081)
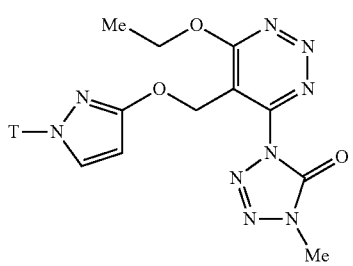
(HA1082)
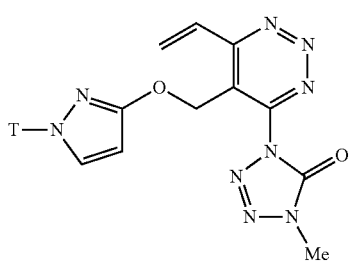
(HA1083)
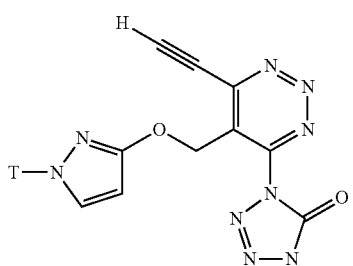
(HA1084)
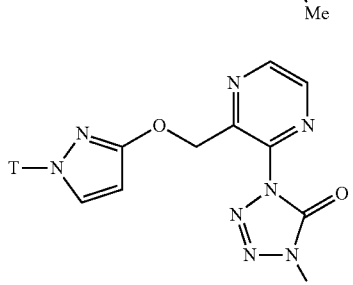
(HA1085)
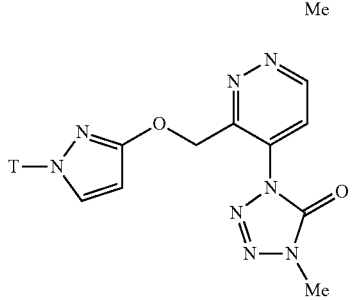
(HA1086)
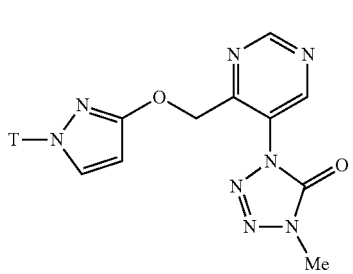
(HA1087)

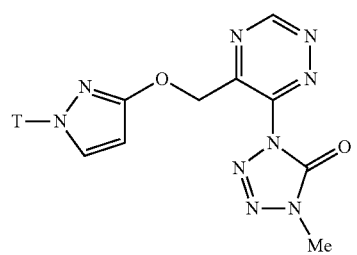 (HA1088)
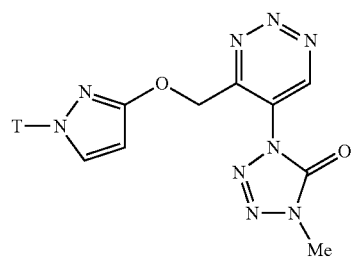 (HA1089)
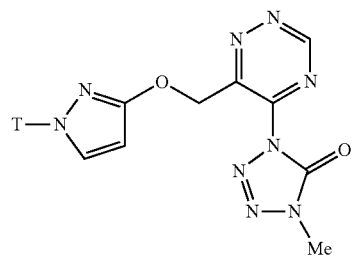 (HA1090)
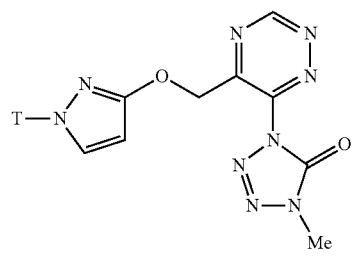 (HA1091)
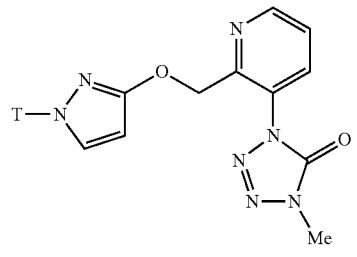 (HA1092)
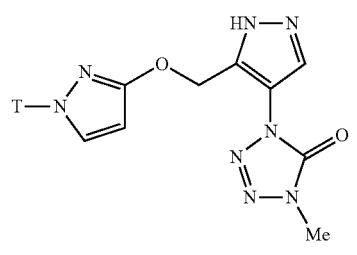 (HA1093)
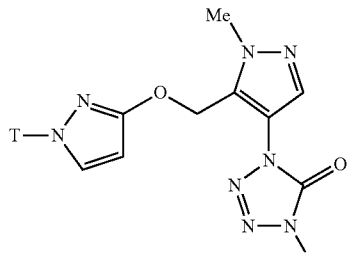 (HA1094)
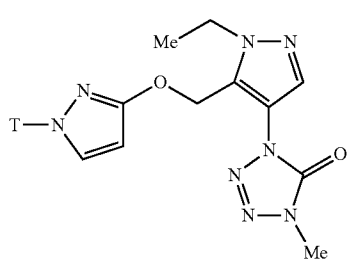 (HA1095)
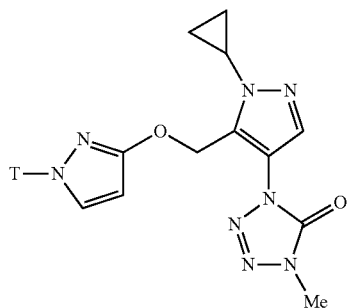 (HA1096)
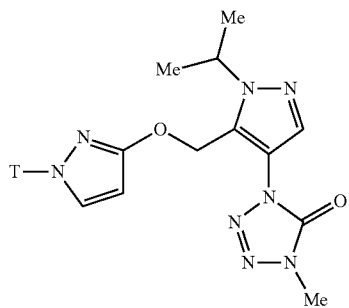 (HA1097)
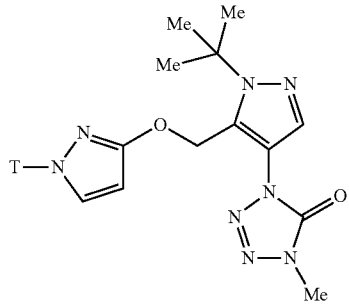 (HA1098)

(HA1099)
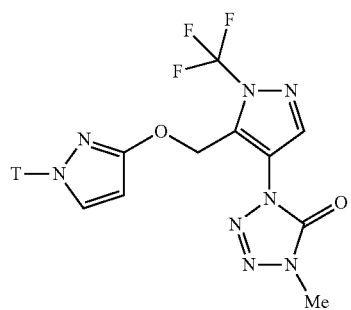
(HA1100)
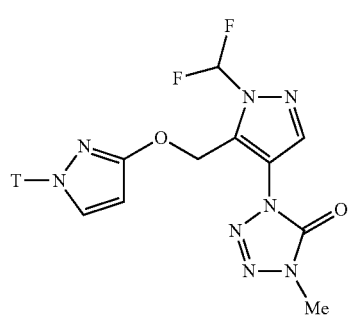
(HA1101)
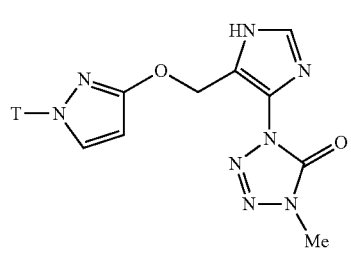
(HA1102)
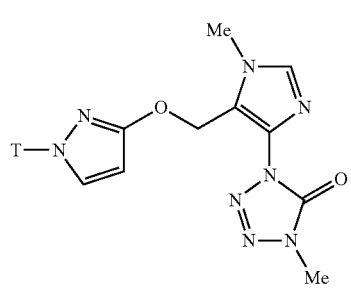
(HA1103)
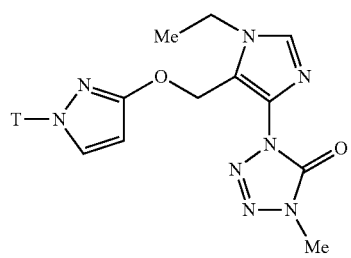
(HA1104)
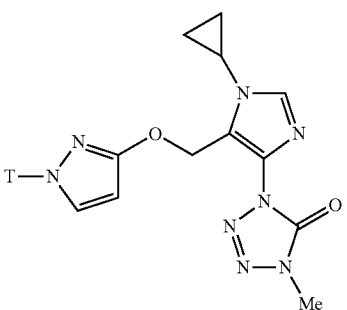
(HA1105)
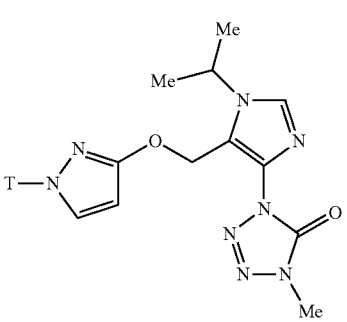
(HA1106)
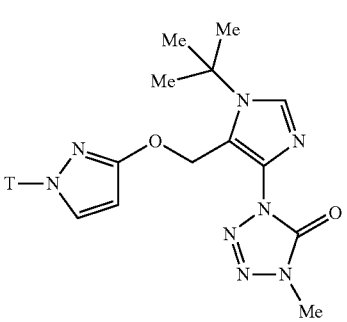
(HA1107)
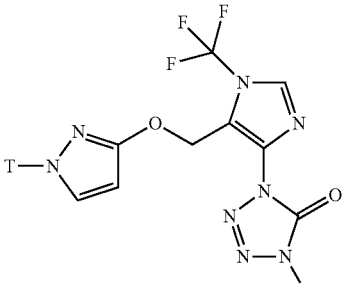
(HA1108)
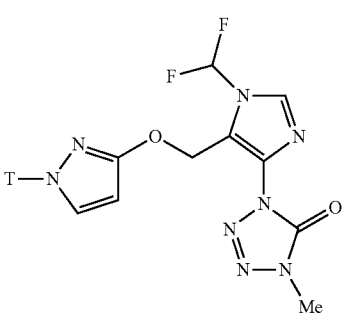

(HA1109) 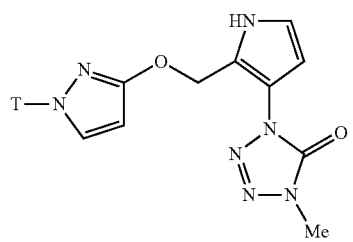
(HA1110) 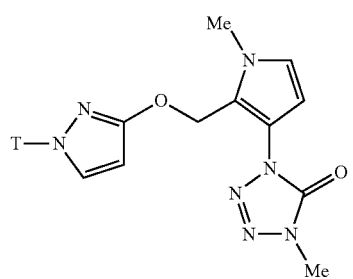
(HA1111) 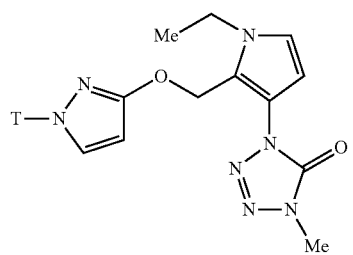
(HA1112) 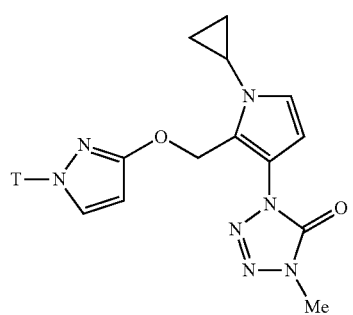
(HA1113) 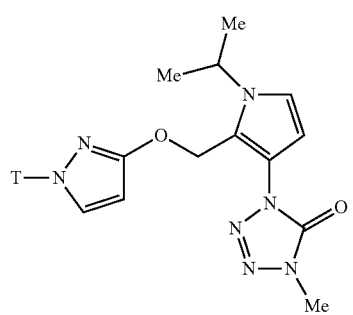
(HA1114) 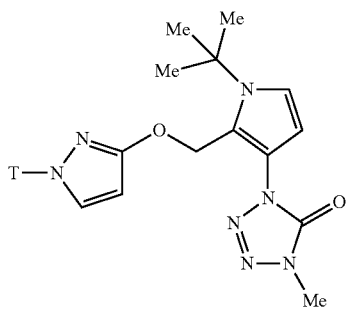
(HA1115) 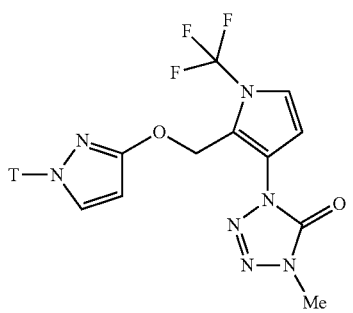
(HA1116) 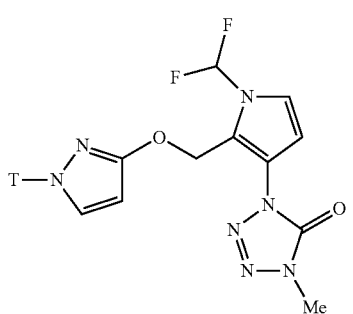
(HA1117) 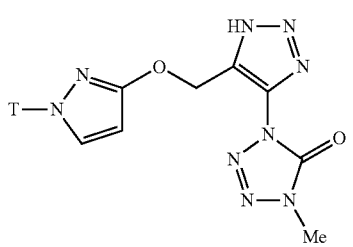
(HA1118) 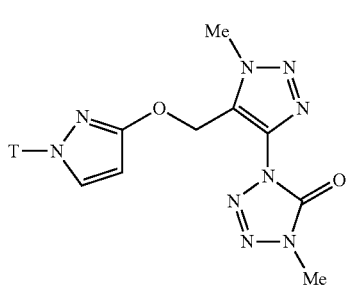

175
-continued
(HA1119)
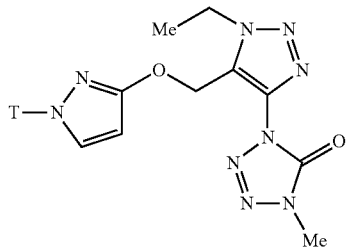
(HA1120)
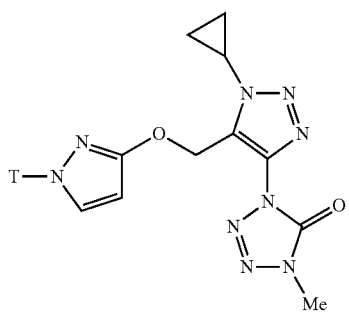
(HA1121)
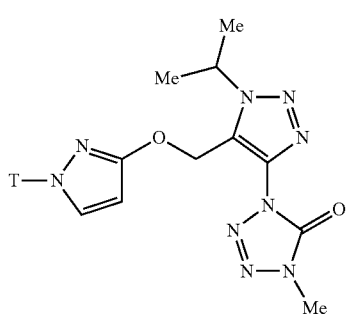
(HA1122)
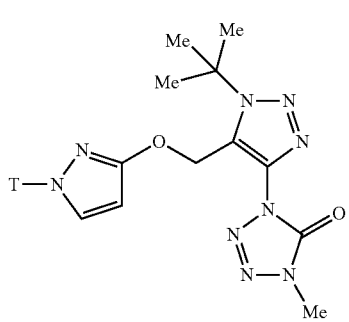
(HA1123)
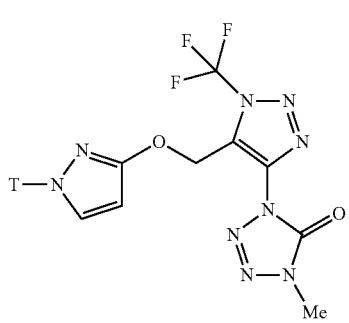
176
-continued
(HA1124)
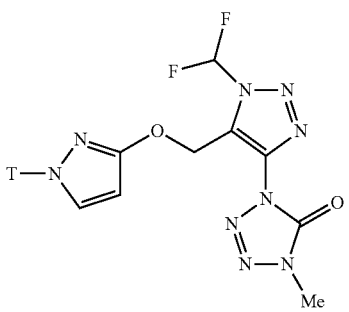
(HA1125)
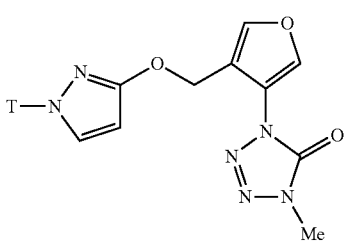
(HA1126)
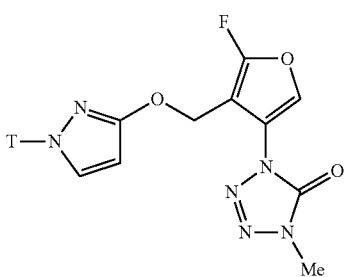
(HA1127)
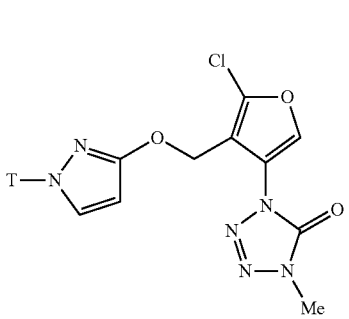
(HA1128)
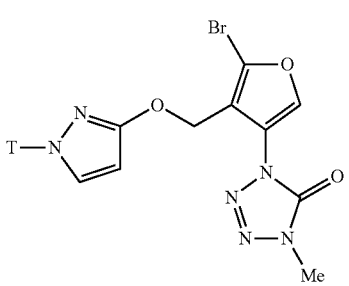

(HA1129)
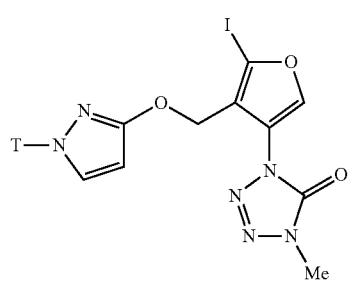
(HA1130)
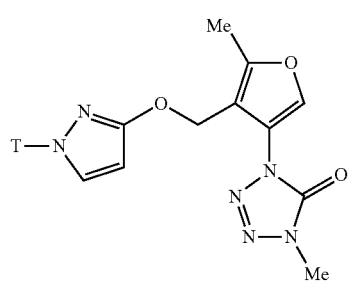
(HA1131)
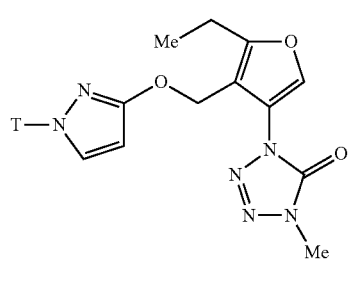
(HA1132)
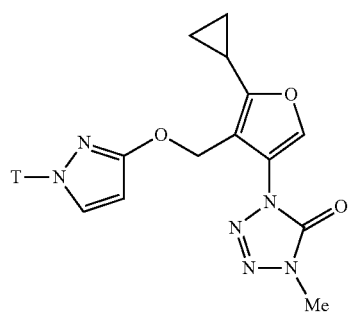
(HA1133)
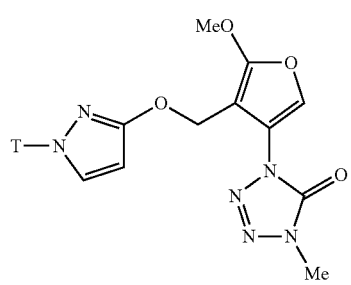
(HA1134)
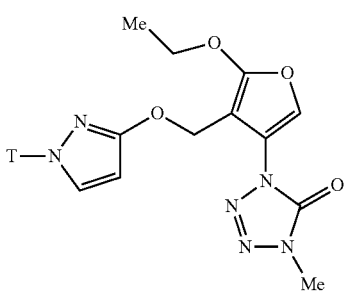
(HA1135)
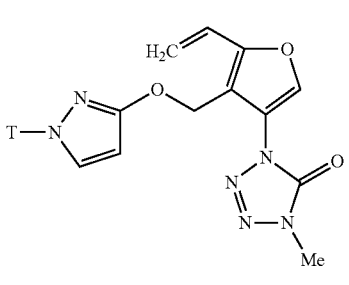
(HA1136)
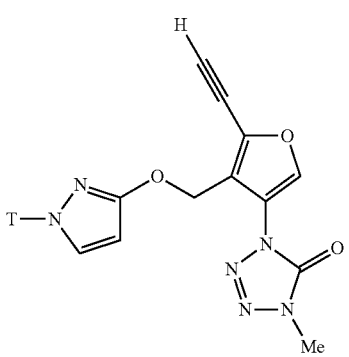
(HA1137)
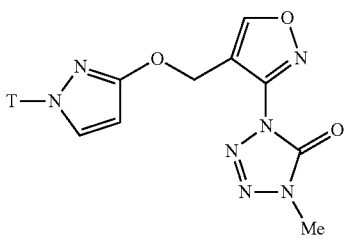
(HA1138)
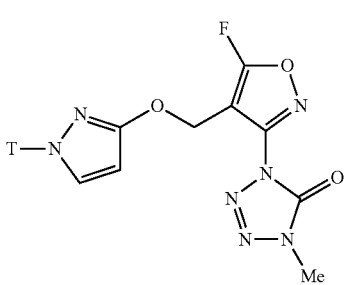

(HA1139)
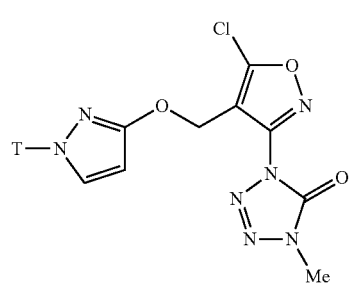
(HA1140)
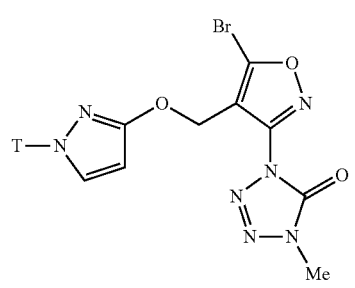
(HA1141)
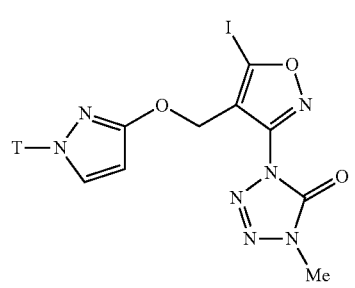
(HA1142)
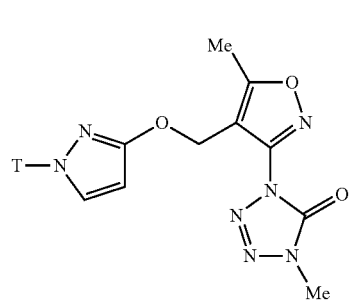
(HA1143)
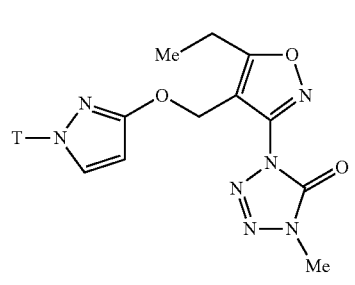
(HA1144)
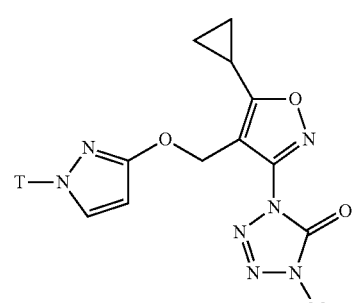
(HA1145)
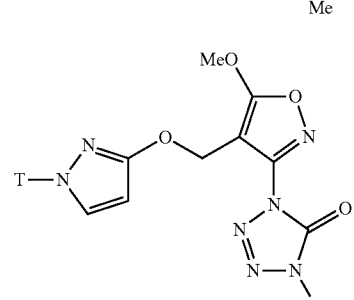
(HA1146)
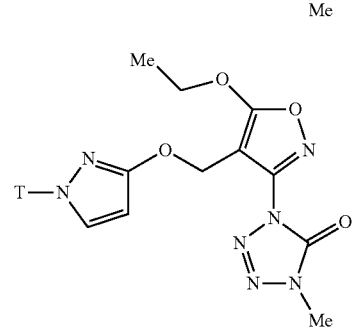
(HA1147)
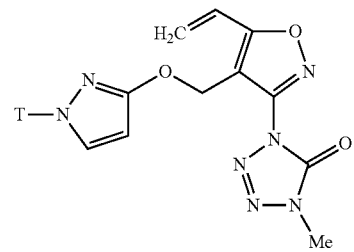
(HA1148)
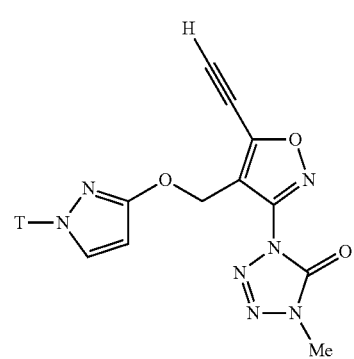

-continued
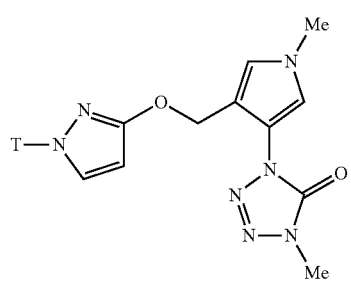 (HA1149)
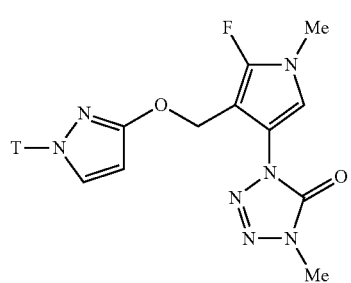 (HA1150)
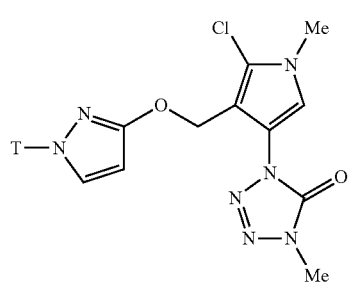 (HA1151)
(HA1152)
(HA1153)
-continued
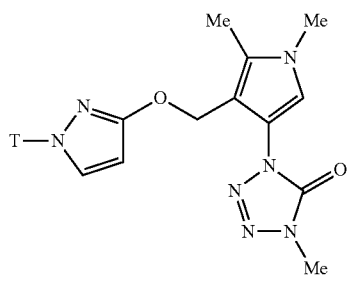 (HA1154)
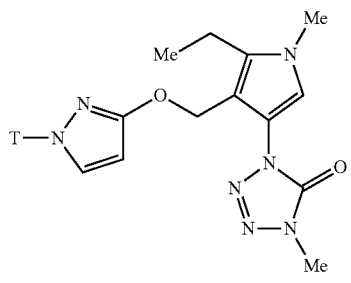 (HA1155)
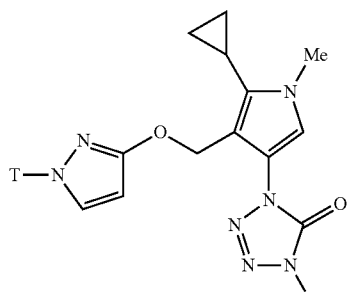 (HA1156)
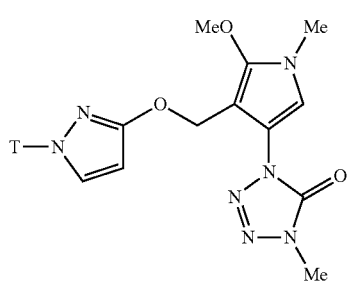 (HA1157)
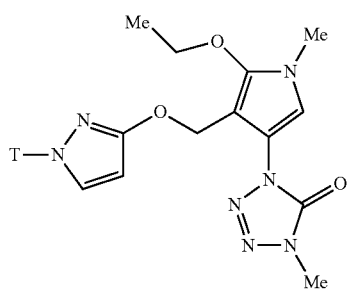 (HA1158)

183
-continued
(HA1159)
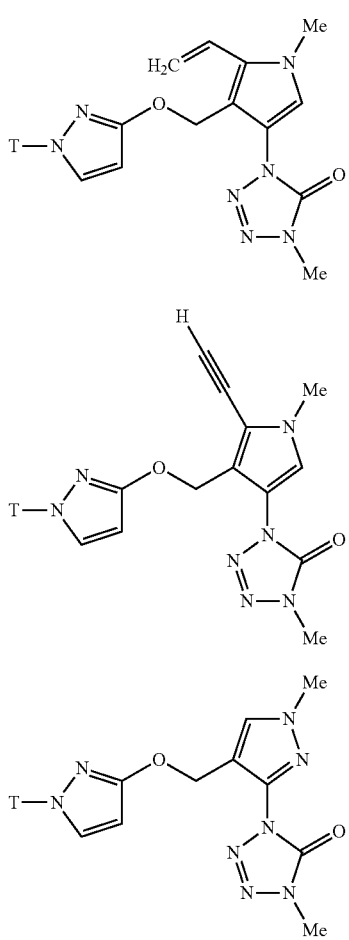
(HA1160)
(HA1161)
(HA1162)
(HA1163)
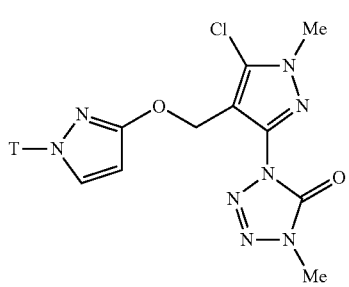
184
-continued
(HA1164)
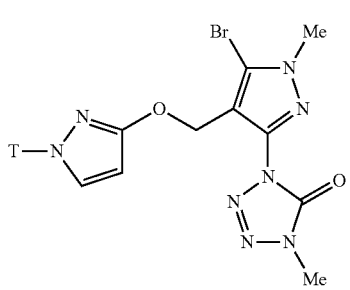
(HA1165)
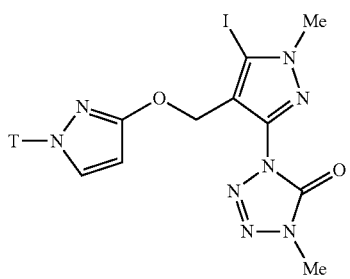
(HA1166)
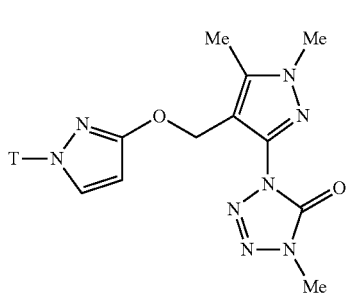
(HA1167)
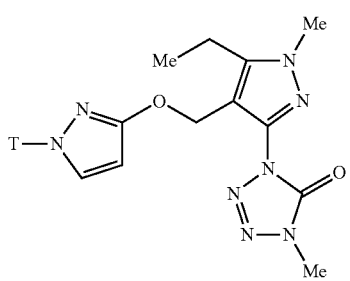
(HA1168)
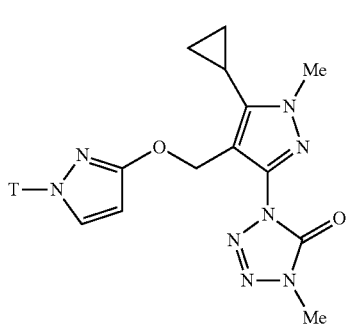

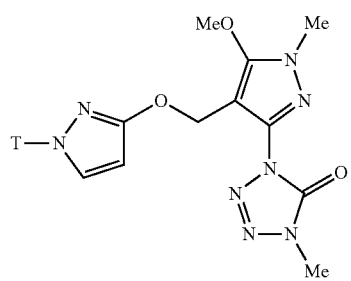 (HA1169)
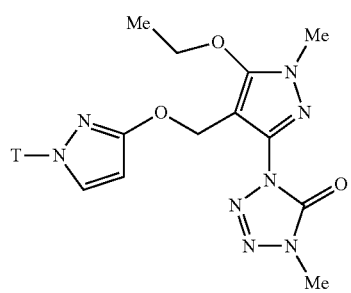 (HA1170)
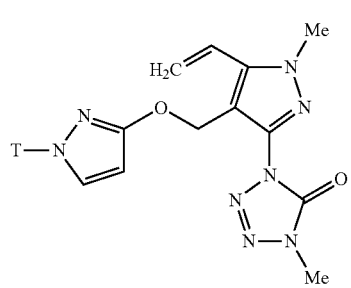 (HA1171)
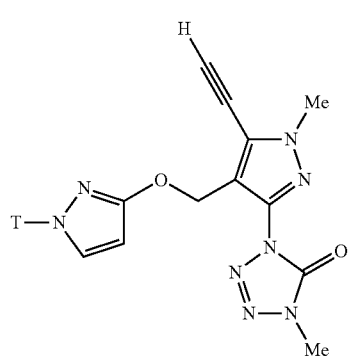 (HA1172)
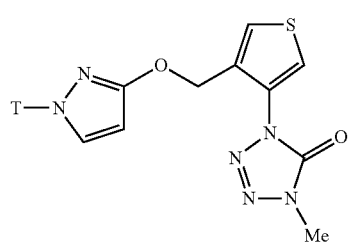 (HA1173)
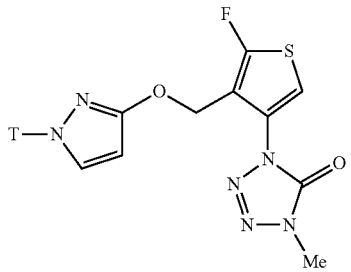 (HA1174)
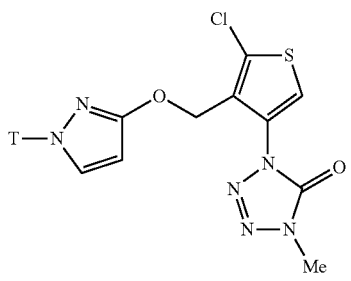 (HA1175)
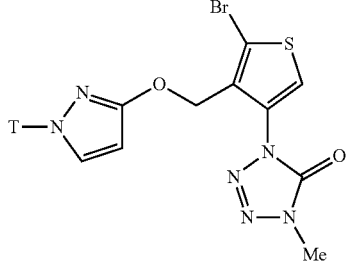 (HA1176)
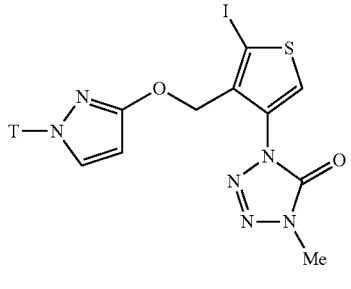 (HA1177)
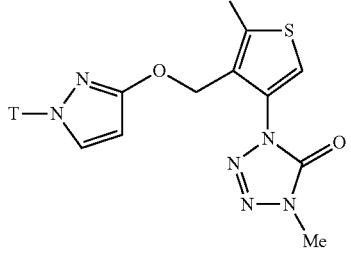 (HA1178)
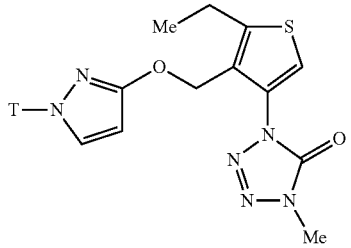 (HA1179)

(HA1180) 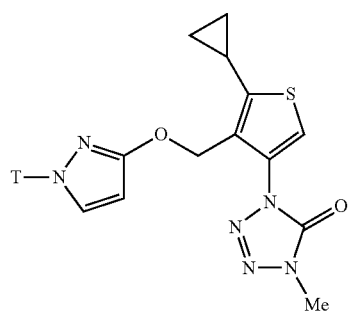
(HA1181) 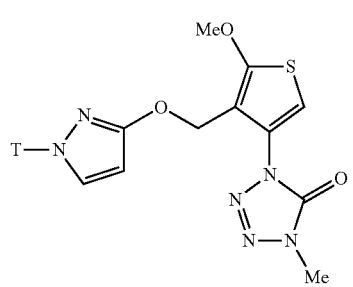
(HA1182) 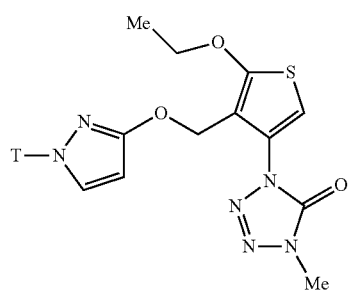
(HA1183) 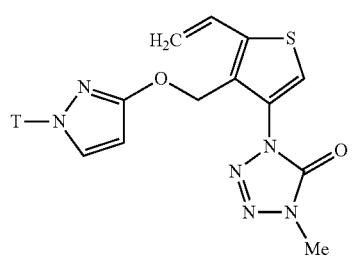
(HA1184) 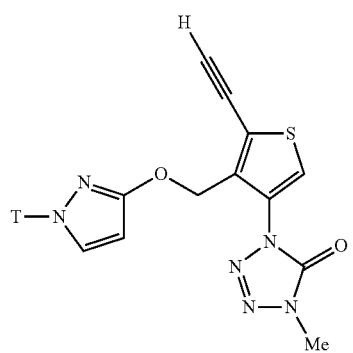
(HA1185) 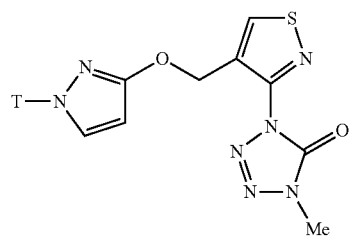
(HA1186) 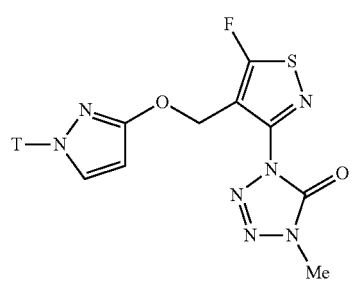
(HA1187) 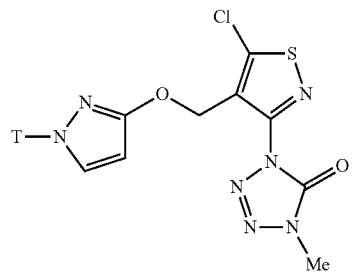
(HA1188) 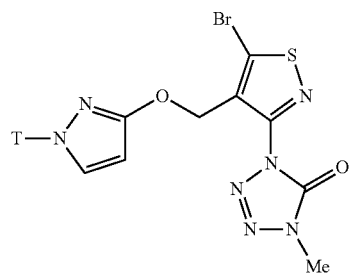
(HA1189) 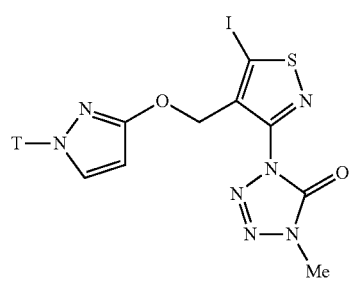
(HA1190) 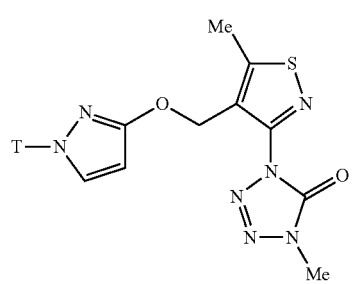

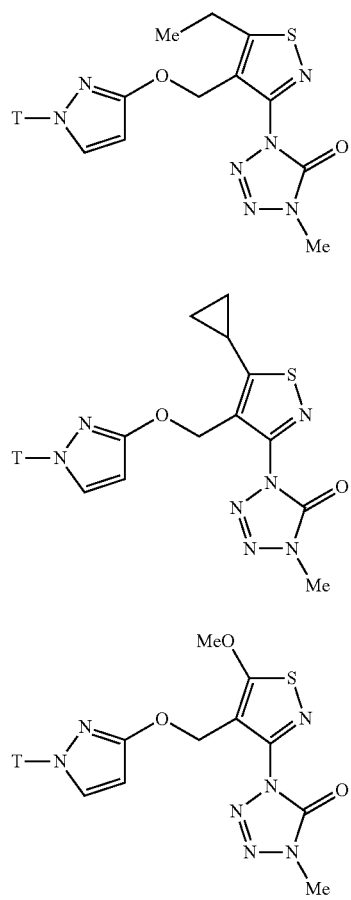
(HA1191)
(HA1192)
(HA1193)
(HA1194)
(HA1195)
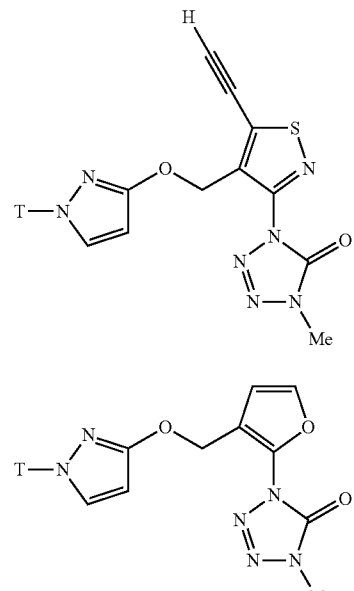
(HA1196)
(HA1197)
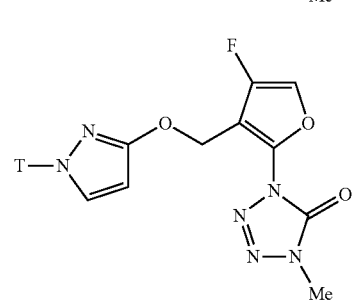
(HA1198)
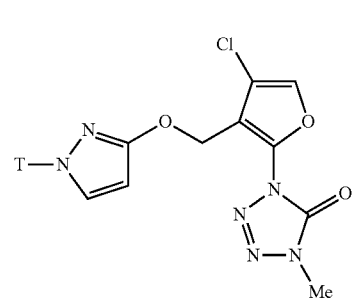
(HA1199)
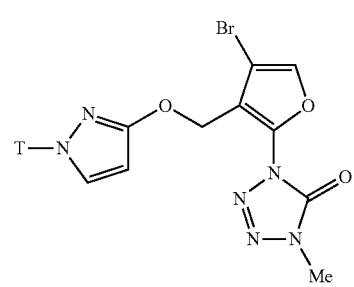
(HA1200)

-continued
(HA1201)
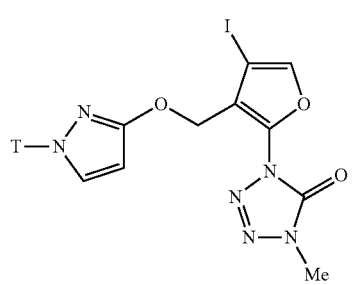
(HA1202)
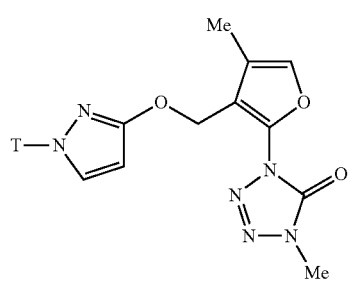
(HA1203)
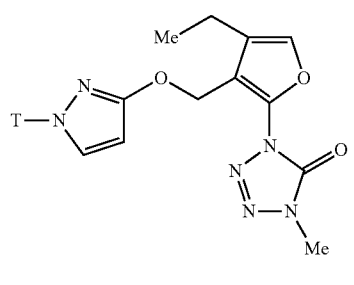
(HA1204)
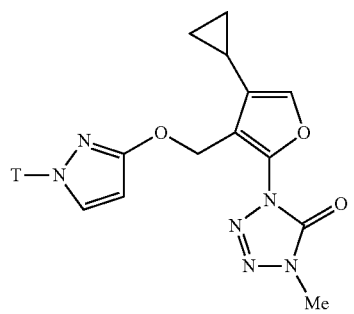
(HA1205)
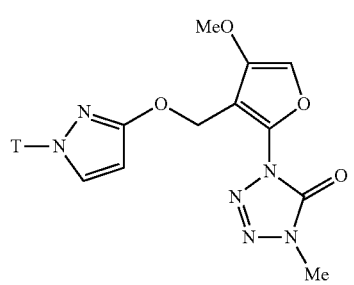
-continued
(HA1206)
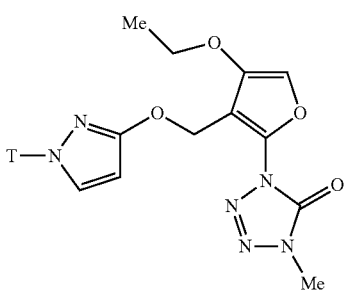
(HA1207)
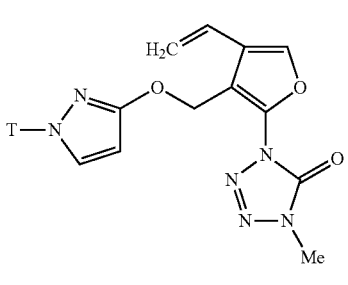
(HA1208)
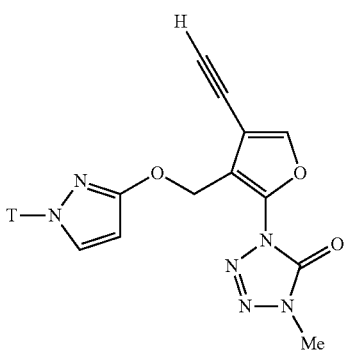
(HA1209)
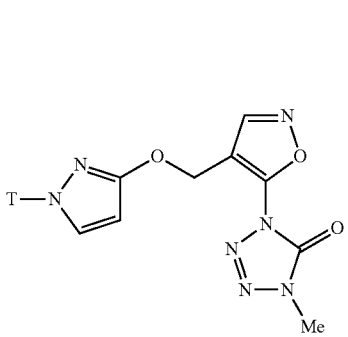
(HA1210)
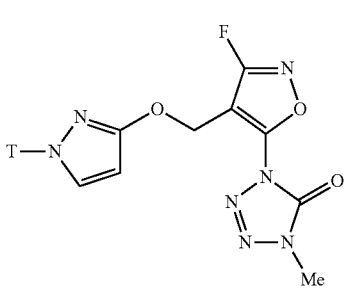

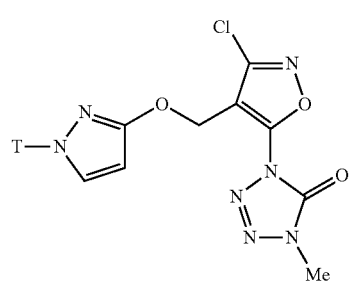
(HA1211)
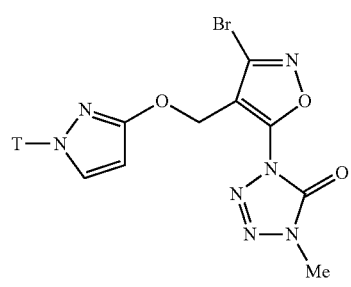
(HA1212)
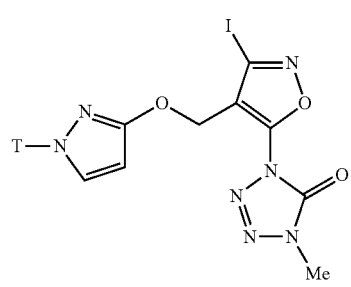
(HA1213)
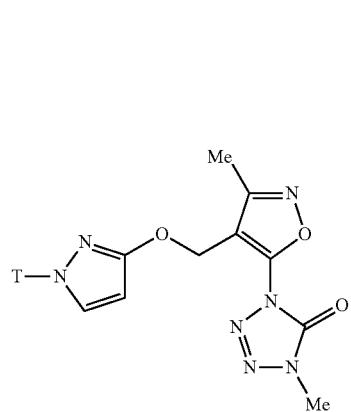
(HA1214)
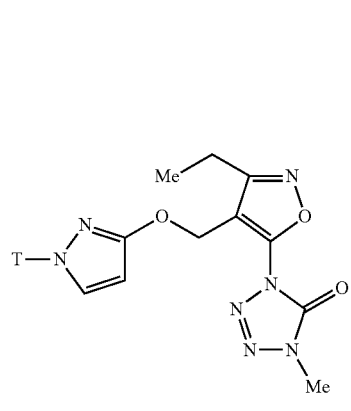
(HA1215)
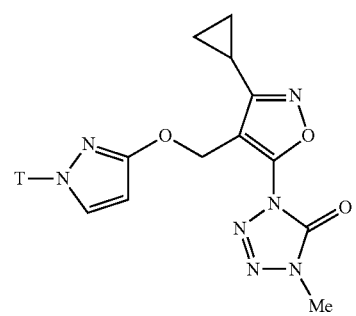
(HA1216)
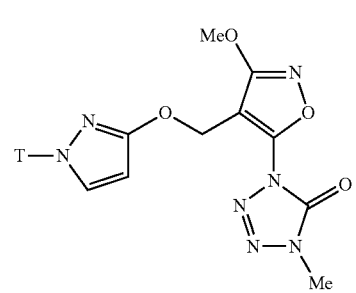
(HA1217)
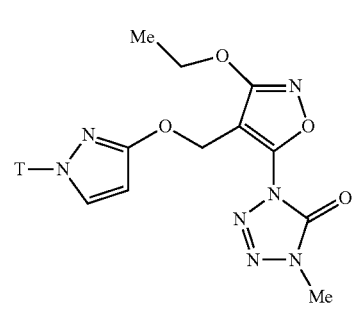
(HA1218)
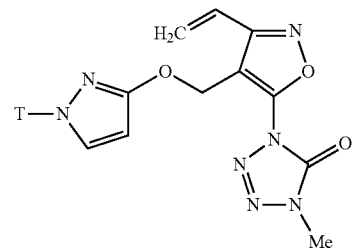
(HA1219)
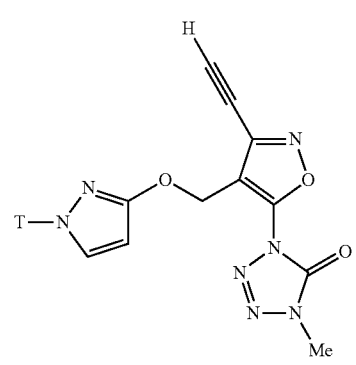
(HA1220)

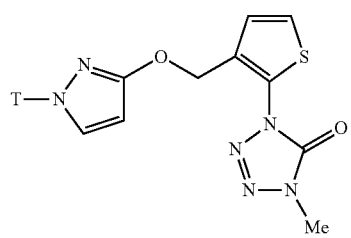
(HA1221)
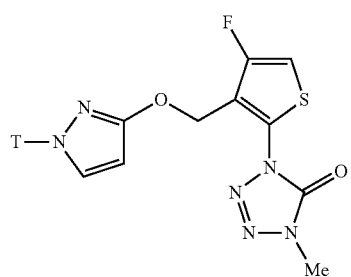
(HA1222)
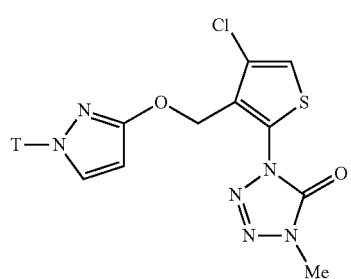
(HA1223)
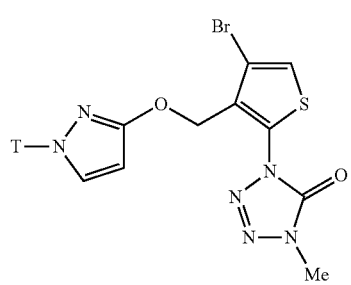
(HA1224)
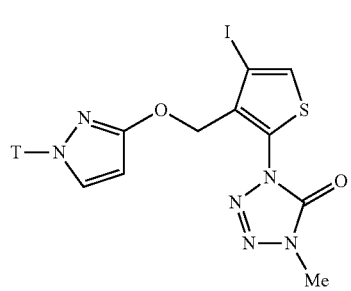
(HA1225)
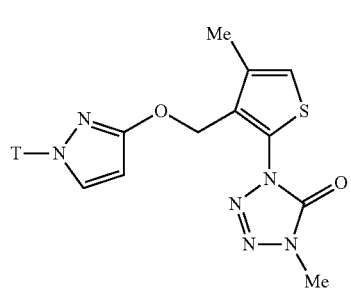
(HA1226)
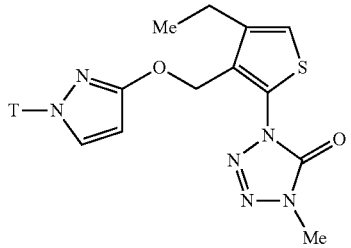
(HA1227)
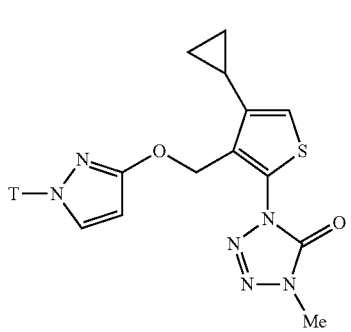
(HA1228)
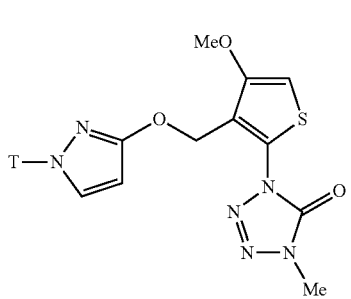
(HA1229)
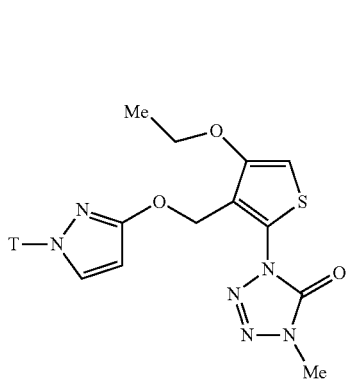
(HA1230)
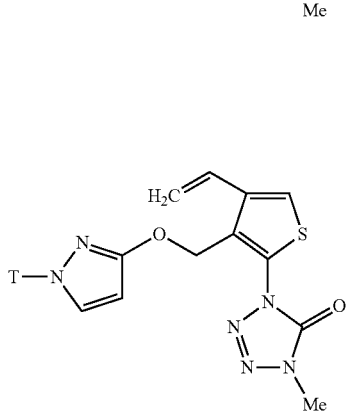
(HA1231)

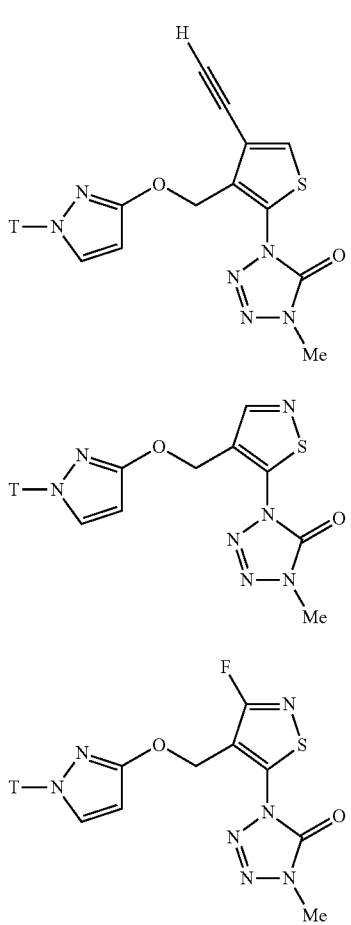
(HA1232)
(HA1233)
(HA1234)
(HA1235)
(HA1236)
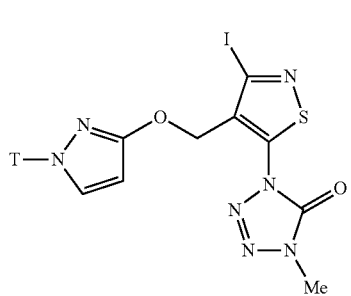
(HA1237)
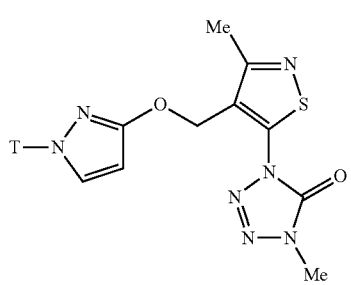
(HA1238)
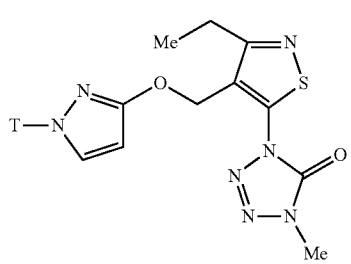
(HA1239)
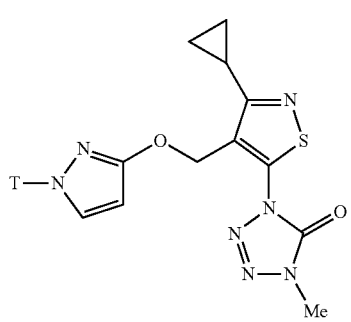
(HA1240)
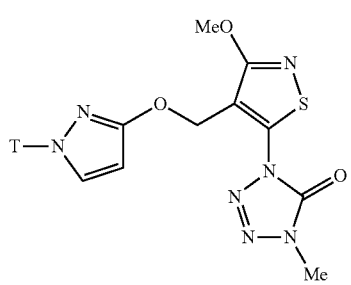
(HA1241)

199
-continued
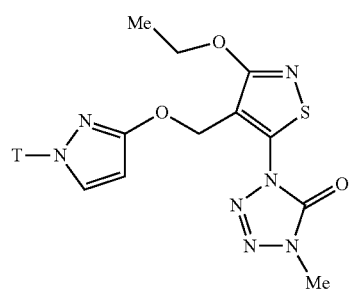
(HA1242)
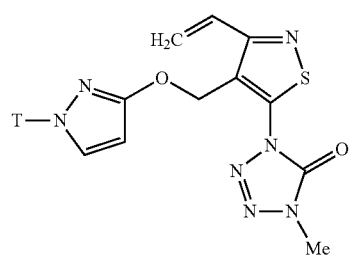
(HA1243)
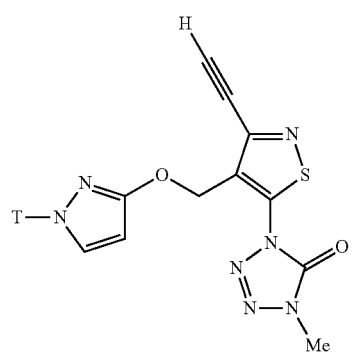
(HA1244)
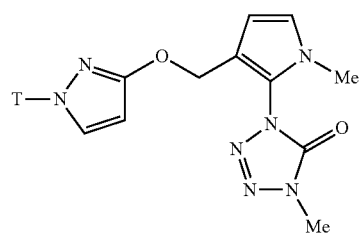
(HA1245)
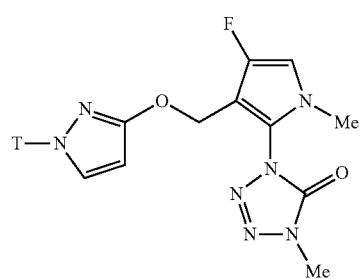
(HA1246)
200
-continued
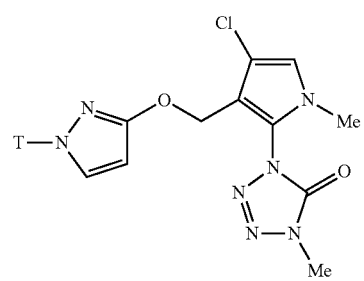
(HA1247)
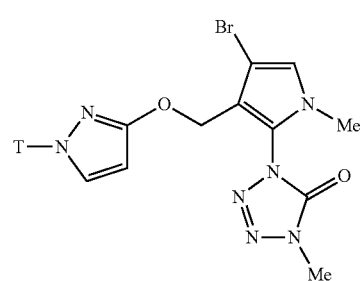
(HA1248)
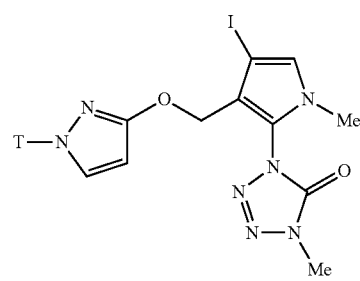
(HA1249)
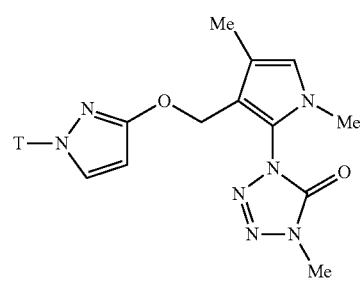
(HA1250)
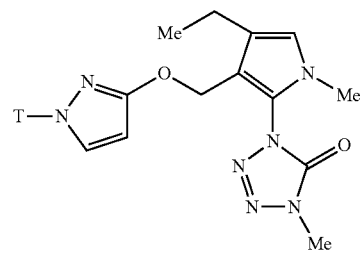
(HA1251)

-continued
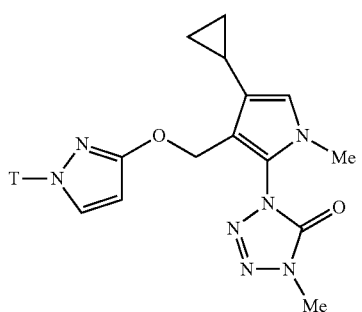
(HA1252)
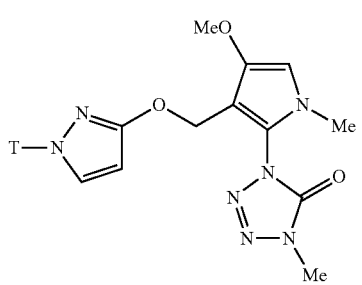
(HA1253)
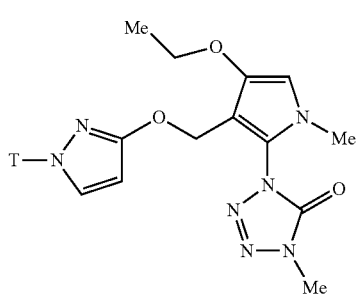
(HA1254)
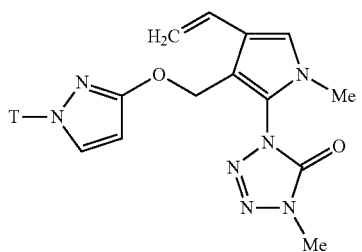
(HA1255)
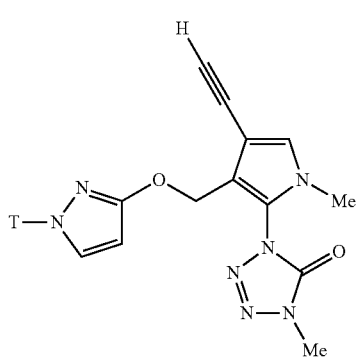
(HA1256)
-continued
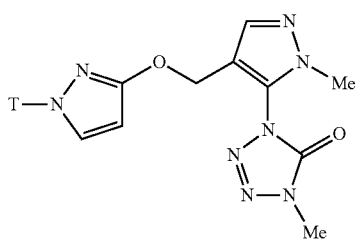
(HA1257)
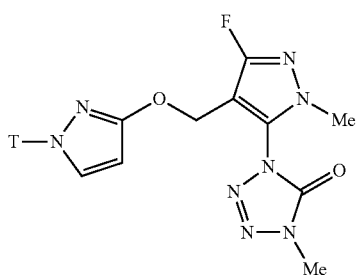
(HA1258)
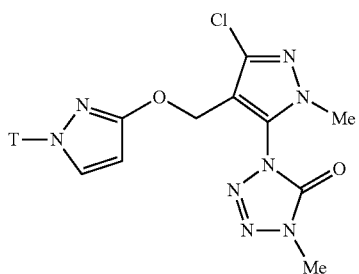
(HA1259)
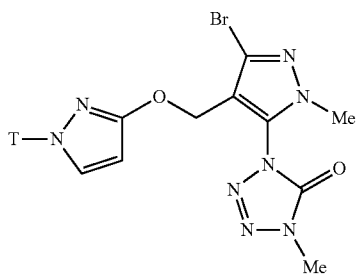
(HA1260)
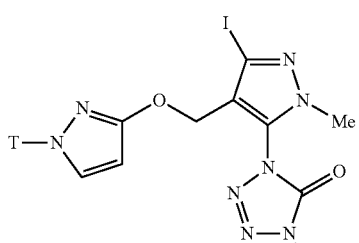
(HA1261)
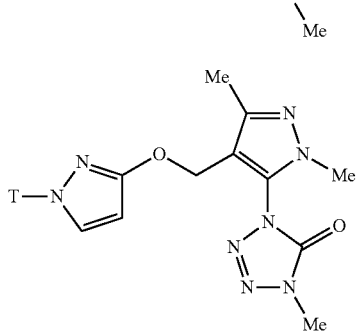
(HA1262)

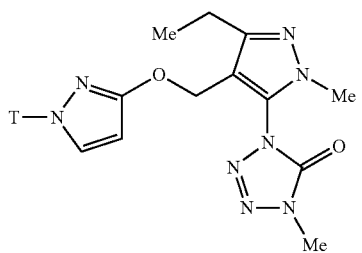
(HA1263)
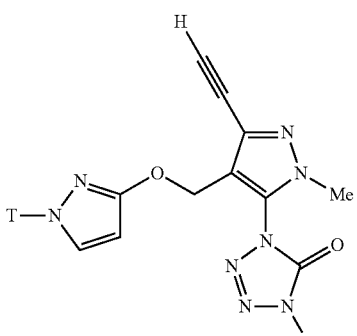
(HA1268)
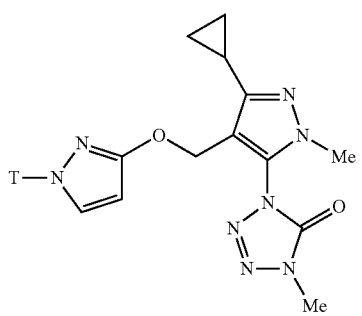
(HA1264)
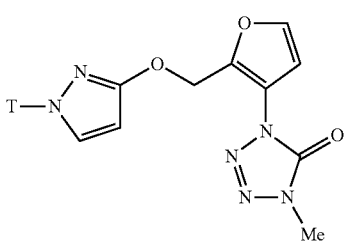
(HA1269)
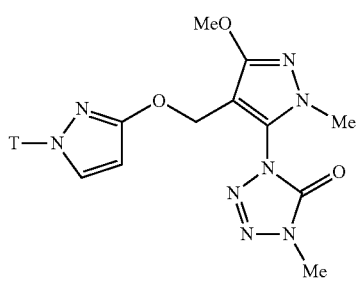
(HA1265)
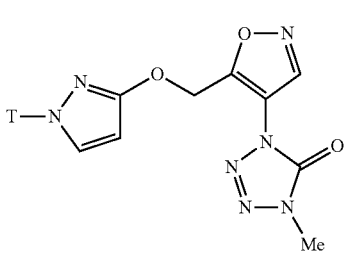
(HA1270)
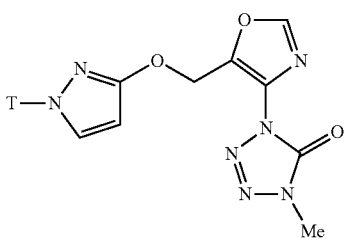
(HA1271)
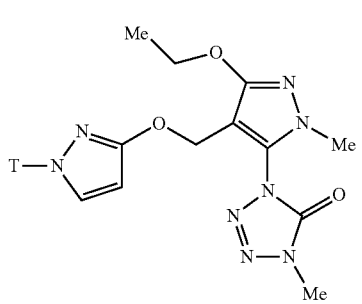
(HA1266)
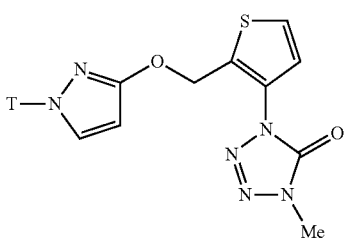
(HA1272)
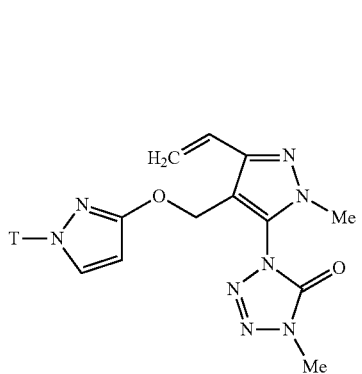
(HA1267)
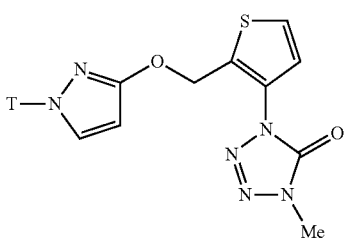
(HA1273)

(HA1274)
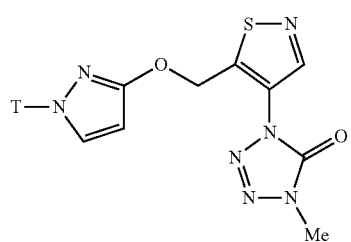
(HA1275)
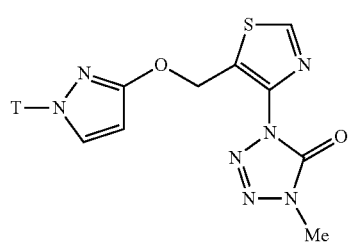
(HA1276)
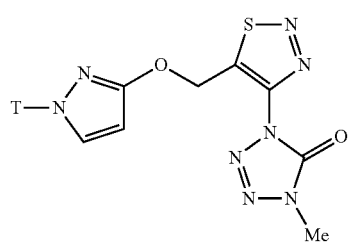
(HA1277)
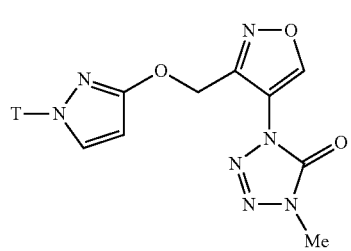
(HA1278)
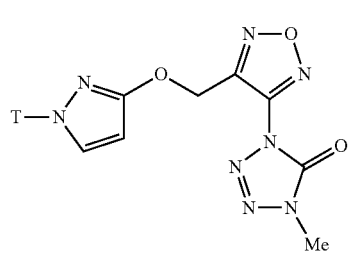
(HA1279)
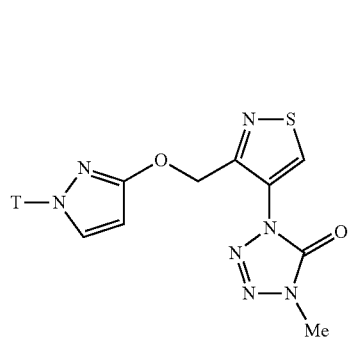
(HA1280)
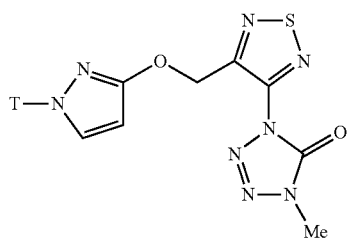
(HA1281)
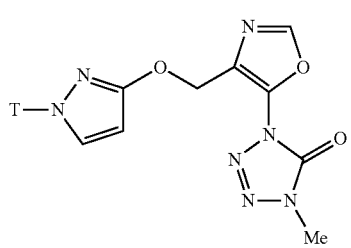
(HA1282)
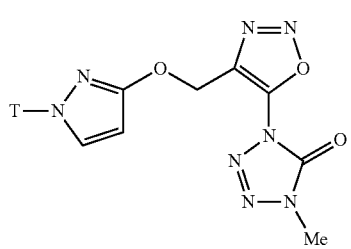
(HA1283)
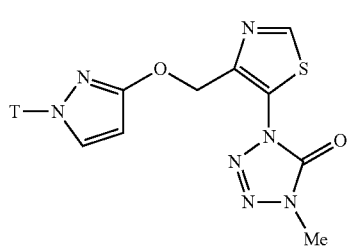
(HA1284)
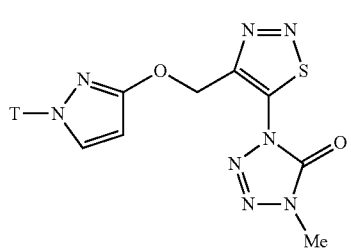
(HA1285)
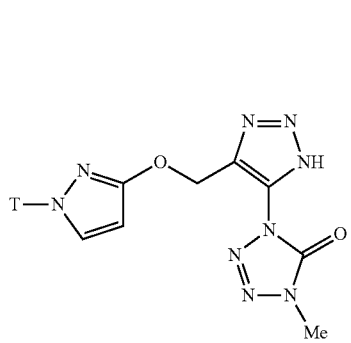

-continued
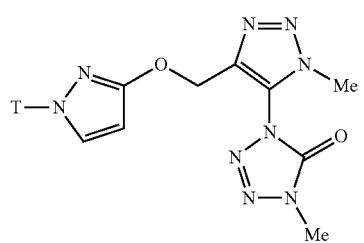 (HA1286)
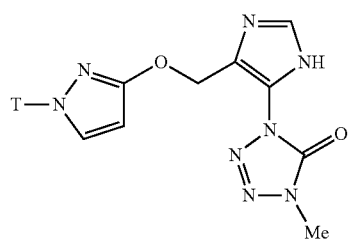 (HA1287)
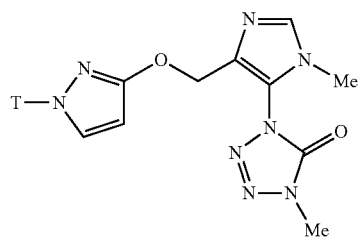 (HA1288)
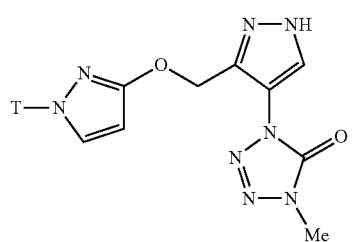 (HA1289)
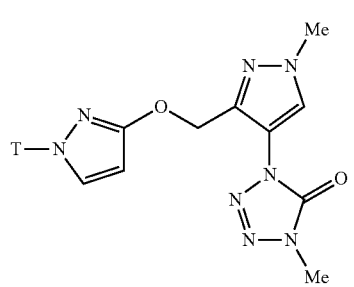 (HA1290)
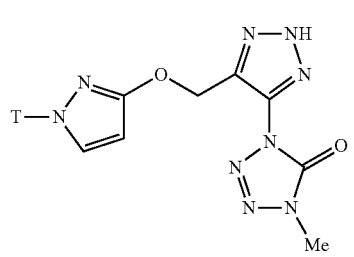 (HA1291)
-continued
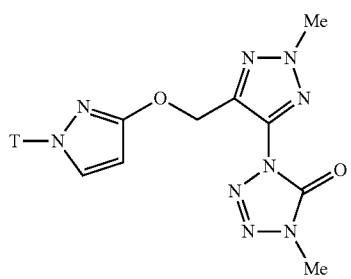 (HA1292)
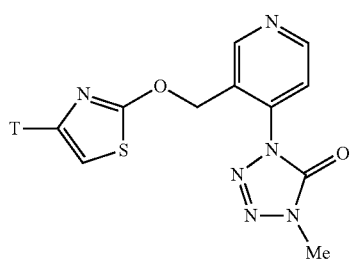 (HA2001)
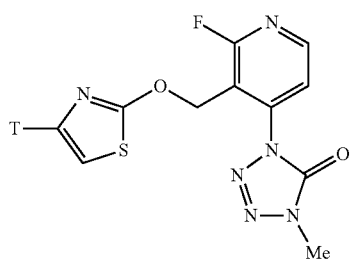 (HA2002)
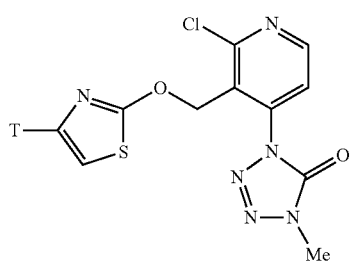 (HA2003)
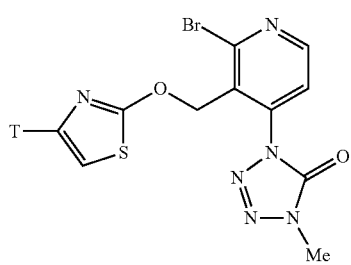 (HA2004)
(HA2005)

209
-continued
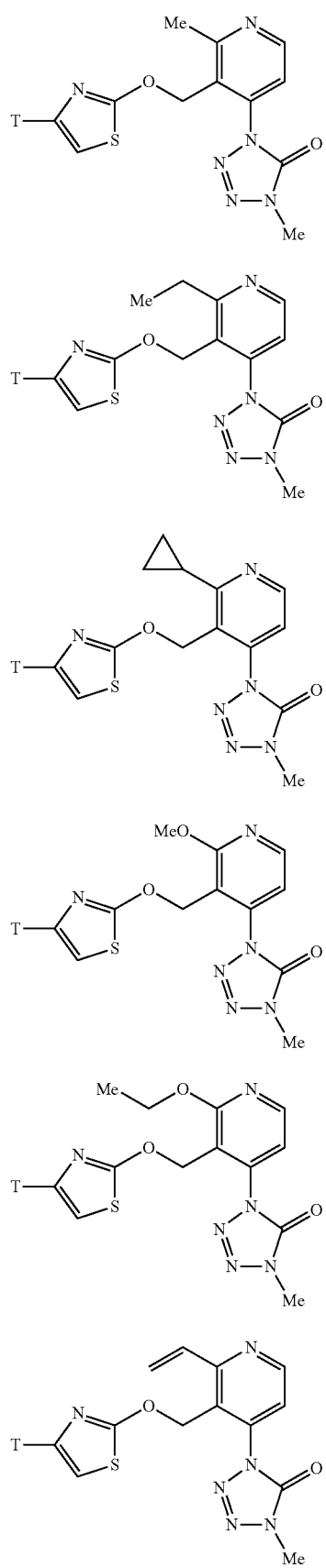
(HA2006)
(HA2007)
(HA2008)
(HA2009)
(HA2010)
(HA2011)
210
-continued
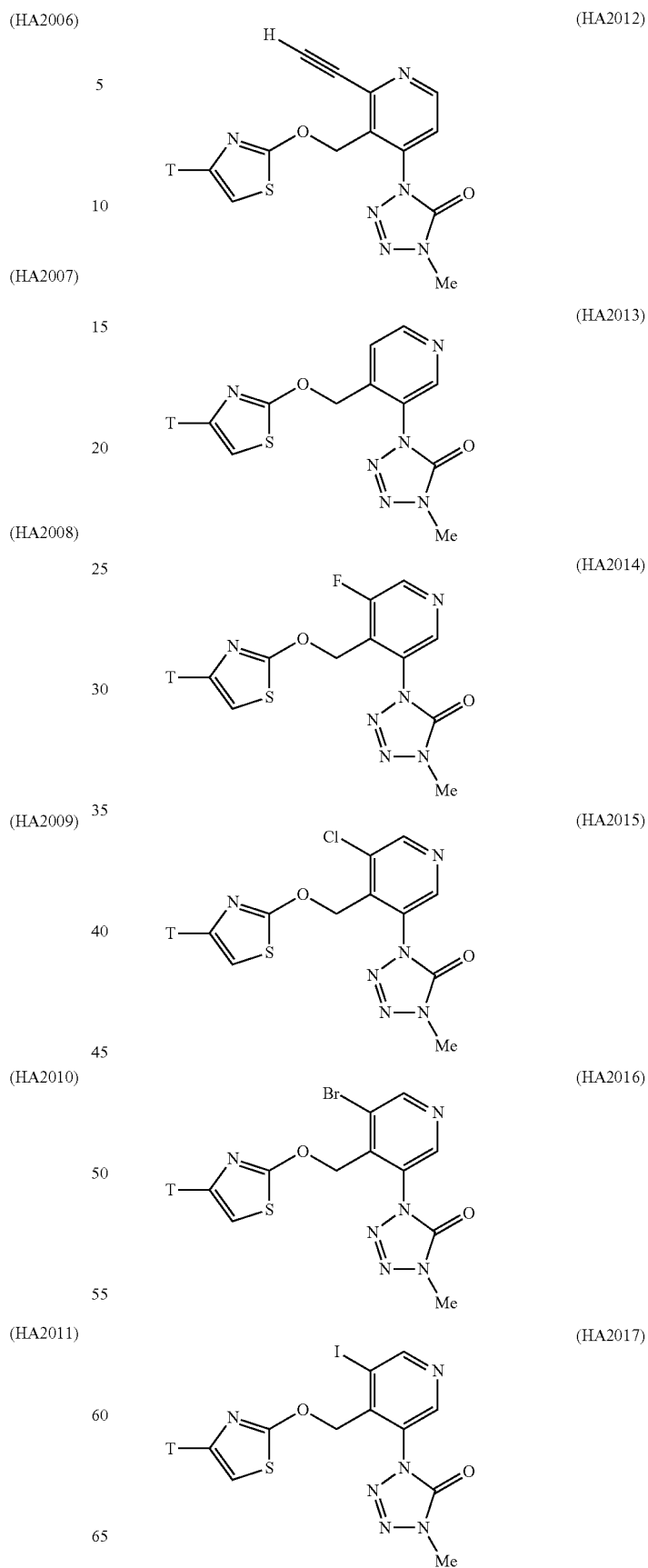
(HA2012)
(HA2013)
(HA2014)
(HA2015)
(HA2016)
(HA2017)

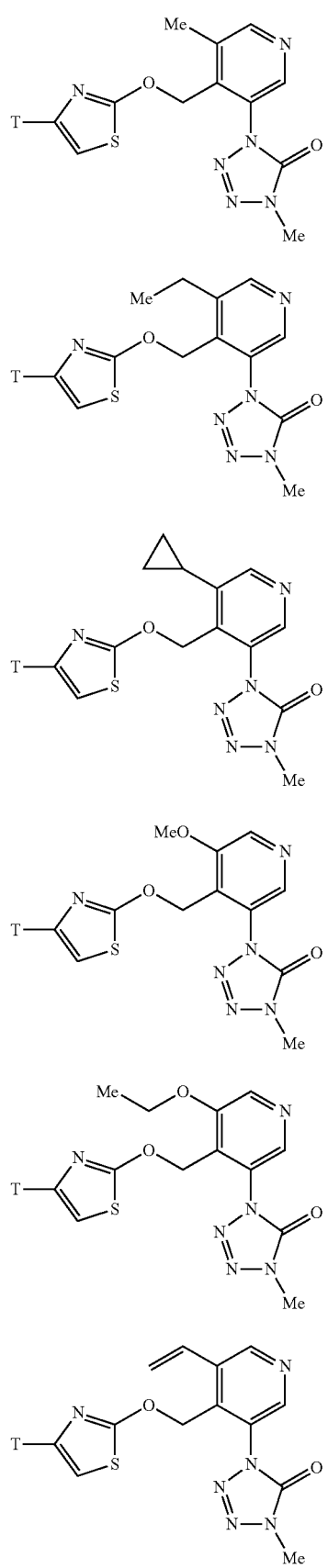
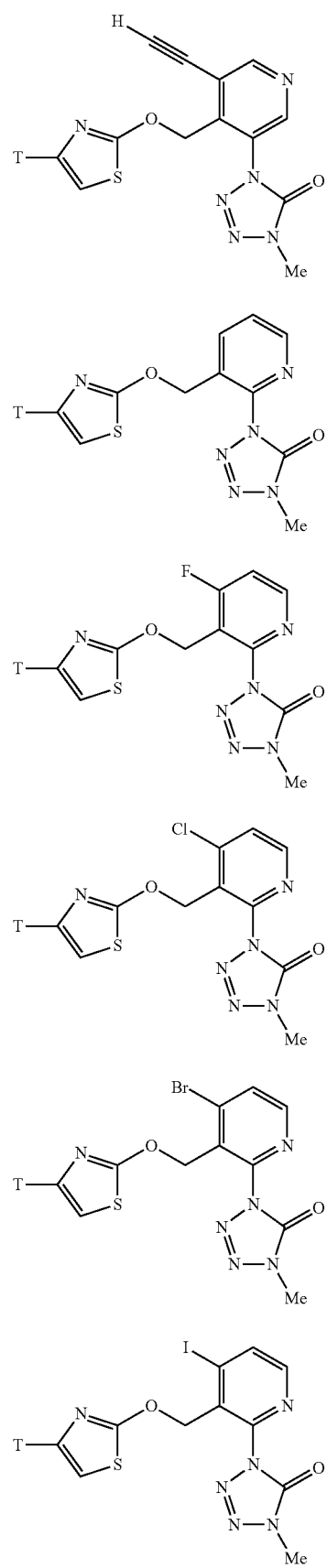

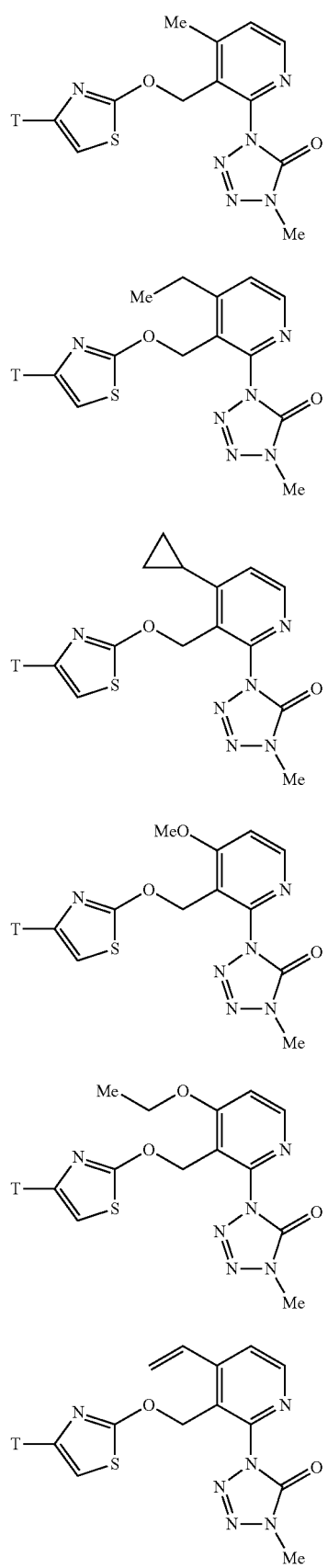
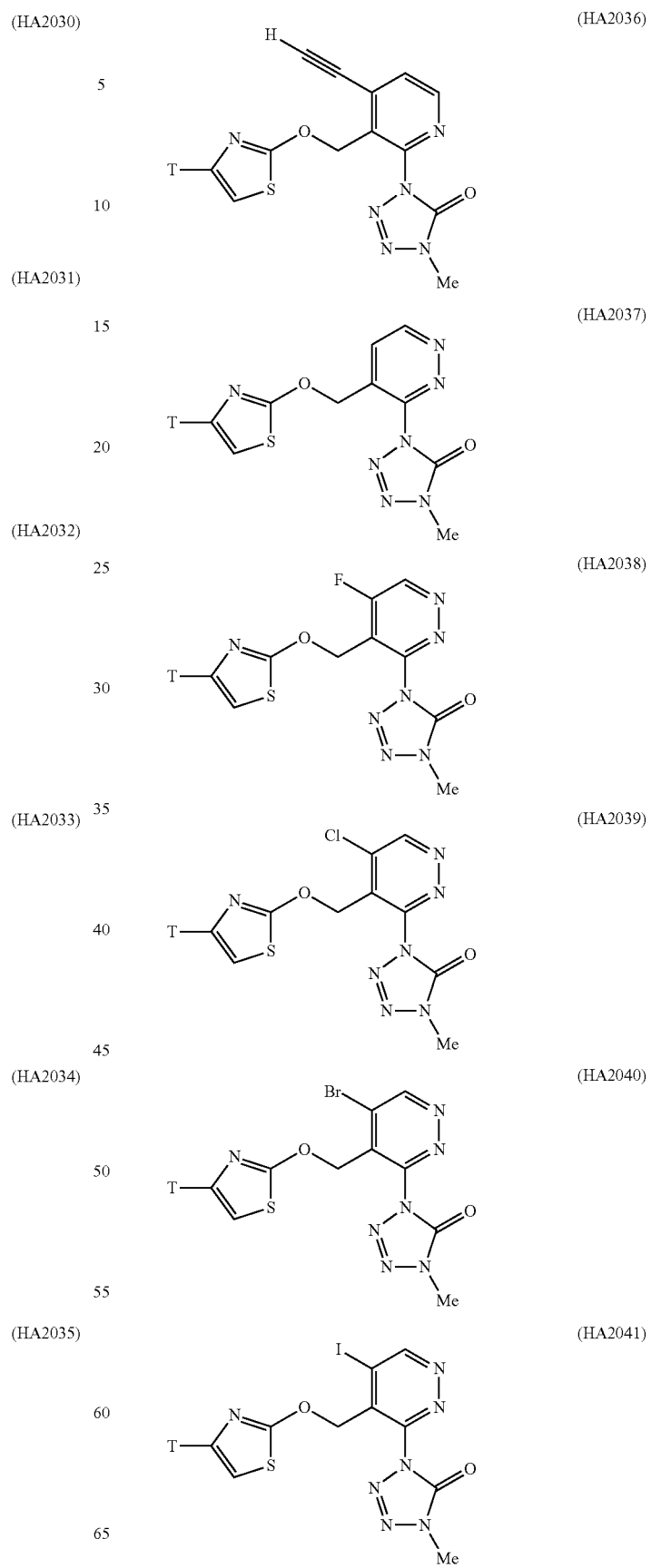

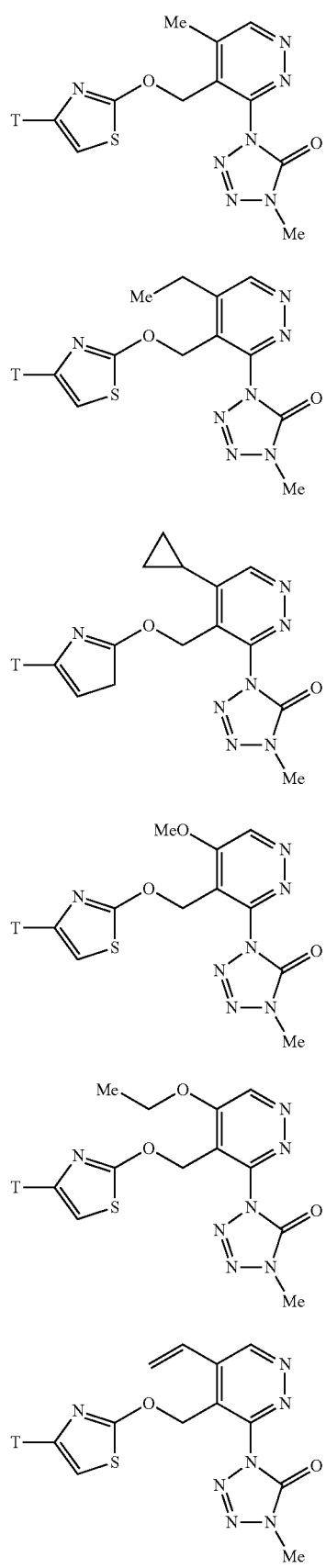
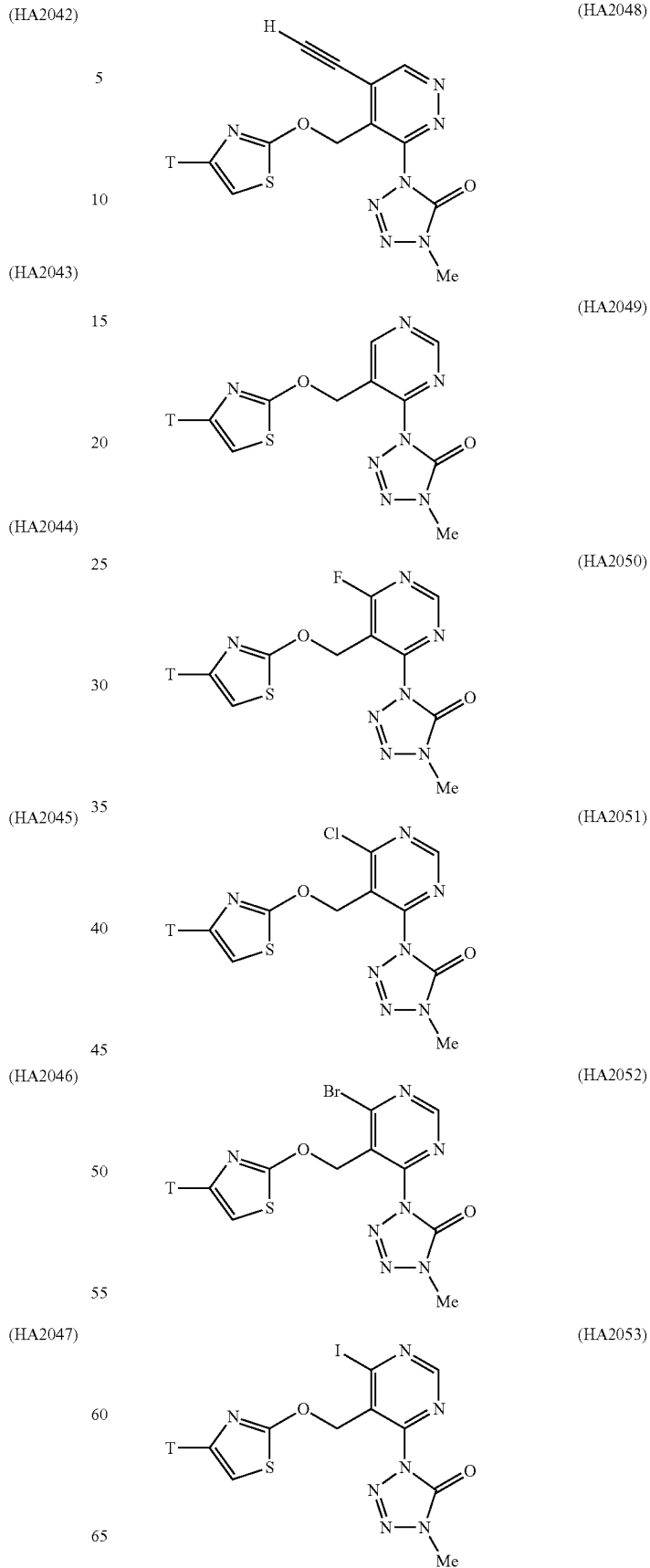

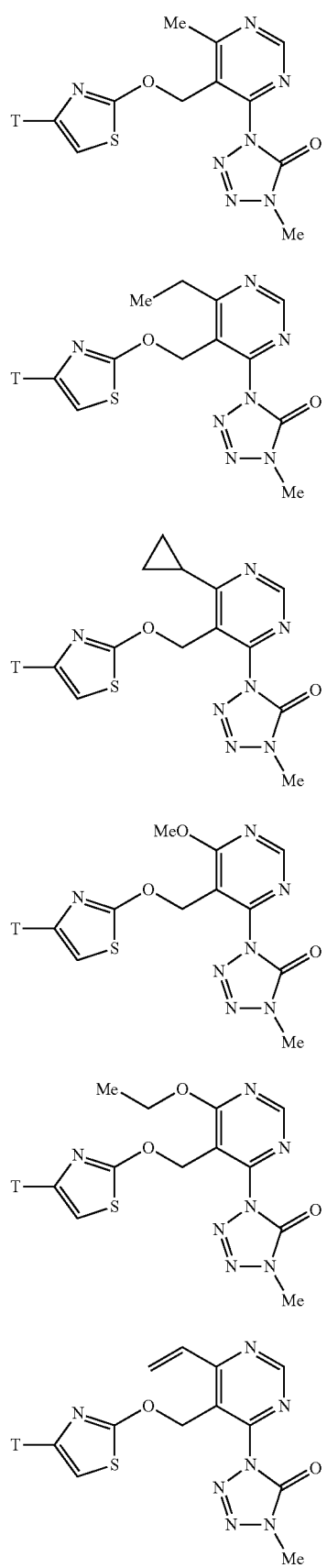
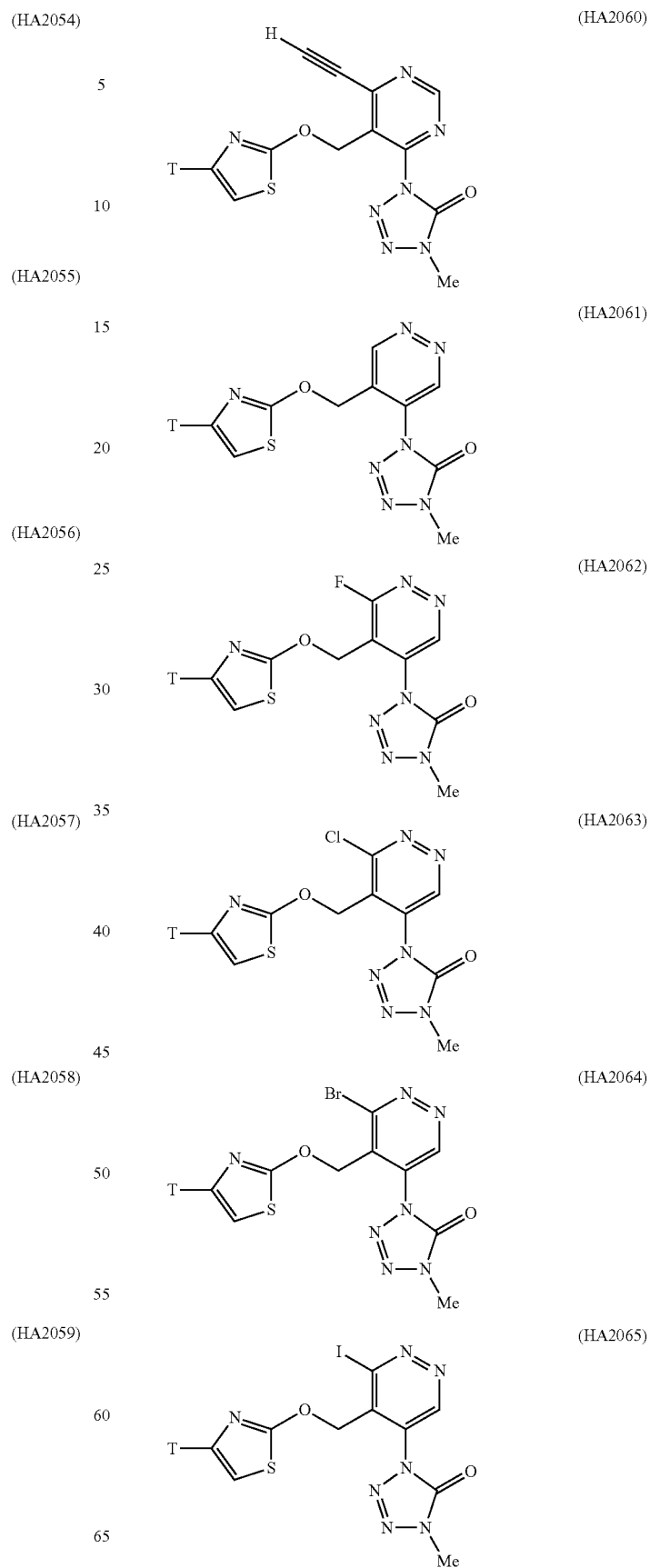

219
-continued
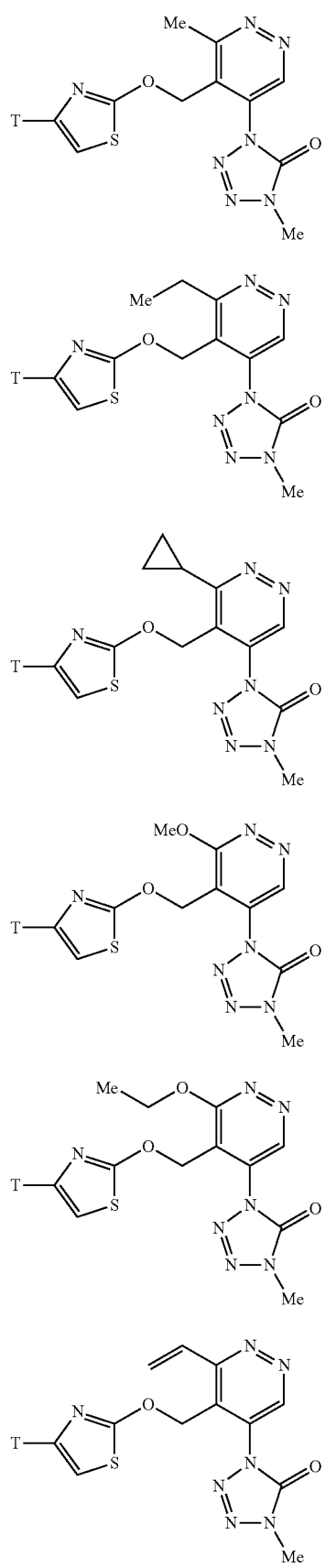
(HA2066)
(HA2067)
(HA2068)
(HA2069)
(HA2070)
(HA2071)
220
-continued
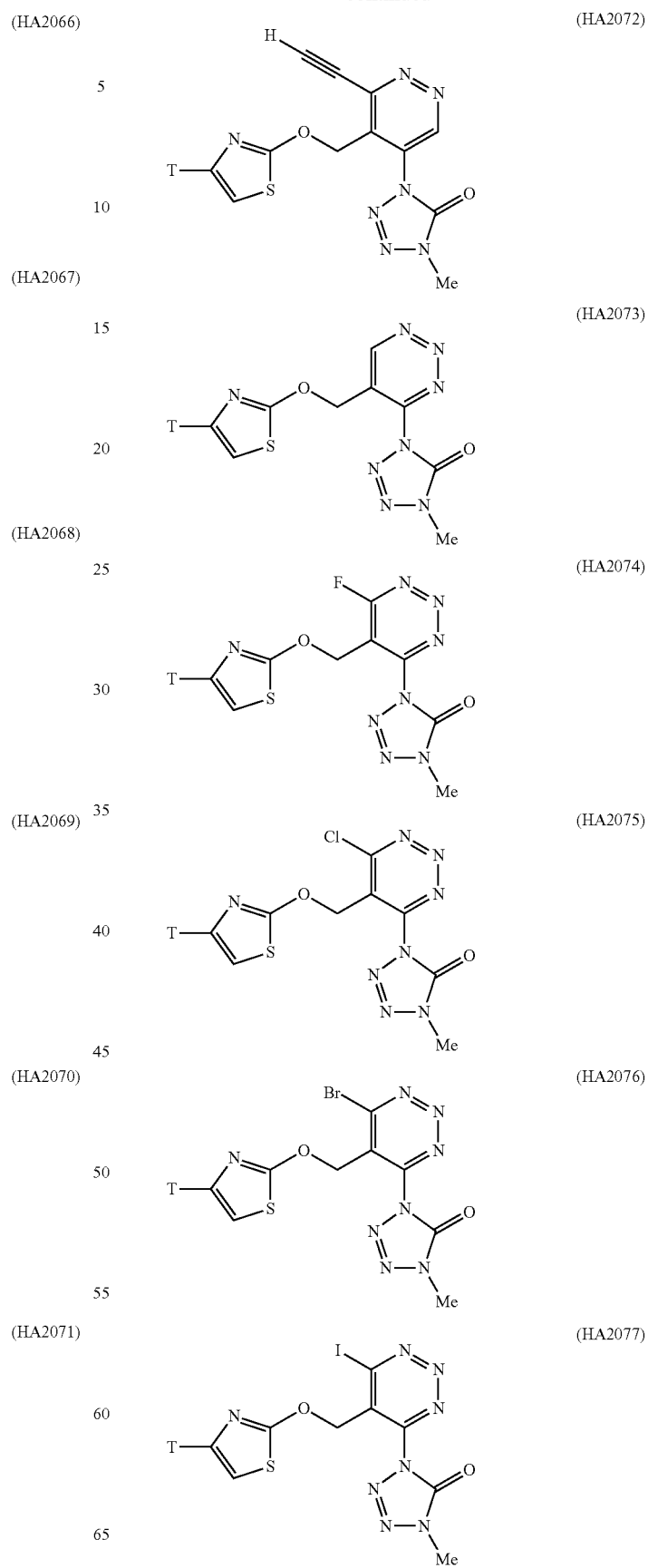
(HA2072)
(HA2073)
(HA2074)
(HA2075)
(HA2076)
(HA2077)

221
-continued
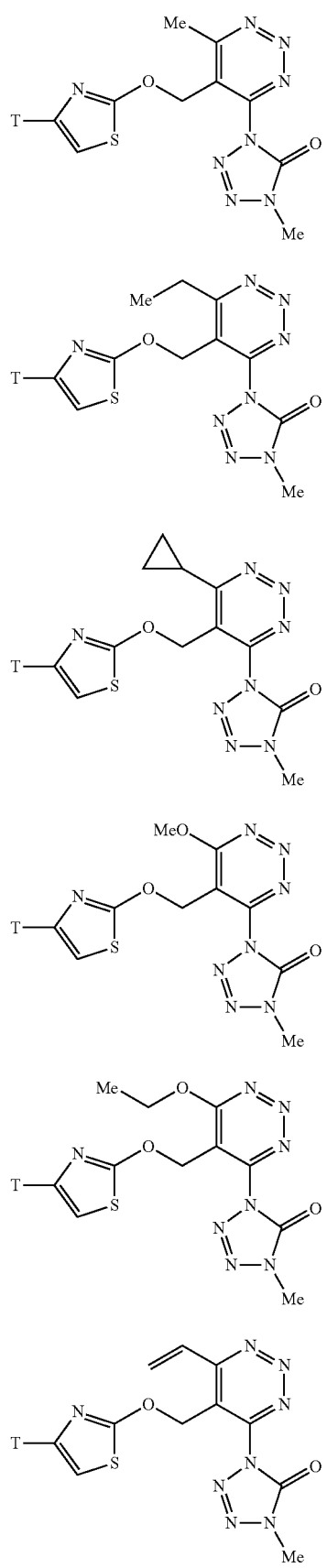
(HA2078)
(HA2079)
(HA2080)
(HA2081)
(HA2082)
(HA2083)
222
-continued
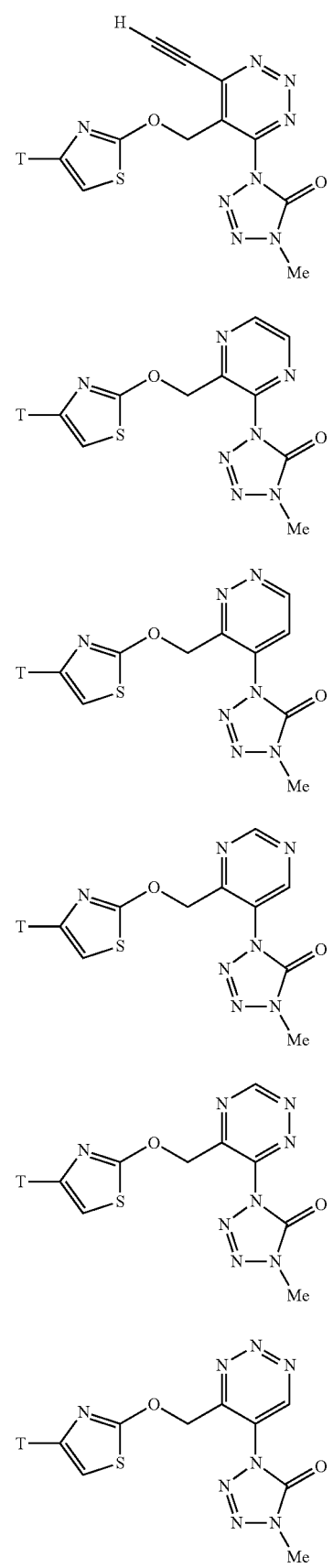
(HA2084)
(HA2085)
(HA2086)
(HA2087)
(HA2088)
(HA2089)

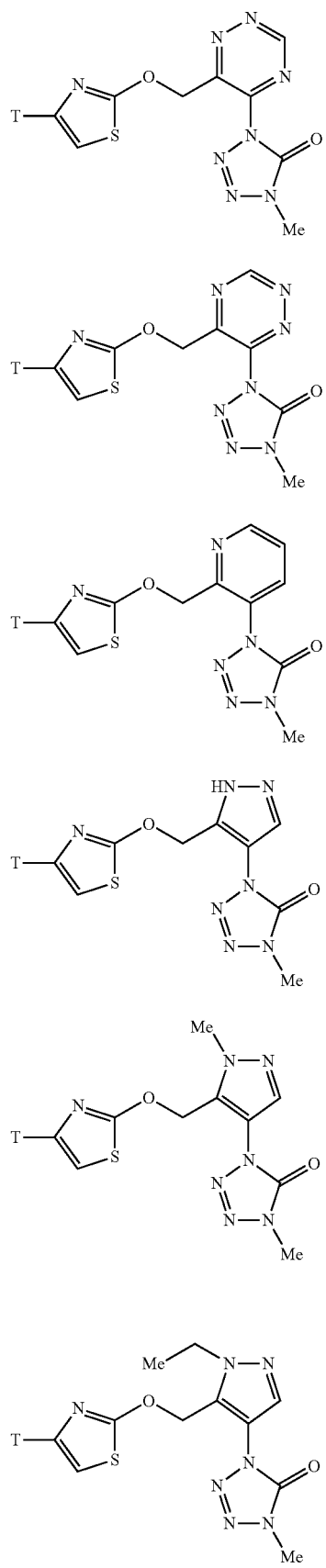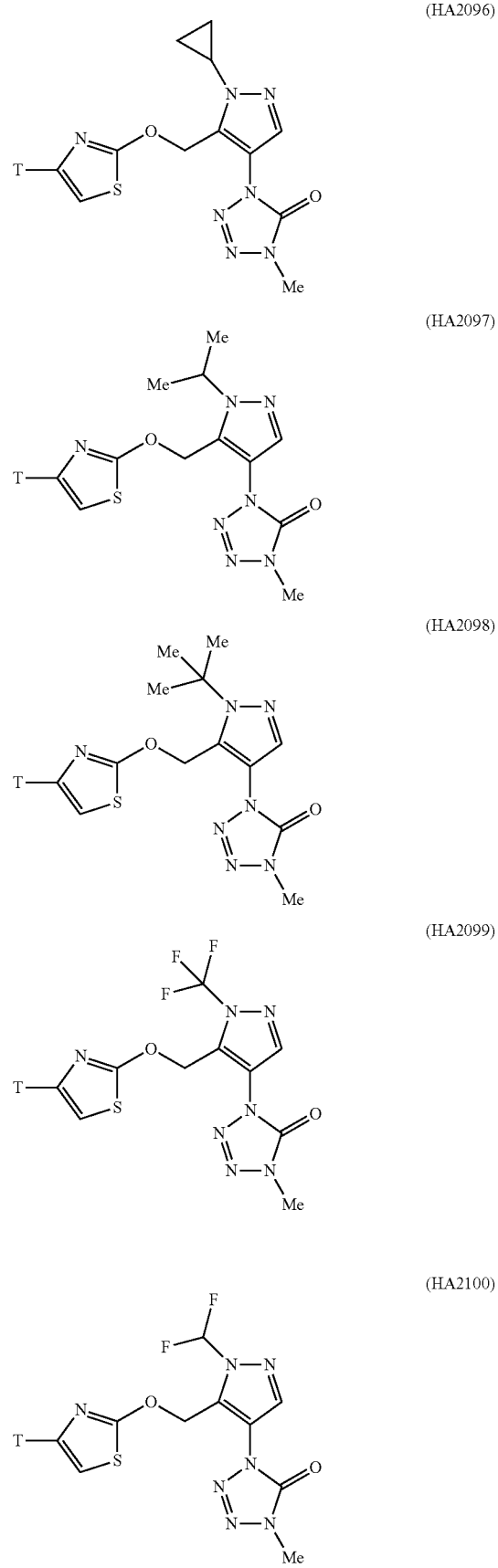

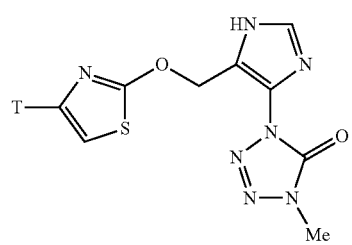
(HA2101)
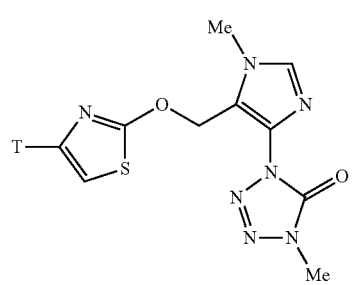
(HA2102)
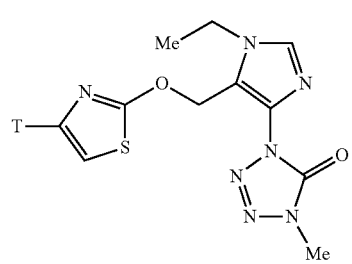
(HA2103)
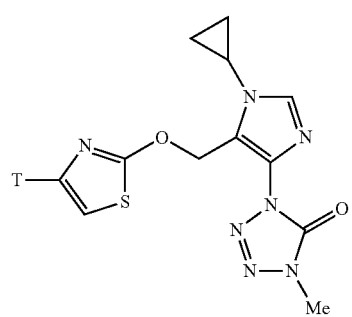
(HA2104)
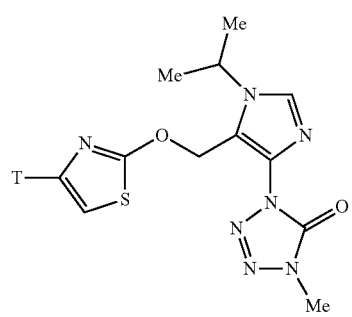
(HA2105)
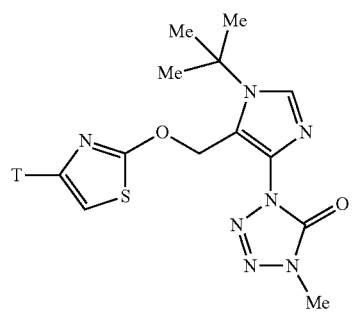
(HA2106)
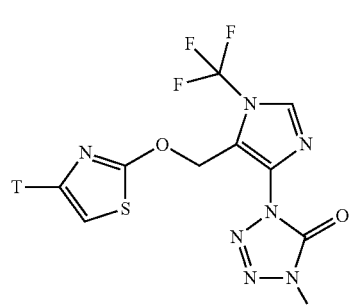
(HA2107)
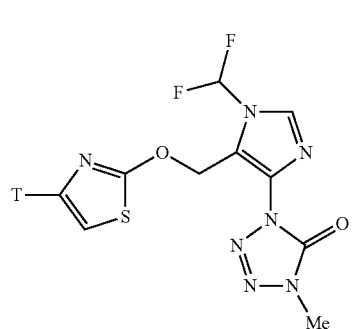
(HA2108)
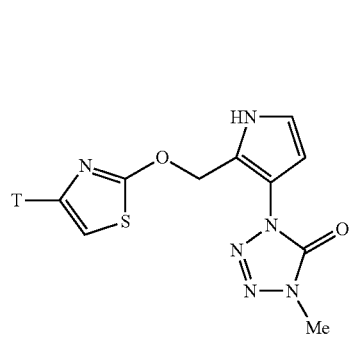
(HA2109)
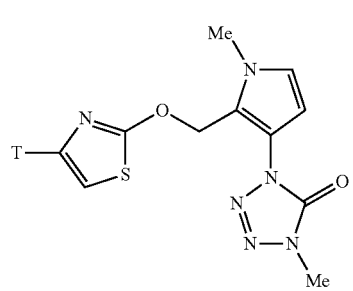
(HA2110)

227
-continued
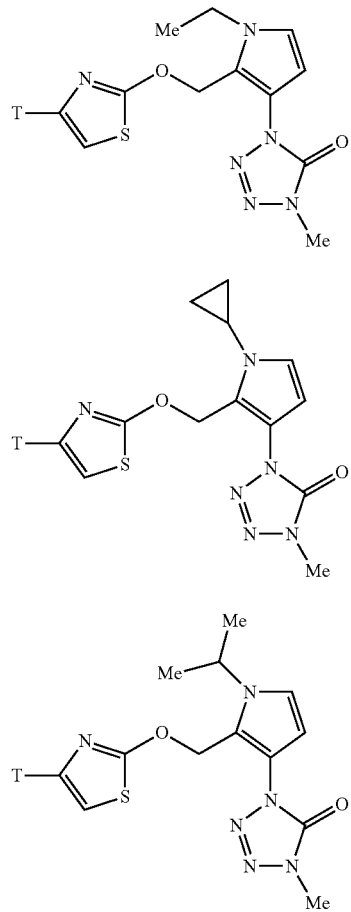
(HA2111)
(HA2112)
(HA2113)
(HA2114)
(HA2115)
228
-continued
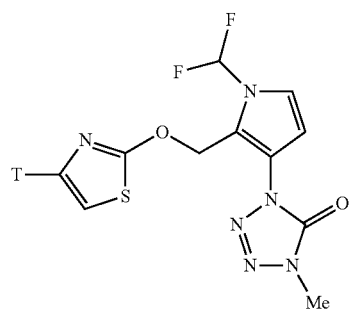
(HA2116)
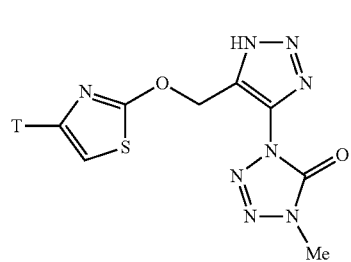
(HA2117)
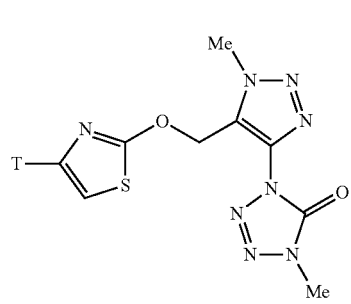
(HA2118)
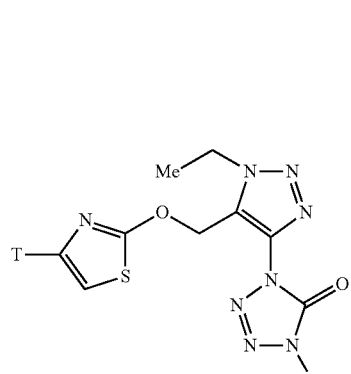
(HA2119)
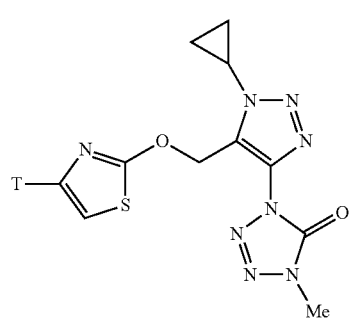
(HA2120)

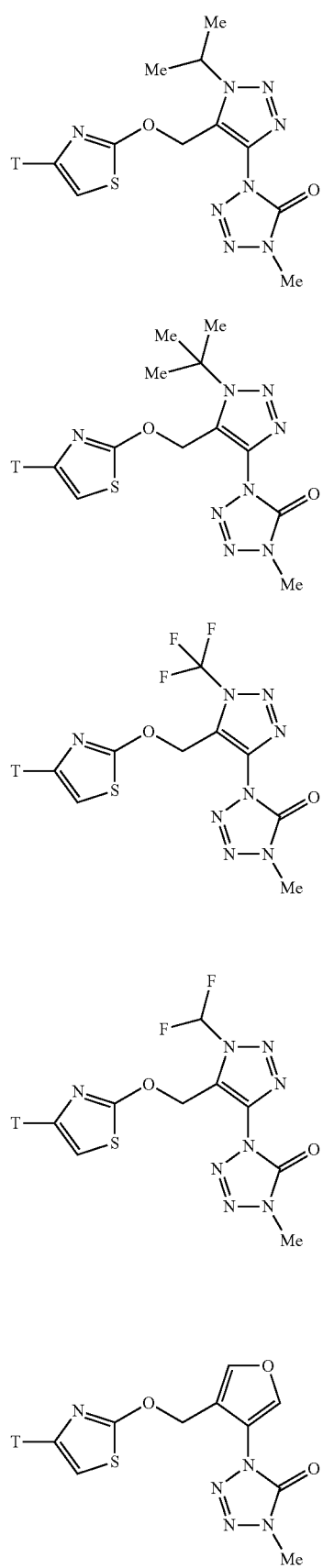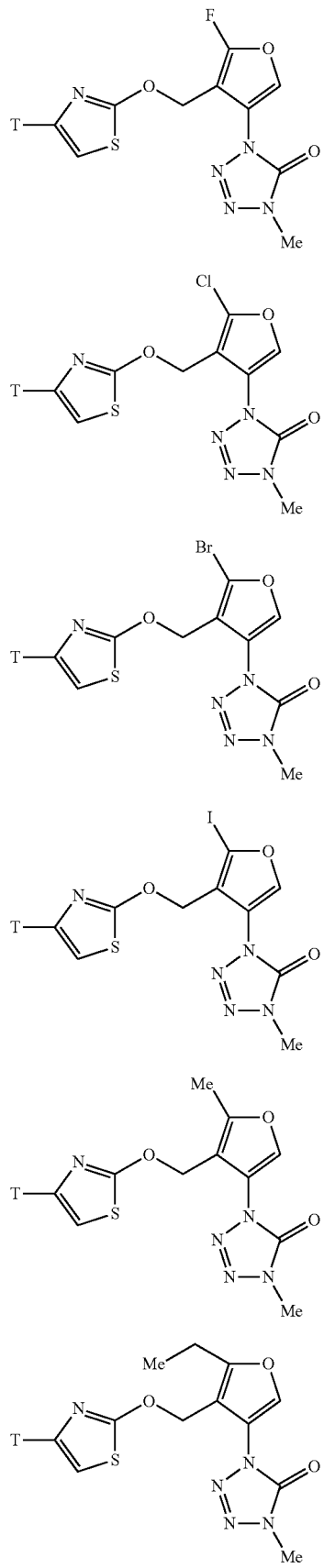

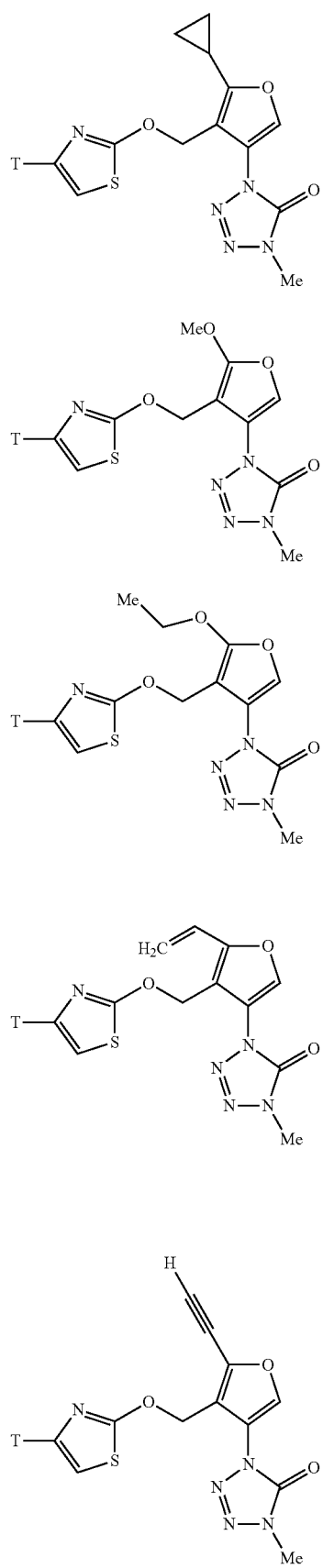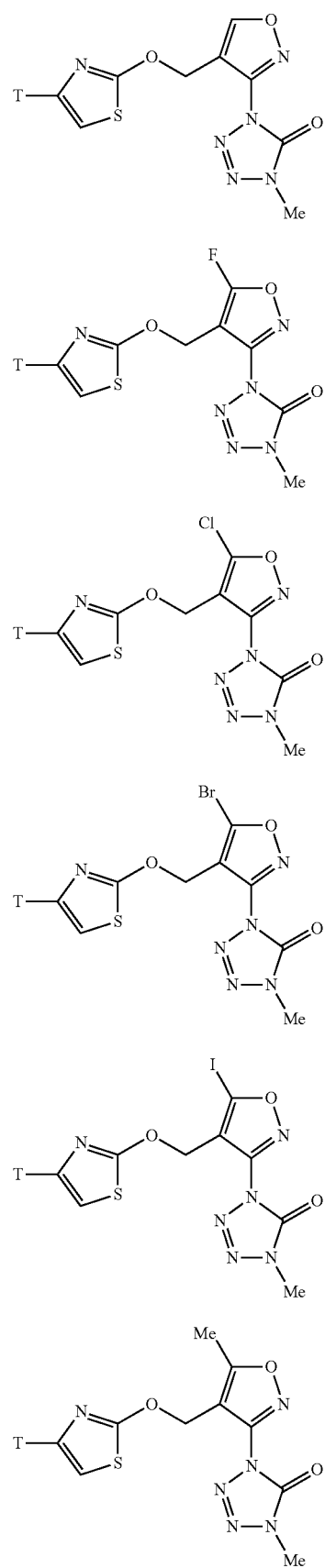

233
-continued
(HA2143)
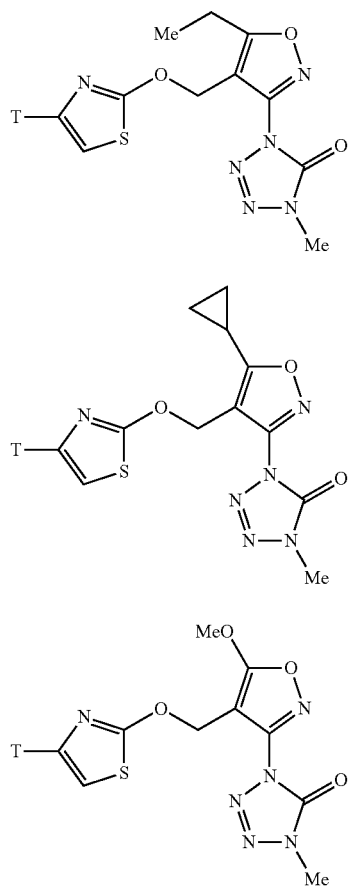
(HA2144)
(HA2145)
(HA2146)
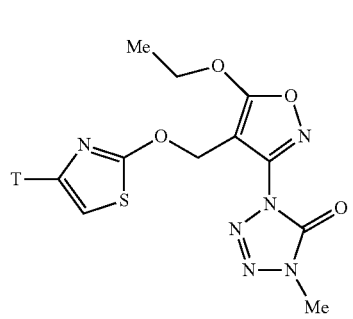
(HA2147)
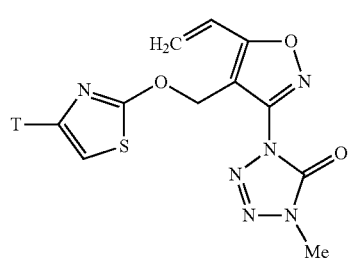
234
-continued
(HA2148)
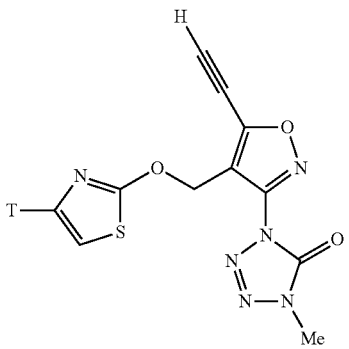
(HA2149)
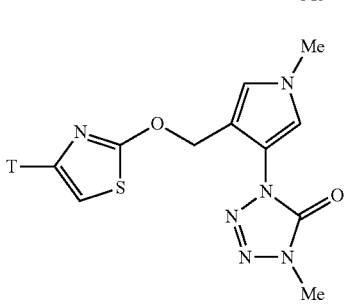
(HA2150)
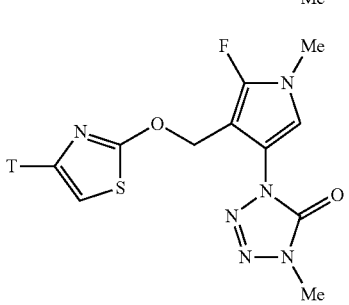
(HA2151)
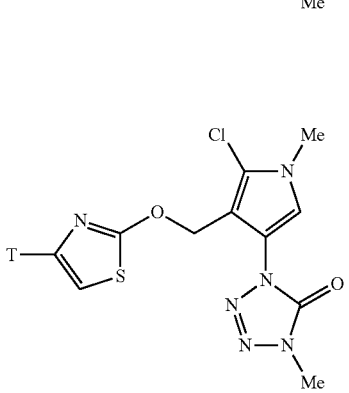
(HA2152)
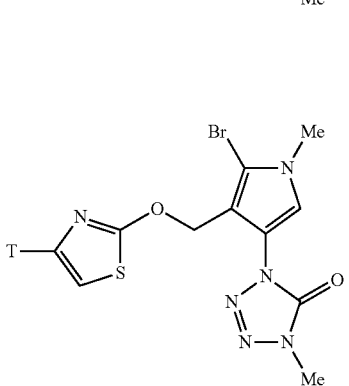

-continued
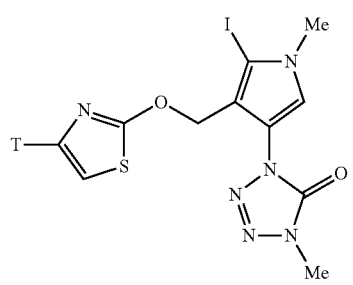
(HA2153)
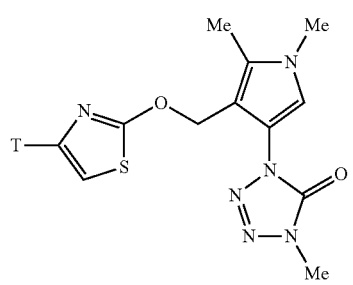
(HA2154)
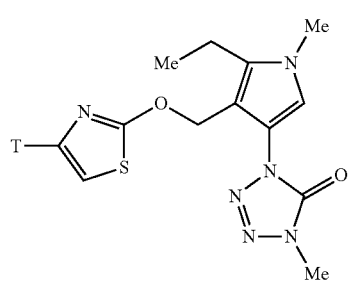
(HA2155)
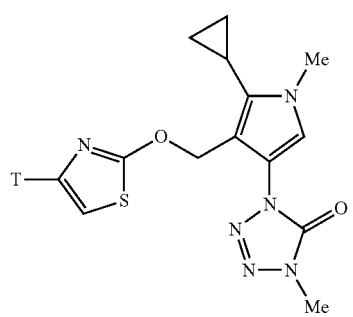
(HA2156)
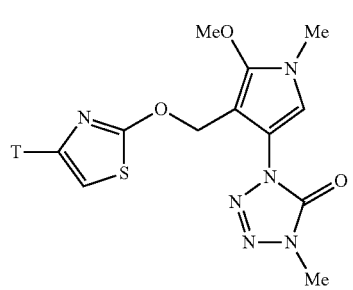
(HA2157)
-continued
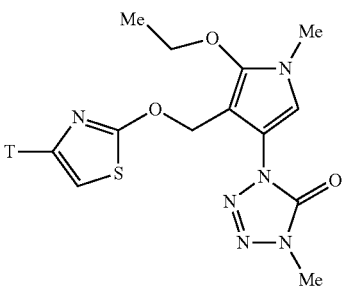
(HA2158)
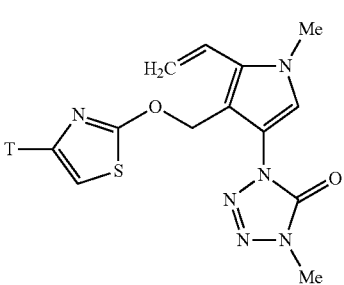
(HA2159)
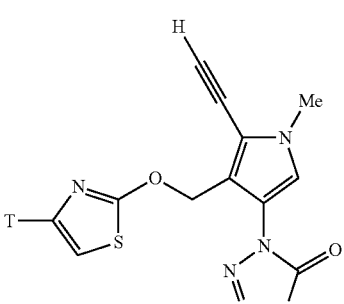
(HA2160)
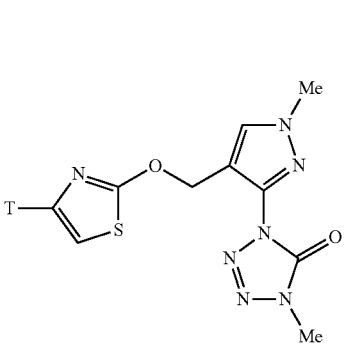
(HA2161)
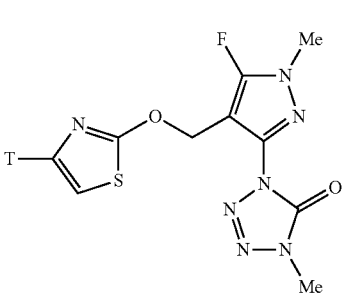
(HA2162)

-continued
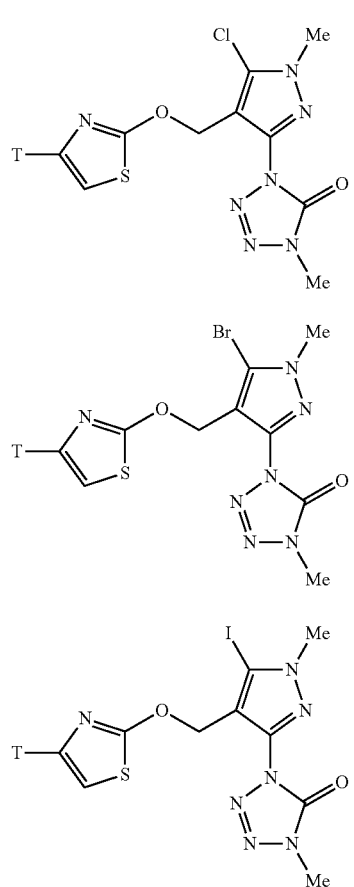
(HA2163)
(HA2164)
(HA2165)
(HA2166)
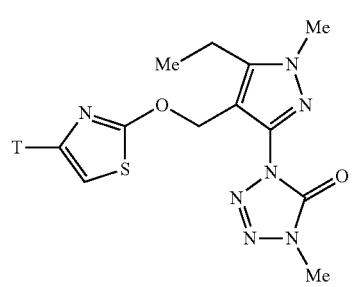
(HA2167)
-continued
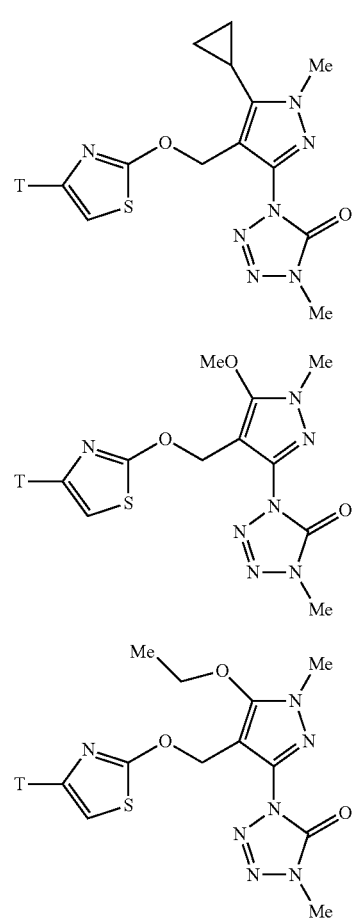
(HA2168)
(HA2169)
(HA2170)
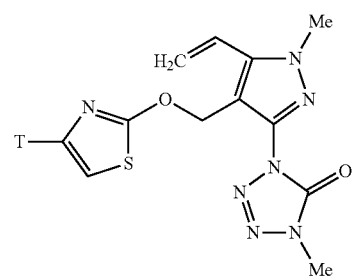
(HA2171)
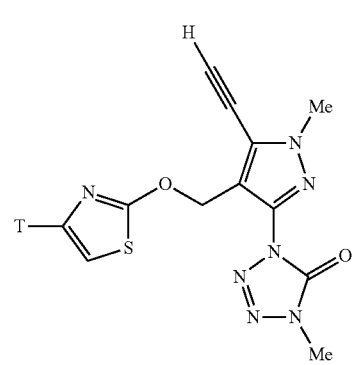
(HA2172)

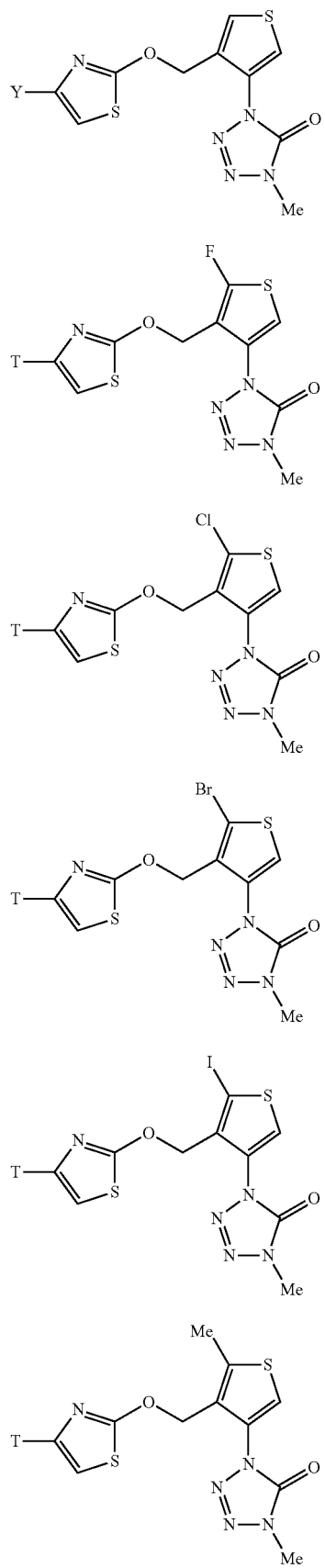
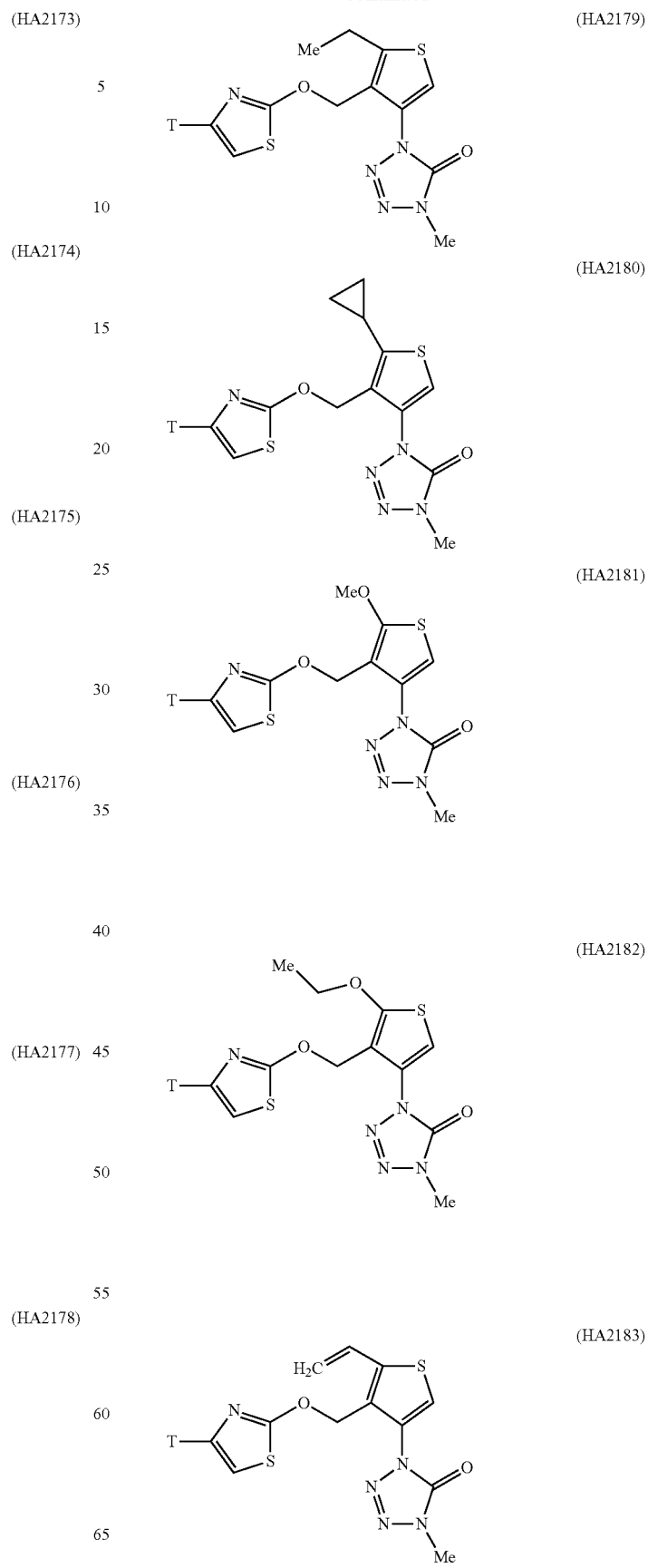

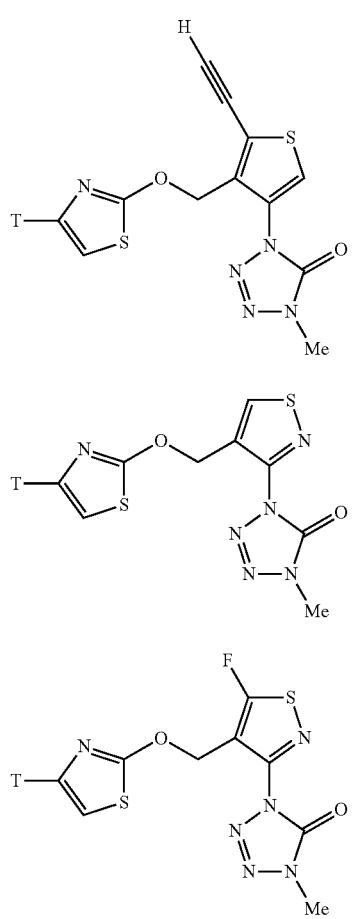
(HA2184)
(HA2185)
(HA2186)
(HA2187)
(HA2188)
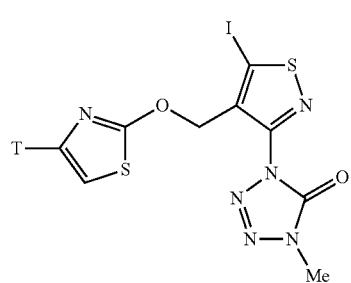
(HA2189)
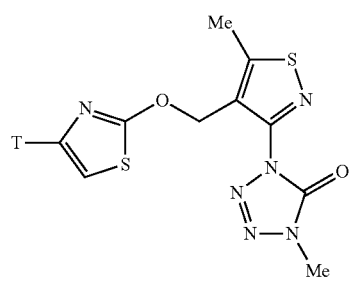
(HA2190)
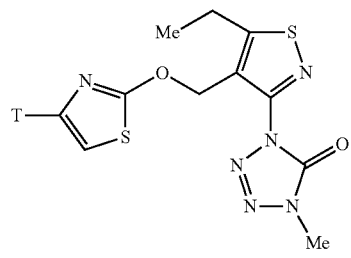
(HA2191)
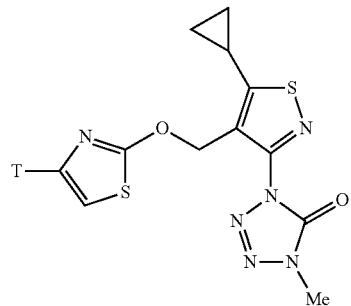
(HA2192)
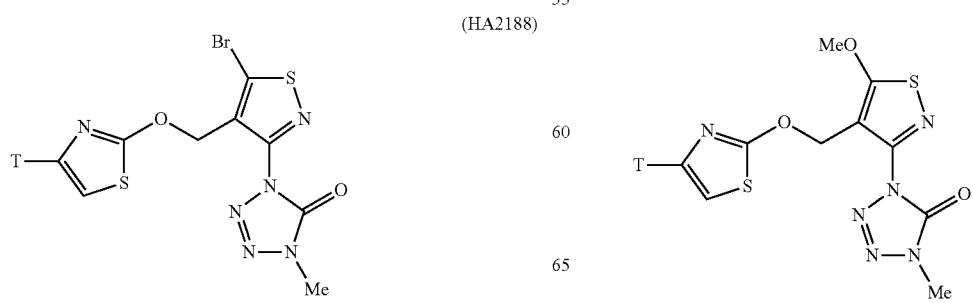
(HA2193)

243
-continued
(HA2194)
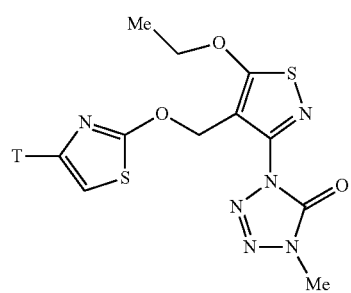
(HA2195)
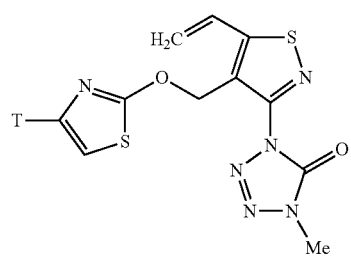
(HA2196)
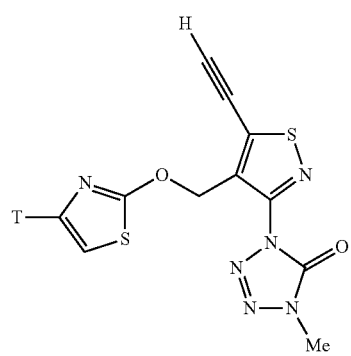
(HA2197)
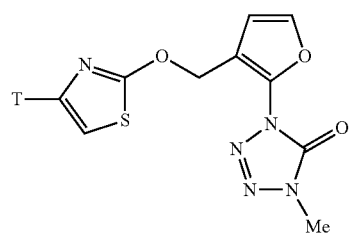
(HA2198)
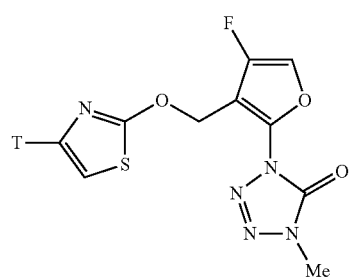
244
-continued
(HA2199)
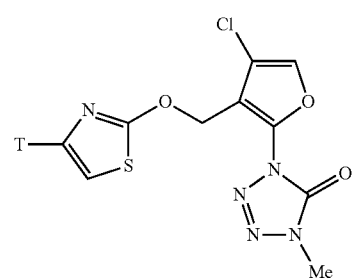
(HA2200)
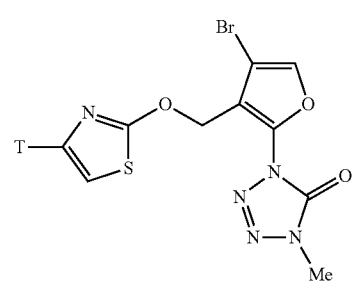
(HA2201)
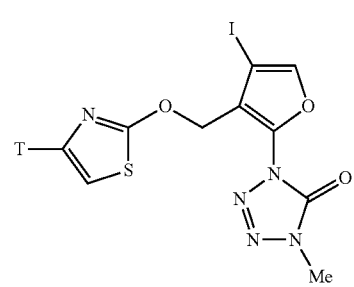
(HA2202)
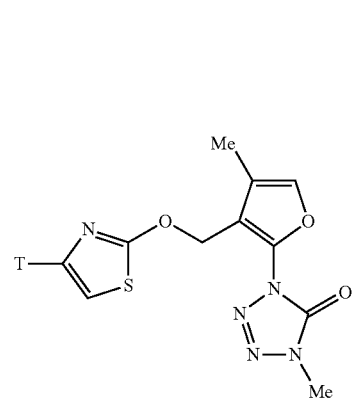
(HA2203)
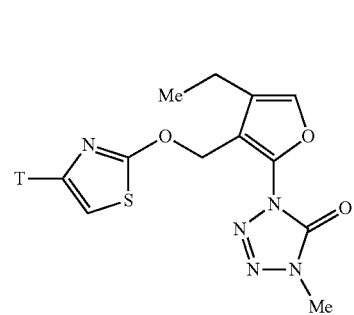

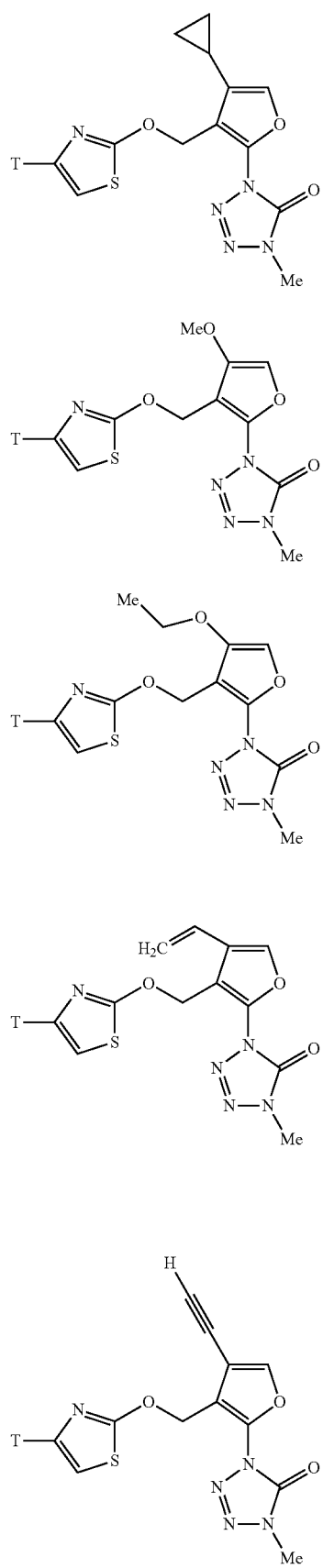
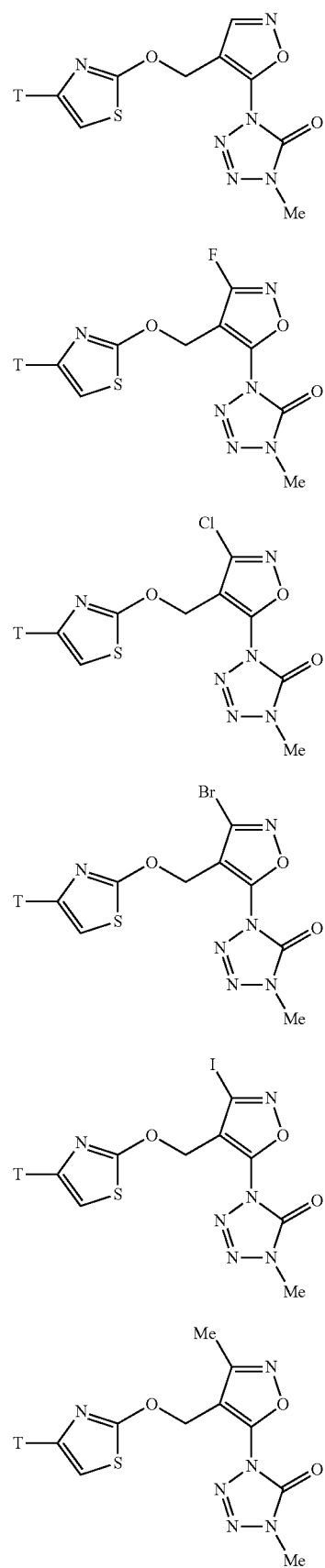

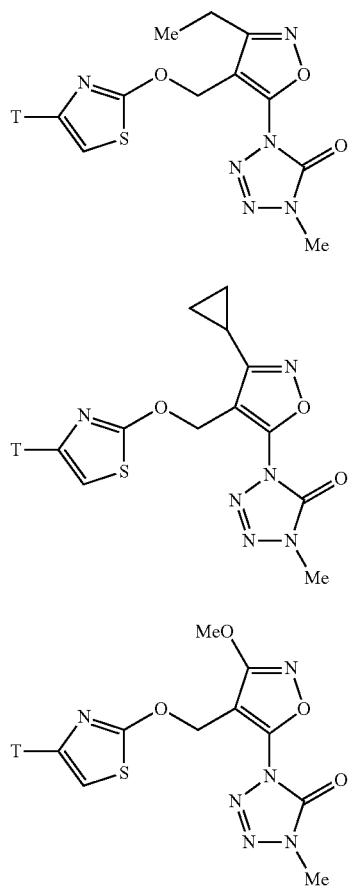
(HA2215)
(HA2216)
(HA2217)
(HA2218)
(HA2219)
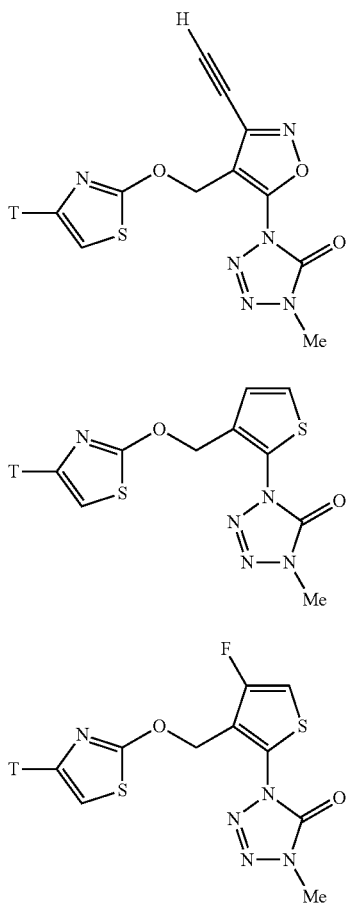
(HA2220)
(HA2221)
(HA2222)
(HA2223)
(HA2224)

(HA2225) 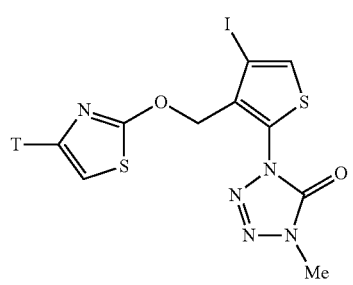
(HA2226) 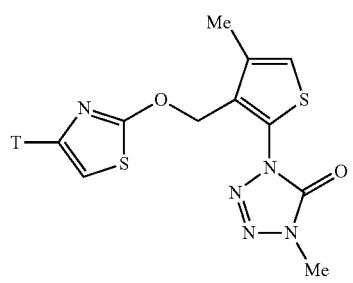
(HA2227) 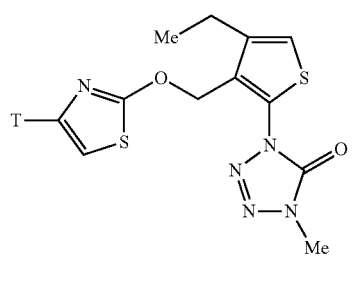
(HA2228) 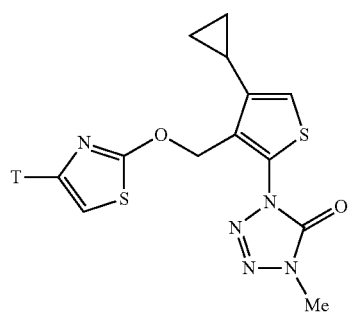
(HA2229) 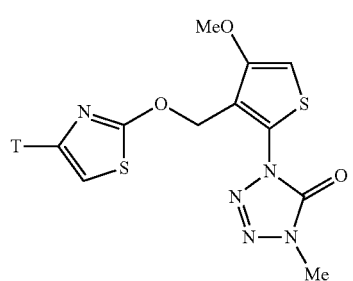
(HA2230) 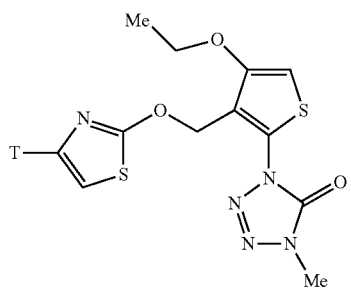
(HA2231) 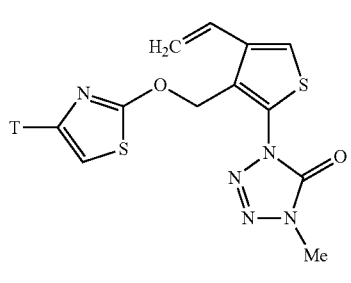
(HA2232) 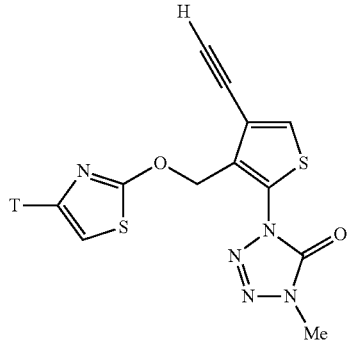
(HA2233) 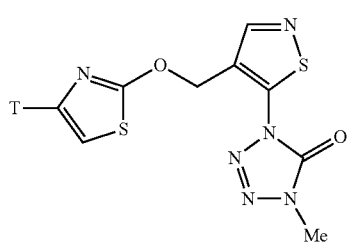
(HA2234) 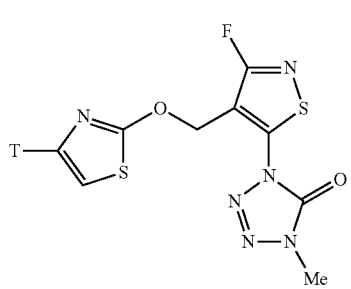

(HA2235)
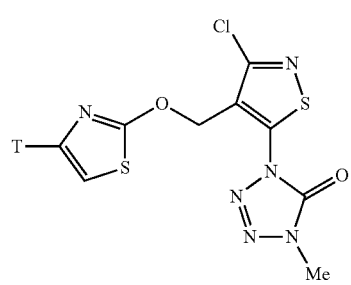
(HA2240)
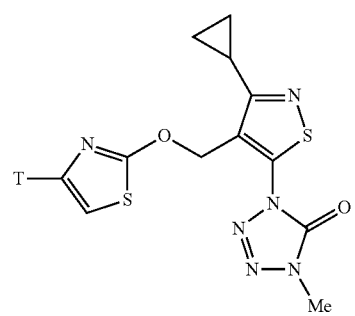
(HA2236)
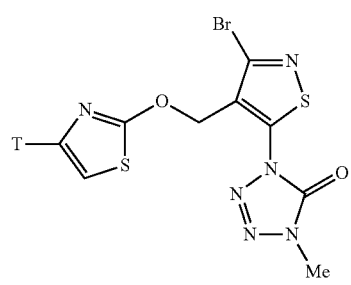
(HA2241)
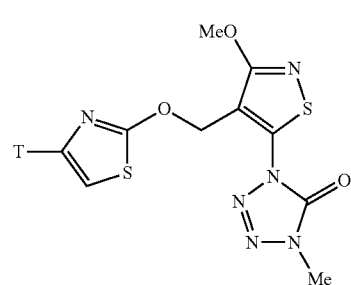
(HA2237)
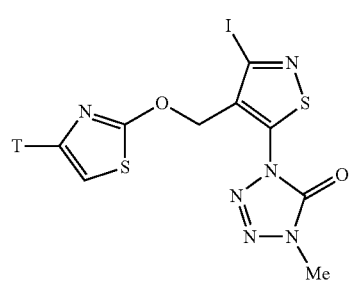
(HA2242)
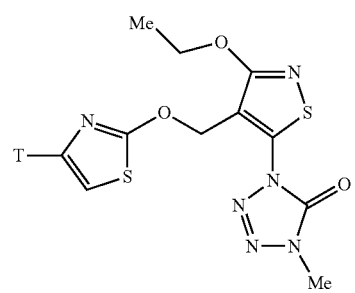
(HA2238)
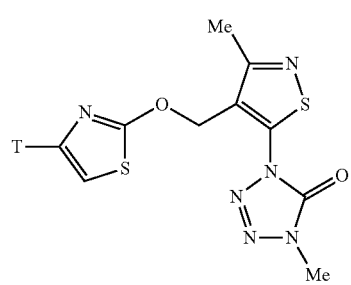
(HA2243)
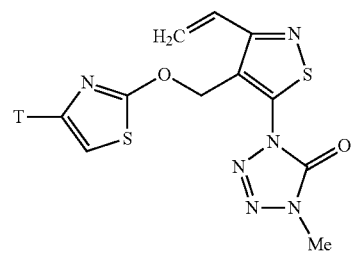
(HA2239)
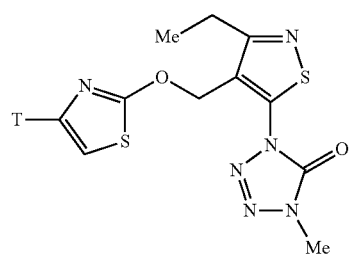
(HA2244)
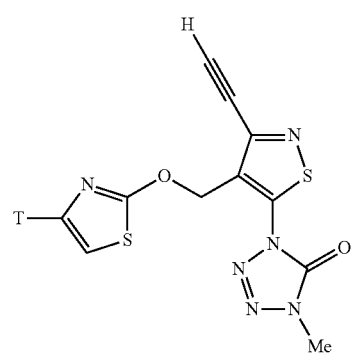

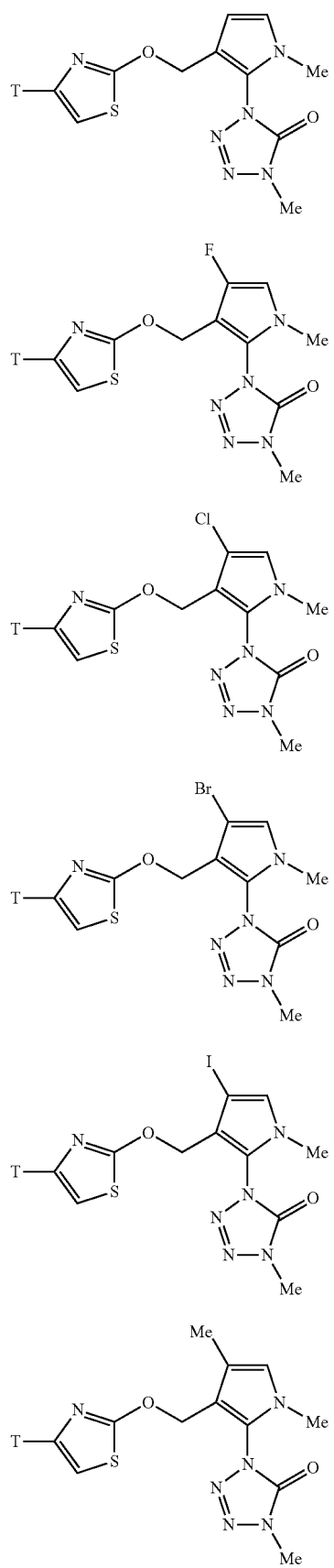
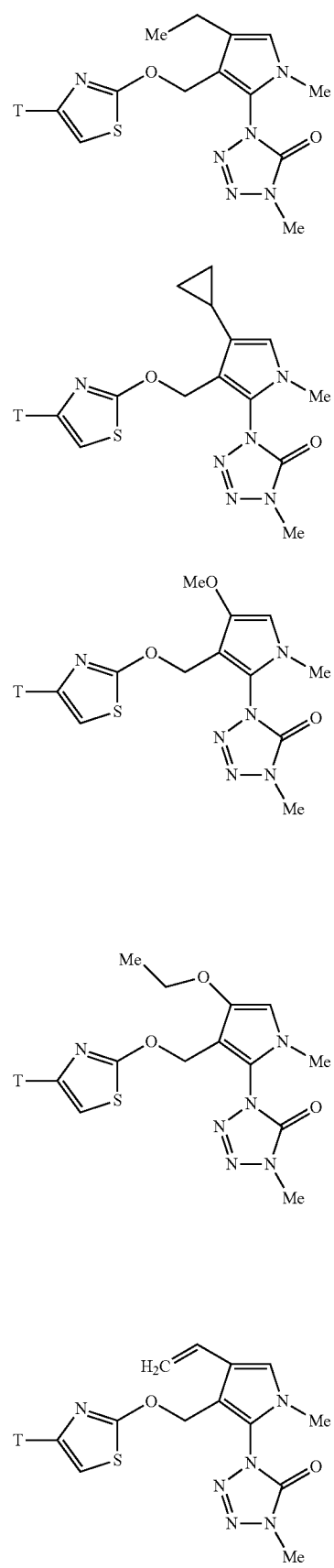

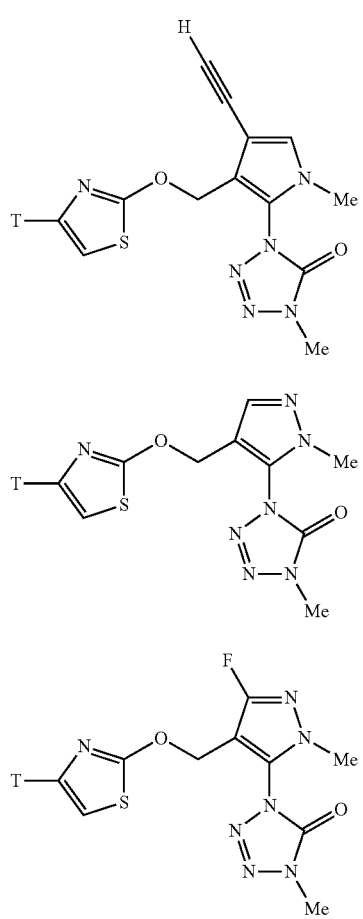
(HA2256)
(HA2257)
(HA2258)
(HA2259)
(HA2260)
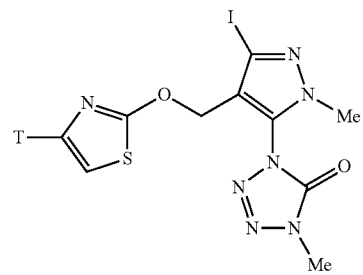
(HA2261)
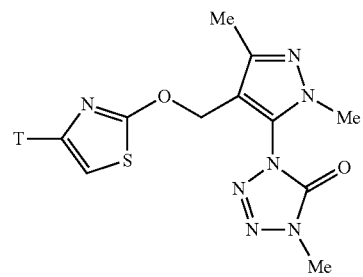
(HA2262)
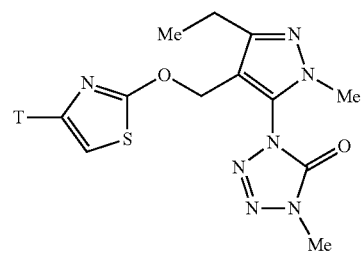
(HA2263)
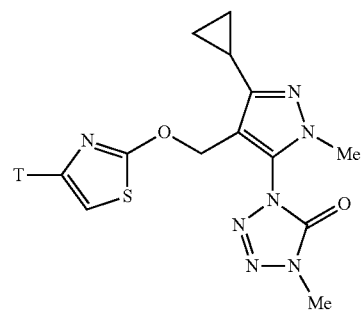
(HA2264)
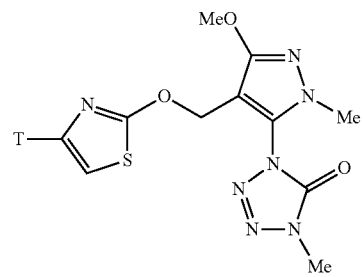
(HA2265)

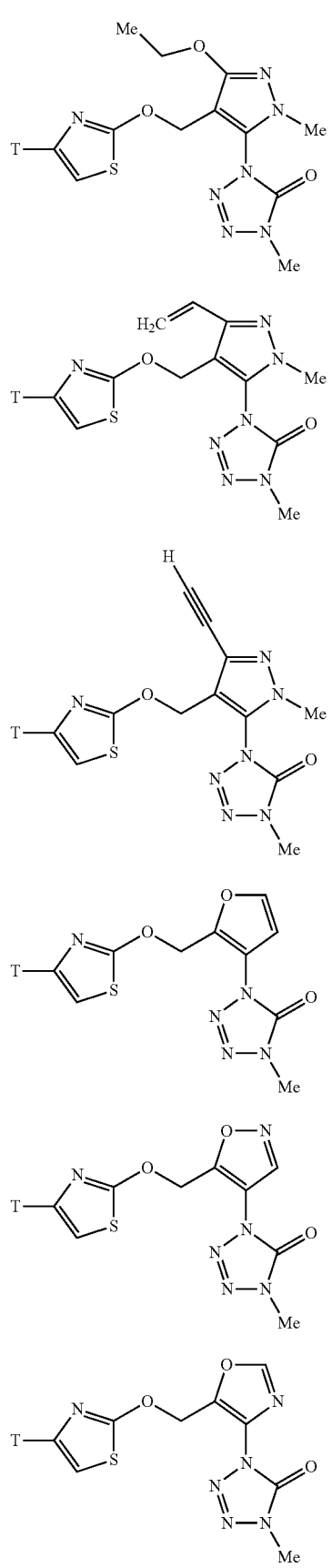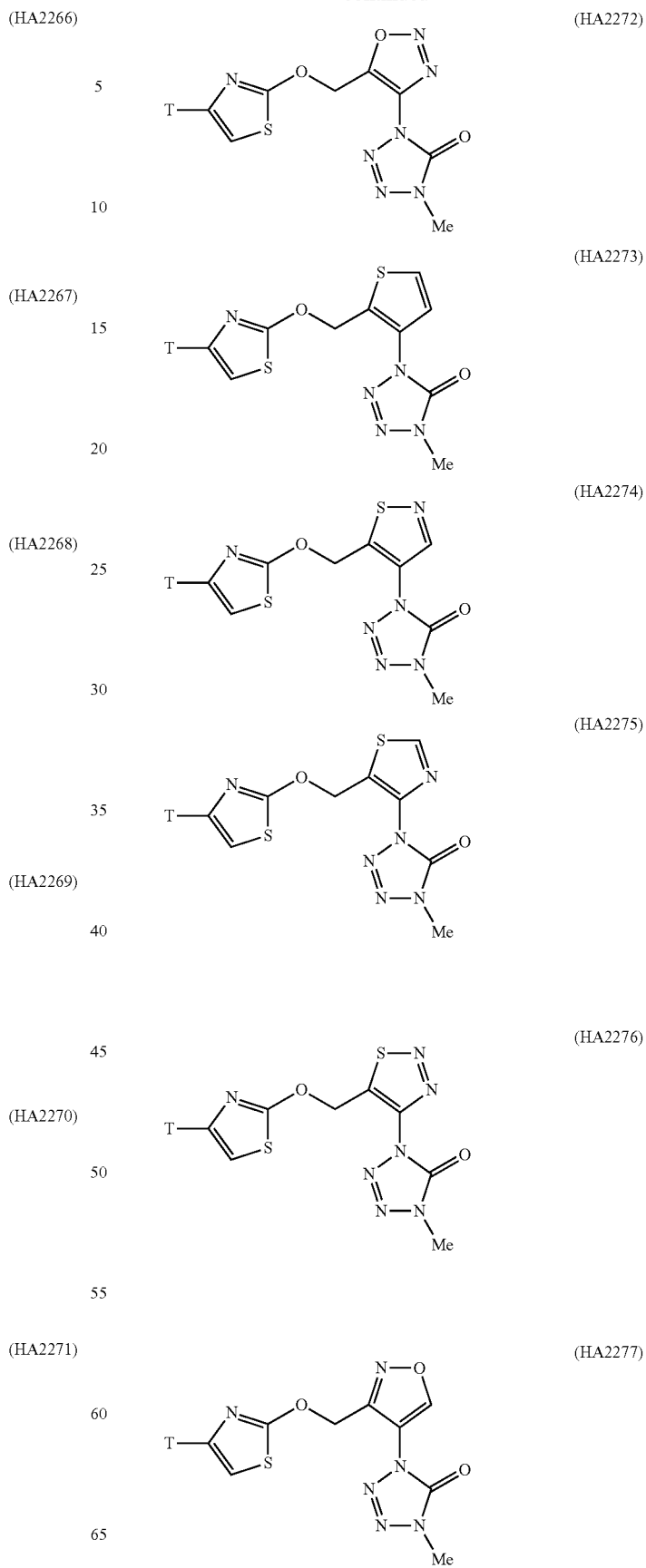

(HA2278) 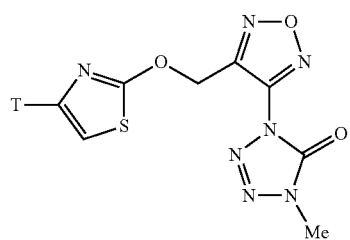
(HA2279) 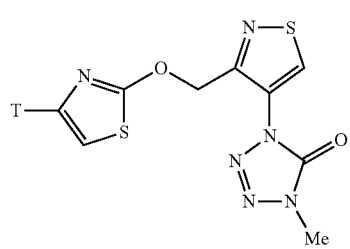
(HA2280) 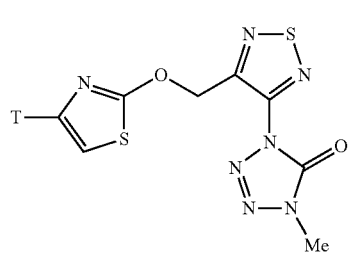
(HA2281) 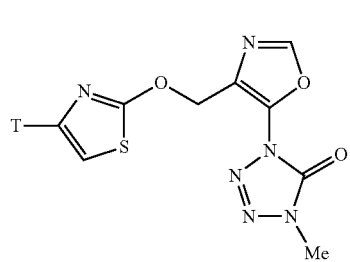
(HA2282) 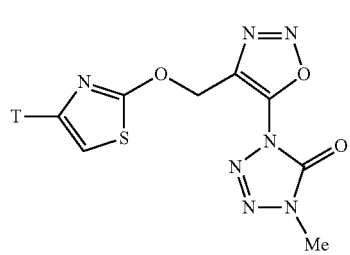
(HA2283) 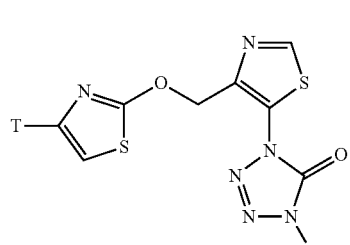
(HA2284) 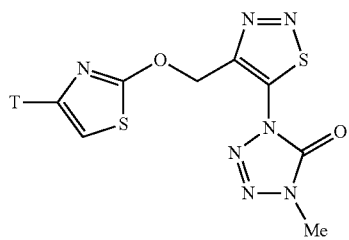
(HA2285) 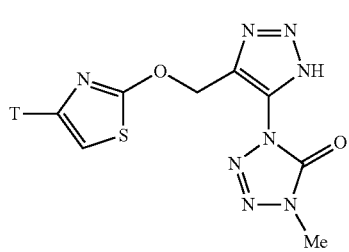
(HA2286) 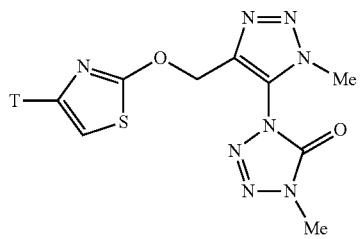
(HA2287) 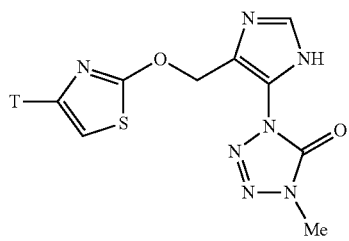
(HA2288) 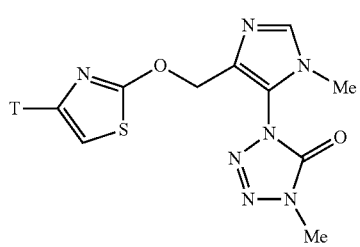
(HA2289) 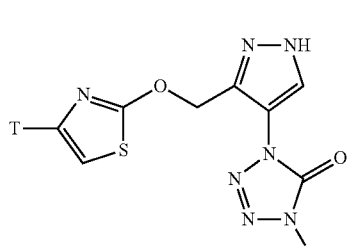

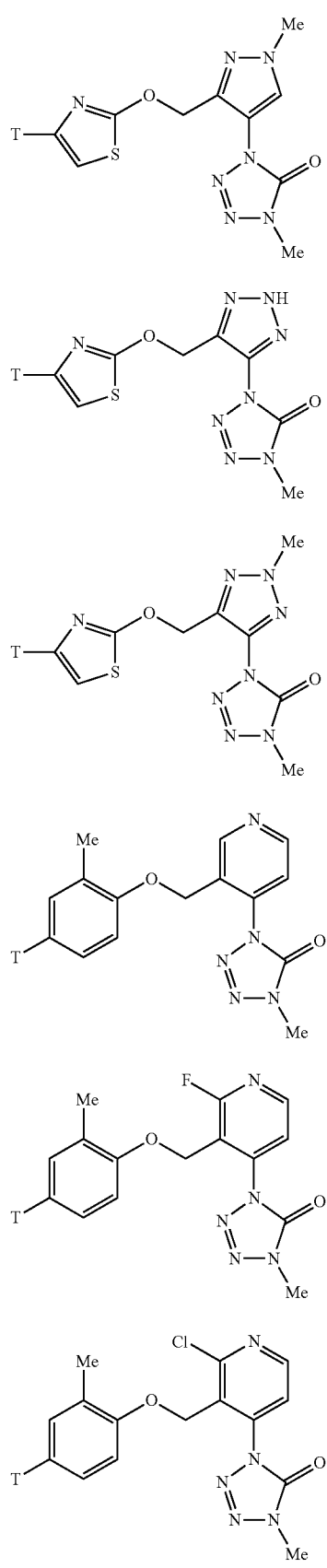
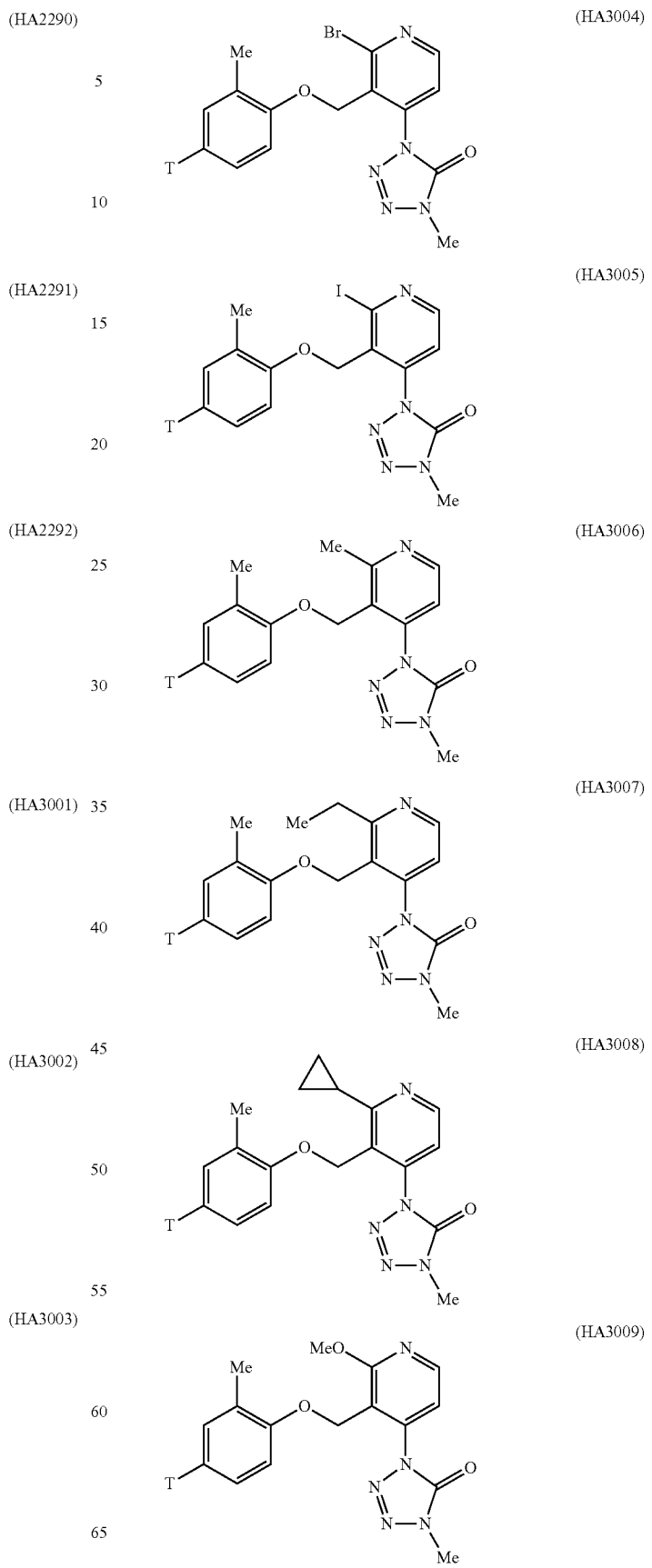

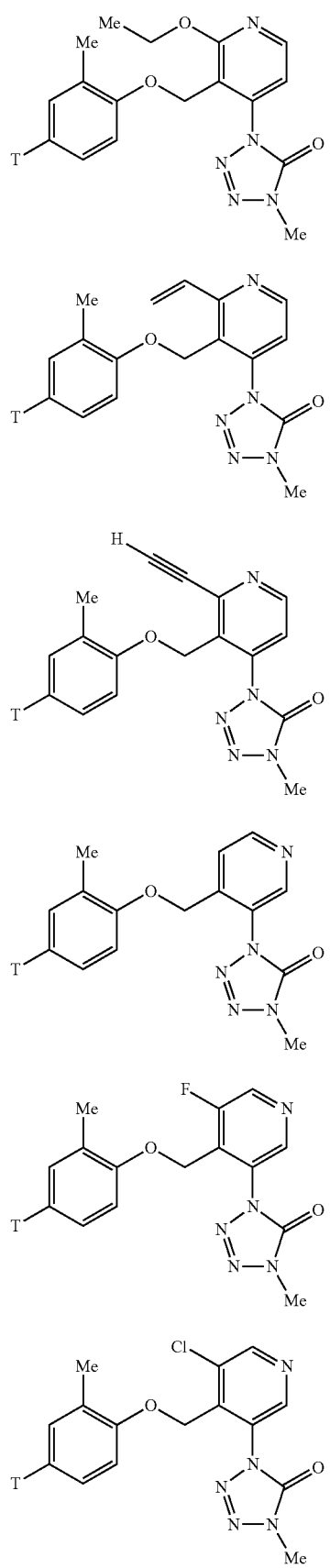
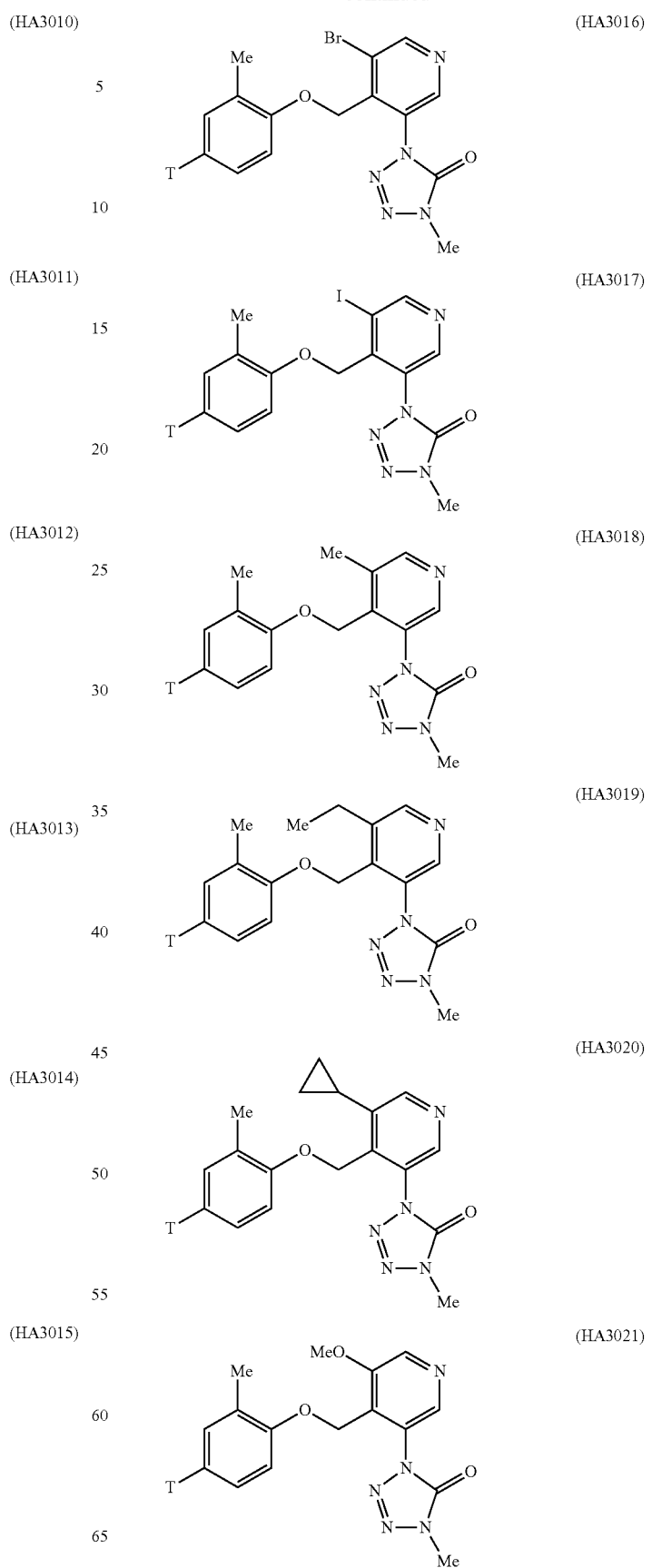

(HA3022)
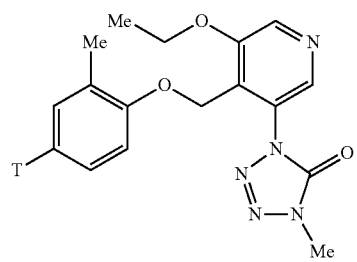
(HA3023)
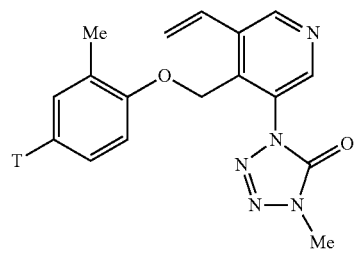
(HA3024)
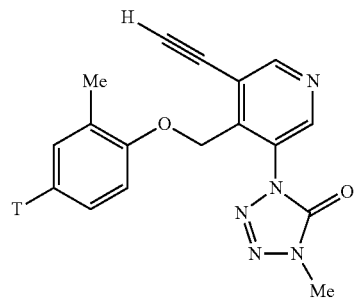
(HA3025)
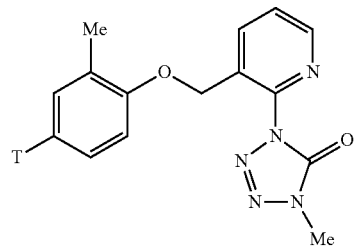
(HA3026)
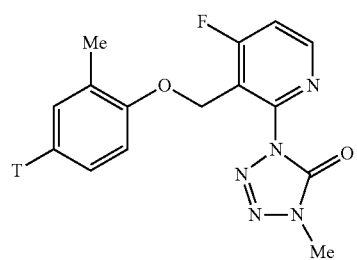
(HA3027)
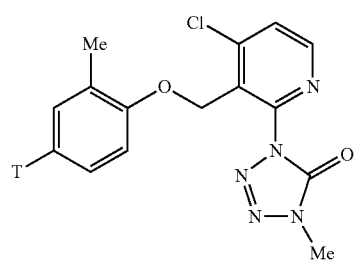
(HA3028)
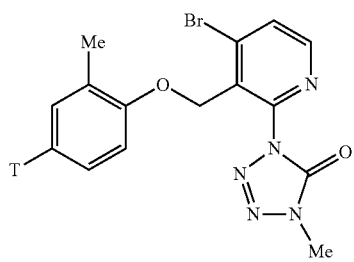
(HA3029)
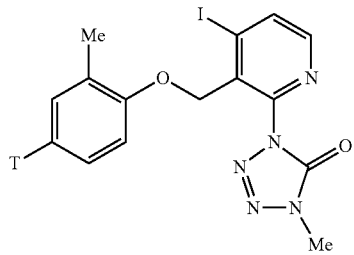
(HA3030)
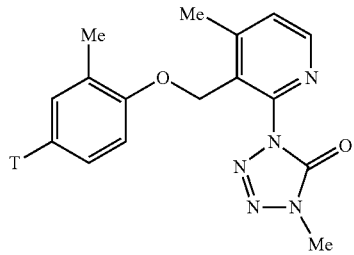
(HA3031)
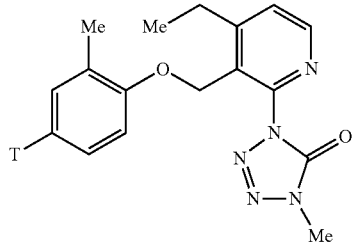
(HA3032)
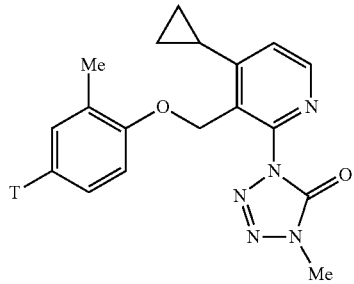
(HA3033)
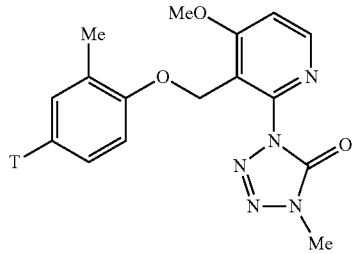

267
-continued
(HA3034)
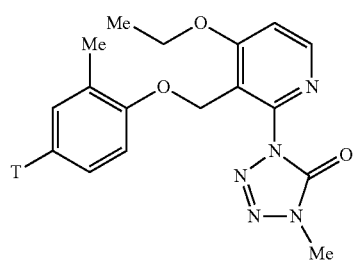
(HA3035)
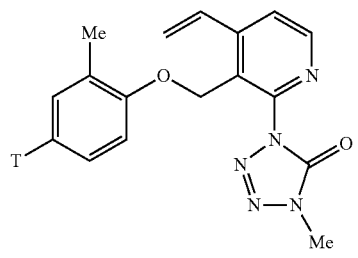
(HA3036)
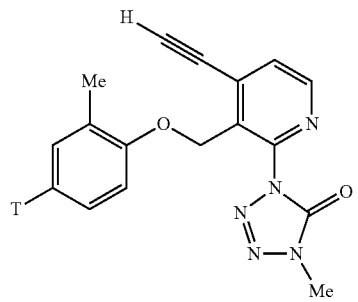
(HA3037)
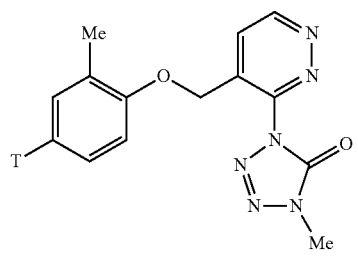
(HA3038)
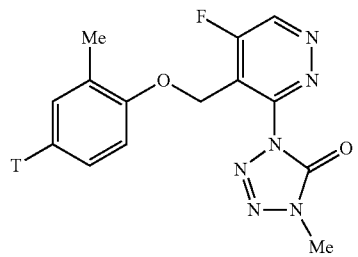
(HA3039)
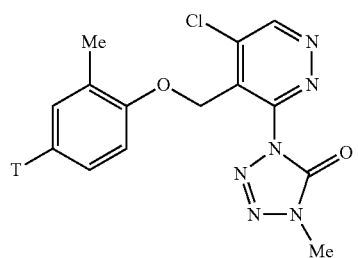
268
-continued
(HA3040)
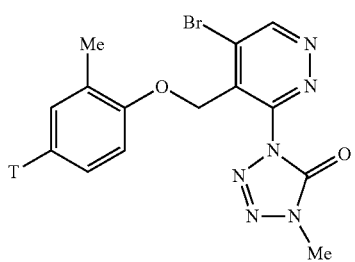
(HA3041)
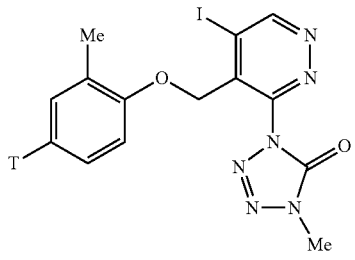
(HA3042)
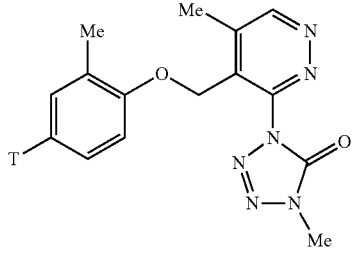
(HA3043)
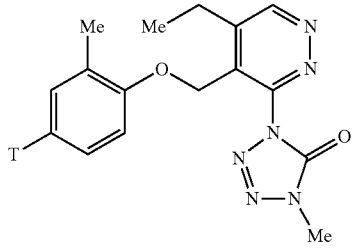
(HA3044)
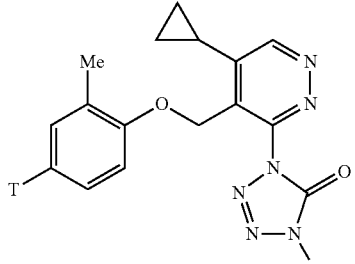
(HA3045)
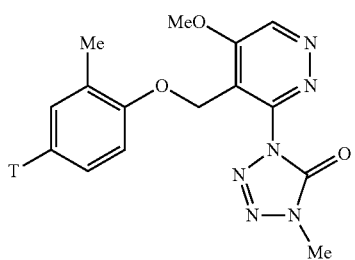

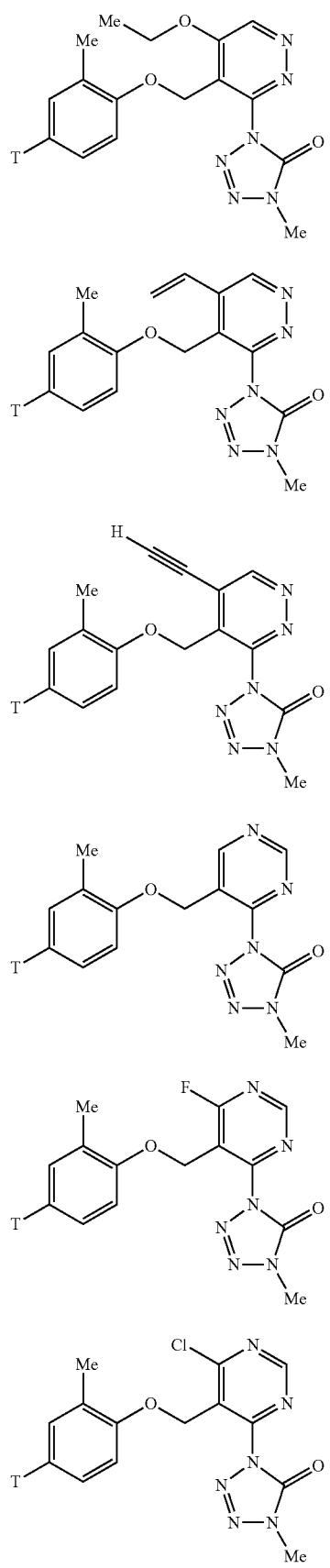
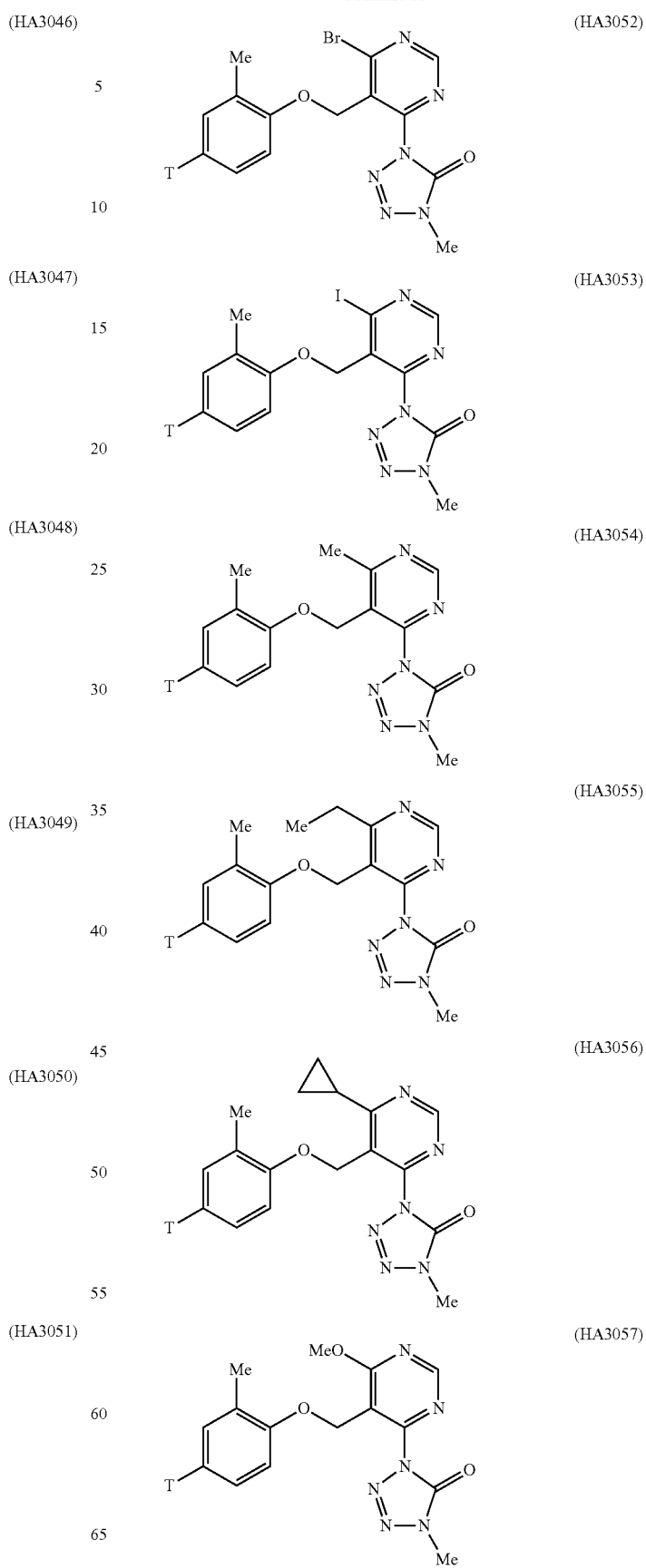

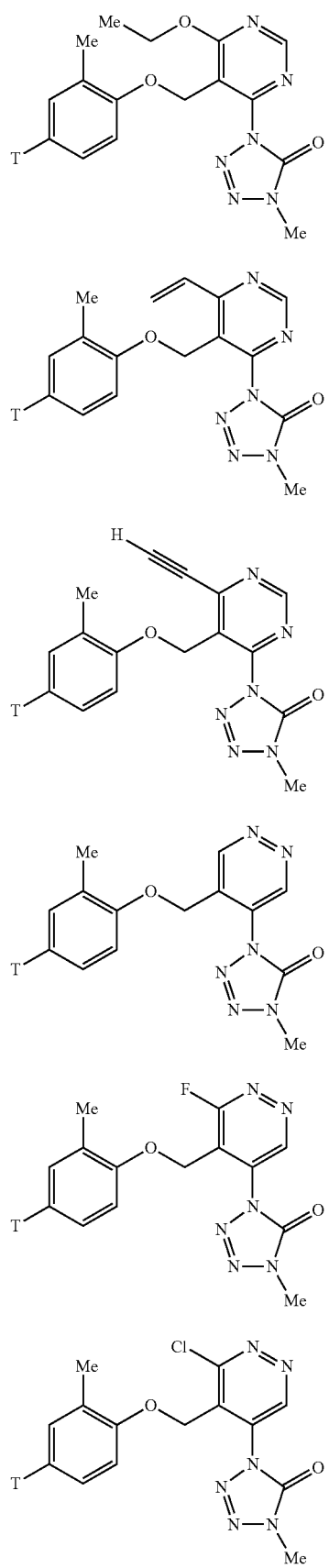
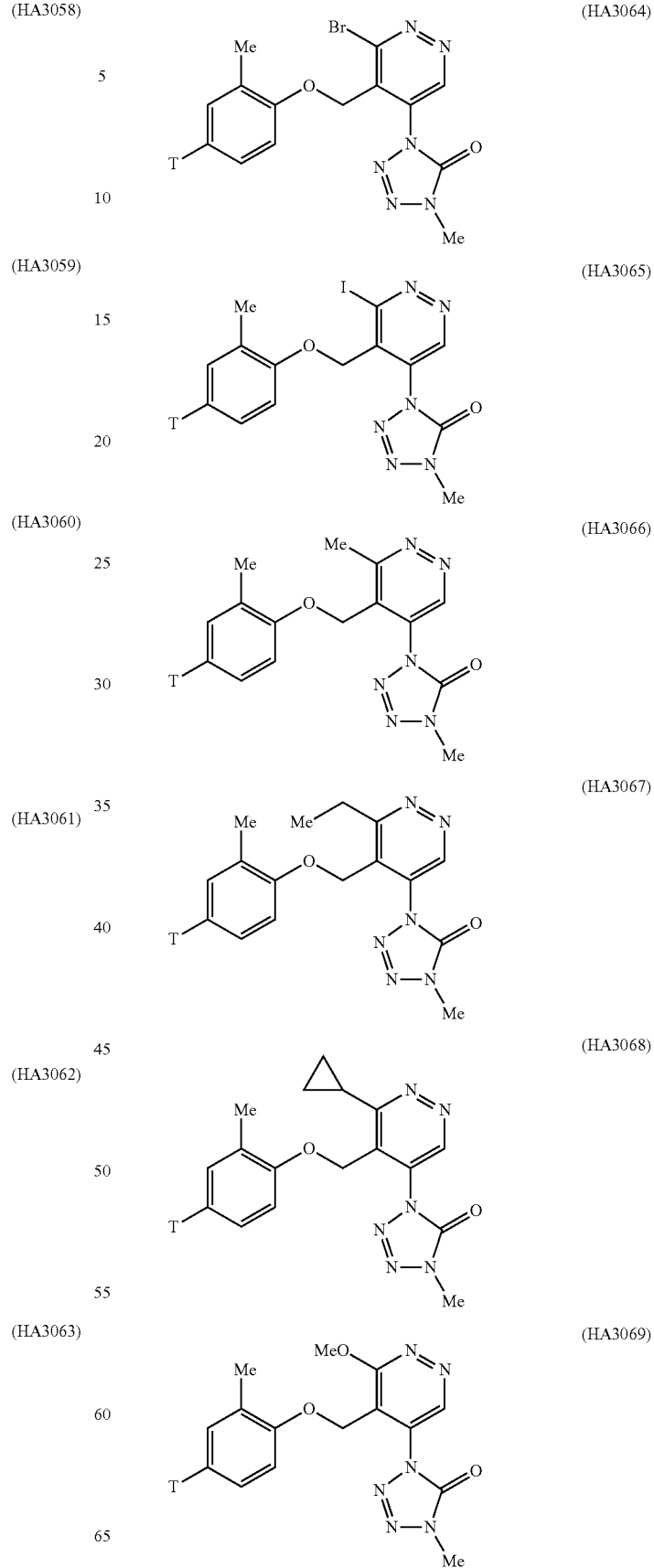

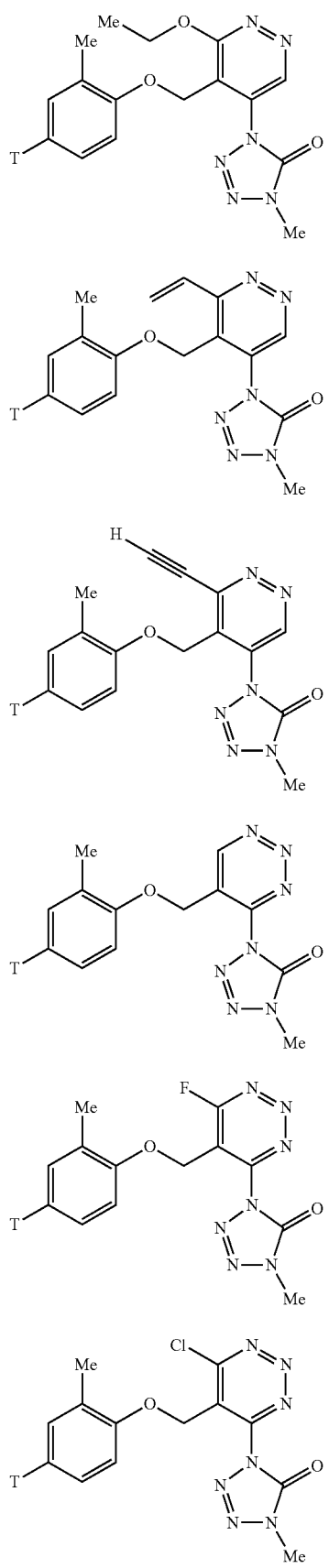
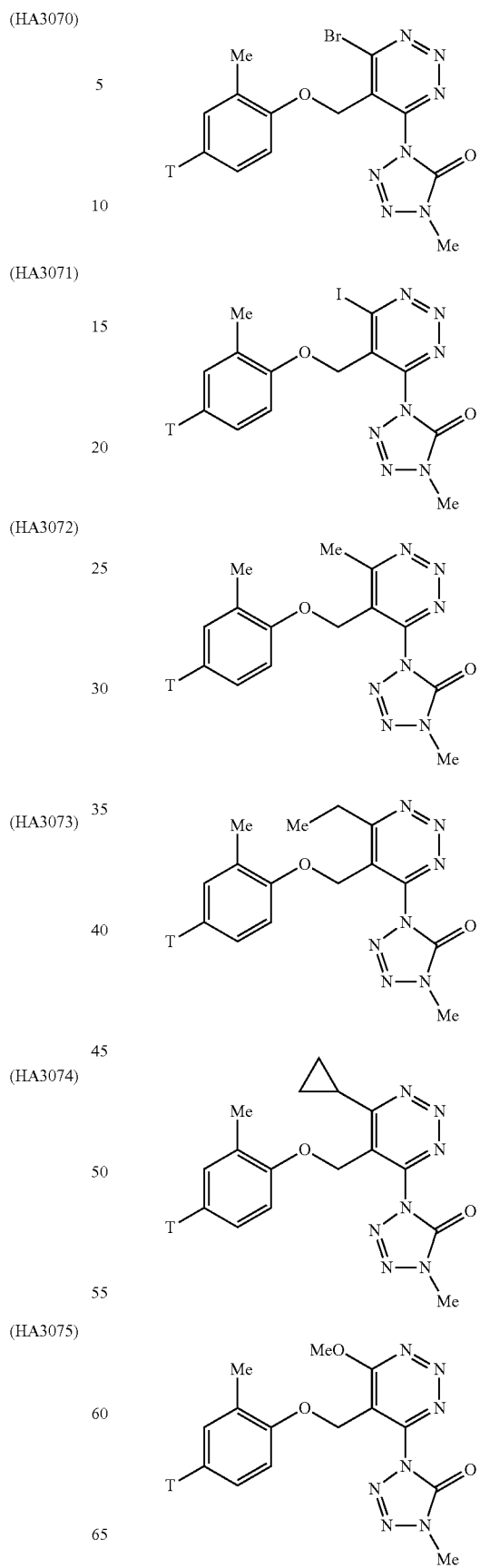

(HA3082) 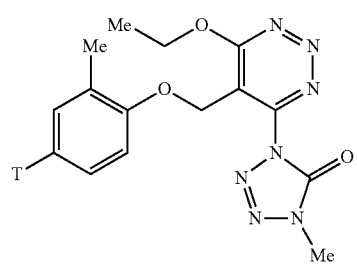
(HA3083) 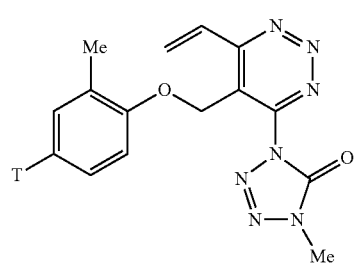
(HA3084) 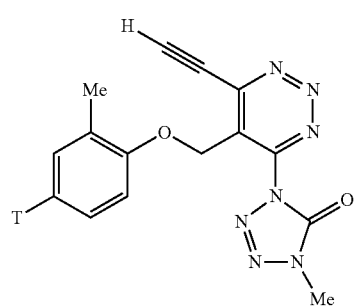
(HA3085) 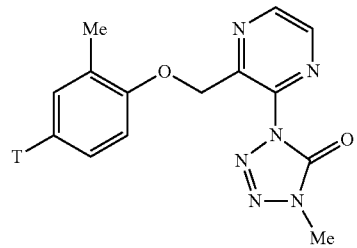
(HA3086) 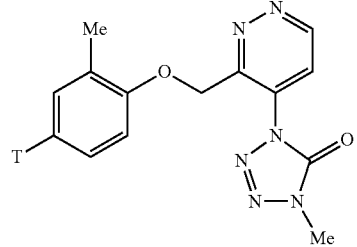
(HA3087) 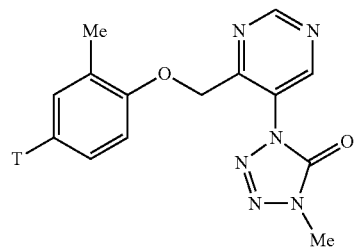
(HA3088) 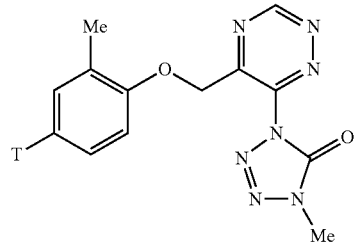
(HA3089) 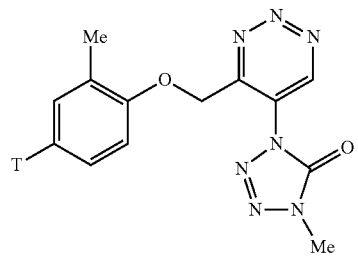
(HA3090) 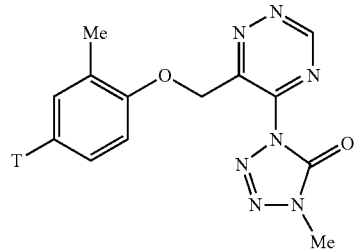
(HA3091) 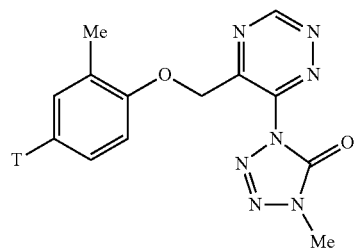
(HA3092) 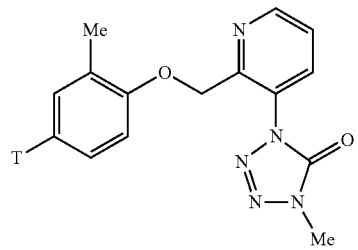
(HA3093) 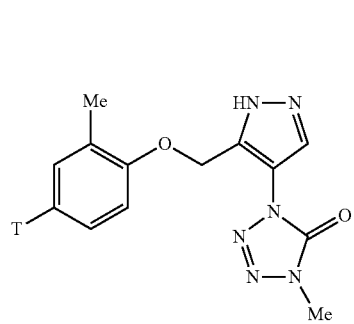

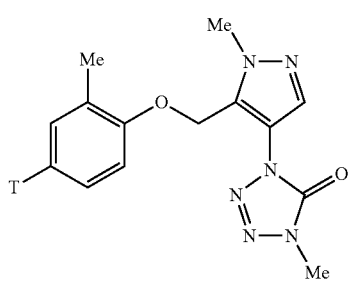
(HA3094)
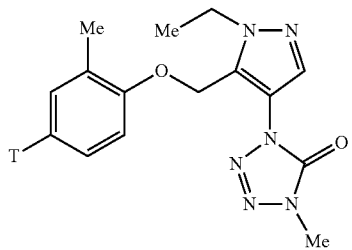
(HA3095)
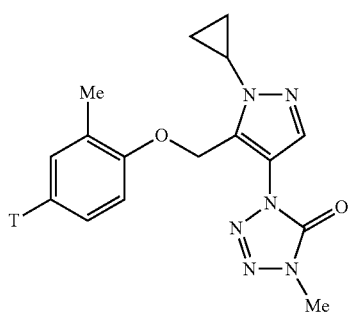
(HA3096)
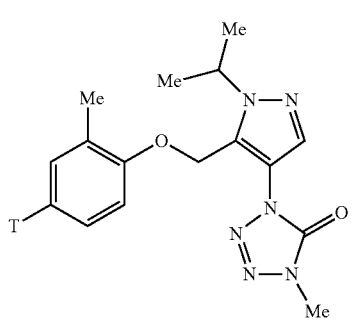
(HA3097)
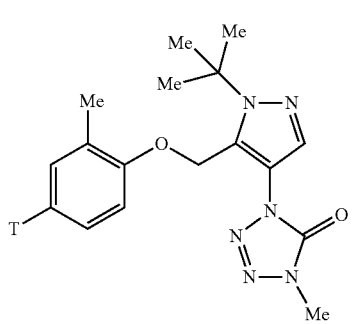
(HA3098)
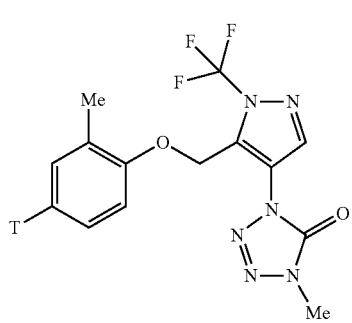
(HA3099)
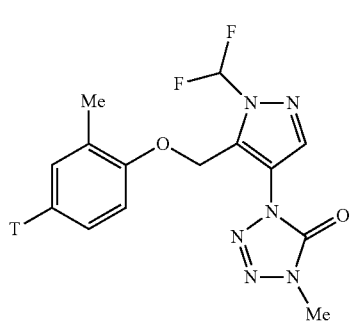
(HA3100)
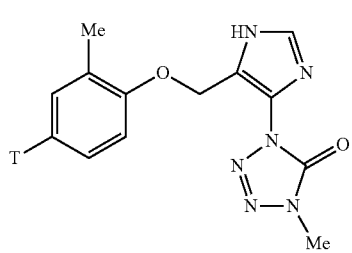
(HA3101)
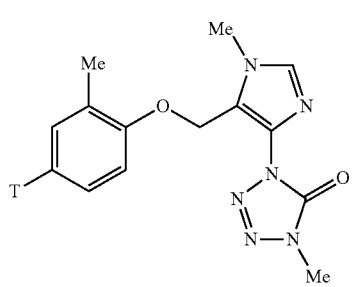
(HA3102)
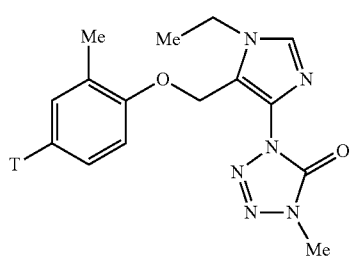
(HA3103)

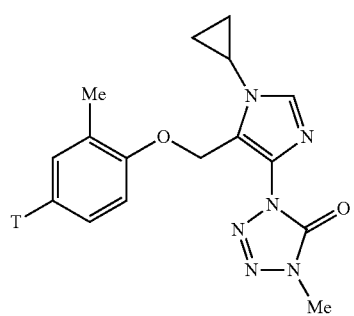
(HA3104)
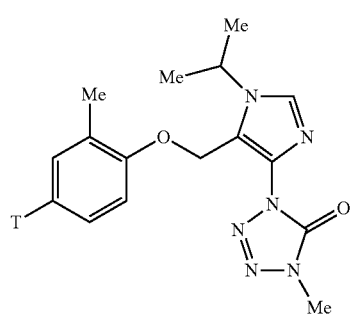
(HA3105)
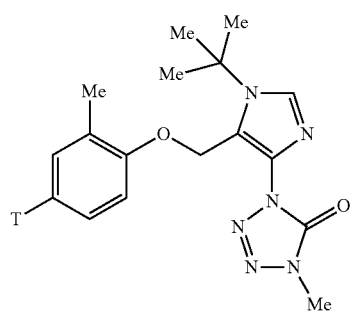
(HA3106)
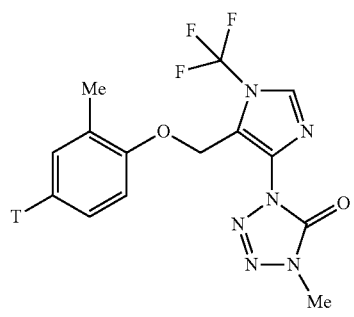
(HA3107)
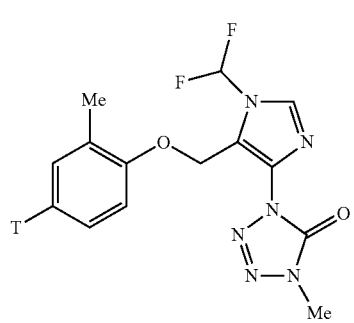
(HA3108)
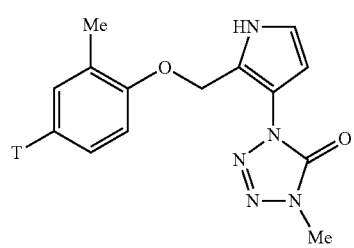
(HA3109)
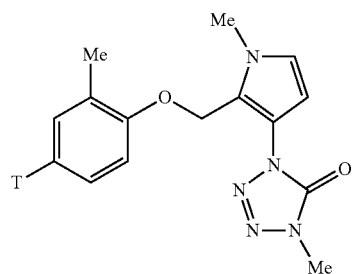
(HA3110)
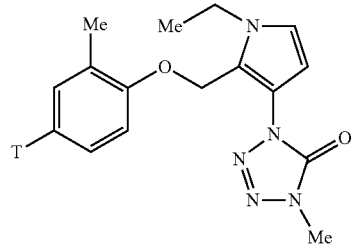
(HA3111)
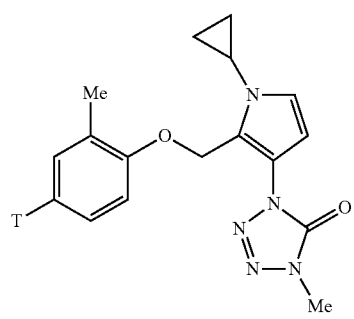
(HA3112)
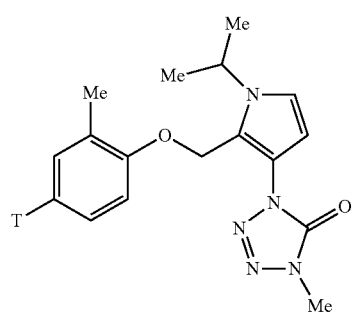
(HA3113)

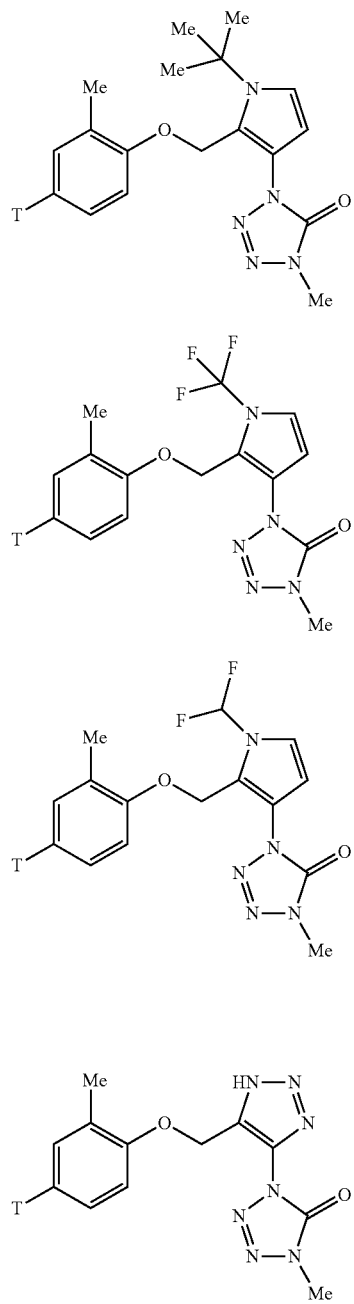
(HA3114)
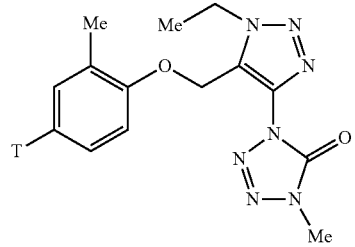
(HA3119)
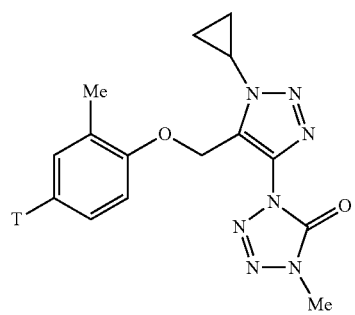
(HA3120)
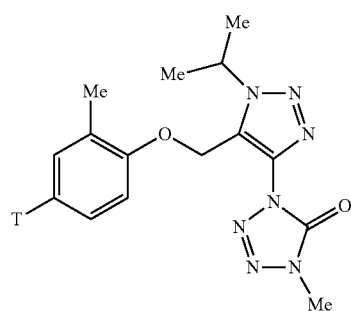
(HA3121)
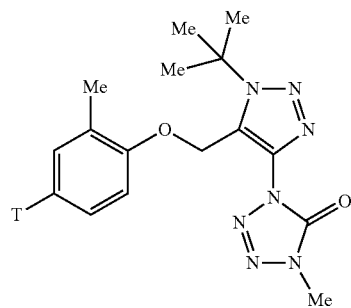
(HA3122)
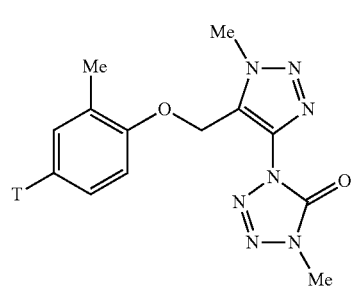
(HA3118)
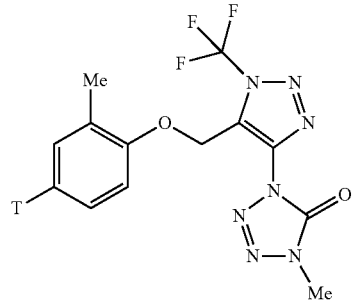
(HA3123)

(HA3124)
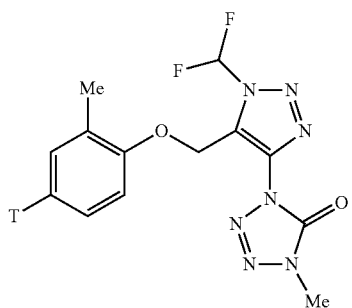
(HA3125)
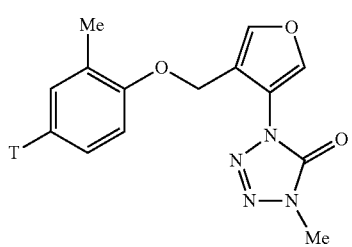
(HA3126)
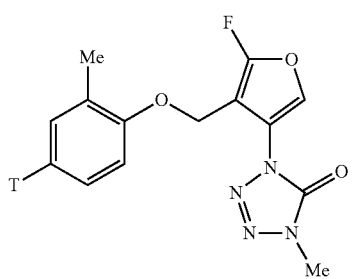
(HA3127)
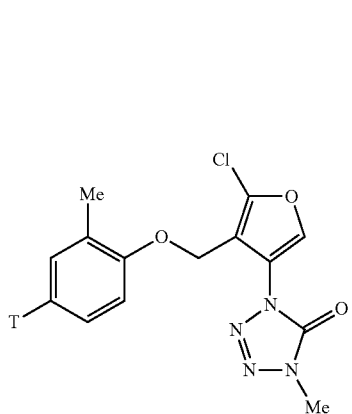
(HA3128)
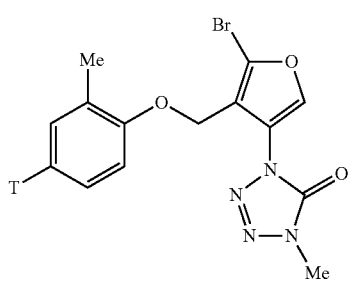
(HA3129)
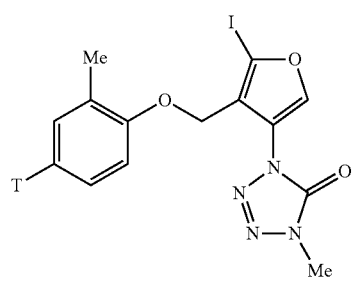
(HA3130)
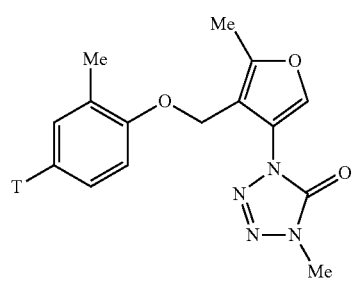
(HA3131)
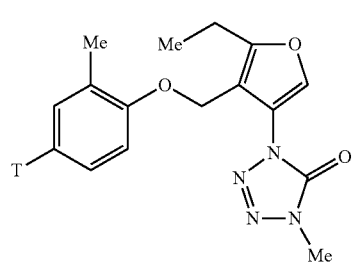
(HA3132)
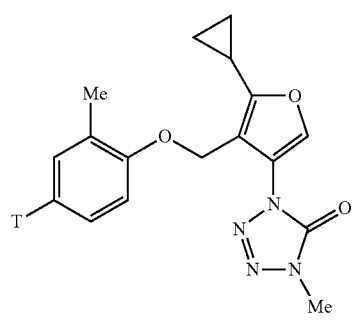
(HA3133)
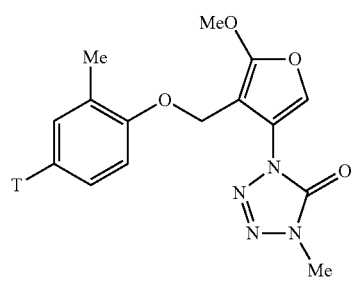

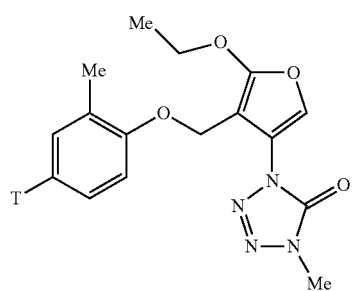
(HA3134)
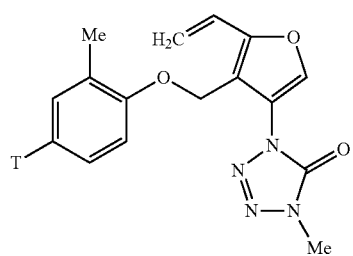
(HA3135)
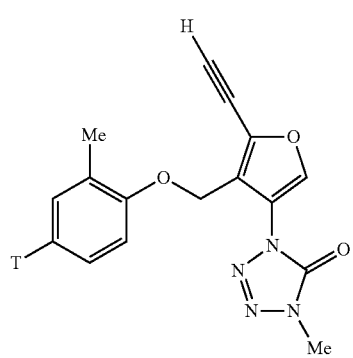
(HA3136)
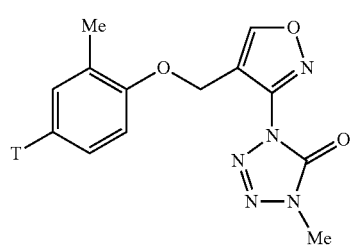
(HA3137)
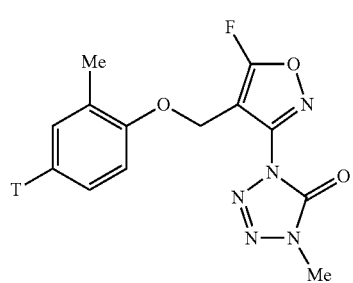
(HA3138)
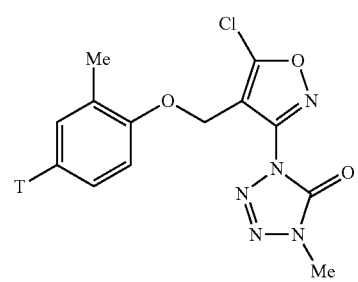
(HA3139)
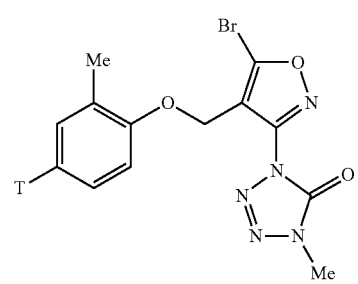
(HA3140)
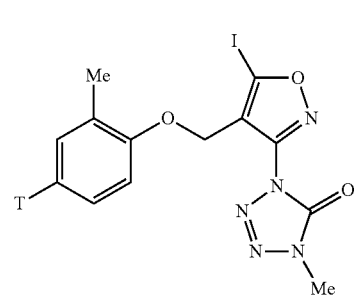
(HA3141)
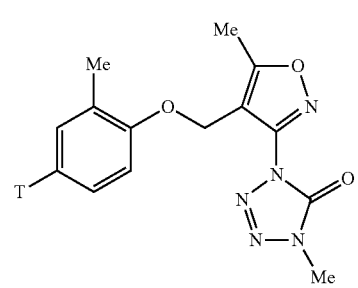
(HA3142)
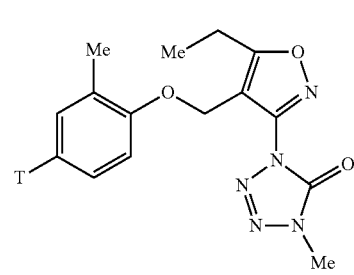
(HA3143)

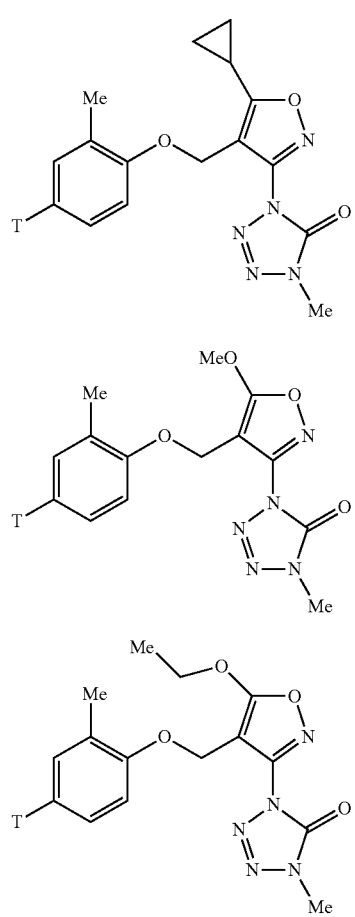
(HA3144)
(HA3145)
(HA3146)
(HA3147)
(HA3148)
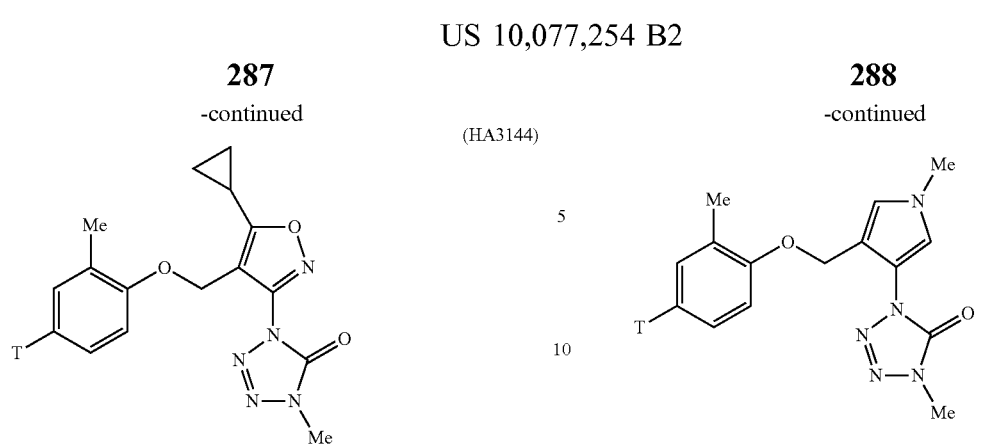
(HA3149)
(HA3150)
(HA3151)
(HA3152)
(HA3153)

289
-continued
(HA3154)
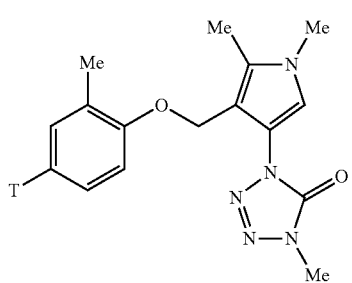
(HA3155)
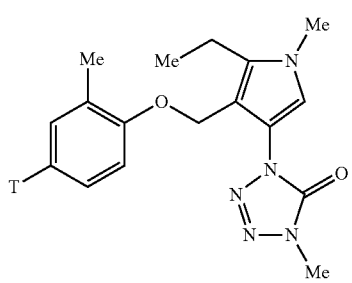
(HA3156)
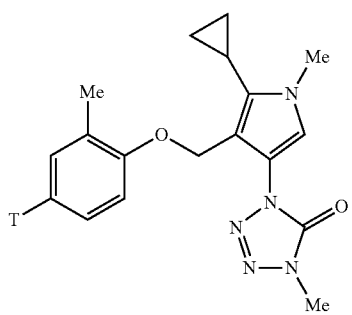
(HA3157)
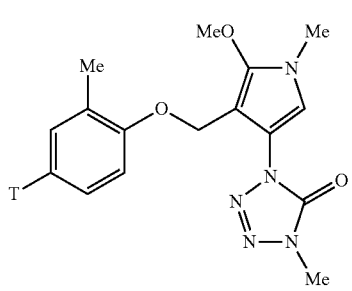
(HA3158)
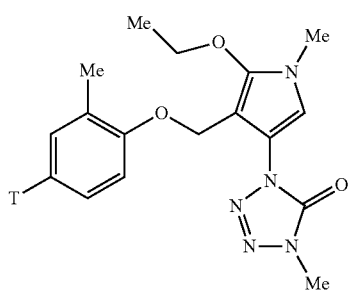
290
-continued
(HA3159)
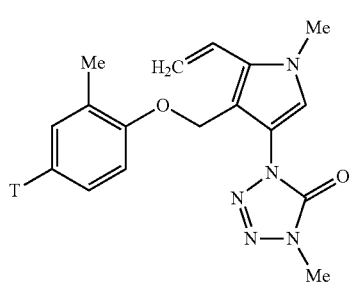
(HA3160)
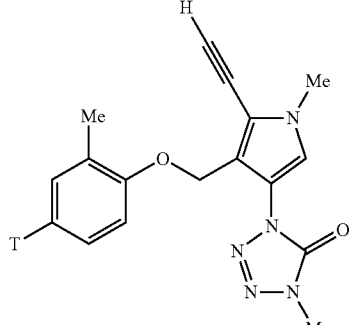
(HA3161)
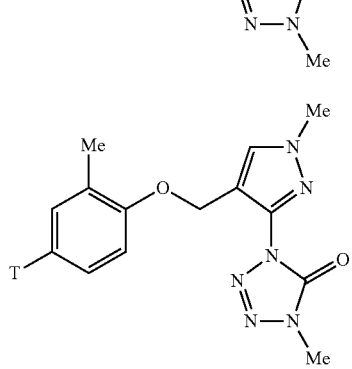
(HA3162)
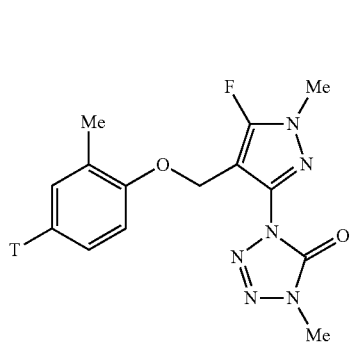
(HA3163)
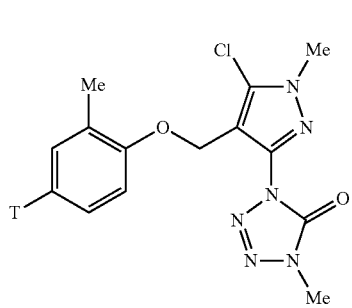

-continued
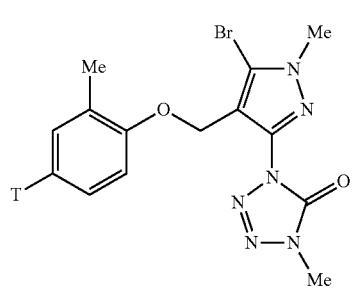 (HA3164)
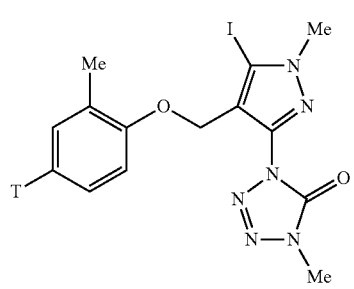 (HA3165)
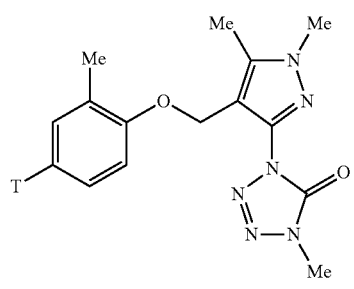 (HA3166)
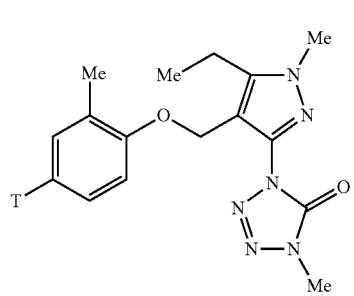 (HA3167)
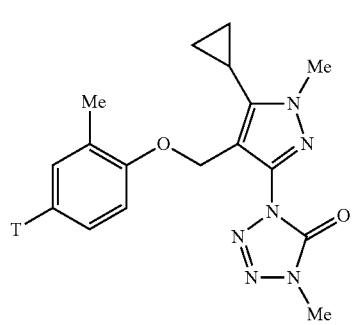 (HA3168)
-continued
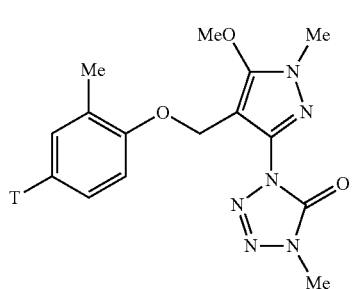 (HA3169)
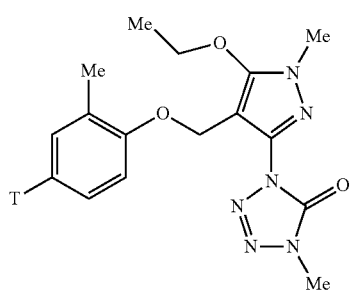 (HA3170)
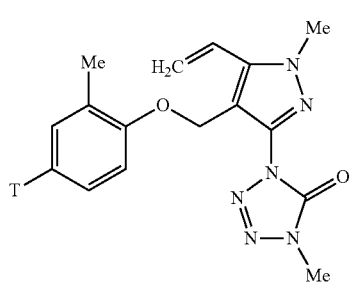 (HA3171)
(HA3172)
(HA3173)

-continued
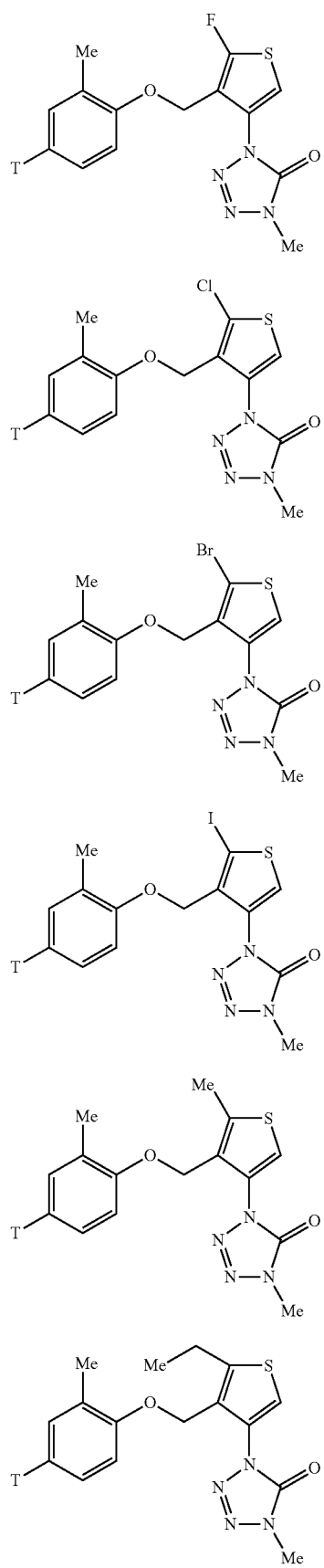
(HA3174)
(HA3175)
(HA3176)
(HA3177)
(HA3178)
(HA3179)
-continued
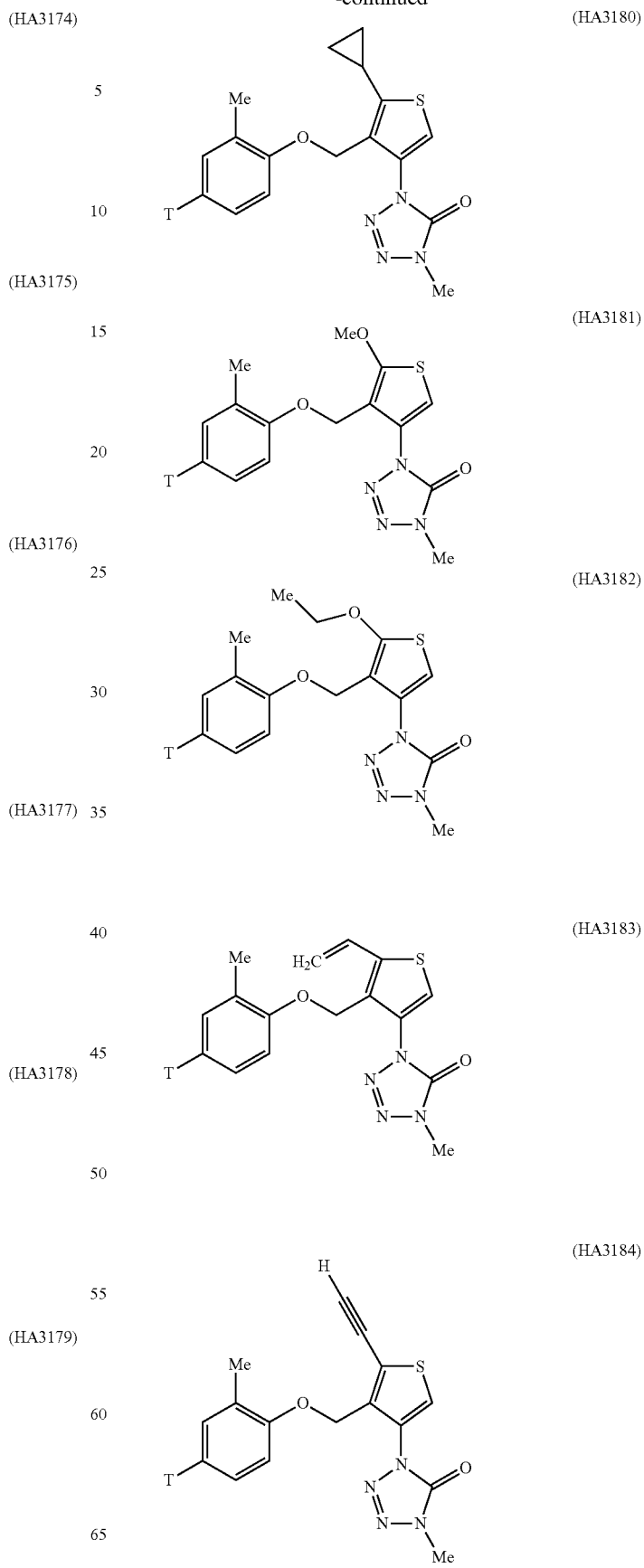
(HA3180)
(HA3181)
(HA3182)
(HA3183)
(HA3184)

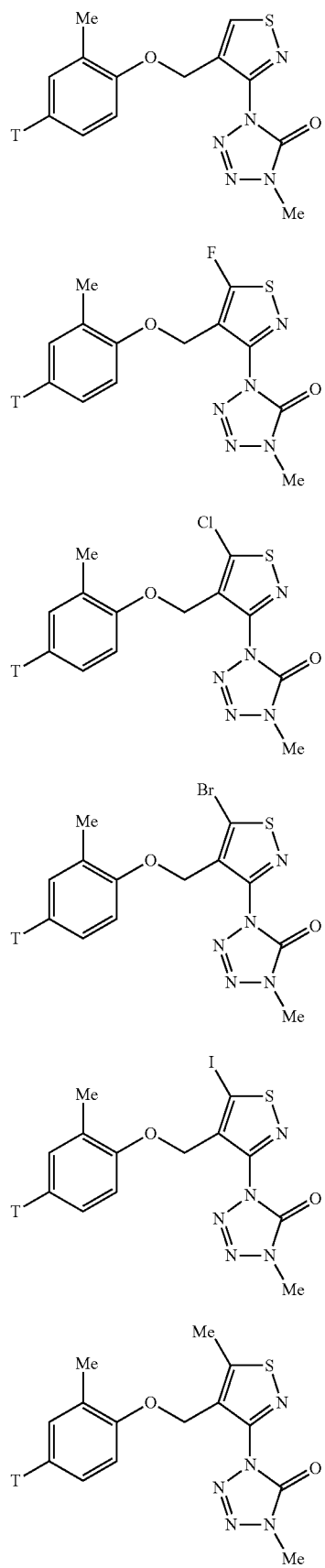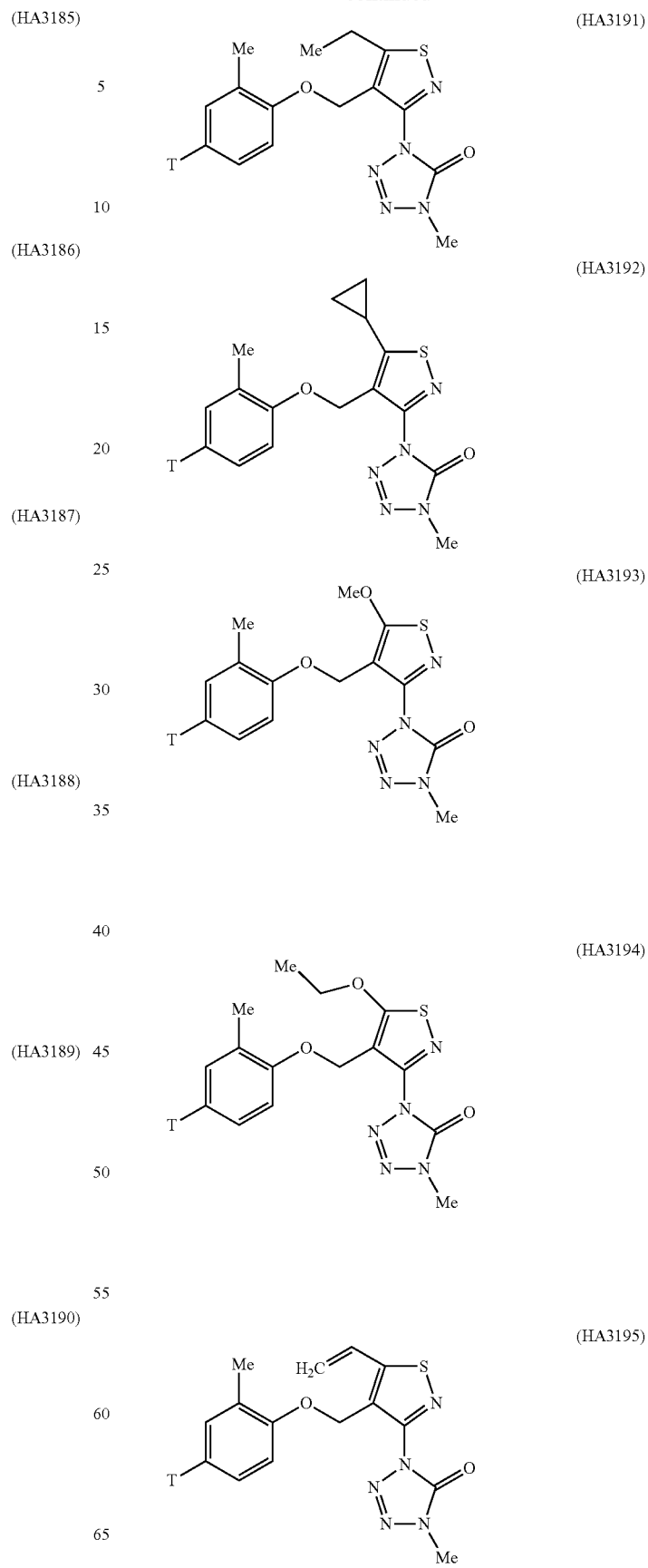

-continued
(HA3196)
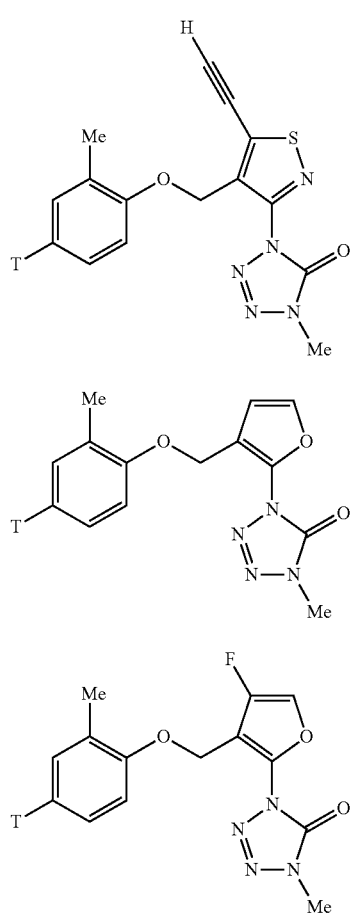
(HA3197)
(HA3198)
(HA3199)
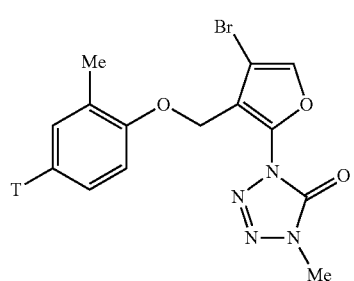
(HA3200)
-continued
(HA3201)
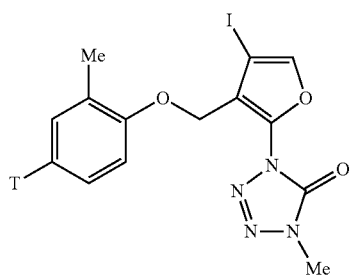
(HA3202)
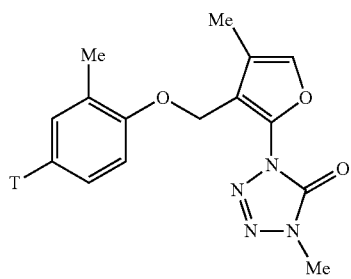
(HA3203)
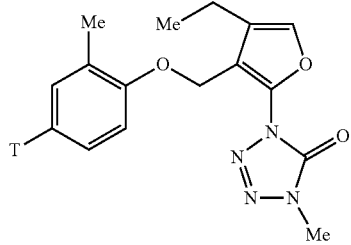
(HA3204)
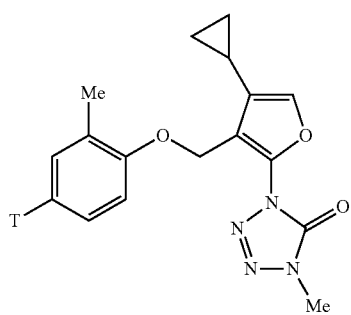
(HA3205)
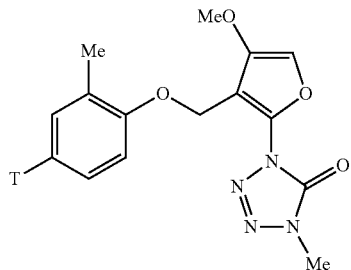

-continued
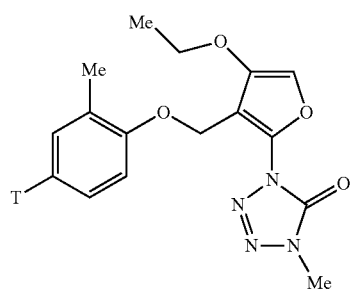
(HA3206)
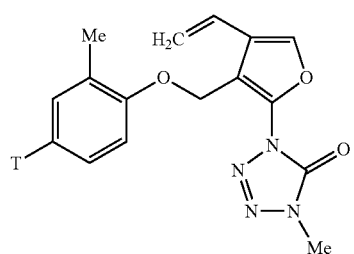
(HA3207)
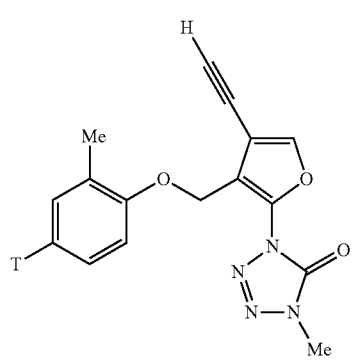
(HA3208)
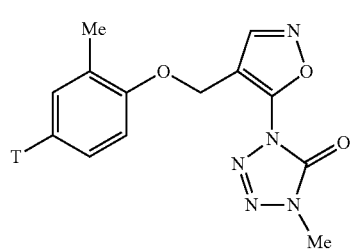
(HA3209)
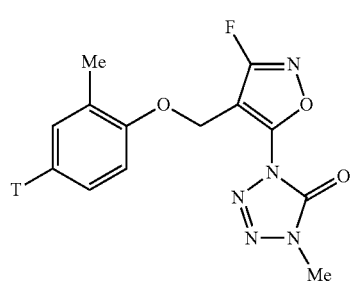
(HA3210)
-continued
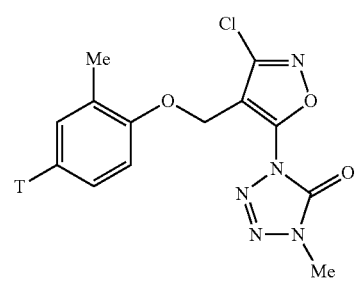
(HA3211)
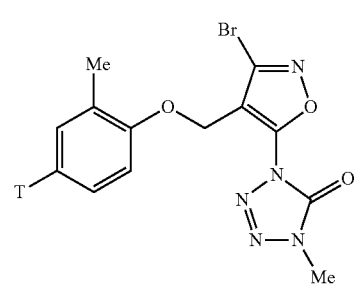
(HA3212)
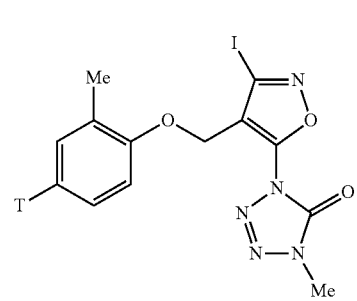
(HA3213)
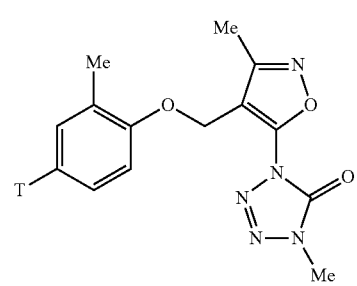
(HA3214)
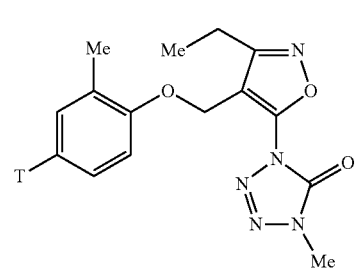
(HA3215)

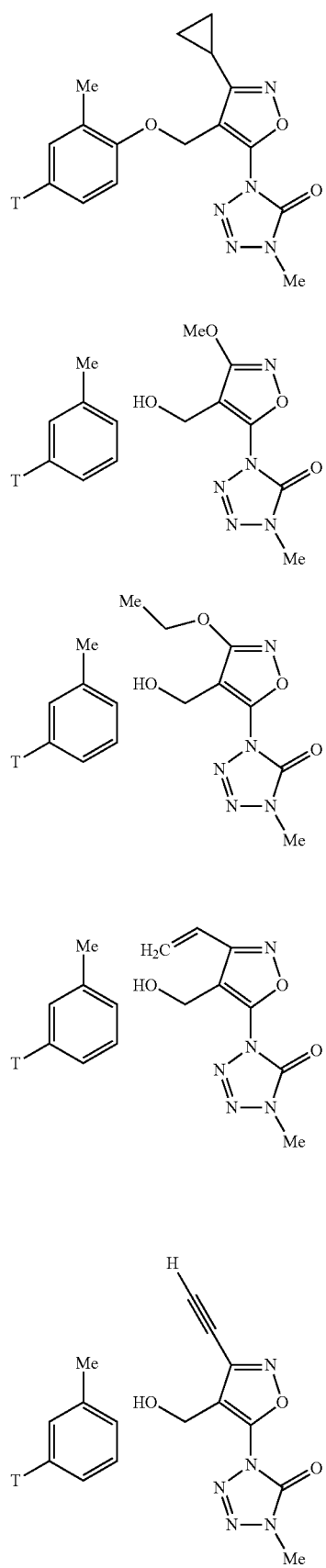
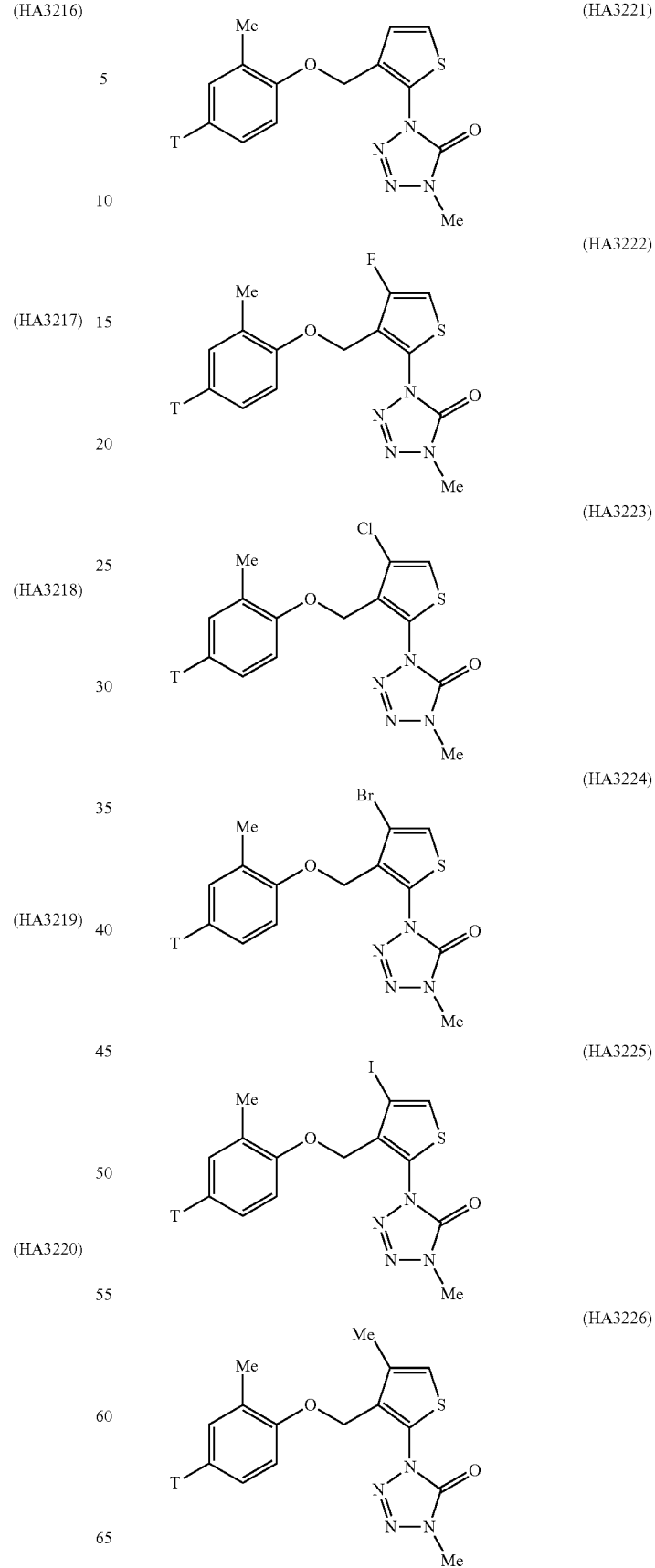

303
-continued
(HA3227)
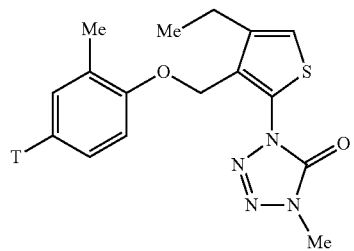
(HA3228)
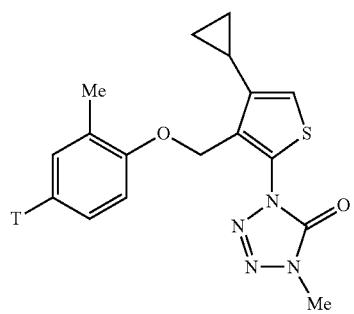
(HA3229)
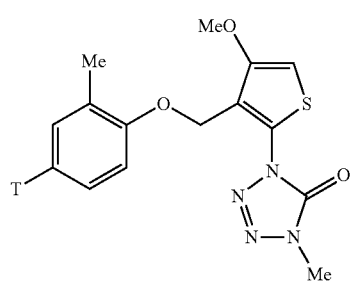
(HA3230)
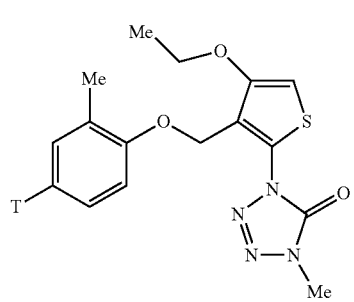
(HA3231)
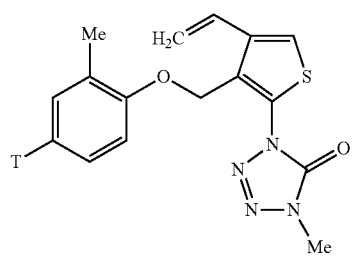
304
-continued
(HA3232)
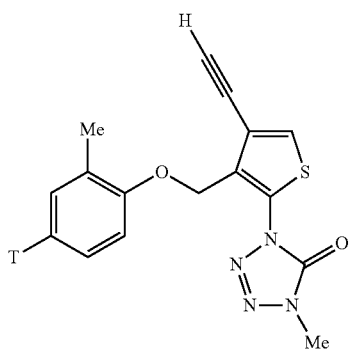
(HA3233)
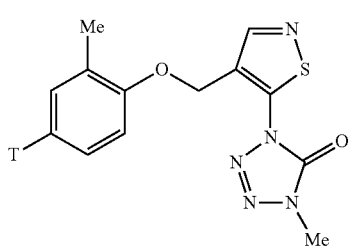
(HA3234)
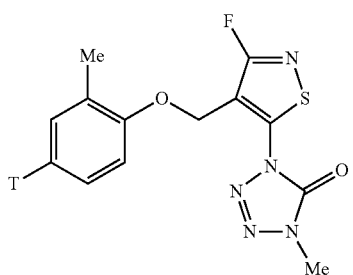
(HA3235)
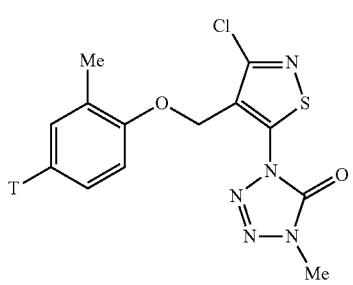
(HA3236)
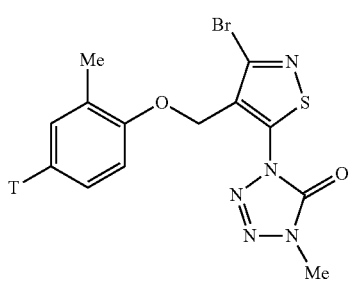

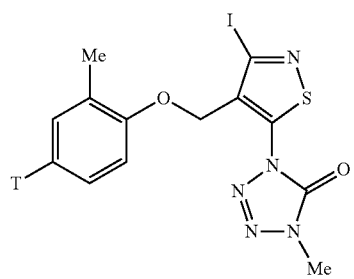
(HA3237)
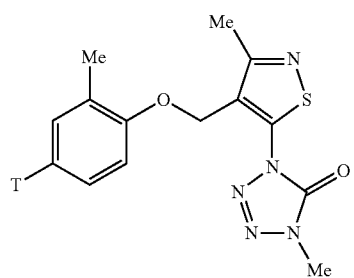
(HA3238)
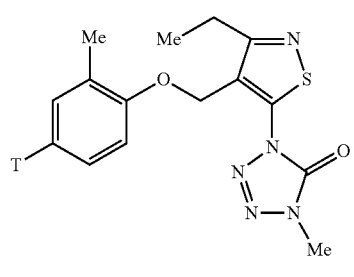
(HA3239)
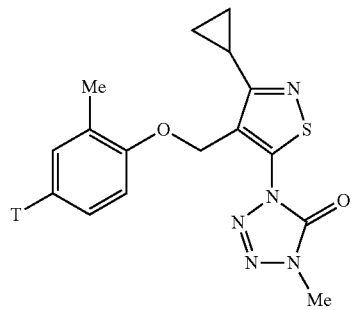
(HA3240)
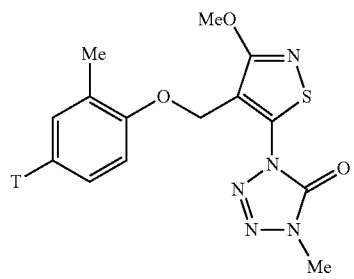
(HA3241)
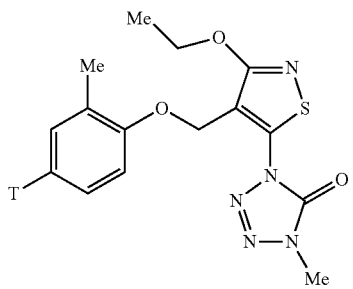
(HA3242)
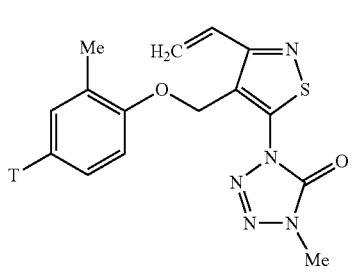
(HA3243)
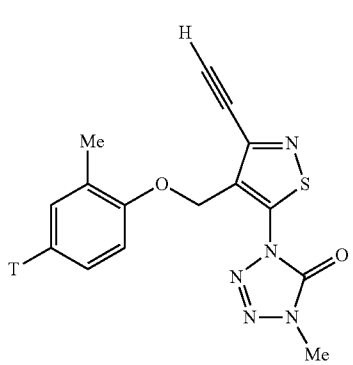
(HA3244)
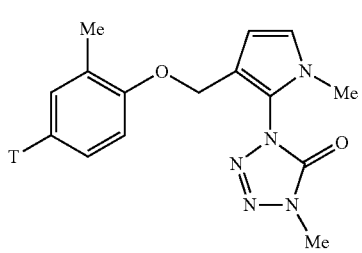
(HA3245)
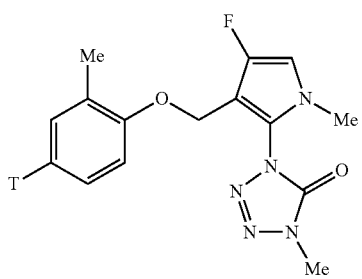
(HA3246)

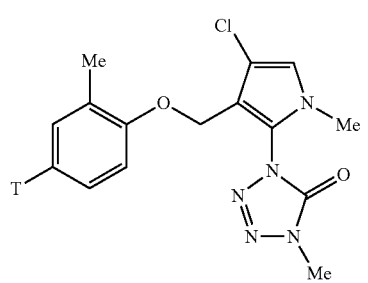
(HA3247)
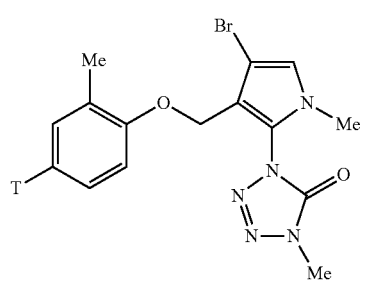
(HA3248)
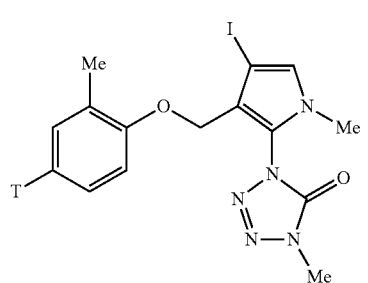
(HA3249)
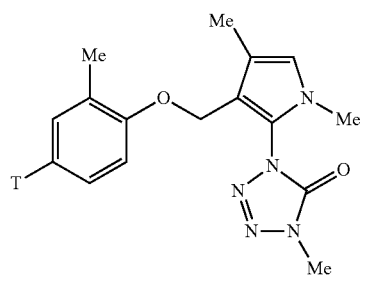
(HA3250)
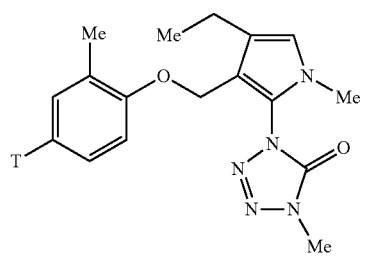
(HA3251)
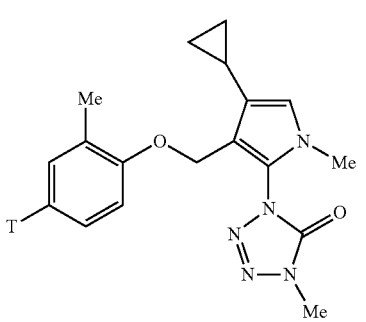
(HA3252)
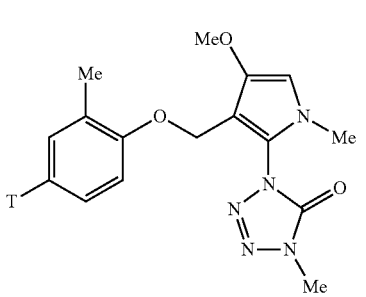
(HA3253)
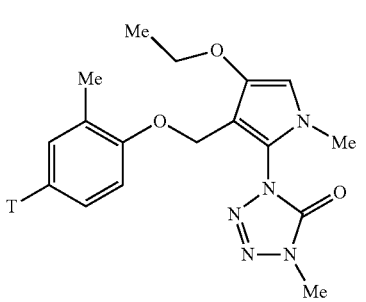
(HA3254)
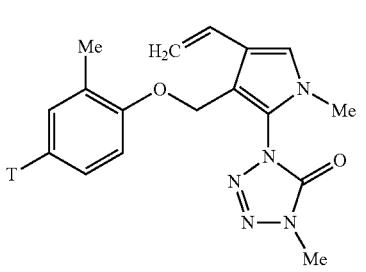
(HA3255)
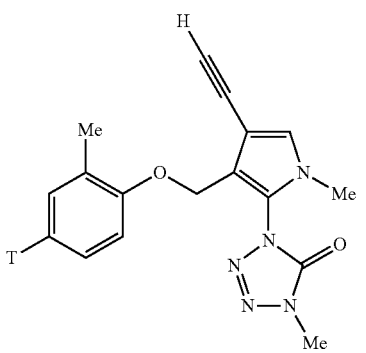
(HA3256)

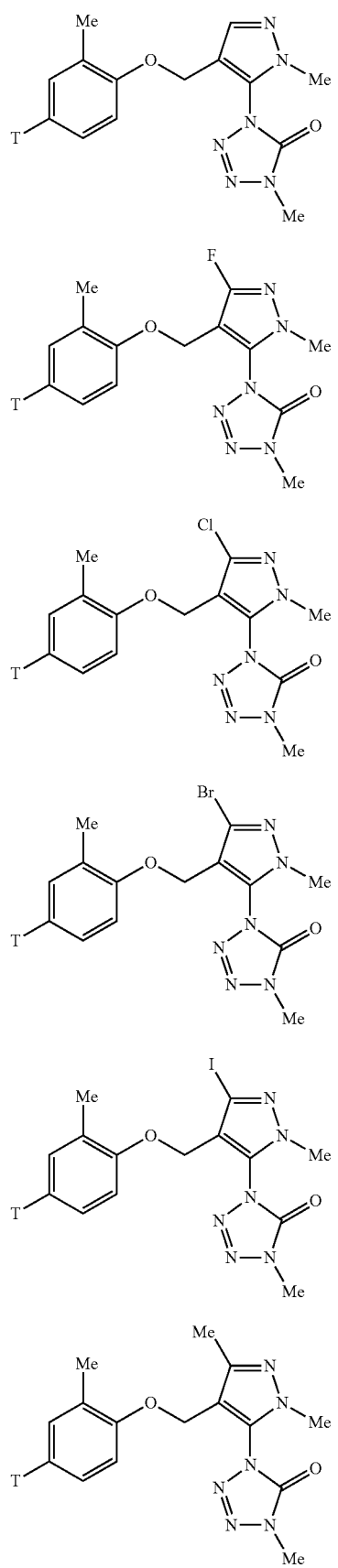
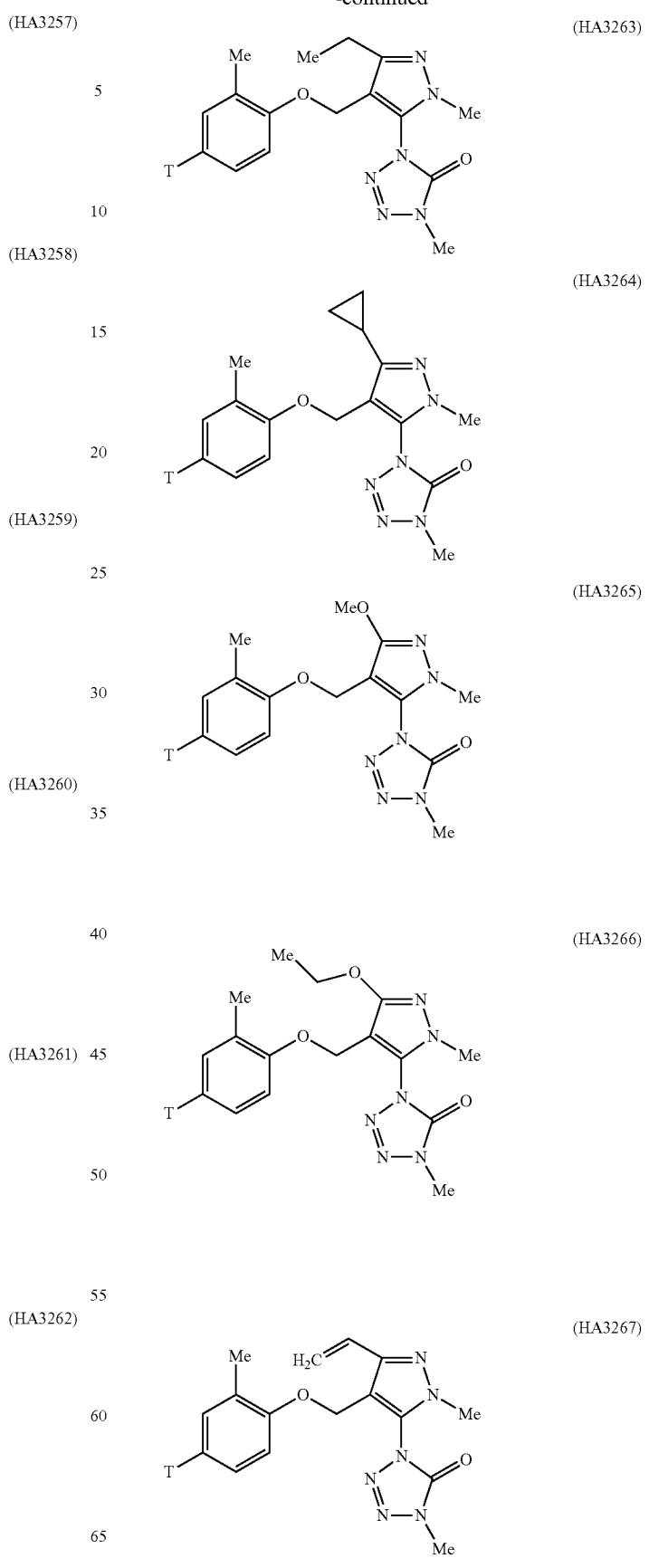

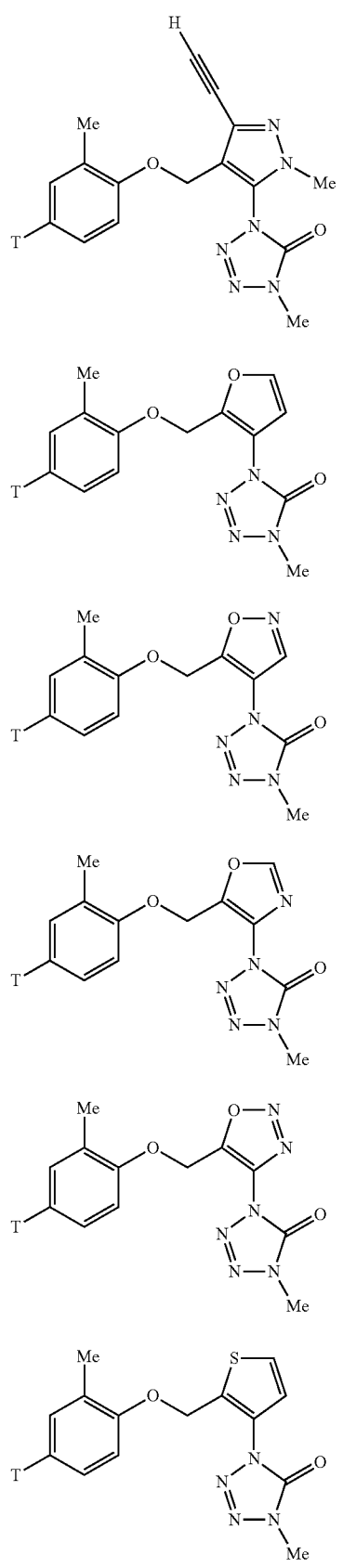
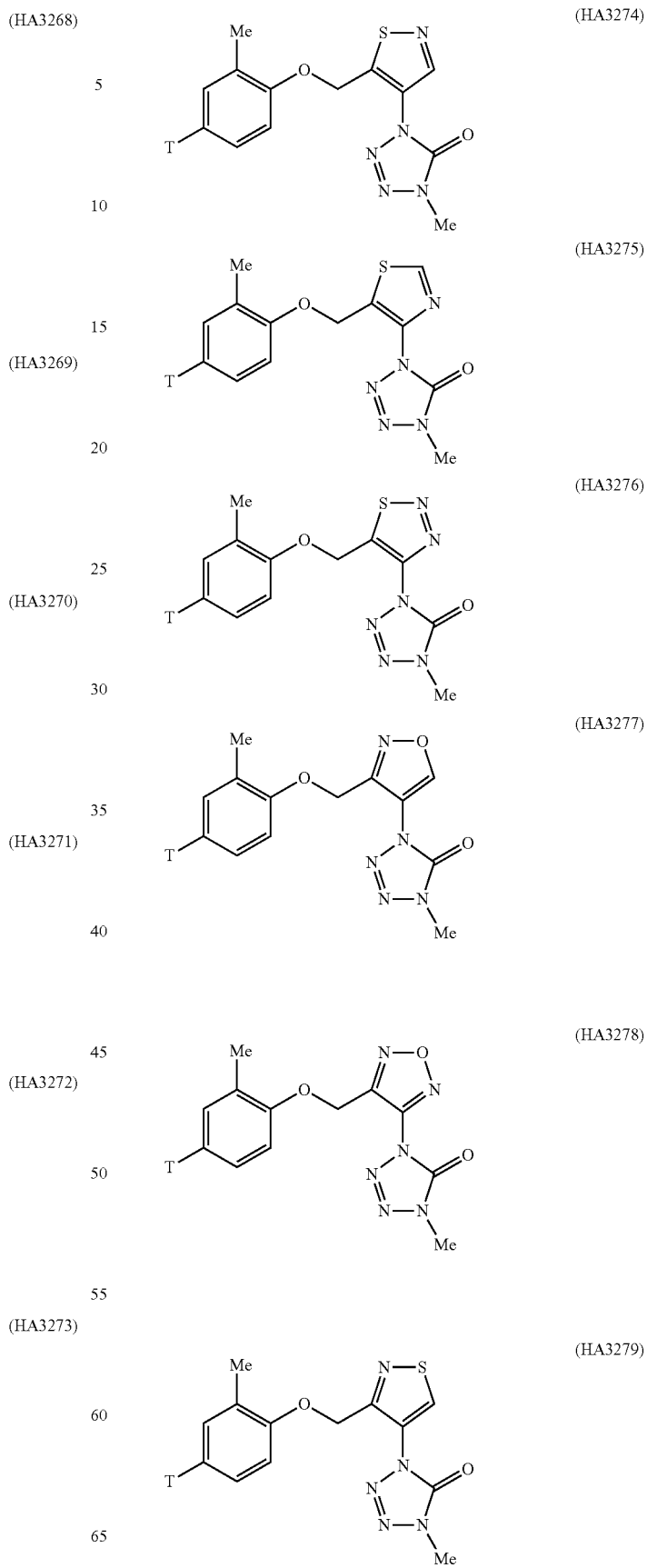

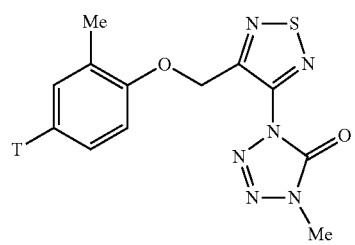 (HA3280)
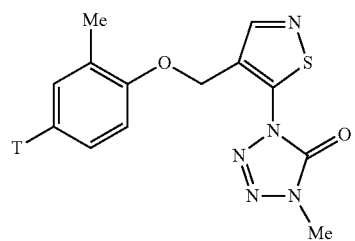 (HA3233)
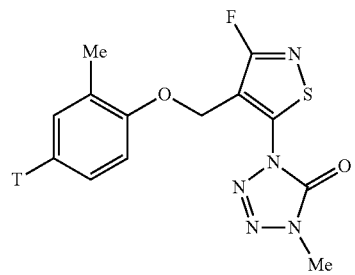 (HA3234)
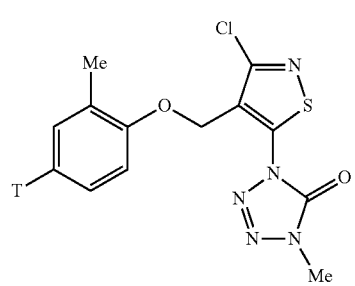 (HA3235)
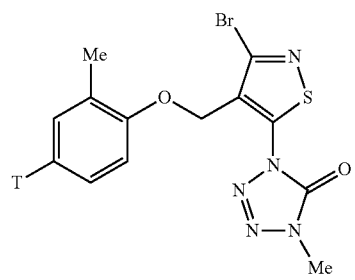 (HA3236)
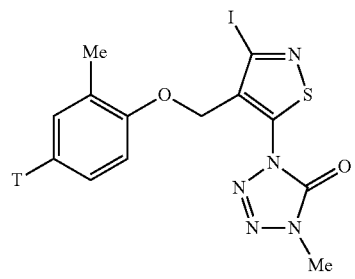 (HA3237)
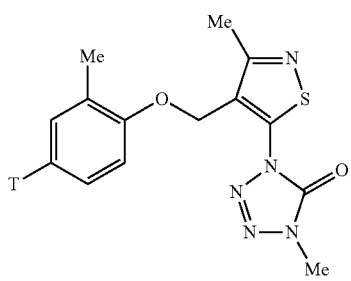 (HA3238)
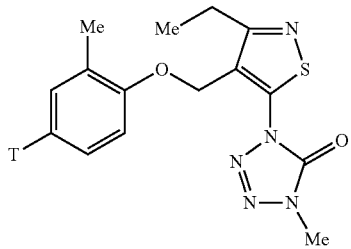 (HA3239)
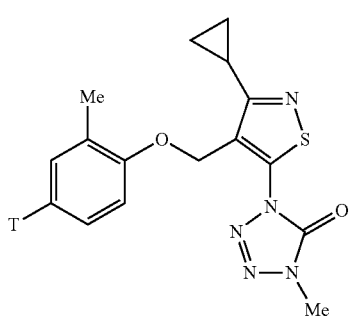 (HA3240)
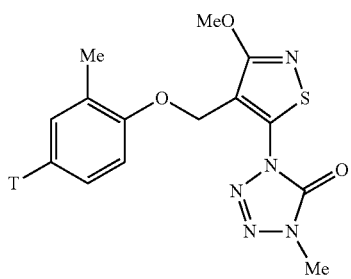 (HA3241)
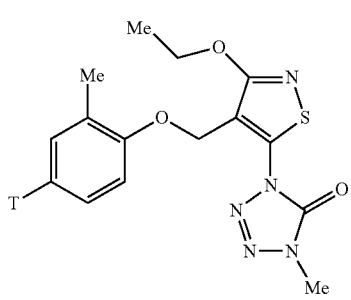 (HA3242)

315
-continued
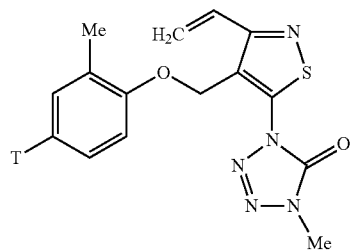
(HA3243)
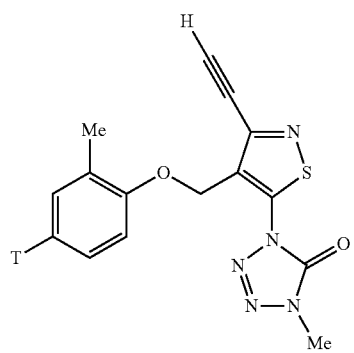
(HA3244)
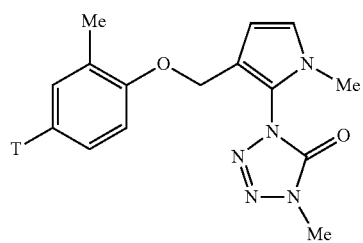
(HA3245)
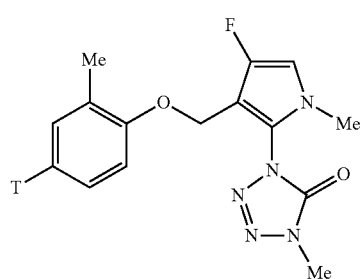
(HA3246)
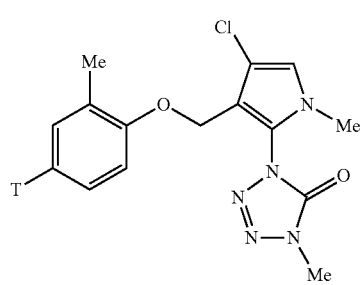
(HA3247)
316
-continued
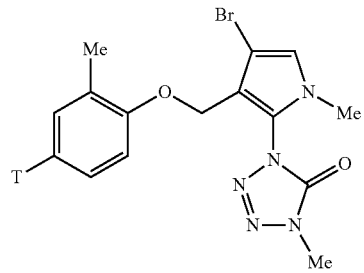
(HA3248)
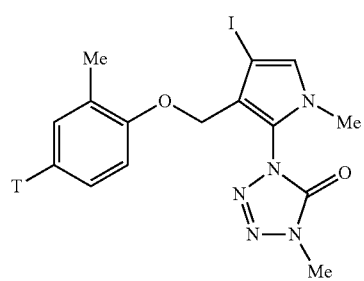
(HA3249)
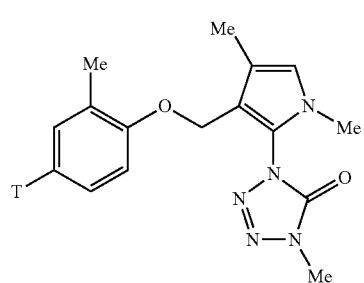
(HA3250)
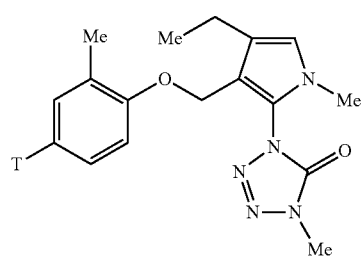
(HA3251)
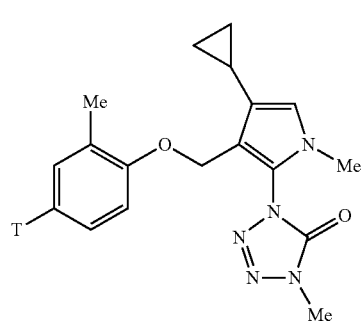
(HA3252)

-continued
(HA3253) 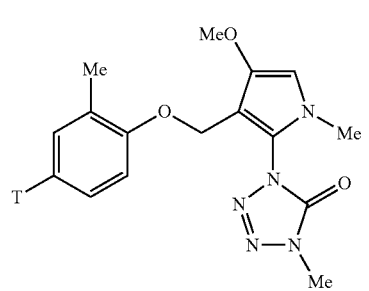
(HA3254) 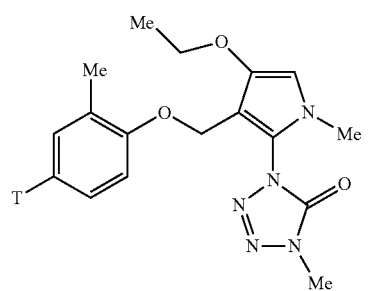
(HA3255) 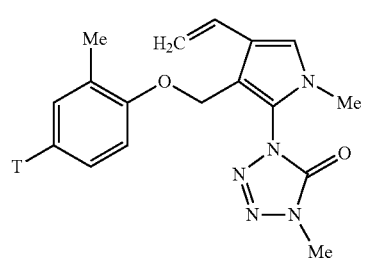
(HA3256) 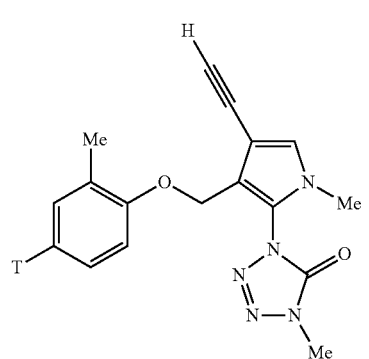
(HA3257) 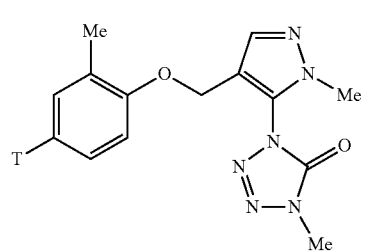
-continued
(HA3258) 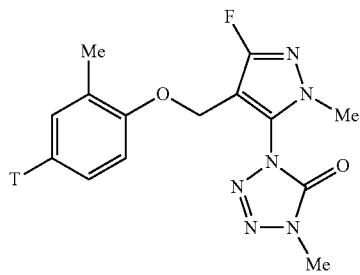
(HA3259) 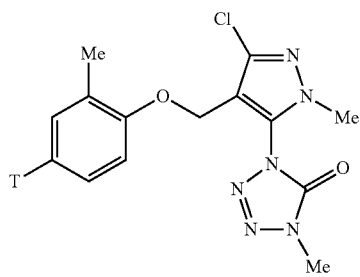
(HA3260) 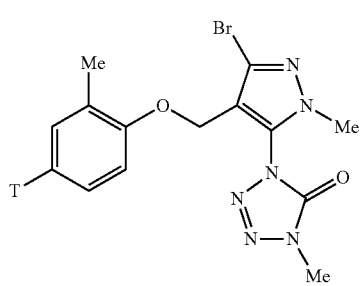
(HA3261) 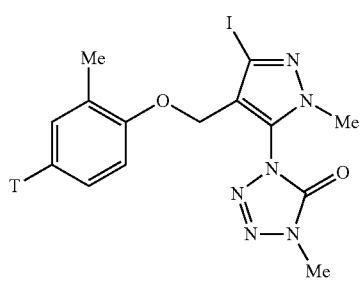
(HA3262) 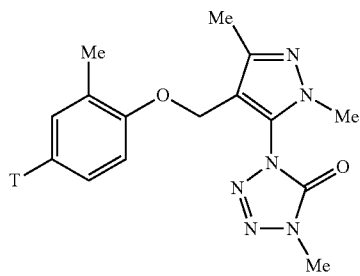
(HA3263) 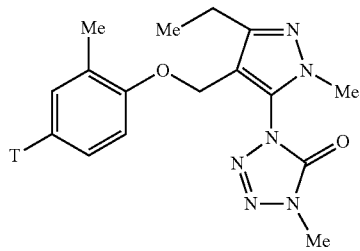

(HA3264)
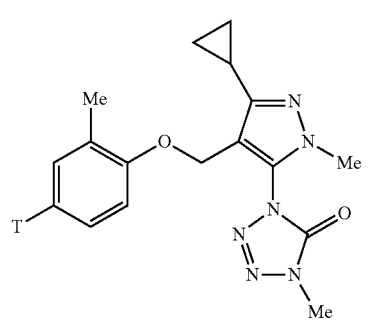
(HA3265)
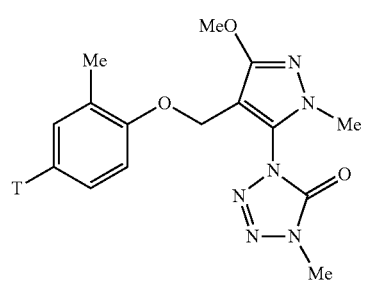
(HA3266)
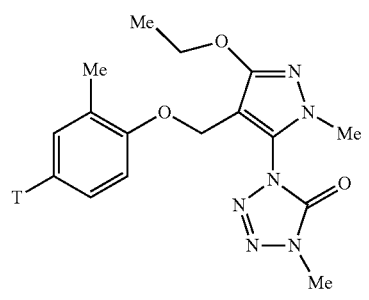
(HA3267)
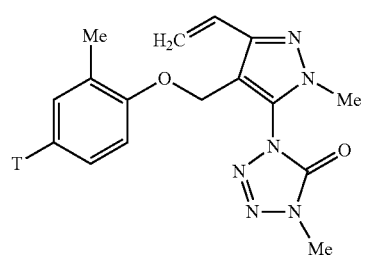
(HA3268)
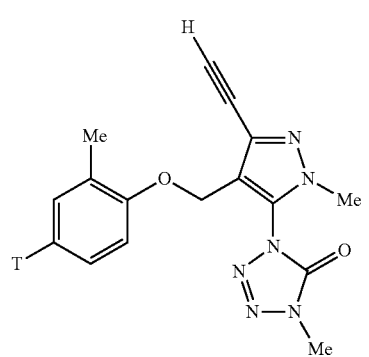
(HA3269)
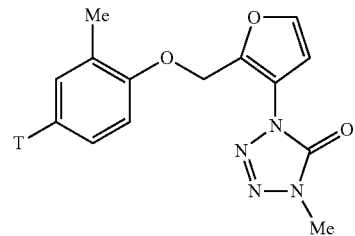
(HA3270)
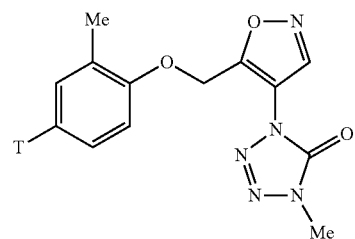
(HA3271)
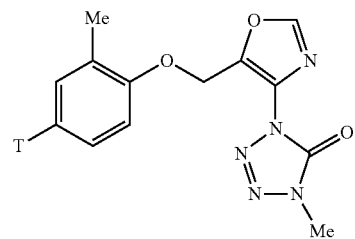
(HA3272)
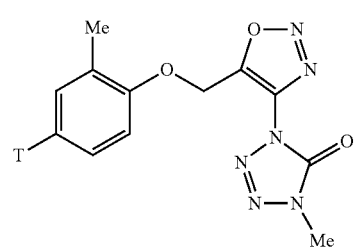
(HA3273)
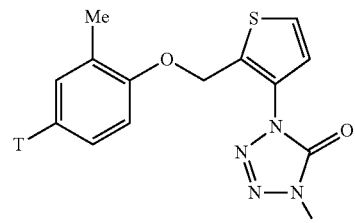
(HA3274)
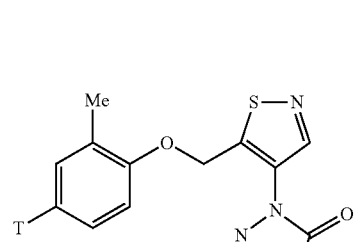

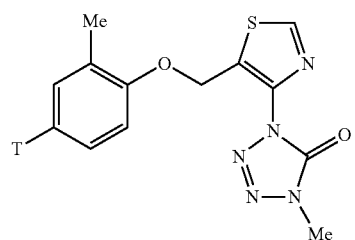
(HA3275)
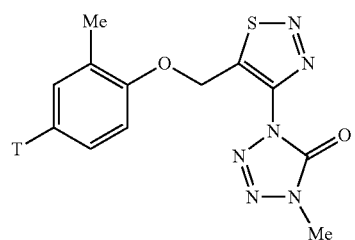
(HA3276)
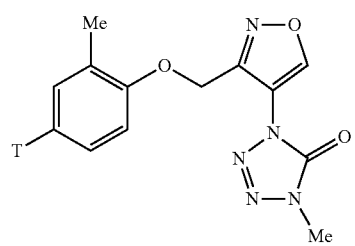
(HA3277)
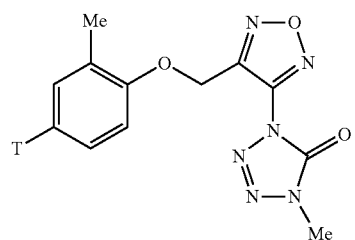
(HA3278)
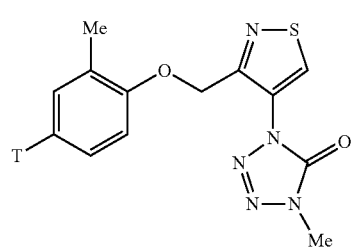
(HA3279)
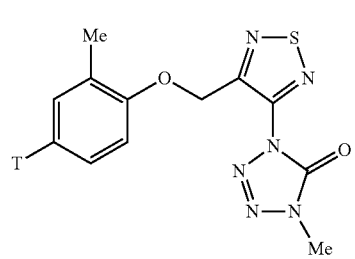
(HA3280)
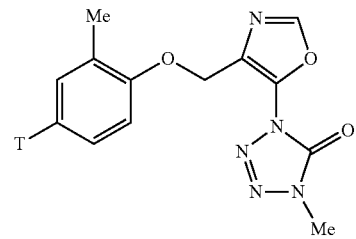
(HA3281)
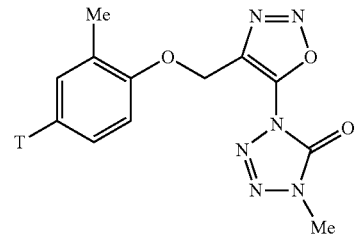
(HA3282)
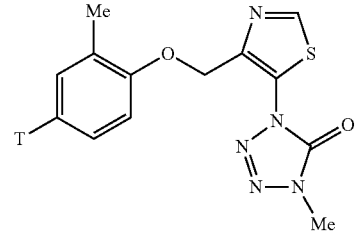
(HA3283)
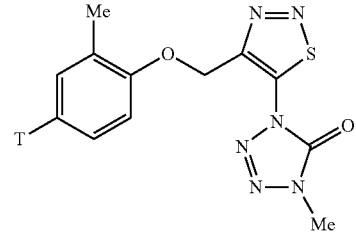
(HA3284)
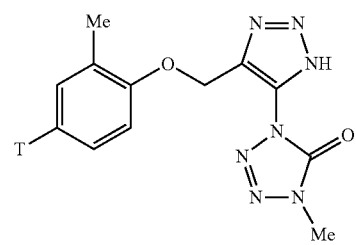
(HA3285)
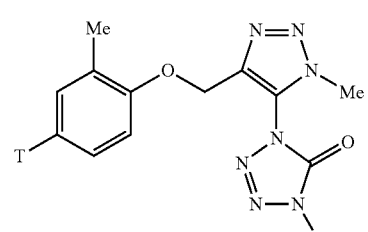
(HA3286)

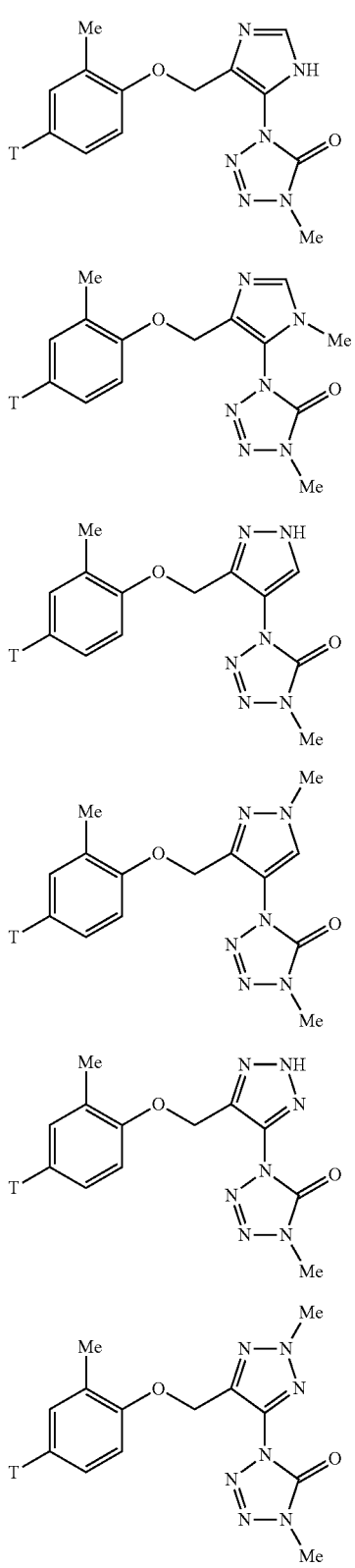

(HA3287)
(HA3288)
(HA3289)
(HA3290)
(HA3291)
(HA3292)

wherein T is a substituent corresponding to each of substituent numbers 1 to 7660. 2-Py mentioned in the following [substituent number; T] represents pyridin-2-yl, 3-Py represents pyridin-3-yl, 4-Py represents pyridin-4-yl, F represents fluoro, Cl represents chloro, Br represents bromo, I represents iodo, CN represents cyano, Me represents methyl, Et represents ethyl, Pr represents propyl, i-Pr represents isopropyl group, CF3 represents trifluoromethyl, CH2CF3 represents 2,2,2-trifluoroethyl, CHF2 represents difluoromethyl, OMe represents methoxy, OCH2CF3 represents 2,2,2-trifluoroethoxy, OEt represents ethoxy, OPr represents propoxy, i-OPr represents isopropoxy, OCF3 represents trifluoromethoxy, OCHF2 represents difluoromethoxy, SMe represents methylthio, S(O)Me represents methylsulfinyl, S(O)2Me represents methylsulfonyl, SCF3 represents trifluoromethylthio, S(O)CF3 represents trifluoromethylsulfinyl, S(O)2CF3 represents trifluoromethylsulfonyl, COOMe represents methoxycarbonyl, NO2 represents nitro, NH2 represents amino, NHMe represents methylamino, NMe2 represents dimethylamino, AC represents acetyl, ACNH represents acetylamino, N-AC-N-Me-N represents N-acetyl-N-methylamino, PYR1 represents pyrazole-1-yl group, PYR3 represents pyrazol-3-yl group, Ph represents phenyl, di represents di, and tri represents tri.

For example, HA1001-0001 represents a compound represented by formula (HA1001) in which T is a substituent number 0001, and is represented by the following formula.

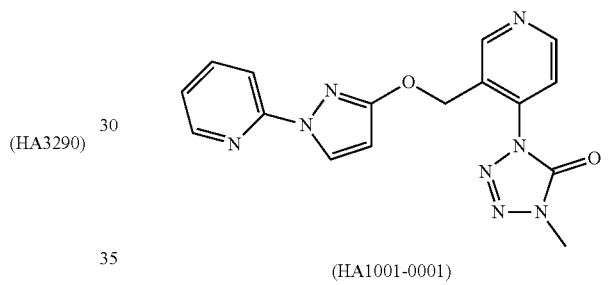

(HA1001-0001)

[0001:2-Py], [0002:3-F-2-Py], [0003:4-Cl-3-F-2-Py], [0004:5-Cl-3-F-2-Py], [0005:6-Cl-3-F-2-Py], [0006:4-Me-3-F-2-Py], [0007:5-Me-3-F-2-Py], [0008:6-Me-3-F-2-Py], [0009:4-CF3-3-F-2-Py], [0010:5-CF3-3-F-2-Py], [0011:6-CF3-3-F-2-Py], [0012:4-CN-3-F-2-Py], [0013:5-CN-3-F-2-Py], [0014:6-CN-3-F-2-Py], [0015:4-OMe-3-F-2-Py], [0016:5-OMe-3-F-2-Py], [0017:6-OMe-3-F-2-Py], [0018:4-F-2-Py], [0019:3-Cl-4-F-2-Py], [0020:5-Cl-4-F-2-Py], [0021:6-Cl-4-F-2-Py], [0022:3-Me-4-F-2-Py], [0023:5-Me-4-F-2-Py], [0024:6-Me-4-F-2-Py], [0025:3-CF3-4-F-2-Py], [0026:5-CF3-4-F-2-Py], [0027:6-CF3-4-F-2-Py], [0028:3-CN-4-F-2-Py], [0029:5-CN-4-F-2-Py], [0030:6-CN-4-F-2-Py], [0031:3-OMe-4-F-2-Py], [0032:5-OMe-4-F-2-Py], [0033:6-OMe-4-F-2-Py], [0034:5-F-2-Py], [0035:3-Cl-5-F-2-Py], [0036:4-Cl-5-F-2-Py], [0037:6-Cl-5-F-2-Py], [0038:3-Me-5-F-2-Py], [0039:4-Me-5-F-2-Py], [0040:6-Me-5-F-2-Py], [0041:3-CF3-5-F-2-Py], [0042:4-CF3-5-F-2-Py], [0043:6-CF3-5-F-2-Py], [0044:3-CN-5-F-2-Py], [0045:4-CN-5-F-2-Py], [0046:6-CN-5-F-2-Py], [0047:3-OMe-5-F-2-Py], [0048:4-OMe-5-F-2-Py], [0049:6-OMe-5-F-2-Py], [0050:6-F-2-Py], [0051:3-Cl-6-F-2-Py], [0052:4-Cl-6-F-2-Py], [0053:5-Cl-6-F-2-Py], [0054:3-Me-6-F-2-Py], [0055:4-Me-6-F-2-Py], [0056:5-Me-6-F-2-Py], [0057:3-CF3-6-F-2-Py], [0058:4-CF3-6-F-2-Py], [0059:5-CF3-6-F-2-Py], [0060:3-CN-6-F-2-Py], [0061:4-CN-6-F-2-Py], [0062:5-CN-6-F-2-Py], [0063:3-OMe-6-F-2-Py], [0064:4-OMe-6-F-2-Py], [0065:5-OMe-6-F-2-Py], [0066:3-Cl-2-Py], [0067:4-Cl-3-Cl-2-Py], [0068:5-Cl-3-Cl-2-Py], [0069:6-Cl-3-Cl-2-Py], [0070:4-Me-3-Cl-2-Py], [0071:5-Me-3-Cl-2-Py], [0072:6-Me-3-Cl-2-Py], [0073:4-CF3-3-Cl-2-Py], [0074:5-

CF3-3-Cl-2-Py], [0075:6-CF3-3-Cl-2-Py], [0076:4-CN-3-Cl-2-Py], [0077:5-CN-3-Cl-2-Py], [0078:6-CN-3-Cl-2-Py], [0079:4-OMe-3-Cl-2-Py], [0080:5-OMe-3-Cl-2-Py], [0081:6-OMe-3-Cl-2-Py], [0082:4-Cl-2-Py], [0083:3-Cl-4-Cl-2-Py], [0084:5-Cl-4-Cl-2-Py], [0085:6-Cl-4-Cl-2-Py], [0086:3-Me-4-Cl-2-Py], [0087:5-Me-4-Cl-2-Py], [0088:6-Me-4-Cl-2-Py], [0089:3-CF3-4-Cl-2-Py], [0090:5-CF3-4-Cl-2-Py], [0091:6-CF3-4-Cl-2-Py], [0092:3-CN-4-Cl-2-Py], [0093:5-CN-4-Cl-2-Py], [0094:6-CN-4-Cl-2-Py], [0095:3-OMe-4-Cl-2-Py], [0096:5-OMe-4-Cl-2-Py], [0097:6-OMe-4-Cl-2-Py], [0098:5-Cl-2-Py], [0099:4-Cl-5-Cl-2-Py], [0100:5-Cl-5-Cl-2-Py],

[0101:6-Cl-5-Cl-2-Py], [0102:4-Me-5-Cl-2-Py], [0103:5-Me-5-Cl-2-Py], [0104:6-Me-5-Cl-2-Py], [0105:4-CF3-5-Cl-2-Py], [0106:5-CF3-5-Cl-2-Py], [0107:6-CF3-5-Cl-2-Py], [0108:4-CN-5-Cl-2-Py], [0109:3-CN-5-Cl-2-Py], [0110:6-CN-5-Cl-2-Py], [0111:4-OMe-5-Cl-2-Py], [0112:5-OMe-5-Cl-2-Py], [0113:6-OMe-5-Cl-2-Py], [0114:6-Cl-2-Py], [0115:3-Cl-6-Cl-2-Py], [0116:4-Cl-6-Cl-2-Py], [0117:5-Cl-6-Cl-2-Py], [0118:3-Me-6-Cl-2-Py], [0119:4-Me-6-Cl-2-Py], [0120:5-Me-6-Cl-2-Py], [0121:3-CF3-6-Cl-2-Py], [0122:4-CF3-6-Cl-2-Py], [0123:5-CF3-6-Cl-2-Py], [0124:3-CN-6-Cl-2-Py], [0125:4-CN-6-Cl-2-Py], [0126:5-CN-6-Cl-2-Py], [0127:3-OMe-6-Cl-2-Py], [0128:4-OMe-6-Cl-2-Py], [0129:5-OMe-6-Cl-2-Py], [0130:3-Br-2-Py], [0131:4-Cl-3-Br-2-Py], [0132:5-Cl-3-Br-2-Py], [0133:6-Cl-3-Br-2-Py], [0134:4-Me-3-Br-2-Py], [0135:5-Me-3-Br-2-Py], [0136:6-Me-3-Br-2-Py], [0137:4-CF3-3-Br-2-Py], [0138:5-CF3-3-Br-2-Py], [0139:6-CF3-3-Br-2-Py], [0140:4-CN-3-Br-2-Py], [0141:5-CN-3-Br-2-Py], [0142:6-CN-3-Br-2-Py], [0143:4-OMe-3-Br-2-Py], [0144:5-OMe-3-Br-2-Py], [0145:6-OMe-3-Br-2-Py], [0146:4-Br-2-Py], [0147:3-Cl-4-Br-2-Py], [0148:5-Cl-4-Br-2-Py], [0149:6-Cl-4-Br-2-Py], [0150:3-Me-4-Br-2-Py], [0151:5-Me-4-Br-2-Py], [0152:6-Me-4-Br-2-Py], [0153:3-CF3-4-Br-2-Py], [0154:5-CF3-4-Br-2-Py], [0155:6-CF3-4-Br-2-Py], [0156:3-CN-4-Br-2-Py], [0157:5-CN-4-Br-2-Py], [0158:6-CN-4-Br-2-Py], [0159:3-OMe-4-Br-2-Py], [0160:5-OMe-4-Br-2-Py], [0161:6-OMe-4-Br-2-Py], [0162:5-Br-2-Py], [0163:3-Cl-5-Br-2-Py], [0164:4-Cl-5-Br-2-Py], [0165:6-Cl-5-Br-2-Py], [0166:3-Me-5-Br-2-Py], [0167:4-Me-5-Br-2-Py], [0168:6-Me-5-Br-2-Py], [0169:3-CF3-5-Br-2-Py], [0170:4-CF3-5-Br-2-Py], [0171:6-CF3-5-Br-2-Py], [0172:3-CN-5-Br-2-Py], [0173:4-CN-5-Br-2-Py], [0174:6-CN-5-Br-2-Py], [0175:3-OMe-5-Br-2-Py], [0176:4-OMe-5-Br-2-Py], [0177:6-OMe-5-Br-2-Py], [0178:6-Br-2-Py], [0179:3-Cl-6-Br-2-Py], [0180:4-Cl-6-Br-2-Py], [0181:5-Cl-6-Br-2-Py], [0182:3-Me-6-Br-2-Py], [0183:4-Me-6-Br-2-Py], [0184:5-Me-6-Br-2-Py], [0185:3-CF3-6-Br-2-Py], [0186:4-CF3-6-Br-2-Py], [0187:5-CF3-6-Br-2-Py], [0188:3-CN-6-Br-2-Py], [0189:4-CN-6-Br-2-Py], [0190:5-CN-6-Br-2-Py], [0191:3-OMe-6-Br-2-Py], [0192:4-OMe-6-Br-2-Py], [0193:5-OMe-6-Br-2-Py], [0194:3-I-2-Py], [0195:4-Cl-3-I-2-Py], [0196:5-Cl-3-I-2-Py], [0197:6-Cl-3-I-2-Py], [0198:4-Me-3-I-2-Py], [0199:5-Me-3-I-2-Py], [0200:6-Me-3-I-2-Py],

[0201:4-CF3-3-I-2-Py], [0202:5-CF3-3-I-2-Py], [0203:6-CF3-3-I-2-Py], [0204:4-CN-3-I-2-Py], [0205:5-CN-3-I-2-Py], [0206:6-CN-3-I-2-Py], [0207:4-OMe-3-I-2-Py], [0208:5-OMe-3-I-2-Py], [0209:6-OMe-3-I-2-Py], [0210:4-I-2-Py], [0211:3-Cl-4-I-2-Py], [0212:5-Cl-4-I-2-Py], [0213:6-Cl-4-I-2-Py], [0214:3-Me-4-I-2-Py], [0215:5-Me-4-I-2-Py], [0216:6-Me-4-I-2-Py], [0217:3-CF3-4-I-2-Py], [0218:5-CF3-4-I-2-Py], [0219:6-CF3-4-I-2-Py], [0220:3-CN-4-I-2-Py], [0221:5-CN-4-I-2-Py], [0222:6-CN-4-I-2-Py], [0223:3-OMe-4-I-2-Py], [0224:5-OMe-4-I-2-Py], [0225:6-OMe-4-I-2-Py], [0226:5-I-2-Py], [0227:3-Cl-5-I-2-Py], [0228:4-Cl-5-I-2-Py], [0229:6-Cl-5-I-2-Py], [0230:3-Me-5-I-2-Py], [0231:4-Me-5-I-2-Py], [0232:6-Me-5-I-2-Py], [0233:3-CF3-5-I-2-Py], [0234:4-CF3-5-I-2-Py], [0235:6-CF3-5-I-2-Py], [0236:3-CN-5-I-2-Py], [0237:4-CN-5-I-2-Py], [0238:6-CN-5-I-2-Py], [0239:3-OMe-5-I-2-Py], [0240:4-OMe-5-I-2-Py], [0241:6-OMe-5-I-2-Py], [0242:6-I-2-Py], [0243:3-Cl-6-I-2-Py], [0244:4-Cl-6-I-2-Py], [0245:5-Cl-6-I-2-Py], [0246:3-Me-6-I-2-Py], [0247:4-Me-6-I-2-Py], [0248:5-Me-6-I-2-Py], [0249:3-CF3-6-I-2-Py], [0250:4-CF3-6-I-2-Py], [0251:5-CF3-6-I-2-Py], [0252:3-CN-6-I-2-Py], [0253:4-CN-6-I-2-Py], [0254:5-CN-6-I-2-Py], [0255:3-OMe-6-I-2-Py], [0256:4-OMe-6-I-2-Py], [0257:5-OMe-6-I-2-Py], [0258:3-Me-2-Py], [0259:4-Cl-3-Me-2-Py], [0260:5-Cl-3-Me-2-Py], [0261:6-Cl-3-Me-2-Py], [0262:4-Me-3-Me-2-Py], [0263:5-Me-3-Me-2-Py], [0264:6-Me-3-Me-2-Py], [0265:4-CF3-3-Me-2-Py], [0266:5-CF3-3-Me-2-Py], [0267:6-CF3-3-Me-2-Py], [0268:4-CN-3-Me-2-Py], [0269:5-CN-3-Me-2-Py], [0270:6-CN-3-Me-2-Py], [0271:4-OMe-3-Me-2-Py], [0272:5-OMe-3-Me-2-Py], [0273:6-OMe-3-Me-2-Py], [0274:4-Me-2-Py], [0275:3-Cl-4-Me-2-Py], [0276:5-Cl-4-Me-2-Py], [0277:6-Cl-4-Me-2-Py], [0278:3-Me-4-Me-2-Py], [0279:5-Me-4-Me-2-Py], [0280:6-Me-4-Me-2-Py], [0281:3-CF3-4-Me-2-Py], [0282:5-CF3-4-Me-2-Py], [0283:6-CF3-4-Me-2-Py], [0284:3-CN-4-Me-2-Py], [0285:5-CN-4-Me-2-Py], [0286:6-CN-4-Me-2-Py], [0287:3-OMe-4-Me-2-Py], [0288:5-OMe-4-Me-2-Py], [0289:6-OMe-4-Me-2-Py], [0290:5-Me-2-Py], [0291:3-Cl-5-Me-2-Py], [0292:4-Cl-5-Me-2-Py], [0293:6-Cl-5-Me-2-Py], [0294:3-Me-5-Me-2-Py], [0295:4-Me-5-Me-2-Py], [0296:6-Me-5-Me-2-Py], [0297:3-CF3-5-Me-2-Py], [0298:4-CF3-5-Me-2-Py], [0299:6-CF3-5-Me-2-Py], [0300:3-CN-5-Me-2-Py],

[0301:4-CN-5-Me-2-Py], [0302:6-CN-5-Me-2-Py], [0303:3-OMe-5-Me-2-Py], [0304:4-OMe-5-Me-2-Py], [0305:6-OMe-5-Me-2-Py], [0306:6-Me-2-Py], [0307:3-Cl-6-Me-2-Py], [0308:4-Cl-6-Me-2-Py], [0309:5-Cl-6-Me-2-Py], [0310:3-Me-6-Me-2-Py], [0311:4-Me-6-Me-2-Py], [0312:5-Me-6-Me-2-Py], [0313:3-CF3-6-Me-2-Py], [0314:4-CF3-6-Me-2-Py], [0315:5-CF3-6-Me-2-Py], [0316:3-CN-6-Me-2-Py], [0317:4-CN-6-Me-2-Py], [0318:5-CN-6-Me-2-Py], [0319:3-OMe-6-Me-2-Py], [0320:4-OMe-6-Me-2-Py], [0321:5-OMe-6-Me-2-Py], [0322:3-OMe-2-Py], [0323:4-Cl-3-OMe-2-Py], [0324:5-Cl-3-OMe-2-Py], [0325:6-Cl-3-OMe-2-Py], [0326:4-Me-3-OMe-2-Py], [0327:5-Me-3-OMe-2-Py], [0328:6-Me-3-OMe-2-Py], [0329:4-CF3-3-OMe-2-Py], [0330:5-CF3-3-OMe-2-Py], [0331:6-CF3-3-OMe-2-Py], [0332:4-CN-3-OMe-2-Py], [0333:5-CN-3-OMe-2-Py], [0334:6-CN-3-OMe-2-Py], [0335:4-OMe-3-OMe-2-Py], [0336:5-OMe-3-OMe-2-Py], [0337:6-OMe-3-OMe-2-Py], [0338:4-OMe-2-Py], [0339:3-Cl-4-OMe-2-Py], [0340:5-Cl-4-OMe-2-Py], [0341:6-Cl-4-OMe-2-Py], [0342:3-Me-4-OMe-2-Py], [0343:5-Me-4-OMe-2-Py], [0344:6-Me-4-OMe-2-Py], [0345:3-CF3-4-OMe-2-Py], [0346:5-CF3-4-OMe-2-Py], [0347:6-CF3-4-OMe-2-Py], [0348:3-CN-4-OMe-2-Py], [0349:5-CN-4-OMe-2-Py], [0350:6-CN-4-OMe-2-Py], [0351:3-OMe-4-OMe-2-Py], [0352:5-OMe-4-OMe-2-Py], [0353:6-OMe-4-OMe-2-Py], [0354:5-OMe-2-Py], [0355:3-Cl-5-OMe-2-Py], [0356:4-Cl-5-OMe-2-Py], [0357:6-Cl-5-OMe-2-Py], [0358:3-Me-5-OMe-2-Py], [0359:4-Me-5-OMe-2-Py], [0360:6-Me-5-OMe-2-Py], [0361:3-CF3-5-OMe-2-Py], [0362:4-CF3-5-OMe-2-Py], [0363:6-CF3-5-OMe-2-Py], [0364:3-CN-5-OMe-2-Py], [0365:4-CN-5-OMe-2-Py], [0366:6-CN-5-OMe-2-Py], [0367:3-OMe-5-OMe-2-Py], [0368:4-OMe-5-OMe-2-Py], [0369:6-OMe-5-OMe-2-Py], [0370:6-OMe-2-Py], [0371:3-Cl-6-OMe-2-Py], [0372:4-Cl-6-OMe-2-Py], [0373:5-Cl-6-OMe-2-Py], [0374:3-Me-6-OMe-2-Py], [0375:4-Me-6-OMe-2-Py], [0376:5-Me-6-OMe-2-Py], [0377:3-CF3-6-OMe-2-Py], [0378:4-CF3-6-OMe-2-Py], [0379:5-CF3-6-

OMe-2-Py], [0380:3-CN-6-OMe-2-Py], [0381:4-CN-6-OMe-2-Py], [0382:5-CN-6-OMe-2-Py], [0383:3-OMe-6-OMe-2-Py], [0384:4-OMe-6-OMe-2-Py], [0385:5-OMe-6-OMe-2-Py], [0386:3-CF3-2-Py], [0387:4-Cl-3-CF3-2-Py], [0388:5-Cl-3-CF3-2-Py], [0389:6-Cl-3-CF3-2-Py], [0390:4-Me-3-CF3-2-Py], [0391:5-Me-3-CF3-2-Py], [0392:6-Me-3-CF3-2-Py], [0393:4-CF3-3-CF3-2-Py], [0394:5-CF3-3-CF3-2-Py], [0395:6-CF3-3-CF3-2-Py], [0396:4-CN-3-CF3-2-Py], [0397:5-CN-3-CF3-2-Py], [0398:6-CN-3-CF3-2-Py], [0399:4-OMe-3-CF3-2-Py], [0400:5-OMe-3-CF3-2-Py], [0401:6-OMe-3-CF3-2-Py], [0402:4-CF3-2-Py], [0403:3-Cl-4-CF3-2-Py], [0404:5-Cl-4-CF3-2-Py], [0405:6-Cl-4-CF3-2-Py], [0406:3-Me-4-CF3-2-Py], [0407:5-Me-4-CF3-2-Py], [0408:6-Me-4-CF3-2-Py], [0409:3-CF3-4-CF3-2-Py], [0410:5-CF3-4-CF3-2-Py], [0411:6-CF3-4-CF3-2-Py], [0412:3-CN-4-CF3-2-Py], [0413:5-CN-4-CF3-2-Py], [0414:6-CN-4-CF3-2-Py], [0415:3-OMe-4-CF3-2-Py], [0416:5-OMe-4-CF3-2-Py], [0417:6-OMe-4-CF3-2-Py], [0418:5-CF3-2-Py], [0419:3-Cl-5-CF3-2-Py], [0420:4-Cl-5-CF3-2-Py], [0421:6-Cl-5-CF3-2-Py], [0422:3-Me-5-CF3-2-Py], [0423:4-Me-5-CF3-2-Py], [0424:6-Me-5-CF3-2-Py], [0425:3-CF3-5-CF3-2-Py], [0426:4-CF3-5-CF3-2-Py], [0427:6-CF3-5-CF3-2-Py], [0428:3-CN-5-CF3-2-Py], [0429:4-CN-5-CF3-2-Py], [0430:6-CN-5-CF3-2-Py], [0431:3-OMe-5-CF3-2-Py], [0432:4-OMe-5-CF3-2-Py], [0433:6-OMe-5-CF3-2-Py], [0434:6-CF3-2-Py], [0435:3-Cl-6-CF3-2-Py], [0436:4-Cl-6-CF3-2-Py], [0437:5-Cl-6-CF3-2-Py], [0438:3-Me-6-CF3-2-Py], [0439:4-Me-6-CF3-2-Py], [0440:5-Me-6-CF3-2-Py], [0441:3-CF3-6-CF3-2-Py], [0442:4-CF3-6-CF3-2-Py], [0443:5-CF3-6-CF3-2-Py], [0444:3-CN-6-CF3-2-Py], [0445:4-CN-6-CF3-2-Py], [0446:5-CN-6-CF3-2-Py], [0447:3-OMe-6-CF3-2-Py], [0448:4-OMe-6-CF3-2-Py], [0449:5-OMe-6-CF3-2-Py], [0450:3-OCF3-2-Py], [0451:4-Cl-3-OCF3-2-Py], [0452:5-Cl-3-OCF3-2-Py], [0453:6-Cl-3-OCF3-2-Py], [0454:4-Me-3-OCF3-2-Py], [0455:5-Me-3-OCF3-2-Py], [0456:6-Me-3-OCF3-2-Py], [0457:4-CF3-3-OCF3-2-Py], [0458:5-CF3-3-OCF3-2-Py], [0459:6-CF3-3-OCF3-2-Py], [0460:4-CN-3-OCF3-2-Py], [0461:5-CN-3-OCF3-2-Py], [0462:6-CN-3-OCF3-2-Py], [0463:4-OMe-3-OCF3-2-Py], [0464:5-OMe-3-OCF3-2-Py], [0465:6-OMe-3-OCF3-2-Py], [0466:4-OCF3-2-Py], [0467:3-Cl-4-OCF3-2-Py], [0468:5-Cl-4-OCF3-2-Py], [0469:6-Cl-4-OCF3-2-Py], [0470:3-Me-4-OCF3-2-Py], [0471:5-Me-4-OCF3-2-Py], [0472:6-Me-4-OCF3-2-Py], [0473:3-CF3-4-OCF3-2-Py], [0474:5-CF3-4-OCF3-2-Py], [0475:6-CF3-4-OCF3-2-Py], [0476:3-CN-4-OCF3-2-Py], [0477:5-CN-4-OCF3-2-Py], [0478:6-CN-4-OCF3-2-Py], [0479:3-OMe-4-OCF3-2-Py], [0480:5-OMe-4-OCF3-2-Py], [0481:6-OMe-4-OCF3-2-Py], [0482:5-OCF3-2-Py], [0483:3-Cl-5-OCF3-2-Py], [0484:4-Cl-5-OCF3-2-Py], [0485:6-Cl-5-OCF3-2-Py], [0486:3-Me-5-OCF3-2-Py], [0487:4-Me-5-OCF3-2-Py], [0488:6-Me-5-OCF3-2-Py], [0489:3-CF3-5-OCF3-2-Py], [0490:4-CF3-5-OCF3-2-Py], [0491:6-CF3-5-OCF3-2-Py], [0492:3-CN-5-OCF3-2-Py], [0493:4-CN-5-OCF3-2-Py], [0494:6-CN-5-OCF3-2-Py], [0495:3-OMe-5-OCF3-2-Py], [0496:4-OMe-5-OCF3-2-Py], [0497:6-OMe-5-OCF3-2-Py], [0498:6-OCF3-2-Py], [0499:3-Cl-6-OCF3-2-Py], [0500:4-Cl-6-OCF3-2-Py], [0501:5-Cl-6-OCF3-2-Py], [0502:3-Me-6-OCF3-2-Py], [0503:4-Me-6-OCF3-2-Py], [0504:5-Me-6-OCF3-2-Py], [0505:3-CF3-6-OCF3-2-Py], [0506:4-CF3-6-OCF3-2-Py], [0507:5-CF3-6-OCF3-2-Py], [0508:3-CN-6-OCF3-2-Py], [0509:4-CN-6-OCF3-2-Py], [0510:5-CN-6-OCF3-2-Py], [0511:3-OMe-6-OCF3-2-Py], [0512:4-OMe-6-OCF3-2-Py], [0513:5-OMe-6-OCF3-2-Py], [0514:3-CHF2-2-Py], [0515:4-CHF2-2-Py], [0516:5-Cl-3-CHF2-2-Py], [0517:6-Cl-3-CHF2-2-Py], [0518:4-Me-3-CHF2-2-Py], [0519:5-Me-3-CHF2-2-Py], [0520:6-Me-3-CHF2-2-Py], [0521:4-CF3-3-CHF2-2-Py], [0522:5-CF3-3-CHF2-2-Py], [0523:6-CF3-3-CHF2-2-Py], [0524:4-CN-3-CHF2-2-Py], [0525:5-CN-3-CHF2-2-Py], [0526:6-CN-3-CHF2-2-Py], [0527:4-OMe-3-CHF2-2-Py], [0528:5-OMe-3-CHF2-2-Py], [0529:6-OMe-3-CHF2-2-Py], [0530:4-CHF2-2-Py], [0531:3-Cl-4-CHF2-2-Py], [0532:5-Cl-4-CHF2-2-Py], [0533:6-Cl-4-CHF2-2-Py], [0534:3-Me-4-CHF2-2-Py], [0535:5-Me-4-CHF2-2-Py], [0536:6-Me-4-CHF2-2-Py], [0537:3-CF3-4-CHF2-2-Py], [0538:5-CF3-4-CHF2-2-Py], [0539:6-CF3-4-CHF2-2-Py], [0540:3-CN-4-CHF2-2-Py], [0541:5-CN-4-CHF2-2-Py], [0542:6-CN-4-CHF2-2-Py], [0543:3-OMe-4-CHF2-2-Py], [0544:5-OMe-4-CHF2-2-Py], [0545:6-OMe-4-CHF2-2-Py], [0546:5-CHF2-2-Py], [0547:3-Cl-5-CHF2-2-Py], [0548:4-Cl-5-CHF2-2-Py], [0549:6-Cl-5-CHF2-2-Py], [0550:3-Me-5-CHF2-2-Py], [0551:4-Me-5-CHF2-2-Py], [0552:6-Me-5-CHF2-2-Py], [0553:3-CF3-5-CHF2-2-Py], [0554:4-CF3-5-CHF2-2-Py], [0555:6-CF3-5-CHF2-2-Py], [0556:3-CN-5-CHF2-2-Py], [0557:4-CN-5-CHF2-2-Py], [0558:6-CN-5-CHF2-2-Py], [0559:3-OMe-5-CHF2-2-Py], [0560:4-OMe-5-CHF2-2-Py], [0561:6-OMe-5-CHF2-2-Py], [0562:6-CHF2-2-Py], [0563:3-Cl-6-CHF2-2-Py], [0564:4-Cl-6-CHF2-2-Py], [0565:5-Cl-6-CHF2-2-Py], [0566:3-Me-6-CHF2-2-Py], [0567:4-Me-6-CHF2-2-Py], [0568:5-Me-6-CHF2-2-Py], [0569:3-CF3-6-CHF2-2-Py], [0570:4-CF3-6-CHF2-2-Py], [0571:5-CF3-6-CHF2-2-Py], [0572:3-CN-6-CHF2-2-Py], [0573:4-CN-6-CHF2-2-Py], [0574:5-CN-6-CHF2-2-Py], [0575:3-OMe-6-CHF2-2-Py], [0576:4-OMe-6-CHF2-2-Py], [0577:5-OMe-6-CHF2-2-Py], [0578:3-OCHF2-2-Py], [0579:4-Cl-3-OCHF2-2-Py], [0580:5-Cl-3-OCHF2-2-Py], [0581:6-Cl-3-OCHF2-2-Py], [0582:4-Me-3-OCHF2-2-Py], [0583:5-Me-3-OCHF2-2-Py], [0584:6-Me-3-OCHF2-2-Py], [0585:4-CF3-3-OCHF2-2-Py], [0586:5-CF3-3-OCHF2-2-Py], [0587:6-CF3-3-OCHF2-2-Py], [0588:4-CN-3-OCHF2-2-Py], [0589:5-CN-3-OCHF2-2-Py], [0590:6-CN-3-OCHF2-2-Py], [0591:4-OMe-3-OCHF2-2-Py], [0592:5-OMe-3-OCHF2-2-Py], [0593:6-OMe-3-OCHF2-2-Py], [0594:4-OCHF2-2-Py], [0595:3-Cl-4-OCHF2-2-Py], [0596:5-Cl-4-OCHF2-2-Py], [0597:6-Cl-4-OCHF2-2-Py], [0598:3-Me-4-OCHF2-2-Py], [0599:5-Me-4-OCHF2-2-Py], [0600:6-Me-4-OCHF2-2-PY], [0601:3-CF3-4-OCHF2-2-Py], [0602:5-CF3-4-OCHF2-2-Py], [0603:6-CF3-4-OCHF2-2-Py], [0604:3-CN-4-OCHF2-2-Py], [0605:5-CN-4-OCHF2-2-Py], [0606:6-CN-4-OCHF2-2-Py], [0607:3-OMe-4-OCHF2-2-Py], [0608:5-OMe-4-OCHF2-2-Py], [0609:6-OMe-4-OCHF2-2-Py], [0610:5-OCHF2-2-Py], [0611:3-Cl-5-OCHF2-2-Py], [0612:4-Cl-5-OCHF2-2-Py], [0613:6-Cl-5-OCHF2-2-Py], [0614:3-Me-5-OCHF2-2-Py], [0615:4-Me-5-OCHF2-2-Py], [0616:6-Me-5-OCHF2-2-Py], [0617:3-CF3-5-OCHF2-2-Py], [0618:4-CF3-5-OCHF2-2-Py], [0619:6-CF3-5-OCHF2-2-Py], [0620:3-CN-5-OCHF2-2-Py], [0621:4-CN-5-OCHF2-2-Py], [0622:6-CN-5-OCHF2-2-Py], [0623:3-OMe-5-OCHF2-2-Py], [0624:4-OMe-5-OCHF2-2-Py], [0625:6-OMe-5-OCHF2-2-Py], [0626:6-OCHF2-2-Py], [0627:3-Cl-6-OCHF2-2-Py], [0628:4-Cl-6-OCHF2-2-Py], [0629:5-Cl-6-OCHF2-2-Py], [0630:3-Me-6-OCHF2-2-Py], [0631:4-Me-6-OCHF2-2-Py], [0632:5-Me-6-OCHF2-2-Py], [0633:3-CF3-6-OCHF2-2-Py], [0634:4-CF3-6-OCHF2-2-Py], [0635:5-CF3-6-OCHF2-2-Py], [0636:3-CN-6-OCHF2-2-Py], [0637:4-CN-6-OCHF2-2-Py], [0638:5-CN-6-OCHF2-2-Py], [0639:3-OMe-6-OCHF2-2-Py], [0640:4-OMe-6-OCHF2-2-Py], [0641:5-OMe-6-OCHF2-2-Py], [0642:3-Et-2-Py], [0643:4-Cl-3-Et-2-Py], [0644:5-Cl-3-Et-2-Py], [0645:6-Cl-3-Et-2-Py], [0646:4-Me-3-Et-2-Py],

[0647:5-Me-3-Et-2-Py], [0648:6-Me-3-Et-2-Py], [0649:4-CF3-3-Et-2-Py], [0650:5-CF3-3-Et-2-Py], [0651:6-CF3-3-Et-2-Py], [0652:4-CN-3-Et-2-Py], [0653:5-CN-3-Et-2-Py], [0654:6-CN-3-Et-2-Py], [0655:4-OMe-3-Et-2-Py], [0656:5-OMe-3-Et-2-Py], [0657:6-OMe-3-Et-2-Py], [0658:4-Et-2-Py], [0659:3-Cl-4-Et-2-Py], [0660:5-Cl-4-Et-2-Py], [0661:6-Cl-4-Et-2-Py], [0662:3-Me-4-Et-2-Py], [0663:5-Me-4-Et-2-Py], [0664:6-Me-4-Et-2-Py], [0665:3-CF3-4-Et-2-Py], [0666:5-CF3-4-Et-2-Py], [0667:6-CF3-4-Et-2-Py], [0668:3-CN-4-Et-2-Py], [0669:5-CN-4-Et-2-Py], [0670:6-CN-4-Et-2-Py], [0671:3-OMe-4-Et-2-Py], [0672:5-OMe-4-Et-2-Py], [0673:6-OMe-4-Et-2-Py], [0674:5-Et-2-Py], [0675:3-Cl-5-Et-2-Py], [0676:4-Cl-5-Et-2-Py], [0677:6-Cl-5-Et-2-Py], [0678:3-Me-5-Et-2-Py], [0679:4-Me-5-Et-2-Py], [0680:6-Me-5-Et-2-Py], [0681:3-CF3-5-Et-2-Py], [0682:4-CF3-5-Et-2-Py], [0683:6-CF3-5-Et-2-Py], [0684:3-CN-5-Et-2-Py], [0685:4-CN-5-Et-2-Py], [0686:6-CN-5-Et-2-Py], [0687:3-OMe-5-Et-2-Py], [0688:4-OMe-5-Et-2-Py], [0689:6-OMe-5-Et-2-Py], [0690:6-Et-2-Py], [0691:3-Cl-6-Et-2-Py], [0692:4-Cl-6-Et-2-Py], [0693:5-Cl-6-Et-2-Py], [0694:3-Me-6-Et-2-Py], [0695:4-Me-6-Et-2-Py], [0696:5-Me-6-Et-2-Py], [0697:3-CF3-6-Et-2-Py], [0698:4-CF3-6-Et-2-Py], [0699:5-CF3-6-Et-2-Py], [0700:3-CN-6-Et-2-Py], [0701:4-CN-6-Et-2-Py], [0702:5-CN-6-Et-2-Py], [0703:3-OMe-6-Et-2-Py], [0704:4-OMe-6-Et-2-Py], [0705:5-OMe-6-Et-2-Py], [0706:3-CH2CF3-2-Py], [0707:4-Cl-3-CH2CF3-2-Py], [0708:5-Cl-3-CH2CF3-2-Py], [0709:6-Cl-3-CH2CF3-2-Py], [0710:4-Me-3-CH2CF3-2-Py], [0711:5-Me-3-CH2CF3-2-Py], [0712:6-Me-3-CH2CF3-2-Py], [0713:4-CF3-3-CH2CF3-2-Py], [0714:5-CF3-3-CH2CF3-2-Py], [0715:6-CF3-3-CH2CF3-2-Py], [0716:4-CN-3-CH2CF3-2-Py], [0717:5-CN-3-CH2CF3-2-Py], [0718:6-CN-3-CH2CF3-2-Py], [0719:4-OMe-3-CH2CF3-2-Py], [0720:5-OMe-3-CH2CF3-2-Py], [0721:6-OMe-3-CH2CF3-2-Py], [0722:4-CH2CF3-2-Py], [0723:3-Cl-4-CH2CF3-2-Py], [0724:5-Cl-4-CH2CF3-2-Py], [0725:6-Cl-4-CH2CF3-2-Py], [0726:3-Me-4-CH2CF3-2-Py], [0727:5-Me-4-CH2CF3-2-Py], [0728:6-Me-4-CH2CF3-2-Py], [0729:3-CF3-4-CH2CF3-2-Py], [0730:5-CF3-4-CH2CF3-2-Py], [0731:6-CF3-4-CH2CF3-2-Py], [0732:3-CN-4-CH2CF3-2-Py], [0733:5-CN-4-CH2CF3-2-Py], [0734:6-CN-4-CH2CF3-2-Py], [0735:3-OMe-4-CH2CF3-2-Py], [0736:5-OMe-4-CH2CF3-2-Py], [0737:6-OMe-4-CH2CF3-2-Py], [0738:5-CH2CF3-2-Py], [0739:3-Cl-5-CH2CF3-2-Py], [0740:4-Cl-5-CH2CF3-2-Py], [0741:6-Cl-5-CH2CF3-2-Py], [0742:3-Me-5-CH2CF3-2-Py], [0743:4-Me-5-CH2CF3-2-Py], [0744:6-Me-5-CH2CF3-2-Py], [0745:3-CF3-5-CH2CF3-2-Py], [0746:4-CF3-5-CH2CF3-2-Py], [0747:6-CF3-5-CH2CF3-2-Py], [0748:3-CN-5-CH2CF3-2-Py], [0749:4-CN-5-CH2CF3-2-Py], [0750:6-CN-5-CH2CF3-2-Py], [0751:3-OMe-5-CH2CF3-2-Py], [0752:4-OMe-5-CH2CF3-2-Py], [0753:6-OMe-5-CH2CF3-2-Py], [0754:6-CH2CF3-2-Py], [0755:3-Cl-6-CH2CF3-2-Py], [0756:4-Cl-6-CH2CF3-2-Py], [0757:5-Cl-6-CH2CF3-2-Py], [0758:3-Me-6-CH2CF3-2-Py], [0759:4-Me-6-CH2CF3-2-Py], [0760:5-Me-6-CH2CF3-2-Py], [0761:3-CF3-6-CH2CF3-2-Py], [0762:4-CF3-6-CH2CF3-2-Py], [0763:5-CF3-6-CH2CF3-2-Py], [0764:3-CN-6-CH2CF3-2-Py], [0765:4-CN-6-CH2CF3-2-Py], [0766:5-CN-6-CH2CF3-2-Py], [0767:3-OMe-6-CH2CF3-2-Py], [0768:4-OMe-6-CH2CF3-2-Py], [0769:5-OMe-6-CH2CF3-2-Py], [0770:3-OEt-2-Py], [0771:4-Cl-3-OEt-2-Py], [0772:5-Cl-3-OEt-2-Py], [0773:6-Cl-3-OEt-2-Py], [0774:4-Me-3-OEt-2-Py], [0775:5-Me-3-OEt-2-Py], [0776:6-Me-3-OEt-2-Py], [0777:4-CF3-3-OEt-2-Py], [0778:5-CF3-3-OEt-2-Py], [0779:6-CF3-3-OEt-2-Py], [0780:4-CN-3-OEt-2-Py], [0781:5-CN-3-OEt-2-Py], [0782:6-CN-3-OEt-2-Py], [0783:4-OMe-3-OEt-2-Py], [0784:5-OMe-3-OEt-2-Py], [0785:6-OMe-3-OEt-2-Py], [0786:4-OEt-2-Py], [0787:3-Cl-4-OEt-2-Py], [0788:5-Cl-4-OEt-2-Py], [0789:6-Cl-4-OEt-2-Py], [0790:3-Me-4-OEt-2-Py], [0791:5-Me-4-OEt-2-Py], [0792:6-Me-4-OEt-2-Py], [0793:3-CF3-4-OEt-2-Py], [0794:5-CF3-4-OEt-2-Py], [0795:6-CF3-4-OEt-2-Py], [0796:3-CN-4-OEt-2-Py], [0797:5-CN-4-OEt-2-Py], [0798:6-CN-4-OEt-2-Py], [0799:3-OMe-4-OEt-2-Py], [0800:5-OMe-4-OEt-2-Py], [0801:6-OMe-4-OEt-2-Py], [0802:5-OEt-2-Py], [0803:3-Cl-5-OEt-2-Py], [0804:4-Cl-5-OEt-2-Py], [0805:6-Cl-5-OEt-2-Py], [0806:3-Me-5-OEt-2-Py], [0807:4-Me-5-OEt-2-Py], [0808:6-Me-5-OEt-2-Py], [0809:3-CF3-5-OEt-2-Py], [0810:4-CF3-5-OEt-2-Py], [0811:6-CF3-5-OEt-2-Py], [0812:3-CN-5-OEt-2-Py], [0813:4-CN-5-OEt-2-Py], [0814:6-CN-5-OEt-2-Py], [0815:3-OMe-5-OEt-2-Py], [0816:4-OMe-5-OEt-2-Py], [0817:6-OMe-5-OEt-2-Py], [0818:6-OEt-2-Py], [0819:3-Cl-6-OEt-2-Py], [0820:4-Cl-6-OEt-2-Py], [0821:5-Cl-6-OEt-2-Py], [0822:3-Me-6-OEt-2-Py], [0823:4-Me-6-OEt-2-Py], [0824:5-Me-6-OEt-2-Py], [0825:3-CF3-6-OEt-2-Py], [0826:4-CF3-6-OEt-2-Py], [0827:5-CF3-6-OEt-2-Py], [0828:3-CN-6-OEt-2-Py], [0829:4-CN-6-OEt-2-Py], [0830:5-CN-6-OEt-2-Py], [0831:3-OMe-6-OEt-2-Py], [0832:4-OMe-6-OEt-2-Py], [0833:5-OMe-6-OEt-2-Py], [0834:3-OCH2CF3-2-Py], [0835:4-Cl-3-OCH2CF3-2-Py], [0836:5-Cl-3-OCH2CF3-2-Py], [0837:6-Cl-3-OCH2CF3-2-Py], [0838:4-Me-3-OCH2CF3-2-Py], [0839:5-Me-3-OCH2CF3-2-Py], [0840:6-Me-3-OCH2CF3-2-Py], [0841:4-CF3-3-OCH2CF3-2-Py], [0842:5-CF3-3-OCH2CF3-2-Py], [0843:6-CF3-3-OCH2CF3-2-Py], [0844:4-CN-3-OCH2CF3-2-Py], [0845:5-CN-3-OCH2CF3-2-Py], [0846:6-CN-3-OCH2CF3-2-Py], [0847:4-OMe-3-OCH2CF3-2-Py], [0848:5-OMe-3-OCH2CF3-2-Py], [0849:6-OMe-3-OCH2CF3-2-Py], [0850:4-OCH2CF3-2-Py], [0851:3-Cl-4-OCH2CF3-2-Py], [0852:5-Cl-4-OCH2CF3-2-Py], [0853:6-Cl-4-OCH2CF3-2-Py], [0854:3-Me-4-OCH2CF3-2-Py], [0855:5-Me-4-OCH2CF3-2-Py], [0856:6-Me-4-OCH2CF3-2-Py], [0857:3-CF3-4-OCH2CF3-2-Py], [0858:5-CF3-4-OCH2CF3-2-Py], [0859:6-CF3-4-OCH2CF3-2-Py], [0860:3-CN-4-OCH2CF3-2-Py], [0861:5-CN-4-OCH2CF3-2-Py], [0862:6-CN-4-OCH2CF3-2-Py], [0863:3-OMe-4-OCH2CF3-2-Py], [0864:5-OMe-4-OCH2CF3-2-Py], [0865:6-OMe-4-OCH2CF3-2-Py], [0866:5-OCH2CF3-2-Py], [0867:3-Cl-5-OCH2CF3-2-Py], [0868:4-Cl-5-OCH2CF3-2-Py], [0869:6-Cl-5-OCH2CF3-2-Py], [0870:3-Me-5-OCH2CF3-2-Py], [0871:4-Me-5-OCH2CF3-2-Py], [0872:6-Me-5-OCH2CF3-2-Py], [0873:3-CF3-5-OCH2CF3-2-Py], [0874:4-CF3-5-OCH2CF3-2-Py], [0875:6-CF3-5-OCH2CF3-2-Py], [0876:3-CN-5-OCH2CF3-2-Py], [0877:4-CN-5-OCH2CF3-2-Py], [0878:6-CN-5-OCH2CF3-2-Py], [0879:3-OMe-5-OCH2CF3-2-Py], [0880:4-OMe-5-OCH2CF3-2-Py], [0881:6-OMe-5-OCH2CF3-2-Py], [0882:6-OCH2CF3-2-Py], [0883:3-Cl-6-OCH2CF3-2-Py], [0884:4-Cl-6-OCH2CF3-2-Py], [0885:5-Cl-6-OCH2CF3-2-Py], [0886:3-Me-6-OCH2CF3-2-Py], [0887:4-Me-6-OCH2CF3-2-Py], [0888:5-Me-6-OCH2CF3-2-Py], [0889:3-CF3-6-OCH2CF3-2-Py], [0890:4-CF3-6-OCH2CF3-2-Py], [0891:5-CF3-6-OCH2CF3-2-Py], [0892:3-CN-6-OCH2CF3-2-Py], [0893:4-CN-6-OCH2CF3-2-Py], [0894:5-CN-6-OCH2CF3-2-Py], [0895:3-OMe-6-OCH2CF3-2-Py], [0896:4-OMe-6-OCH2CF3-2-Py], [0897:5-OMe-6-OCH2CF3-2-Py], [0898:3-Pr-2-Py], [0899:4-Cl-3-Pr-2-Py], [0900:5-Cl-3-Pr-2-Py], [0901:6-Cl-3-Pr-2-Py], [0902:4-Me-3-Pr-2-Py], [0903:5-Me-3-Pr-2-Py], [0904:6-Me-3-Pr-2-Py], [0905:4-CF3-3-Pr-2-Py], [0906:5-CF3-3-Pr-2-Py], [0907:6-CF3-3-Pr-2-Py], [0908:4-CN-3-Pr-2-Py], [0909:5-CN-3-Pr-2-Py], [0910:6-

CN-3-Pr-2-Py], [0911:4-OMe-3-Pr-2-Py], [0912:5-OMe-3-Pr-2-Py], [0913:6-OMe-3-Pr-2-Py], [0914:4-Pr-2-Py], [0915:3-Cl-4-Pr-2-Py], [0916:5-Cl-4-Pr-2-Py], [0917:6-Cl-4-Pr-2-Py], [0918:3-Me-4-Pr-2-Py], [0919:5-Me-4-Pr-2-Py], [0920:6-Me-4-Pr-2-Py], [0921:3-CF3-4-Pr-2-Py], [0922:5-CF3-4-Pr-2-Py], [0923:6-CF3-4-Pr-2-Py], [0924:3-CN-4-Pr-2-Py], [0925:5-CN-4-Pr-2-Py], [0926:6-CN-4-Pr-2-Py], [0927:3-OMe-4-Pr-2-Py], [0928:5-OMe-4-Pr-2-Py], [0929:6-OMe-4-Pr-2-Py], [0930:5-Pr-2-Py], [0931:3-Cl-5-Pr-2-Py], [0932:4-Cl-5-Pr-2-Py], [0933:6-Cl-5-Pr-2-Py], [0934:3-Me-5-Pr-2-Py], [0935:4-Me-5-Pr-2-Py], [0936:6-Me-5-Pr-2-Py], [0937:3-CF3-5-Pr-2-Py], [0938:4-CF3-5-Pr-2-Py], [0939:6-CF3-5-Pr-2-Py], [0940:3-CN-5-Pr-2-Py], [0941:4-CN-5-Pr-2-Py], [0942:6-CN-5-Pr-2-Py], [0943:3-OMe-5-Pr-2-Py], [0944:4-OMe-5-Pr-2-Py], [0945:6-OMe-5-Pr-2-Py], [0946:6-Pr-2-Py], [0947:3-Cl-6-Pr-2-Py], [0948:4-Cl-6-Pr-2-Py], [0949:5-Cl-6-Pr-2-Py], [0950:3-Me-6-Pr-2-Py], [0951:4-Me-6-Pr-2-Py], [0952:5-Me-6-Pr-2-Py], [0953:3-CF3-6-Pr-2-Py], [0954:4-CF3-6-Pr-2-Py], [0955:5-CF3-6-Pr-2-Py], [0956:3-CN-6-Pr-2-Py], [0957:4-CN-6-Pr-2-Py], [0958:5-CN-6-Pr-2-Py], [0959:3-OMe-6-Pr-2-Py], [0960:4-OMe-6-Pr-2-Py], [0961:5-OMe-6-Pr-2-Py], [0962:3-OPr-2-Py], [0963:4-Cl-3-OPr-2-Py], [0964:5-Cl-3-OPr-2-Py], [0965:6-Cl-3-OPr-2-Py], [0966:4-Me-3-OPr-2-Py], [0967:5-Me-3-OPr-2-Py], [0968:6-Me-3-OPr-2-Py], [0969:4-CF3-3-OPr-2-Py], [0970:5-CF3-3-OPr-2-Py], [0971:6-CF3-3-OPr-2-Py], [0972:4-CN-3-OPr-2-Py], [0973:5-CN-3-OPr-2-Py], [0974:6-CN-3-OPr-2-Py], [0975:4-OMe-3-OPr-2-Py], [0976:5-OMe-3-OPr-2-Py], [0977:6-OMe-3-OPr-2-Py], [0978:4-OPr-2-Py], [0979:3-Cl-4-OPr-2-Py], [0980:5-Cl-4-OPr-2-Py], [0981:6-Cl-4-OPr-2-Py], [0982:3-Me-4-OPr-2-Py], [0983:5-Me-4-OPr-2-Py], [0984:6-Me-4-OPr-2-Py], [0985:3-CF3-4-OPr-2-Py], [0986:5-CF3-4-OPr-2-Py], [0987:6-CF3-4-OPr-2-Py], [0988:3-CN-4-OPr-2-Py], [0989:5-CN-4-OPr-2-Py], [0990:6-CN-4-OPr-2-Py], [0991:3-OMe-4-OPr-2-Py], [0992:5-OMe-4-OPr-2-Py], [0993:6-OMe-4-OPr-2-Py], [0994:5-OPr-2-Py], [0995:3-Cl-5-OPr-2-Py], [0996:4-Cl-5-OPr-2-Py], [0997:6-Cl-5-OPr-2-Py], [0998:3-Me-5-OPr-2-Py], [0999:4-Me-5-OPr-2-Py], [1000:6-Me-5-OPr-2-Py],
[1001:3-CF3-5-OPr-2-Py], [1002:4-CF3-5-OPr-2-Py], [1003:6-CF3-5-OPr-2-Py], [1004:3-CN-5-OPr-2-Py], [1005:4-CN-5-OPr-2-Py], [1006:6-CN-5-OPr-2-Py], [1007:3-OMe-5-OPr-2-Py], [1008:4-OMe-5-OPr-2-Py], [1009:6-OMe-5-OPr-2-Py], [1010:6-OPr-2-Py], [1011:3-Cl-6-OPr-2-Py], [1012:4-Cl-6-OPr-2-Py], [1013:5-Cl-6-OPr-2-Py], [1014:3-Me-6-OPr-2-Py], [1015:4-Me-6-OPr-2-Py], [1016:5-Me-6-OPr-2-Py], [1017:3-CF3-6-OPr-2-Py], [1018:4-CF3-6-OPr-2-Py], [1019:5-CF3-6-OPr-2-Py], [1020:3-CN-6-OPr-2-Py], [1021:4-CN-6-OPr-2-Py], [1022:5-CN-6-OPr-2-Py], [1023:3-OMe-6-OPr-2-Py], [1024:4-OMe-6-OPr-2-Py], [1025:5-OMe-6-OPr-2-Py], [1026:3-SMe-2-Py], [1027:4-Cl-3-SMe-2-Py], [1028:5-Cl-3-SMe-2-Py], [1029:6-Cl-3-SMe-2-Py], [1030:4-Me-3-SMe-2-Py], [1031:5-Me-3-SMe-2-Py], [1032:6-Me-3-SMe-2-Py], [1033:4-CF3-3-SMe-2-Py], [1034:5-CF3-3-SMe-2-Py], [1035:6-CF3-3-SMe-2-Py], [1036:4-CN-3-SMe-2-Py], [1037:5-CN-3-SMe-2-Py], [1038:6-CN-3-SMe-2-Py], [1039:4-OMe-3-SMe-2-Py], [1040:5-OMe-3-SMe-2-Py], [1041:6-OMe-3-SMe-2-Py], [1042:4-SMe-2-Py], [1043:3-Cl-4-SMe-2-Py], [1044:5-Cl-4-SMe-2-Py], [1045:6-Cl-4-SMe-2-Py], [1046:3-Me-4-SMe-2-Py], [1047:5-Me-4-SMe-2-Py], [1048:6-Me-4-SMe-2-Py], [1049:3-CF3-4-SMe-2-Py], [1050:5-CF3-4-SMe-2-Py], [1051:6-CF3-4-SMe-2-Py], [1052:3-CN-4-SMe-2-Py], [1053:5-CN-4-SMe-2-Py], [1054:6-CN-4-SMe-2-Py], [1055:3-OMe-4-SMe-2-Py], [1056:5-OMe-4-SMe-2-Py], [1057:6-OMe-4-SMe-2-Py], [1058:5-SMe-2-Py], [1059:3-Cl-5-SMe-2-Py], [1060:4-Cl-5-SMe-2-Py], [1061:6-Cl-5-SMe-2-Py], [1062:3-Me-5-SMe-2-Py], [1063:4-Me-5-SMe-2-Py], [1064:6-Me-5-SMe-2-Py], [1065:3-CF3-5-SMe-2-Py], [1066:4-CF3-5-SMe-2-Py], [1067:6-CF3-5-SMe-2-Py], [1068:3-CN-5-SMe-2-Py], [1069:4-CN-5-SMe-2-Py], [1070:6-CN-5-SMe-2-Py], [1071:3-OMe-5-SMe-2-Py], [1072:4-OMe-5-SMe-2-Py], [1073:6-OMe-5-SMe-2-Py], [1074:6-SMe-2-Py], [1075:3-Cl-6-SMe-2-Py], [1076:4-Cl-6-SMe-2-Py], [1077:5-Cl-6-SMe-2-Py], [1078:3-Me-6-SMe-2-Py], [1079:4-Me-6-SMe-2-Py], [1080:5-Me-6-SMe-2-Py], [1081:3-CF3-6-SMe-2-Py], [1082:4-CF3-6-SMe-2-Py], [1083:5-CF3-6-SMe-2-Py], [1084:3-CN-6-SMe-2-Py], [1085:4-CN-6-SMe-2-Py], [1086:5-CN-6-SMe-2-Py], [1087:3-OMe-6-SMe-2-Py], [1088:4-OMe-6-SMe-2-Py], [1089:5-OMe-6-SMe-2-Py], [1090:3-SCF3-2-Py], [1091:4-Cl-3-SCF3-2-Py], [1092:5-Cl-3-SCF3-2-Py], [1093:6-Cl-3-SCF3-2-Py], [1094:4-Me-3-SCF3-2-Py], [1095:5-Me-3-SCF3-2-Py], [1096:6-Me-3-SCF3-2-Py], [1097:4-CF3-3-SCF3-2-Py], [1098:5-CF3-3-SCF3-2-Py], [1099:6-CF3-3-SCF3-2-Py], [1100:4-CN-3-SCF3-2-Py], [1101:5-CN-3-SCF3-2-Py], [1102:6-CN-3-SCF3-2-Py], [1103:4-OMe-3-SCF3-2-Py], [1104:5-OMe-3-SCF3-2-Py], [1105:6-OMe-3-SCF3-2-Py], [1106:4-SCF3-2-Py], [1107:3-Cl-4-SCF3-2-Py], [1108:5-Cl-4-SCF3-2-Py], [1109:6-Cl-4-SCF3-2-Py], [1110:3-Me-4-SCF3-2-Py], [1111:5-Me-4-SCF3-2-Py], [1112:6-Me-4-SCF3-2-Py], [1113:3-CF3-4-SCF3-2-Py], [1114:5-CF3-4-SCF3-2-Py], [1115:6-CF3-4-SCF3-2-Py], [1116:3-CN-4-SCF3-2-Py], [1117:5-CN-4-SCF3-2-Py], [1118:6-CN-4-SCF3-2-Py], [1119:3-OMe-4-SCF3-2-Py], [1120:5-OMe-4-SCF3-2-Py], [1121:6-OMe-4-SCF3-2-Py], [1122:5-SCF3-2-Py], [1123:3-Cl-5-SCF3-2-Py], [1124:4-Cl-5-SCF3-2-Py], [1125:6-Cl-5-SCF3-2-Py], [1126:3-Me-5-SCF3-2-Py], [1127:4-Me-5-SCF3-2-Py], [1128:6-Me-5-SCF3-2-Py], [1129:3-CF3-5-SCF3-2-Py], [1130:4-CF3-5-SCF3-2-Py], [1131:6-CF3-5-SCF3-2-Py], [1132:3-CN-5-SCF3-2-Py], [1133:4-CN-5-SCF3-2-Py], [1134:6-CN-5-SCF3-2-Py], [1135:3-OMe-5-SCF3-2-Py], [1136:4-OMe-5-SCF3-2-Py], [1137:6-OMe-5-SCF3-2-Py], [1138:6-SCF3-2-Py], [1139:3-Cl-6-SCF3-2-Py], [1140:4-Cl-6-SCF3-2-Py], [1141:6-Cl-6-SCF3-2-Py], [1142:3-Me-6-SCF3-2-Py], [1143:4-Me-6-SCF3-2-Py], [1144:6-Me-6-SCF3-2-Py], [1145:3-CF3-6-SCF3-2-Py], [1146:4-CF3-6-SCF3-2-Py], [1147:6-CF3-6-SCF3-2-Py], [1148:3-CN-6-SCF3-2-Py], [1149:4-CN-6-SCF3-2-Py], [1150:6-CN-6-SCF3-2-Py], [1151:3-OMe-6-SCF3-2-Py], [1152:4-OMe-6-SCF3-2-Py], [1153:6-OMe-6-SCF3-2-Py], [1154:3-S(O)Me-2-Py], [1155:4-Cl-3-S(O)Me-2-Py], [1156:5-Cl-3-S(O)Me-2-Py], [1157:6-Cl-3-S(O)Me-2-Py], [1158:4-Me-3-S(O)Me-2-Py], [1159:5-Me-3-S(O)Me-2-Py], [1160:6-Me-3-S(O)Me-2-Py], [1161:4-CF3-3-S(O)Me-2-Py], [1162:5-CF3-3-S(O)Me-2-Py], [1163:6-CF3-3-S(O)Me-2-Py], [1164:4-CN-3-S(O)Me-2-Py], [1165:5-CN-3-S(O)Me-2-Py], [1166:6-CN-3-S(O)Me-2-Py], [1167:4-OMe-3-S(O)Me-2-Py], [1168:5-OMe-3-S(O)Me-2-Py], [1169:6-OMe-3-S(O)Me-2-Py], [1170:4-S(O)Me-2-Py], [1171:3-Cl-4-S(O)Me-2-Py], [1172:5-Cl-4-S(O)Me-2-Py], [1173:6-Cl-4-S(O)Me-2-Py], [1174:3-Me-4-S(O)Me-2-Py], [1175:5-Me-4-S(O)Me-2-Py], [1176:6-Me-4-S(O)Me-2-Py], [1177:3-CF3-4-S(O)Me-2-Py], [1178:5-CF3-4-S(O)Me-2-Py], [1179:6-CF3-4-S(O)Me-2-Py], [1180:3-CN-4-S(O)Me-2-Py], [1181:5-CN-4-S(O)Me-2-Py], [1182:6-CN-4-S(O)Me-2-Py], [1183:3-OMe-4-S(O)Me-2-Py], [1184:5-OMe-4-S(O)Me-2-Py], [1185:6-OMe-4-S(O)Me-2-Py], [1186:5-S(O)Me-2-Py], [1187:3-Cl-5-S(O)Me-2-Py], [1188:4-Cl-5-S(O)Me-2-Py], [1189:6-Cl-5-S(O)Me-2-Py], [1190:3-Me-5-S(O)Me-2-Py], [1191:4-Me-5-S(O)Me-2-Py], [1192:6-Me-5-S(O)Me-2-Py], [1193:3-CF3-5-S(O)Me-2-Py], [1194:4-CF3-5-S(O)Me-2-Py],

[1195:6-CF3-5-S(O)Me-2-Py], [1196:3-CN-5-S(O)Me-2-Py], [1197:4-CN-5-S(O)Me-2-Py], [1198:6-CN-5-S(O)Me-2-Py], [1199:3-OMe-5-S(O)Me-2-Py], [1200:4-OMe-5-S(O)Me-2-Py], [1201:6-OMe-5-S(O)Me-2-Py], [1202:6-S(O)Me-2-Py], [1203:3-Cl-6-S(O)Me-2-Py], [1204:4-Cl-6-S(O)Me-2-Py], [1205:5-Cl-6-S(O)Me-2-Py], [1206:3-Me-6-S(O)Me-2-Py], [1207:4-Me-6-S(O)Me-2-Py], [1208:5-Me-6-S(O)Me-2-Py], [1209:3-CF3-6-S(O)Me-2-Py], [1210:4-CF3-6-S(O)Me-2-Py], [1211:5-CF3-6-S(O)Me-2-Py], [1212:3-CN-6-S(O)Me-2-Py], [1213:4-CN-6-S(O)Me-2-Py], [1214:5-CN-6-S(O)Me-2-Py], [1215:3-OMe-6-S(O)Me-2-Py], [1216:4-OMe-6-S(O)Me-2-Py], [1217:5-OMe-6-S(O)Me-2-Py], [1218:3-S(O)CF3-2-Py], [1219:4-Cl-3-S(O)CF3-2-Py], [1220:5-Cl-3-S(O)CF3-2-Py], [1221:6-Cl-3-S(O)CF3-2-Py], [1222:4-Me-3-S(O)CF3-2-Py], [1223:5-Me-3-S(O)CF3-2-Py], [1224:6-Me-3-S(O)CF3-2-Py], [1225:4-CF3-3-S(O)CF3-2-Py], [1226:5-CF3-3-S(O)CF3-2-Py], [1227:6-CF3-3-S(O)CF3-2-Py], [1228:4-CN-3-S(O)CF3-2-Py], [1229:5-CN-3-S(O)CF3-2-Py], [1230:6-CN-3-S(O)CF3-2-Py], [1231:4-OMe-3-S(O)CF3-2-Py], [1232:5-OMe-3-S(O)CF3-2-Py], [1233:6-OMe-3-S(O)CF3-2-Py], [1234:4-S(O)CF3-2-Py], [1235:3-Cl-4-S(O)CF3-2-Py], [1236:5-Cl-4-S(O)CF3-2-Py], [1237:6-Cl-4-S(O)CF3-2-Py], [1238:3-Me-4-S(O)CF3-2-Py], [1239:5-Me-4-S(O)CF3-2-Py], [1240:6-Me-4-S(O)CF3-2-Py], [1241:3-CF3-4-S(O)CF3-2-Py], [1242:5-CF3-4-S(O)CF3-2-Py], [1243:6-CF3-4-S(O)CF3-2-Py], [1244:3-CN-4-S(O)CF3-2-Py], [1245:5-CN-4-S(O)CF3-2-Py], [1246:6-CN-4-S(O)CF3-2-Py], [1247:3-OMe-4-S(O)CF3-2-Py], [1248:5-OMe-4-S(O)CF3-2-Py], [1249:6-OMe-4-S(O)CF3-2-Py], [1250:5-S(O)CF3-2-Py], [1251:3-Cl-5-S(O)CF3-2-Py], [1252:4-Cl-5-S(O)CF3-2-Py], [1253:6-Cl-5-S(O)CF3-2-Py], [1254:3-Me-5-S(O)CF3-2-Py], [1255:4-Me-5-S(O)CF3-2-Py], [1256:6-Me-5-S(O)CF3-2-Py], [1257:3-CF3-5-S(O)CF3-2-Py], [1258:4-CF3-5-S(O)CF3-2-Py], [1259:6-CF3-5-S(O)CF3-2-Py], [1260:3-CN-5-S(O)CF3-2-Py], [1261:4-CN-5-S(O)CF3-2-Py], [1262:6-CN-5-S(O)CF3-2-Py], [1263:3-OMe-5-S(O)CF3-2-Py], [1264:4-OMe-5-S(O)CF3-2-Py], [1265:6-OMe-5-S(O)CF3-2-Py], [1266:6-S(O)CF3-2-Py], [1267:3-Cl-6-S(O)CF3-2-Py], [1268:4-Cl-6-S(O)CF3-2-Py], [1269:5-Cl-6-S(O)CF3-2-Py], [1270:3-Me-6-S(O)CF3-2-Py], [1271:4-Me-6-S(O)CF3-2-Py], [1272:5-Me-6-S(O)CF3-2-Py], [1273:3-CF3-6-S(O)CF3-2-Py], [1274:4-CF3-6-S(O)CF3-2-Py], [1275:5-CF3-6-S(O)CF3-2-Py], [1276:3-CN-6-S(O)CF3-2-Py], [1277:4-CN-6-S(O)CF3-2-Py], [1278:5-CN-6-S(O)CF3-2-Py], [1279:3-OMe-6-S(O)CF3-2-Py], [1280:4-OMe-6-S(O)CF3-2-Py], [1281:5-OMe-6-S(O)CF3-2-Py], [1282:3-S(O)2Me-2-Py], [1283:4-Cl-3-S(O)2Me-2-Py], [1284:5-Cl-3-S(O)2Me-2-Py], [1285:6-Cl-3-S(O)2Me-2-Py], [1286:4-Me-3-S(O)2Me-2-Py], [1287:5-Me-3-S(O)2Me-2-Py], [1288:6-Me-3-S(O)2Me-2-Py], [1289:4-CF3-3-S(O)2Me-2-Py], [1290:5-CF3-3-S(O)2Me-2-Py], [1291:6-CF3-3-S(O)2Me-2-Py], [1292:4-CN-3-S(O)2Me-2-Py], [1293:5-CN-3-S(O)2Me-2-Py], [1294:6-CN-3-S(O)2Me-2-Py], [1295:4-OMe-3-S(O)2Me-2-Py], [1296:5-OMe-3-S(O)2Me-2-Py], [1297:6-OMe-3-S(O)2Me-2-Py], [1298:4-S(O)2Me-2-Py], [1299:3-Cl-4-S(O)2Me-2-Py], [1300:5-Cl-4-S(O)2Me-2-Py], [1301:6-Cl-4-S(O)2Me-2-Py], [1302:3-Me-4-S(O)2Me-2-Py], [1303:5-Me-4-S(O)2Me-2-Py], [1304:6-Me-4-S(O)2Me-2-Py], [1305:3-CF3-4-S(O)2Me-2-Py], [1306:5-CF3-4-S(O)2Me-2-Py], [1307:6-CF3-4-S(O)2Me-2-Py], [1308:3-CN-4-S(O)2Me-2-Py], [1309:5-CN-4-S(O)2Me-2-Py], [1310:6-CN-4-S(O)2Me-2-Py], [1311:3-OMe-4-S(O)2Me-2-Py], [1312:5-OMe-4-S(O)2Me-2-Py], [1313:6-OMe-4-S(O)2Me-2-Py], [1314:5-S(O)2Me-2-Py], [1315:3-Cl-5-S(O)2Me-2-Py], [1316:4-Cl-5-S(O)2Me-2-Py], [1317:6-Cl-5-S(O)2Me-2-Py], [1318:3-Me-5-S(O)2Me-2-Py], [1319:4-Me-5-S(O)2Me-2-Py], [1320:6-Me-5-S(O)2Me-2-Py], [1321:3-CF3-5-S(O)2Me-2-Py], [1322:4-CF3-5-S(O)2Me-2-Py], [1323:6-CF3-5-S(O)2Me-2-Py], [1324:3-CN-5-S(O)2Me-2-Py], [1325:4-CN-5-S(O)2Me-2-Py], [1326:6-CN-5-S(O)2Me-2-Py], [1327:3-OMe-5-S(O)2Me-2-Py], [1328:4-OMe-5-S(O)2Me-2-Py], [1329:6-OMe-5-S(O)2Me-2-Py], [1330:6-S(O)2Me-2-Py], [1331:3-Cl-6-S(O)2Me-2-Py], [1332:4-Cl-6-S(O)2Me-2-Py], [1333:5-Cl-6-S(O)2Me-2-Py], [1334:3-Me-6-S(O)2Me-2-Py], [1335:4-Me-6-S(O)2Me-2-Py], [1336:5-Me-6-S(O)2Me-2-Py], [1337:3-CF3-6-S(O)2Me-2-Py], [1338:4-CF3-6-S(O)2Me-2-Py], [1339:5-CF3-6-S(O)2Me-2-Py], [1340:3-CN-6-S(O)2Me-2-Py], [1341:4-CN-6-S(O)2Me-2-Py], [1342:5-CN-6-S(O)2Me-2-Py], [1343:3-OMe-6-S(O)2Me-2-Py], [1344:4-OMe-6-S(O)2Me-2-Py], [1345:5-OMe-6-S(O)2Me-2-Py], [1346:3-S(O)2CF3-2-Py], [1347:4-Cl-3-S(O)2CF3-2-Py], [1348:5-Cl-3-S(O)2CF3-2-Py], [1349:6-Cl-3-S(O)2CF3-2-Py], [1350:4-Me-3-S(O)2CF3-2-Py], [1351:5-Me-3-S(O)2CF3-2-Py], [1352:6-Me-3-S(O)2CF3-2-Py], [1353:4-CF3-3-S(O)2CF3-2-Py], [1354:5-CF3-3-S(O)2CF3-2-Py], [1355:6-CF3-3-S(O)2CF3-2-Py], [1356:4-CN-3-S(O)2CF3-2-Py], [1357:5-CN-3-S(O)2CF3-2-Py], [1358:6-CN-3-S(O)2CF3-2-Py], [1359:4-OMe-3-S(O)2CF3-2-Py], [1360:5-OMe-3-S(O)2CF3-2-Py], [1361:6-OMe-3-S(O)2CF3-2-Py], [1362:4-S(O)2CF3-2-Py], [1363:3-Cl-4-S(O)2CF3-2-Py], [1364:5-Cl-4-S(O)2CF3-2-Py], [1365:6-Cl-4-S(O)2CF3-2-Py], [1366:3-Me-4-S(O)2CF3-2-Py], [1367:5-Me-4-S(O)2CF3-2-Py], [1368:6-Me-4-S(O)2CF3-2-Py], [1369:3-CF3-4-S(O)2CF3-2-Py], [1370:5-CF3-4-S(O)2CF3-2-Py], [1371:6-CF3-4-S(O)2CF3-2-Py], [1372:3-CN-4-S(O)2CF3-2-Py], [1373:5-CN-4-S(O)2CF3-2-Py], [1374:6-CN-4-S(O)2CF3-2-Py], [1375:3-OMe-4-S(O)2CF3-2-Py], [1376:5-OMe-4-S(O)2CF3-2-Py], [1377:6-OMe-4-S(O)2CF3-2-Py], [1378:5-S(O)2CF3-2-Py], [1379:3-Cl-5-S(O)2CF3-2-Py], [1380:4-Cl-5-S(O)2CF3-2-Py], [1381:6-Cl-5-S(O)2CF3-2-Py], [1382:3-Me-5-S(O)2CF3-2-Py], [1383:4-Me-5-S(O)2CF3-2-Py], [1384:6-Me-5-S(O)2CF3-2-Py], [1385:3-CF3-5-S(O)2CF3-2-Py], [1386:4-CF3-5-S(O)2CF3-2-Py], [1387:6-CF3-5-S(O)2CF3-2-Py], [1388:3-CN-5-S(O)2CF3-2-Py], [1389:4-CN-5-S(O)2CF3-2-Py], [1390:6-CN-5-S(O)2CF3-2-Py], [1391:3-OMe-5-S(O)2CF3-2-Py], [1392:4-OMe-5-S(O)2CF3-2-Py], [1393:6-OMe-5-S(O)2CF3-2-Py], [1394:6-S(O)2CF3-2-Py], [1395:3-Cl-6-S(O)2CF3-2-Py], [1396:4-Cl-6-S(O)2CF3-2-Py], [1397:5-Cl-6-S(O)2CF3-2-Py], [1398:3-Me-6-S(O)2CF3-2-Py], [1399:4-Me-6-S(O)2CF3-2-Py], [1400:5-Me-6-S(O)2CF3-2-Py], [1401:3-CF3-6-S(O)2CF3-2-Py], [1402:4-CF3-6-S(O)2CF3-2-Py], [1403:5-CF3-6-S(O)2CF3-2-Py], [1404:3-CN-6-S(O)2CF3-2-Py], [1405:4-CN-6-S(O)2CF3-2-Py], [1406:5-CN-6-S(O)2CF3-2-Py], [1407:3-OMe-6-S(O)2CF3-2-Py], [1408:4-OMe-6-S(O)2CF3-2-Py], [1409:5-OMe-6-S(O)2CF3-2-Py], [1410:3-CN-2-Py], [1411:4-Cl-3-CN-2-Py], [1412:5-Cl-3-CN-2-Py], [1413:6-Cl-3-CN-2-Py], [1414:4-Me-3-CN-2-Py], [1415:5-Me-3-CN-2-Py], [1416:6-Me-3-CN-2-Py], [1417:4-CF3-3-CN-2-Py], [1418:5-CF3-3-CN-2-Py], [1419:6-CF3-3-CN-2-Py], [1420:4-CN-3-CN-2-Py], [1421:5-CN-3-CN-2-Py], [1422:6-CN-3-CN-2-Py], [1423:4-OMe-3-CN-2-Py], [1424:5-OMe-3-CN-2-Py], [1425:6-OMe-3-CN-2-Py], [1426:4-CN-2-Py], [1427:3-Cl-4-CN-2-Py], [1428:5-Cl-4-CN-2-Py], [1429:6-Cl-4-CN-2-Py], [1430:3-Me-4-CN-2-Py], [1431:5-Me-4-CN-2-Py], [1432:6-Me-4-CN-2-Py], [1433:3-CF3-4-CN-2-Py], [1434:5-CF3-4-CN-2-Py], [1435:6-CF3-4-CN-2-Py], [1436:3-CN-4-CN-2-Py], [1437:5-CN-4-CN-2-Py], [1438:6-CN-4-CN-2-Py], [1439:3-OMe-4-CN-2-Py], [1440:5-OMe-4-CN-

2-Py], [1441:6-OMe-4-CN-2-Py], [1442:5-CN-2-Py], [1443:3-Cl-5-CN-2-Py], [1444:4-Cl-5-CN-2-Py], [1445:6-Cl-5-CN-2-Py], [1446:3-Me-5-CN-2-Py], [1447:4-Me-5-CN-2-Py], [1448:6-Me-5-CN-2-Py], [1449:3-CF3-5-CN-2-Py], [1450:4-CF3-5-CN-2-Py], [1451:6-CF3-5-CN-2-Py], [1452:3-CN-5-CN-2-Py], [1453:4-CN-5-CN-2-Py], [1454:6-CN-5-CN-2-Py], [1455:3-OMe-5-CN-2-Py], [1456:4-OMe-5-CN-2-Py], [1457:6-OMe-5-CN-2-Py], [1458:6-CN-2-Py], [1459:3-Cl-6-CN-2-Py], [1460:4-Cl-6-CN-2-Py], [1461:5-Cl-6-CN-2-Py], [1462:3-Me-6-CN-2-Py], [1463:4-Me-6-CN-2-Py], [1464:5-Me-6-CN-2-Py], [1465:3-CF3-6-CN-2-Py], [1466:4-CF3-6-CN-2-Py], [1467:5-CF3-6-CN-2-Py], [1468:3-CN-6-CN-2-Py], [1469:4-CN-6-CN-2-Py], [1470:5-CN-6-CN-2-Py], [1471:3-OMe-6-CN-2-Py], [1472:4-OMe-6-CN-2-Py], [1473:5-OMe-6-CN-2-Py], [1474:3-COOMe-2-Py], [1475:4-Cl-3-COOMe-2-Py], [1476:5-Cl-3-COOMe-2-Py], [1477:6-Cl-3-COOMe-2-Py], [1478:4-Me-3-COOMe-2-Py], [1479:5-Me-3-COOMe-2-Py], [1480:6-Me-3-COOMe-2-Py], [1481:4-CF3-3-COOMe-2-Py], [1482:5-CF3-3-COOMe-2-Py], [1483:6-CF3-3-COOMe-2-Py], [1484:4-CN-3-COOMe-2-Py], [1485:5-CN-3-COOMe-2-Py], [1486:6-CN-3-COOMe-2-Py], [1487:4-OMe-3-COOMe-2-Py], [1488:5-OMe-3-COOMe-2-Py], [1489:6-OMe-3-COOMe-2-Py], [1490:4-COOMe-2-Py], [1491:3-Cl-4-COOMe-2-Py], [1492:5-Cl-4-COOMe-2-Py], [1493:6-Cl-4-COOMe-2-Py], [1494:3-Me-4-COOMe-2-Py], [1495:5-Me-4-COOMe-2-Py], [1496:6-Me-4-COOMe-2-Py], [1497:3-CF3-4-COOMe-2-Py], [1498:5-CF3-4-COOMe-2-Py], [1499:6-CF3-4-COOMe-2-Py], [1500:3-CN-4-COOMe-2-Py],
[1501:5-CN-4-COOMe-2-Py], [1502:6-CN-4-COOMe-2-Py], [1503:3-OMe-4-COOMe-2-Py], [1504:5-OMe-4-COOMe-2-Py], [1505:6-OMe-4-COOMe-2-Py], [1506:5-COOMe-2-Py], [1507:3-Cl-5-COOMe-2-Py], [1508:4-Cl-5-COOMe-2-Py], [1509:6-Cl-5-COOMe-2-Py], [1510:3-Me-5-COOMe-2-Py], [1511:4-Me-5-COOMe-2-Py], [1512:6-Me-5-COOMe-2-Py], [1513:3-CF3-5-COOMe-2-Py], [1514:4-CF3-5-COOMe-2-Py], [1515:6-CF3-5-COOMe-2-Py], [1516:3-CN-5-COOMe-2-Py], [1517:4-CN-5-COOMe-2-Py], [1518:6-CN-5-COOMe-2-Py], [1519:3-OMe-5-COOMe-2-Py], [1520:4-OMe-5-COOMe-2-Py], [1521:6-OMe-5-COOMe-2-Py], [1522:6-COOMe-2-Py], [1523:3-Cl-6-COOMe-2-Py], [1524:4-Cl-6-COOMe-2-Py], [1525:5-Cl-6-COOMe-2-Py], [1526:3-Me-6-COOMe-2-Py], [1527:4-Me-6-COOMe-2-Py], [1528:5-Me-6-COOMe-2-Py], [1529:3-CF3-6-COOMe-2-Py], [1530:4-CF3-6-COOMe-2-Py], [1531:5-CF3-6-COOMe-2-Py], [1532:3-CN-6-COOMe-2-Py], [1533:4-CN-6-COOMe-2-Py], [1534:5-CN-6-COOMe-2-Py], [1535:3-OMe-6-COOMe-2-Py], [1536:4-OMe-6-COOMe-2-Py], [1537:5-OMe-6-COOMe-2-Py], [1538:3-NO2-2-Py], [1539:4-Cl-3-NO2-2-Py], [1540:5-Cl-3-NO2-2-Py], [1541:6-Cl-3-NO2-2-Py], [1542:4-Me-3-NO2-2-Py], [1543:5-Me-3-NO2-2-Py], [1544:6-Me-3-NO2-2-Py], [1545:4-CF3-3-NO2-2-Py], [1546:5-CF3-3-NO2-2-Py], [1547:6-CF3-3-NO2-2-Py], [1548:4-CN-3-NO2-2-Py], [1549:5-CN-3-NO2-2-Py], [1550:6-CN-3-NO2-2-Py], [1551:4-OMe-3-NO2-2-Py], [1552:5-OMe-3-NO2-2-Py], [1553:6-OMe-3-NO2-2-Py], [1554:4-NO2-2-Py], [1555:3-Cl-4-NO2-2-Py], [1556:5-Cl-4-NO2-2-Py], [1557:6-Cl-4-NO2-2-Py], [1558:3-Me-4-NO2-2-Py], [1559:5-Me-4-NO2-2-Py], [1560:6-Me-4-NO2-2-Py], [1561:3-CF3-4-NO2-2-Py], [1562:5-CF3-4-NO2-2-Py], [1563:6-CF3-4-NO2-2-Py], [1564:3-CN-4-NO2-2-Py], [1565:5-CN-4-NO2-2-Py], [1566:6-CN-4-NO2-2-Py], [1567:3-OMe-4-NO2-2-Py], [1568:5-OMe-4-NO2-2-Py], [1569:6-OMe-4-NO2-2-Py], [1570:5-NO2-2-Py], [1571:3-Cl-5-NO2-2-Py], [1572:4-Cl-5-NO2-2-Py], [1573:6-Cl-5-NO2-2-Py], [1574:3-Me-5-NO2-2-Py], [1575:4-Me-5-NO2-2-Py], [1576:6-Me-5-NO2-2-Py], [1577:3-CF3-5-NO2-2-Py], [1578:4-CF3-5-NO2-2-Py], [1579:6-CF3-5-NO2-2-Py], [1580:3-CN-5-NO2-2-Py], [1581:4-CN-5-NO2-2-Py], [1582:6-CN-5-NO2-2-Py], [1583:3-OMe-5-NO2-2-Py], [1584:4-OMe-5-NO2-2-Py], [1585:6-OMe-5-NO2-2-Py], [1586:6-NO2-2-Py], [1587:3-Cl-6-NO2-2-Py], [1588:4-Cl-6-NO2-2-Py], [1589:5-Cl-6-NO2-2-Py], [1590:3-Me-6-NO2-2-Py], [1591:4-Me-6-NO2-2-Py], [1592:5-Me-6-NO2-2-Py], [1593:3-CF3-6-NO2-2-Py], [1594:4-CF3-6-NO2-2-Py], [1595:5-CF3-6-NO2-2-Py], [1596:3-CN-6-NO2-2-Py], [1597:4-CN-6-NO2-2-Py], [1598:5-CN-6-NO2-2-Py], [1599:3-OMe-6-NO2-2-Py], [1600:4-OMe-6-NO2-2-Py],
[1601:5-OMe-6-NO2-2-Py], [1602:3-NH2-2-Py], [1603:4-Cl-3-NH2-2-Py], [1604:5-Cl-3-NH2-2-Py], [1605:6-Cl-3-NH2-2-Py], [1606:4-Me-3-NH2-2-Py], [1607:5-Me-3-NH2-2-Py], [1608:6-Me-3-NH2-2-Py], [1609:4-CF3-3-NH2-2-Py], [1610:5-CF3-3-NH2-2-Py], [1611:6-CF3-3-NH2-2-Py], [1612:4-CN-3-NH2-2-Py], [1613:5-CN-3-NH2-2-Py], [1614:6-CN-3-NH2-2-Py], [1615:4-OMe-3-NH2-2-Py], [1616:5-OMe-3-NH2-2-Py], [1617:6-OMe-3-NH2-2-Py], [1618:4-NH2-2-Py], [1619:3-Cl-4-NH2-2-Py], [1620:5-Cl-4-NH2-2-Py], [1621:6-Cl-4-NH2-2-Py], [1622:3-Me-4-NH2-2-Py], [1623:5-Me-4-NH2-2-Py], [1624:6-Me-4-NH2-2-Py], [1625:3-CF3-4-NH2-2-Py], [1626:5-CF3-4-NH2-2-Py], [1627:6-CF3-4-NH2-2-Py], [1628:3-CN-4-NH2-2-Py], [1629:5-CN-4-NH2-2-Py], [1630:6-CN-4-NH2-2-Py], [1631:3-OMe-4-NH2-2-Py], [1632:5-OMe-4-NH2-2-Py], [1633:6-OMe-4-NH2-2-Py], [1634:5-NH2-2-Py], [1635:3-Cl-5-NH2-2-Py], [1636:4-Cl-5-NH2-2-Py], [1637:6-Cl-5-NH2-2-Py], [1638:3-Me-5-NH2-2-Py], [1639:4-Me-5-NH2-2-Py], [1640:6-Me-5-NH2-2-Py], [1641:3-CF3-5-NH2-2-Py], [1642:4-CF3-5-NH2-2-Py], [1643:6-CF3-5-NH2-2-Py], [1644:3-CN-5-NH2-2-Py], [1645:4-CN-5-NH2-2-Py], [1646:6-CN-5-NH2-2-Py], [1647:3-OMe-5-NH2-2-Py], [1648:4-OMe-5-NH2-2-Py], [1649:6-OMe-5-NH2-2-Py], [1650:6-NH2-2-Py], [1651:3-Cl-6-NH2-2-Py], [1652:4-Cl-6-NH2-2-Py], [1653:5-Cl-6-NH2-2-Py], [1654:3-Me-6-NH2-2-Py], [1655:4-Me-6-NH2-2-Py], [1656:5-Me-6-NH2-2-Py], [1657:3-CF3-6-NH2-2-Py], [1658:4-CF3-6-NH2-2-Py], [1659:5-CF3-6-NH2-2-Py], [1660:3-CN-6-NH2-2-Py], [1661:4-CN-6-NH2-2-Py], [1662:5-CN-6-NH2-2-Py], [1663:3-OMe-6-NH2-2-Py], [1664:4-OMe-6-NH2-2-Py], [1665:5-OMe-6-NH2-2-Py], [1666:3-NHMe-2-Py], [1667:4-Cl-3-NHMe-2-Py], [1668:5-Cl-3-NHMe-2-Py], [1669:6-Cl-3-NHMe-2-Py], [1670:4-Me-3-NHMe-2-Py], [1671:5-Me-3-NHMe-2-Py], [1672:6-Me-3-NHMe-2-Py], [1673:4-CF3-3-NHMe-2-Py], [1674:5-CF3-3-NHMe-2-Py], [1675:6-CF3-3-NHMe-2-Py], [1676:4-CN-3-NHMe-2-Py], [1677:5-CN-3-NHMe-2-Py], [1678:6-CN-3-NHMe-2-Py], [1679:4-OMe-3-NHMe-2-Py], [1680:5-OMe-3-NHMe-2-Py], [1681:6-OMe-3-NHMe-2-Py], [1682:4-NHMe-2-Py], [1683:3-Cl-4-NHMe-2-Py], [1684:5-Cl-4-NHMe-2-Py], [1685:6-Cl-4-NHMe-2-Py], [1686:3-Me-4-NHMe-2-Py], [1687:5-Me-4-NHMe-2-Py], [1688:6-Me-4-NHMe-2-Py], [1689:3-CF3-4-NHMe-2-Py], [1690:5-CF3-4-NHMe-2-Py], [1691:6-CF3-4-NHMe-2-Py], [1692:3-CN-4-NHMe-2-Py], [1693:5-CN-4-NHMe-2-Py], [1694:6-CN-4-NHMe-2-Py], [1695:3-OMe-4-NHMe-2-Py], [1696:5-OMe-4-NHMe-2-Py], [1697:6-OMe-4-NHMe-2-Py], [1698:5-NHMe-2-Py], [1699:3-Cl-5-NHMe-2-Py], [1700:4-Cl-5-NHMe-2-Py],
[1701:6-Cl-5-NHMe-2-Py], [1702:3-Me-5-NHMe-2-Py], [1703:4-Me-5-NHMe-2-Py], [1704:6-Me-5-NHMe-2-Py], [1705:3-CF3-5-NHMe-2-Py], [1706:4-CF3-5-NHMe-2-Py], [1707:6-CF3-5-NHMe-2-Py], [1708:3-CN-5-NHMe-2-

Py], [1709:4-CN-5-NHMe-2-Py], [1710:6-CN-5-NHMe-2-Py], [1711:3-OMe-5-NHMe-2-Py], [1712:4-OMe-5-NHMe-2-Py], [1713:6-OMe-5-NHMe-2-Py], [1714:6-NHMe-2-Py], [1715:3-Cl-6-NHMe-2-Py], [1716:4-Cl-6-NHMe-2-Py], [1717:5-Cl-6-NHMe-2-Py], [1718:3-Me-6-NHMe-2-Py], [1719:4-Me-6-NHMe-2-Py], [1720:5-Me-6-NHMe-2-Py], [1721:3-CF3-6-NHMe-2-Py], [1722:4-CF3-6-NHMe-2-Py], [1723:5-CF3-6-NHMe-2-Py], [1724:3-CN-6-NHMe-2-Py], [1725:4-CN-6-NHMe-2-Py], [1726:5-CN-6-NHMe-2-Py], [1727:3-OMe-6-NHMe-2-Py], [1728:4-OMe-6-NHMe-2-Py], [1729:5-OMe-6-NHMe-2-Py], [1730:3-NMe2-2-Py], [1731:4-Cl-3-NMe2-2-Py], [1732:5-Cl-3-NMe2-2-Py], [1733:6-Cl-3-NMe2-2-Py], [1734:4-Me-3-NMe2-2-Py], [1735:5-Me-3-NMe2-2-Py], [1736:6-Me-3-NMe2-2-Py], [1737:4-CF3-3-NMe2-2-Py], [1738:5-CF3-3-NMe2-2-Py], [1739:6-CF3-3-NMe2-2-Py], [1740:4-CN-3-NMe2-2-Py], [1741:5-CN-3-NMe2-2-Py], [1742:6-CN-3-NMe2-2-Py], [1743:4-OMe-3-NMe2-2-Py], [1744:5-OMe-3-NMe2-2-Py], [1745:6-OMe-3-NMe2-2-Py], [1746:4-NMe2-2-Py], [1747:3-Cl-4-NMe2-2-Py], [1748:5-Cl-4-NMe2-2-Py], [1749:6-Cl-4-NMe2-2-Py], [1750:3-Me-4-NMe2-2-Py], [1751:5-Me-4-NMe2-2-Py], [1752:6-Me-4-NMe2-2-Py], [1753:3-CF3-4-NMe2-2-Py], [1754:5-CF3-4-NMe2-2-Py], [1755:6-CF3-4-NMe2-2-Py], [1756:3-CN-4-NMe2-2-Py], [1757:5-CN-4-NMe2-2-Py], [1758:6-CN-4-NMe2-2-Py], [1759:3-OMe-4-NMe2-2-Py], [1760:5-OMe-4-NMe2-2-Py], [1761:6-OMe-4-NMe2-2-Py], [1762:5-NMe2-2-Py], [1763:3-Cl-5-NMe2-2-Py], [1764:4-Cl-5-NMe2-2-Py], [1765:6-Cl-5-NMe2-2-Py], [1766:3-Me-5-NMe2-2-Py], [1767:4-Me-5-NMe2-2-Py], [1768:6-Me-5-NMe2-2-Py], [1769:3-CF3-5-NMe2-2-Py], [1770:4-CF3-5-NMe2-2-Py], [1771:6-CF3-5-NMe2-2-Py], [1772:3-CN-5-NMe2-2-Py], [1773:4-CN-5-NMe2-2-Py], [1774:6-CN-5-NMe2-2-Py], [1775:3-OMe-5-NMe2-2-Py], [1776:4-OMe-5-NMe2-2-Py], [1777:6-OMe-5-NMe2-2-Py], [1778:6-NMe2-2-Py], [1779:3-Cl-6-NMe2-2-Py], [1780:4-Cl-6-NMe2-2-Py], [1781:5-Cl-6-NMe2-2-Py], [1782:3-Me-6-NMe2-2-Py], [1783:4-Me-6-NMe2-2-Py], [1784:5-Me-6-NMe2-2-Py], [1785:3-CF3-6-NMe2-2-Py], [1786:4-CF3-6-NMe2-2-Py], [1787:5-CF3-6-NMe2-2-Py], [1788:3-CN-6-NMe2-2-Py], [1789:4-CN-6-NMe2-2-Py], [1790:5-CN-6-NMe2-2-Py], [1791:3-OMe-6-NMe2-2-Py], [1792:4-OMe-6-NMe2-2-Py], [1793:5-OMe-6-NMe2-2-Py], [1794:3-ACNH-2-Py], [1795:4-Cl-3-ACNH-2-Py], [1796:5-Cl-3-ACNH-2-Py], [1797:6-Cl-3-ACNH-2-Py], [1798:4-Me-3-ACNH-2-Py], [1799:5-Me-3-ACNH-2-Py], [1800:6-Me-3-ACNH-2-Py],
[1801:4-CF3-3-ACNH-2-Py], [1802:5-CF3-3-ACNH-2-Py], [1803:6-CF3-3-ACNH-2-Py], [1804:4-CN-3-ACNH-2-Py], [1805:5-CN-3-ACNH-2-Py], [1806:6-CN-3-ACNH-2-Py], [1807:4-OMe-3-ACNH-2-Py], [1808:5-OMe-3-ACNH-2-Py], [1809:6-OMe-3-ACNH-2-Py], [1810:4-ACNH-2-Py], [1811:3-Cl-4-ACNH-2-Py], [1812:5-Cl-4-ACNH-2-Py], [1813:6-Cl-4-ACNH-2-Py], [1814:3-Me-4-ACNH-2-Py], [1815:5-Me-4-ACNH-2-Py], [1816:6-Me-4-ACNH-2-Py], [1817:3-CF3-4-ACNH-2-Py], [1818:5-CF3-4-ACNH-2-Py], [1819:6-CF3-4-ACNH-2-Py], [1820:3-CN-4-ACNH-2-Py], [1821:5-CN-4-ACNH-2-Py], [1822:6-CN-4-ACNH-2-Py], [1823:3-OMe-4-ACNH-2-Py], [1824:5-OMe-4-ACNH-2-Py], [1825:6-OMe-4-ACNH-2-Py], [1826:5-ACNH-2-Py], [1827:3-Cl-5-ACNH-2-Py], [1828:4-Cl-5-ACNH-2-Py], [1829:6-Cl-5-ACNH-2-Py], [1830:3-Me-5-ACNH-2-Py], [1831:4-Me-5-ACNH-2-Py], [1832:6-Me-5-ACNH-2-Py], [1833:3-CF3-5-ACNH-2-Py], [1834:4-CF3-5-ACNH-2-Py], [1835:6-CF3-5-ACNH-2-Py], [1836:3-CN-5-ACNH-2-Py], [1837:4-CN-5-ACNH-2-Py], [1838:6-CN-5-ACNH-2-Py], [1839:3-OMe-5-ACNH-2-Py], [1840:4-OMe-5-ACNH-2-Py], [1841:6-OMe-5-ACNH-2-Py], [1842:6-ACNH-2-Py], [1843:3-Cl-6-ACNH-2-Py], [1844:4-Cl-6-ACNH-2-Py], [1845:5-Cl-6-ACNH-2-Py], [1846:3-Me-6-ACNH-2-Py], [1847:4-Me-6-ACNH-2-Py], [1848:5-Me-6-ACNH-2-Py], [1849:3-CF3-6-ACNH-2-Py], [1850:4-CF3-6-ACNH-2-Py], [1851:5-CF3-6-ACNH-2-Py], [1852:3-CN-6-ACNH-2-Py], [1853:4-CN-6-ACNH-2-Py], [1854:5-CN-6-ACNH-2-Py], [1855:3-OMe-6-ACNH-2-Py], [1856:4-OMe-6-ACNH-2-Py], [1857:5-OMe-6-ACNH-2-Py], [1858:3-(N-AC-N-Me-N)-2-Py], [1859:4-Cl-3-(N-AC-N-Me-N)-2-Py], [1860:5-Cl-3-(N-AC-N-Me-N)-2-Py], [1861:6-Cl-3-(N-AC-N-Me-N)-2-Py], [1862:4-Me-3-(N-AC-N-Me-N)-2-Py], [1863:5-Me-3-(N-AC-N-Me-N)-2-Py], [1864:6-Me-3-(N-AC-N-Me-N)-2-Py], [1865:4-CF3-3-(N-AC-N-Me-N)-2-Py], [1866:5-CF3-3-(N-AC-N-Me-N)-2-Py], [1867:6-CF3-3-(N-AC-N-Me-N)-2-Py], [1868:4-CN-3-(N-AC-N-Me-N)-2-Py], [1869:5-CN-3-(N-AC-N-Me-N)-2-Py], [1870:6-CN-3-(N-AC-N-Me-N)-2-Py], [1871:4-OMe-3-(N-AC-N-Me-N)-2-Py], [1872:5-OMe-3-(N-AC-N-Me-N)-2-Py], [1873:6-OMe-3-(N-AC-N-Me-N)-2-Py], [1874:4-(N-AC-N-Me-N)-2-Py], [1875:3-Cl-4-(N-AC-N-Me-N)-2-Py], [1876:5-Cl-4-(N-AC-N-Me-N)-2-Py], [1877:6-Cl-4-(N-AC-N-Me-N)-2-Py], [1878:3-Me-4-(N-AC-N-Me-N)-2-Py], [1879:5-Me-4-(N-AC-N-Me-N)-2-Py], [1880:6-Me-4-(N-AC-N-Me-N)-2-Py], [1881:3-CF3-4-(N-AC-N-Me-N)-2-Py], [1882:5-CF3-4-(N-AC-N-Me-N)-2-Py], [1883:6-CF3-4-(N-AC-N-Me-N)-2-Py], [1884:3-CN-4-(N-AC-N-Me-N)-2-Py], [1885:5-CN-4-(N-AC-N-Me-N)-2-Py], [1886:6-CN-4-(N-AC-N-Me-N)-2-Py], [1887:3-OMe-4-(N-AC-N-Me-N)-2-Py], [1888:5-OMe-4-(N-AC-N-Me-N)-2-Py], [1889:6-OMe-4-(N-AC-N-Me-N)-2-Py], [1890:5-(N-AC-N-Me-N)-2-Py], [1891:3-Cl-5-(N-AC-N-Me-N)-2-Py], [1892:4-Cl-5-(N-AC-N-Me-N)-2-Py], [1893:6-Cl-5-(N-AC-N-Me-N)-2-Py], [1894:3-Me-5-(N-AC-N-Me-N)-2-Py], [1895:4-Me-5-(N-AC-N-Me-N)-2-Py], [1896:6-Me-5-(N-AC-N-Me-N)-2-Py], [1897:3-CF3-5-(N-AC-N-Me-N)-2-Py], [1898:4-CF3-5-(N-AC-N-Me-N)-2-Py], [1899:6-CF3-5-(N-AC-N-Me-N)-2-Py], [1900:3-CN-5-(N-AC-N-Me-N)-2-Py],
[1901:4-CN-5-(N-AC-N-Me-N)-2-Py], [1902:6-CN-5-(N-AC-N-Me-N)-2-Py], [1903:3-OMe-5-(N-AC-N-Me-N)-2-Py], [1904:4-OMe-5-(N-AC-N-Me-N)-2-Py], [1905:6-OMe-5-(N-AC-N-Me-N)-2-Py], [1906:6-(N-AC-N-Me-N)-2-Py], [1907:3-Cl-6-(N-AC-N-Me-N)-2-Py], [1908:4-Cl-6-(N-AC-N-Me-N)-2-Py], [1909:5-Cl-6-(N-AC-N-Me-N)-2-Py], [1910:3-Me-6-(N-AC-N-Me-N)-2-Py], [1911:4-Me-6-(N-AC-N-Me-N)-2-Py], [1912:5-Me-6-(N-AC-N-Me-N)-2-Py], [1913:3-CF3-6-(N-AC-N-Me-N)-2-Py], [1914:4-CF3-6-(N-AC-N-Me-N)-2-Py], [1915:5-CF3-6-(N-AC-N-Me-N)-2-Py], [1916:3-CN-6-(N-AC-N-Me-N)-2-Py], [1917:4-CN-6-(N-AC-N-Me-N)-2-Py], [1918:5-CN-6-(N-AC-N-Me-N)-2-Py], [1919:3-OMe-6-(N-AC-N-Me-N)-2-Py], [1920:4-OMe-6-(N-AC-N-Me-N)-2-Py], [1921:5-OMe-6-(N-AC-N-Me-N)-2-Py], [1922:3-AC-2-Py], [1923:4-Cl-3-AC-2-Py], [1924:5-Cl-3-AC-2-Py], [1925:6-Cl-3-AC-2-Py], [1926:4-Me-3-AC-2-Py], [1927:5-Me-3-AC-2-Py], [1928:6-Me-3-AC-2-Py], [1929:4-CF3-3-AC-2-Py], [1930:5-CF3-3-AC-2-Py], [1931:6-CF3-3-AC-2-Py], [1932:4-CN-3-AC-2-Py], [1933:5-CN-3-AC-2-Py], [1934:6-CN-3-AC-2-Py], [1935:4-OMe-3-AC-2-Py], [1936:5-OMe-3-AC-2-Py], [1937:6-OMe-3-AC-2-Py], [1938:4-AC-2-Py], [1939:3-Cl-4-AC-2-Py], [1940:5-Cl-4-AC-2-Py], [1941:6-Cl-4-AC-2-Py], [1942:3-Me-4-AC-2-Py], [1943:5-Me-4-AC-2-Py], [1944:6-Me-4-AC-2-Py], [1945:3-CF3-4-AC-2-Py], [1946:5-CF3-4-AC-2-Py], [1947:6-CF3-4-AC-2-Py], [1948:3-CN-4-AC-2-Py], [1949:5-CN-4-AC-2-Py], [1950:6-CN-4-AC-2-Py], [1951:3-OMe-4-AC-2-Py], [1952:5-

OMe-4-AC-2-Py], [1953:6-OMe-4-AC-2-Py], [1954:5-AC-2-Py], [1955:3-Cl-5-AC-2-Py], [1956:4-Cl-5-AC-2-Py], [1957:6-Cl-5-AC-2-Py], [1958:3-Me-5-AC-2-Py], [1959:4-Me-5-AC-2-Py], [1960:6-Me-5-AC-2-Py], [1961:3-CF3-5-AC-2-Py], [1962:4-CF3-5-AC-2-Py], [1963:6-CF3-5-AC-2-Py], [1964:3-CN-5-AC-2-Py], [1965:4-CN-5-AC-2-Py], [1966:6-CN-5-AC-2-Py], [1967:3-OMe-5-AC-2-Py], [1968:4-OMe-5-AC-2-Py], [1969:6-OMe-5-AC-2-Py], [1970:6-AC-2-Py], [1971:3-Cl-6-AC-2-Py], [1972:4-Cl-6-AC-2-Py], [1973:5-Cl-6-AC-2-Py], [1974:3-Me-6-AC-2-Py], [1975:4-Me-6-AC-2-Py], [1976:5-Me-6-AC-2-Py], [1977:3-CF3-6-AC-2-Py], [1978:4-CF3-6-AC-2-Py], [1979:5-CF3-6-AC-2-Py], [1980:3-CN-6-AC-2-Py], [1981:4-CN-6-AC-2-Py], [1982:5-CN-6-AC-2-Py], [1983:3-OMe-6-AC-2-Py], [1984:4-OMe-6-AC-2-Py], [1985:5-OMe-6-AC-2-Py], [1986:3-Py], [1987:2-F-3-Py], [1988:4-Cl-2-F-3-Py], [1989:5-Cl-2-F-3-Py], [1990:6-Cl-2-F-3-Py], [1991:4-Me-2-F-3-Py], [1992:5-Me-2-F-3-Py], [1993:6-Me-2-F-3-Py], [1994:4-CF3-2-F-3-Py], [1995:5-CF3-2-F-3-Py], [1996:6-CF3-2-F-3-Py], [1997:4-CN-2-F-3-Py], [1998:5-CN-2-F-3-Py], [1999:6-CN-2-F-3-Py], [2000:4-OMe-2-F-3-Py],
[2001:5-OMe-2-F-3-Py], [2002:6-OMe-2-F-3-Py], [2003:4-F-3-Py], [2004:2-Cl-4-F-3-Py], [2005:5-Cl-4-F-3-Py], [2006:6-Cl-4-F-3-Py], [2007:2-Me-4-F-3-Py], [2008:5-Me-4-F-3-Py], [2009:6-Me-4-F-3-Py], [2010:2-CF3-4-F-3-Py], [2011:5-CF3-4-F-3-Py], [2012:6-CF3-4-F-3-Py], [2013:2-CN-4-F-3-Py], [2014:5-CN-4-F-3-Py], [2015:6-CN-4-F-3-Py], [2016:2-OMe-4-F-3-Py], [2017:5-OMe-4-F-3-Py], [2018:6-OMe-4-F-3-Py], [2019:5-F-3-Py], [2020:2-Cl-5-F-3-Py], [2021:4-Cl-5-F-3-Py], [2022:6-Cl-5-F-3-Py], [2023:2-Me-5-F-3-Py], [2024:4-Me-5-F-3-Py], [2025:6-Me-5-F-3-Py], [2026:2-CF3-5-F-3-Py], [2027:4-CF3-5-F-3-Py], [2028:6-CF3-5-F-3-Py], [2029:2-CN-5-F-3-Py], [2030:4-CN-5-F-3-Py], [2031:6-CN-5-F-3-Py], [2032:2-OMe-5-F-3-Py], [2033:4-OMe-5-F-3-Py], [2034:6-OMe-5-F-3-Py], [2035:6-F-3-Py], [2036:2-Cl-6-F-3-Py], [2037:4-Cl-6-F-3-Py], [2038:5-Cl-6-F-3-Py], [2039:2-Me-6-F-3-Py], [2040:4-Me-6-F-3-Py], [2041:5-Me-6-F-3-Py], [2042:2-CF3-6-F-3-Py], [2043:4-CF3-6-F-3-Py], [2044:5-CF3-6-F-3-Py], [2045:2-CN-6-F-3-Py], [2046:4-CN-6-F-3-Py], [2047:5-CN-6-F-3-Py], [2048:2-OMe-6-F-3-Py], [2049:4-OMe-6-F-3-Py], [2050:5-OMe-6-F-3-Py], [2051:2-Cl-3-Py], [2052:4-Cl-2-Cl-3-Py], [2053:5-Cl-2-Cl-3-Py], [2054:6-Cl-2-Cl-3-Py], [2055:4-Me-2-Cl-3-Py], [2056:5-Me-2-Cl-3-Py], [2057:6-Me-2-Cl-3-Py], [2058:4-CF3-2-Cl-3-Py], [2059:5-CF3-2-Cl-3-Py], [2060:6-CF3-2-Cl-3-Py], [2061:4-CN-2-Cl-3-Py], [2062:5-CN-2-Cl-3-Py], [2063:6-CN-2-Cl-3-Py], [2064:4-OMe-2-Cl-3-Py], [2065:5-OMe-2-Cl-3-Py], [2066:6-OMe-2-Cl-3-Py], [2067:4-Cl-3-Py], [2068:2-Cl-4-Cl-3-Py], [2069:5-Cl-4-Cl-3-Py], [2070:6-Cl-4-Cl-3-Py], [2071:2-Me-4-Cl-3-Py], [2072:5-Me-4-Cl-3-Py], [2073:6-Me-4-Cl-3-Py], [2074:2-CF3-4-Cl-3-Py], [2075:5-CF3-4-Cl-3-Py], [2076:6-CF3-4-Cl-3-Py], [2077:2-CN-4-Cl-3-Py], [2078:5-CN-4-Cl-3-Py], [2079:6-CN-4-Cl-3-Py], [2080:2-OMe-4-Cl-3-Py], [2081:5-OMe-4-Cl-3-Py], [2082:6-OMe-4-Cl-3-Py], [2083:5-Cl-3-Py], [2084:4-Cl-5-Cl-3-Py], [2085:5-Cl-5-Cl-3-Py], [2086:6-Cl-5-Cl-3-Py], [2087:4-Me-5-Cl-3-Py], [2088:5-Me-5-Cl-3-Py], [2089:6-Me-5-Cl-3-Py], [2090:4-CF3-5-Cl-3-Py], [2091:5-CF3-5-Cl-3-Py], [2092:6-CF3-5-Cl-3-Py], [2093:4-CN-5-Cl-3-Py], [2094:3-CN-5-Cl-3-Py], [2095:6-CN-5-Cl-3-Py], [2096:4-OMe-5-Cl-3-Py], [2097:5-OMe-5-Cl-3-Py], [2098:6-OMe-5-Cl-3-Py], [2099:6-Cl-3-Py], [2100:2-Cl-6-Cl-3-Py],
[2101:4-Cl-6-Cl-3-Py], [2102:5-Cl-6-Cl-3-Py], [2103:2-Me-6-Cl-3-Py], [2104:4-Me-6-Cl-3-Py], [2105:5-Me-6-Cl-3-Py], [2106:2-CF3-6-Cl-3-Py], [2107:4-CF3-6-Cl-3-Py], [2108:5-CF3-6-Cl-3-Py], [2109:2-CN-6-Cl-3-Py], [2110:4-CN-6-Cl-3-Py], [2111:5-CN-6-Cl-3-Py], [2112:2-OMe-6-Cl-3-Py], [2113:4-OMe-6-Cl-3-Py], [2114:5-OMe-6-Cl-3-Py], [2115:2-Br-3-Py], [2116:4-Cl-2-Br-3-Py], [2117:5-Cl-2-Br-3-Py], [2118:6-Cl-2-Br-3-Py], [2119:4-Me-2-Br-3-Py], [2120:5-Me-2-Br-3-Py], [2121:6-Me-2-Br-3-Py], [2122:4-CF3-2-Br-3-Py], [2123:5-CF3-2-Br-3-Py], [2124:6-CF3-2-Br-3-Py], [2125:4-CN-2-Br-3-Py], [2126:5-CN-2-Br-3-Py], [2127:6-CN-2-Br-3-Py], [2128:4-OMe-2-Br-3-Py], [2129:5-OMe-2-Br-3-Py], [2130:6-OMe-2-Br-3-Py], [2131:4-Br-3-Py], [2132:2-Cl-4-Br-3-Py], [2133:5-Cl-4-Br-3-Py], [2134:6-Cl-4-Br-3-Py], [2135:2-Me-4-Br-3-Py], [2136:5-Me-4-Br-3-Py], [2137:6-Me-4-Br-3-Py], [2138:2-CF3-4-Br-3-Py], [2139:5-CF3-4-Br-3-Py], [2140:6-CF3-4-Br-3-Py], [2141:2-CN-4-Br-3-Py], [2142:5-CN-4-Br-3-Py], [2143:6-CN-4-Br-3-Py], [2144:2-OMe-4-Br-3-Py], [2145:5-OMe-4-Br-3-Py], [2146:6-OMe-4-Br-3-Py], [2147:5-Br-3-Py], [2148:2-Cl-5-Br-3-Py], [2149:4-Cl-5-Br-3-Py], [2150:6-Cl-5-Br-3-Py], [2151:2-Me-5-Br-3-Py], [2152:4-Me-5-Br-3-Py], [2153:6-Me-5-Br-3-Py], [2154:2-CF3-5-Br-3-Py], [2155:4-CF3-5-Br-3-Py], [2156:6-CF3-5-Br-3-Py], [2157:2-CN-5-Br-3-Py], [2158:4-CN-5-Br-3-Py], [2159:6-CN-5-Br-3-Py], [2160:2-OMe-5-Br-3-Py], [2161:4-OMe-5-Br-3-Py], [2162:6-OMe-5-Br-3-Py], [2163:6-Br-3-Py], [2164:2-Cl-6-Br-3-Py], [2165:4-Cl-6-Br-3-Py], [2166:5-Cl-6-Br-3-Py], [2167:2-Me-6-Br-3-Py], [2168:4-Me-6-Br-3-Py], [2169:5-Me-6-Br-3-Py], [2170:2-CF3-6-Br-3-Py], [2171:4-CF3-6-Br-3-Py], [2172:5-CF3-6-Br-3-Py], [2173:2-CN-6-Br-3-Py], [2174:4-CN-6-Br-3-Py], [2175:5-CN-6-Br-3-Py], [2176:2-OMe-6-Br-3-Py], [2177:4-OMe-6-Br-3-Py], [2178:5-OMe-6-Br-3-Py], [2179:2-I-3-Py], [2180:4-Cl-2-I-3-Py], [2181:5-Cl-2-I-3-Py], [2182:6-Cl-2-I-3-Py], [2183:4-Me-2-I-3-Py], [2184:5-Me-2-I-3-Py], [2185:6-Me-2-I-3-Py], [2186:4-CF3-2-I-3-Py], [2187:5-CF3-2-I-3-Py], [2188:6-CF3-2-I-3-Py], [2189:4-CN-2-I-3-Py], [2190:5-CN-2-I-3-Py], [2191:6-CN-2-I-3-Py], [2192:4-OMe-2-I-3-Py], [2193:5-OMe-2-I-3-Py], [2194:6-OMe-2-I-3-Py], [2195:4-I-3-Py], [2196:2-Cl-4-I-3-Py], [2197:5-Cl-4-I-3-Py], [2198:6-Cl-4-I-3-Py], [2199:2-Me-4-I-3-Py], [2200:5-Me-4-I-3-PY],
[2201:6-Me-4-I-3-Py], [2202:2-CF3-4-I-3-Py], [2203:5-CF3-4-I-3-Py], [2204:6-CF3-4-I-3-Py], [2205:2-CN-4-I-3-Py], [2206:5-CN-4-I-3-Py], [2207:6-CN-4-I-3-Py], [2208:2-OMe-4-I-3-Py], [2209:5-OMe-4-I-3-Py], [2210:6-OMe-4-I-3-Py], [2211:5-I-3-Py], [2212:2-Cl-5-I-3-Py], [2213:4-Cl-5-I-3-Py], [2214:6-Cl-5-I-3-Py], [2215:2-Me-5-I-3-Py], [2216:4-Me-5-I-3-Py], [2217:6-Me-5-I-3-Py], [2218:2-CF3-5-I-3-Py], [2219:4-CF3-5-I-3-Py], [2220:6-CF3-5-I-3-Py], [2221:2-CN-5-I-3-Py], [2222:4-CN-5-I-3-Py], [2223:6-CN-5-I-3-Py], [2224:2-OMe-5-I-3-Py], [2225:4-OMe-5-I-3-Py], [2226:6-OMe-5-I-3-Py], [2227:6-I-3-Py], [2228:2-Cl-6-I-3-Py], [2229:4-Cl-6-I-3-Py], [2230:5-Cl-6-I-3-Py], [2231:2-Me-6-I-3-Py], [2232:4-Me-6-I-3-Py], [2233:5-Me-6-I-3-Py], [2234:2-CF3-6-I-3-Py], [2235:4-CF3-6-I-3-Py], [2236:5-CF3-6-I-3-Py], [2237:2-CN-6-I-3-Py], [2238:4-CN-6-I-3-Py], [2239:5-CN-6-I-3-Py], [2240:2-OMe-6-I-3-Py], [2241:4-OMe-6-I-3-Py], [2242:5-OMe-6-I-3-Py], [2243:2-Me-3-Py], [2244:4-Cl-2-Me-3-Py], [2245:5-Cl-2-Me-3-Py], [2246:6-Cl-2-Me-3-Py], [2247:4-Me-2-Me-3-Py], [2248:5-Me-2-Me-3-Py], [2249:6-Me-2-Me-3-Py], [2250:4-CF3-2-Me-3-Py], [2251:5-CF3-2-Me-3-Py], [2252:6-CF3-2-Me-3-Py], [2253:4-CN-2-Me-3-Py], [2254:5-CN-2-Me-3-Py], [2255:6-CN-2-Me-3-Py], [2256:4-OMe-2-Me-3-Py], [2257:5-OMe-2-Me-3-Py], [2258:6-OMe-2-Me-3-Py], [2259:4-Me-3-Py], [2260:2-Cl-4-Me-3-Py], [2261:5-Cl-4-Me-3-Py], [2262:6-Cl-4-Me-3-Py], [2263:2-Me-4-Me-3-Py], [2264:5-Me-4-Me-3-Py], [2265:6-Me-4-Me-3-Py],

[2266:2-CF3-4-Me-3-Py], [2267:5-CF3-4-Me-3-Py], [2268:6-CF3-4-Me-3-Py], [2269:2-CN-4-Me-3-Py], [2270:5-CN-4-Me-3-Py], [2271:6-CN-4-Me-3-Py], [2272:2-OMe-4-Me-3-Py], [2273:5-OMe-4-Me-3-Py], [2274:6-OMe-4-Me-3-Py], [2275:5-Me-3-Py], [2276:2-Cl-5-Me-3-Py], [2277:4-Cl-5-Me-3-Py], [2278:6-Cl-5-Me-3-Py], [2279:2-Me-5-Me-3-Py], [2280:4-Me-5-Me-3-Py], [2281:6-Me-5-Me-3-Py], [2282:2-CF3-5-Me-3-Py], [2283:4-CF3-5-Me-3-Py], [2284:6-CF3-5-Me-3-Py], [2285:2-CN-5-Me-3-Py], [2286:4-CN-5-Me-3-Py], [2287:6-CN-5-Me-3-Py], [2288:2-OMe-5-Me-3-Py], [2289:4-OMe-5-Me-3-Py], [2290:6-OMe-5-Me-3-Py], [2291:6-Me-3-Py], [2292:2-Cl-6-Me-3-Py], [2293:4-Cl-6-Me-3-Py], [2294:5-Cl-6-Me-3-Py], [2295:2-Me-6-Me-3-Py], [2296:4-Me-6-Me-3-Py], [2297:5-Me-6-Me-3-Py], [2298:2-CF3-6-Me-3-Py], [2299:4-CF3-6-Me-3-Py], [2300:5-CF3-6-Me-3-Py],

[2301:2-CN-6-Me-3-Py], [2302:4-CN-6-Me-3-Py], [2303:5-CN-6-Me-3-Py], [2304:2-OMe-6-Me-3-Py], [2305:4-OMe-6-Me-3-Py], [2306:5-OMe-6-Me-3-Py], [2307:2-OMe-3-Py], [2308:4-Cl-2-OMe-3-Py], [2309:5-Cl-2-OMe-3-Py], [2310:6-Cl-2-OMe-3-Py], [2311:4-Me-2-OMe-3-Py], [2312:5-Me-2-OMe-3-Py], [2313:6-Me-2-OMe-3-Py], [2314:4-CF3-2-OMe-3-Py], [2315:5-CF3-2-OMe-3-Py], [2316:6-CF3-2-OMe-3-Py], [2317:4-CN-2-OMe-3-Py], [2318:5-CN-2-OMe-3-Py], [2319:6-CN-2-OMe-3-Py], [2320:4-OMe-2-OMe-3-Py], [2321:5-OMe-2-OMe-3-Py], [2322:6-OMe-2-OMe-3-Py], [2323:4-OMe-3-Py], [2324:2-Cl-4-OMe-3-Py], [2325:5-Cl-4-OMe-3-Py], [2326:6-Cl-4-OMe-3-Py], [2327:2-Me-4-OMe-3-Py], [2328:5-Me-4-OMe-3-Py], [2329:6-Me-4-OMe-3-Py], [2330:2-CF3-4-OMe-3-Py], [2331:5-CF3-4-OMe-3-Py], [2332:6-CF3-4-OMe-3-Py], [2333:2-CN-4-OMe-3-Py], [2334:5-CN-4-OMe-3-Py], [2335:6-CN-4-OMe-3-Py], [2336:2-OMe-4-OMe-3-Py], [2337:5-OMe-4-OMe-3-Py], [2338:6-OMe-4-OMe-3-Py], [2339:5-OMe-3-Py], [2340:2-Cl-5-OMe-3-Py], [2341:4-Cl-5-OMe-3-Py], [2342:6-Cl-5-OMe-3-Py], [2343:2-Me-5-OMe-3-Py], [2344:4-Me-5-OMe-3-Py], [2345:6-Me-5-OMe-3-Py], [2346:2-CF3-5-OMe-3-Py], [2347:4-CF3-5-OMe-3-Py], [2348:6-CF3-5-OMe-3-Py], [2349:2-CN-5-OMe-3-Py], [2350:4-CN-5-OMe-3-Py], [2351:6-CN-5-OMe-3-Py], [2352:2-OMe-5-OMe-3-Py], [2353:4-OMe-5-OMe-3-Py], [2354:6-OMe-5-OMe-3-Py], [2355:6-OMe-3-Py], [2356:2-Cl-6-OMe-3-Py], [2357:4-Cl-6-OMe-3-Py], [2358:5-Cl-6-OMe-3-Py], [2359:2-Me-6-OMe-3-Py], [2360:4-Me-6-OMe-3-Py], [2361:5-Me-6-OMe-3-Py], [2362:2-CF3-6-OMe-3-Py], [2363:4-CF3-6-OMe-3-Py], [2364:5-CF3-6-OMe-3-Py], [2365:2-CN-6-OMe-3-Py], [2366:4-CN-6-OMe-3-Py], [2367:5-CN-6-OMe-3-Py], [2368:2-OMe-6-OMe-3-Py], [2369:4-OMe-6-OMe-3-Py], [2370:5-OMe-6-OMe-3-Py], [2371:2-CF3-3-Py], [2372:4-Cl-2-CF3-3-Py], [2373:5-Cl-2-CF3-3-Py], [2374:6-Cl-2-CF3-3-Py], [2375:4-Me-2-CF3-3-Py], [2376:5-Me-2-CF3-3-Py], [2377:6-Me-2-CF3-3-Py], [2378:4-CF3-2-CF3-3-Py], [2379:5-CF3-2-CF3-3-Py], [2380:6-CF3-2-CF3-3-Py], [2381:4-CN-2-CF3-3-Py], [2382:5-CN-2-CF3-3-Py], [2383:6-CN-2-CF3-3-Py], [2384:4-OMe-2-CF3-3-Py], [2385:5-OMe-2-CF3-3-Py], [2386:6-OMe-2-CF3-3-Py], [2387:4-CF3-3-Py], [2388:2-Cl-4-CF3-3-Py], [2389:5-Cl-4-CF3-3-Py], [2390:6-Cl-4-CF3-3-Py], [2391:2-Me-4-CF3-3-Py], [2392:5-Me-4-CF3-3-Py], [2393:6-Me-4-CF3-3-Py], [2394:2-CF3-4-CF3-3-Py], [2395:5-CF3-4-CF3-3-Py], [2396:6-CF3-4-CF3-3-Py], [2397:2-CN-4-CF3-3-Py], [2398:5-CN-4-CF3-3-Py], [2399:6-CN-4-CF3-3-Py], [2400:2-OMe-4-CF3-3-Py], [2401:5-OMe-4-CF3-3-Py], [2402:6-OMe-4-CF3-3-Py], [2403:5-CF3-3-Py], [2404:2-Cl-5-CF3-3-Py], [2405:4-Cl-5-CF3-3-Py], [2406:6-Cl-5-CF3-3-Py], [2407:2-Me-5-CF3-3-Py], [2408:4-Me-5-CF3-3-Py], [2409:6-Me-5-CF3-3-Py], [2410:2-CF3-5-CF3-3-Py], [2411:4-CF3-5-CF3-3-Py], [2412:6-CF3-5-CF3-3-Py], [2413:2-CN-5-CF3-3-Py], [2414:4-CN-5-CF3-3-Py], [2415:6-CN-5-CF3-3-Py], [2416:2-OMe-5-CF3-3-Py], [2417:4-OMe-5-CF3-3-Py], [2418:6-OMe-5-CF3-3-Py], [2419:6-CF3-3-Py], [2420:2-Cl-6-CF3-3-Py], [2421:4-Cl-6-CF3-3-Py], [2422:5-Cl-6-CF3-3-Py], [2423:2-Me-6-CF3-3-Py], [2424:4-Me-6-CF3-3-Py], [2425:5-Me-6-CF3-3-Py], [2426:2-CF3-6-CF3-3-Py], [2427:4-CF3-6-CF3-3-Py], [2428:5-CF3-6-CF3-3-Py], [2429:2-CN-6-CF3-3-Py], [2430:4-CN-6-CF3-3-Py], [2431:5-CN-6-CF3-3-Py], [2432:2-OMe-6-CF3-3-Py], [2433:4-OMe-6-CF3-3-Py], [2434:5-OMe-6-CF3-3-Py], [2435:2-OCF3-3-Py], [2436:4-Cl-2-OCF3-3-Py], [2437:5-Cl-2-OCF3-3-Py], [2438:6-Cl-2-OCF3-3-Py], [2439:4-Me-2-OCF3-3-Py], [2440:5-Me-2-OCF3-3-Py], [2441:6-Me-2-OCF3-3-Py], [2442:4-CF3-2-OCF3-3-Py], [2443:5-CF3-2-OCF3-3-Py], [2444:6-CF3-2-OCF3-3-Py], [2445:4-CN-2-OCF3-3-Py], [2446:5-CN-2-OCF3-3-Py], [2447:6-CN-2-OCF3-3-Py], [2448:4-OMe-2-OCF3-3-Py], [2449:5-OMe-2-OCF3-3-Py], [2450:6-OMe-2-OCF3-3-Py], [2451:4-OCF3-3-Py], [2452:2-Cl-4-OCF3-3-Py], [2453:5-Cl-4-OCF3-3-Py], [2454:6-Cl-4-OCF3-3-Py], [2455:2-Me-4-OCF3-3-Py], [2456:5-Me-4-OCF3-3-Py], [2457:6-Me-4-OCF3-3-Py], [2458:2-CF3-4-OCF3-3-Py], [2459:5-CF3-4-OCF3-3-Py], [2460:6-CF3-4-OCF3-3-Py], [2461:2-CN-4-OCF3-3-Py], [2462:5-CN-4-OCF3-3-Py], [2463:6-CN-4-OCF3-3-Py], [2464:2-OMe-4-OCF3-3-Py], [2465:5-OMe-4-OCF3-3-Py], [2466:6-OMe-4-OCF3-3-Py], [2467:5-OCF3-3-Py], [2468:2-Cl-5-OCF3-3-Py], [2469:4-Cl-5-OCF3-3-Py], [2470:6-Cl-5-OCF3-3-Py], [2471:2-Me-5-OCF3-3-Py], [2472:4-Me-5-OCF3-3-Py], [2473:6-Me-5-OCF3-3-Py], [2474:2-CF3-5-OCF3-3-Py], [2475:4-CF3-5-OCF3-3-Py], [2476:6-CF3-5-OCF3-3-Py], [2477:2-CN-5-OCF3-3-Py], [2478:4-CN-5-OCF3-3-Py], [2479:6-CN-5-OCF3-3-Py], [2480:2-OMe-5-OCF3-3-Py], [2481:4-OMe-5-OCF3-3-Py], [2482:6-OMe-5-OCF3-3-Py], [2483:6-OCF3-3-Py], [2484:2-Cl-6-OCF3-3-Py], [2485:4-Cl-6-OCF3-3-Py], [2486:5-Cl-6-OCF3-3-Py], [2487:2-Me-6-OCF3-3-Py], [2488:4-Me-6-OCF3-3-Py], [2489:5-Me-6-OCF3-3-Py], [2490:2-CF3-6-OCF3-3-Py], [2491:4-CF3-6-OCF3-3-Py], [2492:5-CF3-6-OCF3-3-Py], [2493:2-CN-6-OCF3-3-Py], [2494:4-CN-6-OCF3-3-Py], [2495:5-CN-6-OCF3-3-Py], [2496:2-OMe-6-OCF3-3-Py], [2497:4-OMe-6-OCF3-3-Py], [2498:5-OMe-6-OCF3-3-Py], [2499:2-CHF2-3-Py], [2500:4-Cl-2-CHF2-3-Py],
[2501:5-Cl-2-CHF2-3-Py], [2502:6-Cl-2-CHF2-3-Py], [2503:4-Me-2-CHF2-3-Py], [2504:5-Me-2-CHF2-3-Py], [2505:6-Me-2-CHF2-3-Py], [2506:4-CF3-2-CHF2-3-Py], [2507:5-CF3-2-CHF2-3-Py], [2508:6-CF3-2-CHF2-3-Py], [2509:4-CN-2-CHF2-3-Py], [2510:5-CN-2-CHF2-3-Py], [2511:6-CN-2-CHF2-3-Py], [2512:4-OMe-2-CHF2-3-Py], [2513:5-OMe-2-CHF2-3-Py], [2514:6-OMe-2-CHF2-3-Py], [2515:4-CHF2-3-Py], [2516:2-Cl-4-CHF2-3-Py], [2517:5-Cl-4-CHF2-3-Py], [2518:6-Cl-4-CHF2-3-Py], [2519:2-Me-4-CHF2-3-Py], [2520:5-Me-4-CHF2-3-Py], [2521:6-Me-4-CHF2-3-Py], [2522:2-CF3-4-CHF2-3-Py], [2523:5-CF3-4-CHF2-3-Py], [2524:6-CF3-4-CHF2-3-Py], [2525:2-CN-4-CHF2-3-Py], [2526:5-CN-4-CHF2-3-Py], [2527:6-CN-4-CHF2-3-Py], [2528:2-OMe-4-CHF2-3-Py], [2529:5-OMe-4-CHF2-3-Py], [2530:6-OMe-4-CHF2-3-Py], [2531:5-CHF2-3-Py], [2532:2-Cl-5-CHF2-3-Py], [2533:4-Cl-5-CHF2-3-Py], [2534:6-Cl-5-CHF2-3-Py], [2535:2-Me-5-CHF2-3-Py], [2536:4-Me-5-CHF2-3-Py], [2537:6-Me-5-CHF2-3-Py], [2538:2-CF3-5-CHF2-3-Py], [2539:4-CF3-5-CHF2-3-Py], [2540:6-CF3-5-CHF2-3-Py], [2541:2-CN-5-CHF2-3-Py], [2542:4-CN-5-CHF2-3-Py],

[2543:6-CN-5-CHF2-3-Py], [2544:2-OMe-5-CHF2-3-Py], [2545:4-OMe-5-CHF2-3-Py], [2546:6-OMe-5-CHF2-3-Py], [2547:6-CHF2-3-Py], [2548:2-Cl-6-CHF2-3-Py], [2549:4-Cl-6-CHF2-3-Py], [2550:5-Cl-6-CHF2-3-Py], [2551:2-Me-6-CHF2-3-Py], [2552:4-Me-6-CHF2-3-Py], [2553:5-Me-6-CHF2-3-Py], [2554:2-CF3-6-CHF2-3-Py], [2555:4-CF3-6-CHF2-3-Py], [2556:5-CF3-6-CHF2-3-Py], [2557:2-CN-6-CHF2-3-Py], [2558:4-CN-6-CHF2-3-Py], [2559:5-CN-6-CHF2-3-Py], [2560:2-OMe-6-CHF2-3-Py], [2561:4-OMe-6-CHF2-3-Py], [2562:5-OMe-6-CHF2-3-Py], [2563:2-OCHF2-3-Py], [2564:4-Cl-2-OCHF2-3-Py], [2565:5-Cl-2-OCHF2-3-Py], [2566:6-Cl-2-OCHF2-3-Py], [2567:4-Me-2-OCHF2-3-Py], [2568:5-Me-2-OCHF2-3-Py], [2569:6-Me-2-OCHF2-3-Py], [2570:4-CF3-2-OCHF2-3-Py], [2571:5-CF3-2-OCHF2-3-Py], [2572:6-CF3-2-OCHF2-3-Py], [2573:4-CN-2-OCHF2-3-Py], [2574:5-CN-2-OCHF2-3-Py], [2575:6-CN-2-OCHF2-3-Py], [2576:4-OMe-2-OCHF2-3-Py], [2577:5-OMe-2-OCHF2-3-Py], [2578:6-OMe-2-OCHF2-3-Py], [2579:4-OCHF2-3-Py], [2580:2-Cl-4-OCHF2-3-Py], [2581:5-Cl-4-OCHF2-3-Py], [2582:6-Cl-4-OCHF2-3-Py], [2583:2-Me-4-OCHF2-3-Py], [2584:5-Me-4-OCHF2-3-Py], [2585:6-Me-4-OCHF2-3-Py], [2586:2-CF3-4-OCHF2-3-Py], [2587:5-CF3-4-OCHF2-3-Py], [2588:6-CF3-4-OCHF2-3-Py], [2589:2-CN-4-OCHF2-3-Py], [2590:5-CN-4-OCHF2-3-Py], [2591:6-CN-4-OCHF2-3-Py], [2592:2-OMe-4-OCHF2-3-Py], [2593:5-OMe-4-OCHF2-3-Py], [2594:6-OMe-4-OCHF2-3-Py], [2595:5-OCHF2-3-Py], [2596:2-Cl-5-OCHF2-3-Py], [2597:4-Cl-5-OCHF2-3-Py], [2598:6-Cl-5-OCHF2-3-Py], [2599:2-Me-5-OCHF2-3-Py], [2600:4-Me-5-OCHF2-3-Py],
[2601:6-Me-5-OCHF2-3-Py], [2602:2-CF3-5-OCHF2-3-Py], [2603:4-CF3-5-OCHF2-3-Py], [2604:6-CF3-5-OCHF2-3-Py], [2605:2-CN-5-OCHF2-3-Py], [2606:4-CN-5-OCHF2-3-Py], [2607:6-CN-5-OCHF2-3-Py], [2608:2-OMe-5-OCHF2-3-Py], [2609:4-OMe-5-OCHF2-3-Py], [2610:6-OMe-5-OCHF2-3-Py], [2611:6-OCHF2-3-Py], [2612:2-Cl-6-OCHF2-3-Py], [2613:4-Cl-6-OCHF2-3-Py], [2614:5-Cl-6-OCHF2-3-Py], [2615:2-Me-6-OCHF2-3-Py], [2616:4-Me-6-OCHF2-3-Py], [2617:5-Me-6-OCHF2-3-Py], [2618:2-CF3-6-OCHF2-3-Py], [2619:4-CF3-6-OCHF2-3-Py], [2620:5-CF3-6-OCHF2-3-Py], [2621:2-CN-6-OCHF2-3-Py], [2622:4-CN-6-OCHF2-3-Py], [2623:5-CN-6-OCHF2-3-Py], [2624:2-OMe-6-OCHF2-3-Py], [2625:4-OMe-6-OCHF2-3-Py], [2626:5-OMe-6-OCHF2-3-Py], [2627:2-Et-3-Py], [2628:4-Cl-2-Et-3-Py], [2629:5-Cl-2-Et-3-Py], [2630:6-Cl-2-Et-3-Py], [2631:4-Me-2-Et-3-Py], [2632:5-Me-2-Et-3-Py], [2633:6-Me-2-Et-3-Py], [2634:4-CF3-2-Et-3-Py], [2635:5-CF3-2-Et-3-Py], [2636:6-CF3-2-Et-3-Py], [2637:4-CN-2-Et-3-Py], [2638:5-CN-2-Et-3-Py], [2639:6-CN-2-Et-3-Py], [2640:4-OMe-2-Et-3-Py], [2641:5-OMe-2-Et-3-Py], [2642:6-OMe-2-Et-3-Py], [2643:4-Et-3-Py], [2644:2-Cl-4-Et-3-Py], [2645:5-Cl-4-Et-3-Py], [2646:6-Cl-4-Et-3-Py], [2647:2-Me-4-Et-3-Py], [2648:5-Me-4-Et-3-Py], [2649:6-Me-4-Et-3-Py], [2650:2-CF3-4-Et-3-Py], [2651:5-CF3-4-Et-3-Py], [2652:6-CF3-4-Et-3-Py], [2653:2-CN-4-Et-3-Py], [2654:5-CN-4-Et-3-Py], [2655:6-CN-4-Et-3-Py], [2656:2-OMe-4-Et-3-Py], [2657:5-OMe-4-Et-3-Py], [2658:6-OMe-4-Et-3-Py], [2659:5-Et-3-Py], [2660:2-Cl-5-Et-3-Py], [2661:4-Cl-5-Et-3-Py], [2662:6-Cl-5-Et-3-Py], [2663:2-Me-5-Et-3-Py], [2664:4-Me-5-Et-3-Py], [2665:6-Me-5-Et-3-Py], [2666:2-CF3-5-Et-3-Py], [2667:4-CF3-5-Et-3-Py], [2668:6-CF3-5-Et-3-Py], [2669:2-CN-5-Et-3-Py], [2670:4-CN-5-Et-3-Py], [2671:6-CN-5-Et-3-Py], [2672:2-OMe-5-Et-3-Py], [2673:4-OMe-5-Et-3-Py], [2674:6-OMe-5-Et-3-Py], [2675:6-Et-3-Py], [2676:2-Cl-6-Et-3-Py], [2677:4-Cl-6-Et-3-Py], [2678:5-Cl-6-Et-3-Py], [2679:2-Me-6-Et-3-Py], [2680:4-Me-6-Et-3-Py], [2681:5-Me-6-Et-3-Py], [2682:2-CF3-6-Et-3-Py], [2683:4-CF3-6-Et-3-Py], [2684:5-CF3-6-Et-3-Py], [2685:2-CN-6-Et-3-Py], [2686:4-CN-6-Et-3-Py], [2687:5-CN-6-Et-3-Py], [2688:2-OMe-6-Et-3-Py], [2689:4-OMe-6-Et-3-Py], [2690:5-OMe-6-Et-3-Py], [2691:2-CH2CF3-3-Py], [2692:4-Cl-2-CH2CF3-3-Py], [2693:5-Cl-2-CH2CF3-3-Py], [2694:6-Cl-2-CH2CF3-3-Py], [2695:4-Me-2-CH2CF3-3-Py], [2696:5-Me-2-CH2CF3-3-Py], [2697:6-Me-2-CH2CF3-3-Py], [2698:4-CF3-2-CH2CF3-3-Py], [2699:5-CF3-2-CH2CF3-3-Py], [2700:6-CF3-2-CH2CF3-3-Py],
[2701:4-CN-2-CH2CF3-3-Py], [2702:5-CN-2-CH2CF3-3-Py], [2703:6-CN-2-CH2CF3-3-Py], [2704:4-OMe-2-CH2CF3-3-Py], [2705:5-OMe-2-CH2CF3-3-Py], [2706:6-OMe-2-CH2CF3-3-Py], [2707:4-CH2CF3-3-Py], [2708:2-Cl-4-CH2CF3-3-Py], [2709:5-Cl-4-CH2CF3-3-Py], [2710:6-Cl-4-CH2CF3-3-Py], [2711:2-Me-4-CH2CF3-3-Py], [2712:5-Me-4-CH2CF3-3-Py], [2713:6-Me-4-CH2CF3-3-Py], [2714:2-CF3-4-CH2CF3-3-Py], [2715:5-CF3-4-CH2CF3-3-Py], [2716:6-CF3-4-CH2CF3-3-Py], [2717:2-CN-4-CH2CF3-3-Py], [2718:5-CN-4-CH2CF3-3-Py], [2719:6-CN-4-CH2CF3-3-Py], [2720:2-OMe-4-CH2CF3-3-Py], [2721:5-OMe-4-CH2CF3-3-Py], [2722:6-OMe-4-CH2CF3-3-Py], [2723:5-CH2CF3-3-Py], [2724:2-Cl-5-CH2CF3-3-Py], [2725:4-Cl-5-CH2CF3-3-Py], [2726:6-Cl-5-CH2CF3-3-Py], [2727:2-Me-5-CH2CF3-3-Py], [2728:4-Me-5-CH2CF3-3-Py], [2729:6-Me-5-CH2CF3-3-Py], [2730:2-CF3-5-CH2CF3-3-Py], [2731:4-CF3-5-CH2CF3-3-Py], [2732:6-CF3-5-CH2CF3-3-Py], [2733:2-CN-5-CH2CF3-3-Py], [2734:4-CN-5-CH2CF3-3-Py], [2735:6-CN-5-CH2CF3-3-Py], [2736:2-OMe-5-CH2CF3-3-Py], [2737:4-OMe-5-CH2CF3-3-Py], [2738:6-OMe-5-CH2CF3-3-Py], [2739:6-CH2CF3-3-Py], [2740:2-Cl-6-CH2CF3-3-Py], [2741:4-Cl-6-CH2CF3-3-Py], [2742:5-Cl-6-CH2CF3-3-Py], [2743:2-Me-6-CH2CF3-3-Py], [2744:4-Me-6-CH2CF3-3-Py], [2745:5-Me-6-CH2CF3-3-Py], [2746:2-CF3-6-CH2CF3-3-Py], [2747:4-CF3-6-CH2CF3-3-Py], [2748:5-CF3-6-CH2CF3-3-Py], [2749:2-CN-6-CH2CF3-3-Py], [2750:4-CN-6-CH2CF3-3-Py], [2751:5-CN-6-CH2CF3-3-Py], [2752:2-OMe-6-CH2CF3-3-Py], [2753:4-OMe-6-CH2CF3-3-Py], [2754:5-OMe-6-CH2CF3-3-Py], [2755:2-OEt-3-Py], [2756:4-Cl-2-OEt-3-Py], [2757:5-Cl-2-OEt-3-Py], [2758:6-Cl-2-OEt-3-Py], [2759:4-Me-2-OEt-3-Py], [2760:5-Me-2-OEt-3-Py], [2761:6-Me-2-OEt-3-Py], [2762:4-CF3-2-OEt-3-Py], [2763:5-CF3-2-OEt-3-Py], [2764:6-CF3-2-OEt-3-Py], [2765:4-CN-2-OEt-3-Py], [2766:5-CN-2-OEt-3-Py], [2767:6-CN-2-OEt-3-Py], [2768:4-OMe-2-OEt-3-Py], [2769:5-OMe-2-OEt-3-Py], [2770:6-OMe-2-OEt-3-Py], [2771:4-OEt-3-Py], [2772:2-Cl-4-OEt-3-Py], [2773:5-Cl-4-OEt-3-Py], [2774:6-Cl-4-OEt-3-Py], [2775:2-Me-4-OEt-3-Py], [2776:5-Me-4-OEt-3-Py], [2777:6-Me-4-OEt-3-Py], [2778:2-CF3-4-OEt-3-Py], [2779:5-CF3-4-OEt-3-Py], [2780:6-CF3-4-OEt-3-Py], [2781:2-CN-4-OEt-3-Py], [2782:5-CN-4-OEt-3-Py], [2783:6-CN-4-OEt-3-Py], [2784:2-OMe-4-OEt-3-Py], [2785:5-OMe-4-OEt-3-Py], [2786:6-OMe-4-OEt-3-Py], [2787:5-OEt-3-Py], [2788:2-Cl-5-OEt-3-Py], [2789:4-Cl-5-OEt-3-Py], [2790:6-Cl-5-OEt-3-Py], [2791:2-Me-5-OEt-3-Py], [2792:4-Me-5-OEt-3-Py], [2793:6-Me-5-OEt-3-Py], [2794:2-CF3-5-OEt-3-Py], [2795:4-CF3-5-OEt-3-Py], [2796:6-CF3-5-OEt-3-Py], [2797:2-CN-5-OEt-3-Py], [2798:4-CN-5-OEt-3-Py], [2799:6-CN-5-OEt-3-Py], [2800:2-OMe-5-OEt-3-Py],
[2801:4-OMe-5-OEt-3-Py], [2802:6-OMe-5-OEt-3-Py], [2803:6-OEt-3-Py], [2804:2-Cl-6-OEt-3-Py], [2805:4-Cl-6-OEt-3-Py], [2806:5-Cl-6-OEt-3-Py], [2807:2-Me-6-OEt-3-Py], [2808:4-Me-6-OEt-3-Py], [2809:5-Me-6-OEt-3-Py], [2810:2-CF3-6-OEt-3-Py], [2811:4-CF3-6-OEt-3-Py],

[2812:5-CF3-6-OEt-3-Py], [2813:2-CN-6-OEt-3-Py], [2814:4-CN-6-OEt-3-Py], [2815:5-CN-6-OEt-3-Py], [2816:2-OMe-6-OEt-3-Py], [2817:4-OMe-6-OEt-3-Py], [2818:5-OMe-6-OEt-3-Py], [2819:2-OCH2CF3-3-Py], [2820:4-Cl-2-OCH2CF3-3-Py], [2821:5-Cl-2-OCH2CF3-3-Py], [2822:6-Cl-2-OCH2CF3-3-Py], [2823:4-Me-2-OCH2CF3-3-Py], [2824:5-Me-2-OCH2CF3-3-Py], [2825:6-Me-2-OCH2CF3-3-Py], [2826:4-CF3-2-OCH2CF3-3-Py], [2827:5-CF3-2-OCH2CF3-3-Py], [2828:6-CF3-2-OCH2CF3-3-Py], [2829:4-CN-2-OCH2CF3-3-Py], [2830:5-CN-2-OCH2CF3-3-Py], [2831:6-CN-2-OCH2CF3-3-Py], [2832:4-OMe-2-OCH2CF3-3-Py], [2833:5-OMe-2-OCH2CF3-3-Py], [2834:6-OMe-2-OCH2CF3-3-Py], [2835:4-OCH2CF3-3-Py], [2836:2-Cl-4-OCH2CF3-3-Py], [2837:5-Cl-4-OCH2CF3-3-Py], [2838:6-Cl-4-OCH2CF3-3-Py], [2839:2-Me-4-OCH2CF3-3-Py], [2840:5-Me-4-OCH2CF3-3-Py], [2841:6-Me-4-OCH2CF3-3-Py], [2842:2-CF3-4-OCH2CF3-3-Py], [2843:5-CF3-4-OCH2CF3-3-Py], [2844:6-CF3-4-OCH2CF3-3-Py], [2845:2-CN-4-OCH2CF3-3-Py], [2846:5-CN-4-OCH2CF3-3-Py], [2847:6-CN-4-OCH2CF3-3-Py], [2848:2-OMe-4-OCH2CF3-3-Py], [2849:5-OMe-4-OCH2CF3-3-Py], [2850:6-OMe-4-OCH2CF3-3-Py], [2851:5-OCH2CF3-3-Py], [2852:2-Cl-5-OCH2CF3-3-Py], [2853:4-Cl-5-OCH2CF3-3-Py], [2854:6-Cl-5-OCH2CF3-3-Py], [2855:2-Me-5-OCH2CF3-3-Py], [2856:4-Me-5-OCH2CF3-3-Py], [2857:6-Me-5-OCH2CF3-3-Py], [2858:2-CF3-5-OCH2CF3-3-Py], [2859:4-CF3-5-OCH2CF3-3-Py], [2860:6-CF3-5-OCH2CF3-3-Py], [2861:2-CN-5-OCH2CF3-3-Py], [2862:4-CN-5-OCH2CF3-3-Py], [2863:6-CN-5-OCH2CF3-3-Py], [2864:2-OMe-5-OCH2CF3-3-Py], [2865:4-OMe-5-OCH2CF3-3-Py], [2866:6-OMe-5-OCH2CF3-3-Py], [2867:6-OCH2CF3-3-Py], [2868:2-Cl-6-OCH2CF3-3-Py], [2869:4-Cl-6-OCH2CF3-3-Py], [2870:5-Cl-6-OCH2CF3-3-Py], [2871:2-Me-6-OCH2CF3-3-Py], [2872:4-Me-6-OCH2CF3-3-Py], [2873:5-Me-6-OCH2CF3-3-Py], [2874:2-CF3-6-OCH2CF3-3-Py], [2875:4-CF3-6-OCH2CF3-3-Py], [2876:5-CF3-6-OCH2CF3-3-Py], [2877:2-CN-6-OCH2CF3-3-Py], [2878:4-CN-6-OCH2CF3-3-Py], [2879:5-CN-6-OCH2CF3-3-Py], [2880:2-OMe-6-OCH2CF3-3-Py], [2881:4-OMe-6-OCH2CF3-3-Py], [2882:5-OMe-6-OCH2CF3-3-Py], [2883:2-Pr-3-Py], [2884:4-Cl-2-Pr-3-Py], [2885:5-Cl-2-Pr-3-Py], [2886:6-Cl-2-Pr-3-Py], [2887:4-Me-2-Pr-3-Py], [2888:5-Me-2-Pr-3-Py], [2889:6-Me-2-Pr-3-Py], [2890:4-CF3-2-Pr-3-Py], [2891:5-CF3-2-Pr-3-Py], [2892:6-CF3-2-Pr-3-Py], [2893:4-CN-2-Pr-3-Py], [2894:5-CN-2-Pr-3-Py], [2895:6-CN-2-Pr-3-Py], [2896:4-OMe-2-Pr-3-Py], [2897:5-OMe-2-Pr-3-Py], [2898:6-OMe-2-Pr-3-Py], [2899:4-Pr-3-Py], [2900:2-Cl-4-Pr-3-Py], [2901:5-Cl-4-Pr-3-Py], [2902:6-Cl-4-Pr-3-Py], [2903:2-Me-4-Pr-3-Py], [2904:5-Me-4-Pr-3-Py], [2905:6-Me-4-Pr-3-Py], [2906:2-CF3-4-Pr-3-Py], [2907:5-CF3-4-Pr-3-Py], [2908:6-CF3-4-Pr-3-Py], [2909:2-CN-4-Pr-3-Py], [2910:5-CN-4-Pr-3-Py], [2911:6-CN-4-Pr-3-Py], [2912:2-OMe-4-Pr-3-Py], [2913:5-OMe-4-Pr-3-Py], [2914:6-OMe-4-Pr-3-Py], [2915:5-Pr-3-Py], [2916:2-Cl-5-Pr-3-Py], [2917:4-Cl-5-Pr-3-Py], [2918:6-Cl-5-Pr-3-Py], [2919:2-Me-5-Pr-3-Py], [2920:4-Me-5-Pr-3-Py], [2921:6-Me-5-Pr-3-Py], [2922:2-CF3-5-Pr-3-Py], [2923:4-CF3-5-Pr-3-Py], [2924:6-CF3-5-Pr-3-Py], [2925:2-CN-5-Pr-3-Py], [2926:4-CN-5-Pr-3-Py], [2927:6-CN-5-Pr-3-Py], [2928:2-OMe-5-Pr-3-Py], [2929:4-OMe-5-Pr-3-Py], [2930:6-OMe-5-Pr-3-Py], [2931:6-Pr-3-Py], [2932:2-Cl-6-Pr-3-Py], [2933:4-Cl-6-Pr-3-Py], [2934:5-Cl-6-Pr-3-Py], [2935:2-Me-6-Pr-3-Py], [2936:4-Me-6-Pr-3-Py], [2937:5-Me-6-Pr-3-Py], [2938:2-CF3-6-Pr-3-Py], [2939:4-CF3-6-Pr-3-Py], [2940:5-CF3-6-Pr-3-Py], [2941:2-CN-6-Pr-3-Py], [2942:4-CN-6-Pr-3-Py], [2943:5-CN-6-Pr-3-Py], [2944:2-OMe-6-Pr-3-Py], [2945:4-OMe-6-Pr-3-Py], [2946:5-OMe-6-Pr-3-Py], [2947:2-OPr-3-Py], [2948:4-Cl-2-OPr-3-Py], [2949:5-Cl-2-OPr-3-Py], [2950:6-Cl-2-OPr-3-Py], [2951:4-Me-2-OPr-3-Py], [2952:5-Me-2-OPr-3-Py], [2953:6-Me-2-OPr-3-Py], [2954:4-CF3-2-OPr-3-Py], [2955:5-CF3-2-OPr-3-Py], [2956:6-CF3-2-OPr-3-Py], [2957:4-CN-2-OPr-3-Py], [2958:5-CN-2-OPr-3-Py], [2959:6-CN-2-OPr-3-Py], [2960:4-OMe-2-OPr-3-Py], [2961:5-OMe-2-OPr-3-Py], [2962:6-OMe-2-OPr-3-Py], [2963:4-OPr-3-Py], [2964:2-Cl-4-OPr-3-Py], [2965:5-Cl-4-OPr-3-Py], [2966:6-Cl-4-OPr-3-Py], [2967:2-Me-4-OPr-3-Py], [2968:5-Me-4-OPr-3-Py], [2969:6-Me-4-OPr-3-Py], [2970:2-CF3-4-OPr-3-Py], [2971:5-CF3-4-OPr-3-Py], [2972:6-CF3-4-OPr-3-Py], [2973:2-CN-4-OPr-3-Py], [2974:5-CN-4-OPr-3-Py], [2975:6-CN-4-OPr-3-Py], [2976:2-OMe-4-OPr-3-Py], [2977:5-OMe-4-OPr-3-Py], [2978:6-OMe-4-OPr-3-Py], [2979:5-OPr-3-Py], [2980:2-Cl-5-OPr-3-Py], [2981:4-Cl-5-OPr-3-Py], [2982:6-Cl-5-OPr-3-Py], [2983:2-Me-5-OPr-3-Py], [2984:4-Me-5-OPr-3-Py], [2985:6-Me-5-OPr-3-Py], [2986:2-CF3-5-OPr-3-Py], [2987:4-CF3-5-OPr-3-Py], [2988:6-CF3-5-OPr-3-Py], [2989:2-CN-5-OPr-3-Py], [2990:4-CN-5-OPr-3-Py], [2991:6-CN-5-OPr-3-Py], [2992:2-OMe-5-OPr-3-Py], [2993:4-OMe-5-OPr-3-Py], [2994:6-OMe-5-OPr-3-Py], [2995:6-OPr-3-Py], [2996:2-Cl-6-OPr-3-Py], [2997:4-Cl-6-OPr-3-Py], [2998:5-Cl-6-OPr-3-Py], [2999:2-Me-6-OPr-3-Py], [3000:4-Me-6-OPr-3-Py], [3001:5-Me-6-OPr-3-Py], [3002:2-CF3-6-OPr-3-Py], [3003:4-CF3-6-OPr-3-Py], [3004:5-CF3-6-OPr-3-Py], [3005:2-CN-6-OPr-3-Py], [3006:4-CN-6-OPr-3-Py], [3007:5-CN-6-OPr-3-Py], [3008:2-OMe-6-OPr-3-Py], [3009:4-OMe-6-OPr-3-Py], [3010:5-OMe-6-OPr-3-Py], [3011:2-SMe-3-Py], [3012:4-Cl-2-SMe-3-Py], [3013:5-Cl-2-SMe-3-Py], [3014:6-Cl-2-SMe-3-Py], [3015:4-Me-2-SMe-3-Py], [3016:5-Me-2-SMe-3-Py], [3017:6-Me-2-SMe-3-Py], [3018:4-CF3-2-SMe-3-Py], [3019:5-CF3-2-SMe-3-Py], [3020:6-CF3-2-SMe-3-Py], [3021:4-CN-2-SMe-3-Py], [3022:5-CN-2-SMe-3-Py], [3023:6-CN-2-SMe-3-Py], [3024:4-OMe-2-SMe-3-Py], [3025:5-OMe-2-SMe-3-Py], [3026:6-OMe-2-SMe-3-Py], [3027:4-SMe-3-Py], [3028:2-Cl-4-SMe-3-Py], [3029:5-Cl-4-SMe-3-Py], [3030:6-Cl-4-SMe-3-Py], [3031:2-Me-4-SMe-3-Py], [3032:5-Me-4-SMe-3-Py], [3033:6-Me-4-SMe-3-Py], [3034:2-CF3-4-SMe-3-Py], [3035:5-CF3-4-SMe-3-Py], [3036:6-CF3-4-SMe-3-Py], [3037:2-CN-4-SMe-3-Py], [3038:5-CN-4-SMe-3-Py], [3039:6-CN-4-SMe-3-Py], [3040:2-OMe-4-SMe-3-Py], [3041:5-OMe-4-SMe-3-Py], [3042:6-OMe-4-SMe-3-Py], [3043:5-SMe-3-Py], [3044:2-Cl-5-SMe-3-Py], [3045:4-Cl-5-SMe-3-Py], [3046:6-Cl-5-SMe-3-Py], [3047:2-Me-5-SMe-3-Py], [3048:4-Me-5-SMe-3-Py], [3049:6-Me-5-SMe-3-Py], [3050:2-CF3-5-SMe-3-Py], [3051:4-CF3-5-SMe-3-Py], [3052:6-CF3-5-SMe-3-Py], [3053:2-CN-5-SMe-3-Py], [3054:4-CN-5-SMe-3-Py], [3055:6-CN-5-SMe-3-Py], [3056:2-OMe-5-SMe-3-Py], [3057:4-OMe-5-SMe-3-Py], [3058:6-OMe-5-SMe-3-Py], [3059:6-SMe-3-Py], [3060:2-Cl-6-SMe-3-Py], [3061:4-Cl-6-SMe-3-Py], [3062:5-Cl-6-SMe-3-Py], [3063:2-Me-6-SMe-3-Py], [3064:4-Me-6-SMe-3-Py], [3065:5-Me-6-SMe-3-Py], [3066:2-CF3-6-SMe-3-Py], [3067:4-CF3-6-SMe-3-Py], [3068:5-CF3-6-SMe-3-Py], [3069:2-CN-6-SMe-3-Py], [3070:4-CN-6-SMe-3-Py], [3071:5-CN-6-SMe-3-Py], [3072:2-OMe-6-SMe-3-Py], [3073:4-OMe-6-SMe-3-Py], [3074:5-OMe-6-SMe-3-Py], [3075:2-SCF3-3-Py], [3076:4-Cl-2-SCF3-3-Py], [3077:5-Cl-2-SCF3-3-Py], [3078:6-Cl-2-SCF3-3-Py], [3079:4-Me-2-SCF3-3-Py], [3080:5-Me-2-SCF3-3-Py], [3081:6-Me-2-SCF3-3-Py], [3082:4-CF3-2-SCF3-3-Py], [3083:5-CF3-2-SCF3-3-Py], [3084:6-CF3-2-SCF3-3-Py], [3085:4-CN-2-SCF3-3-Py], [3086:5-CN-2-SCF3-3-Py], [3087:6-CN-2-SCF3-3-Py], [3088:4-OMe-2-SCF3-3-Py], [3089:5-OMe-2-

SCF3-3-Py], [3090:6-OMe-2-SCF3-3-Py], [3091:4-SCF3-3-Py], [3092:2-Cl-4-SCF3-3-Py], [3093:5-Cl-4-SCF3-3-Py], [3094:6-Cl-4-SCF3-3-Py], [3095:2-Me-4-SCF3-3-Py], [3096:5-Me-4-SCF3-3-Py], [3097:6-Me-4-SCF3-3-Py], [3098:2-CF3-4-SCF3-3-Py], [3099:5-CF3-4-SCF3-3-Py], [3100:6-CF3-4-SCF3-3-Py], [3101:2-CN-4-SCF3-3-Py], [3102:5-CN-4-SCF3-3-Py], [3103:6-CN-4-SCF3-3-Py], [3104:2-OMe-4-SCF3-3-Py], [3105:5-OMe-4-SCF3-3-Py], [3106:6-OMe-4-SCF3-3-Py], [3107:5-SCF3-3-Py], [3108:2-Cl-5-SCF3-3-Py], [3109:4-Cl-5-SCF3-3-Py], [3110:6-Cl-5-SCF3-3-Py], [3111:2-Me-5-SCF3-3-Py], [3112:4-Me-5-SCF3-3-Py], [3113:6-Me-5-SCF3-3-Py], [3114:2-CF3-5-SCF3-3-Py], [3115:4-CF3-5-SCF3-3-Py], [3116:6-CF3-5-SCF3-3-Py], [3117:2-CN-5-SCF3-3-Py], [3118:4-CN-5-SCF3-3-Py], [3119:6-CN-5-SCF3-3-Py], [3120:2-OMe-5-SCF3-3-Py], [3121:4-OMe-5-SCF3-3-Py], [3122:6-OMe-5-SCF3-3-Py], [3123:6-SCF3-3-Py], [3124:2-Cl-6-SCF3-3-Py], [3125:4-Cl-6-SCF3-3-Py], [3126:6-Cl-6-SCF3-3-Py], [3127:2-Me-6-SCF3-3-Py], [3128:4-Me-6-SCF3-3-Py], [3129:6-Me-6-SCF3-3-Py], [3130:2-CF3-6-SCF3-3-Py], [3131:4-CF3-6-SCF3-3-Py], [3132:6-CF3-6-SCF3-3-Py], [3133:2-CN-6-SCF3-3-Py], [3134:4-CN-6-SCF3-3-Py], [3135:6-CN-6-SCF3-3-Py], [3136:2-OMe-6-SCF3-3-Py], [3137:4-OMe-6-SCF3-3-Py], [3138:6-OMe-6-SCF3-3-Py], [3139:2-S(O)Me-3-Py], [3140:4-Cl-2-S(O)Me-3-Py], [3141:5-Cl-2-S(O)Me-3-Py], [3142:6-Cl-2-S(O)Me-3-Py], [3143:4-Me-2-S(O)Me-3-Py], [3144:5-Me-2-S(O)Me-3-Py], [3145:6-Me-2-S(O)Me-3-Py], [3146:4-CF3-2-S(O)Me-3-Py], [3147:5-CF3-2-S(O)Me-3-Py], [3148:6-CF3-2-S(O)Me-3-Py], [3149:4-CN-2-S(O)Me-3-Py], [3150:5-CN-2-S(O)Me-3-Py], [3151:6-CN-2-S(O)Me-3-Py], [3152:4-OMe-2-S(O)Me-3-Py], [3153:5-OMe-2-S(O)Me-3-Py], [3154:6-OMe-2-S(O)Me-3-Py], [3155:4-S(O)Me-3-Py], [3156:2-Cl-4-S(O)Me-3-Py], [3157:5-Cl-4-S(O)Me-3-Py], [3158:6-Cl-4-S(O)Me-3-Py], [3159:2-Me-4-S(O)Me-3-Py], [3160:5-Me-4-S(O)Me-3-Py], [3161:6-Me-4-S(O)Me-3-Py], [3162:2-CF3-4-S(O)Me-3-Py], [3163:5-CF3-4-S(O)Me-3-Py], [3164:6-CF3-4-S(O)Me-3-Py], [3165:2-CN-4-S(O)Me-3-Py], [3166:5-CN-4-S(O)Me-3-Py], [3167:6-CN-4-S(O)Me-3-Py], [3168:2-OMe-4-S(O)Me-3-Py], [3169:5-OMe-4-S(O)Me-3-Py], [3170:6-OMe-4-S(O)Me-3-Py], [3171:5-S(O)Me-3-Py], [3172:2-Cl-5-S(O)Me-3-Py], [3173:4-Cl-5-S(O)Me-3-Py], [3174:6-Cl-5-S(O)Me-3-Py], [3175:2-Me-5-S(O)Me-3-Py], [3176:4-Me-5-S(O)Me-3-Py], [3177:6-Me-5-S(O)Me-3-Py], [3178:2-CF3-5-S(O)Me-3-Py], [3179:4-CF3-5-S(O)Me-3-Py], [3180:6-CF3-5-S(O)Me-3-Py], [3181:2-CN-5-S(O)Me-3-Py], [3182:4-CN-5-S(O)Me-3-Py], [3183:6-CN-5-S(O)Me-3-Py], [3184:2-OMe-5-S(O)Me-3-Py], [3185:4-OMe-5-S(O)Me-3-Py], [3186:6-OMe-5-S(O)Me-3-Py], [3187:6-S(O)Me-3-Py], [3188:2-Cl-6-S(O)Me-3-Py], [3189:4-Cl-6-S(O)Me-3-Py], [3190:5-Cl-6-S(O)Me-3-Py], [3191:2-Me-6-S(O)Me-3-Py], [3192:4-Me-6-S(O)Me-3-Py], [3193:5-Me-6-S(O)Me-3-Py], [3194:2-CF3-6-S(O)Me-3-Py], [3195:4-CF3-6-S(O)Me-3-Py], [3196:5-CF3-6-S(O)Me-3-Py], [3197:2-CN-6-S(O)Me-3-Py], [3198:4-CN-6-S(O)Me-3-Py], [3199:5-CN-6-S(O)Me-3-Py], [3200:2-OMe-6-S(O)Me-3-Py], [3201:4-OMe-6-S(O)Me-3-Py], [3202:5-OMe-6-S(O)Me-3-Py], [3203:2-S(O)CF3-3-Py], [3204:4-Cl-2-S(O)CF3-3-Py], [3205:5-Cl-2-S(O)CF3-3-Py], [3206:6-Cl-2-S(O)CF3-3-Py], [3207:4-Me-2-S(O)CF3-3-Py], [3208:5-Me-2-S(O)CF3-3-Py], [3209:6-Me-2-S(O)CF3-3-Py], [3210:4-CF3-2-S(O)CF3-3-Py], [3211:5-CF3-2-S(O)CF3-3-Py], [3212:6-CF3-2-S(O)CF3-3-Py], [3213:4-CN-2-S(O)CF3-3-Py], [3214:5-CN-2-S(O)CF3-3-Py], [3215:6-CN-2-S(O)CF3-3-Py], [3216:4-OMe-2-S(O)CF3-3-Py], [3217:5-OMe-2-S(O)CF3-3-Py], [3218:6-OMe-2-S(O)CF3-3-Py], [3219:4-S(O)CF3-3-Py], [3220:2-Cl-4-S(O)CF3-3-Py], [3221:5-Cl-4-S(O)CF3-3-Py], [3222:6-Cl-4-S(O)CF3-3-Py], [3223:2-Me-4-S(O)CF3-3-Py], [3224:5-Me-4-S(O)CF3-3-Py], [3225:6-Me-4-S(O)CF3-3-Py], [3226:2-CF3-4-S(O)CF3-3-Py], [3227:5-CF3-4-S(O)CF3-3-Py], [3228:6-CF3-4-S(O)CF3-3-Py], [3229:2-CN-4-S(O)CF3-3-Py], [3230:5-CN-4-S(O)CF3-3-Py], [3231:6-CN-4-S(O)CF3-3-Py], [3232:2-OMe-4-S(O)CF3-3-Py], [3233:5-OMe-4-S(O)CF3-3-Py], [3234:6-OMe-4-S(O)CF3-3-Py], [3235:5-S(O)CF3-3-Py], [3236:2-Cl-5-5(O)CF3-3-Py], [3237:4-Cl-5-S(O)CF3-3-Py], [3238:6-Cl-5-S(O)CF3-3-Py], [3239:2-Me-5-S(O)CF3-3-Py], [3240:4-Me-5-S(O)CF3-3-Py], [3241:6-Me-5-S(O)CF3-3-Py], [3242:2-CF3-5-S(O)CF3-3-Py], [3243:4-CF3-5-S(O)CF3-3-Py], [3244:6-CF3-5-S(O)CF3-3-Py], [3245:2-CN-5-S(O)CF3-3-Py], [3246:4-CN-5-S(O)CF3-3-Py], [3247:6-CN-5-S(O)CF3-3-Py], [3248:2-OMe-5-S(O)CF3-3-Py], [3249:4-OMe-5-S(O)CF3-3-Py], [3250:6-OMe-5-S(O)CF3-3-Py], [3251:6-S(O)CF3-3-Py], [3252:2-Cl-6-S(O)CF3-3-Py], [3253:4-Cl-6-S(O)CF3-3-Py], [3254:5-Cl-6-S(O)CF3-3-Py], [3255:2-Me-6-S(O)CF3-3-Py], [3256:4-Me-6-S(O)CF3-3-Py], [3257:5-Me-6-S(O)CF3-3-Py], [3258:2-CF3-6-S(O)CF3-3-Py], [3259:4-CF3-6-S(O)CF3-3-Py], [3260:5-CF3-6-S(O)CF3-3-Py], [3261:2-CN-6-S(O)CF3-3-Py], [3262:4-CN-6-S(O)CF3-3-Py], [3263:5-CN-6-S(O)CF3-3-Py], [3264:2-OMe-6-S(O)CF3-3-Py], [3265:4-OMe-6-S(O)CF3-3-Py], [3266:5-OMe-6-S(O)CF3-3-Py], [3267:2-S(O)2Me-3-Py], [3268:4-Cl-2-S(O)2Me-3-Py], [3269:5-Cl-2-S(O)2Me-3-Py], [3270:6-Cl-2-S(O)2Me-3-Py], [3271:4-Me-2-S(O)2Me-3-Py], [3272:5-Me-2-S(O)2Me-3-Py], [3273:6-Me-2-S(O)2Me-3-Py], [3274:4-CF3-2-S(O)2Me-3-Py], [3275:5-CF3-2-S(O)2Me-3-Py], [3276:6-CF3-2-S(O)2Me-3-Py], [3277:4-CN-2-S(O)2Me-3-Py], [3278:5-CN-2-S(O)2Me-3-Py], [3279:6-CN-2-S(O)2Me-3-Py], [3280:4-OMe-2-S(O)2Me-3-Py], [3281:5-OMe-2-S(O)2Me-3-Py], [3282:6-OMe-2-S(O)2Me-3-Py], [3283:4-S(O)2Me-3-Py], [3284:2-Cl-4-S(O)2Me-3-Py], [3285:5-Cl-4-S(O)2Me-3-Py], [3286:6-Cl-4-S(O)2Me-3-Py], [3287:2-Me-4-S(O)2Me-3-Py], [3288:5-Me-4-S(O)2Me-3-Py], [3289:6-Me-4-S(O)2Me-3-Py], [3290:2-CF3-4-S(O)2Me-3-Py], [3291:5-CF3-4-S(O)2Me-3-Py], [3292:6-CF3-4-S(O)2Me-3-Py], [3293:2-CN-4-S(O)2Me-3-Py], [3294:5-CN-4-S(O)2Me-3-Py], [3295:6-CN-4-S(O)2Me-3-Py], [3296:2-OMe-4-S(O)2Me-3-Py], [3297:5-OMe-4-S(O)2Me-3-Py], [3298:6-OMe-4-S(O)2Me-3-Py], [3299:5-S(O)2Me-3-Py], [3300:2-Cl-5-S(O)2Me-3-Py], [3301:4-Cl-5-S(O)2Me-3-Py], [3302:6-Cl-5-S(O)2Me-3-Py], [3303:2-Me-5-S(O)2Me-3-Py], [3304:4-Me-5-S(O)2Me-3-Py], [3305:6-Me-5-S(O)2Me-3-Py], [3306:2-CF3-5-S(O)2Me-3-Py], [3307:4-CF3-5-S(O)2Me-3-Py], [3308:6-CF3-5-S(O)2Me-3-Py], [3309:2-CN-5-S(O)2Me-3-Py], [3310:4-CN-5-S(O)2Me-3-Py], [3311:6-CN-5-S(O)2Me-3-Py], [3312:2-OMe-5-S(O)2Me-3-Py], [3313:4-OMe-5-S(O)2Me-3-Py], [3314:6-OMe-5-S(O)2Me-3-Py], [3315:6-S(O)2Me-3-Py], [3316:2-Cl-6-S(O)2Me-3-Py], [3317:4-Cl-6-S(O)2Me-3-Py], [3318:5-Cl-6-S(O)2Me-3-Py], [3319:2-Me-6-S(O)2Me-3-Py], [3320:4-Me-6-S(O)2Me-3-Py], [3321:5-Me-6-S(O)2Me-3-Py], [3322:2-CF3-6-S(O)2Me-3-Py], [3323:4-CF3-6-S(O)2Me-3-Py], [3324:5-CF3-6-S(O)2Me-3-Py], [3325:2-CN-6-S(O)2Me-3-Py], [3326:4-CN-6-S(O)2Me-3-Py], [3327:5-CN-6-S(O)2Me-3-Py], [3328:2-OMe-6-S(O)2Me-3-Py], [3329:4-OMe-6-S(O)2Me-3-Py], [3330:5-OMe-6-S(O)2Me-3-Py], [3331:2-S(O)2CF3-3-Py], [3332:4-Cl-2-S(O)2CF3-3-Py], [3333:5-Cl-2-S(O)2CF3-3-Py], [3334:6-Cl-2-S(O)2CF3-3-Py], [3335:4-Me-2-S(O)2CF3-3-Py], [3336:5-Me-2-S(O)2CF3-3-Py], [3337:6-Me-2-S(O)2CF3-3-Py], [3338:4-CF3-2-S(O)2CF3-3-Py],

[3339:5-CF3-2-S(O)2CF3-3-Py], [3340:6-CF3-2-S(O)2CF3-3-Py], [3341:4-CN-2-S(O)2CF3-3-Py], [3342:5-CN-2-S(O)2CF3-3-Py], [3343:6-CN-2-S(O)2CF3-3-Py], [3344:4-OMe-2-S(O)2CF3-3-Py], [3345:5-OMe-2-S(O)2CF3-3-Py], [3346:6-OMe-2-S(O)2CF3-3-Py], [3347:4-S(O)2CF3-3-Py], [3348:2-Cl-4-S(O)2CF3-3-Py], [3349:5-Cl-4-S(O)2CF3-3-Py], [3350:6-Cl-4-S(O)2CF3-3-Py], [3351:2-Me-4-S(O)2CF3-3-Py], [3352:5-Me-4-S(O)2CF3-3-Py], [3353:6-Me-4-S(O)2CF3-3-Py], [3354:2-CF3-4-S(O)2CF3-3-Py], [3355:5-CF3-4-S(O)2CF3-3-Py], [3356:6-CF3-4-S(O)2CF3-3-Py], [3357:2-CN-4-S(O)2CF3-3-Py], [3358:5-CN-4-S(O)2CF3-3-Py], [3359:6-CN-4-S(O)2CF3-3-Py], [3360:2-OMe-4-S(O)2CF3-3-Py], [3361:5-OMe-4-S(O)2CF3-3-Py], [3362:6-OMe-4-S(O)2CF3-3-Py], [3363:5-S(O)2CF3-3-Py], [3364:2-Cl-5-S(O)2CF3-3-Py], [3365:4-Cl-5-S(O)2CF3-3-Py], [3366:6-Cl-5-S(O)2CF3-3-Py], [3367:2-Me-5-S(O)2CF3-3-Py], [3368:4-Me-5-S(O)2CF3-3-Py], [3369:6-Me-5-S(O)2CF3-3-Py], [3370:2-CF3-5-S(O)2CF3-3-Py], [3371:4-CF3-5-S(O)2CF3-3-Py], [3372:6-CF3-5-S(O)2CF3-3-Py], [3373:2-CN-5-S(O)2CF3-3-Py], [3374:4-CN-5-S(O)2CF3-3-Py], [3375:6-CN-5-S(O)2CF3-3-Py], [3376:2-OMe-5-S(O)2CF3-3-Py], [3377:4-OMe-5-S(O)2CF3-3-Py], [3378:6-OMe-5-S(O)2CF3-3-Py], [3379:6-S(O)2CF3-3-Py], [3380:2-Cl-6-S(O)2CF3-3-Py], [3381:4-Cl-6-S(O)2CF3-3-Py], [3382:5-Cl-6-S(O)2CF3-3-Py], [3383:2-Me-6-S(O)2CF3-3-Py], [3384:4-Me-6-S(O)2CF3-3-Py], [3385:5-Me-6-S(O)2CF3-3-Py], [3386:2-CF3-6-S(O)2CF3-3-Py], [3387:4-CF3-6-S(O)2CF3-3-Py], [3388:5-CF3-6-S(O)2CF3-3-Py], [3389:2-CN-6-S(O)2CF3-3-Py], [3390:4-CN-6-S(O)2CF3-3-Py], [3391:5-CN-6-S(O)2CF3-3-Py], [3392:2-OMe-6-S(O)2CF3-3-Py], [3393:4-OMe-6-S(O)2CF3-3-Py], [3394:5-OMe-6-S(O)2CF3-3-Py][3395:2-CN-3-Py], [3396:4-Cl-2-CN-3-Py], [3397:5-Cl-2-CN-3-Py], [3398:6-Cl-2-CN-3-Py], [3399:4-Me-2-CN-3-Py], [3400:5-Me-2-CN-3-Py],
[3401:6-Me-2-CN-3-Py], [3402:4-CF3-2-CN-3-Py], [3403:5-CF3-2-CN-3-Py], [3404:6-CF3-2-CN-3-Py], [3405:4-CN-2-CN-3-Py], [3406:5-CN-2-CN-3-Py], [3407:6-CN-2-CN-3-Py], [3408:4-OMe-2-CN-3-Py], [3409:5-OMe-2-CN-3-Py], [3410:6-OMe-2-CN-3-Py], [3411:4-CN-3-Py], [3412:2-Cl-4-CN-3-Py], [3413:5-Cl-4-CN-3-Py], [3414:6-Cl-4-CN-3-Py], [3415:2-Me-4-CN-3-Py], [3416:5-Me-4-CN-3-Py], [3417:6-Me-4-CN-3-Py], [3418:2-CF3-4-CN-3-Py], [3419:5-CF3-4-CN-3-Py], [3420:6-CF3-4-CN-3-Py], [3421:2-CN-4-CN-3-Py], [3422:5-CN-4-CN-3-Py], [3423:6-CN-4-CN-3-Py], [3424:2-OMe-4-CN-3-Py], [3425:5-OMe-4-CN-3-Py], [3426:6-OMe-4-CN-3-Py], [3427:5-CN-3-Py], [3428:2-Cl-5-CN-3-Py], [3429:4-Cl-5-CN-3-Py], [3430:6-Cl-5-CN-3-Py], [3431:2-Me-5-CN-3-Py], [3432:4-Me-5-CN-3-Py], [3433:6-Me-5-CN-3-Py], [3434:2-CF3-5-CN-3-Py], [3435:4-CF3-5-CN-3-Py], [3436:6-CF3-5-CN-3-Py], [3437:2-CN-5-CN-3-Py], [3438:4-CN-5-CN-3-Py], [3439:6-CN-5-CN-3-Py], [3440:2-OMe-5-CN-3-Py], [3441:4-OMe-5-CN-3-Py], [3442:6-OMe-5-CN-3-Py], [3443:6-CN-3-Py], [3444:2-Cl-6-CN-3-Py], [3445:4-Cl-6-CN-3-Py], [3446:5-Cl-6-CN-3-Py], [3447:2-Me-6-CN-3-Py], [3448:4-Me-6-CN-3-Py], [3449:5-Me-6-CN-3-Py], [3450:2-CF3-6-CN-3-Py], [3451:4-CF3-6-CN-3-Py], [3452:5-CF3-6-CN-3-Py], [3453:2-CN-6-CN-3-Py], [3454:4-CN-6-CN-3-Py], [3455:5-CN-6-CN-3-Py], [3456:2-OMe-6-CN-3-Py], [3457:4-OMe-6-CN-3-Py], [3458:5-OMe-6-CN-3-Py], [3459:2-COOMe-3-Py], [3460:4-Cl-2-COOMe-3-Py], [3461:5-Cl-2-COOMe-3-Py], [3462:6-Cl-2-COOMe-3-Py], [3463:4-Me-2-COOMe-3-Py], [3464:5-Me-2-COOMe-3-Py], [3465:6-Me-2-COOMe-3-Py], [3466:4-CF3-2-COOMe-3-Py], [3467:5-CF3-2-COOMe-3-Py], [3468:6-CF3-2-COOMe-3-Py], [3469:4-CN-2-COOMe-3-Py], [3470:5-CN-2-COOMe-3-Py], [3471:6-CN-2-COOMe-3-Py], [3472:4-OMe-2-COOMe-3-Py], [3473:5-OMe-2-COOMe-3-Py], [3474:6-OMe-2-COOMe-3-Py], [3475:4-COOMe-3-Py], [3476:2-Cl-4-COOMe-3-Py], [3477:5-Cl-4-COOMe-3-Py], [3478:6-Cl-4-COOMe-3-Py], [3479:2-Me-4-COOMe-3-Py], [3480:5-Me-4-COOMe-3-Py], [3481:6-Me-4-COOMe-3-Py], [3482:2-CF3-4-COOMe-3-Py], [3483:5-CF3-4-COOMe-3-Py], [3484:6-CF3-4-COOMe-3-Py], [3485:2-CN-4-COOMe-3-Py], [3486:5-CN-4-COOMe-3-Py], [3487:6-CN-4-COOMe-3-Py], [3488:2-OMe-4-COOMe-3-Py], [3489:5-OMe-4-COOMe-3-Py], [3490:6-OMe-4-COOMe-3-Py], [3491:5-COOMe-3-Py], [3492:2-Cl-5-COOMe-3-Py], [3493:4-Cl-5-COOMe-3-Py], [3494:6-Cl-5-COOMe-3-Py], [3495:2-Me-5-COOMe-3-Py], [3496:4-Me-5-COOMe-3-Py], [3497:6-Me-5-COOMe-3-Py], [3498:2-CF3-5-COOMe-3-Py], [3499:4-CF3-5-COOMe-3-Py], [3500:6-CF3-5-COOMe-3-Py],
[3501:2-CN-5-COOMe-3-Py], [3502:4-CN-5-COOMe-3-Py], [3503:6-CN-5-COOMe-3-Py], [3504:2-OMe-5-COOMe-3-Py], [3505:4-OMe-5-COOMe-3-Py], [3506:6-OMe-5-COOMe-3-Py], [3507:6-COOMe-3-Py], [3508:2-Cl-6-COOMe-3-Py], [3509:4-Cl-6-COOMe-3-Py], [3510:5-Cl-6-COOMe-3-Py], [3511:2-Me-6-COOMe-3-Py], [3512:4-Me-6-COOMe-3-Py], [3513:5-Me-6-COOMe-3-Py], [3514:2-CF3-6-COOMe-3-Py], [3515:4-CF3-6-COOMe-3-Py], [3516:5-CF3-6-COOMe-3-Py], [3517:2-CN-6-COOMe-3-Py], [3518:4-CN-6-COOMe-3-Py], [3519:5-CN-6-COOMe-3-Py], [3520:2-OMe-6-COOMe-3-Py], [3521:4-OMe-6-COOMe-3-Py], [3522:5-OMe-6-COOMe-3-Py], [3523:2-NO2-3-Py], [3524:4-Cl-2-NO2-3-Py], [3525:5-Cl-2-NO2-3-Py], [3526:6-Cl-2-NO2-3-Py], [3527:4-Me-2-NO2-3-Py], [3528:5-Me-2-NO2-3-Py], [3529:6-Me-2-NO2-3-Py], [3530:4-CF3-2-NO2-3-Py], [3531:5-CF3-2-NO2-3-Py], [3532:6-CF3-2-NO2-3-Py], [3533:4-CN-2-NO2-3-Py], [3534:5-CN-2-NO2-3-Py], [3535:6-CN-2-NO2-3-Py], [3536:4-OMe-2-NO2-3-Py], [3537:5-OMe-2-NO2-3-Py], [3538:6-OMe-2-NO2-3-Py], [3539:4-NO2-3-Py], [3540:2-Cl-4-NO2-3-Py], [3541:5-Cl-4-NO2-3-Py], [3542:6-Cl-4-NO2-3-Py], [3543:2-Me-4-NO2-3-Py], [3544:5-Me-4-NO2-3-Py], [3545:6-Me-4-NO2-3-Py], [3546:2-CF3-4-NO2-3-Py], [3547:5-CF3-4-NO2-3-Py], [3548:6-CF3-4-NO2-3-Py], [3549:2-CN-4-NO2-3-Py], [3550:5-CN-4-NO2-3-Py], [3551:6-CN-4-NO2-3-Py], [3552:2-OMe-4-NO2-3-Py], [3553:5-OMe-4-NO2-3-Py], [3554:6-OMe-4-NO2-3-Py], [3555:5-NO2-3-Py], [3556:2-Cl-5-NO2-3-Py], [3557:4-Cl-5-NO2-3-Py], [3558:6-Cl-5-NO2-3-Py], [3559:2-Me-5-NO2-3-Py], [3560:4-Me-5-NO2-3-Py], [3561:6-Me-5-NO2-3-Py], [3562:2-CF3-5-NO2-3-Py], [3563:4-CF3-5-NO2-3-Py], [3564:6-CF3-5-NO2-3-Py], [3565:2-CN-5-NO2-3-Py], [3566:4-CN-5-NO2-3-Py], [3567:6-CN-5-NO2-3-Py], [3568:2-OMe-5-NO2-3-Py], [3569:4-OMe-5-NO2-3-Py], [3570:6-OMe-5-NO2-3-Py], [3571:6-NO2-3-Py], [3572:2-Cl-6-NO2-3-Py], [3573:4-Cl-6-NO2-3-Py], [3574:5-Cl-6-NO2-3-Py], [3575:2-Me-6-NO2-3-Py], [3576:4-Me-6-NO2-3-Py], [3577:5-Me-6-NO2-3-Py], [3578:2-CF3-6-NO2-3-Py], [3579:4-CF3-6-NO2-3-Py], [3580:5-CF3-6-NO2-3-Py], [3581:2-CN-6-NO2-3-Py], [3582:4-CN-6-NO2-3-Py], [3583:5-CN-6-NO2-3-Py], [3584:2-OMe-6-NO2-3-Py], [3585:4-OMe-6-NO2-3-Py], [3586:5-OMe-6-NO2-3-Py], [3587:2-NH2-3-Py], [3588:4-Cl-2-NH2-3-Py], [3589:5-Cl-2-NH2-3-Py], [3590:6-Cl-2-NH2-3-Py], [3591:4-Me-2-NH2-3-Py], [3592:5-Me-2-NH2-3-Py], [3593:6-Me-2-NH2-3-Py], [3594:4-CF3-2-NH2-3-Py], [3595:5-CF3-2-NH2-3-Py], [3596:6-

CF3-2-NH2-3-Py], [3597:4-CN-2-NH2-3-Py], [3598:5-CN-2-NH2-3-Py], [3599:6-CN-2-NH2-3-Py], [3600:4-OMe-2-NH2-3-Py],
[3601:5-OMe-2-NH2-3-Py], [3602:6-OMe-2-NH2-3-Py], [3603:4-NH2-3-Py], [3604:2-Cl-4-NH2-3-Py], [3605:5-Cl-4-NH2-3-Py], [3606:6-Cl-4-NH2-3-Py], [3607:2-Me-4-NH2-3-Py], [3608:5-Me-4-NH2-3-Py], [3609:6-Me-4-NH2-3-Py], [3610:2-CF3-4-NH2-3-Py], [3611:5-CF3-4-NH2-3-Py], [3612:6-CF3-4-NH2-3-Py], [3613:2-CN-4-NH2-3-Py], [3614:5-CN-4-NH2-3-Py], [3615:6-CN-4-NH2-3-Py], [3616:2-OMe-4-NH2-3-Py], [3617:5-OMe-4-NH2-3-Py], [3618:6-OMe-4-NH2-3-Py], [3619:5-NH2-3-Py], [3620:2-Cl-5-NH2-3-Py], [3621:4-Cl-5-NH2-3-Py], [3622:6-Cl-5-NH2-3-Py], [3623:2-Me-5-NH2-3-Py], [3624:4-Me-5-NH2-3-Py], [3625:6-Me-5-NH2-3-Py], [3626:2-CF3-5-NH2-3-Py], [3627:4-CF3-5-NH2-3-Py], [3628:6-CF3-5-NH2-3-Py], [3629:2-CN-5-NH2-3-Py], [3630:4-CN-5-NH2-3-Py], [3631:6-CN-5-NH2-3-Py], [3632:2-OMe-5-NH2-3-Py], [3633:4-OMe-5-NH2-3-Py], [3634:6-OMe-5-NH2-3-Py], [3635:6-NH2-3-Py], [3636:2-Cl-6-NH2-3-Py], [3637:4-Cl-6-NH2-3-Py], [3638:5-Cl-6-NH2-3-Py], [3639:2-Me-6-NH2-3-Py], [3640:4-Me-6-NH2-3-Py], [3641:5-Me-6-NH2-3-Py], [3642:2-CF3-6-NH2-3-Py], [3643:4-CF3-6-NH2-3-Py], [3644:5-CF3-6-NH2-3-Py], [3645:2-CN-6-NH2-3-Py], [3646:4-CN-6-NH2-3-Py], [3647:5-CN-6-NH2-3-Py], [3648:2-OMe-6-NH2-3-Py], [3649:4-OMe-6-NH2-3-Py], [3650:5-OMe-6-NH2-3-Py], [3651:2-NHMe-3-Py], [3652:4-Cl-2-NHMe-3-Py], [3653:5-Cl-2-NHMe-3-Py], [3654:6-Cl-2-NHMe-3-Py], [3655:4-Me-2-NHMe-3-Py], [3656:5-Me-2-NHMe-3-Py], [3657:6-Me-2-NHMe-3-Py], [3658:4-CF3-2-NHMe-3-Py], [3659:5-CF3-2-NHMe-3-Py], [3660:6-CF3-2-NHMe-3-Py], [3661:4-CN-2-NHMe-3-Py], [3662:5-CN-2-NHMe-3-Py], [3663:6-CN-2-NHMe-3-Py], [3664:4-OMe-2-NHMe-3-Py], [3665:5-OMe-2-NHMe-3-Py], [3666:6-OMe-2-NHMe-3-Py], [3667:4-NHMe-3-Py], [3668:2-Cl-4-NHMe-3-Py], [3669:5-Cl-4-NHMe-3-Py], [3670:6-Cl-4-NHMe-3-Py], [3671:2-Me-4-NHMe-3-Py], [3672:5-Me-4-NHMe-3-Py], [3673:6-Me-4-NHMe-3-Py], [3674:2-CF3-4-NHMe-3-Py], [3675:5-CF3-4-NHMe-3-Py], [3676:6-CF3-4-NHMe-3-Py], [3677:2-CN-4-NHMe-3-Py], [3678:5-CN-4-NHMe-3-Py], [3679:6-CN-4-NHMe-3-Py], [3680:2-OMe-4-NHMe-3-Py], [3681:5-OMe-4-NHMe-3-Py], [3682:6-OMe-4-NHMe-3-Py], [3683:5-NHMe-3-Py], [3684:2-Cl-5-NHMe-3-Py], [3685:4-Cl-5-NHMe-3-Py], [3686:6-Cl-5-NHMe-3-Py], [3687:2-Me-5-NHMe-3-Py], [3688:4-Me-5-NHMe-3-Py], [3689:6-Me-5-NHMe-3-Py], [3690:2-CF3-5-NHMe-3-Py], [3691:4-CF3-5-NHMe-3-Py], [3692:6-CF3-5-NHMe-3-Py], [3693:2-CN-5-NHMe-3-Py], [3694:4-CN-5-NHMe-3-Py], [3695:6-CN-5-NHMe-3-Py], [3696:2-OMe-5-NHMe-3-Py], [3697:4-OMe-5-NHMe-3-Py], [3698:6-OMe-5-NHMe-3-Py], [3699:6-NHMe-3-Py], [3700:2-Cl-6-NHMe-3-Py], [3701:4-Cl-6-NHMe-3-Py], [3702:5-Cl-6-NHMe-3-Py], [3703:2-Me-6-NHMe-3-Py], [3704:4-Me-6-NHMe-3-Py], [3705:5-Me-6-NHMe-3-Py], [3706:2-CF3-6-NHMe-3-Py], [3707:4-CF3-6-NHMe-3-Py], [3708:5-CF3-6-NHMe-3-Py], [3709:2-CN-6-NHMe-3-Py], [3710:4-CN-6-NHMe-3-Py], [3711:5-CN-6-NHMe-3-Py], [3712:2-OMe-6-NHMe-3-Py], [3713:4-OMe-6-NHMe-3-Py], [3714:5-OMe-6-NHMe-3-Py], [3715:2-NMe2-3-Py], [3716:4-Cl-2-NMe2-3-Py], [3717:5-Cl-2-NMe2-3-Py], [3718:6-Cl-2-NMe2-3-Py], [3719:4-Me-2-NMe2-3-Py], [3720:5-Me-2-NMe2-3-Py], [3721:6-Me-2-NMe2-3-Py], [3722:4-CF3-2-NMe2-3-Py], [3723:5-CF3-2-NMe2-3-Py], [3724:6-CF3-2-NMe2-3-Py], [3725:4-CN-2-NMe2-3-Py], [3726:5-CN-2-NMe2-3-Py], [3727:6-CN-2-NMe2-3-Py], [3728:4-OMe-2-NMe2-3-Py], [3729:5-OMe-2-NMe2-3-Py], [3730:6-OMe-2-NMe2-3-Py], [3731:4-NMe2-3-Py], [3732:2-Cl-4-NMe2-3-Py], [3733:5-Cl-4-NMe2-3-Py], [3734:6-Cl-4-NMe2-3-Py], [3735:2-Me-4-NMe2-3-Py], [3736:5-Me-4-NMe2-3-Py], [3737:6-Me-4-NMe2-3-Py], [3738:2-CF3-4-NMe2-3-Py], [3739:5-CF3-4-NMe2-3-Py], [3740:6-CF3-4-NMe2-3-Py], [3741:2-CN-4-NMe2-3-Py], [3742:5-CN-4-NMe2-3-Py], [3743:6-CN-4-NMe2-3-Py], [3744:2-OMe-4-NMe2-3-Py], [3745:5-OMe-4-NMe2-3-Py], [3746:6-OMe-4-NMe2-3-Py], [3747:5-NMe2-3-Py], [3748:2-Cl-5-NMe2-3-Py], [3749:4-Cl-5-NMe2-3-Py], [3750:6-Cl-5-NMe2-3-Py], [3751:2-Me-5-NMe2-3-Py], [3752:4-Me-5-NMe2-3-Py], [3753:6-Me-5-NMe2-3-Py], [3754:2-CF3-5-NMe2-3-Py], [3755:4-CF3-5-NMe2-3-Py], [3756:6-CF3-5-NMe2-3-Py], [3757:2-CN-5-NMe2-3-Py], [3758:4-CN-5-NMe2-3-Py], [3759:6-CN-5-NMe2-3-Py], [3760:2-OMe-5-NMe2-3-Py], [3761:4-OMe-5-NMe2-3-Py], [3762:6-OMe-5-NMe2-3-Py], [3763:6-NMe2-3-Py], [3764:2-Cl-6-NMe2-3-Py], [3765:4-Cl-6-NMe2-3-Py], [3766:5-Cl-6-NMe2-3-Py], [3767:2-Me-6-NMe2-3-Py], [3768:4-Me-6-NMe2-3-Py], [3769:5-Me-6-NMe2-3-Py], [3770:2-CF3-6-NMe2-3-Py], [3771:4-CF3-6-NMe2-3-Py], [3772:5-CF3-6-NMe2-3-Py], [3773:2-CN-6-NMe2-3-Py], [3774:4-CN-6-NMe2-3-Py], [3775:5-CN-6-NMe2-3-Py], [3776:2-OMe-6-NMe2-3-Py], [3777:4-OMe-6-NMe2-3-Py], [3778:5-OMe-6-NMe2-3-Py], [3779:2-ACNH-3-Py], [3780:4-Cl-2-ACNH-3-Py], [3781:5-Cl-2-ACNH-3-Py], [3782:6-Cl-2-ACNH-3-Py], [3783:4-Me-2-ACNH-3-Py], [3784:5-Me-2-ACNH-3-Py], [3785:6-Me-2-ACNH-3-Py], [3786:4-CF3-2-ACNH-3-Py], [3787:5-CF3-2-ACNH-3-Py], [3788:6-CF3-2-ACNH-3-Py], [3789:4-CN-2-ACNH-3-Py], [3790:5-CN-2-ACNH-3-Py], [3791:6-CN-2-ACNH-3-Py], [3792:4-OMe-2-ACNH-3-Py], [3793:5-OMe-2-ACNH-3-Py], [3794:6-OMe-2-ACNH-3-Py], [3795:4-ACNH-3-Py], [3796:2-Cl-4-ACNH-3-Py], [3797:5-Cl-4-ACNH-3-Py], [3798:6-Cl-4-ACNH-3-Py], [3799:2-Me-4-ACNH-3-Py], [3800:5-Me-4-ACNH-3-Py],
[3801:6-Me-4-ACNH-3-Py], [3802:2-CF3-4-ACNH-3-Py], [3803:5-CF3-4-ACNH-3-Py], [3804:6-CF3-4-ACNH-3-Py], [3805:2-CN-4-ACNH-3-Py], [3806:5-CN-4-ACNH-3-Py], [3807:6-CN-4-ACNH-3-Py], [3808:2-OMe-4-ACNH-3-Py], [3809:5-OMe-4-ACNH-3-Py], [3810:6-OMe-4-ACNH-3-Py], [3811:5-ACNH-3-Py], [3812:2-Cl-5-ACNH-3-Py], [3813:4-Cl-5-ACNH-3-Py], [3814:6-Cl-5-ACNH-3-Py], [3815:2-Me-5-ACNH-3-Py], [3816:4-Me-5-ACNH-3-Py], [3817:6-Me-5-ACNH-3-Py], [3818:2-CF3-5-ACNH-3-Py], [3819:4-CF3-5-ACNH-3-Py], [3820:6-CF3-5-ACNH-3-Py], [3821:2-CN-5-ACNH-3-Py], [3822:4-CN-5-ACNH-3-Py], [3823:6-CN-5-ACNH-3-Py], [3824:2-OMe-5-ACNH-3-Py], [3825:4-OMe-5-ACNH-3-Py], [3826:6-OMe-5-ACNH-3-Py], [3827:6-ACNH-3-Py], [3828:2-Cl-6-ACNH-3-Py], [3829:4-Cl-6-ACNH-3-Py], [3830:5-Cl-6-ACNH-3-Py], [3831:2-Me-6-ACNH-3-Py], [3832:4-Me-6-ACNH-3-Py], [3833:5-Me-6-ACNH-3-Py], [3834:2-CF3-6-ACNH-3-Py], [3835:4-CF3-6-ACNH-3-Py], [3836:5-CF3-6-ACNH-3-Py], [3837:2-CN-6-ACNH-3-Py], [3838:4-CN-6-ACNH-3-Py], [3839:5-CN-6-ACNH-3-Py], [3840:2-OMe-6-ACNH-3-Py], [3841:4-OMe-6-ACNH-3-Py], [3842:5-OMe-6-ACNH-3-Py], [3843:2-(N-AC-N-Me-N)-3-Py], [3844:4-Cl-2-(N-AC-N-Me-N)-3-Py], [3845:5-Cl-2-(N-AC-N-Me-N)-3-Py], [3846:6-Cl-2-(N-AC-N-Me-N)-3-Py], [3847:4-Me-2-(N-AC-N-Me-N)-3-Py], [3848:5-Me-2-(N-AC-N-Me-N)-3-Py], [3849:6-Me-2-(N-AC-N-Me-N)-3-Py], [3850:4-CF3-2-(N-AC-N-Me-N)-3-Py], [3851:5-CF3-2-(N-AC-N-Me-N)-3-Py], [3852:6-CF3-2-(N-AC-N-Me-N)-3-Py], [3853:4-CN-2-(N-AC-N-Me-N)-3-Py], [3854:5-CN-2-(N-AC-N-Me-N)-3-Py], [3855:6-CN-2-(N-AC-N-Me-N)-3-Py], [3856:4-OMe-2-(N-AC-N-Me-N)-3-Py],

[3857:5-OMe-2-(N-AC-N-Me-N)-3-Py], [3858:6-OMe-2-(N-AC-N-Me-N)-3-Py], [3859:4-(N-AC-N-Me-N)-3-Py], [3860:2-Cl-4-(N-AC-N-Me-N)-3-Py], [3861:5-Cl-4-(N-AC-N-Me-N)-3-Py], [3862:6-Cl-4-(N-AC-N-Me-N)-3-Py], [3863:2-Me-4-(N-AC-N-Me-N)-3-Py], [3864:5-Me-4-(N-AC-N-Me-N)-3-Py], [3865:6-Me-4-(N-AC-N-Me-N)-3-Py], [3866:2-CF3-4-(N-AC-N-Me-N)-3-Py], [3867:5-CF3-4-(N-AC-N-Me-N)-3-Py], [3868:6-CF3-4-(N-AC-N-Me-N)-3-Py], [3869:2-CN-4-(N-AC-N-Me-N)-3-Py], [3870:5-CN-4-(N-AC-N-Me-N)-3-Py], [3871:6-CN-4-(N-AC-N-Me-N)-3-Py], [3872:2-OMe-4-(N-AC-N-Me-N)-3-Py], [3873:5-OMe-4-(N-AC-N-Me-N)-3-Py], [3874:6-OMe-4-(N-AC-N-Me-N)-3-Py], [3875:5-(N-AC-N-Me-N)-3-Py], [3876:2-Cl-5-(N-AC-N-Me-N)-3-Py], [3877:4-Cl-5-(N-AC-N-Me-N)-3-Py], [3878:6-Cl-5-(N-AC-N-Me-N)-3-Py], [3879:2-Me-5-(N-AC-N-Me-N)-3-Py], [3880:4-Me-5-(N-AC-N-Me-N)-3-Py], [3881:6-Me-5-(N-AC-N-Me-N)-3-Py], [3882:2-CF3-5-(N-AC-N-Me-N)-3-Py], [3883:4-CF3-5-(N-AC-N-Me-N)-3-Py], [3884:6-CF3-5-(N-AC-N-Me-N)-3-Py], [3885:2-CN-5-(N-AC-N-Me-N)-3-Py], [3886:4-CN-5-(N-AC-N-Me-N)-3-Py], [3887:6-CN-5-(N-AC-N-Me-N)-3-Py], [3888:2-OMe-5-(N-AC-N-Me-N)-3-Py], [3889:4-OMe-5-(N-AC-N-Me-N)-3-Py], [3890:6-OMe-5-(N-AC-N-Me-N)-3-Py], [3891:6-(N-AC-N-Me-N)-3-Py], [3892:2-Cl-6-(N-AC-N-Me-N)-3-Py], [3893:4-Cl-6-(N-AC-N-Me-N)-3-Py], [3894:5-Cl-6-(N-AC-N-Me-N)-3-Py], [3895:2-Me-6-(N-AC-N-Me-N)-3-Py], [3896:4-Me-6-(N-AC-N-Me-N)-3-Py], [3897:5-Me-6-(N-AC-N-Me-N)-3-Py], [3898:2-CF3-6-(N-AC-N-Me-N)-3-Py], [3899:4-CF3-6-(N-AC-N-Me-N)-3-Py], [3900:5-CF3-6-(N-AC-N-Me-N)-3-Py],

[3901:2-CN-6-(N-AC-N-Me-N)-3-Py], [3902:4-CN-6-(N-AC-N-Me-N)-3-Py], [3903:5-CN-6-(N-AC-N-Me-N)-3-Py], [3904:2-OMe-6-(N-AC-N-Me-N)-3-Py], [3905:4-OMe-6-(N-AC-N-Me-N)-3-Py], [3906:5-OMe-6-(N-AC-N-Me-N)-3-Py]

[3907:2-AC-3-Py], [3908:4-Cl-2-AC-3-Py], [3909:5-Cl-2-AC-3-Py], [3910:6-Cl-2-AC-3-Py], [3911:4-Me-2-AC-3-Py], [3912:5-Me-2-AC-3-Py], [3913:6-Me-2-AC-3-Py], [3914:4-CF3-2-AC-3-Py], [3915:5-CF3-2-AC-3-Py], [3916:6-CF3-2-AC-3-Py], [3917:4-CN-2-AC-3-Py], [3918:5-CN-2-AC-3-Py], [3919:6-CN-2-AC-3-Py], [3920:4-OMe-2-AC-3-Py], [3921:5-OMe-2-AC-3-Py], [3922:6-OMe-2-AC-3-Py], [3923:4-AC-3-Py], [3924:2-Cl-4-AC-3-Py], [3925:5-Cl-4-AC-3-Py], [3926:6-Cl-4-AC-3-Py], [3927:2-Me-4-AC-3-Py], [3928:5-Me-4-AC-3-Py], [3929:6-Me-4-AC-3-Py], [3930:2-CF3-4-AC-3-Py], [3931:5-CF3-4-AC-3-Py], [3932:6-CF3-4-AC-3-Py], [3933:2-CN-4-AC-3-Py], [3934:5-CN-4-AC-3-Py], [3935:6-CN-4-AC-3-Py], [3936:2-OMe-4-AC-3-Py], [3937:5-OMe-4-AC-3-Py], [3938:6-OMe-4-AC-3-Py], [3939:5-AC-3-Py], [3940:2-Cl-5-AC-3-Py], [3941:4-Cl-5-AC-3-Py], [3942:6-Cl-5-AC-3-Py], [3943:2-Me-5-AC-3-Py], [3944:4-Me-5-AC-3-Py], [3945:6-Me-5-AC-3-Py], [3946:2-CF3-5-AC-3-Py], [3947:4-CF3-5-AC-3-Py], [3948:6-CF3-5-AC-3-Py], [3949:2-CN-5-AC-3-Py], [3950:4-CN-5-AC-3-Py], [3951:6-CN-5-AC-3-Py], [3952:2-OMe-5-AC-3-Py], [3953:4-OMe-5-AC-3-Py], [3954:6-OMe-5-AC-3-Py], [3955:6-AC-3-Py], [3956:2-Cl-6-AC-3-Py], [3957:4-Cl-6-AC-3-Py], [3958:5-Cl-6-AC-3-Py], [3959:2-Me-6-AC-3-Py], [3960:4-Me-6-AC-3-Py], [3961:5-Me-6-AC-3-Py], [3962:2-CF3-6-AC-3-Py], [3963:4-CF3-6-AC-3-Py], [3964:5-CF3-6-AC-3-Py], [3965:2-CN-6-AC-3-Py], [3966:4-CN-6-AC-3-Py], [3967:5-CN-6-AC-3-Py], [3968:2-OMe-6-AC-3-Py], [3969:4-OMe-6-AC-3-Py], [3970:5-OMe-6-AC-3-Py], [3971:4-Py], [3972:3-F-4-Py], [3973:2-Cl-3-F-4-Py], [3974:5-Cl-3-F-4-Py], [3975:6-Cl-3-F-4-Py], [3976:2-Me-3-F-4-Py], [3977:5-Me-3-F-4-Py], [3978:6-Me-3-F-4-Py], [3979:2-CF3-3-F-4-Py], [3980:5-CF3-3-F-4-Py], [3981:6-CF3-3-F-4-Py], [3982:2-CN-3-F-4-Py], [3983:5-CN-3-F-4-Py], [3984:6-CN-3-F-4-Py], [3985:2-OMe-3-F-4-Py], [3986:5-OMe-3-F-4-Py], [3987:6-OMe-3-F-4-Py], [3988:2-F-4-Py], [3989:3-Cl-2-F-4-Py], [3990:5-Cl-2-F-4-Py], [3991:6-Cl-2-F-4-Py], [3992:3-Me-2-F-4-Py], [3993:5-Me-2-F-4-Py], [3994:6-Me-2-F-4-Py], [3995:3-CF3-2-F-4-Py], [3996:5-CF3-2-F-4-Py], [3997:6-CF3-2-F-4-Py], [3998:3-CN-2-F-4-Py], [3999:5-CN-2-F-4-Py], [4000:6-CN-2-F-4-Py],

[4001:3-OMe-2-F-4-Py], [4002:5-OMe-2-F-4-Py], [4003:6-OMe-2-F-4-Py], [4004:5-F-4-Py], [4005:3-Cl-5-F-4-Py], [4006:2-Cl-5-F-4-Py], [4007:6-Cl-5-F-4-Py], [4008:3-Me-5-F-4-Py], [4009:2-Me-5-F-4-Py], [4010:6-Me-5-F-4-Py], [4011:3-CF3-5-F-4-Py], [4012:2-CF3-5-F-4-Py], [4013:6-CF3-5-F-4-Py], [4014:3-CN-5-F-4-Py], [4015:2-CN-5-F-4-Py], [4016:6-CN-5-F-4-Py], [4017:3-OMe-5-F-4-Py], [4018:2-OMe-5-F-4-Py], [4019:6-OMe-5-F-4-Py], [4020:6-F-4-Py], [4021:3-Cl-6-F-4-Py], [4022:2-Cl-6-F-4-Py], [4023:5-Cl-6-F-4-Py], [4024:3-Me-6-F-4-Py], [4025:2-Me-6-F-4-Py], [4026:5-Me-6-F-4-Py], [4027:3-CF3-6-F-4-Py], [4028:2-CF3-6-F-4-Py], [4029:5-CF3-6-F-4-Py], [4030:3-CN-6-F-4-Py], [4031:2-CN-6-F-4-Py], [4032:5-CN-6-F-4-Py], [4033:3-OMe-6-F-4-Py], [4034:2-OMe-6-F-4-Py], [4035:5-OMe-6-F-4-Py], [4036:3-Cl-4-Py], [4037:2-Cl-3-Cl-4-Py], [4038:5-Cl-3-Cl-4-Py], [4039:6-Cl-3-Cl-4-Py], [4040:2-Me-3-Cl-4-Py], [4041:5-Me-3-Cl-4-Py], [4042:6-Me-3-Cl-4-Py], [4043:2-CF3-3-Cl-4-Py], [4044:5-CF3-3-Cl-4-Py], [4045:6-CF3-3-Cl-4-Py], [4046:2-CN-3-Cl-4-Py], [4047:5-CN-3-Cl-4-Py], [4048:6-CN-3-Cl-4-Py], [4049:2-OMe-3-Cl-4-Py], [4050:5-OMe-3-Cl-4-Py], [4051:6-OMe-3-Cl-4-Py], [4052:2-Cl-4-Py], [4053:3-Cl-2-Cl-4-Py], [4054:5-Cl-2-Cl-4-Py], [4055:6-Cl-2-Cl-4-Py], [4056:3-Me-2-Cl-4-Py], [4057:5-Me-2-Cl-4-Py], [4058:6-Me-2-Cl-4-Py], [4059:3-CF3-2-Cl-4-Py], [4060:5-CF3-2-Cl-4-Py], [4061:6-CF3-2-Cl-4-Py], [4062:3-CN-2-Cl-4-Py], [4063:5-CN-2-Cl-4-Py], [4064:6-CN-2-Cl-4-Py], [4065:3-OMe-2-Cl-4-Py], [4066:5-OMe-2-Cl-4-Py], [4067:6-OMe-2-Cl-4-Py], [4068:5-Cl-4-Py], [4069:2-Cl-5-Cl-4-Py], [4070:5-Cl-5-Cl-4-Py], [4071:6-Cl-5-Cl-4-Py], [4072:2-Me-5-Cl-4-Py], [4073:5-Me-5-Cl-4-Py], [4074:6-Me-5-Cl-4-Py], [4075:2-CF3-5-Cl-4-Py], [4076:5-CF3-5-Cl-4-Py], [4077:6-CF3-5-Cl-4-Py], [4078:2-CN-5-Cl-4-Py], [4079:3-CN-5-Cl-4-Py], [4080:6-CN-5-Cl-4-Py], [4081:2-OMe-5-Cl-4-Py], [4082:5-OMe-5-Cl-4-Py], [4083:6-OMe-5-Cl-4-Py], [4084:6-Cl-4-Py], [4085:3-Cl-6-Cl-4-Py], [4086:2-Cl-6-Cl-4-Py], [4087:5-Cl-6-Cl-4-Py], [4088:3-Me-6-Cl-4-Py], [4089:2-Me-6-Cl-4-Py], [4090:5-Me-6-Cl-4-Py], [4091:3-CF3-6-Cl-4-Py], [4092:2-CF3-6-Cl-4-Py], [4093:5-CF3-6-Cl-4-Py], [4094:3-CN-6-Cl-4-Py], [4095:2-CN-6-Cl-4-Py], [4096:5-CN-6-Cl-4-Py], [4097:3-OMe-6-Cl-4-Py], [4098:2-OMe-6-Cl-4-Py], [4099:5-OMe-6-Cl-4-Py], [4100:3-Br-4-Py],

[4101:2-Cl-3-Br-4-Py], [4102:5-Cl-3-Br-4-Py], [4103:6-Cl-3-Br-4-Py], [4104:2-Me-3-Br-4-Py], [4105:5-Me-3-Br-4-Py], [4106:6-Me-3-Br-4-Py], [4107:2-CF3-3-Br-4-Py], [4108:5-CF3-3-Br-4-Py], [4109:6-CF3-3-Br-4-Py], [4110:2-CN-3-Br-4-Py], [4111:5-CN-3-Br-4-Py], [4112:6-CN-3-Br-4-Py], [4113:2-OMe-3-Br-4-Py], [4114:5-OMe-3-Br-4-Py], [4115:6-OMe-3-Br-4-Py], [4116:2-Br-4-Py], [4117:3-Cl-2-Br-4-Py], [4118:5-Cl-2-Br-4-Py], [4119:6-Cl-2-Br-4-Py], [4120:3-Me-2-Br-4-Py], [4121:5-Me-2-Br-4-Py], [4122:6-Me-2-Br-4-Py], [4123:3-CF3-2-Br-4-Py], [4124:5-CF3-2-Br-4-Py], [4125:6-CF3-2-Br-4-Py], [4126:3-CN-2-Br-4-Py], [4127:5-CN-2-Br-4-Py], [4128:6-CN-2-Br-4-Py], [4129:3-OMe-2-Br-4-Py], [4130:5-OMe-2-Br-4-Py], [4131:6-OMe-2-Br-4-Py], [4132:5-Br-4-Py], [4133:3-Cl-5-Br-4-Py], [4134:2-Cl-5-Br-4-Py], [4135:6-Cl-5-Br-4-Py], [4136:

3-Me-5-Br-4-Py], [4137:2-Me-5-Br-4-Py], [4138:6-Me-5-Br-4-Py], [4139:3-CF3-5-Br-4-Py], [4140:2-CF3-5-Br-4-Py], [4141:6-CF3-5-Br-4-Py], [4142:3-CN-5-Br-4-Py], [4143:2-CN-5-Br-4-Py], [4144:6-CN-5-Br-4-Py], [4145:3-OMe-5-Br-4-Py], [4146:2-OMe-5-Br-4-Py], [4147:6-OMe-5-Br-4-Py], [4148:6-Br-4-Py], [4149:3-Cl-6-Br-4-Py], [4150:2-Cl-6-Br-4-Py], [4151:5-Cl-6-Br-4-Py], [4152:3-Me-6-Br-4-Py], [4153:2-Me-6-Br-4-Py], [4154:5-Me-6-Br-4-Py], [4155:3-CF3-6-Br-4-Py], [4156:2-CF3-6-Br-4-Py], [4157:5-CF3-6-Br-4-Py], [4158:3-CN-6-Br-4-Py], [4159:2-CN-6-Br-4-Py], [4160:5-CN-6-Br-4-Py], [4161:3-OMe-6-Br-4-Py], [4162:2-OMe-6-Br-4-Py], [4163:5-OMe-6-Br-4-Py], [4164:3-I-4-Py], [4165:2-Cl-3-I-4-Py], [4166:5-Cl-3-I-4-Py], [4167:6-Cl-3-I-4-Py], [4168:2-Me-3-I-4-Py], [4169:5-Me-3-I-4-Py], [4170:6-Me-3-I-4-Py], [4171:2-CF3-3-I-4-Py], [4172:5-CF3-3-I-4-Py], [4173:6-CF3-3-I-4-Py], [4174:2-CN-3-I-4-Py], [4175:5-CN-3-I-4-Py], [4176:6-CN-3-I-4-Py], [4177:2-OMe-3-I-4-Py], [4178:5-OMe-3-I-4-Py], [4179:6-OMe-3-I-4-Py], [4180:2-I-4-Py], [4181:3-Cl-2-I-4-Py], [4182:5-Cl-2-I-4-Py], [4183:6-Cl-2-I-4-Py], [4184:3-Me-2-I-4-Py], [4185:5-Me-2-I-4-Py], [4186:6-Me-2-I-4-Py], [4187:3-CF3-2-I-4-Py], [4188:5-CF3-2-I-4-Py], [4189:6-CF3-2-I-4-Py], [4190:3-CN-2-I-4-Py], [4191:5-CN-2-I-4-Py], [4192:6-CN-2-I-4-Py], [4193:3-OMe-2-I-4-Py], [4194:5-OMe-2-I-4-Py], [4195:6-OMe-2-I-4-Py], [4196:5-I-4-Py], [4197:3-Cl-5-I-4-Py], [4198:2-Cl-5-I-4-Py], [4199:6-Cl-5-I-4-Py], [4200:3-Me-5-I-4-Py],

[4201:2-Me-5-I-4-Py], [4202:6-Me-5-I-4-Py], [4203:3-CF3-5-I-4-Py], [4204:2-CF3-5-I-4-Py], [4205:6-CF3-5-I-4-Py], [4206:3-CN-5-I-4-Py], [4207:2-CN-5-I-4-Py], [4208:6-CN-5-I-4-Py], [4209:3-OMe-5-I-4-Py], [4210:2-OMe-5-I-4-Py], [4211:6-OMe-5-I-4-Py], [4212:6-I-4-Py], [4213:3-Cl-6-I-4-Py], [4214:2-Cl-6-I-4-Py], [4215:5-Cl-6-I-4-Py], [4216:3-Me-6-I-4-Py], [4217:2-Me-6-I-4-Py], [4218:5-Me-6-I-4-Py], [4219:3-CF3-6-I-4-Py], [4220:2-CF3-6-I-4-Py], [4221:5-CF3-6-I-4-Py], [4222:3-CN-6-I-4-Py], [4223:2-CN-6-I-4-Py], [4224:5-CN-6-I-4-Py], [4225:3-OMe-6-I-4-Py], [4226:2-OMe-6-I-4-Py], [4227:5-OMe-6-I-4-Py], [4228:3-Me-4-Py], [4229:2-Cl-3-Me-4-Py], [4230:5-Cl-3-Me-4-Py], [4231:6-Cl-3-Me-4-Py], [4232:2-Me-3-Me-4-Py], [4233:5-Me-3-Me-4-Py], [4234:6-Me-3-Me-4-Py], [4235:2-CF3-3-Me-4-Py], [4236:5-CF3-3-Me-4-Py], [4237:6-CF3-3-Me-4-Py], [4238:2-CN-3-Me-4-Py], [4239:5-CN-3-Me-4-Py], [4240:6-CN-3-Me-4-Py], [4241:2-OMe-3-Me-4-Py], [4242:5-OMe-3-Me-4-Py], [4243:6-OMe-3-Me-4-Py], [4244:2-Me-4-Py], [4245:3-Cl-2-Me-4-Py], [4246:5-Cl-2-Me-4-Py], [4247:6-Cl-2-Me-4-Py], [4248:3-Me-2-Me-4-Py], [4249:5-Me-2-Me-4-Py], [4250:6-Me-2-Me-4-Py], [4251:3-CF3-2-Me-4-Py], [4252:5-CF3-2-Me-4-Py], [4253:6-CF3-2-Me-4-Py], [4254:3-CN-2-Me-4-Py], [4255:5-CN-2-Me-4-Py], [4256:6-CN-2-Me-4-Py], [4257:3-OMe-2-Me-4-Py], [4258:5-OMe-2-Me-4-Py], [4259:6-OMe-2-Me-4-Py], [4260:5-Me-4-Py], [4261:3-Cl-5-Me-4-Py], [4262:2-Cl-5-Me-4-Py], [4263:6-Cl-5-Me-4-Py], [4264:3-Me-5-Me-4-Py], [4265:2-Me-5-Me-4-Py], [4266:6-Me-5-Me-4-Py], [4267:3-CF3-5-Me-4-Py], [4268:2-CF3-5-Me-4-Py], [4269:6-CF3-5-Me-4-Py], [4270:3-CN-5-Me-4-Py], [4271:2-CN-5-Me-4-Py], [4272:6-CN-5-Me-4-Py], [4273:3-OMe-5-Me-4-Py], [4274:2-OMe-5-Me-4-Py], [4275:6-OMe-5-Me-4-Py], [4276:6-Me-4-Py], [4277:3-Cl-6-Me-4-Py], [4278:2-Cl-6-Me-4-Py], [4279:5-Cl-6-Me-4-Py], [4280:3-Me-6-Me-4-Py], [4281:2-Me-6-Me-4-Py], [4282:5-Me-6-Me-4-Py], [4283:3-CF3-6-Me-4-Py], [4284:2-CF3-6-Me-4-Py], [4285:5-CF3-6-Me-4-Py], [4286:3-CN-6-Me-4-Py], [4287:2-CN-6-Me-4-Py], [4288:5-CN-6-Me-4-Py], [4289:3-OMe-6-Me-4-Py], [4290:2-OMe-6-Me-4-Py], [4291:5-OMe-6-Me-4-Py], [4292:3-OMe-4-Py], [4293:2-Cl-3-OMe-4-Py], [4294:5-Cl-3-OMe-4-Py], [4295:6-Cl-3-OMe-4-Py], [4296:2-Me-3-OMe-4-Py], [4297:5-Me-3-OMe-4-Py], [4298:6-Me-3-OMe-4-Py], [4299:2-CF3-3-OMe-4-Py], [4300:5-CF3-3-OMe-4-Py],

[4301:6-CF3-3-OMe-4-Py], [4302:2-CN-3-OMe-4-Py], [4303:5-CN-3-OMe-4-Py], [4304:6-CN-3-OMe-4-Py], [4305:2-OMe-3-OMe-4-Py], [4306:5-OMe-3-OMe-4-Py], [4307:6-OMe-3-OMe-4-Py], [4308:2-OMe-4-Py], [4309:3-Cl-2-OMe-4-Py], [4310:5-Cl-2-OMe-4-Py], [4311:6-Cl-2-OMe-4-Py], [4312:3-Me-2-OMe-4-Py], [4313:5-Me-2-OMe-4-Py], [4314:6-Me-2-OMe-4-Py], [4315:3-CF3-2-OMe-4-Py], [4316:5-CF3-2-OMe-4-Py], [4317:6-CF3-2-OMe-4-Py], [4318:3-CN-2-OMe-4-Py], [4319:5-CN-2-OMe-4-Py], [4320:6-CN-2-OMe-4-Py], [4321:3-OMe-2-OMe-4-Py], [4322:5-OMe-2-OMe-4-Py], [4323:6-OMe-2-OMe-4-Py], [4324:5-OMe-4-Py], [4325:3-Cl-5-OMe-4-Py], [4326:2-Cl-5-OMe-4-Py], [4327:6-Cl-5-OMe-4-Py], [4328:3-Me-5-OMe-4-Py], [4329:2-Me-5-OMe-4-Py], [4330:6-Me-5-OMe-4-Py], [4331:3-CF3-5-OMe-4-Py], [4332:2-CF3-5-OMe-4-Py], [4333:6-CF3-5-OMe-4-Py], [4334:3-CN-5-OMe-4-Py], [4335:2-CN-5-OMe-4-Py], [4336:6-CN-5-OMe-4-Py], [4337:3-OMe-5-OMe-4-Py], [4338:2-OMe-5-OMe-4-Py], [4339:6-OMe-5-OMe-4-Py], [4340:6-OMe-4-Py], [4341:3-Cl-6-OMe-4-Py], [4342:2-Cl-6-OMe-4-Py], [4343:5-Cl-6-OMe-4-Py], [4344:6-Me-6-OMe-4-Py], [4345:2-Me-6-OMe-4-Py], [4346:5-Me-6-OMe-4-Py], [4347:3-CF3-6-OMe-4-Py], [4348:2-CF3-6-OMe-4-Py], [4349:5-CF3-6-OMe-4-Py], [4350:3-CN-6-OMe-4-Py], [4351:2-CN-6-OMe-4-Py], [4352:5-CN-6-OMe-4-Py], [4353:3-OMe-6-OMe-4-Py], [4354:2-OMe-6-OMe-4-Py], [4355:5-OMe-6-OMe-4-Py], [4356:3-CF3-4-Py], [4357:2-Cl-3-CF3-4-Py], [4358:5-Cl-3-CF3-4-Py], [4359:6-Cl-3-CF3-4-Py], [4360:2-Me-3-CF3-4-Py], [4361:5-Me-3-CF3-4-Py], [4362:6-Me-3-CF3-4-Py], [4363:2-CF3-3-CF3-4-Py], [4364:5-CF3-3-CF3-4-Py], [4365:6-CF3-3-CF3-4-Py], [4366:2-CN-3-CF3-4-Py], [4367:5-CN-3-CF3-4-Py], [4368:6-CN-3-CF3-4-Py], [4369:2-OMe-3-CF3-4-Py], [4370:5-OMe-3-CF3-4-Py], [4371:6-OMe-3-CF3-4-Py], [4372:2-CF3-4-Py], [4373:3-Cl-2-CF3-4-Py], [4374:5-Cl-2-CF3-4-Py], [4375:6-Cl-2-CF3-4-Py], [4376:3-Me-2-CF3-4-Py], [4377:5-Me-2-CF3-4-Py], [4378:6-Me-2-CF3-4-Py], [4379:3-CF3-2-CF3-4-Py], [4380:5-CF3-2-CF3-4-Py], [4381:6-CF3-2-CF3-4-Py], [4382:3-CN-2-CF3-4-Py], [4383:5-CN-2-CF3-4-Py], [4384:6-CN-2-CF3-4-Py], [4385:3-OMe-2-CF3-4-Py], [4386:5-OMe-2-CF3-4-Py], [4387:6-OMe-2-CF3-4-Py], [4388:5-CF3-4-Py], [4389:3-Cl-5-CF3-4-Py], [4390:2-Cl-5-CF3-4-Py], [4391:6-Cl-5-CF3-4-Py], [4392:3-Me-5-CF3-4-Py], [4393:2-Me-5-CF3-4-Py], [4394:6-Me-5-CF3-4-Py], [4395:3-CF3-5-CF3-4-Py], [4396:2-CF3-5-CF3-4-Py], [4397:6-CF3-5-CF3-4-Py], [4398:3-CN-5-CF3-4-Py], [4399:2-CN-5-CF3-4-Py], [4400:6-CN-5-CF3-4-Py],

[4401:3-OMe-5-CF3-4-Py], [4402:2-OMe-5-CF3-4-Py], [4403:6-OMe-5-CF3-4-Py], [4404:6-CF3-4-Py], [4405:3-Cl-6-CF3-4-Py], [4406:2-Cl-6-CF3-4-Py], [4407:5-Cl-6-CF3-4-Py], [4408:3-Me-6-CF3-4-Py], [4409:2-Me-6-CF3-4-Py], [4410:5-Me-6-CF3-4-Py], [4411:3-CF3-6-CF3-4-Py], [4412:2-CF3-6-CF3-4-Py], [4413:5-CF3-6-CF3-4-Py], [4414:3-CN-6-CF3-4-Py], [4415:2-CN-6-CF3-4-Py], [4416:5-CN-6-CF3-4-Py], [4417:3-OMe-6-CF3-4-Py], [4418:2-OMe-6-CF3-4-Py], [4419:5-OMe-6-CF3-4-Py], [4420:3-OCF3-4-Py], [4421:2-Cl-3-OCF3-4-Py], [4422:5-Cl-3-OCF3-4-Py], [4423:6-Cl-3-OCF3-4-Py], [4424:2-Me-3-OCF3-4-Py], [4425:5-Me-3-OCF3-4-Py], [4426:6-Me-3-OCF3-4-Py], [4427:2-CF3-3-OCF3-4-Py], [4428:5-CF3-3-OCF3-4-Py], [4429:6-CF3-3-OCF3-4-Py], [4430:2-CN-3-OCF3-4-Py], [4431:5-CN-3-OCF3-4-Py], [4432:6-CN-3-

OCF3-4-Py], [4433:2-OMe-3-OCF3-4-Py], [4434:5-OMe-3-OCF3-4-Py], [4435:6-OMe-3-OCF3-4-Py], [4436:2-OCF3-4-Py], [4437:3-Cl-2-OCF3-4-Py], [4438:5-Cl-2-OCF3-4-Py], [4439:6-Cl-2-OCF3-4-Py], [4440:3-Me-2-OCF3-4-Py], [4441:5-Me-2-OCF3-4-Py], [4442:6-Me-2-OCF3-4-Py], [4443:3-CF3-2-OCF3-4-Py], [4444:5-CF3-2-OCF3-4-Py], [4445:6-CF3-2-OCF3-4-Py], [4446:3-CN-2-OCF3-4-Py], [4447:5-CN-2-OCF3-4-Py], [4448:6-CN-2-OCF3-4-Py], [4449:3-OMe-2-OCF3-4-Py], [4450:5-OMe-2-OCF3-4-Py], [4451:6-OMe-2-OCF3-4-Py], [4452:5-OCF3-4-Py], [4453:3-Cl-5-OCF3-4-Py], [4454:2-Cl-5-OCF3-4-Py], [4455:6-Cl-5-OCF3-4-Py], [4456:3-Me-5-OCF3-4-Py], [4457:2-Me-5-OCF3-4-Py], [4458:6-Me-5-OCF3-4-Py], [4459:3-CF3-5-OCF3-4-Py], [4460:2-CF3-5-OCF3-4-Py], [4461:6-CF3-5-OCF3-4-Py], [4462:3-CN-5-OCF3-4-Py], [4463:2-CN-5-OCF3-4-Py], [4464:6-CN-5-OCF3-4-Py], [4465:3-OMe-5-OCF3-4-Py], [4466:2-OMe-5-OCF3-4-Py], [4467:6-OMe-5-OCF3-4-Py], [4468:6-OCF3-4-Py], [4469:3-Cl-6-OCF3-4-Py], [4470:2-Cl-6-OCF3-4-Py], [4471:5-Cl-6-OCF3-4-Py], [4472:3-Me-6-OCF3-4-Py], [4473:2-Me-6-OCF3-4-Py], [4474:5-Me-6-OCF3-4-Py], [4475:3-CF3-6-OCF3-4-Py], [4476:2-CF3-6-OCF3-4-Py], [4477:5-CF3-6-OCF3-4-Py], [4478:3-CN-6-OCF3-4-Py], [4479:2-CN-6-OCF3-4-Py], [4480:5-CN-6-OCF3-4-Py], [4481:3-OMe-6-OCF3-4-Py], [4482:2-OMe-6-OCF3-4-Py], [4483:5-OMe-6-OCF3-4-Py], [4484:3-CHF2-4-Py], [4485:2-Cl-3-CHF2-4-Py], [4486:5-Cl-3-CHF2-4-Py], [4487:6-Cl-3-CHF2-4-Py], [4488:2-Me-3-CHF2-4-Py], [4489:5-Me-3-CHF2-4-Py], [4490:6-Me-3-CHF2-4-Py], [4491:2-CF3-3-CHF2-4-Py], [4492:5-CF3-3-CHF2-4-Py], [4493:6-CF3-3-CHF2-4-Py], [4494:2-CN-3-CHF2-4-Py], [4495:5-CN-3-CHF2-4-Py], [4496:6-CN-3-CHF2-4-Py], [4497:2-OMe-3-CHF2-4-Py], [4498:5-OMe-3-CHF2-4-Py], [4499:6-OMe-3-CHF2-4-Py], [4500:4-CHF2-4-Py],
[4501:3-Cl-4-CHF2-4-Py], [4502:5-Cl-4-CHF2-4-Py], [4503:6-Cl-4-CHF2-4-Py], [4504:3-Me-4-CHF2-4-Py], [4505:5-Me-4-CHF2-4-Py], [4506:6-Me-4-CHF2-4-Py], [4507:3-CF3-4-CHF2-4-Py], [4508:5-CF3-4-CHF2-4-Py], [4509:6-CF3-4-CHF2-4-Py], [4510:3-CN-4-CHF2-4-Py], [4511:5-CN-4-CHF2-4-Py], [4512:6-CN-4-CHF2-4-Py], [4513:3-OMe-4-CHF2-4-Py], [4514:5-OMe-4-CHF2-4-Py], [4515:6-OMe-4-CHF2-4-Py], [4516:5-CHF2-4-Py], [4517:3-Cl-5-CHF2-4-Py], [4518:2-Cl-5-CHF2-4-Py], [4519:6-Cl-5-CHF2-4-Py], [4520:3-Me-5-CHF2-4-Py], [4521:2-Me-5-CHF2-4-Py], [4522:6-Me-5-CHF2-4-Py], [4523:3-CF3-5-CHF2-4-Py], [4524:2-CF3-5-CHF2-4-Py], [4525:6-CF3-5-CHF2-4-Py], [4526:3-CN-5-CHF2-4-Py], [4527:2-CN-5-CHF2-4-Py], [4528:6-CN-5-CHF2-4-Py], [4529:3-OMe-5-CHF2-4-Py], [4530:2-OMe-5-CHF2-4-Py], [4531:6-OMe-5-CHF2-4-Py], [4532:6-CHF2-4-Py], [4533:3-Cl-6-CHF2-4-Py], [4534:2-Cl-6-CHF2-4-Py], [4535:5-Cl-6-CHF2-4-Py], [4536:3-Me-6-CHF2-4-Py], [4537:2-Me-6-CHF2-4-Py], [4538:5-Me-6-CHF2-4-Py], [4539:3-CF3-6-CHF2-4-Py], [4540:2-CF3-6-CHF2-4-Py], [4541:5-CF3-6-CHF2-4-Py], [4542:3-CN-6-CHF2-4-Py], [4543:2-CN-6-CHF2-4-Py], [4544:5-CN-6-CHF2-4-Py], [4545:3-OMe-6-CHF2-4-Py], [4546:2-OMe-6-CHF2-4-Py], [4547:5-OMe-6-CHF2-4-Py], [4548:3-OCHF2-4-Py], [4549:2-Cl-3-OCHF2-4-Py], [4550:5-Cl-3-OCHF2-4-Py], [4551:6-Cl-3-OCHF2-4-Py], [4552:2-Me-3-OCHF2-4-Py], [4553:5-Me-3-OCHF2-4-Py], [4554:6-Me-3-OCHF2-4-Py], [4555:2-CF3-3-OCHF2-4-Py], [4556:5-CF3-3-OCHF2-4-Py], [4557:6-CF3-3-OCHF2-4-Py], [4558:2-CN-3-OCHF2-4-Py], [4559:5-CN-3-OCHF2-4-Py], [4560:6-CN-3-OCHF2-4-Py], [4561:2-OMe-3-OCHF2-4-Py], [4562:5-OMe-3-OCHF2-4-Py], [4563:6-OMe-3-OCHF2-4-Py], [4564:4-OCHF2-4-Py], [4565:3-Cl-4-OCHF2-4-Py], [4566:5-Cl-4-OCHF2-4-Py], [4567:6-Cl-4-OCHF2-4-Py], [4568:3-Me-4-OCHF2-4-Py], [4569:5-Me-4-OCHF2-4-Py], [4570:6-Me-4-OCHF2-4-Py], [4571:3-CF3-4-OCHF2-4-Py], [4572:5-CF3-4-OCHF2-4-Py], [4573:6-CF3-4-OCHF2-4-Py], [4574:3-CN-4-OCHF2-4-Py], [4575:5-CN-4-OCHF2-4-Py], [4576:6-CN-4-OCHF2-4-Py], [4577:3-OMe-4-OCHF2-4-Py], [4578:5-OMe-4-OCHF2-4-Py], [4579:6-OMe-4-OCHF2-4-Py], [4580:5-OCHF2-4-Py], [4581:3-Cl-5-OCHF2-4-Py], [4582:2-Cl-5-OCHF2-4-Py], [4583:6-Cl-5-OCHF2-4-Py], [4584:3-Me-5-OCHF2-4-Py], [4585:2-Me-5-OCHF2-4-Py], [4586:6-Me-5-OCHF2-4-Py], [4587:3-CF3-5-OCHF2-4-Py], [4588:2-CF3-5-OCHF2-4-Py], [4589:6-CF3-5-OCHF2-4-Py], [4590:3-CN-5-OCHF2-4-Py], [4591:2-CN-5-OCHF2-4-Py], [4592:6-CN-5-OCHF2-4-Py], [4593:3-OMe-5-OCHF2-4-Py], [4594:2-OMe-5-OCHF2-4-Py], [4595:6-OMe-5-OCHF2-4-Py], [4596:6-OCHF2-4-Py], [4597:3-Cl-6-OCHF2-4-Py], [4598:2-Cl-6-OCHF2-4-Py], [4599:5-Cl-6-OCHF2-4-Py], [4600:3-Me-6-OCHF2-4-PY],
[4601:2-Me-6-OCHF2-4-Py], [4602:5-Me-6-OCHF2-4-Py], [4603:3-CF3-6-OCHF2-4-Py], [4604:2-CF3-6-OCHF2-4-Py], [4605:5-CF3-6-OCHF2-4-Py], [4606:3-CN-6-OCHF2-4-Py], [4607:2-CN-6-OCHF2-4-Py], [4608:5-CN-6-OCHF2-4-Py], [4609:3-OMe-6-OCHF2-4-Py], [4610:2-OMe-6-OCHF2-4-Py], [4611:5-OMe-6-OCHF2-4-Py], [4612:3-Et-4-Py], [4613:2-Cl-3-Et-4-Py], [4614:5-Cl-3-Et-4-Py], [4615:6-Cl-3-Et-4-Py], [4616:2-Me-3-Et-4-Py], [4617:5-Me-3-Et-4-Py], [4618:6-Me-3-Et-4-Py], [4619:2-CF3-3-Et-4-Py], [4620:5-CF3-3-Et-4-Py], [4621:6-CF3-3-Et-4-Py], [4622:2-CN-3-Et-4-Py], [4623:5-CN-3-Et-4-Py], [4624:6-CN-3-Et-4-Py], [4625:2-OMe-3-Et-4-Py], [4626:5-OMe-3-Et-4-Py], [4627:6-OMe-3-Et-4-Py], [4628:2-Et-4-Py], [4629:3-Cl-2-Et-4-Py], [4630:5-Cl-2-Et-4-Py], [4631:6-Cl-2-Et-4-Py], [4632:3-Me-2-Et-4-Py], [4633:5-Me-2-Et-4-Py], [4634:6-Me-2-Et-4-Py], [4635:3-CF3-2-Et-4-Py], [4636:5-CF3-2-Et-4-Py], [4637:6-CF3-2-Et-4-Py], [4638:3-CN-2-Et-4-Py], [4639:5-CN-2-Et-4-Py], [4640:6-CN-2-Et-4-Py], [4641:3-OMe-2-Et-4-Py], [4642:5-OMe-2-Et-4-Py], [4643:6-OMe-2-Et-4-Py], [4644:5-Et-4-Py], [4645:3-Cl-5-Et-4-Py], [4646:2-Cl-5-Et-4-Py], [4647:6-Cl-5-Et-4-Py], [4648:3-Me-5-Et-4-Py], [4649:2-Me-5-Et-4-Py], [4650:6-Me-5-Et-4-Py], [4651:3-CF3-5-Et-4-Py], [4652:2-CF3-5-Et-4-Py], [4653:6-CF3-5-Et-4-Py], [4654:3-CN-5-Et-4-Py], [4655:2-CN-5-Et-4-Py], [4656:6-CN-5-Et-4-Py], [4657:3-OMe-5-Et-4-Py], [4658:2-OMe-5-Et-4-Py], [4659:6-OMe-5-Et-4-Py], [4660:6-Et-4-Py], [4661:3-Cl-6-Et-4-Py], [4662:2-Cl-6-Et-4-Py], [4663:5-Cl-6-Et-4-Py], [4664:3-Me-6-Et-4-Py], [4665:2-Me-6-Et-4-Py], [4666:5-Me-6-Et-4-Py], [4667:3-CF3-6-Et-4-Py], [4668:2-CF3-6-Et-4-Py], [4669:5-CF3-6-Et-4-Py], [4670:3-CN-6-Et-4-Py], [4671:2-CN-6-Et-4-Py], [4672:5-CN-6-Et-4-Py], [4673:3-OMe-6-Et-4-Py], [4674:2-OMe-6-Et-4-Py], [4675:5-OMe-6-Et-4-Py], [4676:3-CH2CF3-4-Py], [4677:2-Cl-3-CH2CF3-4-Py], [4678:5-Cl-3-CH2CF3-4-Py], [4679:6-Cl-3-CH2CF3-4-Py], [4680:2-Me-3-CH2CF3-4-Py], [4681:5-Me-3-CH2CF3-4-Py], [4682:6-Me-3-CH2CF3-4-Py], [4683:2-CF3-3-CH2CF3-4-Py], [4684:5-CF3-3-CH2CF3-4-Py], [4685:6-CF3-3-CH2CF3-4-Py], [4686:2-CN-3-CH2CF3-4-Py], [4687:5-CN-3-CH2CF3-4-Py], [4688:6-CN-3-CH2CF3-4-Py], [4689:2-OMe-3-CH2CF3-4-Py], [4690:5-OMe-3-CH2CF3-4-Py], [4691:6-OMe-3-CH2CF3-4-Py], [4692:2-CH2CF3-4-Py], [4693:3-Cl-2-CH2CF3-4-Py], [4694:5-Cl-2-CH2CF3-4-Py], [4695:6-Cl-2-CH2CF3-4-Py], [4696:3-Me-2-CH2CF3-4-Py], [4697:5-Me-2-CH2CF3-4-Py], [4698:6-Me-2-CH2CF3-4-Py], [4699:3-CF3-2-CH2CF3-4-Py], [4700:5-CF3-2-CH2CF3-4-Py],

[4701:6-CF3-2-CH2CF3-4-Py], [4702:3-CN-2-CH2CF3-4-Py], [4703:5-CN-2-CH2CF3-4-Py], [4704:6-CN-2-CH2CF3-4-Py], [4705:3-OMe-2-CH2CF3-4-Py], [4706:5-OMe-2-CH2CF3-4-Py], [4707:6-OMe-2-CH2CF3-4-Py], [4708:5-CH2CF3-4-Py], [4709:3-Cl-5-CH2CF3-4-Py], [4710:2-Cl-5-CH2CF3-4-Py], [4711:6-Cl-5-CH2CF3-4-Py], [4712:3-Me-5-CH2CF3-4-Py], [4713:2-Me-5-CH2CF3-4-Py], [4714:6-Me-5-CH2CF3-4-Py], [4715:3-CF3-5-CH2CF3-4-Py], [4716:2-CF3-5-CH2CF3-4-Py], [4717:6-CF3-5-CH2CF3-4-Py], [4718:3-CN-5-CH2CF3-4-Py], [4719:2-CN-5-CH2CF3-4-Py], [4720:6-CN-5-CH2CF3-4-Py], [4721:3-OMe-5-CH2CF3-4-Py], [4722:2-OMe-5-CH2CF3-4-Py], [4723:6-OMe-5-CH2CF3-4-Py], [4724:6-CH2CF3-4-Py], [4725:3-Cl-6-CH2CF3-4-Py], [4726:2-Cl-6-CH2CF3-4-Py], [4727:5-Cl-6-CH2CF3-4-Py], [4728:3-Me-6-CH2CF3-4-Py], [4729:2-Me-6-CH2CF3-4-Py], [4730:5-Me-6-CH2CF3-4-Py], [4731:3-CF3-6-CH2CF3-4-Py], [4732:2-CF3-6-CH2CF3-4-Py], [4733:5-CF3-6-CH2CF3-4-Py], [4734:3-CN-6-CH2CF3-4-Py], [4735:2-CN-6-CH2CF3-4-Py], [4736:5-CN-6-CH2CF3-4-Py], [4737:3-OMe-6-CH2CF3-4-Py], [4738:2-OMe-6-CH2CF3-4-Py], [4739:5-OMe-6-CH2CF3-4-Py], [4740:3-OEt-4-Py], [4741:2-Cl-3-OEt-4-Py], [4742:5-Cl-3-OEt-4-Py], [4743:6-Cl-3-OEt-4-Py], [4744:2-Me-3-OEt-4-Py], [4745:5-Me-3-OEt-4-Py], [4746:6-Me-3-OEt-4-Py], [4747:2-CF3-3-OEt-4-Py], [4748:5-CF3-3-OEt-4-Py], [4749:6-CF3-3-OEt-4-Py], [4750:2-CN-3-OEt-4-Py], [4751:5-CN-3-OEt-4-Py], [4752:6-CN-3-OEt-4-Py], [4753:2-OMe-3-OEt-4-Py], [4754:5-OMe-3-OEt-4-Py], [4755:6-OMe-3-OEt-4-Py], [4756:2-OEt-4-Py], [4757:3-Cl-2-OEt-4-Py], [4758:5-Cl-2-OEt-4-Py], [4759:6-Cl-2-OEt-4-Py], [4760:3-Me-2-OEt-4-Py], [4761:5-Me-2-OEt-4-Py], [4762:6-Me-2-OEt-4-Py], [4763:3-CF3-2-OEt-4-Py], [4764:5-CF3-2-OEt-4-Py], [4765:6-CF3-2-OEt-4-Py], [4766:3-CN-2-OEt-4-Py], [4767:5-CN-2-OEt-4-Py], [4768:6-CN-2-OEt-4-Py], [4769:3-OMe-2-OEt-4-Py], [4770:5-OMe-2-OEt-4-Py], [4771:6-OMe-2-OEt-4-Py], [4772:5-OEt-4-Py], [4773:3-Cl-5-OEt-4-Py], [4774:2-Cl-5-OEt-4-Py], [4775:6-Cl-5-OEt-4-Py], [4776:3-Me-5-OEt-4-Py], [4777:2-Me-5-OEt-4-Py], [4778:6-Me-5-OEt-4-Py], [4779:3-CF3-5-OEt-4-Py], [4780:2-CF3-5-OEt-4-Py], [4781:6-CF3-5-OEt-4-Py], [4782:3-CN-5-OEt-4-Py], [4783:2-CN-5-OEt-4-Py], [4784:6-CN-5-OEt-4-Py], [4785:3-OMe-5-OEt-4-Py], [4786:2-OMe-5-OEt-4-Py], [4787:6-OMe-5-OEt-4-Py], [4788:6-OEt-4-Py], [4789:3-Cl-6-OEt-4-Py], [4790:2-Cl-6-OEt-4-Py], [4791:5-Cl-6-OEt-4-Py], [4792:3-Me-6-OEt-4-Py], [4793:2-Me-6-OEt-4-Py], [4794:5-Me-6-OEt-4-Py], [4795:3-CF3-6-OEt-4-Py], [4796:2-CF3-6-OEt-4-Py], [4797:5-CF3-6-OEt-4-Py], [4798:3-CN-6-OEt-4-Py], [4799:2-CN-6-OEt-4-Py], [4800:5-CN-6-OEt-4-Py],
[4801:3-OMe-6-OEt-4-Py], [4802:2-OMe-6-OEt-4-Py], [4803:5-OMe-6-OEt-4-Py], [4804:3-OCH2CF3-4-Py], [4805:2-Cl-3-OCH2CF3-4-Py], [4806:5-Cl-3-OCH2CF3-4-Py], [4807:6-Cl-3-OCH2CF3-4-Py], [4808:2-Me-3-OCH2CF3-4-Py], [4809:5-Me-3-OCH2CF3-4-Py], [4810:6-Me-3-OCH2CF3-4-Py], [4811:2-CF3-3-OCH2CF3-4-Py], [4812:5-CF3-3-OCH2CF3-4-Py], [4813:6-CF3-3-OCH2CF3-4-Py], [4814:2-CN-3-OCH2CF3-4-Py], [4815:5-CN-3-OCH2CF3-4-Py], [4816:6-CN-3-OCH2CF3-4-Py], [4817:2-OMe-3-OCH2CF3-4-Py], [4818:5-OMe-3-OCH2CF3-4-Py], [4819:6-OMe-3-OCH2CF3-4-Py], [4820:2-OCH2CF3-4-Py], [4821:3-Cl-2-OCH2CF3-4-Py], [4822:5-Cl-2-OCH2CF3-4-Py], [4823:6-Cl-2-OCH2CF3-4-Py], [4824:3-Me-2-OCH2CF3-4-Py], [4825:5-Me-2-OCH2CF3-4-Py], [4826:6-Me-2-OCH2CF3-4-Py], [4827:3-CF3-2-OCH2CF3-4-Py], [4828:5-CF3-2-OCH2CF3-4-Py], [4829:6-CF3-2-OCH2CF3-4-Py], [4830:3-CN-2-OCH2CF3-4-Py], [4831:5-CN-2-OCH2CF3-4-Py], [4832:6-CN-2-OCH2CF3-4-Py], [4833:3-OMe-2-OCH2CF3-4-Py], [4834:5-OMe-2-OCH2CF3-4-Py], [4835:6-OMe-2-OCH2CF3-4-Py], [4836:5-OCH2CF3-4-Py], [4837:3-Cl-5-OCH2CF3-4-Py], [4838:2-Cl-5-OCH2CF3-4-Py], [4839:6-Cl-5-OCH2CF3-4-Py], [4840:3-Me-5-OCH2CF3-4-Py], [4841:2-Me-5-OCH2CF3-4-Py], [4842:6-Me-5-OCH2CF3-4-Py], [4843:3-CF3-5-OCH2CF3-4-Py], [4844:2-CF3-5-OCH2CF3-4-Py], [4845:6-CF3-5-OCH2CF3-4-Py], [4846:3-CN-5-OCH2CF3-4-Py], [4847:2-CN-5-OCH2CF3-4-Py], [4848:6-CN-5-OCH2CF3-4-Py], [4849:3-OMe-5-OCH2CF3-4-Py], [4850:2-OMe-5-OCH2CF3-4-Py], [4851:6-OMe-5-OCH2CF3-4-Py], [4852:6-OCH2CF3-4-Py], [4853:3-Cl-6-OCH2CF3-4-Py], [4854:2-Cl-6-OCH2CF3-4-Py], [4855:5-Cl-6-OCH2CF3-4-Py], [4856:3-Me-6-OCH2CF3-4-Py], [4857:2-Me-6-OCH2CF3-4-Py], [4858:5-Me-6-OCH2CF3-4-Py], [4859:3-CF3-6-OCH2CF3-4-Py], [4860:2-CF3-6-OCH2CF3-4-Py], [4861:5-CF3-6-OCH2CF3-4-Py], [4862:3-CN-6-OCH2CF3-4-Py], [4863:2-CN-6-OCH2CF3-4-Py], [4864:5-CN-6-OCH2CF3-4-Py], [4865:3-OMe-6-OCH2CF3-4-Py], [4866:2-OMe-6-OCH2CF3-4-Py], [4867:5-OMe-6-OCH2CF3-4-Py], [4868:3-Pr-4-Py], [4869:2-Cl-3-Pr-4-Py], [4870:5-Cl-3-Pr-4-Py], [4871:6-Cl-3-Pr-4-Py], [4872:2-Me-3-Pr-4-Py], [4873:5-Me-3-Pr-4-Py], [4874:6-Me-3-Pr-4-Py], [4875:2-CF3-3-Pr-4-Py], [4876:5-CF3-3-Pr-4-Py], [4877:6-CF3-3-Pr-4-Py], [4878:2-CN-3-Pr-4-Py], [4879:5-CN-3-Pr-4-Py], [4880:6-CN-3-Pr-4-Py], [4881:2-OMe-3-Pr-4-Py], [4882:5-OMe-3-Pr-4-Py], [4883:6-OMe-3-Pr-4-Py], [4884:2-Pr-4-Py], [4885:3-Cl-2-Pr-4-Py], [4886:5-Cl-2-Pr-4-Py], [4887:6-Cl-2-Pr-4-Py], [4888:3-Me-2-Pr-4-Py], [4889:5-Me-2-Pr-4-Py], [4890:6-Me-2-Pr-4-Py], [4891:3-CF3-2-Pr-4-Py], [4892:5-CF3-2-Pr-4-Py], [4893:6-CF3-2-Pr-4-Py], [4894:3-CN-2-Pr-4-Py], [4895:5-CN-2-Pr-4-Py], [4896:6-CN-2-Pr-4-Py], [4897:3-OMe-2-Pr-4-Py], [4898:5-OMe-2-Pr-4-Py], [4899:6-OMe-2-Pr-4-Py], [4900:5-Pr-4-Py],
[4901:3-Cl-5-Pr-4-Py], [4902:2-Cl-5-Pr-4-Py], [4903:6-Cl-5-Pr-4-Py], [4904:3-Me-5-Pr-4-Py], [4905:2-Me-5-Pr-4-Py], [4906:6-Me-5-Pr-4-Py], [4907:3-CF3-5-Pr-4-Py], [4908:2-CF3-5-Pr-4-Py], [4909:6-CF3-5-Pr-4-Py], [4910:3-CN-5-Pr-4-Py], [4911:2-CN-5-Pr-4-Py], [4912:6-CN-5-Pr-4-Py], [4913:3-OMe-5-Pr-4-Py], [4914:2-OMe-5-Pr-4-Py], [4915:6-OMe-5-Pr-4-Py], [4916:6-Pr-4-Py], [4917:3-Cl-6-Pr-4-Py], [4918:2-Cl-6-Pr-4-Py], [4919:5-Cl-6-Pr-4-Py], [4920:3-Me-6-Pr-4-Py], [4921:2-Me-6-Pr-4-Py], [4922:5-Me-6-Pr-4-Py], [4923:3-CF3-6-Pr-4-Py], [4924:2-CF3-6-Pr-4-Py], [4925:5-CF3-6-Pr-4-Py], [4926:3-CN-6-Pr-4-Py], [4927:2-CN-6-Pr-4-Py], [4928:5-CN-6-Pr-4-Py], [4929:3-OMe-6-Pr-4-Py], [4930:2-OMe-6-Pr-4-Py], [4931:5-OMe-6-Pr-4-Py], [4932:3-OPr-4-Py], [4933:2-Cl-3-OPr-4-Py], [4934:5-Cl-3-OPr-4-Py], [4935:6-Cl-3-OPr-4-Py], [4936:2-Me-3-OPr-4-Py], [4937:5-Me-3-OPr-4-Py], [4938:6-Me-3-OPr-4-Py], [4939:2-CF3-3-OPr-4-Py], [4940:5-CF3-3-OPr-4-Py], [4941:6-CF3-3-OPr-4-Py], [4942:2-CN-3-OPr-4-Py], [4943:5-CN-3-OPr-4-Py], [4944:6-CN-3-OPr-4-Py], [4945:2-OMe-3-OPr-4-Py], [4946:5-OMe-3-OPr-4-Py], [4947:6-OMe-3-OPr-4-Py], [4948:2-OPr-4-Py], [4949:3-Cl-2-OPr-4-Py], [4950:5-Cl-2-OPr-4-Py], [4951:6-Cl-2-OPr-4-Py], [4952:3-Me-2-OPr-4-Py], [4953:5-Me-2-OPr-4-Py], [4954:6-Me-2-OPr-4-Py], [4955:3-CF3-2-OPr-4-Py], [4956:5-CF3-2-OPr-4-Py], [4957:6-CF3-2-OPr-4-Py], [4958:3-CN-2-OPr-4-Py], [4959:5-CN-2-OPr-4-Py], [4960:6-CN-2-OPr-4-Py], [4961:3-OMe-2-OPr-4-Py], [4962:5-OMe-2-OPr-4-Py], [4963:6-OMe-2-OPr-4-Py], [4964:5-OPr-4-Py], [4965:3-Cl-5-OPr-4-Py], [4966:2-Cl-5-OPr-4-Py], [4967:6-Cl-5-OPr-4-Py], [4968:3-Me-5-OPr-4-Py], [4969:2-Me-5-OPr-4-Py], [4970:6-Me-5-OPr-4-Py], [4971:3-CF3-5-OPr-4-Py],

[4972:2-CF3-5-OPr-4-Py], [4973:6-CF3-5-OPr-4-Py], [4974:3-CN-5-OPr-4-Py], [4975:2-CN-5-OPr-4-Py], [4976:6-CN-5-OPr-4-Py], [4977:3-OMe-5-OPr-4-Py], [4978:2-OMe-5-OPr-4-Py], [4979:6-OMe-5-OPr-4-Py], [4980:6-OPr-4-Py], [4981:3-Cl-6-OPr-4-Py], [4982:2-Cl-6-OPr-4-Py], [4983:5-Cl-6-OPr-4-Py], [4984:3-Me-6-OPr-4-Py], [4985:2-Me-6-OPr-4-Py], [4986:5-Me-6-OPr-4-Py], [4987:3-CF3-6-OPr-4-Py], [4988:2-CF3-6-OPr-4-Py], [4989:5-CF3-6-OPr-4-Py], [4990:3-CN-6-OPr-4-Py], [4991:2-CN-6-OPr-4-Py], [4992:5-CN-6-OPr-4-Py], [4993:3-OMe-6-OPr-4-Py], [4994:2-OMe-6-OPr-4-Py], [4995:5-OMe-6-OPr-4-Py], [4996:3-SMe-4-Py], [4997:2-Cl-3-SMe-4-Py], [4998:5-Cl-3-SMe-4-Py], [4999:6-Cl-3-SMe-4-Py], [5000:2-Me-3-SMe-4-Py],

[5001:5-Me-3-SMe-4-Py], [5002:6-Me-3-SMe-4-Py], [5003:2-CF3-3-SMe-4-Py], [5004:5-CF3-3-SMe-4-Py], [5005:6-CF3-3-SMe-4-Py], [5006:2-CN-3-SMe-4-Py], [5007:5-CN-3-SMe-4-Py], [5008:6-CN-3-SMe-4-Py], [5009:2-OMe-3-SMe-4-Py], [5010:5-OMe-3-SMe-4-Py], [5011:6-OMe-3-SMe-4-Py], [5012:2-SMe-4-Py], [5013:3-Cl-2-SMe-4-Py], [5014:5-Cl-2-SMe-4-Py], [5015:6-Cl-2-SMe-4-Py], [5016:3-Me-2-SMe-4-Py], [5017:5-Me-2-SMe-4-Py], [5018:6-Me-2-SMe-4-Py], [5019:3-CF3-2-SMe-4-Py], [5020:5-CF3-2-SMe-4-Py], [5021:6-CF3-2-SMe-4-Py], [5022:3-CN-2-SMe-4-Py], [5023:5-CN-2-SMe-4-Py], [5024:6-CN-2-SMe-4-Py], [5025:3-OMe-2-SMe-4-Py], [5026:5-OMe-2-SMe-4-Py], [5027:6-OMe-2-SMe-4-Py], [5028:5-SMe-4-Py], [5029:3-Cl-5-SMe-4-Py], [5030:2-Cl-5-SMe-4-Py], [5031:6-Cl-5-SMe-4-Py], [5032:3-Me-5-SMe-4-Py], [5033:2-Me-5-SMe-4-Py], [5034:6-Me-5-SMe-4-Py], [5035:3-CF3-5-SMe-4-Py], [5036:2-CF3-5-SMe-4-Py], [5037:6-CF3-5-SMe-4-Py], [5038:3-CN-5-SMe-4-Py], [5039:2-CN-5-SMe-4-Py], [5040:6-CN-5-SMe-4-Py], [5041:3-OMe-5-SMe-4-Py], [5042:2-OMe-5-SMe-4-Py], [5043:6-OMe-5-SMe-4-Py], [5044:6-SMe-4-Py], [5045:3-Cl-6-SMe-4-Py], [5046:2-Cl-6-SMe-4-Py], [5047:5-Cl-6-SMe-4-Py], [5048:3-Me-6-SMe-4-Py], [5049:2-Me-6-SMe-4-Py], [5050:5-Me-6-SMe-4-Py], [5051:3-CF3-6-SMe-4-Py], [5052:2-CF3-6-SMe-4-Py], [5053:5-CF3-6-SMe-4-Py], [5054:3-CN-6-SMe-4-Py], [5055:2-CN-6-SMe-4-Py], [5056:5-CN-6-SMe-4-Py], [5057:3-OMe-6-SMe-4-Py], [5058:2-OMe-6-SMe-4-Py], [5059:5-OMe-6-SMe-4-Py], [5060:3-SCF3-4-Py], [5061:2-Cl-3-SCF3-4-Py], [5062:5-Cl-3-SCF3-4-Py], [5063:6-Cl-3-SCF3-4-Py], [5064:2-Me-3-SCF3-4-Py], [5065:5-Me-3-SCF3-4-Py], [5066:6-Me-3-SCF3-4-Py], [5067:2-CF3-3-SCF3-4-Py], [5068:5-CF3-3-SCF3-4-Py], [5069:6-CF3-3-SCF3-4-Py], [5070:2-CN-3-SCF3-4-Py], [5071:5-CN-3-SCF3-4-Py], [5072:6-CN-3-SCF3-4-Py], [5073:2-OMe-3-SCF3-4-Py], [5074:5-OMe-3-SCF3-4-Py], [5075:6-OMe-3-SCF3-4-Py], [5076:2-SCF3-4-Py], [5077:3-Cl-2-SCF3-4-Py], [5078:5-Cl-2-SCF3-4-Py], [5079:6-Cl-2-SCF3-4-Py], [5080:3-Me-2-SCF3-4-Py], [5081:5-Me-2-SCF3-4-Py], [5082:6-Me-2-SCF3-4-Py], [5083:3-CF3-2-SCF3-4-Py], [5084:5-CF3-2-SCF3-4-Py], [5085:6-CF3-2-SCF3-4-Py], [5086:3-CN-2-SCF3-4-Py], [5087:5-CN-2-SCF3-4-Py], [5088:6-CN-2-SCF3-4-Py], [5089:3-OMe-2-SCF3-4-Py], [5090:5-OMe-2-SCF3-4-Py], [5091:6-OMe-2-SCF3-4-Py], [5092:5-SCF3-4-Py], [5093:3-Cl-5-SCF3-4-Py], [5094:2-Cl-5-SCF3-4-Py], [5095:6-Cl-5-SCF3-4-Py], [5096:3-Me-5-SCF3-4-Py], [5097:2-Me-5-SCF3-4-Py], [5098:6-Me-5-SCF3-4-Py], [5099:3-CF3-5-SCF3-4-Py], [5100:2-CF3-5-SCF3-4-Py],

[5101:6-CF3-5-SCF3-4-Py], [5102:3-CN-5-SCF3-4-Py], [5103:2-CN-5-SCF3-4-Py], [5104:6-CN-5-SCF3-4-Py], [5105:3-OMe-5-SCF3-4-Py], [5106:2-OMe-5-SCF3-4-Py], [5107:6-OMe-5-SCF3-4-Py], [5108:6-SCF3-4-Py], [5109:3-Cl-6-SCF3-4-Py], [5110:2-Cl-6-SCF3-4-Py], [5111:6-Cl-6-SCF3-4-Py], [5112:3-Me-6-SCF3-4-Py], [5113:2-Me-6-SCF3-4-Py], [5114:6-Me-6-SCF3-4-Py], [5115:3-CF3-6-SCF3-4-Py], [5116:2-CF3-6-SCF3-4-Py], [5117:6-CF3-6-SCF3-4-Py], [5118:3-CN-6-SCF3-4-Py], [5119:2-CN-6-SCF3-4-Py], [5120:6-CN-6-SCF3-4-Py], [5121:3-OMe-6-SCF3-4-Py], [5122:2-OMe-6-SCF3-4-Py], [5123:6-OMe-6-SCF3-4-Py], [5124:3-S(O)Me-4-Py], [5125:2-Cl-3-S(O)Me-4-Py], [5126:5-Cl-3-S(O)Me-4-Py], [5127:6-Cl-3-S(O)Me-4-Py], [5128:2-Me-3-S(O)Me-4-Py], [5129:5-Me-3-S(O)Me-4-Py], [5130:6-Me-3-S(O)Me-4-Py], [5131:2-CF3-3-S(O)Me-4-Py], [5132:5-CF3-3-S(O)Me-4-Py], [5133:6-CF3-3-S(O)Me-4-Py], [5134:2-CN-3-S(O)Me-4-Py], [5135:5-CN-3-S(O)Me-4-Py], [5136:6-CN-3-S(O)Me-4-Py], [5137:2-OMe-3-S(O)Me-4-Py], [5138:5-OMe-3-S(O)Me-4-Py], [5139:6-OMe-3-S(O)Me-4-Py], [5140:2-S(O)Me-4-Py], [5141:3-Cl-2-S(O)Me-4-Py], [5142:5-Cl-2-S(O)Me-4-Py], [5143:6-Cl-2-S(O)Me-4-Py], [5144:3-Me-2-S(O)Me-4-Py], [5145:5-Me-2-S(O)Me-4-Py], [5146:6-Me-2-S(O)Me-4-Py], [5147:3-CF3-2-S(O)Me-4-Py], [5148:5-CF3-2-S(O)Me-4-Py], [5149:6-CF3-2-S(O)Me-4-Py], [5150:3-CN-2-S(O)Me-4-Py], [5151:5-CN-2-S(O)Me-4-Py], [5152:6-CN-2-S(O)Me-4-Py], [5153:3-OMe-2-S(O)Me-4-Py], [5154:5-OMe-2-S(O)Me-4-Py], [5155:6-OMe-2-S(O)Me-4-Py], [5156:5-S(O)Me-4-Py], [5157:3-Cl-5-S(O)Me-4-Py], [5158:2-Cl-5-S(O)Me-4-Py], [5159:6-Cl-5-S(O)Me-4-Py], [5160:3-Me-5-S(O)Me-4-Py], [5161:2-Me-5-S(O)Me-4-Py], [5162:6-Me-5-S(O)Me-4-Py], [5163:3-CF3-5-S(O)Me-4-Py], [5164:2-CF3-5-S(O)Me-4-Py], [5165:6-CF3-5-S(O)Me-4-Py], [5166:3-CN-5-S(O)Me-4-Py], [5167:2-CN-5-S(O)Me-4-Py], [5168:6-CN-5-S(O)Me-4-Py], [5169:3-OMe-5-S(O)Me-4-Py], [5170:2-OMe-5-S(O)Me-4-Py], [5171:6-OMe-5-S(O)Me-4-Py], [5172:6-S(O)Me-4-Py], [5173:3-Cl-6-S(O)Me-4-Py], [5174:2-Cl-6-S(O)Me-4-Py], [5175:5-Cl-6-S(O)Me-4-Py], [5176:3-Me-6-S(O)Me-4-Py], [5177:2-Me-6-S(O)Me-4-Py], [5178:5-Me-6-S(O)Me-4-Py], [5179:3-CF3-6-S(O)Me-4-Py], [5180:2-CF3-6-S(O)Me-4-Py], [5181:5-CF3-6-S(O)Me-4-Py], [5182:3-CN-6-S(O)Me-4-Py], [5183:2-CN-6-S(O)Me-4-Py], [5184:5-CN-6-S(O)Me-4-Py], [5185:3-OMe-6-S(O)Me-4-Py], [5186:2-OMe-6-S(O)Me-4-Py], [5187:5-OMe-6-S(O)Me-4-Py], [5188:3-S(O)CF3-4-Py], [5189:2-Cl-3-S(O)CF3-4-Py], [5190:5-Cl-3-S(O)CF3-4-Py], [5191:6-Cl-3-S(O)CF3-4-Py], [5192:2-Me-3-S(O)CF3-4-Py], [5193:5-Me-3-S(O)CF3-4-Py], [5194:6-Me-3-S(O)CF3-4-Py], [5195:2-CF3-3-S(O)CF3-4-Py], [5196:5-CF3-3-S(O)CF3-4-Py], [5197:6-CF3-3-S(O)CF3-4-Py], [5198:2-CN-3-S(O)CF3-4-Py], [5199:5-CN-3-S(O)CF3-4-Py], [5200:6-CN-3-S(O)CF3-4-Py],

[5201:2-OMe-3-S(O)CF3-4-Py], [5202:5-OMe-3-S(O)CF3-4-Py], [5203:6-OMe-3-S(O)CF3-4-Py], [5204:2-S(O)CF3-4-Py], [5205:3-Cl-2-S(O)CF3-4-Py], [5206:5-Cl-2-S(O)CF3-4-Py], [5207:6-Cl-2-S(O)CF3-4-Py], [5208:3-Me-2-S(O)CF3-4-Py], [5209:5-Me-2-S(O)CF3-4-Py], [5210:6-Me-2-S(O)CF3-4-Py], [5211:3-CF3-2-S(O)CF3-4-Py], [5212:5-CF3-2-S(O)CF3-4-Py], [5213:6-CF3-2-S(O)CF3-4-Py], [5214:3-CN-2-S(O)CF3-4-Py], [5215:5-CN-2-S(O)CF3-4-Py], [5216:6-CN-2-S(O)CF3-4-Py], [5217:3-OMe-2-S(O)CF3-4-Py], [5218:5-OMe-2-S(O)CF3-4-Py], [5219:6-OMe-2-S(O)CF3-4-Py], [5220:5-S(O)CF3-4-Py], [5221:3-Cl-5-S(O)CF3-4-Py], [5222:2-Cl-5-S(O)CF3-4-Py], [5223:6-Cl-5-S(O)CF3-4-Py], [5224:3-Me-5-S(O)CF3-4-Py], [5225:2-Me-5-S(O)CF3-4-Py], [5226:6-Me-5-S(O)CF3-4-Py], [5227:3-CF3-5-S(O)CF3-4-Py], [5228:2-CF3-5-S(O)CF3-4-Py], [5229:6-CF3-5-S(O)CF3-4-Py], [5230:3-CN-5-S(O)CF3-4-Py], [5231:2-CN-5-S(O)CF3-4-Py], [5232:6-CN-5-S(O)CF3-4-Py], [5233:3-OMe-5-S(O)CF3-4-Py], [5234:2-OMe-5-S(O)CF3-4-Py], [5235:6-OMe-5-S(O)CF3-4-Py],

[5236:6-S(O)CF3-4-Py], [5237:3-Cl-6-S(O)CF3-4-Py], [5238:2-Cl-6-S(O)CF3-4-Py], [5239:5-Cl-6-S(O)CF3-4-Py], [5240:3-Me-6-S(O)CF3-4-Py], [5241:2-Me-6-S(O)CF3-4-Py], [5242:5-Me-6-S(O)CF3-4-Py], [5243:3-CF3-6-S(O)CF3-4-Py], [5244:2-CF3-6-S(O)CF3-4-Py], [5245:5-CF3-6-S(O)CF3-4-Py], [5246:3-CN-6-S(O)CF3-4-Py], [5247:2-CN-6-S(O)CF3-4-Py], [5248:5-CN-6-S(O)CF3-4-Py], [5249:3-OMe-6-S(O)CF3-4-Py], [5250:2-OMe-6-S(O)CF3-4-Py], [5251:5-OMe-6-S(O)CF3-4-Py], [5252:3-S(O)2Me-4-Py], [5253:2-Cl-3-S(O)2Me-4-Py], [5254:5-Cl-3-S(O)2Me-4-Py], [5255:6-Cl-3-S(O)2Me-4-Py], [5256:2-Me-3-S(O)2Me-4-Py], [5257:5-Me-3-S(O)2Me-4-Py], [5258:6-Me-3-S(O)2Me-4-Py], [5259:2-CF3-3-S(O)2Me-4-Py], [5260:5-CF3-3-S(O)2Me-4-Py], [5261:6-CF3-3-S(O)2Me-4-Py], [5262:2-CN-3-S(O)2Me-4-Py], [5263:5-CN-3-S(O)2Me-4-Py], [5264:6-CN-3-S(O)2Me-4-Py], [5265:2-OMe-3-S(O)2Me-4-Py], [5266:5-OMe-3-S(O)2Me-4-Py], [5267:6-OMe-3-S(O)2Me-4-Py], [5268:2-S(O)2Me-4-Py], [5269:3-Cl-2-S(O)2Me-4-Py], [5270:5-Cl-2-S(O)2Me-4-Py], [5271:6-Cl-2-S(O)2Me-4-Py], [5272:3-Me-2-S(O)2Me-4-Py], [5273:5-Me-2-S(O)2Me-4-Py], [5274:6-Me-2-S(O)2Me-4-Py], [5275:3-CF3-2-S(O)2Me-4-Py], [5276:5-CF3-2-S(O)2Me-4-Py], [5277:6-CF3-2-S(O)2Me-4-Py], [5278:3-CN-2-S(O)2Me-4-Py], [5279:5-CN-2-S(O)2Me-4-Py], [5280:6-CN-2-S(O)2Me-4-Py], [5281:3-OMe-2-S(O)2Me-4-Py], [5282:5-OMe-2-S(O)2Me-4-Py], [5283:6-OMe-2-S(O)2Me-4-Py], [5284:5-S(O)2Me-4-Py], [5285:3-Cl-5-S(O)2Me-4-Py], [5286:2-Cl-5-S(O)2Me-4-Py], [5287:6-Cl-5-S(O)2Me-4-Py], [5288:3-Me-5-S(O)2Me-4-Py], [5289:2-Me-5-S(O)2Me-4-Py], [5290:6-Me-5-S(O)2Me-4-Py], [5291:3-CF3-5-S(O)2Me-4-Py], [5292:2-CF3-5-S(O)2Me-4-Py], [5293:6-CF3-5-S(O)2Me-4-Py], [5294:3-CN-5-S(O)2Me-4-Py], [5295:2-CN-5-S(O)2Me-4-Py], [5296:6-CN-5-S(O)2Me-4-Py], [5297:3-OMe-5-S(O)2Me-4-Py], [5298:2-OMe-5-S(O)2Me-4-Py], [5299:6-OMe-5-S(O)2Me-4-Py], [5300:6-S(O)2Me-4-Py],
[5301:3-Cl-6-S(O)2Me-4-Py], [5302:2-Cl-6-S(O)2Me-4-Py], [5303:5-Cl-6-S(O)2Me-4-Py], [5304:3-Me-6-S(O)2Me-4-Py], [5305:2-Me-6-S(O)2Me-4-Py], [5306:5-Me-6-S(O)2Me-4-Py], [5307:3-CF3-6-S(O)2Me-4-Py], [5308:2-CF3-6-S(O)2Me-4-Py], [5309:5-CF3-6-S(O)2Me-4-Py], [5310:3-CN-6-S(O)2Me-4-Py], [5311:2-CN-6-S(O)2Me-4-Py], [5312:5-CN-6-S(O)2Me-4-Py], [5313:3-OMe-6-S(O)2Me-4-Py], [5314:2-OMe-6-S(O)2Me-4-Py], [5315:5-OMe-6-S(O)2Me-4-Py], [5316:3-S(O)2CF3-4-Py], [5317:2-Cl-3-S(O)2CF3-4-Py], [5318:5-Cl-3-S(O)2CF3-4-Py], [5319:6-Cl-3-S(O)2CF3-4-Py], [5320:2-Me-3-S(O)2CF3-4-Py], [5321:5-Me-3-S(O)2CF3-4-Py], [5322:6-Me-3-S(O)2CF3-4-Py], [5323:2-CF3-3-S(O)2CF3-4-Py], [5324:5-CF3-3-S(O)2CF3-4-Py], [5325:6-CF3-3-S(O)2CF3-4-Py], [5326:2-CN-3-S(O)2CF3-4-Py], [5327:5-CN-3-S(O)2CF3-4-Py], [5328:6-CN-3-S(O)2CF3-4-Py], [5329:2-OMe-3-S(O)2CF3-4-Py], [5330:5-OMe-3-S(O)2CF3-4-Py], [5331:6-OMe-3-S(O)2CF3-4-Py], [5332:2-S(O)2CF3-4-Py], [5333:3-Cl-2-S(O)2CF3-4-Py], [5334:5-Cl-2-S(O)2CF3-4-Py], [5335:6-Cl-2-S(O)2CF3-4-Py], [5336:3-Me-2-S(O)2CF3-4-Py], [5337:5-Me-2-S(O)2CF3-4-Py], [5338:6-Me-2-S(O)2CF3-4-Py], [5339:3-CF3-2-S(O)2CF3-4-Py], [5340:5-CF3-2-S(O)2CF3-4-Py], [5341:6-CF3-2-S(O)2CF3-4-Py], [5342:3-CN-2-S(O)2CF3-4-Py], [5343:5-CN-2-S(O)2CF3-4-Py], [5344:6-CN-2-S(O)2CF3-4-Py], [5345:3-OMe-2-S(O)2CF3-4-Py], [5346:5-OMe-2-S(O)2CF3-4-Py], [5347:6-OMe-2-S(O)2CF3-4-Py], [5348:5-S(O)2CF3-4-Py], [5349:3-Cl-5-S(O)2CF3-4-Py], [5350:2-Cl-5-S(O)2CF3-4-Py], [5351:6-Cl-5-S(O)2CF3-4-Py], [5352:3-Me-5-S(O)2CF3-4-Py], [5353:2-Me-5-S(O)2CF3-4-Py], [5354:6-Me-5-S(O)2CF3-4-Py], [5355:3-CF3-5-S(O)2CF3-4-Py], [5356:2-CF3-5-S(O)2CF3-4-Py], [5357:6-CF3-5-S(O)2CF3-4-Py], [5358:3-CN-5-S(O)2CF3-4-Py], [5359:2-CN-5-S(O)2CF3-4-Py], [5360:6-CN-5-S(O)2CF3-4-Py], [5361:3-OMe-5-S(O)2CF3-4-Py], [5362:2-OMe-5-S(O)2CF3-4-Py], [5363:6-OMe-5-S(O)2CF3-4-Py], [5364:6-S(O)2CF3-4-Py], [5365:3-Cl-6-S(O)2CF3-4-Py], [5366:2-Cl-6-S(O)2CF3-4-Py], [5367:5-Cl-6-S(O)2CF3-4-Py], [5368:3-Me-6-S(O)2CF3-4-Py], [5369:2-Me-6-S(O)2CF3-4-Py], [5370:5-Me-6-S(O)2CF3-4-Py], [5371:3-CF3-6-S(O)2CF3-4-Py], [5372:2-CF3-6-S(O)2CF3-4-Py], [5373:5-CF3-6-S(O)2CF3-4-Py], [5374:3-CN-6-S(O)2CF3-4-Py], [5375:2-CN-6-S(O)2CF3-4-Py], [5376:5-CN-6-S(O)2CF3-4-Py], [5377:3-OMe-6-S(O)2CF3-4-Py], [5378:2-OMe-6-S(O)2CF3-4-Py], [5379:5-OMe-6-S(O)2CF3-4-Py], [5380:3-CN-4-Py], [5381:2-Cl-3-CN-4-Py], [5382:5-Cl-3-CN-4-Py], [5383:6-Cl-3-CN-4-Py], [5384:2-Me-3-CN-4-Py], [5385:5-Me-3-CN-4-Py], [5386:6-Me-3-CN-4-Py], [5387:2-CF3-3-CN-4-Py], [5388:5-CF3-3-CN-4-Py], [5389:6-CF3-3-CN-4-Py], [5390:2-CN-3-CN-4-Py], [5391:5-CN-3-CN-4-Py], [5392:6-CN-3-CN-4-Py], [5393:2-OMe-3-CN-4-Py], [5394:5-OMe-3-CN-4-Py], [5395:6-OMe-3-CN-4-Py], [5396:2-CN-4-Py], [5397:3-Cl-2-CN-4-Py], [5398:5-Cl-2-CN-4-Py], [5399:6-Cl-2-CN-4-Py], [5400:3-Me-2-CN-4-Py],
[5401:5-Me-2-CN-4-Py], [5402:6-Me-2-CN-4-Py], [5403:3-CF3-2-CN-4-Py], [5404:5-CF3-2-CN-4-Py], [5405:6-CF3-2-CN-4-Py], [5406:3-CN-2-CN-4-Py], [5407:5-CN-2-CN-4-Py], [5408:6-CN-2-CN-4-Py], [5409:3-OMe-2-CN-4-Py], [5410:5-OMe-2-CN-4-Py], [5411:6-OMe-2-CN-4-Py], [5412:5-CN-4-Py], [5413:3-Cl-5-CN-4-Py], [5414:2-Cl-5-CN-4-Py], [5415:6-Cl-5-CN-4-Py], [5416:3-Me-5-CN-4-Py], [5417:2-Me-5-CN-4-Py], [5418:6-Me-5-CN-4-Py], [5419:3-CF3-5-CN-4-Py], [5420:2-CF3-5-CN-4-Py], [5421:6-CF3-5-CN-4-Py], [5422:3-CN-5-CN-4-Py], [5423:2-CN-5-CN-4-Py], [5424:6-CN-5-CN-4-Py], [5425:3-OMe-5-CN-4-Py], [5426:2-OMe-5-CN-4-Py], [5427:6-OMe-5-CN-4-Py], [5428:6-CN-4-Py], [5429:3-Cl-6-CN-4-Py], [5430:2-Cl-6-CN-4-Py], [5431:5-Cl-6-CN-4-Py], [5432:3-Me-6-CN-4-Py], [5433:2-Me-6-CN-4-Py], [5434:5-Me-6-CN-4-Py], [5435:3-CF3-6-CN-4-Py], [5436:2-CF3-6-CN-4-Py], [5437:5-CF3-6-CN-4-Py], [5438:3-CN-6-CN-4-Py], [5439:2-CN-6-CN-4-Py], [5440:5-CN-6-CN-4-Py], [5441:3-OMe-6-CN-4-Py], [5442:2-OMe-6-CN-4-Py], [5443:5-OMe-6-CN-4-Py], [5444:3-COOMe-4-Py], [5445:2-Cl-3-COOMe-4-Py], [5446:5-Cl-3-COOMe-4-Py], [5447:6-Cl-3-COOMe-4-Py], [5448:2-Me-3-COOMe-4-Py], [5449:5-Me-3-COOMe-4-Py], [5450:6-Me-3-COOMe-4-Py], [5451:2-CF3-3-COOMe-4-Py], [5452:5-CF3-3-COOMe-4-Py], [5453:6-CF3-3-COOMe-4-Py], [5454:2-CN-3-COOMe-4-Py], [5455:5-CN-3-COOMe-4-Py], [5456:6-CN-3-COOMe-4-Py], [5457:2-OMe-3-COOMe-4-Py], [5458:5-OMe-3-COOMe-4-Py], [5459:6-OMe-3-COOMe-4-Py], [5460:2-COOMe-4-Py], [5461:3-Cl-2-COOMe-4-Py], [5462:5-Cl-2-COOMe-4-Py], [5463:6-Cl-2-COOMe-4-Py], [5464:3-Me-2-COOMe-4-Py], [5465:5-Me-2-COOMe-4-Py], [5466:6-Me-2-COOMe-4-Py], [5467:3-CF3-2-COOMe-4-Py], [5468:5-CF3-2-COOMe-4-Py], [5469:6-CF3-2-COOMe-4-Py], [5470:3-CN-2-COOMe-4-Py], [5471:5-CN-2-COOMe-4-Py], [5472:6-CN-2-COOMe-4-Py], [5473:3-OMe-2-COOMe-4-Py], [5474:5-OMe-2-COOMe-4-Py], [5475:6-OMe-2-COOMe-4-Py], [5476:5-COOMe-4-Py], [5477:3-Cl-5-COOMe-4-Py], [5478:2-Cl-5-COOMe-4-Py], [5479:6-Cl-5-COOMe-4-Py], [5480:3-Me-5-COOMe-4-Py], [5481:2-Me-5-COOMe-4-Py], [5482:6-Me-5-COOMe-4-Py], [5483:3-CF3-5-COOMe-4-Py], [5484:2-CF3-5-COOMe-4-Py], [5485:6-CF3-5-COOMe-4-Py], [5486:3-CN-5-COOMe-4-Py], [5487:2-CN-5-COOMe-4-Py], [5488:6-CN-5-COOMe-4-Py], [5489:3-

OMe-5-COOMe-4-Py], [5490:2-OMe-5-COOMe-4-Py], [5491:6-OMe-5-COOMe-4-Py], [5492:6-COOMe-4-Py], [5493:3-Cl-6-COOMe-4-Py], [5494:2-Cl-6-COOMe-4-Py], [5495:5-Cl-6-COOMe-4-Py], [5496:3-Me-6-COOMe-4-Py], [5497:2-Me-6-COOMe-4-Py], [5498:5-Me-6-COOMe-4-Py], [5499:3-CF3-6-COOMe-4-Py], [5500:2-CF3-6-COOMe-4-Py],
[5501:5-CF3-6-COOMe-4-Py], [5502:3-CN-6-COOMe-4-Py], [5503:2-CN-6-COOMe-4-Py], [5504:5-CN-6-COOMe-4-Py], [5505:3-OMe-6-COOMe-4-Py], [5506:2-OMe-6-COOMe-4-Py], [5507:5-OMe-6-COOMe-4-Py], [5508:3-NO2-4-Py], [5509:2-Cl-3-NO2-4-Py], [5510:5-Cl-3-NO2-4-Py], [5511:6-Cl-3-NO2-4-Py], [5512:2-Me-3-NO2-4-Py], [5513:5-Me-3-NO2-4-Py], [5514:6-Me-3-NO2-4-Py], [5515:2-CF3-3-NO2-4-Py], [5516:5-CF3-3-NO2-4-Py], [5517:6-CF3-3-NO2-4-Py], [5518:2-CN-3-NO2-4-Py], [5519:5-CN-3-NO2-4-Py], [5520:6-CN-3-NO2-4-Py], [5521:2-OMe-3-NO2-4-Py], [5522:5-OMe-3-NO2-4-Py], [5523:6-OMe-3-NO2-4-Py], [5524:2-NO2-4-Py], [5525:3-Cl-2-NO2-4-Py], [5526:5-Cl-2-NO2-4-Py], [5527:6-Cl-2-NO2-4-Py], [5528:3-Me-2-NO2-4-Py], [5529:5-Me-2-NO2-4-Py], [5530:6-Me-2-NO2-4-Py], [5531:3-CF3-2-NO2-4-Py], [5532:5-CF3-2-NO2-4-Py], [5533:6-CF3-2-NO2-4-Py], [5534:3-CN-2-NO2-4-Py], [5535:5-CN-2-NO2-4-Py], [5536:6-CN-2-NO2-4-Py], [5537:3-OMe-2-NO2-4-Py], [5538:5-OMe-2-NO2-4-Py], [5539:6-OMe-2-NO2-4-Py], [5540:5-NO2-4-Py], [5541:3-Cl-5-NO2-4-Py], [5542:2-Cl-5-NO2-4-Py], [5543:6-Cl-5-NO2-4-Py], [5544:3-Me-5-NO2-4-Py], [5545:2-Me-5-NO2-4-Py], [5546:6-Me-5-NO2-4-Py], [5547:3-CF3-5-NO2-4-Py], [5548:2-CF3-5-NO2-4-Py], [5549:6-CF3-5-NO2-4-Py], [5550:3-CN-5-NO2-4-Py], [5551:2-CN-5-NO2-4-Py], [5552:6-CN-5-NO2-4-Py], [5553:3-OMe-5-NO2-4-Py], [5554:2-OMe-5-NO2-4-Py], [5555:6-OMe-5-NO2-4-Py], [5556:6-NO2-4-Py], [5557:3-Cl-6-NO2-4-Py], [5558:2-Cl-6-NO2-4-Py], [5559:5-Cl-6-NO2-4-Py], [5560:3-Me-6-NO2-4-Py], [5561:2-Me-6-NO2-4-Py], [5562:5-Me-6-NO2-4-Py], [5563:3-CF3-6-NO2-4-Py], [5564:2-CF3-6-NO2-4-Py], [5565:5-CF3-6-NO2-4-Py], [5566:3-CN-6-NO2-4-Py], [5567:2-CN-6-NO2-4-Py], [5568:5-CN-6-NO2-4-Py], [5569:3-OMe-6-NO2-4-Py], [5570:2-OMe-6-NO2-4-Py], [5571:5-OMe-6-NO2-4-Py], [5572:3-NH2-4-Py], [5573:2-Cl-3-NH2-4-Py], [5574:5-Cl-3-NH2-4-Py], [5575:6-Cl-3-NH2-4-Py], [5576:2-Me-3-NH2-4-Py], [5577:5-Me-3-NH2-4-Py], [5578:6-Me-3-NH2-4-Py], [5579:2-CF3-3-NH2-4-Py], [5580:5-CF3-3-NH2-4-Py], [5581:6-CF3-3-NH2-4-Py], [5582:2-CN-3-NH2-4-Py], [5583:5-CN-3-NH2-4-Py], [5584:6-CN-3-NH2-4-Py], [5585:2-OMe-3-NH2-4-Py], [5586:5-OMe-3-NH2-4-Py], [5587:6-OMe-3-NH2-4-Py], [5588:2-NH2-4-Py], [5589:3-Cl-2-NH2-4-Py], [5590:5-Cl-2-NH2-4-Py], [5591:6-Cl-2-NH2-4-Py], [5592:3-Me-2-NH2-4-Py], [5593:5-Me-2-NH2-4-Py], [5594:6-Me-2-NH2-4-Py], [5595:3-CF3-2-NH2-4-Py], [5596:5-CF3-2-NH2-4-Py], [5597:6-CF3-2-NH2-4-Py], [5598:3-CN-2-NH2-4-Py], [5599:5-CN-2-NH2-4-Py], [5600:6-CN-2-NH2-4-Py],
[5601:3-OMe-2-NH2-4-Py], [5602:5-OMe-2-NH2-4-Py], [5603:6-OMe-2-NH2-4-Py], [5604:5-NH2-4-Py], [5605:3-Cl-5-NH2-4-Py], [5606:2-Cl-5-NH2-4-Py], [5607:6-Cl-5-NH2-4-Py], [5608:3-Me-5-NH2-4-Py], [5609:2-Me-5-NH2-4-Py], [5610:6-Me-5-NH2-4-Py], [5611:3-CF3-5-NH2-4-Py], [5612:2-CF3-5-NH2-4-Py], [5613:6-CF3-5-NH2-4-Py], [5614:3-CN-5-NH2-4-Py], [5615:2-CN-5-NH2-4-Py], [5616:6-CN-5-NH2-4-Py], [5617:3-OMe-5-NH2-4-Py], [5618:2-OMe-5-NH2-4-Py], [5619:6-OMe-5-NH2-4-Py], [5620:6-NH2-4-Py], [5621:3-Cl-6-NH2-4-Py], [5622:2-Cl-6-NH2-4-Py], [5623:5-Cl-6-NH2-4-Py], [5624:3-Me-6-NH2-4-Py], [5625:2-Me-6-NH2-4-Py], [5626:5-Me-6-NH2-4-Py], [5627:3-CF3-6-NH2-4-Py], [5628:2-CF3-6-NH2-4-Py], [5629:5-CF3-6-NH2-4-Py], [5630:3-CN-6-NH2-4-Py], [5631:2-CN-6-NH2-4-Py], [5632:5-CN-6-NH2-4-Py], [5633:3-OMe-6-NH2-4-Py], [5634:2-OMe-6-NH2-4-Py], [5635:5-OMe-6-NH2-4-Py], [5636:3-NHMe-4-Py], [5637:2-Cl-3-NHMe-4-Py], [5638:5-Cl-3-NHMe-4-Py], [5639:6-Cl-3-NHMe-4-Py], [5640:2-Me-3-NHMe-4-Py], [5641:5-Me-3-NHMe-4-Py], [5642:6-Me-3-NHMe-4-Py], [5643:2-CF3-3-NHMe-4-Py], [5644:5-CF3-3-NHMe-4-Py], [5645:6-CF3-3-NHMe-4-Py], [5646:2-CN-3-NHMe-4-Py], [5647:5-CN-3-NHMe-4-Py], [5648:6-CN-3-NHMe-4-Py], [5649:2-OMe-3-NHMe-4-Py], [5650:5-OMe-3-NHMe-4-Py], [5651:6-OMe-3-NHMe-4-Py], [5652:2-NHMe-4-Py], [5653:3-Cl-2-NHMe-4-Py], [5654:5-Cl-2-NHMe-4-Py], [5655:6-Cl-2-NHMe-4-Py], [5656:3-Me-2-NHMe-4-Py], [5657:5-Me-2-NHMe-4-Py], [5658:6-Me-2-NHMe-4-Py], [5659:3-CF3-2-NHMe-4-Py], [5660:5-CF3-2-NHMe-4-Py], [5661:6-CF3-2-NHMe-4-Py], [5662:3-CN-2-NHMe-4-Py], [5663:5-CN-2-NHMe-4-Py], [5664:6-CN-2-NHMe-4-Py], [5665:3-OMe-2-NHMe-4-Py], [5666:5-OMe-2-NHMe-4-Py], [5667:6-OMe-2-NHMe-4-Py], [5668:5-NHMe-4-Py], [5669:3-Cl-5-NHMe-4-Py], [5670:2-Cl-5-NHMe-4-Py], [5671:6-Cl-5-NHMe-4-Py], [5672:3-Me-5-NHMe-4-Py], [5673:2-Me-5-NHMe-4-Py], [5674:6-Me-5-NHMe-4-Py], [5675:3-CF3-5-NHMe-4-Py], [5676:2-CF3-5-NHMe-4-Py], [5677:6-CF3-5-NHMe-4-Py], [5678:3-CN-5-NHMe-4-Py], [5679:2-CN-5-NHMe-4-Py], [5680:6-CN-5-NHMe-4-Py], [5681:3-OMe-5-NHMe-4-Py], [5682:2-OMe-5-NHMe-4-Py], [5683:6-OMe-5-NHMe-4-Py], [5684:6-NHMe-4-Py], [5685:3-Cl-6-NHMe-4-Py], [5686:2-Cl-6-NHMe-4-Py], [5687:5-Cl-6-NHMe-4-Py], [5688:3-Me-6-NHMe-4-Py], [5689:2-Me-6-NHMe-4-Py], [5690:5-Me-6-NHMe-4-Py], [5691:3-CF3-6-NHMe-4-Py], [5692:2-CF3-6-NHMe-4-Py], [5693:5-CF3-6-NHMe-4-Py], [5694:3-CN-6-NHMe-4-Py], [5695:2-CN-6-NHMe-4-Py], [5696:5-CN-6-NHMe-4-Py], [5697:3-OMe-6-NHMe-4-Py], [5698:2-OMe-6-NHMe-4-Py], [5699:5-OMe-6-NHMe-4-Py], [5700:3-NMe2-4-Py],
[5701:2-Cl-3-NMe2-4-Py], [5702:5-Cl-3-NMe2-4-Py], [5703:6-Cl-3-NMe2-4-Py], [5704:2-Me-3-NMe2-4-Py], [5705:5-Me-3-NMe2-4-Py], [5706:6-Me-3-NMe2-4-Py], [5707:2-CF3-3-NMe2-4-Py], [5708:5-CF3-3-NMe2-4-Py], [5709:6-CF3-3-NMe2-4-Py], [5710:2-CN-3-NMe2-4-Py], [5711:5-CN-3-NMe2-4-Py], [5712:6-CN-3-NMe2-4-Py], [5713:2-OMe-3-NMe2-4-Py], [5714:5-OMe-3-NMe2-4-Py], [5715:6-OMe-3-NMe2-4-Py], [5716:4-NMe2-4-Py], [5717:3-Cl-4-NMe2-4-Py], [5718:5-Cl-4-NMe2-4-Py], [5719:6-Cl-4-NMe2-4-Py], [5720:3-Me-4-NMe2-4-Py], [5721:5-Me-4-NMe2-4-Py], [5722:6-Me-4-NMe2-4-Py], [5723:3-CF3-4-NMe2-4-Py], [5724:5-CF3-4-NMe2-4-Py], [5725:6-CF3-4-NMe2-4-Py], [5726:3-CN-4-NMe2-4-Py], [5727:5-CN-4-NMe2-4-Py], [5728:6-CN-4-NMe2-4-Py], [5729:3-OMe-4-NMe2-4-Py], [5730:5-OMe-4-NMe2-4-Py], [5731:6-OMe-4-NMe2-4-Py], [5732:5-NMe2-4-Py], [5733:3-Cl-5-NMe2-4-Py], [5734:2-Cl-5-NMe2-4-Py], [5735:6-Cl-5-NMe2-4-Py], [5736:3-Me-5-NMe2-4-Py], [5737:2-Me-5-NMe2-4-Py], [5738:6-Me-5-NMe2-4-Py], [5739:3-CF3-5-NMe2-4-Py], [5740:2-CF3-5-NMe2-4-Py], [5741:6-CF3-5-NMe2-4-Py], [5742:3-CN-5-NMe2-4-Py], [5743:2-CN-5-NMe2-4-Py], [5744:6-CN-5-NMe2-4-Py], [5745:3-OMe-5-NMe2-4-Py], [5746:2-OMe-5-NMe2-4-Py], [5747:6-OMe-5-NMe2-4-Py], [5748:6-NMe2-4-Py], [5749:3-Cl-6-NMe2-4-Py], [5750:2-Cl-6-NMe2-4-Py], [5751:5-Cl-6-NMe2-4-Py], [5752:3-Me-6-NMe2-4-Py], [5753:2-Me-6-NMe2-4-Py], [5754:5-Me-6-NMe2-4-Py], [5755:3-CF3-6-NMe2-4-Py], [5756:2-CF3-6-NMe2-4-Py], [5757:5-CF3-6-NMe2-4-Py], [5758:3-CN-6-NMe2-4-Py],

[5759:2-CN-6-NMe2-4-Py], [5760:5-CN-6-NMe2-4-Py], [5761:3-OMe-6-NMe2-4-Py], [5762:2-OMe-6-NMe2-4-Py], [5763:5-OMe-6-NMe2-4-Py], [5764:3-ACNH-4-Py], [5765:2-Cl-3-ACNH-4-Py], [5766:5-Cl-3-ACNH-4-Py], [5767:6-Cl-3-ACNH-4-Py], [5768:2-Me-3-ACNH-4-Py], [5769:5-Me-3-ACNH-4-Py], [5770:6-Me-3-ACNH-4-Py], [5771:2-CF3-3-ACNH-4-Py], [5772:5-CF3-3-ACNH-4-Py], [5773:6-CF3-3-ACNH-4-Py], [5774:2-CN-3-ACNH-4-Py], [5775:5-CN-3-ACNH-4-Py], [5776:6-CN-3-ACNH-4-Py], [5777:2-OMe-3-ACNH-4-Py], [5778:5-OMe-3-ACNH-4-Py], [5779:6-OMe-3-ACNH-4-Py], [5780:2-ACNH-4-Py], [5781:3-Cl-2-ACNH-4-Py], [5782:5-Cl-2-ACNH-4-Py], [5783:6-Cl-2-ACNH-4-Py], [5784:3-Me-2-ACNH-4-Py], [5785:5-Me-2-ACNH-4-Py], [5786:6-Me-2-ACNH-4-Py], [5787:3-CF3-2-ACNH-4-Py], [5788:5-CF3-2-ACNH-4-Py], [5789:6-CF3-2-ACNH-4-Py], [5790:3-CN-2-ACNH-4-Py], [5791:5-CN-2-ACNH-4-Py], [5792:6-CN-2-ACNH-4-Py], [5793:3-OMe-2-ACNH-4-Py], [5794:5-OMe-2-ACNH-4-Py], [5795:6-OMe-2-ACNH-4-Py], [5796:5-ACNH-4-Py], [5797:3-Cl-5-ACNH-4-Py], [5798:2-Cl-5-ACNH-4-Py], [5799:6-Cl-5-ACNH-4-Py], [5800:3-Me-5-ACNH-4-Py]
[5801:2-Me-5-ACNH-4-Py], [5802:6-Me-5-ACNH-4-Py], [5803:3-CF3-5-ACNH-4-Py], [5804:2-CF3-5-ACNH-4-Py], [5805:6-CF3-5-ACNH-4-Py], [5806:3-CN-5-ACNH-4-Py], [5807:2-CN-5-ACNH-4-Py], [5808:6-CN-5-ACNH-4-Py], [5809:3-OMe-5-ACNH-4-Py], [5810:2-OMe-5-ACNH-4-Py], [5811:6-OMe-5-ACNH-4-Py], [5812:6-ACNH-4-Py], [5813:3-Cl-6-ACNH-4-Py], [5814:2-Cl-6-ACNH-4-Py], [5815:5-Cl-6-ACNH-4-Py], [5816:3-Me-6-ACNH-4-Py], [5817:2-Me-6-ACNH-4-Py], [5818:5-Me-6-ACNH-4-Py], [5819:3-CF3-6-ACNH-4-Py], [5820:2-CF3-6-ACNH-4-Py], [5821:5-CF3-6-ACNH-4-Py], [5822:3-CN-6-ACNH-4-Py], [5823:2-CN-6-ACNH-4-Py], [5824:5-CN-6-ACNH-4-Py], [5825:3-OMe-6-ACNH-4-Py], [5826:2-OMe-6-ACNH-4-Py], [5827:5-OMe-6-ACNH-4-Py], [5828:3-(N-AC-N-Me-N)-4-Py], [5829:2-Cl-3-(N-AC-N-Me-N)-4-Py], [5830:5-Cl-3-(N-AC-N-Me-N)-4-Py], [5831:6-Cl-3-(N-AC-N-Me-N)-4-Py], [5832:2-Me-3-(N-AC-N-Me-N)-4-Py], [5833:5-Me-3-(N-AC-N-Me-N)-4-Py], [5834:6-Me-3-(N-AC-N-Me-N)-4-Py], [5835:2-CF3-3-(N-AC-N-Me-N)-4-Py], [5836:5-CF3-3-(N-AC-N-Me-N)-4-Py], [5837:6-CF3-3-(N-AC-N-Me-N)-4-Py], [5838:2-CN-3-(N-AC-N-Me-N)-4-Py], [5839:5-CN-3-(N-AC-N-Me-N)-4-Py], [5840:6-CN-3-(N-AC-N-Me-N)-4-Py], [5841:2-OMe-3-(N-AC-N-Me-N)-4-Py], [5842:5-OMe-3-(N-AC-N-Me-N)-4-Py], [5843:6-OMe-3-(N-AC-N-Me-N)-4-Py], [5844:2-(N-AC-N-Me-N)-4-Py], [5845:3-Cl-2-(N-AC-N-Me-N)-4-Py], [5846:5-Cl-2-(N-AC-N-Me-N)-4-Py], [5847:6-Cl-2-(N-AC-N-Me-N)-4-Py], [5848:3-Me-2-(N-AC-N-Me-N)-4-Py], [5849:5-Me-2-(N-AC-N-Me-N)-4-Py], [5850:6-Me-2-(N-AC-N-Me-N)-4-Py], [5851:3-CF3-2-(N-AC-N-Me-N)-4-Py], [5852:5-CF3-2-(N-AC-N-Me-N)-4-Py], [5853:6-CF3-2-(N-AC-N-Me-N)-4-Py], [5854:3-CN-2-(N-AC-N-Me-N)-4-Py], [5855:5-CN-2-(N-AC-N-Me-N)-4-Py], [5856:6-CN-2-(N-AC-N-Me-N)-4-Py], [5857:3-OMe-2-(N-AC-N-Me-N)-4-Py], [5858:5-OMe-2-(N-AC-N-Me-N)-4-Py], [5859:6-OMe-2-(N-AC-N-Me-N)-4-Py], [5860:5-(N-AC-N-Me-N)-4-Py], [5861:3-Cl-5-(N-AC-N-Me-N)-4-Py], [5862:2-Cl-5-(N-AC-N-Me-N)-4-Py], [5863:6-Cl-5-(N-AC-N-Me-N)-4-Py], [5864:3-Me-5-(N-AC-N-Me-N)-4-Py], [5865:2-Me-5-(N-AC-N-Me-N)-4-Py], [5866:6-Me-5-(N-AC-N-Me-N)-4-Py], [5867:3-CF3-5-(N-AC-N-Me-N)-4-Py], [5868:2-CF3-5-(N-AC-N-Me-N)-4-Py], [5869:6-CF3-5-(N-AC-N-Me-N)-4-Py], [5870:3-CN-5-(N-AC-N-Me-N)-4-Py], [5871:2-CN-5-(N-AC-N-Me-N)-4-Py], [5872:6-CN-5-(N-AC-N-Me-N)-4-Py], [5873:3-OMe-5-(N-AC-N-Me-N)-4-Py], [5874:2-OMe-5-(N-AC-N-Me-N)-4-Py], [5875:6-OMe-5-(N-AC-N-Me-N)-4-Py], [5876:6-(N-AC-N-Me-N)-4-Py], [5877:3-Cl-6-(N-AC-N-Me-N)-4-Py], [5878:2-Cl-6-(N-AC-N-Me-N)-4-Py], [5879:5-Cl-6-(N-AC-N-Me-N)-4-Py], [5880:3-Me-6-(N-AC-N-Me-N)-4-Py], [5881:2-Me-6-(N-AC-N-Me-N)-4-Py], [5882:5-Me-6-(N-AC-N-Me-N)-4-Py], [5883:3-CF3-6-(N-AC-N-Me-N)-4-Py], [5884:2-CF3-6-(N-AC-N-Me-N)-4-Py], [5885:5-CF3-6-(N-AC-N-Me-N)-4-Py], [5886:3-CN-6-(N-AC-N-Me-N)-4-Py], [5887:2-CN-6-(N-AC-N-Me-N)-4-Py], [5888:5-CN-6-(N-AC-N-Me-N)-4-Py], [5889:3-OMe-6-(N-AC-N-Me-N)-4-Py], [5890:2-OMe-6-(N-AC-N-Me-N)-4-Py], [5891:5-OMe-6-(N-AC-N-Me-N)-4-Py], [5892:3-AC-4-Py], [5893:2-Cl-3-AC-4-Py], [5894:5-Cl-3-AC-4-Py], [5895:6-Cl-3-AC-4-Py], [5896:2-Me-3-AC-4-Py], [5897:5-Me-3-AC-4-Py], [5898:6-Me-3-AC-4-Py], [5899:2-CF3-3-AC-4-Py], [5900:5-CF3-3-AC-4-Py], [5901:6-CF3-3-AC-4-Py], [5902:2-CN-3-AC-4-Py], [5903:5-CN-3-AC-4-Py], [5904:6-CN-3-AC-4-Py], [5905:2-OMe-3-AC-4-Py], [5906:5-OMe-3-AC-4-Py], [5907:6-OMe-3-AC-4-Py], [5908:2-AC-4-Py], [5909:3-Cl-2-AC-4-Py], [5910:5-Cl-2-AC-4-Py], [5911:6-Cl-2-AC-4-Py], [5912:3-Me-2-AC-4-Py], [5913:5-Me-2-AC-4-Py], [5914:6-Me-2-AC-4-Py], [5915:3-CF3-2-AC-4-Py], [5916:5-CF3-2-AC-4-Py], [5917:6-CF3-2-AC-4-Py], [5918:3-CN-2-AC-4-Py], [5919:5-CN-2-AC-4-Py], [5920:6-CN-2-AC-4-Py], [5921:3-OMe-2-AC-4-Py], [5922:5-OMe-2-AC-4-Py], [5923:6-OMe-2-AC-4-Py], [5924:5-AC-4-Py], [5925:3-Cl-5-AC-4-Py], [5926:2-Cl-5-AC-4-Py], [5927:6-Cl-5-AC-4-Py], [5928:3-Me-5-AC-4-Py], [5929:2-Me-5-AC-4-Py], [5930:6-Me-5-AC-4-Py], [5931:3-CF3-5-AC-4-Py], [5932:2-CF3-5-AC-4-Py], [5933:6-CF3-5-AC-4-Py], [5934:3-CN-5-AC-4-Py], [5935:2-CN-5-AC-4-Py], [5936:6-CN-5-AC-4-Py], [5937:3-OMe-5-AC-4-Py], [5938:2-OMe-5-AC-4-Py], [5939:6-OMe-5-AC-4-Py], [5940:6-AC-4-Py], [5941:3-Cl-6-AC-4-Py], [5942:2-Cl-6-AC-4-Py], [5943:5-Cl-6-AC-4-Py], [5944:3-Me-6-AC-4-Py], [5945:2-Me-6-AC-4-Py], [5946:5-Me-6-AC-4-Py], [5947:3-CF3-6-AC-4-Py], [5948:2-CF3-6-AC-4-Py], [5949:5-CF3-6-AC-4-Py], [5950:3-CN-6-AC-4-Py], [5951:2-CN-6-AC-4-Py], [5952:5-CN-6-AC-4-Py], [5953:3-OMe-6-AC-4-Py], [5954:2-OMe-6-AC-4-Py], [5955:5-OMe-6-AC-4-Py], [5956:1,2-(methylenedioxy)phenyl-4-yl], [5957:2,3-dihydrobenzofuran-5-yl], [5958:2,3-dihydrobenzofuran-6-yl], [5959:1,3-dihydroisobenzofuran-5-yl], [5960:benzofuran-5-yl], [5961:benzofuran-6-yl], [5962:2,3-dihydrobenzothiophen-5-yl], [5963:2,3-dihydrobenzothiophen-6-yl], [5964:1,3-dihydroisobenzothiophen-5-yl], [5965:benzothiophen-5-yl], [5966:benzothiophen-6-yl], [5967:benzodioxane-4-yl], [5968:chroman-6-yl], [5969:chroman-7-yl], [5970:isochroman-6-yl], [5971:isochroman-7-yl], [5972:phenyl], [5973:2-fluorophenyl], [5974:3-fluorophenyl], [5975:4-fluorophenyl], [5976:2,4-difluorophenyl], [5977:2,4,6-trifluorophenyl], [5978:2,3,4,5,6-pentafluorophenyl], [5979:2,3-difluorophenyl], [5980:2-chlorophenyl], [5981:3-chlorophenyl], [5982:4-chlorophenyl], [5983:2,3-dichlorophenyl], [5984:2,4-dichlorophenyl], [5985:2,5-dichlorophenyl], [5986:2,6-dichlorophenyl], [5987:3,4-dichlorophenyl], [5988:3,5-dichlorophenyl], [5989:2,3,4-trichlorophenyl], [5990:2,3,5-trichlorophenyl], [5991:2,3,6-trichlorophenyl], [5992:2,4,5-trichlorophenyl], [5993:2,4,6-trichlorophenyl], [5994:3,4,5-trichlorophenyl], [5995:2,3,4,6-tetrachlorophenyl], [5996:2,3,5,6-tetrachlorophenyl], [5997:2,3,4,5,6-pentachlorophenyl], [5998:2-bromophenyl], [5999:3-bromophenyl], [6000:4-bromophenyl],

[6001:2,4-dibromophenyl], [6002:2,5-dibromophenyl], [6003:2,6-dibromophenyl], [6004:2,4,6-tribromophenyl], [6005:2,3,4,5,6-pentabromophenyl], [6006:2-iodophenyl], [6007:3-iodophenyl], [6008:4-iodophenyl], [6009:2,4-diiodophenyl], [6010:2-chloro-3-fluorophenyl], [6011:2-chloro-4-fluorophenyl], [6012:2-chloro-5-fluorophenyl], [6013:2-chloro-6-fluorophenyl], [6014:2-chloro-3-bromophenyl], [6015:2-chloro-4-bromophenyl], [6016:2-chloro-5-bromophenyl], [6017:2-chloro-6-bromophenyl], [6018:2-bromo-3-chlorophenyl], [6019:2-bromo-4-chlorophenyl], [6020:2-bromo-5-chlorophenyl], [6021:2-bromo-3-fluorophenyl], [6022:2-bromo-4-fluorophenyl], [6023:2-bromo-5-fluorophenyl], [6024:2-bromo-6-fluorophenyl], [6025:2-fluoro-3-chlorophenyl], [6026:2-fluoro-4-chlorophenyl], [6027:2-fluoro-5-chlorophenyl], [6028:2-fluoro-4-bromophenyl], [6029:3-chloro-4-fluorophenyl], [6030:3-chloro-5-fluorophenyl], [6031:3-chloro-4-bromophenyl], [6032:3-chloro-5-bromophenyl], [6033:3-fluoro-4-chlorophenyl], [6034:3-fluoro-4-bromophenyl], [6035:3-bromo-4-chlorophenyl], [6036:3-bromo-4-fluorophenyl], [6037:2,6-dichloro-4-bromophenyl], [6038:2,3-difluoro-4-chlorophenyl], [6039:2,6-difluoro-4-chlorophenyl], [6040:2,5-difluoro-4-chlorophenyl], [6041:3,5-difluoro-4-chlorophenyl], [6042:2,3,5-trifluoro-4-chlorophenyl], [6043:2,3,6-trifluoro-4-chlorophenyl], [6044:2,3,5-tetrafluoro-4-chlorophenyl], [6045:2-fluoro-4-bromophenyl], [6046:2,3-difluoro-4-bromophenyl], [6047:2,6-difluoro-4-bromophenyl], [6048:2,5-difluoro-4-bromophenyl], [6049:3,5-difluoro-4-bromophenyl], [6050:2,3,5-trifluoro-4-bromophenyl], [6051:2,3,6-trifluoro-4-bromophenyl], [6052:2,3,5,6-tetrafluoro-4-bromophenyl], [6053:2-fluoro-4-iodophenyl], [6054:3-fluoro-4-iodophenyl], [6055:2,3-difluoro-4-iodophenyl], [6056:2,6-difluoro-4-iodophenyl], [6057:2,5-difluoro-4-iodophenyl], [6058:3,5-difluoro-4-iodophenyl], [6059:2,3,5-trifluoro-4-iodophenyl], [6060:2,3,6-trifluoro-4-iodophenyl], [6061:2,3,5,6-tetrafluoro-4-iodophenyl], [6062:2-methylphenyl], [6063:3-methylphenyl], [6064:4-methylphenyl], [6065:2,3-dimethylphenyl], [6066:2,4-dimethylphenyl], [6067:2,5-dimethylphenyl], [6068:2,6-dimethylphenyl], [6069:3,4-dimethylphenyl], [6070:3,5-dimethylphenyl], [6071:2,3,5-trimethylphenyl], [6072:2,3,4-trimethylphenyl], [6073:2,3,6-trimethylphenyl], [6074:2,4,5-trimethylphenyl], [6075:2,4,6-trimethylphenyl], [6076:3,4,5-trimethylphenyl], [6077:2,3,4,6-tetramethylphenyl], [6078:2,3,5,6-tetramethylphenyl], [6079:2,3,4,5,6-pentamethylphenyl], [6080:2-ethylphenyl], [6081:3-ethylphenyl], [6082:4-ethylphenyl], [6083:2,4-diethylphenyl], [6084:2,6-diethylphenyl], [6085:3,5-diethylphenyl], [6086:2,4,6-triethylphenyl], [6087:2-n-propylphenyl], [6088:3-n-propylphenyl], [6089:4-n-propylphenyl], [6090:2-isopropylphenyl], [6091:3-isopropylphenyl], [6092:4-isopropylphenyl], [6093:2,4-diisopropylphenyl], [6094:2,6-diisopropylphenyl], [6095:3,5-diisopropylphenyl], [6096:2-s-butylphenyl], [6097:3-s-butylphenyl], [6098:4-s-butylphenyl], [6099:2-t-butylphenyl], [6100:3-t-butylphenyl], [6101:4-t-butylphenyl], [6102:4-n-butylphenyl], [6103:4-n-nonylphenyl], [6104:2-methyl-4-t-butylphenyl], [6105:2-methyl-6-t-butylphenyl], [6106:2-methyl-4-isopropylphenyl], [6107:2-methyl-5-isopropylphenyl], [6108:3-methyl-4-isopropylphenyl], [6109:2-cyclohexylphenyl], [6110:3-cyclohexylphenyl], [6111:4-cyclohexylphenyl], [6112:4-cyclopropylphenyl], [6113:4-cyclobutylphenyl], [6114:4-cyclopentylphenyl], [6115:2-chloro-4-phenylphenyl], [6116:2-bromo-4-phenylphenyl], [6117:4-hydroxyphenyl], [6118:2-methoxyphenyl], [6119:3-methoxyphenyl], [6120:4-methoxyphenyl], [6121:2-ethoxyphenyl], [6122:3-ethoxyphenyl], [6123:4-ethoxyphenyl], [6124:2-n-propyloxyphenyl], [6125:3-n-propyloxyphenyl], [6126:4-n-propyloxyphenyl], [6127:2-isopropyloxyphenyl], [6128:3-isopropyloxyphenyl], [6129:4-isopropyloxyphenyl], [6130:2-n-hexyloxyphenyl], [6131:3-n-hexyloxyphenyl], [6132:4-n-hexyloxyphenyl], [6133:2-benzyloxyphenyl], [6134:3-benzyloxyphenyl], [6135:4-benzyloxyphenyl], [6136:2,3-dimethoxyphenyl], [6137:2,4-dimethoxyphenyl], [6138:2,5-dimethoxyphenyl], [6139:2,6-dimethoxyphenyl], [6140:3,4-dimethoxyphenyl], [6141:3,5-dimethoxyphenyl], [6142:2-t-butoxyphenyl], [6143:3-t-butoxyphenyl], [6144:4-t-butoxyphenyl], [6145:3-(3'-chlorophenyl)phenyl], [6146:4-(4'-chlorophenyl)phenyl], [6147:2-phenoxyphenyl], [6148:3-phenoxyphenyl], [6149:4-phenoxyphenyl], [6150:2-(2'-fluorophenoxy)phenyl], [6151:3-(3'-chlorophenoxy)phenyl], [6152:4-(4'-chlorophenoxy)phenyl], [6153:2,3,6-trimethyl-4-fluorophenyl], [6154:2,3,6-trimethyl-4-chlorophenyl], [6155:2,3,6-trimethyl-4-bromophenyl], [6156:2,4-dimethyl-6-fluorophenyl], [6157:2,4-dimethyl-6-chlorophenyl], [6158:2,4-dimethyl-6-bromophenyl], [6159:2-isopropyl-4-chloro-5-methylphenyl], [6160:2-chloro-4-nitrophenyl], [6161:2-nitro-4-chlorophenyl], [6162:2-methoxy-5-nitrophenyl], [6163:2,4-dichloro-5-nitrophenyl], [6164:2,4-dichloro-6-nitrophenyl], [6165:2,6-dichloro-4-nitrophenyl], [6166:2,6-dibromo-4-nitrophenyl], [6167:2,6-diiodo-4-nitrophenyl], [6168:2-methyl-5-isopropyl-4-chlorophenyl], [6169:2-methoxycarbonylphenyl], [6170:3-methoxycarbonylphenyl], [6171:4-methoxycarbonylphenyl], [6172:4-acetoxyphenyl], [6173:2-methoxymethylphenyl], [6174:3-methoxymethylphenyl], [6175:4-methoxymethylphenyl], [6176:2-phenylphenyl], [6177:3-phenylphenyl], [6178:4-phenylphenyl], [6179:2-(2'-fluorophenyl)phenyl], [6180:2-methyl-5-bromophenyl], [6181:2-methyl-6-bromophenyl], [6182:2-chloro-3-methylphenyl], [6183:2-chloro-4-methylphenyl], [6184:2-chloro-5-methylphenyl], [6185:2-fluoro-3-methylphenyl], [6186:2-fluoro-4-methylphenyl], [6187:2-fluoro-5-methylphenyl], [6188:2-bromo-3-methylphenyl], [6189:2-bromo-4-methylphenyl], [6190:2-bromo-5-methylphenyl], [6191:3-methyl-4-chlorophenyl], [6192:3-methyl-5-chlorophenyl], [6193:3-methyl-4-fluorophenyl], [6194:3-methyl-5-fluorophenyl], [6195:3-methyl-4-bromophenyl], [6196:3-methyl-5-bromophenyl], [6197:3-fluoro-4-methylphenyl], [6198:3-chloro-4-methylphenyl], [6199:3-bromo-4-methylphenyl], [6200:2-chloro-4,5-dimethylphenyl], [6201:2-bromo-4,5-dimethylphenyl], [6202:2-chloro-3,5-dimethylphenyl], [6203:2-bromo-3,5-dimethylphenyl], [6204:2,6-dibromo-4-methylphenyl], [6205:2,4-dichloro-6-methylphenyl], [6206:2,4-difluoro-6-methylphenyl], [6207:2,4-dibromo-6-methylphenyl], [6208:2,6-dimethyl-4-fluorophenyl], [6209:2,6-dimethyl-4-chlorophenyl], [6210:2,6-dimethyl-4-bromophenyl], [6211:3,5-dimethyl-4-fluorophenyl], [6212:3,5-dimethyl-4-chlorophenyl], [6213:3,5-dimethyl-4-bromophenyl], [6214:2,3-difluoro-4-methylphenyl], [6215:2,5-difluoro-4-methylphenyl], [6216:3,5-difluoro-4-methylphenyl], [6217:2,3,5-trifluoro-4-methylphenyl], [6218:2,3,6-trifluoro-4-methylphenyl], [6219:2,3,5,6-tetrafluoro-4-methylphenyl], [6220:2-fluoro-4-ethylphenyl], [6221:3-fluoro-4-ethylphenyl], [6222:2,3-difluoro-4-ethylphenyl], [6223:2,6-difluoro-4-ethylphenyl], [6224:2,5-difluoro-4-ethylphenyl], [6225:3,5-difluoro-4-ethylphenyl], [6226:2,3,5-trifluoro-4-ethylphenyl], [6227:2,3,6-trifluoro-4-ethylphenyl], [6228:2,3,5,6-tetrafluoro-4-ethylphenyl], [6229:2-trifluoromethylphenyl], [6230:3-trifluoromethylphenyl], [6231:4-trifluoromethylphenyl], [6232:4-(2,2,2-trifluoro-1-trifluoromethyl-ethyl)phenyl], [6233:2-trifluoromethoxyphenyl], [6234:3-trifluoromethoxyphenyl], [6235:4-trifluoromethoxyphenyl], [6236:4-(2,2-difluoroethoxy)phenyl], [6237:4-(2,2,2-trifluoroethoxy)phenyl], [6238:2-nitrophenyl], [6239:3-nitrophenyl], [6240:4-nitrophenyl], [6241:2-cyanophenyl], [6242:3-cyanophenyl], [6243:4-cyanophenyl], [6244:2-methyl-3-chlorophenyl], [6245:2-methyl-4-chlorophenyl], [6246:2-methyl-5-chlorophenyl], [6247:2-methyl-6-chlorophenyl], [6248:2-methyl-3-fluorophenyl], [6249:2-methyl-4-fluorophenyl], [6250:2-methyl-5-fluorophenyl], [6251:2-methyl-6-fluorophenyl], [6252:2-methyl-3-bromophenyl], [6253:2-methyl-4-bromophenyl], [6254:4-methylthiophenyl], [6255:4-methylsulfonylphenyl], [6256:4-methylsulfinylphenyl], [6257:4-trifluoromethylthiophenyl], [6258:4-ethynylphenyl], [6259:4-(1-propynyl)phenyl], [6260:4-vinylphenyl], [6261:4-(2,2-dichlorovinyl)phenyl], [6262:4-(2,2-difluorovinyl)phenyl], [6263:cyclohexyl], [6264:2-chlorocyclohexyl], [6265:3-chlorocyclohexyl], [6266:4-chlorocyclohexyl], [6267:4,4-dichlorocyclohexyl], [6268:2-bromocyclohexyl], [6269:3-bromocyclohexyl], [6270:4-bromocyclohexyl], [6271:4,4-dibromocyclohexyl], [6272:2-iodocyclohexyl], [6273:3-iodocyclohexyl], [6274:4-iodocyclohexyl], [6275:2-fluorocyclohexyl], [6276:3-fluorocyclohexyl], [6277:4-fluorocyclohexyl], [6278:4,4-difluorocyclohexyl], [6279:4-methylcyclohexyl], [6280:4-ethylcyclohexyl], [6281:1-cyclohexenyl], [6282:2-cyclohexenyl], [6283:3-cyclohexenyl], [6284:2-chloro-1-cyclohexenyl], [6285:3-chloro-1-cyclohexenyl], [6286:4-chloro-1-cyclohexenyl], [6287:5-chloro-1-cyclohexenyl], [6288:6-chloro-1-cyclohexenyl], [6289:1-chloro-2-cyclohexenyl], [6290:2-chloro-2-cyclohexenyl], [6291:3-chloro-2-cyclohexenyl], [6292:4-chloro-2-cyclohexenyl], [6293:5-chloro-2-cyclohexenyl], [6294:6-chloro-2-cyclohexenyl], [6295:1-chloro-3-cyclohexenyl], [6296:2-chloro-3-cyclohexenyl], [6297:3-chloro-3-cyclohexenyl], [6298:4-chloro-3-cyclohexenyl], [6299:5-chloro-3-cyclohexenyl], [6300:6-chloro-3-cyclohexenyl],
[6301:4-bromo-1-cyclohexenyl], [6302:4-bromo-2-cyclohexenyl], [6303:4-bromo-3-cyclohexenyl], [6304:4-methyl-1-cyclohexenyl], [6305:4-methyl-2-cyclohexenyl], [6306:4-methyl-3-cyclohexenyl], [6307:4-ethyl-1-cyclohexenyl], [6308:4-ethyl-2-cyclohexenyl], [6309:4-ethyl-3-cyclohexenyl], [6310:trifluoromethyl], [6311:tert-butyl], [6312:3-fluoro-2-methoxyphenyl], [6313:4-fluoro-2-methoxyphenyl], [6314:5-fluoro-2-methoxyphenyl], [6315:6-fluoro-2-methoxyphenyl], [6316:3-chloro-2-methoxyphenyl], [6317:4-chloro-2-methoxyphenyl], [6318:5-chloro-2-methoxyphenyl], [6319:6-chloro-2-methoxyphenyl], [6320:3-bromo-2-methoxyphenyl], [6321:4-bromo-2-methoxyphenyl], [6322:5-bromo-2-methoxyphenyl], [6323:6-bromo-2-methoxyphenyl], [6324:3-iodo-2-methoxyphenyl], [6325:4-iodo-2-methoxyphenyl], [6326:5-iodo-2-methoxyphenyl], [6327:6-iodo-2-methoxyphenyl], [6328:2,3-dimethoxyphenyl], [6329:2,4-dimethoxyphenyl], [6330:2,5-dimethoxyphenyl], [6331:2,6-dimethoxyphenyl], [6332:3-methyl-2-methoxyphenyl], [6333:4-methyl-2-methoxyphenyl], [6334:5-methyl-2-methoxyphenyl], [6335:6-methyl-2-methoxyphenyl], [6336:3-ethyl-2-methoxyphenyl], [6337:4-ethyl-2-methoxyphenyl], [6338:5-ethyl-2-methoxyphenyl], [6339:6-ethyl-2-methoxyphenyl], [6340:3-trifluoromethoxy-2-methoxyphenyl], [6341:4-trifluoromethoxy-2-methoxyphenyl], [6342:5-trifluoromethoxy-2-methoxyphenyl], [6343:6-trifluoromethoxy-2-methoxyphenyl], [6344:3-trifluoromethyl-2-methoxyphenyl], [6345:4-trifluoromethyl-2-methoxyphenyl], [6346:5-trifluoromethyl-2-methoxyphenyl], [6347:6-trifluoromethyl-2-methoxyphenyl], [6348:3-methylthio-2-methoxyphenyl], [6349:4-methylthio-2-methoxyphenyl], [6350:5-methylthio-2-methoxyphenyl], [6351:6-methylthio-2-methoxyphenyl], [6352:3-trifluoromethylthio-2-methoxyphenyl], [6353:4-trifluoromethylthio-2-methoxyphenyl], [6354:5-trifluoromethylthio-2-methoxyphenyl], [6355:6-trifluoromethylthio-2-methoxyphenyl], [6356:3-ethynyl-2-methoxyphenyl], [6357:4-ethynyl-2-methoxyphenyl], [6358:5-ethynyl-2-methoxyphenyl], [6359:6-ethynyl-2-methoxyphenyl], [6360:3-cyclopropyl-2-methoxyphenyl], [6361:4-cyclopropyl-2-methoxyphenyl], [6362:5-cyclopropyl-2-methoxyphenyl], [6363:6-cyclopropyl-2-methoxyphenyl], [6364:3-cyclopropyloxy-2-methoxyphenyl], [6365:4-cyclopropyloxy-2-methoxyphenyl], [6366:5-cyclopropyloxy-2-methoxyphenyl], [6367:6-cyclopropyloxy-2-methoxyphenyl], [6368:2-ethoxy-3-fluorophenyl], [6369:2-ethoxy-4-fluorophenyl], [6370:2-ethoxy-5-fluorophenyl], [6371:2-ethoxy-6-fluorophenyl], [6372:3-chloro-2-ethoxyphenyl], [6373:4-chloro-2-ethoxyphenyl], [6374:5-chloro-2-ethoxyphenyl], [6375:6-chloro-2-ethoxyphenyl], [6376:3-bromo-2-ethoxyphenyl], [6377:4-bromo-2-ethoxyphenyl], [6378:5-bromo-2-ethoxyphenyl], [6379:6-bromo-2-ethoxyphenyl], [6380:2-ethoxy-3-iodophenyl], [6381:2-ethoxy-4-iodophenyl], [6382:2-ethoxy-5-iodophenyl], [6383:2-ethoxy-6-iodophenyl], [6384:2,3-diethoxyphenyl], [6385:2,4-diethoxyphenyl], [6386:2,5-diethoxyphenyl], [6387:2,6-diethoxyphenyl], [6388:2-ethoxy-3-methylphenyl], [6389:2-ethoxy-4-methylphenyl], [6390:2-ethoxy-5-methylphenyl], [6391:2-ethoxy-6-methylphenyl], [6392:3-ethyl-2-ethoxyphenyl], [6393:4-ethyl-2-ethoxyphenyl], [6394:5-ethyl-2-ethoxyphenyl], [6395:6-ethyl-2-ethoxyphenyl], [6396:2-ethoxy-3-trifluoromethoxyphenyl], [6397:2-ethoxy-4-trifluoromethoxyphenyl], [6398:2-ethoxy-5-trifluoromethoxyphenyl], [6399:2-ethoxy-6-trifluoromethoxyphenyl], [6400:2-ethoxy-3-trifluoromethylphenyl], [6401:2-ethoxy-4-trifluoromethylphenyl], [6402:2-ethoxy-5-trifluoromethylphenyl], [6403:2-ethoxy-6-trifluoromethylphenyl], [6404:2-ethoxy-3-methylthiophenyl], [6405:2-ethoxy-4-methylthiophenyl], [6406:2-ethoxy-5-methylthiophenyl], [6407:2-ethoxy-6-methylthiophenyl], [6408:2-ethoxy-3-trifluoromethylthiophenyl], [6409:2-ethoxy-4-trifluoromethylthiophenyl], [6410:2-ethoxy-5-trifluoromethylthiophenyl], [6411:2-ethoxy-6-trifluoromethylthiophenyl], [6412:3-ethynyl-2-ethoxyphenyl], [6413:4-ethynyl-2-ethoxyphenyl], [6414:5-ethynyl-2-ethoxyphenyl], [6415:6-ethynyl-2-ethoxyphenyl], [6416:3-cyclopropyl-2-ethoxyphenyl], [6417:4-cyclopropyl-2-ethoxyphenyl], [6418:5-cyclopropyl-2-ethoxyphenyl], [6419:6-cyclopropyl-2-ethoxyphenyl], [6420:3-cyclopropyloxy-2-ethoxyphenyl], [6421:4-cyclopropyloxy-2-ethoxyphenyl], [6422:5-cyclopropyloxy-2-ethoxyphenyl], [6423:6-cyclopropyloxy-2-ethoxyphenyl], [6424:3-methoxy-2-methylphenyl], [6425:4-methoxy-2-methylphenyl], [6426:5-methoxy-2-methylphenyl], [6427:6-methoxy-2-methylphenyl], [6428:3-ethoxy-2-methylphenyl], [6429:4-ethoxy-2-methylphenyl], [6430:5-ethoxy-2-methylphenyl], [6431:6-ethoxy-2-methylphenyl], [6432:3-ethyl-2-methylphenyl], [6433:4-ethyl-2-methylphenyl], [6434:5-ethyl-2-methylphenyl], [6435:6-ethyl-2-methylphenyl], [6436:3-trifluoromethoxy-2-methylphenyl], [6437:4-trifluoromethoxy-2-methylphenyl], [6438:5-trifluoromethoxy-2-methylphenyl], [6439:6-trifluoromethoxy-2-methylphenyl], [6440:3-trifluoromethyl-2-methylphenyl], [6441:4-trifluoromethyl-2-methylphenyl], [6442:5-trifluoromethyl-2-methylphenyl], [6443:6-trifluoromethyl-2-methylphenyl], [6444:3-methylthio-2-methylphenyl], [6445:4-methylthio- 2-methylphenyl], [6446:5-methylthio-2-methylphenyl], [6447:6-methylthio-2-methylphenyl], [6448:4-fluoro-2-isopropyloxyphenyl], [6449:4-chloro-2-isopropyloxyphenyl], [6450:4-bromo-2-isopropyloxyphenyl], [6451:4-iodo-2-isopropyloxyphenyl], [6452:4-methyl-2-isopropyloxyphenyl], [6453:4-ethyl-2-isopropyloxyphenyl], [6454:4-methoxy-2-isopropyloxyphenyl], [6455:4-ethoxy-2-isopropyloxyphenyl], [6456:4-trifluoromethyl-2-isopropyloxyphenyl], [6457:4-trifluoromethoxy-2-isopropyloxyphenyl], [6458:4-methylthio-2-isopropyloxyphenyl], [6459:4-cyclopropyl-2-isopropyloxyphenyl], [6460:4-fluoro-2-cyclopropyloxyphenyl], [6461:4-chloro-2-cyclopropyloxyphenyl], [6462:4-bromo-2-cyclopropyloxyphenyl], [6463:4-iodo-2-cyclopropyloxyphenyl], [6464:4-methyl-2-cyclopropyloxyphenyl], [6465:4-ethyl-2-cyclopropyloxyphenyl], [6466:4-methoxy-2-cyclopropyloxyphenyl], [6467:4-ethoxy-2-cyclopropyloxyphenyl], [6468:4-trifluoromethyl-2-cyclopropyloxyphenyl], [6469:4-trifluoromethoxy-2-cyclopropyloxyphenyl], [6470:4-methylthio-2-cyclopropyloxyphenyl], [6471:4-cyclopropyl-2-cyclopropyloxyphenyl], [6472:3,4-difluoro-2-methoxyphenyl], [6473:4,5-difluoro-2-methoxyphenyl], [6474:4,6-difluoro-2-methoxyphenyl], [6475:3,4,5-trifluoro-2-methoxyphenyl], [6476:3,4,5,6-tetrafluoro-2-methoxyphenyl], [6477:4-chloro-3-fluoro-2-methoxyphenyl], [6478:4-chloro-5-fluoro-2-methoxyphenyl], [6479:4-chloro-6-fluoro-2-methoxyphenyl], [6480:4-bromo-3-fluoro-2-methoxyphenyl], [6481:4-bromo-5-fluoro-2-methoxyphenyl], [6482:4-bromo-6-fluoro-2-methoxyphenyl], [6483:3,4-difluoro-2-ethoxyphenyl], [6484:4,5-difluoro-2-ethoxyphenyl], [6485:4,6-difluoro-2-ethoxyphenyl], [6486:3,4,5-trifluoro-2-ethoxyphenyl], [6487:3,4,5,6-tetrafluoro-2-ethoxyphenyl], [6488:4-chloro-3-fluoro-2-ethoxyphenyl], [6489:4-chloro-5-fluoro-2-ethoxyphenyl], [6490:4-chloro-6-fluoro-2-ethoxyphenyl], [6491:4-bromo-3-fluoro-2-ethoxyphenyl], [6492:4-bromo-5-fluoro-2-ethoxyphenyl], [6493:4-bromo-6-fluoro-2-ethoxyphenyl], [6494:3,4-difluoro-2-isopropyloxyphenyl], [6495:4,5-difluoro-2-isopropyloxyphenyl], [6496:4,6-difluoro-2-isopropyloxyphenyl], [6497:3,4,5-trifluoro-2-isopropyloxyphenyl], [6498:3,4,5,6-tetrafluoro-2-isopropyloxyphenyl], [6499:4-chloro-3-fluoro-2-isopropyloxyphenyl], [6500:4-chloro-5-fluoro-2-isopropyloxyphenyl], [6501:4-chloro-6-fluoro-2-isopropyloxyphenyl], [6502:4-bromo-3-fluoro-2-isopropyloxyphenyl], [6503:4-bromo-5-fluoro-2-isopropyloxyphenyl], [6504:4-bromo-6-fluoro-2-isopropyloxyphenyl], [6505:3,4-difluoro-2-cyclopropyloxyphenyl], [6506:4,5-difluoro-2-cyclopropyloxyphenyl], [6507:4,6-difluoro-2-cyclopropyloxyphenyl], [6508:3,4,5-trifluoro-2-cyclopropyloxyphenyl], [6509:3,4,5,6-tetrafluoro-2-cyclopropyloxyphenyl], [6510:4-chloro-3-fluoro-2-cyclopropyloxyphenyl], [6511:4-chloro-5-fluoro-2-cyclopropyloxyphenyl], [6512:4-chloro-6-fluoro-2-cyclopropyloxyphenyl], [6513:4-bromo-3-fluoro-2-cyclopropyloxyphenyl], [6514:4-bromo-5-fluoro-2-cyclopropyloxyphenyl], [6515:4-bromo-6-fluoro-2-cyclopropyloxyphenyl], [6516:3-ethynyl-2-methylphenyl], [6517:4-ethynyl-2-methylphenyl], [6518:5-ethynyl-2-methylphenyl], [6519:6-ethynyl-2-methylphenyl], [6520:3-cyclopropyl-2-methylphenyl], [6521:4-cyclopropyl-2-methylphenyl], [6522:5-cyclopropyl-2-methylphenyl], [6523:6-cyclopropyl-2-methylphenyl], [6524:3-cyclopropyloxy-2-methylphenyl], [6525:4-cyclopropyloxy-2-methylphenyl], [6526:5-cyclopropyloxy-2-methylphenyl], [6527:6-cyclopropyloxy-2-methylphenyl], [6528:3-methoxy-2-fluorophenyl], [6529:4-methoxy-2-fluorophenyl], [6530:5-methoxy-2-fluorophenyl], [6531:6-methoxy-2-fluorophenyl], [6532:3-ethoxy-2-fluorophenyl], [6533:4-ethoxy-2-fluorophenyl], [6534:5-ethoxy-2-fluorophenyl], [6535:6-ethoxy-2-fluorophenyl], [6536:3-ethyl-2-fluorophenyl], [6537:5-ethyl-2-fluorophenyl], [6538:6-ethyl-2-fluorophenyl], [6539:2-fluoro-3-trifluoromethoxyphenyl], [6540:2-fluoro-4-trifluoromethoxyphenyl], [6541:2-fluoro-5-trifluoromethoxyphenyl], [6542:2-fluoro-6-trifluoromethoxyphenyl], [6543:2-fluoro-3-trifluoromethylphenyl], [6544:2-fluoro-4-trifluoromethylphenyl], [6545:2-fluoro-5-trifluoromethylphenyl], [6546:2-fluoro-6-trifluoromethylphenyl], [6547:2-fluoro-3-fluorothiophenyl], [6548:2-fluoro-4-fluorothiophenyl], [6549:2-fluoro-5-fluorothiophenyl], [6550:2-fluoro-6-fluorothiophenyl], [6551:3-ethynyl-2-fluorophenyl], [6552:4-ethynyl-2-fluorophenyl], [6553:5-ethynyl-2-fluorophenyl], [6554:6-ethynyl-2-fluorophenyl], [6555:3-cyclopropyl-2-fluorophenyl], [6556:4-cyclopropyl-2-fluorophenyl], [6557:5-cyclopropyl-2-fluorophenyl], [6558:6-cyclopropyl-2-fluorophenyl], [6559:3-cyclopropyloxy-2-fluorophenyl], [6560:4-cyclopropyloxy-2-fluorophenyl], [6561:5-cyclopropyloxy-2-fluorophenyl], [6562:6-cyclopropyloxy-2-fluorophenyl], [6563:2-ethyl-3-fluorophenyl], [6564:2-ethyl-4-fluorophenyl], [6565:2-ethyl-5-fluorophenyl], [6566:2-ethyl-6-fluorophenyl], [6567:3-chloro-2-ethylphenyl], [6568:4-chloro-2-ethylphenyl], [6569:5-chloro-2-ethylphenyl], [6570:6-chloro-2-ethylphenyl], [6571:3-bromo-2-ethylphenyl], [6572:4-bromo-2-ethylphenyl], [6573:5-bromo-2-ethylphenyl], [6574:6-bromo-2-ethylphenyl], [6575:2-ethyl-3-iodophenyl], [6576:2-ethyl-4-iodophenyl], [6577:2-ethyl-5-iodophenyl], [6578:2-ethyl-6-iodophenyl], [6579:2-ethyl-3-ethoxyphenyl], [6580:2-ethyl-4-ethoxyphenyl], [6581:2-ethyl-5-ethoxyphenyl], [6582:2-ethyl-6-ethoxyphenyl], [6583:2-ethyl-3-methylphenyl], [6584:2-ethyl-4-methylphenyl], [6585:2-ethyl-5-methylphenyl], [6586:2-ethyl-6-methylphenyl], [6587:2,3-diethylphenyl], [6588:2,4-diethylphenyl], [6589:2,5-diethylphenyl], [6590:2,6-diethylphenyl], [6591:2-ethyl-3-trifluoromethoxyphenyl], [6592:2-ethyl-4-trifluoromethoxyphenyl], [6593:2-ethyl-5-trifluoromethoxyphenyl], [6594:2-ethyl-6-trifluoromethoxyphenyl], [6595:2-ethyl-3-trifluoromethylphenyl], [6596:2-ethyl-4-trifluoromethylphenyl], [6597:2-ethyl-5-trifluoromethylphenyl], [6598:2-ethyl-6-trifluoromethylphenyl], [6599:2-ethyl-3-methylthiophenyl], [6600:2-ethyl-4-methylthiophenyl], [6601:2-ethyl-5-methylthiophenyl], [6602:2-ethyl-6-methylthiophenyl], [6603:2-ethyl-3-trifluoromethylthiophenyl], [6604:2-ethyl-4-trifluoromethylthiophenyl], [6605:2-ethyl-5-trifluoromethylthiophenyl], [6606:2-ethyl-6-trifluoromethylthiophenyl], [6607:3-ethynyl-2-ethylphenyl], [6608:4-ethynyl-2-ethylphenyl], [6609:5-ethynyl-2-ethylphenyl], [6610:6-ethynyl-2-ethylphenyl], [6611:3-cyclopropyl-2-ethylphenyl], [6612:4-cyclopropyl-2-ethylphenyl], [6613:5-cyclopropyl-2-ethylphenyl], [6614:6-cyclopropyl-2-ethylphenyl], [6615:3-cyclopropyloxy-2-ethylphenyl], [6616:4-cyclopropyloxy-2-ethylphenyl], [6617:5-cyclopropyloxy-2-ethylphenyl], [6618:6-cyclopropyloxy-2-ethylphenyl], [6619:3-fluoro-2-trifluoromethylphenyl], [6620:4-fluoro-2-trifluoromethylphenyl], [6621:5-fluoro-2-trifluoromethylphenyl], [6622:6-fluoro-2-trifluoromethylphenyl], [6623:3-chloro-2-trifluoromethylphenyl], [6624:4-chloro-2-trifluoromethylphenyl], [6625:5-chloro-2-trifluoromethylphenyl], [6626:6-chloro-2- trifluoromethylphenyl], [6628:4-bromo-2-trifluoromethylphenyl], [6629:5-bromo-2-trifluoromethylphenyl], [6630:6-bromo-2-trifluoromethylphenyl], [6631:3-iodo-2-trifluoromethylphenyl], [6632:4-iodo-2-trifluoromethylphenyl], [6633:5-iodo-2-trifluoromethylphenyl], [6634:6-iodo-2-trifluoromethylphenyl], [6635:3-ethoxy-2-trifluoromethylphenyl], [6636:4-ethoxy-2-trifluoromethylphenyl], [6637:5-ethoxy-2-trifluoromethylphenyl], [6638:6-ethoxy-2-trifluoromethylphenyl], [6639:3-methyl-2-trifluoromethylphenyl], [6640:4-methyl-2-trifluoromethylphenyl], [6641:5-methyl-2-trifluoromethylphenyl], [6642:6-methyl-2-trifluoromethylphenyl], [6643:2,3-ditrifluoromethylphenyl], [6644:2,4-ditrifluoromethylphenyl], [6645:2,5-ditrifluoromethylphenyl], [6646:2,6-ditrifluoromethylphenyl], [6647:2-trifluoromethyl-3-trifluoromethoxyphenyl], [6648:2-trifluoromethyl-4-trifluoromethoxyphenyl], [6649:2-trifluoromethyl-5-trifluoromethoxyphenyl], [6650:2-trifluoromethyl-6-trifluoromethoxyphenyl], [6651:2-ethyl-3-trifluoromethylphenyl], [6652:2-ethyl-4-trifluoromethylphenyl], [6653:2-ethyl-5-trifluoromethylphenyl], [6654:2-ethyl-6-trifluoromethylphenyl], [6655:3-methylthio-2-trifluoromethylphenyl], [6656:4-methylthio-2-trifluoromethylphenyl], [6657:5-methylthio-2-trifluoromethylphenyl], [6658:6-methylthio-2-trifluoromethylphenyl], [6659:2-trifluoromethyl-3-trifluoromethylthiophenyl], [6660:2-trifluoromethyl-4-trifluoromethylthiophenyl], [6661:2-trifluoromethyl-5-trifluoromethylthiophenyl], [6662:2-trifluoromethyl-6-trifluoromethylthiophenyl], [6663:3-ethynyl-2-trifluoromethylphenyl], [6664:4-ethynyl-2-trifluoromethylphenyl], [6665:5-ethynyl-2-trifluoromethylphenyl], [6666:6-ethynyl-2-trifluoromethylphenyl], [6667:3-cyclopropyl-2-trifluoromethylphenyl], [6668:4-cyclopropyl-2-trifluoromethylphenyl], [6669:5-cyclopropyl-2-trifluoromethylphenyl], [6670:6-cyclopropyl-2-trifluoromethylphenyl], [6671:3-cyclopropyloxy-2-trifluoromethylphenyl], [6672:4-cyclopropyloxy-2-trifluoromethylphenyl], [6673:5-cyclopropyloxy-2-trifluoromethylphenyl], [6674:6-cyclopropyloxy-2-trifluoromethylphenyl], [6675:3-methoxynaphthalen-2-yl], [6676:6-chloro-3-methoxynaphthalen-2-yl], [6677:6-fluoro-3-methoxynaphthalen-2-yl], [6678:7-chloro-3-methoxynaphthalen-2-yl], [6679:7-fluoro-3-methoxynaphthalen-2-yl], [6680:8-chloro-3-methoxynaphthalen-2-yl], [6681:8-fluoro-3-methoxynaphthalen-2-yl], [6682:1-chloro-3-methoxynaphthalen-2-yl], [6683:1-fluoro-3-methoxynaphthalen-2-yl], [6684:4-chloro-3-methoxynaphthalen-2-yl], [6685:4-fluoro-3-methoxynaphthalen-2-yl], [6686:5-chloro-3-methoxynaphthalen-2-yl], [6687:5-fluoro-3-methoxynaphthalen-2-yl], [6688:1-naphthyl], [6689:2-naphthyl], [6690:adamantan-1-yl], [6691:3-methyladamantan-1-yl], [6692:5-methyladamantan-1-yl], [6693:5,7-dimethyladamantan-1-yl], [6694:3,5-dimethyladamantan-1-yl], [6695:3,5,7-trimethyladamantan-1-yl], [6696:5-methyladamantan-1-yl], [6697:5,7-dimethyladamantan-1-yl], [6698:3,5-dimethyladamantan-1-yl], [6699:3,5,7-trimethyladamantan-1-yl], [6700:PYR1], [6701:3-Me-PYR1], [6702:3-Me-4-F-PYR1], [6703:3-Me-4-Cl-PYR1], [6704:3-Me-4-Br-PYR1], [6705:3-Me-4-Me-PYR1], [6706:3-Me-4-Et-PYR1], [6707:3-Me-4-OMe-PYR1], [6708:3-Me-4-OEt-PYR1], [6709:3-Me-4-CN-PYR1], [6710:3-Me-4-c-Pr-PYR1], [6711:3-Me-4-CHF2-PYR1], [6712:3-Me-4-CF3-PYR1], [6713:3-Me-5-F-PYR1], [6714:3-Me-4-F-5-F-PYR1], [6715:3-Me-4-Cl-5-F-PYR1], [6716:3-Me-4-Br-5-F-PYR1], [6717:3-Me-4-Me-5-F-PYR1], [6718:3-Me-4-Et-5-F-PYR1], [6719:3-Me-4-OMe-5-F-PYR1], [6720:3-Me-4-OEt-5-F-PYR1], [6721:3-Me-4-CN-5-F-PYR1], [6722:3-Me-4-c-Pr-5-F-PYR1], [6723:3-Me-4-CHF2-5-F-PYR1], [6724:3-Me-4-CF3-5-F-PYR1], [6725:3-Me-5-Cl-PYR1], [6726:3-Me-4-F-5-Cl-PYR1], [6727:3-Me-4-Cl-5-Cl-PYR1], [6728:3-Me-4-Br-5-Cl-PYR1], [6729:3-Me-4-Me-5-Cl-PYR1], [6730:3-Me-4-Et-5-Cl-PYR1], [6731:3-Me-4-OMe-5-Cl-PYR1], [6732:3-Me-4-OEt-5-Cl-PYR1], [6733:3-Me-4-CN-5-Cl-PYR1], [6734:3-Me-4-c-Pr-5-Cl-PYR1], [6735:3-Me-4-CHF2-5-Cl-PYR1], [6736:3-Me-4-CF3-5-Cl-PYR1], [6737:3-Me-5-Br-PYR1], [6738:3-Me-4-F-5-Br-PYR1], [6739:3-Me-4-Cl-5-Br-PYR1], [6740:3-Me-4-Br-5-Br-PYR1], [6741:3-Me-4-Me-5-Br-PYR1], [6742:3-Me-4-Et-5-Br-PYR1], [6743:3-Me-4-OMe-5-Br-PYR1], [6744:3-Me-4-OEt-5-Br-PYR1], [6745:3-Me-4-CN-5-Br-PYR1], [6746:3-Me-4-c-Pr-5-Br-PYR1], [6747:3-Me-4-CHF2-5-Br-PYR1], [6748:3-Me-4-CF3-5-Br-PYR1], [6749:3-Me-5-Me-PYR1], [6750:3-Me-4-F-5-Me-PYR1], [6751:3-Me-4-Cl-5-Me-PYR1], [6752:3-Me-4-Br-5-Me-PYR1], [6753:3-Me-4-Me-5-Me-PYR1], [6754:3-Me-4-Et-5-Me-PYR1], [6755:3-Me-4-OMe-5-Me-PYR1], [6756:3-Me-4-OEt-5-Me-PYR1], [6757:3-Me-4-CN-5-Me-PYR1], [6758:3-Me-4-c-Pr-5-Me-PYR1], [6759:3-Me-4-CHF2-5-Me-PYR1], [6760:3-Me-4-CF3-5-Me-PYR1], [6761:3-Me-5-Et-PYR1], [6762:3-Me-4-F-5-Et-PYR1], [6763:3-Me-4-Cl-5-Et-PYR1], [6764:3-Me-4-Br-5-Et-PYR1], [6765:3-Me-4-Me-5-Et-PYR1], [6766:3-Me-4-Et-5-Et-PYR1], [6767:3-Me-4-OMe-5-Et-PYR1], [6768:3-Me-4-OEt-5-Et-PYR1], [6769:3-Me-4-CN-5-Et-PYR1], [6770:3-Me-4-c-Pr-5-Et-PYR1], [6771:3-Me-4-CHF2-5-Et-PYR1], [6772:3-Me-4-CF3-5-Et-PYR1], [6773:3-Me-5-OMe-PYR1], [6774:3-Me-4-F-5-OMe-PYR1], [6775:3-Me-4-Cl-5-OMe-PYR1], [6776:3-Me-4-Br-5-OMe-PYR1], [6777:3-Me-4-Me-5-OMe-PYR1], [6778:3-Me-4-Et-5-OMe-PYR1], [6779:3-Me-4-OMe-5-OMe-PYR1], [6780:3-Me-4-OEt-5-OMe-PYR1], [6781:3-Me-4-CN-5-OMe-PYR1], [6782:3-Me-4-c-Pr-5-OMe-PYR1], [6783:3-Me-4-CHF2-5-OMe-PYR1], [6784:3-Me-4-CF3-5-OMe-PYR1], [6785:3-Me-5-OEt-PYR1], [6786:3-Me-4-F-5-OEt-PYR1], [6787:3-Me-4-Cl-5-OEt-PYR1], [6788:3-Me-4-Br-5-OEt-PYR1], [6789:3-Me-4-Me-5-OEt-PYR1], [6790:3-Me-4-Et-5-OEt-PYR1], [6791:3-Me-4-OMe-5-OEt-PYR1], [6792:3-Me-4-OEt-5-OEt-PYR1], [6793:3-Me-4-CN-5-OEt-PYR1], [6794:3-Me-4-c-Pr-5-OEt-PYR1], [6795:3-Me-4-CHF2-5-OEt-PYR1], [6796:3-Me-4-CF3-5-OEt-PYR1], [6797:3-Me-5-CN-PYR1], [6798:3-Me-4-F-5-CN-PYR1], [6799:3-Me-4-Cl-5-CN-PYR1], [6800:3-Me-4-Br-5-CN-PYR1], [6801:3-Me-4-Me-5-CN-PYR1], [6802:3-Me-4-Et-5-CN-PYR1], [6803:3-Me-4-OMe-5-CN-PYR1], [6804:3-Me-4-OEt-5-CN-PYR1], [6805:3-Me-4-CN-5-CN-PYR1], [6806:3-Me-4-c-Pr-5-CN-PYR1], [6807:3-Me-4-CHF2-5-CN-PYR1], [6808:3-Me-4-CF3-5-CN-PYR1], [6809:3-Me-5-c-Pr-PYR1], [6810:3-Me-4-F-5-c-Pr-PYR1], [6811:3-Me-4-Cl-5-c-Pr-PYR1], [6812:3-Me-4-Br-5-c-Pr-PYR1], [6813:3-Me-4-Me-5-c-Pr-PYR1], [6814:3-Me-4-Et-5-c-Pr-PYR1], [6815:3-Me-4-OMe-5-c-Pr-PYR1], [6816:3-Me-4-OEt-5-c-Pr-PYR1], [6817:3-Me-4-CN-5-c-Pr-PYR1], [6818:3-Me-4-c-Pr-5-c-Pr-PYR1], [6819:3-Me-4-CHF2-5-c-Pr-PYR1], [6820:3-Me-4-CF3-5-c-Pr-PYR1], [6821:3-Me-5-CHF2-PYR1], [6822:3-Me-4-F-5-CHF2-PYR1], [6823:3-Me-4-Cl-5-CHF2-PYR1], [6824:3-Me-4-Br-5-CHF2-PYR1], [6825:3-Me-4-Me-5-CHF2-PYR1], [6826:3-

Me-4-Et-5-CHF2-PYR1], [6827:3-Me-4-OMe-5-CHF2-PYR1], [6828:3-Me-4-OEt-5-CHF2-PYR1], [6829:3-Me-4-CN-5-CHF2-PYR1], [6830:3-Me-4-c-Pr-5-CHF2-PYR1], [6831:3-Me-4-CHF2-5-CHF2-PYR1], [6832:3-Me-4-CF3-5-CHF2-PYR1], [6833:3-Me-5-CF3-PYR1], [6834:3-Me-4-F-5-CF3-PYR1], [6835:3-Me-4-Cl-5-CF3-PYR1], [6836:3-Me-4-Br-5-CF3-PYR1], [6837:3-Me-4-Me-5-CF3-PYR1], [6838:3-Me-4-Et-5-CF3-PYR1], [6839:3-Me-4-OMe-5-CF3-PYR1], [6840:3-Me-4-OEt-5-CF3-PYR1], [6841:3-Me-4-CN-5-CF3-PYR1], [6842:3-Me-4-c-Pr-5-CF3-PYR1], [6843:3-Me-4-CHF2-5-CF3-PYR1], [6844:3-Me-4-CF3-5-CF3-PYR1], [6845:3-Et-PYR1], [6846:3-Et-4-F-PYR1], [6847:3-Et-4-Cl-PYR1], [6848:3-Et-4-Br-PYR1], [6849:3-Et-4-Me-PYR1], [6850:3-Et-4-Et-PYR1], [6851:3-Et-4-OMe-PYR1], [6852:3-Et-4-OEt-PYR1], [6853:3-Et-4-CN-PYR1], [6854:3-Et-4-c-Pr-PYR1], [6855:3-Et-4-CHF2-PYR1], [6856:3-Et-4-CF3-PYR1], [6857:3-Et-5-F-PYR1], [6858:3-Et-4-F-5-F-PYR1], [6859:3-Et-4-Cl-5-F-PYR1], [6860:3-Et-4-Br-5-F-PYR1], [6861:3-Et-4-Me-5-F-PYR1], [6862:3-Et-4-Et-5-F-PYR1], [6863:3-Et-4-OMe-5-F-PYR1], [6864:3-Et-4-OEt-5-F-PYR1], [6865:3-Et-4-CN-5-F-PYR1], [6866:3-Et-4-c-Pr-5-F-PYR1], [6867:3-Et-4-CHF2-5-F-PYR1], [6868:3-Et-4-CF3-5-F-PYR1], [6869:3-Et-5-Cl-PYR1], [6870:3-Et-4-F-5-Cl-PYR1], [6871:3-Et-4-Cl-5-Cl-PYR1], [6872:3-Et-4-Br-5-Cl-PYR1], [6873:3-Et-4-Me-5-Cl-PYR1], [6874:3-Et-4-Et-5-Cl-PYR1], [6875:3-Et-4-OMe-5-Cl-PYR1], [6876:3-Et-4-OEt-5-Cl-PYR1], [6877:3-Et-4-CN-5-Cl-PYR1], [6878:3-Et-4-c-Pr-5-Cl-PYR1], [6879:3-Et-4-CHF2-5-Cl-PYR1], [6880:3-Et-4-CF3-5-Cl-PYR1], [6881:3-Et-5-Br-PYR1], [6882:3-Et-4-F-5-Br-PYR1], [6883:3-Et-4-Cl-5-Br-PYR1], [6884:3-Et-4-Br-5-Br-PYR1], [6885:3-Et-4-Me-5-Br-PYR1], [6886:3-Et-4-Et-5-Br-PYR1], [6887:3-Et-4-OMe-5-Br-PYR1], [6888:3-Et-4-OEt-5-Br-PYR1], [6889:3-Et-4-CN-5-Br-PYR1], [6890:3-Et-4-c-Pr-5-Br-PYR1], [6891:3-Et-4-CHF2-5-Br-PYR1], [6892:3-Et-4-CF3-5-Br-PYR1], [6893:3-Et-5-Me-PYR1], [6894:3-Et-4-F-5-Me-PYR1], [6895:3-Et-4-Cl-5-Me-PYR1], [6896:3-Et-4-Br-5-Me-PYR1], [6897:3-Et-4-Me-5-Me-PYR1], [6898:3-Et-4-Et-5-Me-PYR1], [6899:3-Et-4-OMe-5-Me-PYR1], [6900:3-Et-4-OEt-5-Me-PYR1],

[6901:3-Et-4-CN-5-Me-PYR1], [6902:3-Et-4-c-Pr-5-Me-PYR1], [6903:3-Et-4-CHF2-5-Me-PYR1], [6904:3-Et-4-CF3-5-Me-PYR1], [6905:3-Et-5-Et-PYR1], [6906:3-Et-4-F-5-Et-PYR1], [6907:3-Et-4-Cl-5-Et-PYR1], [6908:3-Et-4-Br-5-Et-PYR1], [6909:3-Et-4-Me-5-Et-PYR1], [6910:3-Et-4-Et-5-Et-PYR1], [6911:3-Et-4-OMe-5-Et-PYR1], [6912:3-Et-4-OEt-5-Et-PYR1], [6913:3-Et-4-CN-5-Et-PYR1], [6914:3-Et-4-c-Pr-5-Et-PYR1], [6915:3-Et-4-CHF2-5-Et-PYR1], [6916:3-Et-4-CF3-5-Et-PYR1], [6917:3-Et-5-OMe-PYR1], [6918:3-Et-4-F-5-OMe-PYR1], [6919:3-Et-4-Cl-5-OMe-PYR1], [6920:3-Et-4-Br-5-OMe-PYR1], [6921:3-Et-4-Me-5-OMe-PYR1], [6922:3-Et-4-Et-5-OMe-PYR1], [6923:3-Et-4-OMe-5-OMe-PYR1], [6924:3-Et-4-OEt-5-OMe-PYR1], [6925:3-Et-4-CN-5-OMe-PYR1], [6926:3-Et-4-c-Pr-5-OMe-PYR1], [6927:3-Et-4-CHF2-5-OMe-PYR1], [6928:3-Et-4-CF3-5-OMe-PYR1], [6929:3-Et-5-OEt-PYR1], [6930:3-Et-4-F-5-OEt-PYR1], [6931:3-Et-4-Cl-5-OEt-PYR1], [6932:3-Et-4-Br-5-OEt-PYR1], [6933:3-Et-4-Me-5-OEt-PYR1], [6934:3-Et-4-Et-5-OEt-PYR1], [6935:3-Et-4-OMe-5-OEt-PYR1], [6936:3-Et-4-OEt-5-OEt-PYR1], [6937:3-Et-4-CN-5-OEt-PYR1], [6938:3-Et-4-c-Pr-5-OEt-PYR1], [6939:3-Et-4-CHF2-5-OEt-PYR1], [6940:3-Et-4-CF3-5-OEt-PYR1], [6941:3-Et-5-CN-PYR1], [6942:3-Et-4-F-5-CN-PYR1], [6943:3-Et-4-Cl-5-CN-PYR1], [6944:3-Et-4-Br-5-CN-PYR1], [6945:3-Et-4-Me-5-CN-PYR1], [6946:3-Et-4-Et-5-CN-PYR1], [6947:3-Et-4-OMe-5-CN-PYR1], [6948:3-Et-4-OEt-5-CN-PYR1], [6949:3-Et-4-CN-5-CN-PYR1], [6950:3-Et-4-c-Pr-5-CN-PYR1], [6951:3-Et-4-CHF2-5-CN-PYR1], [6952:3-Et-4-CF3-5-CN-PYR1], [6953:3-Et-5-c-Pr-PYR1], [6954:3-Et-4-F-5-c-Pr-PYR1], [6955:3-Et-4-Cl-5-c-Pr-PYR1], [6956:3-Et-4-Br-5-c-Pr-PYR1], [6957:3-Et-4-Me-5-c-Pr-PYR1], [6958:3-Et-4-Et-5-c-Pr-PYR1], [6959:3-Et-4-OMe-5-c-Pr-PYR1], [6960:3-Et-4-OEt-5-c-Pr-PYR1], [6961:3-Et-4-CN-5-c-Pr-PYR1], [6962:3-Et-4-c-Pr-5-c-Pr-PYR1], [6963:3-Et-4-CHF2-5-c-Pr-PYR1], [6964:3-Et-4-CF3-5-c-Pr-PYR1], [6965:3-Et-5-CHF2-PYR1], [6966:3-Et-4-F-5-CHF2-PYR1], [6967:3-Et-4-Cl-5-CHF2-PYR1], [6968:3-Et-4-Br-5-CHF2-PYR1], [6969:3-Et-4-Me-5-CHF2-PYR1], [6970:3-Et-4-Et-5-CHF2-PYR1], [6971:3-Et-4-OMe-5-CHF2-PYR1], [6972:3-Et-4-OEt-5-CHF2-PYR1], [6973:3-Et-4-CN-5-CHF2-PYR1], [6974:3-Et-4-c-Pr-5-CHF2-PYR1], [6975:3-Et-4-CHF2-5-CHF2-PYR1], [6976:3-Et-4-CF3-5-CHF2-PYR1], [6977:3-Et-5-CF3-PYR1], [6978:3-Et-4-F-5-CF3-PYR1], [6979:3-Et-4-Cl-5-CF3-PYR1], [6980:3-Et-4-Br-5-CF3-PYR1], [6981:3-Et-4-Me-5-CF3-PYR1], [6982:3-Et-4-Et-5-CF3-PYR1], [6983:3-Et-4-OMe-5-CF3-PYR1], [6984:3-Et-4-OEt-5-CF3-PYR1], [6985:3-Et-4-CN-5-CF3-PYR1], [6986:3-Et-4-c-Pr-5-CF3-PYR1], [6987:3-Et-4-CHF2-5-CF3-PYR1], [6988:3-Et-4-CF3-5-CF3-PYR1], [6989:5-Me-PYR1], [6990:3-F-5-Me-PYR1], [6991:3-Cl-5-Me-PYR1], [6992:3-Br-5-Me-PYR1], [6993:3-OMe-5-Me-PYR1], [6994:3-OEt-5-Me-PYR1], [6995:3-CN-5-Me-PYR1], [6996:3-c-Pr-5-Me-PYR1], [6997:3-CHF2-5-Me-PYR1], [6998:3-CF3-5-Me-PYR1], [6999:4-F-5-Me-PYR1], [7000:3-F-4-F-5-Me-PYR1], [7001:3-Cl-4-F-5-Me-PYR1], [7002:3-Br-4-F-5-Me-PYR1], [7003:3-OMe-4-F-5-Me-PYR1], [7004:3-OEt-4-F-5-Me-PYR1], [7005:3-CN-4-F-5-Me-PYR1], [7006:3-c-Pr-4-F-5-Me-PYR1], [7007:3-CHF2-4-F-5-Me-PYR1], [7008:3-CF3-4-F-5-Me-PYR1], [7009:4-Cl-5-Me-PYR1], [7010:3-F-4-Cl-5-Me-PYR1], [7011:3-Cl-4-Cl-5-Me-PYR1], [7012:3-Br-4-Cl-5-Me-PYR1], [7013:3-OMe-4-Cl-5-Me-PYR1], [7014:3-OEt-4-Cl-5-Me-PYR1], [7015:3-CN-4-Cl-5-Me-PYR1], [7016:3-c-Pr-4-Cl-5-Me-PYR1], [7017:3-CHF2-4-Cl-5-Me-PYR1], [7018:3-CF3-4-Cl-5-Me-PYR1], [7019:4-Br-5-Me-PYR1], [7020:3-F-4-Br-5-Me-PYR1], [7021:3-Cl-4-Br-5-Me-PYR1], [7022:3-Br-4-Br-5-Me-PYR1], [7023:3-OMe-4-Br-5-Me-PYR1], [7024:3-OEt-4-Br-5-Me-PYR1], [7025:3-CN-4-Br-5-Me-PYR1], [7026:3-c-Pr-4-Br-5-Me-PYR1], [7027:3-CHF2-4-Br-5-Me-PYR1], [7028:3-CF3-4-Br-5-Me-PYR1], [7029:4-Me-5-Me-PYR1], [7030:3-F-4-Me-5-Me-PYR1], [7031:3-Cl-4-Me-5-Me-PYR1], [7032:3-Br-4-Me-5-Me-PYR1], [7033:3-OMe-4-Me-5-Me-PYR1], [7034:3-OEt-4-Me-5-Me-PYR1], [7035:3-CN-4-Me-5-Me-PYR1], [7036:3-c-Pr-4-Me-5-Me-PYR1], [7037:3-CHF2-4-Me-5-Me-PYR1], [7038:3-CF3-4-Me-5-Me-PYR1], [7039:4-Et-5-Me-PYR1], [7040:3-F-4-Et-5-Me-PYR1], [7041:3-Cl-4-Et-5-Me-PYR1], [7042:3-Br-4-Et-5-Me-PYR1], [7043:3-OMe-4-Et-5-Me-PYR1], [7044:3-OEt-4-Et-5-Me-PYR1], [7045:3-CN-4-Et-5-Me-PYR1], [7046:3-c-Pr-4-Et-5-Me-PYR1], [7047:3-CHF2-4-Et-5-Me-PYR1], [7048:3-CF3-4-Et-5-Me-PYR1], [7049:4-OMe-5-Me-PYR1], [7050:3-F-4-OMe-5-Me-PYR1], [7051:3-Cl-4-OMe-5-Me-PYR1], [7052:3-Br-4-OMe-5-Me-PYR1], [7053:3-OMe-4-OMe-5-Me-PYR1], [7054:3-OEt-4-OMe-5-Me-PYR1], [7055:3-CN-4-OMe-5-Me-PYR1], [7056:3-c-Pr-4-OMe-5-Me-PYR1], [7057:3-CHF2-4-OMe-5-Me-PYR1], [7058:3-CF3-4-OMe-5-Me-PYR1], [7059:4-OEt-5-Me-PYR1], [7060:3-F-4-OEt-5-Me-PYR1], [7061:3-Cl-4-OEt-5-Me-PYR1], [7062:3-Br-4-OEt-5-Me-PYR1], [7063:3-OMe-4-OEt-5-Me-PYR1], [7064:3-OEt-4-OEt-5-Me-PYR1], [7065:3-CN-4-OEt-5-Me-PYR1], [7066:3-c-Pr-

4-OEt-5-Me-PYR1], [7067:3-CHF2-4-OEt-5-Me-PYR1], [7068:3-CF3-4-OEt-5-Me-PYR1], [7069:4-CN-5-Me-PYR1], [7070:3-F-4-CN-5-Me-PYR1], [7071:3-Cl-4-CN-5-Me-PYR1], [7072:3-Br-4-CN-5-Me-PYR1], [7073:3-OMe-4-CN-5-Me-PYR1], [7074:3-OEt-4-CN-5-Me-PYR1], [7075:3-CN-4-CN-5-Me-PYR1], [7076:3-c-Pr-4-CN-5-Me-PYR1], [7077:3-CHF2-4-CN-5-Me-PYR1], [7078:3-CF3-4-CN-5-Me-PYR1], [7079:4-c-Pr-5-Me-PYR1], [7080:3-F-4-c-Pr-5-Me-PYR1], [7081:3-Cl-4-c-Pr-5-Me-PYR1], [7082:3-Br-4-c-Pr-5-Me-PYR1], [7083:3-OMe-4-c-Pr-5-Me-PYR1], [7084:3-OEt-4-c-Pr-5-Me-PYR1], [7085:3-CN-4-c-Pr-5-Me-PYR1], [7086:3-c-Pr-4-c-Pr-5-Me-PYR1], [7087:3-CHF2-4-c-Pr-5-Me-PYR1], [7088:3-CF3-4-c-Pr-5-Me-PYR1], [7089:4-CHF2-5-Me-PYR1], [7090:3-F-4-CHF2-5-Me-PYR1], [7091:3-Cl-4-CHF2-5-Me-PYR1], [7092:3-Br-4-CHF2-5-Me-PYR1], [7093:3-OMe-4-CHF2-5-Me-PYR1], [7094:3-OEt-4-CHF2-5-Me-PYR1], [7095:3-CN-4-CHF2-5-Me-PYR1], [7096:3-c-Pr-4-CHF2-5-Me-PYR1], [7097:3-CHF2-4-CHF2-5-Me-PYR1], [7098:3-CF3-4-CHF2-5-Me-PYR1], [7099:4-CF3-5-Me-PYR1], [7100:3-F-4-CF3-5-Me-PYR1], [7101:3-Cl-4-CF3-5-Me-PYR1], [7102:3-Br-4-CF3-5-Me-PYR1], [7103:3-OMe-4-CF3-5-Me-PYR1], [7104:3-OEt-4-CF3-5-Me-PYR1], [7105:3-CN-4-CF3-5-Me-PYR1], [7106:3-c-Pr-4-CF3-5-Me-PYR1], [7107:3-CHF2-4-CF3-5-Me-PYR1], [7108:3-CF3-4-CF3-5-Me-PYR1], [7109:5-Et-PYR1], [7110:3-F-5-Et-PYR1], [7111:3-Cl-5-Et-PYR1], [7112:3-Br-5-Et-PYR1], [7113:3-OMe-5-Et-PYR1], [7114:3-OEt-5-Et-PYR1], [7115:3-CN-5-Et-PYR1], [7116:3-c-Pr-5-Et-PYR1], [7117:3-CHF2-5-Et-PYR1], [7118:3-CF3-5-Et-PYR1], [7119:4-F-5-Et-PYR1], [7120:3-F-4-F-5-Et-PYR1], [7121:3-Cl-4-F-5-Et-PYR1], [7122:3-Br-4-F-5-Et-PYR1], [7123:3-OMe-4-F-5-Et-PYR1], [7124:3-OEt-4-F-5-Et-PYR1], [7125:3-CN-4-F-5-Et-PYR1], [7126:3-c-Pr-4-F-5-Et-PYR1], [7127:3-CHF2-4-F-5-Et-PYR1], [7128:3-CF3-4-F-5-Et-PYR1], [7129:4-Cl-5-Et-PYR1], [7130:3-F-4-Cl-5-Et-PYR1], [7131:3-Cl-4-Cl-5-Et-PYR1], [7132:3-Br-4-Cl-5-Et-PYR1], [7133:3-OMe-4-Cl-5-Et-PYR1], [7134:3-OEt-4-Cl-5-Et-PYR1], [7135:3-CN-4-Cl-5-Et-PYR1], [7136:3-c-Pr-4-Cl-5-Et-PYR1], [7137:3-CHF2-4-Cl-5-Et-PYR1], [7138:3-CF3-4-Cl-5-Et-PYR1], [7139:4-Br-5-Et-PYR1], [7140:3-F-4-Br-5-Et-PYR1], [7141:3-Cl-4-Br-5-Et-PYR1], [7142:3-Br-4-Br-5-Et-PYR1], [7143:3-OMe-4-Br-5-Et-PYR1], [7144:3-OEt-4-Br-5-Et-PYR1], [7145:3-CN-4-Br-5-Et-PYR1], [7146:3-c-Pr-4-Br-5-Et-PYR1], [7147:3-CHF2-4-Br-5-Et-PYR1], [7148:3-CF3-4-Br-5-Et-PYR1], [7149:4-Me-5-Et-PYR1], [7150:3-F-4-Me-5-Et-PYR1], [7151:3-Cl-4-Me-5-Et-PYR1], [7152:3-Br-4-Me-5-Et-PYR1], [7153:3-OMe-4-Me-5-Et-PYR1], [7154:3-OEt-4-Me-5-Et-PYR1], [7155:3-CN-4-Me-5-Et-PYR1], [7156:3-c-Pr-4-Me-5-Et-PYR1], [7157:3-CHF2-4-Me-5-Et-PYR1], [7158:3-CF3-4-Me-5-Et-PYR1], [7159:4-Et-5-Et-PYR1], [7160:3-F-4-Et-5-Et-PYR1], [7161:3-Cl-4-Et-5-Et-PYR1], [7162:3-Br-4-Et-5-Et-PYR1], [7163:3-OMe-4-Et-5-Et-PYR1], [7164:3-OEt-4-Et-5-Et-PYR1], [7165:3-CN-4-Et-5-Et-PYR1], [7166:3-c-Pr-4-Et-5-Et-PYR1], [7167:3-CHF2-4-Et-5-Et-PYR1], [7168:3-CF3-4-Et-5-Et-PYR1], [7169:4-OMe-5-Et-PYR1], [7170:3-F-4-OMe-5-Et-PYR1], [7171:3-Cl-4-OMe-5-Et-PYR1], [7172:3-Br-4-OMe-5-Et-PYR1], [7173:3-OMe-4-OMe-5-Et-PYR1], [7174:3-OEt-4-OMe-5-Et-PYR1], [7175:3-CN-4-OMe-5-Et-PYR1], [7176:3-c-Pr-4-OMe-5-Et-PYR1], [7177:3-CHF2-4-OMe-5-Et-PYR1], [7178:3-CF3-4-OMe-5-Et-PYR1], [7179:4-OEt-5-Et-PYR1], [7180:3-F-4-OEt-5-Et-PYR1], [7181:3-Cl-4-OEt-5-Et-PYR1], [7182:3-Br-4-OEt-5-Et-PYR1], [7183:3-OMe-4-OEt-5-Et-PYR1], [7184:3-OEt-4-OEt-5-Et-PYR1], [7185:3-CN-4-OEt-5-Et-PYR1], [7186:3-c-Pr-4-OEt-5-Et-PYR1], [7187:3-CHF2-4-OEt-5-Et-PYR1], [7188:3-CF3-4-OEt-5-Et-PYR1], [7189:4-CN-5-Et-PYR1], [7190:3-F-4-CN-5-Et-PYR1], [7191:3-Cl-4-CN-5-Et-PYR1], [7192:3-Br-4-CN-5-Et-PYR1], [7193:3-OMe-4-CN-5-Et-PYR1], [7194:3-OEt-4-CN-5-Et-PYR1], [7195:3-CN-4-CN-5-Et-PYR1], [7196:3-c-Pr-4-CN-5-Et-PYR1], [7197:3-CHF2-4-CN-5-Et-PYR1], [7198:3-CF3-4-CN-5-Et-PYR1], [7199:4-c-Pr-5-Et-PYR1], [7200:3-F-4-c-Pr-5-Et-PYR1], [7201:3-Cl-4-c-Pr-5-Et-PYR1], [7202:3-Br-4-c-Pr-5-Et-PYR1], [7203:3-OMe-4-c-Pr-5-Et-PYR1], [7204:3-OEt-4-c-Pr-5-Et-PYR1], [7205:3-CN-4-c-Pr-5-Et-PYR1], [7206:3-c-Pr-4-c-Pr-5-Et-PYR1], [7207:3-CHF2-4-c-Pr-5-Et-PYR1], [7208:3-CF3-4-c-Pr-5-Et-PYR1], [7209:4-CHF2-5-Et-PYR1], [7210:3-F-4-CHF2-5-Et-PYR1], [7211:3-Cl-4-CHF2-5-Et-PYR1], [7212:3-Br-4-CHF2-5-Et-PYR1], [7213:3-OMe-4-CHF2-5-Et-PYR1], [7214:3-OEt-4-CHF2-5-Et-PYR1], [7215:3-CN-4-CHF2-5-Et-PYR1], [7216:3-c-Pr-4-CHF2-5-Et-PYR1], [7217:3-CHF2-4-CHF2-5-Et-PYR1], [7218:3-CF3-4-CHF2-5-Et-PYR1], [7219:4-CF3-5-Et-PYR1], [7220:3-F-4-CF3-5-Et-PYR1], [7221:3-Cl-4-CF3-5-Et-PYR1], [7222:3-Br-4-CF3-5-Et-PYR1], [7223:3-OMe-4-CF3-5-Et-PYR1], [7224:3-OEt-4-CF3-5-Et-PYR1], [7225:3-CN-4-CF3-5-Et-PYR1], [7226:3-c-Pr-4-CF3-5-Et-PYR1], [7227:3-CHF2-4-CF3-5-Et-PYR1], [7228:3-CF3-4-CF3-5-Et-PYR1], [7229:1-Me-PYR3], [7230:1-Me-4-F-PYR3], [7231:1-Me-4-Cl-PYR3], [7232:1-Me-4-Br-PYR3], [7233:1-Me-4-Me-PYR3], [7234:1-Me-4-Et-PYR3], [7235:1-Me-4-OMe-PYR3], [7236:1-Me-4-OEt-PYR3], [7237:1-Me-4-CN-PYR3], [7238:1-Me-4-c-Pr-PYR3], [7239:1-Me-4-CHF2-PYR3], [7240:1-Me-4-CF3-PYR3], [7241:1-Me-5-F-PYR3], [7242:1-Me-4-F-5-F-PYR3], [7243:1-Me-4-Cl-5-F-PYR3], [7244:1-Me-4-Br-5-F-PYR3], [7245:1-Me-4-Me-5-F-PYR3], [7246:1-Me-4-Et-5-F-PYR3], [7247:1-Me-4-OMe-5-F-PYR3], [7248:1-Me-4-OEt-5-F-PYR3], [7249:1-Me-4-CN-5-F-PYR3], [7250:1-Me-4-c-Pr-5-F-PYR3], [7251:1-Me-4-CHF2-5-F-PYR3], [7252:1-Me-4-CF3-5-F-PYR3], [7253:1-Me-5-Cl-PYR3], [7254:1-Me-4-F-5-Cl-PYR3], [7255:1-Me-4-Cl-5-Cl-PYR3], [7256:1-Me-4-Br-5-Cl-PYR3], [7257:1-Me-4-Me-5-Cl-PYR3], [7258:1-Me-4-Et-5-Cl-PYR3], [7259:1-Me-4-OMe-5-Cl-PYR3], [7260:1-Me-4-OEt-5-Cl-PYR3], [7261:1-Me-4-CN-5-Cl-PYR3], [7262:1-Me-4-c-Pr-5-Cl-PYR3], [7263:1-Me-4-CHF2-6-Cl-PYR3], [7264:1-Me-4-CF3-7-Cl-PYR3], [7265:1-Me-5-Br-PYR3], [7266:1-Me-4-F-5-Br-PYR3], [7267:1-Me-4-Cl-5-Br-PYR3], [7268:1-Me-4-Br-5-Br-PYR3], [7269:1-Me-4-Me-5-Br-PYR3], [7270:1-Me-4-Et-5-Br-PYR3], [7271:1-Me-4-OMe-5-Br-PYR3], [7272:1-Me-4-OEt-5-Br-PYR3], [7273:1-Me-4-CN-5-Br-PYR3], [7274:1-Me-4-c-Pr-5-Br-PYR3], [7275:1-Me-4-CHF2-5-Br-PYR3], [7276:1-Me-4-CF3-5-Br-PYR3], [7277:1-Me-5-Me-PYR3], [7278:1-Me-4-F-5-Me-PYR3], [7279:1-Me-4-Cl-5-Me-PYR3], [7280:1-Me-4-Br-5-Me-PYR3], [7281:1-Me-4-Me-5-Me-PYR3], [7282:1-Me-4-Et-5-Me-PYR3], [7283:1-Me-4-OMe-5-Me-PYR3], [7284:1-Me-4-OEt-5-Me-PYR3], [7285:1-Me-4-CN-5-Me-PYR3], [7286:1-Me-4-c-Pr-5-Me-PYR3], [7287:1-Me-4-CHF2-5-Me-PYR3], [7288:1-Me-4-CF3-5-Me-PYR3], [7289:1-Me-5-Et-PYR3], [7290:1-Me-4-F-5-Et-PYR3], [7291:1-Me-4-Cl-5-Et-PYR3], [7292:1-Me-4-Br-5-Et-PYR3], [7293:1-Me-4-Me-5-Et-PYR3], [7294:1-Me-4-Et-5-Et-PYR3], [7295:1-Me-4-OMe-5-Et-PYR3], [7296:1-Me-4-OEt-5-Et-PYR3], [7297:1-Me-4-CN-5-Et-PYR3], [7298:1-Me-4-c-Pr-5-Et-PYR3], [7299:1-Me-4-CHF2-5-Et-PYR3], [7300:1-Me-4-CF3-5-Et-PYR3], [7301:1-Me-5-OMe-PYR3], [7302:1-Me-4-F-5-OMe-PYR3], [7303:1-Me-4-Cl-5-OMe-PYR3], [7304:1-Me-4-Br-5-OMe-PYR3], [7305:1-Me-4-Me-5-OMe-PYR3], [7306:1-Me-4-Et-5-OMe-PYR3], [7307:1-Me-4-OMe-5-

OMe-PYR3], [7308:1-Me-4-OEt-5-OMe-PYR3], [7309:1-Me-4-CN-5-OMe-PYR3], [7310:1-Me-4-c-Pr-5-OMe-PYR3], [7311:1-Me-4-CHF2-5-OMe-PYR3], [7312:1-Me-4-CF3-5-OMe-PYR3], [7313:1-Me-5-OEt-PYR3], [7314:1-Me-4-F-5-OEt-PYR3], [7315:1-Me-4-Cl-5-OEt-PYR3], [7316:1-Me-4-Br-5-OEt-PYR3], [7317:1-Me-4-Me-5-OEt-PYR3], [7318:1-Me-4-Et-5-OEt-PYR3], [7319:1-Me-4-OMe-5-OEt-PYR3], [7320:1-Me-4-OEt-5-OEt-PYR3], [7321:1-Me-4-CN-5-OEt-PYR3], [7322:1-Me-4-c-Pr-5-OEt-PYR3], [7323:1-Me-4-CHF2-5-OEt-PYR3], [7324:1-Me-4-CF3-5-OEt-PYR3], [7325:1-Me-5-CN-PYR3], [7326:1-Me-4-F-5-CN-PYR3], [7327:1-Me-4-Cl-5-CN-PYR3], [7328:1-Me-4-Br-5-CN-PYR3], [7329:1-Me-4-Me-5-CN-PYR3], [7330:1-Me-4-Et-5-CN-PYR3], [7331:1-Me-4-OMe-5-CN-PYR3], [7332:1-Me-4-OEt-5-CN-PYR3], [7333:1-Me-4-CN-5-CN-PYR3], [7334:1-Me-4-c-Pr-5-CN-PYR3], [7335:1-Me-4-CHF2-5-CN-PYR3], [7336:1-Me-4-CF3-5-CN-PYR3], [7337:1-Me-5-c-Pr-PYR3], [7338:1-Me-4-F-5-c-Pr-PYR3], [7339:1-Me-4-Cl-5-c-Pr-PYR3], [7340:1-Me-4-Br-5-c-Pr-PYR3], [7341:1-Me-4-Me-5-c-Pr-PYR3], [7342:1-Me-4-Et-5-c-Pr-PYR3], [7343:1-Me-4-OMe-5-c-Pr-PYR3], [7344:1-Me-4-OEt-5-c-Pr-PYR3], [7345:1-Me-4-CN-5-c-Pr-PYR3], [7346:1-Me-4-c-Pr-5-c-Pr-PYR3], [7347:1-Me-4-CHF2-5-c-Pr-PYR3], [7348:1-Me-4-CF3-5-c-Pr-PYR3], [7349:1-Me-5-CHF2-PYR3], [7350:1-Me-4-F-5-CHF2-PYR3], [7351:1-Me-4-Cl-5-CHF2-PYR3], [7352:1-Me-4-Br-5-CHF2-PYR3], [7353:1-Me-4-Me-5-CHF2-PYR3], [7354:1-Me-4-Et-5-CHF2-PYR3], [7355:1-Me-4-OMe-5-CHF2-PYR3], [7356:1-Me-4-OEt-5-CHF2-PYR3], [7357:1-Me-4-CN-5-CHF2-PYR3], [7358:1-Me-4-c-Pr-5-CHF2-PYR3], [7359:1-Me-4-CHF2-5-CHF2-PYR3], [7360:1-Me-4-CF3-5-CHF2-PYR3], [7361:1-Me-5-CF3-PYR3], [7362:1-Me-4-F-5-CF3-PYR3], [7363:1-Me-4-Cl-5-CF3-PYR3], [7364:1-Me-4-Br-5-CF3-PYR3], [7365:1-Me-4-Me-5-CF3-PYR3], [7366:1-Me-4-Et-5-CF3-PYR3], [7367:1-Me-4-OMe-5-CF3-PYR3], [7368:1-Me-4-OEt-5-CF3-PYR3], [7369:1-Me-4-CN-5-CF3-PYR3], [7370:1-Me-4-c-Pr-5-CF3-PYR3], [7371:1-Me-4-CHF2-5-CF3-PYR3], [7372:1-Me-4-CF3-5-CF3-PYR3], [7373:1-Me-5-OPr-PYR3], [7374:1-Me-4-F-5-OPr-PYR3], [7375:1-Me-4-Cl-5-OPr-PYR3], [7376:1-Me-4-Br-5-OPr-PYR3], [7377:1-Me-4-Me-5-OPr-PYR3], [7378:1-Me-4-Et-5-OPr-PYR3], [7379:1-Me-4-OMe-5-OPr-PYR3], [7380:1-Me-4-OEt-5-OPr-PYR3], [7381:1-Me-4-CN-5-OPr-PYR3], [7382:1-Me-4-c-Pr-5-OPr-PYR3], [7383:1-Me-4-CHF2-5-OPr-PYR3], [7384:1-Me-4-CF3-5-OPr-PYR3], [7385:1-Me-5-OCH2CH=CH2-PYR3], [7386:1-Me-4-F-5-OCH2CH=CH2-PYR3], [7387:1-Me-4-Cl-5-OCH2CH=CH2-PYR3], [7388:1-Me-4-Br-5-OCH2CH=CH2-PYR3], [7389:1-Me-4-Me-5-OCH2CH=CH2-PYR3], [7390:1-Me-4-Et-5-OCH2CH=CH2-PYR3], [7391:1-Me-4-OMe-5-OCH2CH=CH2-PYR3], [7392:1-Me-4-OEt-5-OCH2CH=CH2-PYR3], [7393:1-Me-4-CN-5-OCH2CH=CH2-PYR3], [7394:1-Me-4-c-Pr-5-OCH2CH=CH2-PYR3], [7395:1-Me-4-CHF2-5-OCH2CH=CH2-PYR3], [7396:1-Me-4-CF3-5-OCH2CH=CH2-PYR3], [7397:1-Me-5-OCH2CH=CCl2-PYR3], [7398:1-Me-4-F-5-OCH2CH=CCl2-PYR3], [7399:1-Me-4-Cl-5-OCH2CH=CCl2-PYR3], [7400:1-Me-4-Br-5-OCH2CH=CCl2-PYR3], [7401:1-Me-4-Me-5-OCH2CH=CCl2-PYR3], [7402:1-Me-4-Et-5-OCH2CH=CCl2-PYR3], [7403:1-Me-4-OMe-5-OCH2CH=CCl2-PYR3], [7404:1-Me-4-OEt-5-OCH2CH=CCl2-PYR3], [7405:1-Me-4-CN-5-OCH2CH=CCl2-PYR3], [7406:1-Me-4-c-Pr-5-OCH2CH=CCl2-PYR3], [7407:1-Me-4-CHF2-5-OCH2CH=CCl2-PYR3], [7408:1-Me-4-CF3-5-OCH2CH=CCl2-PYR3], [7409:1-Me-5-OCH2C≡CH-PYR3], [7410:1-Me-4-F-5-OCH2C≡CH-PYR3], [7411:1-Me-4-Cl-5-OCH2C≡CH-PYR3], [7412:1-Me-4-Br-5-OCH2C≡CH-PYR3], [7413:1-Me-4-Me-5-OCH2C≡CH-PYR3], [7414:1-Me-4-Et-5-OCH2C≡CH-PYR3], [7415:1-Me-4-OMe-5-OCH2C≡CH-PYR3], [7416:1-Me-4-OEt-5-OCH2C≡CH-PYR3], [7417:1-Me-4-CN-5-OCH2C≡CH-PYR3], [7418:1-Me-4-c-Pr-5-OCH2C≡CH-PYR3], [7419:1-Me-4-CHF2-5-OCH2C≡CH-PYR3], [7420:1-Me-4-CF3-5-OCH2C≡CH-PYR3], [7421:1-Me-5-OCH2CF3-PYR3], [7422:1-Me-4-F-5-OCH2CF3-PYR3], [7423:1-Me-4-Cl-5-OCH2CF3-PYR3], [7424:1-Me-4-Br-5-OCH2CF3-PYR3], [7425:1-Me-4-Me-5-OCH2CF3-PYR3], [7426:1-Me-4-Et-5-OCH2CF3-PYR3], [7427:1-Me-4-OMe-5-OCH2CF3-PYR3], [7428:1-Me-4-OEt-5-OCH2CF3-PYR3], [7429:1-Me-4-CN-5-OCH2CF3-PYR3], [7430:1-Me-4-c-Pr-5-OCH2CF3-PYR3], [7431:1-Me-4-CHF2-5-OCH2CF3-PYR3], [7432:1-Me-4-CF3-5-OCH2CF3-PYR3], [7433:1-Me-5-CH2OCH3-PYR3], [7434:1-Me-4-F-5-CH2OCH3-PYR3], [7435:1-Me-4-Cl-5-CH2OCH3-PYR3], [7436:1-Me-4-Br-5-CH2OCH3-PYR3], [7437:1-Me-4-Me-5-CH2OCH3-PYR3], [7438:1-Me-4-Et-5-CH2OCH3-PYR3], [7439:1-Me-4-OMe-5-CH2OCH3-PYR3], [7440:1-Me-4-OEt-5-CH2OCH3-PYR3], [7441:1-Me-4-CN-5-CH2OCH3-PYR3], [7442:1-Me-4-c-Pr-5-CH2OCH3-PYR3], [7443:1-Me-4-CHF2-5-CH2OCH3-PYR3], [7444:1-Me-4-CF3-5-CH2OCH3-PYR3], [7445:1-Et-PYR3], [7446:1-Et-4-F-PYR3], [7447:1-Et-4-Cl-PYR3], [7448:1-Et-4-Br-PYR3], [7449:1-Et-4-Me-PYR3], [7450:1-Et-4-Et-PYR3], [7451:1-Et-4-OMe-PYR3], [7452:1-Et-4-OEt-PYR3], [7453:1-Et-4-CN-PYR3], [7454:1-Et-4-c-Pr-PYR3], [7455:1-Et-4-CHF2-PYR3], [7456:1-Et-4-CF3-PYR3], [7457:1-Et-5-F-PYR3], [7458:1-Et-4-F-5-F-PYR3], [7459:1-Et-4-Cl-5-F-PYR3], [7460:1-Et-4-Br-5-F-PYR3], [7461:1-Et-4-Me-5-F-PYR3], [7462:1-Et-4-Et-5-F-PYR3], [7463:1-Et-4-OMe-5-F-PYR3], [7464:1-Et-4-OEt-5-F-PYR3], [7465:1-Et-4-CN-5-F-PYR3], [7466:1-Et-4-c-Pr-5-F-PYR3], [7467:1-Et-4-CHF2-5-F-PYR3], [7468:1-Et-4-CF3-5-F-PYR3], [7469:1-Et-5-Cl-PYR3], [7470:1-Et-4-F-5-Cl-PYR3], [7471:1-Et-4-Cl-5-Cl-PYR3], [7472:1-Et-4-Br-5-Cl-PYR3], [7473:1-Et-4-Me-5-Cl-PYR3], [7474:1-Et-4-Et-5-Cl-PYR3], [7475:1-Et-4-OMe-5-Cl-PYR3], [7476:1-Et-4-OEt-5-Cl-PYR3], [7477:1-Et-4-CN-5-Cl-PYR3], [7478:1-Et-4-c-Pr-5-Cl-PYR3], [7479:1-Et-4-CHF2-5-Cl-PYR3], [7480:1-Et-4-CF3-5-Cl-PYR3], [7481:1-Et-5-Br-PYR3], [7482:1-Et-4-F-5-Br-PYR3], [7483:1-Et-4-Cl-5-Br-PYR3], [7484:1-Et-4-Br-5-Br-PYR3], [7485:1-Et-4-Me-5-Br-PYR3], [7486:1-Et-4-Et-5-Br-PYR3], [7487:1-Et-4-OMe-5-Br-PYR3], [7488:1-Et-4-OEt-5-Br-PYR3], [7489:1-Et-4-CN-5-Br-PYR3], [7490:1-Et-4-c-Pr-5-Br-PYR3], [7491:1-Et-4-CHF2-5-Br-PYR3], [7492:1-Et-4-CF3-5-Br-PYR3], [7493:1-Et-5-Me-PYR3], [7494:1-Et-4-F-5-Me-PYR3], [7495:1-Et-4-Cl-5-Me-PYR3], [7496:1-Et-4-Br-5-Me-PYR3], [7497:1-Et-4-Me-5-Me-PYR3], [7498:1-Et-4-Et-5-Me-PYR3], [7499:1-Et-4-OMe-5-Me-PYR3], [7500:1-Et-4-OEt-5-Me-PYR3], [7501:1-Et-4-CN-5-Me-PYR3], [7502:1-Et-4-c-Pr-5-Me-PYR3], [7503:1-Et-4-CHF2-5-Me-PYR3], [7504:1-Et-4-CF3-5-Me-PYR3], [7505:1-Et-5-Et-PYR3], [7506:1-Et-4-F-5-Et-PYR3], [7507:1-Et-4-Cl-5-Et-PYR3], [7508:1-Et-4-Br-5-Et-PYR3], [7509:1-Et-4-Me-5-Et-PYR3], [7510:1-Et-4-Et-5-Et-PYR3], [7511:1-Et-4-OMe-5-Et-PYR3], [7512:1-Et-4-OEt-5-Et-PYR3], [7513:1-Et-4-CN-5-Et-PYR3], [7514:1-Et-4-c-Pr-5-Et-PYR3], [7515:1-Et-4-CHF2-5-Et-PYR3], [7516:1-Et-4-CF3-5-Et-PYR3], [7517:1-Et-5-OMe-PYR3], [7518:1-Et-4-F-5-OMe-PYR3], [7519:1-Et-4-Cl-5-

OMe-PYR3], [7520:1-Et-4-Br-5-OMe-PYR3], [7521:1-Et-4-Me-5-OMe-PYR3], [7522:1-Et-4-Et-5-OMe-PYR3], [7523:1-Et-4-OMe-5-OMe-PYR3], [7524:1-Et-4-OEt-5-OMe-PYR3], [7525:1-Et-4-CN-5-OMe-PYR3], [7526:1-Et-4-c-Pr-5-OMe-PYR3], [7527:1-Et-4-CHF2-5-OMe-PYR3], [7528:1-Et-4-CF3-5-OMe-PYR3], [7529:1-Et-5-OEt-PYR3], [7530:1-Et-4-F-5-OEt-PYR3], [7531:1-Et-4-Cl-5-OEt-PYR3], [7532:1-Et-4-Br-5-OEt-PYR3], [7533:1-Et-4-Me-5-OEt-PYR3], [7534:1-Et-4-Et-5-OEt-PYR3], [7535:1-Et-4-OMe-5-OEt-PYR3], [7536:1-Et-4-OEt-5-OEt-PYR3], [7537:1-Et-4-CN-5-OEt-PYR3], [7538:1-Et-4-c-Pr-5-OEt-PYR3], [7539:1-Et-4-CHF2-5-OEt-PYR3], [7540:1-Et-4-CF3-5-OEt-PYR3], [7541:1-Et-5-CN-PYR3], [7542:1-Et-4-F-5-CN-PYR3], [7543:1-Et-4-Cl-5-CN-PYR3], [7544:1-Et-4-Br-5-CN-PYR3], [7545:1-Et-4-Me-5-CN-PYR3], [7546:1-Et-4-Et-5-CN-PYR3], [7547:1-Et-4-OMe-5-CN-PYR3], [7548:1-Et-4-OEt-5-CN-PYR3], [7549:1-Et-4-CN-5-CN-PYR3], [7550:1-Et-4-c-Pr-5-CN-PYR3], [7551:1-Et-4-CHF2-5-CN-PYR3], [7552:1-Et-4-CF3-5-CN-PYR3], [7553:1-Et-5-c-Pr-PYR3], [7554:1-Et-4-F-5-c-Pr-PYR3], [7555:1-Et-4-Cl-5-c-Pr-PYR3], [7556:1-Et-4-Br-5-c-Pr-PYR3], [7557:1-Et-4-Me-5-c-Pr-PYR3], [7558:1-Et-4-Et-5-c-Pr-PYR3], [7559:1-Et-4-OMe-5-c-Pr-PYR3], [7560:1-Et-4-OEt-5-c-Pr-PYR3], [7561:1-Et-4-CN-5-c-Pr-PYR3], [7562:1-Et-4-c-Pr-5-c-Pr-PYR3], [7563:1-Et-4-CHF2-5-c-Pr-PYR3], [7564:1-Et-4-CF3-5-c-Pr-PYR3], [7565:1-Et-5-CHF2-PYR3], [7566:1-Et-4-F-5-CHF2-PYR3], [7567:1-Et-4-Cl-5-CHF2-PYR3], [7568:1-Et-4-Br-5-CHF2-PYR3], [7569:1-Et-4-Me-5-CHF2-PYR3], [7570:1-Et-4-Et-5-CHF2-PYR3], [7571:1-Et-4-OMe-5-CHF2-PYR3], [7572:1-Et-4-OEt-5-CHF2-PYR3], [7573:1-Et-4-CN-5-CHF2-PYR3], [7574:1-Et-4-c-Pr-5-CHF2-PYR3], [7575:1-Et-4-CHF2-5-CHF2-PYR3], [7576:1-Et-4-CF3-5-CHF2-PYR3], [7577:1-Et-5-CF3-PYR3], [7578:1-Et-4-F-5-CF3-PYR3], [7579:1-Et-4-Cl-5-CF3-PYR3], [7580:1-Et-4-Br-5-CF3-PYR3], [7581:1-Et-4-Me-5-CF3-PYR3], [7582:1-Et-4-Et-5-CF3-PYR3], [7583:1-Et-4-OMe-5-CF3-PYR3], [7584:1-Et-4-OEt-5-CF3-PYR3], [7585:1-Et-4-CN-5-CF3-PYR3], [7586:1-Et-4-c-Pr-5-CF3-PYR3], [7587:1-Et-4-CHF2-5-CF3-PYR3], [7588:1-Et-4-CF3-5-CF3-PYR3], [7589:1-Et-5-OPr-PYR3], [7590:1-Et-4-F-5-OPr-PYR3], [7591:1-Et-4-Cl-5-OPr-PYR3], [7592:1-Et-4-Br-5-OPr-PYR3], [7593:1-Et-4-Me-5-OPr-PYR3], [7594:1-Et-4-Et-5-OPr-PYR3], [7595:1-Et-4-OMe-5-OPr-PYR3], [7596:1-Et-4-OEt-5-OPr-PYR3], [7597:1-Et-4-CN-5-OPr-PYR3], [7598:1-Et-4-c-Pr-5-OPr-PYR3], [7599:1-Et-4-CHF2-5-OPr-PYR3], [7600:1-Et-4-CF3-5-OPr-PYR3], [7601:1-Et-5-OCH2CH=CH2-PYR3], [7602:1-Et-4-F-5-OCH2CH=CH2-PYR3], [7603:1-Et-4-Cl-5-OCH2CH=CH2-PYR3], [7604:1-Et-4-Br-5-OCH2CH=CH2-PYR3], [7605:1-Et-4-Me-5-OCH2CH=CH2-PYR3], [7606:1-Et-4-Et-5-OCH2CH=CH2-PYR3], [7607:1-Et-4-OMe-5-OCH2CH=CH2-PYR3], [7608:1-Et-4-OEt-5-OCH2CH=CH2-PYR3], [7609:1-Et-4-CN-5-OCH2CH=CH2-PYR3], [7610:1-Et-4-c-Pr-5-OCH2CH=CH2-PYR3], [7611:1-Et-4-CHF2-5-OCH2CH=CH2-PYR3], [7612:1-Et-4-CF3-5-OCH2CH=CH2-PYR3], [7613:1-Et-5-OCH2CH=CCl2-PYR3], [7614:1-Et-4-F-5-OCH2CH=CCl2-PYR3], [7615:1-Et-4-Cl-5-OCH2CH=CCl2-PYR3], [7616:1-Et-4-Br-5-OCH2CH=CCl2-PYR3], [7617:1-Et-4-Me-5-OCH2CH=CCl2-PYR3], [7618:1-Et-4-Et-5-OCH2CH=CCl2-PYR3], [7619:1-Et-4-OMe-5-OCH2CH=CCl2-PYR3], [7620:1-Et-4-OEt-5-OCH2CH=CCl2-PYR3], [7621:1-Et-4-CN-5-OCH2CH=CCl2-PYR3], [7622:1-Et-4-c-Pr-5-OCH2CH=CCl2-PYR3], [7623:1-Et-4-CHF2-5-OCH2CH=CCl2-PYR3], [7624:1-Et-4-CF3-5-OCH2CH=CCl2-PYR3], [7625:1-Et-5-OCH2C≡CH-PYR3], [7626:1-Et-4-F-5-OCH2C≡CH-PYR3], [7627:1-Et-4-Cl-5-OCH2C≡CH-PYR3], [7628:1-Et-4-Br-5-OCH2C≡CH-PYR3], [7629:1-Et-4-Me-5-OCH2C≡CH-PYR3], [7630:1-Et-4-Et-5-OCH2C≡CH-PYR3], [7631:1-Et-4-OMe-5-OCH2C≡CH-PYR3], [7632:1-Et-4-OEt-5-OCH2C≡CH-PYR3], [7633:1-Et-4-CN-5-OCH2C≡CH-PYR3], [7634:1-Et-4-c-Pr-5-OCH2C≡CH-PYR3], [7635:1-Et-4-CHF2-5-OCH2C≡CH-PYR3], [7636:1-Et-4-CF3-5-OCH2C≡CH-PYR3], [7637:1-Et-5-OCH2CF3-PYR3], [7638:1-Et-4-F-5-OCH2CF3-PYR3], [7639:1-Et-4-Cl-5-OCH2CF3-PYR3], [7640:1-Et-4-Br-5-OCH2CF3-PYR3], [7641:1-Et-4-Me-5-OCH2CF3-PYR3], [7642:1-Et-4-Et-5-OCH2CF3-PYR3], [7643:1-Et-4-OMe-5-OCH2CF3-PYR3], [7644:1-Et-4-OEt-5-OCH2CF3-PYR3], [7645:1-Et-4-CN-5-OCH2CF3-PYR3], [7646:1-Et-4-c-Pr-5-OCH2CF3-PYR3], [7647:1-Et-4-CHF2-5-OCH2CF3-PYR3], [7648:1-Et-4-CF3-5-OCH2CF3-PYR3], [7649:1-Et-5-CH2OCH3-PYR3], [7650:1-Et-4-F-5-CH2OCH3-PYR3], [7651:1-Et-4-Cl-5-CH2OCH3-PYR3], [7652:1-Et-4-Br-5-CH2OCH3-PYR3], [7653:1-Et-4-Me-5-CH2OCH3-PYR3], [7654:1-Et-4-Et-5-CH2OCH3-PYR3], [7655:1-Et-4-OMe-5-CH2OCH3-PYR3], [7656:1-Et-4-OEt-5-CH2OCH3-PYR3], [7657:1-Et-4-CN-5-CH2OCH3-PYR3], [7658:1-Et-4-c-Pr-5-CH2OCH3-PYR3], [7659:1-Et-4-CHF2-5-CH2OCH3-PYR3], [7660:1-Et-4-CF3-5-CH2OCH3-PYR3]

Formulation Examples will be shown below.

Formulation Example 1

Fifty parts (50 parts) of any one of the present compounds A, 3 parts of calcium ligninsulfonate, 2 parts of laurylmagnesium sulfate, and 45 parts of synthetic hydrated silicon oxide are thoroughly ground and mixed to obtain each formulation.

Formulation Example 2

Twenty parts (20 parts) of any one of the present compounds A and 1.5 parts of sorbitan trioleate are mixed with 28.5 parts of an aqueous solution containing 2 parts of polyvinyl alcohol, and the mixture was finely ground by a wet grinding method. Then, 40 parts of an aqueous solution containing 0.05 part of xanthan gum and 0.1 part of aluminum magnesium silicate is added thereto and 10 parts of propylene glycol is further added, followed by stirring and mixing to obtain each formulation.

Formulation Example 3

Two parts (2 parts) of any one of the present compounds A, 88 parts of kaolin clay, and 10 parts of talc are thoroughly ground and mixed to obtain each formulation.

Formulation Example 4

Five parts (5 parts) of any one of the present compounds A, 14 parts of polyoxyethylene styryl phenyl ether, 6 parts of calcium dodecylbenzenesulfonate, and 75 parts of xylene are thoroughly ground and mixed to obtain each formulation.

Formulation Example 5

Two parts (2 parts) of any one of the present compounds A, 1 part of synthetic hydrated silicon oxide, 2 parts of calcium ligninsulfonate, 30 parts of bentonite, and 65 parts of kaolin clay are thoroughly ground and mixed. After the addition of water, the mixture is thoroughly kneaded and further granulated and dried to obtain each formulation.

Formulation Example 6

Ten parts (10 parts) of any one of the present compounds A, 35 parts of white carbon containing 50 parts of a polyoxyethylene alkyl ether sulfate ammonium salt, and 55 parts of water were finely ground by a wet grinding method to obtain each formulation.

The following Test Examples will show that the present compounds are useful for controlling plant diseases.

The control effect was evaluated by visually observing the area of lesion on each of test plants at the time of investigation, and comparing the area of lesion spots on a plant treated with the present compound with that on an untreated plant.

Test Example 1

Each of plastic pots was filled with soil and rice (cultivar: NIHONBARE) was sowed and grown in a greenhouse for 20 days. Then, each water dilution prepared by adjusting so as to contain a predetermined concentration (500 ppm) of any one compound of the present compounds 11, 13, and 16 was sprayed over stems and leaves so that it sufficiently adhered to the surface of the leaves of the rice. After spraying, the plant was air-dried and placed for 6 days at 24° C. in the daytime and 20° C. at night under high humidity condition, while being in contact with the rice seedling (cultivar: NIHONBARE) infected by the rice blast fungus (*Magnaporthe grisea*), and then the area of lesion was investigated. As a result, the lesion areas on the plant treated with the present compound 11, 13, or 16 were 30% or less with respect to the lesion area on the non-treated plant.

Test Example 2

Each of plastic pots was filled with soil and rice (cultivar: NIHONBARE) was sowed and grown in a greenhouse for 20 days. Then, each water dilution prepared by adjusting so as to contain a predetermined concentration (200 ppm) of any one compound of the present compounds 1, 10, and 15 was sprayed over stems and leaves so that it sufficiently adhered to the surface of the leaves of the rice. After spraying, the plant was air-dried and placed for 6 days at 24° C. in the daytime and 20° C. at night under high humidity condition, while being in contact with the rice seedling (cultivar: NIHONBARE) infected by the rice blast fungus (*Magnaporthe grisea*), and then the area of lesion was investigated. As a result, the lesion areas on the plant treated with the present compound 1, 10, or 15 were 30% or less with respect to the lesion area on the non-treated plant.

Test Example 3

Each of plastic pots was filled with soil and barley (cultivar: NISHINOHOSHI) was sowed and grown in a greenhouse for 7 days. Then, each water dilution prepared by adjusting so as to contain a predetermined concentration (500 ppm) of any one compound of the present compounds 1, and 3 to 16 was sprayed over stems and leaves of the barley so that it sufficiently adhered to the surface of the leaves of the barley. After spraying, the plant was air-dried. After 2 days, an aqueous suspension containing spores of barley net blotch fungus (*Pyrenophora teres*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, the area of lesion on the plant treated with the present compound(s) 1, or 3 to 16 was 30% or less of that on an untreated plant.

Test Example 4

Each of plastic pots was filled with soil and kidney bean (cultivar: NAGAUZURA SAITOU) was sowed and grown in a greenhouse for 8 days. Then, each water dilution prepared by adjusting so as to contain a predetermined concentration (500 ppm) of any one compound of the present compounds 4 and 6 was sprayed over stems and leaves of the kidney bean so that it sufficiently adhered to the surface of the leaves of the kidney bean. After spraying, the plant was air-dried and a PDA medium containing hyphae of the kidney bean stem rot fungus (*Sclerotinia sclerotiorum*) was placed on the leaves of the kidney bean. After the inoculation, all kidney beans were placed under high humidity condition only at night. Four days after the inoculation, the area of lesion was investigated. As a result, the area of lesion on the plant treated with the present compound 4 or 6 was 30% or less of that on an untreated plant.

Test Example 5

Each of plastic pots was filled with soil and wheat (cultivar: APOGEE) was sowed and grown in a greenhouse for 10 days. Then, each water dilution prepared by adjusting so as to contain a predetermined concentration (500 ppm) of any one compound of the present compounds 1 to 8 and 10 to 16 was sprayed over stems and leaves of the wheat so that it sufficiently adhered to the surface of the leaves of the wheat. After spraying, the plant was air-dried. After 4 days, an aqueous suspension containing spores of wheat leaf blotch fungus (*Septoria tritici*) was sprayed to inoculate the spores. After completion of the inoculation, the plant was placed at 18° C. under high humidity condition for 3 days and placed under illumination for 14 to 18 days, and then the area of lesion was investigated. As a result, the area of lesion on the plant treated with the present compound(s) 1 to 8 or 10 to 16 was 30% or less of that on an untreated plant.

Test Example 6

Each of plastic pots was filled with soil and wheat (cultivar: APOGEE) was sowed and grown in a greenhouse for 10 days. Thereafter, an aqueous suspension containing spores of wheat leaf blotch fungus (*Septoria tritici*) was sprayed over the wheat to inoculate the spores. The wheat was placed at 18° C. under high humidity condition for 3 days and then air-dried. Each water dilution prepared by adjusting so as to contain a predetermined concentration (200 ppm) of any one compound of the present compounds 1, 7, 8, 12, and 14 to 16 was sprayed over stems and leaves of the wheat so that it sufficiently adhered to the surface of the leaves of the wheat. After spraying, the plant was air-dried. The plant was placed under illumination for 14 to 18 days, and then the area of lesion was investigated. As a result, the area of lesion on the plant treated with the present compound(s) 1, 7, 8, 12, or 14 to 16 was 30% or less of that on an untreated plant.

Test Example 7

Each of plastic pots was filled with soil and wheat (cultivar: APOGEE) was sowed and grown in a greenhouse for 10 days. Thereafter, an aqueous suspension containing spores of wheat leaf blotch fungus (*Septoria tritici*) was sprayed over the wheat to inoculate the spores. The wheat was placed at 18° C. under high humidity condition for 3 days and then air-dried. Each water dilution prepared by adjusting so as to contain a predetermined concentration (50 ppm) of the present compound 3 was sprayed over stems and leaves of the wheat so that it sufficiently adhered to the surface of the leaves of the wheat. After spraying, the plant was air-dried. The plant was placed under illumination for 14 to 18 days, and then the area of lesion was investigated. As a result, the area of lesion on the plant treated with the present compound 3 was 30% or less of that on an untreated plant.

Test Example 8

Each of plastic pots was filled with soil and wheat (cultivar: SHIROGANE) was sowed and grown in a greenhouse for 9 days. Then, each water dilution prepared by adjusting so as to contain a predetermined concentration (200 ppm) of any one compound of the present compounds 12, and 14 to 16 was sprayed over stems and leaves of the wheat so that it sufficiently adhered to the surface of the leaves of the wheat. After spraying, the plant was air-dried and cultivated at 20° C. for 5 days under illumination, and then inoculated by sprinkling with spores of wheat rust fungus (*Puccinia recondita*). After the inoculation, the plant was placed at 23° C. for one day under dark and high humidity condition, and cultivated under illumination at 20° C. for 8 days, and then the area of lesion was investigated. As a result, it has been found that the area of lesion on the plant treated with the present compound(s) 12, or 14 to 16 was 30% or less of that on an untreated plant.

Test Example 9

Each of plastic pots was filled with soil and barley (cultivar: MIKAMO GOLDEN) was sowed and grown in a greenhouse for 7 days. Then, each water dilution prepared by adjusting so as to contain a predetermined concentration (200 ppm) of any one compound of the present compounds 14, 15, and 16 was sprayed over stems and leaves of the barley so that it sufficiently adhered to the surface of the leaves of the barley. After spraying, the plant was air-dried. After 2 days, an aqueous suspension containing spores of barley scald fungus (*Rhynchosporium secalis*) was sprayed to inoculate the spores. After completion of the inoculation, the plant was placed for 3 days in a greenhouse at 23° C. in the daytime and 20° C. at night under high humidity condition and cultivated in a greenhouse for 7 days, and then the area of lesion was investigated. As a result, it has been found that the area of lesion on the plant treated with of the present compound 14, 15, or 16 was 30% or less of that on an untreated plant.

Test Example 10

Each of plastic pots was filled with soil and cucumber (cultivar: SAGAMI HANJIRO) was sowed and grown in a greenhouse for 12 days. Then, each water dilution prepared by adjusting so as to contain a predetermined concentration (500 ppm) of any one compound of the present compounds 3 to 5, 12, 14, and 16 was sprayed over stems and leaves of the cucumber so that it sufficiently adhered to the surface of the leaves of the cucumber. After spraying, the plant was air-dried and then inoculated by sprinkling with spores of cucumber powdery mildew fungus (*Sphaerotheca fuliginea*). After the inoculation, the plant was cultivated in a greenhouse at 24° C. in the daytime and 20° C. at night for 8 days, and then the area of lesion was investigated. As a result, the area of lesion on the plant treated with the present compound 3 to 5, 12, 14, or 16 was 30% or less of that on an untreated plant.

Test Example 11

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of the present compound 6 was sprayed over stems and leaves of the cucumber so that it sufficiently adhered to the surface of the leaves of the cucumber. After spraying, the plant was air-dried. After one day, an aqueous suspension containing spores of target spot fungus (*Corynespora cassiicola*). After the inoculation, the plant was cultivated in a greenhouse at 24° C. in the daytime and 20° C. at night for 7 days, and then the area of lesion was investigated. As a result, the area of lesion on the plant treated with the present compound 6 was 30% or less of that on an untreated plant.

Test Example 12

Each of plastic pots was filled with soil and cucumber (cultivar: SAGAMI HANJIRO) was sowed and grown in a greenhouse for 19 days. Then, each water dilution prepared by adjusting so as to contain a predetermined concentration (200 ppm) of any one compound of the present compounds 11 to 13, 15, and 16 was sprayed over stems and leaves of the cucumber so that it sufficiently adhered to the surface of the leaves of the cucumber. After spraying, the plant was air-dried. After one day, an aqueous suspension containing spores of anthracnose fungus (*Colletotrichum lagenarium*) was sprayed to inoculate the spores. After the inoculation, the plant was cultivated in a greenhouse at 24° C. in the daytime and 20° C. at night for 6 days, and then the area of lesion was investigated. As a result, the area of lesion on the plant treated with the present compound(s) 11 to 13, 15, or 16 was 30% or less of that on an untreated plant.

Test Example 13

The present compound 9 was diluted with water so as to contain 500 ppm of an active ingredient to prepare a test chemical solution.

On the bottom a polyethylene cup having a diameter of 5.5 cm, a filter paper having the same size was laid. Then, 0.7 mL of the above test chemical solution was dropped on the filter paper and 30 mg of sucrose as a bait was uniformly put therein. Ten (10) heads of female adults of house fly (*Musca domestica*) were released and then a lid was put on the cup. After 24 hours, life and death of house fly were examined and mortality was calculated by the following equation.

Mortality(%)=(number of dead insects/number of tested insects)×100

As a result, in a treatment with the present compound 9, 100% of mortality was shown.

Test Example 14

The present compound 12 or 14 was diluted with water so as to contain 500 ppm of an active ingredient to prepare a test chemical solution.

Cabbage (cultivar: GREEN BALL) was sowed and grown in a polyethylene cup until the third to fourth true leaf was developed. The test chemical solution was sprayed over the cabbage at a rate of 20 mL per cup. After drying the chemical solution, the cabbage cut from the base was disposed in a polyethylene cup (5.5 cm in diameter) with a filter paper laid on the bottom. Five (5) heads of third-instar larvae of diamondback moth (*Plutella xylostella*) were released and then a lid was put on the cup. After storage at 25° C. for 5 days, the number of the surviving insects was counted and mortality was calculated by the following equation.

Mortality(%)=(number of dead insects/number of tested insects)×100

As a result, the present compound 12 or 14 showed 80% or more of mortality in the area treated with the test chemical solution.

Test Example 15

The present compound 12 was diluted with water so as to contain 500 ppm of an active ingredient to prepare a test chemical solution.

Thirty (30) heads of cotton aphid (*Aphis gossypii*) (including adults and larvae) were released on the leaves of cucumber (cultivar: SAGAMI HANJIRO FUSHINARI) grown in a polyethylene cup until the first true leaf was developed. Next day, 20 mL of the test chemical solution was sprayed. After 6 days, the number of the surviving insects was counted and the control value was calculated by the following equation.

Control value(%)={1−(Cb×Tai)/(Cai×Tb)}×100 wherein symbols in the equation represent the followings:
Cb: Number of insects before spraying chemical solution in untreated area;
Cai: Number of surviving insects in untreated area;
Tb: Number of insects before spraying chemical solution in treated area; and
Tai: Number of surviving insects in treated area.

As a result, the present compound 12 showed 90% or more of the control value.

The invention claimed is:
1. A tetrazolinone compound represented by formula (1):

$$A-Q-Y-E-N\underset{N=N}{\overset{X}{\underset{\|}{\bigvee}}}\!\!\!\!\!\!\!\!\!\underset{}{\overset{R^5}{\diagdown N}} \quad (1)$$

wherein
$R^5$ represents a C1-C3 alkyl group optionally having one or more halogen atoms;

E represents a group selected from the following group:

E16

E36

E44

E45 wherein the symbol # represents a binding site for a tetrazolinone ring, and the symbol $ represents a binding site for Y;
$R^1$ represents a hydrogen atom, a C1-C6 alkyl group, a C3-C6 cycloalkyl group, a halogen atom, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, a thiol group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group;
$R^3$ represents a hydrogen atom, a halogen atom, a C1-C3 alkyl group, a C1-C3 haloalkyl group, a C2-C3 alkenyl group, a C2-C3 haloalkenyl group, or a C1-C3 alkoxy group;
$R^6$ and $R^7$ each independently represents a hydrogen atom, a C1-C3 alkyl group, a C1-C3 haloalkyl group, a C2-C3 alkenyl group, a C2-C3 haloalkenyl group, or a C1-C3 alkoxy group;

R⁸ represents a hydrogen atom, a C1-C6 alkyl group, a C3-C6 cycloalkyl group, a C1-C6 haloalkyl group, a C2-C6 alkenyl group, a C1-C6 alkoxy group, a C1-C6 alkylthio group, a C2-C6 alkynyl group, a nitro group, a cyano group, an aminocarbonyl group optionally having a C1-C6 alkyl group, a C2-C6 haloalkenyl group, a C2-C6 haloalkynyl group, a C3-C6 halocycloalkyl group, a C1-C6 haloalkoxy group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a C2-C6 alkoxycarbonyl group, a hydroxy group, an amino group optionally having a C1-C6 alkyl group, a pentafluorosulfanyl group, a C3-C9 trialkylsilyl group, a C5-C14 trialkylsilylethynyl group, a C1-C4 alkylsulfonyl group, a C1-C4 haloalkylsulfonyl group, a C1-C4 alkylsulfinyl group, a C1-C4 haloalkylsulfinyl group, a C2-C5 alkoxyalkyl group, or a C2-C5 alkylthioalkyl group;

Y represents *—(CH₂)$_n$-G-&, wherein G represents an oxygen atom, n represents an integer 1, and the symbol * in Y represents a binding site for Q, and the symbol & represents a binding site for E;

Q represents Q46:

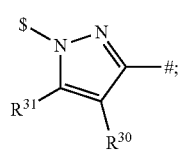

wherein R³⁰ and R³¹ each independently represents a hydrogen atom, a halogen atom, a cyano group, a C3-C6 cycloalkyl group, a C3-C6 halocycloalkyl group, a C1-C4 alkoxy group, a C1-C4 haloalkoxy group, a C1-C4 alkylthio group, or a C1-C4 haloalkylthio group;

X represents an oxygen atom or a sulfur atom;

A represents a C6-C10 aryl group, an adamantyl group, a C6-C10 aryloxy group, a C6-C10 arylthio group, a C6-C10 arylamino group, a C3-C10 cycloalkyl group, a 5- to 10-membered heterocyclic group, a 5- to 10-membered heteroaryloxy group, a 5- to 10-membered heteroarylthio group, a 5- to 10-membered heteroarylamino group, a C6-C10 arylsulfonyl group, a C6-C10 arylsulfinyl group, or —CH=NH optionally having one or two groups selected from Group P³, wherein the 5- to 10-membered heterocyclic group, the 5- to 10-membered heteroaryloxy group, the 5- to 10-membered heteroarylthio group, and the 5- to 10-membered heteroarylamino group have, as a ring-constituent atom, one or more atoms selected from the group consisting of a nitrogen atom, an oxygen atom, and a sulfur atom, and, when two or more atoms are present, the atoms may be the same or different to each other, and the 5- to 10-membered heterocyclic group, the 5- to 10-membered heteroaryloxy group, the 5- to 10-membered heteroarylthio group, and the 5- to 10-membered heteroarylamino group optionally have one or more atoms or groups selected from Group P¹, and, when two or more atoms or groups are present, the atoms or groups may be the same or different to each other, when —CH=NH has two groups selected from Group P³, the groups may be the same or different to each other, and the C6-C10 aryl group, the adamantyl group, the C6-C10 aryloxy group, the C6-C10 arylthio group, the C6-C10 arylamino group, the C3-C10 cycloalkyl group, the C6-C10 arylsulfonyl group, and the C6-C10 arylsulfinyl group optionally have one or more atoms or groups selected from Group P¹, and, when two or more atoms or groups are present, the atoms or groups may be the same or different to each other:

Group P¹: Group consisting of a halogen atom, a C1-C6 alkyl group, a C1-C6 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C1-C6 alkoxy group, a C1-C6 haloalkoxy group, a C1-C6 alkylthio group, a C1-C6 haloalkylthio group, a C3-C6 cycloalkyloxy group, a C3-C6 halocycloalkyloxy group, a C3-C6 cycloalkylthio group, a C3-C6 alkenyloxy group, a C3-C6 alkynyloxy group, a C3-C6 haloalkenyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C2-C6 alkylcarbonyl group, a C2-C6 haloalkylcarbonyl group, a C2-C6 alkylcarbonyloxy group, a C2-C6 alkylcarbonylthio group, a carboxy group, a formyl group, a C2-C6 alkoxycarbonyl group, a nitro group, a cyano group, a hydroxy group, a C1-C6 alkylsulfonyl group, a C1-C6 haloalkylsulfonyl group, a C1-C6 alkylsulfinyl group, a C1-C6 haloalkylsulfinyl group, an amino group optionally having a C1-C6 alkyl group, an aminosulfonyl group optionally having a C1-C6 alkyl group, and an aminocarbonyl group optionally having a C1-C6 alkyl group; and Group P³: Group consisting of a C1-C6 alkyl group, a C1-C6 haloalkyl group, a C3-C6 cycloalkyl group, and a C3-C6 halocycloalkyl group.

2. A pest control agent comprising the tetrazolinone compound according to claim 1.

3. A method for controlling pests, which comprises applying an effective amount of the tetrazolinone compound according to claim 1 to plants or soil.

4. The tetrazolinone compound according to claim 1, wherein E is E16, E36, E44, or E45.

5. The tetrazolinone compound according to claim 1, wherein in Q46, R³⁰ and R³¹ are hydrogen.

* * * * *